US010793561B2

(12) United States Patent
Pham et al.

(10) Patent No.: US 10,793,561 B2
(45) Date of Patent: Oct. 6, 2020

(54) 1,8-NAPHTHYRIDINONE COMPOUNDS AND USES THEREOF

(71) Applicant: NUVATION BIO INC., New York, NY (US)

(72) Inventors: Son Minh Pham, San Francisco, CA (US); Jiyun Chen, Moraga, CA (US); Amantullah Ansari, Noida (IN); Pradeep S. Jadhavar, Greater Noida (IN); Varshavekumar S. Patil, Greater Noida (IN); Farha Khan, New Delhi (IN); Sreekanth A. Ramachandran, Greater Noida (IN); Anil Kumar Agarwal, Noida (IN); Sarvajit Chakravarty, Edmond, OK (US)

(73) Assignee: NUVATION BIO INC., New York, NY (US)

( * ) Notice: Subject to any disclaimer, the term of this patent is extended or adjusted under 35 U.S.C. 154(b) by 0 days.

(21) Appl. No.: 16/039,301

(22) Filed: Jul. 18, 2018

(65) Prior Publication Data

US 2019/0023702 A1 Jan. 24, 2019

Related U.S. Application Data

(60) Provisional application No. 62/534,185, filed on Jul. 18, 2017.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ... C07D 471/04; C07D 519/00; A61K 31/444
See application file for complete search history.

(56) References Cited

U.S. PATENT DOCUMENTS

| | | | |
|---|---|---|---|
| 6,992,087 B2 | 1/2006 | Verhoest | |
| 7,407,961 B2 | 8/2008 | Yonishi et al. | |
| 7,728,141 B2 * | 6/2010 | Debenham | A61K 31/4375 546/123 |
| 7,790,728 B2 | 9/2010 | Vidal Juan et al. | |
| 8,754,085 B2 * | 6/2014 | Charlton | A61K 31/4375 514/249 |
| 9,132,127 B2 * | 9/2015 | Charlton | A61K 31/4375 |
| 10,112,923 B2 | 10/2018 | Congreve et al. | |
| RE47,351 E | 4/2019 | Zablocki | |
| 10,253,044 B2 | 4/2019 | Wang | |
| 10,292,968 B2 | 5/2019 | Brown | |
| 10,307,407 B2 | 6/2019 | Wang | |
| 10,328,074 B2 | 6/2019 | Engelhardt | |
| 10,336,697 B2 | 7/2019 | Ujjinamatada | |
| 10,336,722 B2 | 7/2019 | Bair | |
| 10,363,257 B2 | 7/2019 | Quinn | |
| 10,370,356 B2 | 8/2019 | Atkinson | |
| 10,370,374 B2 | 8/2019 | Ibrahim | |
| 10,377,769 B2 | 8/2019 | Bair | |
| 10,391,175 B2 | 8/2019 | Wang | |
| 10,399,962 B2 | 9/2019 | Beatty | |
| 10,472,347 B2 | 11/2019 | Kuang et al. | |
| 2006/0293339 A1 | 12/2006 | Chakravarty et al. | |
| 2007/0072874 A1 | 3/2007 | Cui | |
| 2009/0247567 A1 | 10/2009 | Do et al. | |
| 2014/0174537 A1 | 6/2014 | Fadhel | |
| 2014/0243346 A1 | 8/2014 | Charlton et al. | |
| 2015/0094312 A1 | 4/2015 | Adcock | |
| 2016/0130253 A1 | 5/2016 | Arancio et al. | |
| 2016/0311784 A1 | 10/2016 | Leach et al. | |
| 2019/0023666 A1 | 1/2019 | Pham et al. | |
| 2019/0135784 A1 | 5/2019 | Strum | |
| 2019/0135811 A1 | 5/2019 | Strum | |
| 2019/0135820 A1 | 5/2019 | Smith | |
| 2019/0248795 A1 | 8/2019 | Burkamp | |
| 2019/0276473 A1 | 9/2019 | Crosignani | |
| 2019/0292188 A1 | 9/2019 | Wang et al. | |
| 2019/0337957 A1 | 11/2019 | Wang et al. | |

FOREIGN PATENT DOCUMENTS

| | | |
|---|---|---|
| AU | 2019205984 A1 | 8/2019 |
| CN | 104341386 A | 2/2015 |
| CN | 107221611 A | 9/2017 |
| EP | 3230277 B1 | 9/2019 |
| WO | WO2003030909 A1 | 4/2003 |
| WO | WO-2005/040151 A1 | 5/2005 |
| WO | WO-2007/017096 A1 | 2/2007 |
| WO | WO-2011/095625 A1 | 8/2011 |
| WO | WO-2012/168358 A1 | 12/2012 |
| WO | WO-2014/145485 A2 | 9/2014 |
| WO | WO-2014/145485 A3 | 9/2014 |
| WO | WO-2015/017335 A1 | 2/2015 |
| WO | WO-2016/081290 A1 | 5/2016 |
| WO | WO-2017/025918 A1 | 2/2017 |
| WO | WO-2017/112917 A1 | 6/2017 |
| WO | WO-2018/081863 A1 | 5/2018 |
| WO | WO-2018/178338 A1 | 10/2018 |
| WO | WO-2019/002606 A1 | 1/2019 |
| WO | WO-2019/090347 A1 | 5/2019 |
| WO | WO2019096322 A1 | 5/2019 |
| WO | WO2019118313 A1 | 6/2019 |
| WO | WO2019120234 A2 | 6/2019 |
| WO | WO2019134539 A1 | 7/2019 |
| WO | WO2019141131 A1 | 7/2019 |
| WO | WO2019148161 A1 | 8/2019 |
| WO | WO2019154294 A1 | 8/2019 |
| WO | WO2019158070 A1 | 8/2019 |

(Continued)

OTHER PUBLICATIONS

Lin,CA160:536900, abstract only of Gaodeng Xuexiao Huaxue Xuebao, 2013, 34(5), 1240-1245. (Year: 2013).*

(Continued)

*Primary Examiner* — D Margaret M Seaman
(74) *Attorney, Agent, or Firm* — Morrison & Foerster LLP

(57) ABSTRACT 1,8-naphthyridinone compounds as modulators of an adenosine receptor are provided. The compounds may find use as therapeutic agents for the treatment of diseases mediated through a G-protein-coupled receptor signaling pathway and may find particular use in oncology.

76 Claims, No Drawings

(56) References Cited

FOREIGN PATENT DOCUMENTS

| WO | WO2019160829 A1 | 8/2019 |
|----|----|----|
| WO | WO2019165204 A1 | 8/2019 |
| WO | WO2019169065 A2 | 9/2019 |
| WO | WO2019173082 A1 | 9/2019 |

OTHER PUBLICATIONS

Ferrarini, Il Farmaco vol. 55, 603-610, 2010. (Year: 2010).*
Kang, Bioorg & Med Chem Lett, vol. 19, 2990-2996, 2009. (Year: 2009).*
Madsen-Duggen, Bioorg & Med Chem Lett, vol. 20, 2010, 3750-3754. (Year: 2010).*
Iyer, Med Chem Res, vol. 21, 788-795, 2012. (Year: 2012).*
Chen, Angew Chem Int Ed, 2017, 56, 14232-14236. (Year: 2017).*
Debenhann, Bioorg & Med Chem Lett, VOI 16, 681-685, 2006. (Year: 2006).*
Badawneh, Il Farmaco, vol. 58, 2003, 859-866. (Year: 2003).*
Allard, B. et al. (2013; e-pub. Aug. 27, 2013). "Targeting CD73 Enhances the Antitumor Activity of Anti-PD-1 and Anti-CTLA-4 mAbs," Clinical Cancer Research 19(20):1-10.
Allard, B. et al. (2016). "Immunosuppressive Activities of Adenosine in Cancer," Current Opinion in Pharmacology 29:7-16.
Allard, D. et al. (Feb. 2016; e-pub. Jan. 25, 2016). "CD73—Adenosine: A Next-Generation Target in Immuno-Oncology," Immunotherapy 8(2):143-163, 19 pages.
Allard, D. et al. (Apr. 2017; e-published Feb. 8, 2017). "Targeting A2 Adenosine Receptors in Cancer," Immunology and Cell Biology 95(4):333-339; 34 pages.
Allard, D. et al. (Jan. 2019; e-pub. May 24, 2018). "Targeting the CD73-Adenosine Axis in Immuno-Oncology," Immunology Letters 205:31-39.
Arab, S. et al. (Mar. 2017). "Increased Efficacy of a Dendritic Cell-based Therapeutic Cancer Vaccine with Adenosine Receptor Antagonist and CD73 Inhibitor," Tumor Biology, pp. 1-8.
Azambuja, J.H. et al. (May 2019; e-pub. Aug. 16, 2018). "CD73 Downregulation Decreases In Vitro and In Vivo Glioblastoma Growth," Molecular Neurobiology 56(5):3260-3279, 20 pages.
Banuelos, J. et al. (Feb. 18-22, 2019). "Targeting Innate Immune Cells for the Treatment of Cancer," #1008, Poster presented at Keystone Conference, Uncovering Mechanisms of Immune-Based Therapy in Cancer and Autoimmunity, Breckenridge, CO, 1 page.
Bastid, J. et al. (2014). "Inhibition of CD39 Enzymatic Function at the Surface of Tumor Cells Alleviates Their Immunosuppressive Activity," Cancer Immunology Research 3(3):254-265.
Beavis, P.A. et al. (Mar. 2017). "Targeting the Adenosine 2A Receptor Enhances Chimeric Antigen Receptor T Cell Efficacy," The Journal of Clinical Investigation 127(3):929-941.
Beavis, P.A. et al. (May 2015; e-pub. Feb. 11, 2015). "Adenosine Receptor 2A Blockade Increases the Efficacy of Anti-PD-1 through Enhanced Antitumor T-cell Responses," Cancer Immunology Research 3(5):506-517.
Beavis, P.A. et al. (Nov. 2015). "CD73: A Potential Biomarker for Anti-PD-1 Therapy," OncoImmunology 4(11):e1046675, 3 pages.
Beavis, P.V. et al. (Sep. 3, 2013). "Blockade of A2A Receptors Potently Suppresses the Metabolism of CD73+ Tumors," Proc. Natl. Acad. Sci. 110(36):14711-14716.
Becker, A. et al. (2018). "CD73 Inhibitors (CD73i) Reverse the AMP/Adenosine-Mediated Impairment of Immune Effector Cell Activation by Immune Checkpoint Inhibitors (ICI)," Abstract No. 710, Poster present at Annual Meeting of the American Association of Cancer Research, Chicago, IL,1 page.
Bendell, J. et al. (Mar. 29-Apr. 4, 2019). "Evidence of Immune Activation in the First-in-Human Phase Ia Dose Escalation Study of the Adenosine 2a Receptor Antagonist, AZD4635, in Patients with Advanced Solid Tumors " Poster presented at the American Association for Cancer Research Annual Meeting, Atlanta, GA, 1 page.

Blay, J. et al. (Jul. 1, 1997). "The Extracellular Fluid of Solid Carcinomas Contains Immunosuppressive Concentrations of Adenosine," Cancer Research 57(13):2602-2605.
Borodovsky, A. et al. (Apr. 5, 2017). "Preclinical Pharmacodynamics and Antitumor Activity of AZD4635, a Novel Adenosine 2A Receptor Inhibitor that Reverses Adenosine Mediated T Cell Suppression," Poster Presented at the AACR Annual Meeting, Washington, D.C., 1 page.
Borodovsky, A. et al. (Apr. 17, 2018). "Inhibition of $A_{2A}R$ by AZD4635 Induces Anti-tumor Immunity Alone and in Combination with Anti-PD-L1 in Preclinical Models," Poster Presented at the AACR Annual Meeting, Chicago, IL, 1 page.
Burkholder, B. et al. (2014; e-pub. Jan. 17, 2014). "Tumor-induced Perturbations of Cytokines and Immune Cell Networks," Biochimica Biophysica Acta 1845:182-201.
Cekic, C. et al. (2011). Adenosine $A_{2B}$ Receptor Blockade Slows Growth of Bladder and Breast Tumors, J. Immunol. 188(1):198-205.
Cekic, C. et al. (Mar. 2016). "Purinergic Regulation of the Immune System," Nature Reviews 16:177-192.
Chen, J.-F. et al. (Apr. 2013). "Adenosine Receptors as Drug Targets—What are the Challenges'?," Nature Reviews 12:265-286.
Congreve, M. et al. (2012). "Discovery of 1,2,4-Triazine Derivatives as Adenosine $A_{2A}$ Antagonists using Structure Based Drug Design," Journal of Medicinal Chemistry 55:1898-1903, (with Supplementary material, 18 pages).
Congreve, M. et al. (Nov. 2018; e-pub. Oct. 18, 2018). "Targeting Adenosine $A_{2A}$ Receptor Antagonism for Treatment of Cancer," Expert Opinion on Drug Discovery 13(11):997-1003, 8 pages.
Corvus Pharmaceuticals. (Oct. 2, 2018). Corporate Presentation at Cantor Global Healthcare Conference, 25 pages.
De Lera Ruiz, M. et al. (May 8, 2014; e-pub. Nov. 15, 2013). "Adenosine $A_{2A}$ Receptor as a Drug Discovery Target," J. Med. Chem. 57(9):3623-3650, 28 pages.
De Mendonca, A. et al. (2000). "Adenosine: Does it have a Neuroprotective Role After All?," Brain Research Reviews 33:258-274.
Dosa, P.I. et al. (Feb. 11, 2016; e-pub. Sep. 21, 2015). "Tactical Approaches to Interconverting GPCR Agonists and Antagonists," Journal of Medicinal Chemistry 59(3):810-840, 31 pages.
Draper-Joyce, C.J. et al. (2018). "Structure of the Adenosine-bound Human Adenosine $A_1$ Receptor—$G_i$ Complex," Nature 558:559-563, 21 pages.
Eastwood, P. et al. (2010; e-pub. Jan. 20, 2010). "Discovery of N-(5,6-diarylpyridin-2-yl)amide Derivatives as Potent and Selective $A_{2B}$ Adenosine Receptor Antagonists," Bioorganic & Medicinal Chemistry Letters 20:1697-1700.
Eastwood, P. et al. (2011; e-pub. Dec. 20, 2010). "Discovery of LAS101057: A Potent, Selective, and Orally Efficacious A2B Adenosine Receptor Antagonist," Bioorganic & Medicinal Chemistry Letters 2:213-218.
Garapaty, S. et al. (Jun. 2018). "Novel, Heterocyclic Small Molecule Inhibitors of PD-1/PD-L1 Pathway," Jubliant Biosys Ltd., Poster presented at AACR, 1 page.
Gessi, S. et al. (Dec. 1, 2017). "Inhibition of $A_{2A}$ Adenosine Receptor Signaling in Cancer Cells Proliferation by the Novel Antagonist TP455," Frontiers in Pharmacology 8(Article 888), 13 pages.
Gessi, S. et al. (May 2011; e-pub. Oct. 1, 2010). "Adenosine Receptors and Cancer," Biochim Biophys Acta 1808(5):1400-1412.
Glukhova, A. et al. (Feb. 23, 2017). "Structure of the Adenosine A1 Receptor Reveals the Basis for Subtype Selectivity," Cell 168:867-877.
Goulding, J. et al. (2018; e-pub. Oct. 26, 2017). "Characterisation of Endogenous $A_{2A}$ and $A_{2B}$ Receptor-mediated Cyclic AMP Responses in HEK 293 Cells Using the GloSensor™ Biosensor: Evidence for an Allosteric Mechanism of Action for the A2B-Selective Antagonist PSB 603," Biochemical Pharmacology 147:55-66.
Gutierrez-De-Teran, H. et al. (2017). "Structure-Based Rational Design of Adenosine Receptor Ligands," Current Topics in Medicinal Chemistry 17:40-58.

(56) References Cited

OTHER PUBLICATIONS

Hausler, S. et al. (2014). "Anti-CD39 and Anti-CD73 Antibodies A1 and 7G2 Improve Targeted Therapy in Ovarian Cancer by Blocking Adenosine-Dependent Immune Evasion," Am J Transl Res 6(2):129-139.

Hinz, S. et al. (2018). "Adenosine $A_{2A}$ Receptor Ligand Recognition and Signaling is Blocked by $A_{2B}$ Receptors," Oncotarget 9(17):13593-13611.

Hocher, B. (2010; e-pub. Jun. 30, 2010). "Adenosine A1 Receptor Antagonists in Clinical Research and Development," Kidney International 78:438-445.

Houthuys, E. et al. (Sep. 2017). "A Novel Non-Competitive and Non-Brain Penetrant Adenosine A2A Receptor Antagonist Designed to Reverse Adenosinemediated Suppression of Anti-tumor Immunity," Poster presented at ICIC, 1 page.

Huang, S. et al. (Aug. 15, 1997). "Role of A2a Extracellular Adenosine Receptor-Mediated Signaling in Adenosine-Mediated Inhibition of T-Cell Activation and Expansion," Blood 90(4):1600-1610.

Iannone, R. et al. (Dec. 2013). Blockade of $A_{2B}$ Adenosine Receptor Reduces Tumor Growth and Immune Suppression Mediated by Myeloid-Derived Suppressor Cells in a Mouse Model of Melanoma, Neoplasia, 15(12):1400-14009.

Iannone, R. et al. (Mar. 15, 2014; e-pub. Mar. 1, 2014). "Adenosine Limits the Therapeutic Effectiveness of Anti-CTLA4 mAb in a Mouse Melanoma Model," Am J Cancer Res 4(2):172-181.

International Search Report and Written Opinion dated Nov. 1, 2018 for PCT Application No. PCT/US2018/042777 filed on Jul. 18, 2018, 10 pages.

International Search Report and Written Opinion dated Oct. 26, 2018 for PCT Application No. PCT/US2018/042776 filed on Jul. 18, 2018, 10 pages.

Invitrogen. (Dec. 1, 2010). "GeneBLAzer ADORA2A CHO-K1 DA Cell-Based Assay" 12 pages.

Invitrogen. (Sep. 1, 2008). "GeneBLAzer ADORA2A CHO-K1 DA Assay Kit," 5 pages.

Ismayilova, N. et al. (2004). "Effects of Adenosine $Al_1$ Dopamine D1 and Metabotropic Glutamate 5 Receptors-modulating Agents on Locomotion of the Reserpinised Rats," European Journal of Pharmacology 497:187-195.

Jaakola, V.-P. et al. (Nov. 21, 2008). "The 2.6 Angstrom Crystal Structure of a Human A2A Adenosine Receptor Bound to an Antagonist," Science 322:1211-1217.

Jajoo, S. et al. (Nov. 2009). "Adenosine A3 Receptor Suppresses Prostate Cancer Metastasis by Inhibiting NADPH Oxidase Activity," Neoplasia 11(11):1132-1145.

Jazayeri, A. et al. (Jan. 11, 2017; e-pub. Jun. 22, 2016). "Structurally Enabled Discovery of Adenosine $A_{2A}$ Receptor Antagonists," Chemical Reviews 117(1):21-37, 17 pages.

Katritch, V. et al. (Feb. 25, 2010). "Structure-Based Discovery of Novel Chemotypes for Adenosine $A_{2A}$ Receptor Antagonists," J Med Chem. 53(4):1799-1809, 30 pages.

Kjaergaard, J. et al. (Jul. 15, 2018; e-pub. May 25, 2018). "$A_{2A}$ Adenosine Receptor Gene Deletion or Synthetic A2A Antagonist Liberate Tumor-Reactive CD8$^+$T Cells from Tumor-Induced Immunosuppression," The Journal of Immunology 201(2):782-791, 10 pages.

Köse, M. et al. (May 24, 2018; e-pub. May 15, 2018). "Fluorescent-Labeled Selective Adenosine $A_{2B}$ Receptor Antagonist Enables Competition Binding Assay by Flow Cytometry," Journal of Medicinal Chemistry 61(10):4301-4316, 16 pages.

Koszalka, P. et al. (2014). "Inhibition of CD73 Stimulates the Migration and Invasion of B16F10 Melanoma Cells In Vitro, but Results in Impaired Angiogenesis and Reduced Melanoma Growth In Vivo," Oncology Reports 31:819-827.

Kumar, V. (2013; e-pub. Dec. 28, 2012). "Adenosine as an Endogenous Immunoregulator in Cancer Pathogenesis: Where to go?," Purinergic Signalling 9(2):145-165.

Lappas, C.M. et al. (2005). "$A_{2A}$ Adenosine Receptor Induction Inhibits IFN-γ Production in Murine CD4$^+$T Cells," The Journal of Immunology 174:1073-1080.

Leclerc, B.G. et al. (2015; e-pub. Aug. 7, 2015). "CD73 Expression Is an Independent Prognostic Factor in Prostate Cancer," Clinical Cancer Research 22(1):158-166.

Leone, R.D. et al. (2015; e-pub. Apr. 8, 2015). "A2aR Antagonists: Next Generation Checkpoint Blockade for Cancer Immunotherapy," Computational and Structural Biotechnology Journal 13:265-272.

Leone, R.D. et al. (2018). "Targeting Adenosine for Cancer Immunotherapy," Journal for ImmunoTherapy of Cancer 6:57, 9 pages.

Leone, R.D. et al. (Aug. 2018; e-pub. Jun. 19, 2018). "Inhibition of the Adenosine A2a Receptor Modulates Expression of T Cell Coinhibitory Receptors and Improves Effector Function for Enhanced Checkpoint Blockade and ACT in Murine Cancer Models," Cancer Immunology Immunotherapy 67(8):1271-1284, 14 pages.

Lertsuwan, K. et al. (2017). "Purinergic Receptor Expression and Cellular Responses to Purinergic Agonists in Human Prostate Cancer Cells," Anticancer Research 37:529-538.

Li, Q.-X. et al. (May 2017; e-pub. Feb. 4, 2017). "Experimental Animal Modeling for Immuno-Oncology," Pharmacology & Therapeutics 173:34-46, 13 pages.

Lin, Z. et al. (Feb. 25, 2010). "Adenosine A1 Receptor, a Target and Regulator of ERα Action, Mediates the Proliferative Effects of Estradiol in Breast Cancer," Oncogene 29(8):1114-1122, 18 pages.

Linden, J. et al. (1999). "Characterization of Human $A_{2B}$ Adenosine Receptors: Radioligand Binding, Western Blotting, and Coupling to $G_q$ in Human Embryonic Kidney 293 Cells and HMC-1 Mast Cells," Molecular Pharmacology 56:705-713.

Lingam, V.S. et al. (Oct. 22, 2015; e-pub.Sep. 30, 2015). "Design, Synthesis and Pharmacological Evaluation of 5,6-Disubstituted Pyridin-2(1 H)-one Derivatives as Phosphodiesterase 10A (PDE10A) Antagonists," J. Med. Chem 58(20):8292-8308.

Ma, S.-R. et al. (2017). "Blockade of Adenosine A2A Receptor Enhances CD8$^+$T Cells Response and Decreases Regulatory T Cells in Head and Neck Squamous Cell Carcinoma," Molecular Cancer 16:99, 15 pages.

Maemoto, T. et al. (2004). "Pharmacological Characterization of FR194921, a New Potent, Selective, and Orally Active Antagonist for Central Adenosine $A_1$ Receptors," J Pharmacol 96:42-52.

Mantri, M. et al. (2008; e-pub. Jul. 19, 2008). "2-Amino-6-furan-2-yl-4-substituted Nicotinonitriles as $A_{2A}$ Adenosine Receptor Antagonists," J. Med. Chem. 51(15):4449-4455.

Massie, B.M. et al. (Oct. 7, 2010). "Rolofylline, an Adenosine $A_1$—Receptor Antagonist, in Acute Heart Failure," The New England Journal of Medicine 363(15):1419-1428.

McCoull, W. et al. (Nov. 16, 2018; e-pub. Oct. 17, 2018). "Development of a Novel B-Cell Lymphoma 6 (BCL6) PROTAC to Provide Insight into Small Molecule Targeting of BCL6," ACS Chem. Biol. 13(11):3131-3141, 11 pages.

Medialvilla-Varela, M. et al. (Jul. 2017). "A Novel Antagonist of the Immune Checkpoint Protein Adenosine A2a Receptor Restores Tumor-Infiltrating Lymphocyte Activity in the Context of the Tumor Microenvironment," Neoplasia 19(7):530-536.

Medialvilla-Varela, M. et al. (Sep. 2013; e-pub. Jul. 17, 2013). "Antagonism of Adenosine A2A Receptor Expressed by Lung Adenocarcinoma Tumor Cells and Cancer Associated Fibroblasts Inhibits Their Growth," Cancer Biology & Therapy 14(9):860-868.

Mendonca, A.D. et al. (2000). "Adenosine: Does it Have a Neuroprotective Role After All?," Brain Research Reviews 33:258-274.

Mihara, T. et al. (2007). "Pharmacological Characterization of a Novel, Potent Adenosine $A_1$ and $A_{2A}$ Receptor Dual Antagonist, 5[5-Amino-3-(4-fluorophenyl)pyrazin-2-yl]-1-isopropylpyridine-2(1 H)-one (ASP5854), in Models of Parkinson's Disease and Cognition," The Journal of Pharmacology and Experimental Therapeutics 323(2):708-719.

Mittal, D. et al. (Aug. 1, 2016; e-pub. May 24, 2016). "Adenosine 2B Receptor Expression on Cancer Cells Promotes Metastasis," Cancer Research 76(15):1-11.

Mittal, D. et al. (Jul. 15, 2014; e-pub. Jul. 1, 2014). "Antimetastatic Effects of Blocking PD-1 and the Adenosine A2A Receptor," Cancer Research 74(14):3652-3658.

(56) References Cited

OTHER PUBLICATIONS

Mokyr, M.B. et al. (Dec. 1, 1998). "Realization of the Therapeutic Potential of CTLA-4 Blockade in Low-Dose Chemotherapy-treated Tumor-bearing Mice," Cancer Research 58:5301-5304.

Moriyama, K. et al. (Dec. 10, 2010). "Adenosine A2A Receptor Is Involved in Cell Surface Expression of A2B Receptor," The Journal of Biology Chemistry 285(50):39271-39288.

Mousavi, S. et al. (2015; e-pub. Feb. 20, 2015). "Expression of Adenosine Receptor Subclasses in Malignant and Adjacent Normal Human Prostate Tissues," The Prostate 75:735-747.

Nikbakht, D.M. et al. (2016). "Adenosine A1 Receptor Modifies P53 Expression and Apoptosis in Breast Cancer Cell Line Mcf-7," Bratisl Med J 117(4):242-246.

Novío S. et al. (2017; e-pub. Mar. 30, 2017). "Adenosine Signaling Pathways as Potential Therapeutic Targets in Prostate Cancer Disease," Molecular Oncology: Underlying Mechanisms and Translational Advancements pp. 93-107.

Ohana, G. et al. (2001; e-pub. Nov. 30, 2000). "Differential Effect of Adenosine on Tumor and Normal Cell Growth: Focus on the A3 Adenosine Receptor," Journal of Cellular Physiology 186:19-23.

Ohta, A. (Mar. 29, 2016). "A Metabolic Immune Checkpoint: Adenosine in Tumor Microenvironment," Frontiers in Immunology 7(Article 109), 11 pages.

Panjehpour, M. et al. (2010). "Adenosine Receptor Expression in Two Different Human Cancer Cell Lines at Molecular Level," Iran J Cancer Prev 3(3):111-116.

Pinna, A. et al. (2014; e-pub. Apr. 1, 2014). "Adenosine $A_{2A}$ Receptor Antagonists in Parkinson's Disease: Progress in Clinical Trials from the Newly Approved Istradefylline to Drugs in Early Development and Those Already Discontinued," CNS Drugs 28:455-474.

Popoli, P. et al. (Mar. 1, 2002). "Blockade of Striatal Adenosine $A_{2A}$ Receptor Reduces, Through a Presynaptic Mechanism, Quinolinic Acid-Induced Excitotoxicity: Possible Relevance to Neuroprotective Interventions in Neurodegenerative Diseases of the Striatum," J. Neurosci 22(5):1967-1975.

Preti, D. et al. (Jul. 2015; e-pub. Mar. 27, 2015). "History and Perspectives of $A_{2A}$ Adenosine Receptor Antagonists as Potential Therapeutic Agents," Med. Res. Rev. 35(4):790-848, 59 pages.

Pubchem. CID 66665902 (Nov. 30, 2012). Located at <https://pubchem.ncbi.nlm.nih.gov/compound/66665902>, last visited on Sep. 1, 2018, 13 pages.

Rahimova, R. et al. (Jan. 29, 2018). "Identification of Allosteric Inhibitors of the Ecto-5'-Nucleotidase (CD73) Targeting the Dimer Interface," PLoS Comput Biol 14(1):e1005943, 23 pages.

Remington's Pharmaceutical Sciences, Mack Publishing Company, Philadelphia, PA, 21th ed. (2000) TOC, 4 pages.

Rosse, G. (Dec. 8, 2016; e-pub. Nov. 2, 2016); "Quinazoline Carboxamides as Selective Antagonists of Adenosine 2A Receptor," ACS Med. Chem. Lett. 7(12):1014-1015.

Rusinov, V.L. et al., (Dec. 2005). "Synthesis and Antiviral Activity of 2-Amino-3-Ethoxycarbonylpyrazine Derivatives," Pharmaceutical Chemistry Journal 39(12):630-635.

Schuler, P.J. et al. (2014). "Human $CD_4^+CD_{39}^+$Regulatory T Cells Produce Adenosine Upon Co-Expression of Surface $CD_{73}$ or Contact with $CD_{73+}$Exosomes or CD73$^+$Cells," Clinical and Experimental Immunology 177:531-543.

Segala, E. et al. (Jul. 14, 2016; e-published Jul. 1, 2016). "Controlling the Dissociation of Ligands from the Adenosine A2A Receptor Through Modulation of Salt Bridge Strength," J. Med. Chem. 59(13):6470-6479, 41 pages.

Sek, K. et al. (Dec. 2, 2018). "Targeting Adenosine Receptor Signaling in Cancer Immunotherapy," Int. J. Mol. Sci. 19:3837, 23 pages.

Shook, B.C. et al. (2010; e-pub. Oct. 25, 2010). "In Vivo Characterization of a Dual Adenosine $A_{2A}/A_1$ Receptor Antagonist in Animal Models of Parkinson's Disease," J. Med. Chem. 53(22):8104-8115.

Sitkowsky, M. et al. (Jul. 2014). "Hostile, Hypoxia-A2-Adenosinergic Tumor Biology as the Next Barrier to Overcome for Tumor Immunologists," Cancer Immunol. Res. 2(7):598-605, 15 pages.

Sorrentino, C. et al. (Jul. 17, 2017). "Role of Adenosine in Tumor Progression: Focus on $A_{2B}$ Receptor as Potential Therapeutic Target," Journal of Cancer Metastasis and Treatment 3:127-138.

Sorrentino, C. et al. (Sep. 29, 2015; e-pub. Jul. 25, 2015). "Myeloid-Derived Suppressor Cells Contribute to A2B Adenosine Receptor-Induced VEGF Production and Angiogenesis in a Mouse Melanoma Model," Oncotarget 6(29):27478-27489.

Tuite, P. et al. (Aug. 2003). "Recent Developments in the Pharmacological Treatment of Parkinson's Disease," Expert Opin. Investig. Drugs 12(8):1335-1352.

Van Waarde, A. et al. (Jan. 2018; e-pub. Jan. 27, 2017). "Potential Therapeutic Applications of Adenosine $A_{2A}$ Receptor Ligands and Opportunities for $A_{2A}$ Receptor Imaging," Med. Res. Rev. 38(1):5-56, 52 pages.

Varani, K. et al. (1997). "Characterization of $A_{2A}$ Adenosine Receptors in Human Lymphocyte Membranes by [$^3$H]-SCH 58261 Binding," British Journal of Pharmacology 122:386-392.

Vaupel, P. et al. (Dec. 21, 2017). "Accomplices of the Hypoxic Tumor Microenvironment Compromising Antitumor immunity: Adenosine, Lactate, Acidosis, Vascular Endothelial Growth Factor, Potassium Ions, and Phosphatidylserine," Frontiers in Immunology 8(Article 1887), 6 pages.

Vecchio, E. A. et al. (Apr. 2016). "Ligand-Independent Adenosine A2B Receptor Constitutive Activity as a Promoter of Prostate Cancer Cell Proliferation," J Pharmacol Exp Ther 357:36-44.

Vecchio, E.A. et al. (Jun. 2019). "The Adenosine $A_{2B}$ G Protein-Coupled Receptor: Recent Advances and Therapeutic Implications," Pharmacology and Therapeutics 198:20-33, 50 pages.

Vijayan, D. et al. (Dec. 2017; e-pub. Oct. 23, 2017). "Targeting Immunosuppressive Adenosine in Cancer," Nature Rev Cancer 17(12):709-724.

Virgilio, F.D. et al. (2017; e-pub. Jun. 20, 2016). "Extracellular Purines, Purinergic Receptors and Tumor Growth," Oncogene 36:293-303.

Voors, A.A. et al. (May 10, 2011). "Effects of the Adenosine $A_1$ Receptor Antagonist Rolofylline on Renal Function in Patients With Acute Heart Failure and Renal Dysfunction," J Am Coll Cardiol 57(19):1899-1907.

Waickman, A.T. et al. (Jun. 2012). "Enhancement of Tumor Immunotherapy by Deletion of the $A_{2A}$ Adenosine Receptor," Cancer Immunol Immunother. 61(6):917-926, 17 pages.

Walters, M.J. et al. (2017). "Characterization of AB928, an $A_2$R Antagonist for the Treatment of Cancer," Poster presented at AACR, 1 page.

Walters, M.J. et al. (2018). "Combining Adenosine Receptor Inhibition, with AB928, and Chemotherapy Results in Greater Immune Activation and Tumor Control," Abstract 5556, Poster presented at AACR, 1 page.

Wang, J. et al. (Sep. 2018; e-pub. Aug. 1, 2018). "Adenosinergic Signaling as a Target for Natural Killer Cell Immunotherapy," Journal of Molecular Medicine 96(9):903-913, 11 pages.

Wei, Q. et al. (2013; e-pub. Jan. 15, 2013). "$A_{2B}$ Adenosine Receptor Blockade Inhibits Growth of Prostate Cancer Cells," Purinergic Signalling 9:271-280.

Whiteside, T.L. et al. (Jun. 2017; e-pub. Apr. 27, 2017). "Targeting Adenosine in Cancer Immunotherapy: A Review of Recent Progress," Expert Review of Anticancer Therapy 17(6):527-535, 36 pages.

Willingham, S.B. et al. (Oct. 2018; e-pub. Aug. 21, 2018). "A2AR Antagonism with CPI-444 Induces Antitumor Responses and Augments Efficacy to Anti-PD-(L)1 and Anti-CTLA-4 in Preclinical Models," Cancer Immunol Res. 6(10):1136-1149, (with Supplementary material, 30 pages).

Willingham, S.B. et al. (Oct. 2018; e-pub. Aug. 21, 2018). "A2AR Antagonism with CPI-444 Induces Antitumor Responses and Augments Efficacy to Anti-PD-(L)1 and Anti-CTLA-4 in Preclinical Models," Cancer Immunol Res. 6(10):1-14.

(56) References Cited

OTHER PUBLICATIONS

Yang, X. et al. (2017). "Tiamulin Inhibits Breast Cancer Growth and Pulmonary Metastasis by Decreasing the Activity of CD73," BMC Cancer 17:255, 12 pages.

Yang_X. et al. (2018; e-pub. Aug. 6, 2018). "An Affinity-Based Probe for the Human Adenosine $A_{2A}$ Receptor," J. Med. Chem. 61:7892-7901.

Yuan, G. et al. (2014). "Towards Next Generation Adenosine $A_{2A}$ Receptor Antagonists," Current Medicinal Chemistry 21(34):3918-3935.

Zhou, J.Z. et al. (Apr. 2, 2015). "Differential Impact of Adenosine Nucleotides Released by Osteocytes on Breast Cancer Growth and Bone Metastasis," Oncogene 34(14):1831-1842, 31 pages.

Barbosa, R.S.S. et al. (2019). "Sequential Combination of Bortezomib and WEE1 Inhibitor, MK-1775, Induced Apoptosis in Multiple Myeloma Cell Lines," Biochemical and Biophysical Research Communication pp. 1-8.

Borodovsky, A. et al. (Apr. 5, 2017). "Preclinical Pharmacodynamics and Antitumor Activity of AZD4635, A Novel Adenosine 2A Receptor Inhibitor That Reverses Adenosine Mediated T Cell Suppression," AACR 2017 Annual Meeting, Washington, D.C, Poster 5580, 1 page.

Cretella, D. et al. (2019, e-pub. Sep. 10, 2019). "Pre-Treatment With the CDK4/6 Inhibitor Palbociclib Improves the Efficacy of Paclitaxel in TNBC Cells," Scientific Reports 9(13014)1-11.

Dastjerdi, N. eta l. (2016). "Adenosine Al Receptor Modifies PTE Expression and Apoptosis in Breast Cancer Cell Line Mcf-7," Bratisl. Med. J. 117(4):242-246.

Di Sante, G. et al. (2019). "Recent Advances With Cyclin-Dependent Kinase Inhibitors: Therapeutic Agents for Breast Cancer and Their Role in Immuno-Oncology," Expert Review of Anticancer Therapy 19(7):569-587.

Fang, Y. et al. (Jun. 10, 2019). "Sequential Therapy with Parp and WEE1 Inhibitors Minimizes Toxicity while Maintaining Efficacy," Cancer Cell 35:851-867.

Hafner, M. et al. (Aug. 15, 2019). "Multiomics Profiling Establishes the Polypharmacology of FDA-Approved CDK4/6 Inhibitors and the Potential for Differential Clinical Activity," Cell Chemical Biology 26:1-14.

Harter, M. et al. (2019). "Novel non-xanthine antagonist of the A2B adenosine receptor: From HTS hit to lead structure," European Journal of Medicinal Chemistry 163:763-778.

Hu, Y. et al. (2018, e-pub. Dec. 24, 2018). "Pharmacophore Modeling, Multiple Docking, and Molecular Dynamics Studies on Wee1 Kinase Inhibitors," Journal of Biomolecular Structure and Dynamics 1-14.

Jin, M.N. et al. (2019). "Therapeutic Co-Targeting of WEE1 and ATM Downregulates PD-L1 Expression in Pancreatic Cancer," Cancer Research and Treatment (CRT) pp. 1-40.

Kuzu, O.F. et al. (2017). "Improving Pharmacological targeting of AKT in Melanoma," Cancer Letters 404:29-36.

Liang, J. et al. (Sep. 24, 2019). "Genome-Wide Cripsr-cas9 Screen Reveals Selective Vulnerability of ATRX-Vlutant Cancers to WEE1 Inhibition," State Key Laboratory of Medical Molecular Biology, Institute of Basic Medical Sciences, Chinese Academy of Medical Sciences, Peking Union Medical School, Manuscript, 42 pages.

Liu, D. et al.(2019). "Enhancement of Chemosensitivity by WEE1 Inhibition in EGFR-TKIs Resistant Non-Small Cell Lung Cancer," Biomedicine & Pharmacotherapy 117(109185):1-8.

Liu, W. • et al (2019, e-pub. Jun. 13, 2019). "Targeting the WEE1 kinase strengthens the antitumor activity of imatinib via promoting Kit autophagic degradation in gastrointestinal stromal tumors," Gastric Cancer pp. 1-13.

Lübbehüsen, c. et al. (2019, e-pub. Apr. 23, 2019). "Characterization of Three Novel H3F3A-mutated Giant Cell Tumor Cell Lines and Targeting of Their Wee1 Pathway," Scientific Reports 9(6458):1-10.

Mastracchio, A. et al. (2019). "Investigation of Biaryl Heterocycles as Inhibitors of Wee1 Kinase," Bioorganic & Medicinal Chemistry Letters 29:1481-1486.

McCoull, A et al. (2018). "Development of a Novel B-Cell Lymphoma 6 (BCL6) PROTAC to Provide Insight into Small Molecule Targeting of BCL6," ACS Chemical Biology 11 pages.

Palmer, B.D. et al. (2006, e-pub. Jul. 15, 2006). "4-Phenylpyrrolo[3,4-c]carbazole-1,3(2H,6H)-dione Inhibitors of the Checkpoint Kinase Wee1. Structure-Activity Relationships for Chromophore Modification and Phenyl Ring Substitution," J. Med. Chem. 49:4896-4911.

Pandey, K. et al. (2019). "Molecular Mechanisms of Resistance to CDK4/6 Inhibitors in Breast Cancer: A Review," International Journal of Cancer 145:1179-1188.

Powderly, J. et al. (May 2019). "AB928, a Novel Dual Adenosine Receptor Antagonist, Combined With Chemotherapy or AB122 (anti-PD-1) in Patients With Advanced Tumors: Preliminary Results From Ongoing Phase I Studies," ASCO 2019, Abstract No. 2604, 1 page.

Restelli, V. et al. (2019, e-pub. May 7, 2019). "Dna Damage Response Inhibitor Combinations Exert Synergistic Antitumor Activity in Aggressive B Cell Lymphomas," American Association for Cancer Research Manuscript pp. 1-25.

Serpico, A.F. et al. (2019, e-pub. Jun. 13, 2019). "Wee1 Rather Than Plk1 Is Inhibited by AZD1775 at Therapeutically Relevant Concentrations," Cancers 11:1-1.

Takashima, Y. et al. (2019). "Bromodomain and Extraterminal Domain Inhibition Synergizes with WEE1-Inhibitor AZD1775 Effect by Impairing Non-Homologous End Joining and Enhancing DNA Damage in Non-Small Cell Lung Cancer," Department of Respiratory Medicine, Faculty of Medicine and Graduate School of Medicine, Hokkaido University pp. 1-33.

Tarkhov, et al. (2005). "Photoluminescence of Some Indolylpyrazines." Materialovedenie 4:16-22. with English Translation.

Tarkhov, et al., (2005). "Analysis of Electronic Transitions During Photoluminescence for some Indolylpyrazines," Materialovedenie 10:18-21. with English Translation.

Thomas, A. et al. (Oct. 4, 2015, e-pub. Sep. 30, 2015). "Design, Synthesis and Pharmacological Evaluation of 5,6-Disubstituted Pyridin-2(1H)-one Derivatives as Phosphodiesterase 10A (PDE10A) Antagonists," Journal of Medicinal Chemistry 62 pages.

Vilgelm, A.E. (2019). "MDM2 Antagonists Overcome Intrinsic resistance to CDK4/6 Inhibition by Inducing p21," Sci. Transl. Med. 11(3aav7171):1-15.

Walters, M.J. et al. (2018). "Combining Adenosine Receptor Inhibition, With AB928, and Chemotherapy Results in greater Immune Activation and Tumor Control," AACR 2018, Abstract 5556, 1 page.

Wichapong, K. K et al.(2009, e-pub. Sep. 20, 2008). "Receptor-based 3D-QSAR studies of checkpoint Wee1 kinase inhibitors," European Journal of Medicinal Chemistry 44:1383-1395.

Yang, Q. et al. (2013, e-pub. May 8, 2013). "Overexpression of CD73 in Prostate Cancer is Associated with Lymph Node Metastasis," Pathol. Oncol. Res. 4 pages.

Young, A et al. (Sep. 12, 2016). "Co-inhibition of CD73 and A2AR Adenosine Signaling Improves Anti-tumor Immune Responses," Cancer Cell 30:391-403.

Zhang, P. et al. (2019, e-pub. Jul. 21, 2019). "BRD4 Inhibitor AZD5153 Suppresses the Proliferation of Colorectal Cancer Cells and Sensitizes the Anticancer Effect of PARP Inhibitor," Int. J. Biol. Sci. 15(9):1942-1954.

Dörwald, F.Z. (2005). "Side Reactions in Organic Synthesis: A Guide to Successful Synthesis Design," Weinheim: Wiley-Vch, 4 pages.

International Preliminary Report on Patentability, dated Jan. 21, 2020, for PCT Application No. PCT/US2018/042776, 6 pages.

* cited by examiner

1,8-NAPHTHYRIDINONE COMPOUNDS AND USES THEREOF

CROSS-REFERENCE TO RELATED APPLICATIONS

This application claims priority to U.S. Provisional Application No. 62/534,185, filed Jul. 18, 2017, the contents of which are incorporated by reference in their entirety.

FIELD OF THE INVENTION

This disclosure relates generally to therapeutics for treatment mediated through a G-protein-coupled receptor (GPCR) signaling pathway and, more particularly, to compounds that inhibit an adenosine receptor (such as an $A_{2A}$ antagonist). The disclosure also provides pharmaceutically acceptable compositions comprising such compounds and methods of using the compounds or compositions in the treatment of a disease associated with a GPCR signaling pathway.

BACKGROUND OF THE INVENTION

Adenosine receptors (ARs) are distributed throughout the body and are responsible for numerous biological functions. The seven trans-membrane G-protein-coupled receptors (GPCRs) have been divided into four different subtypes: $A_1$, $A_{2A}$, $A_{2B}$, and $A_3$. The $A_{2A}$ and $A_{2B}$ ARs stimulate activity of the adenylyl cyclase, inducing an increase of cAMP levels. $A_{2A}$ ARs have a distinct tissue localization, different biochemical pathways, and specific pharmacological profiles.

Adenosine is one of the human body's most important neuromodulators in both the central and the peripheral nervous systems. Adenosine is released from tumor cells and its concentration in the extracellular fluid of tumors can reach immunosuppressive levels (Blay et al. (1997), *Cancer Res.*, 57(13), pp. 2602-5). The extracellular fluid of solid carcinomas contains immunosuppressive concentrations of adenosine. Id. This increase in adenosine concentration is a result of increases in CD73 (ecto-5'-nucleotidase) and CD39 (nucleoside triphosphate dephosphorylase) enzymes, which are responsible for directly catabolizing ATP into adenosine. These upregulations are triggered by hypoxia and the generation of HIF-1α. High levels of adenosine around tumor cells act to regulate multiple immune cells (e.g., CD4+ T-cells and cytotoxic CD8+ T-cells) via activation of multiple adenosine receptor subtypes, but particularly $A_{2A}$ receptors, resulting the suppressing of pro-inflammatory activities and upregulation of anti-inflammatory molecules and immunoregulatory cells (Kumar et al. (2013), Adenosine as an endogenous immunoregulator in cancer pathogenesis: where to go? *Purinergic Signal.*, 9(2), pp 145-65 and Sitkowsky et al., Hostile, hypoxia-A2-adenosinergic tumor biology as the next barrier to overcome for tumor immunologists. *Cancer Immunol. Res.* 2(7), pp 598-605; Ohta (2016), A Metabolic Immune Checkpoint: Adenosine in Tumor Microenvironment. *Frontiers in Immunology*, 7 article#109, pp 1-11). It was demonstrated that chimeric antigen receptor (CAR) T cells upregulate A2ARs upon antigen-specific stimulation in vitro and in vivo (Beavls (2017), Targeting the Adenosine 2A Receptor Enhances Chimeric Antigen Receptor T Cell Efficacy. *J of Clin Invest.* 127 (3): pp 929-941).

Survival of cancer cells is dependent on their ability to avoid attack by the immune system. In addition, tumor cells can overtake the immune system to facilitate tumor survival and metastasis. Adenosine, whose concentration increases within hypoxic regions of solid tumors, has been recognized as being able to interfere with the recognition of tumor cells by cytolytic effector cells of the immune system. (Tuite and Riss (2013). Recent developments in the pharmacological treatment of Parkinson's disease. *Expert Opin. Investig. Drugs*, 12(8) pp 1335-52, Popoli et al. (2002). Blockade of striatal adenosine $A_{2A}$ receptor reduces, through a presynaptic mechanism, quinolinic acid-induced excitotoxicity: possible relevance to neuroprotective interventions in neurodegenerative diseases of the striatum, *J. Neurosci*, 22(5) pp. 1967-75, Gessi et al. (2011). Adenosine receptors and cancer. *Biochim Biophys Acta*, 1808(5), pp. 1400-12).

Although all adenosine receptors now have an increasing number of recognized biological roles in tumors, the $A_{2A}$ and $A_3$ subtypes appear promising targets for therapeutic development. In particular, activation of $A_{2A}$ receptors leads to immunosuppressive effects, which decreases anti-tumoral immunity and thereby encourages tumor growth.

The $A_{2B}$ receptor is another potential target for therapeutic development. Autocrine/paracrine stimulation of $A_{2B}$ expressed on tumor cells is believed to enhance their metastatic potential and $A_{2B}$ blockade may reduce tumor metastasis in an immune-independent manner (Beavis et al. (2013). Blockade of $A_{2A}$ receptors potently suppresses the metabolism of CD73+ Tumors. *Proc. Natl. Acad. Sci.*, 110 (36) pp. 14711-6). $A_{2B}$ expression also correlates with relapse-free survival (RFS) in triple negative breast cancer suggesting that this pathway may be clinically relevant. $A_{2B}$ blockade also has the potential to modulate the immunosuppressive properties of tumor-associated immune cells including dendritic cells and myeloid-derived suppressor cells (MDSCs) (Cekic et al. (2011). Adenosine A2B receptor blockade slows growth of bladder and breast tumors. *J. Immunol.* 188(1), pp. 198-205; Sorrentino et al. (2015). Myeloid-derived suppressor cells contribute to $A_{2B}$ adenosine receptor-induced VEGF production and angiogenesis in a mouse melanoma model. *Oncotarget* 6(29), pp. 27478-89; Iannone et al. (2013). Blockade of $A_{2B}$ adenosine receptor reduces tumor growth and immune suppression mediated by myeloid-derived suppressor cells in a mouse model of melanoma. *Neoplasia*, 15(12), pp. 1400-9.

There remains a continuing need for new therapies for the treatment of diseases and disorders related to the adenosine signaling pathway.

BRIEF SUMMARY OF THE INVENTION

In one aspect, provided is a compound of the formula (I):

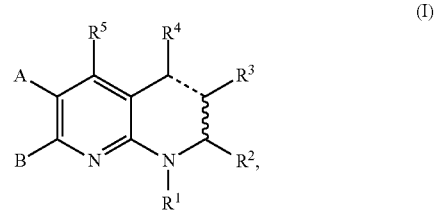

or a tautomer or isomer thereof, or a pharmaceutically acceptable salt of any of the foregoing, wherein A, B, $R^1$, $R^2$, $R^3$, $R^4$, and $R^5$ are as detailed herein.

In some embodiments, the compound of the formula (I), or a tautomer or isomer thereof, or a pharmaceutically acceptable salt of any of the foregoing, is of the formula (II) or (III), or a tautomer or isomer thereof, or a pharmaceutically acceptable salt of any of the foregoing, as detailed herein. In some embodiments, the compound of the formula (I), or a tautomer thereof, or a salt of any of the foregoing, is of the formula (II). In some embodiments, the compound of the formula (I), or a tautomer thereof, or a salt of any of the foregoing, is of the formula (III).

In another aspect, provided is a method for any one or more of: (a) treating a disease, such as a proliferative disease, in an individual in need thereof; (b) enhancing an immune response in an individual in need thereof; (c) inhibiting tumor metastasis in an individual in need thereof; (d) modulating the activity of a G protein coupled receptor signaling pathway in an individual in need thereof; (e) modulating the activity of an adenosine receptor, such as an $A_{2A}$ receptor, in an individual in need thereof; and (f) increasing the activity of a natural killer cell in an individual in need thereof, wherein the method comprises administering to the individual an effective amount of a compound of formula (I), or a tautomer or isomer thereof, or a pharmaceutically acceptable salt of any of the foregoing. In some embodiments, provided is a method for any one or more of: (a) treating a disease, such as a proliferative disease, in an individual in need thereof; (b) enhancing an immune response in an individual in need thereof; (c) inhibiting tumor metastasis in an individual in need thereof; (d) modulating the activity of a G protein coupled receptor signaling pathway in an individual in need thereof; (e) modulating the activity of an adenosine receptor, such as an $A_{2A}$ receptor, in an individual in need thereof; and (f) increasing the activity of a natural killer cell in an individual in need thereof, wherein the method comprises administering to the individual an effective amount of a compound of formula (I), or a tautomer thereof, or a or a salt of any of the foregoing. In one aspect, the compound of formula (I) or a tautomer thereof, or a salt of any of the foregoing, is administered to the individual in combination with another therapeutic agent. In some embodiments, the compound of formula (I) or a tautomer or isomer thereof, or a pharmaceutically acceptable salt of any of the foregoing is administered to the individual in combination with another therapeutic agent. In a further aspect of the methods, the compound of formula (I) or a salt thereof is a compound of the formula (II) or (III) or a tautomer thereof, or a or a salt of any of the foregoing. In some embodiments, the compound of formula (I) or a tautomer or isomer thereof, or a pharmaceutically acceptable salt of any of the foregoing is a compound of the formula (II) or (III), or a tautomer or isomer thereof, or a pharmaceutically acceptable salt of any of the foregoing.

Also provided are pharmaceutical compositions comprising (A) a compound detailed herein, such as a compound of formula (I) or a tautomer or isomer thereof, or a pharmaceutically acceptable salt of any of the foregoing, or a compound of formula (II) or a tautomer or isomer thereof, or a pharmaceutically acceptable salt of any of the foregoing, or a compound of formula (III) or a tautomer or isomer thereof, or a pharmaceutically acceptable salt of any of the foregoing, and (B) a pharmaceutically acceptable carrier or excipient. In some embodiments, provided are pharmaceutical compositions comprising (A) a compound detailed herein, such as a compound of formula (I) or a tautomer thereof, or a or a salt of any of the foregoing, or a compound of formula (II) or a tautomer thereof, or a or a salt of any of the foregoing, or a compound of formula (III) or a tautomer thereof, or a or a salt of any of the foregoing, and (B) a pharmaceutically acceptable carrier or excipient. Kits comprising a compound detailed herein or a tautomer or isomer thereof, or a pharmaceutically acceptable salt of any of the foregoing and instructions for use are also provided. Kits comprising a compound detailed herein or a salt thereof and instructions for use are also provided. A compound detailed herein or a tautomer or isomer thereof, or a pharmaceutically acceptable salt of any of the foregoing is also provided for the manufacture of a medicament for the treatment of cancer. Compounds as detailed herein or a pharmaceutically acceptable salt thereof are also provided for the manufacture of a medicament for the treatment of cancer.

DETAILED DESCRIPTION OF THE INVENTION

Definitions

For use herein, unless clearly indicated otherwise, use of the terms "a", "an" and the like refers to one or more.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

The term "alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

The term "aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

The terms "cycloalkyl" or "carbocycle" are used interchangeably and refer to and include cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl or carbocycle groups can consist of one ring, such as cyclohexyl, or multiple rings, such as adamantyl, but excludes aryl groups. A cycloalkyl or carbocycle comprising more than one ring may be fused, spiro or bridged, or combinations thereof. A preferred cycloalkyl or carbocycle is a cyclic hydrocarbon having from 3 to 13 annular carbon atoms. A more preferred cycloalkyl or carbocycle is a cyclic hydrocarbon having from 3 to 8 annular carbon atoms (a "$C_3$-$C_8$ cycloalkyl"). Examples of cycloalkyl or carbocycle groups include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

The term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like. Examples of heteroaryl groups also include, but are not limited to, pyridyl, pyrimidyl, thiophenyl, furanyl, thiazolyl, oxazolyl, isoxazolyl, thiophenyl, pyrrolyl, pyrazolyl, 1,3,4-oxadiazolyl, imidazolyl, isothiazolyl, triazolyl, 1,3,4-thiadiazolyl, tetrazolyl, benzofuranyl, benzothiophenyl, pyrazolopyridinyl, indazolyl, benzothiazolyl, benzooxazolyl or benzoimidazolyl and the like In one variation, a heteroaryl containing at least one additional fused ring that is nonaromatic (e.g., cycloakyl or heterocyclyl) is attached to the parent structure at an annular atom of the additional ring. In another variation, a heteroaryl containing at least one additional ring that is nonaromatic (e.g., cycloakyl or heterocyclyl) is attached to the parent structure at an annular atom of the aromatic ring.

The term "heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl, cycloalkyl or heterocyclyl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1 (2H)-yl, and the like.

In one variation, a heterocyclyl containing at least one additional ring (such as a fused additional ring) that does not contain a heteroatom is attached to the parent structure at an annular atom of the additional ring. In another variation, a heterocyclyl containing at least one additional ring (such as a fused additional ring) that does not contain a heteroatom is attached to the parent structure at an annular atom of the ring containing a heteroatom.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying occurrence and/or recurrence, such as of unwanted cell proliferation.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

Compounds

In one aspect, provided is a compound of the Formula (I):

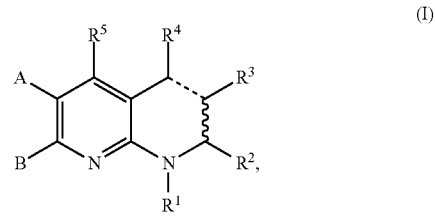

or a tautomer or isomer thereof, or a pharmaceutically acceptable salt of any of the foregoing, wherein:

$R^1$ is H or $C_1$-$C_6$ alkyl wherein the $C_1$-$C_6$ alkyl of $R^1$ is optionally substituted with oxo or $R^a$;

$R^2$ and $R^4$ are each independently H, $R^b$ or oxo;

$R^3$ and $R^5$ are each independently H or $R^c$;

each $R^a$, $R^b$, and $R^c$ is independently $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$NO_2$, —C=$NH(OR^8)$, —$C(O)R^8$, —$OC(O)R^8$, —$C(O)OR^8$, —$C(O)NR^9R^{10}$, —$OC(O)NR^9R^{10}$, —$NR^8C(O)R^9$, —$NR^8C(O)OR^9$, —$NR^8C(O)NR^9R^{10}$, —$S(O)R^8$, —$S(O)_2R^8$, —$NR^8S(O)R^9$, —$C(O)NR^8S(O)R^9$, —$NR^8S(O)_2R^9$, —$C(O)NR^8S(O)_2R^9$, —$S(O)NR^9R^{10}$, —$S(O)_2NR^9R^{10}$, —$P(O)(OR^9)(OR^{10})$, $C_3$-$C_6$ cycloalkyl, 3-12-membered heterocyclyl, 5- to 10-membered heteroaryl, $C_6$-$C_{14}$ aryl, —$(C_1$-$C_3$ alkylene)CN, —$(C_1$-$C_3$ alkylene)$OR^8$, —$(C_1$-$C_3$ alkylene)$SR^8$, —$(C_1$-$C_3$ alkylene)$NR^9R^{10}$, —$(C_1$-$C_3$ alkylene)$CF_3$, —$(C_1$-$C_3$ alkylene)$NO_2$, —C=$NH(OR^8)$, —$(C_1$-$C_3$ alkylene)$C(O)R^8$, —$(C_1$-$C_3$ alkylene)$OC(O)R^8$, —$(C_1$-$C_3$ alkylene)$C(O)OR^8$, —$(C_1$-$C_3$ alkylene)$C(O)NR^9R^{10}$, —$(C_1$-$C_3$ alkylene)$OC(O)NR^9R^{10}$, —$(C_1$-$C_3$ alkylene)$NR^8C(O)R^9$, —$(C_1$-$C_3$ alkylene)$NR^8C(O)OR^9$, —$(C_1$-$C_3$ alkylene)$NR^8C(O)NR^9R^{10}$, —$(C_1$-$C_3$ alkylene)$S(O)R^8$, —$(C_1$-$C_3$ alkylene)$S(O)_2R^8$, —$(C_1$-$C_3$ alkylene)$NR^8S(O)R^9$, —$C(O)(C_1$-$C_3$ alkylene)$NR^8S(O)R^9$, —$(C_1$-$C_3$ alkylene)$NR^8S(O)_2R^9$, —$(C_1$-$C_3$ alkylene)$C(O)NR^8S(O)_2R^9$, —$(C_1$-$C_3$ alkylene)$S(O)NR^9R^{10}$, —$(C_1$-$C_3$ alkylene)$S(O)_2NR^9R^{10}$, —$(C_1$-$C_3$ alkylene)$P(O)(OR^9)(OR^{10})$, —$(C_1$-$C_3$ alkylene)($C_3$-$C_6$ cycloalkyl), —$(C_1$-$C_3$ alkylene)(3-12-membered heterocyclyl), —$(C_1$-$C_3$ alkylene)(5-10-membered heteroaryl) or —$(C_1$-$C_3$ alkylene)($C_6$-$C_{14}$ aryl), wherein each $R^a$, $R^b$, and $R^c$ is independently optionally substituted by halogen, oxo, —OR, —$NR^{11}R^{12}$, —$C(O)R^{11}$, —CN, —$S(O)R^{11}$, —$S(O)_2R^{11}$, —$P(O)(OR^{11})(OR^{12})$, —$(C_1$-$C_3$ alkylene)$OR^{11}$, —$(C_1$-$C_3$ alkylene)$NR^{11}R^{12}$, —$(C_1$-$C_3$ alkylene)$C(O)R^{11}$, —$(C_1$-$C_3$ alkylene)

S(O)R$^{11}$, —(C$_1$-C$_3$ alkylene)S(O)$_2$R$^{11}$, —(C$_1$-C$_3$ alkylene)P(O)(OR)(OR$^{12}$), C$_3$-C$_8$ cycloalkyl, or C$_1$-C$_6$ alkyl optionally substituted by oxo, —OH or halogen;
  wherein when R$^1$ is C$_1$-C$_6$ alkyl, R$^4$ is other than —NR$^9$R$^{10}$ and R$^3$ is other than —C(O)R$^8$;
  ------ is a single bond or a double bond, wherein when ------ is a double bond, R$^2$ is oxo;
  ⁓⁓⁓ is a single bond or a double bond, wherein when ⁓⁓⁓ is a double bond, R$^4$ is oxo;
  one of ------ and ⁓⁓⁓ is a double bond and the other is a single bond;

A is C$_6$-C$_{12}$ aryl, 5- to 10-membered heteroaryl, 9- to 10-membered carbocycle, or 9- to 10-membered heterocycle, wherein the C$_6$-C$_{12}$ aryl, 5- to 10-membered heteroaryl, 9- to 10-membered carbocycle, or 9- to 10-membered heterocycle of A is optionally further substituted with R$^6$;

B is phenyl, 5- to 6-membered heteroaryl, 5- to 6-membered carbocycle, 5- to 6-membered heterocycle, or 9- to 10-membered heteroaryl, wherein the phenyl, 5- to 6-membered heteroaryl, 5- to 6-membered carbocycle, 5- to 6-membered heterocycle, or 9- to 10-membered heteroaryl of B is optionally further substituted with R$^7$;
  wherein when B is 5- to 6-membered heterocycle, A is other than phenyl or pyridyl optionally further substituted with R$^7$;

each R$^6$ and R$^7$ is independently oxo, C$_1$-C$_6$ alkyl, C$_2$-C$_6$ alkenyl, C$_2$-C$_6$ alkynyl, halogen, —CN, —OR$^8$, —SR$^8$, —NR$^9$R$^{10}$, —NO$_2$, —C=NH(OR$^8$), —C(O)R$^8$, —OC(O)R$^8$, —C(O)OR$^8$, —C(O)NR$^9$R$^{10}$, —OC(O)NR$^9$R$^{10}$, —NR$^8$C(O)R$^9$, —NR$^8$C(O)OR$^9$, —NR$^8$C(O)NR$^9$R$^{10}$, —S(O)R$^8$, —S(O)$_2$R$^8$, —NR$^8$S(O)R$^9$, —C(O)NR$^8$S(O)R$^9$, —NR$^8$S(O)$_2$R$^9$, —C(O)NR$^8$S(O)$_2$R$^9$, —S(O)NR$^9$R$^{10}$, —S(O)$_2$NR$^9$R$^{10}$, —P(O)(OR$^9$)(OR$^{10}$), C$_3$-C$_6$ cycloalkyl, 3-12-membered heterocyclyl, 5- to 10-membered heteroaryl, C$_6$-C$_{14}$ aryl, —(C$_1$-C$_3$ alkylene)CN, —(C$_1$-C$_3$ alkylene)OR$^8$, —(C$_1$-C$_3$ alkylene)SR$^8$, —(C$_1$-C$_3$ alkylene)NR$^9$R$^{10}$, —(C$_1$-C$_3$ alkylene)CF$_3$, —(C$_1$-C$_3$ alkylene)NO$_2$, —C=NH(OR$^8$), —(C$_1$-C$_3$ alkylene)C(O)R$^8$, —(C$_1$-C$_3$ alkylene)OC(O)R$^8$, —(C$_1$-C$_3$ alkylene)C(O)OR$^8$, —(C$_1$-C$_3$ alkylene)C(O)NR$^9$R$^{10}$, —(C$_1$-C$_3$ alkylene)OC(O)NR$^9$R$^{10}$, —(C$_1$-C$_3$ alkylene)NR$^8$C(O)R$^9$, —(C$_1$-C$_3$ alkylene)NR$^8$C(O)OR$^9$, —(C$_1$-C$_3$ alkylene)NR$^8$C(O)NR$^9$R$^{10}$, —(C$_1$-C$_3$ alkylene)S(O)R$^8$, —(C$_1$-C$_3$ alkylene)S(O)$_2$R$^8$, —(C$_1$-C$_3$ alkylene)NR$^8$S(O)R$^9$, —C(O)(C$_1$-C$_3$ alkylene)NR$^8$S(O)R$^9$, —(C$_1$-C$_3$ alkylene)NR$^8$S(O)$_2$R$^9$, —(C$_1$-C$_3$ alkylene)C(O)NR$^8$S(O)$_2$R$^9$, —(C$_1$-C$_3$ alkylene)S(O)NR$^9$R$^{10}$, —(C$_1$-C$_3$ alkylene)S(O)$_2$NR$^9$R$^{10}$, —(C$_1$-C$_3$ alkylene)P(O)(OR$^9$)(OR$^{10}$), —(C$_1$-C$_3$ alkylene)(C$_3$-C$_6$ cycloalkyl), —(C$_1$-C$_3$ alkylene)(3-12-membered heterocyclyl), —(C$_1$-C$_3$ alkylene)(5-10-membered heteroaryl) or —(C$_1$-C$_3$ alkylene)(C$_6$-C$_{14}$ aryl), wherein each R$^6$ and R$^7$ is independently optionally substituted by halogen, oxo, —OR$^{11}$, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —(C$_1$-C$_3$ alkylene)OR$^{11}$, —(C$_1$-C$_3$ alkylene)NR$^{11}$R$^{12}$, —(C$_1$-C$_3$ alkylene)C(O)R$^{11}$, —(C$_1$-C$_3$ alkylene)S(O)R$^{11}$, —(C$_1$-C$_3$ alkylene)S(O)$_2$R$^{11}$, —(C$_1$-C$_3$ alkylene)P(O)(OR$^{11}$)(OR$^{12}$), C$_3$-C$_8$ cycloalkyl, or C$_1$-C$_6$ alkyl optionally substituted by oxo, —OH or halogen;

each R$^8$ is independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl, 3-6-membered heterocyclyl, —(C$_1$-C$_3$ alkylene)(C$_3$-C$_6$ cycloalkyl), —(C$_1$-C$_3$ alkylene)(C$_6$-C$_{14}$ aryl), —(C$_1$-C$_3$ alkylene)(5-6-membered heteroaryl), or —(C$_1$-C$_3$ alkylene)(3-6-membered heterocyclyl), wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl, 3-6-membered heterocyclyl, —(C$_1$-C$_3$ alkylene)(C$_3$-C$_6$ cycloalkyl), —(C$_1$-C$_3$ alkylene)(C$_6$-C$_{14}$ aryl), —(C$_1$-C$_3$ alkylene)(5-6-membered heteroaryl), and —(C$_1$-C$_3$ alkylene)(3-6-membered heterocyclyl) of R$^8$ are independently optionally substituted by halogen, oxo, —CN, —OR$^{13}$, —NR$^{13}$R$^{14}$, —P(O)(OR$^{13}$)(OR$^{14}$), phenyl optionally substituted by halogen, or C$_1$-C$_6$ alkyl optionally substituted by halogen, —OH or oxo;

R$^9$ and R$^{10}$ are each independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl, 3-6 membered heterocyclyl, —(C$_1$-C$_3$ alkylene)NR$^{11}$R$^{12}$, —(C$_1$-C$_3$ alkylene)(C$_3$-C$_6$ cycloalkyl), —(C$_1$-C$_3$ alkylene)(3-6-membered heterocyclyl), —(C$_1$-C$_3$ alkylene)(5-6-membered heteroaryl) or —(C$_1$-C$_3$ alkylene)(C$_6$ aryl), wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl, 3-6 membered heterocyclyl, —(C$_1$-C$_3$ alkylene)(C$_3$-C$_6$ cycloalkyl), —(C$_1$-C$_3$ alkylene)(3-6-membered heterocyclyl), —(C$_1$-C$_3$ alkylene)(5-6-membered heteroaryl) and —(C$_1$-C$_3$ alkylene)(C$_6$ aryl) of R$^9$ and R$^{10}$ are independently optionally substituted by halogen, oxo, —CN, —OR$^{13}$, —NR$^{13}$R$^{14}$ or C$_1$-C$_6$ alkyl optionally substituted by halogen, —OH or oxo;
  or R$^9$ and R$^{10}$ are taken together with the atom to which they attached to form a 3-6 membered heterocyclyl optionally substituted by halogen, oxo, —OR$^{13}$, —NR$^{13}$R$^{14}$ or C$_1$-C$_6$ alkyl optionally substituted by halogen, oxo or —OH;

R$^{11}$ and R$^{12}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo; or R$^{11}$ and R$^{12}$ are taken together with the atom to which they attached to form a 3-6 membered heterocyclyl optionally substituted by halogen, oxo or C$_1$-C$_6$ alkyl optionally substituted by halogen or oxo; and R$^{13}$ and R$^{14}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;
  or R$^{13}$ and R$^{14}$ are taken together with the atom to which they attached to form a 3-6 membered heterocyclyl optionally substituted by halogen, oxo or C$_1$-C$_6$ alkyl optionally substituted by oxo or halogen.

In some embodiments of a compound of the Formula (I):

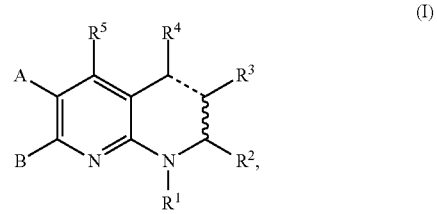

or a tautomer thereof, or a salt of any of the foregoing, wherein:
R$^1$ is H or C$_1$-C$_6$ alkyl wherein the C$_1$-C$_6$ alkyl of R$^1$ is optionally substituted with oxo or R$^a$;
R$^2$ and R$^4$ are each independently H, R$^b$ or oxo;
R$^3$ and R$^5$ are each independently H or R$^c$;
each R$^a$, R$^b$, and R$^c$ is independently C$_1$-C$_6$ alkyl, C$_2$-C$_6$ alkenyl, C$_2$-C$_6$ alkynyl, halogen, —CN, —OR$^8$, —SR$^8$, —NR$^9$R$^{10}$, —NO$_2$, —C=NH(OR$^8$), —C(O)R$^8$, —OC(O)R$^8$, —C(O)OR$^8$, —C(O)NR$^9$R$^{10}$, —OC(O)NR$^9$R$^{10}$, —NR$^8$C(O)R$^9$, —NR$^8$C(O)OR$^9$, —NR$^8$C(O)NR$^9$R$^{10}$, —S(O)R$^8$, —S(O)$_2$R$^8$, —NR$^8$S(O)R$^9$, —C(O)NR$^8$S(O)R$^9$, —NR$^8$S(O)$_2$R$^9$, —C(O)NR$^8$S(O)$_2$R$^9$, —S(O)NR$^9$R$^{10}$, —S(O)$_2$NR$^9$R$^{10}$, —P(O)(OR$^9$)(OR$^{10}$), C$_3$-C$_6$ cycloalkyl, 3-12-membered heterocyclyl, 5- to 10-membered heteroaryl, C$_6$-C$_{14}$ aryl, —(C$_1$-C$_3$ alkylene)CN, —(C$_1$-C$_3$ alkylene)OR$^8$, —(C$_1$-C$_3$ alkylene)SR$^8$, —(C$_1$-C$_3$ alkylene)NR$^9$R$^{10}$, —(C$_1$-C$_3$ alkylene)CF$_3$, —(C$_1$-C$_3$ alkylene)NO$_2$, —C=NH(OR$^8$), —(C$_1$-C$_3$ alkylene)C(O)R$^8$, —(C$_1$-C$_3$ alkylene)OC(O)R$^8$, —(C$_1$-C$_3$ alkylene)C(O)OR$^8$, —(C$_1$-C$_3$ alkylene)C(O)NR$^9$R$^{10}$, —(C$_1$-C$_3$ alkylene)OC(O)NR$^9$R$^{10}$, —(C$_1$-C$_3$ alkylene)NR$^8$C(O)R$^9$, —(C$_1$-C$_3$ alkylene)NR$^8$C(O)OR$^9$, —(C$_1$-C$_3$ alkylene)NR$^8$C(O)NR$^9$R$^{10}$, —(C$_1$-C$_3$ alkylene)S(O)R$^8$, —(C$_1$-C$_3$ alkylene)S(O)$_2$R$^8$, —(C$_1$-C$_3$ alkylene)NR$^8$S(O)R$^9$, —C(O)(C$_1$-C$_3$ alkylene)NR$^8$S(O)R$^9$, —(C$_1$-C$_3$ alkylene)NR$^8$S(O)$_2$R$^9$, —(C$_1$-C$_3$ alkylene)C(O)NR$^8$S(O)$_2$R$^9$, —(C$_1$-C$_3$ alkylene)S(O)NR$^9$R$^{10}$, —(C$_1$-C$_3$ alkylene)S(O)$_2$NR$^9$R$^{10}$, —(C$_1$-C$_3$ alkylene)P(O)(OR$^9$)(OR$^{10}$), —(C$_1$-C$_3$ alkylene)(C$_3$-C$_6$ cycloalkyl), —(C$_1$-C$_3$ alkylene)(3-12-membered heterocyclyl), —(C$_1$-C$_3$ alkylene)(5-10-membered heteroaryl) or —(C$_1$-C$_3$ alkylene)(C$_6$-C$_{14}$ aryl), wherein each R$^a$, R$^b$, and R$^c$ is independently optionally substituted by halogen, oxo, —OR, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —(C$_1$-C$_3$ alkylene)OR$^{11}$, —(C$_1$-C$_3$ alkylene)NR$^{11}$R$^{12}$, —(C$_1$-C$_3$ alkylene)C(O)R$^{11}$, —(C$_1$-C$_3$ alkylene)S(O)R$^{11}$, —(C$_1$-C$_3$ alkylene)S(O)$_2$R$^{11}$, —(C$_1$-C$_3$ alkylene)P(O)(OR$^{11}$)(OR$^{12}$), C$_3$-C$_8$ cycloalkyl, or C$_1$-C$_6$ alkyl optionally substituted by oxo, —OH or halogen;

wherein when R$^1$ is C$_1$-C$_6$ alkyl, R$^4$ is other than —NR$^9$R$^{10}$ and R$^3$ is other than —OC(O)R$^8$;

------ is a single bond or a double bond, wherein when ------ is a double bond, R$^2$ is OXO;

⁓⁓⁓ is a single bond or a double bond, wherein when ⁓⁓⁓ is a double bond, R$^4$ is oxo;

one of ------ and ⁓⁓⁓ is a double bond and the other is a single bond;

A is C$_6$-C$_{12}$ aryl, 5- to 10-membered heteroaryl, 9- to 10-membered carbocycle, or 9- to 10-membered heterocycle, wherein the C$_6$-C$_{12}$ aryl, 5- to 10-membered heteroaryl, 9- to 10-membered carbocycle, or 9- to 10-membered heterocycle of A is optionally further substituted with R$^6$;

B is phenyl, 5- to 6-membered heteroaryl, 5- to 6-membered carbocycle, 5- to 6-membered heterocycle, or 9- to 10-membered heteroaryl, wherein the phenyl, 5- to 6-membered heteroaryl, 5- to 6-membered carbocycle, 5- to 6-membered heterocycle, or 9- to 10-membered heteroaryl of B is optionally further substituted with R$^7$;

wherein when B is 5- to 6-membered heterocycle, A is other than phenyl or pyridyl optionally further substituted with R$^7$;

each R$^6$ and R$^7$ is independently oxo, C$_1$-C$_6$ alkyl, C$_2$-C$_6$ alkenyl, C$_2$-C$_6$ alkynyl, halogen, —CN, —OR$^8$, —SR$^8$, —NR$^9$R$^{10}$, —NO$_2$, —C=NH(OR$^8$), —C(O)R$^8$, —OC(O)R$^8$, —C(O)OR$^8$, —C(O)NR$^9$R$^{10}$, —OC(O)NR$^9$R$^{10}$, —NR$^8$C(O)R$^9$, —NR$^8$C(O)OR$^9$, —NR$^8$C(O)NR$^9$R$^{10}$, —S(O)R$^8$, —S(O)$_2$R$^8$, —NR$^8$S(O)R$^9$, —C(O)NR$^8$S(O)R$^9$, —NR$^8$S(O)$_2$R$^9$, —C(O)NR$^8$S(O)$_2$R$^9$, —S(O)NR$^9$R$^{10}$, —S(O)$_2$NR$^9$R$^{10}$, —P(O)(OR$^9$)(OR$^{10}$), C$_3$-C$_6$ cycloalkyl, 3-12-membered heterocyclyl, 5- to 10-membered heteroaryl, C$_6$-C$_{14}$ aryl, —(C$_1$-C$_3$ alkylene)CN, —(C$_1$-C$_3$ alkylene)OR$^8$, —(C$_1$-C$_3$ alkylene)SR$^8$, —(C$_1$-C$_3$ alkylene)NR$^9$R$^{10}$, —(C$_1$-C$_3$ alkylene)CF$_3$, —(C$_1$-C$_3$ alkylene)NO$_2$, —C=NH(OR$^8$), —(C$_1$-C$_3$ alkylene)C(O)R$^8$, —(C$_1$-C$_3$ alkylene)OC(O)R$^8$, —(C$_1$-C$_3$ alkylene)C(O)OR$^8$, —(C$_1$-C$_3$ alkylene)C(O)NR$^9$R$^{10}$, —(C$_1$-C$_3$ alkylene)OC(O)NR$^9$R$^{10}$, —(C$_1$-C$_3$ alkylene)NR$^8$C(O)R$^9$, —(C$_1$-C$_3$ alkylene)NR$^8$C(O)OR$^9$, —(C$_1$-C$_3$ alkylene)NR$^8$C(O)NR$^9$R$^{10}$, —(C$_1$-C$_3$ alkylene)S(O)R$^8$, —(C$_1$-C$_3$ alkylene)S(O)$_2$R$^8$, —(C$_1$-C$_3$ alkylene)NR$^8$S(O)R$^9$, —C(O)(C$_1$-C$_3$ alkylene)NR$^8$S(O)R$^9$, —(C$_1$-C$_3$ alkylene)NR$^8$S(O)$_2$R$^9$, —(C$_1$-C$_3$ alkylene)C(O)NR$^8$S(O)$_2$R$^9$, —(C$_1$-C$_3$ alkylene)S(O)NR$^9$R$^{10}$, —(C$_1$-C$_3$ alkylene)S(O)$_2$NR$^9$R$^{10}$, —(C$_1$-C$_3$ alkylene)P(O)(OR$^9$)(OR$^{10}$), —(C$_1$-C$_3$ alkylene)(C$_3$-C$_6$ cycloalkyl), —(C$_1$-C$_3$ alkylene)(3-12-membered heterocyclyl), —(C$_1$-C$_3$ alkylene)(5-10-membered heteroaryl) or —(C$_1$-C$_3$ alkylene)(C$_6$-C$_{14}$ aryl), wherein each R$^6$ and R$^7$ is independently optionally substituted by halogen, oxo, —OR$^{11}$, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —(C$_1$-C$_3$ alkylene)OR$^{11}$, —(C$_1$-C$_3$ alkylene)NR$^{11}$R$^{12}$, —(C$_1$-C$_3$ alkylene)C(O)R$^{11}$, —(C$_1$-C$_3$ alkylene)S(O)R$^{11}$, —(C$_1$-C$_3$ alkylene)S(O)$_2$R$^{11}$, —(C$_1$-C$_3$ alkylene)P(O)(OR$^{11}$)(OR$^{12}$), C$_3$-C$_8$ cycloalkyl, or C$_1$-C$_6$ alkyl optionally substituted by oxo, —OH or halogen;

R$^8$ is independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl or 3-6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl and 3-6-membered heterocyclyl are independently optionally substituted by halogen, oxo, —CN, —OR$^{13}$, —NR$^{13}$R$^{14}$, —P(O)(OR$^{13}$)(OR$^{14}$), phenyl optionally substituted by halogen, or C$_1$-C$_6$ alkyl optionally substituted by halogen, —OH or oxo;

R$^9$ and R$^{10}$ are each independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl or 3-6 membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl and 3-6 membered heterocyclyl are independently optionally substituted by halogen, oxo, —CN, —OR$^{13}$, —NR$^{13}$R$^{14}$ or C$_1$-C$_6$ alkyl optionally substituted by halogen, —OH or oxo;

or R$^9$ and R$^{10}$ are taken together with the atom to which they attached to form a 3-6 membered heterocyclyl optionally substituted by halogen, oxo, —OR$^{13}$, —NR$^{13}$R$^{14}$ or C$_1$-C$_6$ alkyl optionally substituted by halogen, oxo or —OH;

R$^{11}$ and R$^{12}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{11}$ and R$^{12}$ are taken together with the atom to which they attached to form a 3-6 membered heterocyclyl optionally substituted by halogen, oxo or C$_1$-C$_6$ alkyl optionally substituted by halogen or oxo; and R$^{13}$ and R$^{14}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{13}$ and R$^{14}$ are taken together with the atom to which they attached to form a 3-6 membered heterocyclyl optionally substituted by halogen, oxo or C$_1$-C$_6$ alkyl optionally substituted by oxo or halogen.

In some embodiments of the compound of Formula (I), A is selected from the group consisting of C$_6$-C$_{12}$ aryl and 5- to 10-membered heteroaryl, wherein the C$_6$-C$_{12}$ aryl and 5- to 10-membered heteroaryl of A is optionally further substituted with R$^6$. In some embodiments of the compound of Formula (I), B is selected from the group consisting of phenyl and 5- to 6-membered heteroaryl, wherein the phenyl and 5- to 6-membered heteroaryl of B is optionally further substituted with R$^7$. In some embodiments of the compound of Formula (I), A is selected from the group consisting of $C_6$-$C_{12}$ aryl and 5- to 10-membered heteroaryl, wherein the $C_6$-$C_{12}$ aryl and 5- to 10-membered heteroaryl of A is optionally further substituted with $R^6$ and B is selected from the group consisting of phenyl and 5- to 6-membered heteroaryl, wherein the phenyl and 5- to 6-membered heteroaryl of B is optionally further substituted with $R^7$.

In some embodiments of Formula (I), $R^a$, $R^b$, and $R^c$ are independently $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$C(O)NR^9R^{10}$, —$NR^8C(O)R^9$, —$NR^8C(O)NR^9R^{10}$, —$S(O)R^8$, —$S(O)_2R$, —$NR^8S(O)R^9$, —$NR^8S(O)_2R^9$, —$S(O)NR^9R^{10}$, —$S(O)_2NR^9R^{10}$, $C_3$-$C_6$ cycloalkyl, 3-12-membered heterocyclyl, 5- to 10-membered heteroaryl or $C_6$-$C_{14}$ aryl.

In some embodiments of Formula (I), $R^a$, $R^b$, and $R^c$ are independently $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$C(O)NR^9R^{10}$, —$NR^8C(O)R^9$, $C_3$-$C_6$ cycloalkyl, 3-12-membered heterocyclyl, 5- to 10-membered heteroaryl or $C_6$-$C_{14}$ aryl.

In some embodiments of Formula (I), $R^a$, $R^b$, and $R^c$ are independently $C_1$-$C_6$ alkyl, halogen, —CN, —$OR^8$, —$SR^8$ or —$NR^9R^{10}$, In some embodiments of Formula (I), $R^a$, $R^b$, and $R^c$ are independently —$CH_3$, halogen, —CN or —$OCH_3$.

In some embodiments of the compound of Formula (I), $R^1$ is H or methyl.

In some embodiments of the compound of Formula (I), $R^5$ is H, $C_1$-$C_6$ alkyl, halogen, —CN, or —$OR^8$.

In some embodiments of the compound of Formula (I), $R^1$, $R^2$, $R^3$, and $R^5$ are each H and $R^4$ is oxo. In some embodiments of the compound of Formula (I), $R^1$, $R^3$, $R^4$, and $R^5$ are each H and $R^2$ is oxo.

In some embodiments, provided is a compound of Formula (II):

(II)

or a tautomer or isomer thereof, or a pharmaceutically acceptable salt of any of the foregoing, wherein A, B, $R^1$, $R^3$, $R^4$, and $R^5$ are as defined for Formula (I).

In some embodiments of a compound of Formula (II), at least one of $R^3$, $R^4$, and $R^5$ is not H. In some embodiments, at least one of $R^3$, $R^4$, and $R^5$ is $C_1$-$C_6$ alkyl, halogen, $C_6$-$C_{14}$ aryl, —CN, or —$OR^8$. In some embodiments, $R^1$, $R^3$, $R^4$, and $R^5$ are each H.

In some embodiments, provided is a compound of Formula (III):

(III)

or a tautomer or isomer thereof, or a pharmaceutically acceptable salt of any of the foregoing, wherein A, B, $R^1$, $R^2$, $R^3$, and $R^5$ are as defined for Formula (I).

In some embodiments of a compound of Formula (III), at least one of $R^2$, $R^3$, and $R^5$ is not H. In some embodiments, at least one of $R^2$, $R^3$, and $R^5$ is $C_1$-$C_6$ alkyl, halogen, $C_6$-$C_{14}$ aryl, —CN, or —$OR^8$. In some embodiments, $R^1$, $R^2$, $R^3$, and $R^5$ are each H.

In some embodiments of a compound of Formula (I), (II), or (III), $R^1$ is $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$C(O)NR^9R^{10}$, —$NR^8C(O)R^9$, —$NR^8C(O)NR^9R^{10}$, —$S(O)R^8$, —$S(O)_2R^8$, —$NR^8S(O)R^9$, —$NR^8S(O)_2R^9$, —$S(O)NR^9R^{10}$, —$S(O)_2NR^9R^{10}$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^1$ is $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$C(O)NR^9R^{10}$, —$NR^8C(O)R^9$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^1$ is $C_1$-$C_6$ alkyl, halogen, —CN, —OR, —$SR^8$ or —$NR^9R^{10}$. In some embodiments of a compound of Formula (I), (II), or (III), $R^1$ is —$CH_3$, halogen, —CN or —$OCH_3$. In some embodiments of a compound of Formula (I), (II), or (III), $R^1$ is H or methyl. In some embodiments of a compound of Formula (I), (II), or (III), $R^1$ is H, $C_1$-$C_6$ alkyl, halogen, —CN, or —$OR^8$. In some embodiments of a compound of Formula (I), (II), or (III), $R^1$ is H or $C_1$-$C_6$ alkyl. In some embodiments of a compound of Formula (I), (II), or (III), $R^1$ is H or methyl. In some embodiments, $R^1$ is H.

In some embodiments of a compound of Formula (I), (II), or (III), $R^2$ is $C_1$-$C_6$ alkyl, $C_2$-$C_6$ alkenyl, $C_2$-$C_6$ alkynyl, halogen, —CN, —OR, —$SR^8$, —$NR^9R^{10}$, —$C(O)NR^9R^{10}$, —$NR^8C(O)R^9$, —$NR^8C(O)NR^9R^{10}$, —$S(O)R^8$, —$S(O)_2R^8$, —$NR^8S(O)R^9$, —$NR^8S(O)_2R^9$, —$S(O)NR^9R^{10}$, —$S(O)_2NR^9R^{10}$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^2$ is $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$C(O)NR^9R^{10}$, —$NR^8C(O)R^9$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^2$ is $C_1$-$C_6$ alkyl, halogen, —CN, —$OR^8$, —$SR^8$ or —$NR^9R^{10}$. In some embodiments of a compound of Formula (I), (II), or (III), $R^2$ is —$CH_3$, halogen, —CN or —$OCH_3$. In some embodiments of a compound of Formula (I), (II), or (III), $R^2$ is H or methyl. In some embodiments of a compound of Formula (I), (II), or (III), $R^2$ is H, $C_1$-$C_6$ alkyl, halogen, —CN, or —$OR^8$. In some embodiments of a compound of Formula (I), (II), or (III), $R^2$ is oxo.

In some embodiments of a compound of Formula (I), (II), or (III), $R^3$ is $C_1$-$C_6$ alkyl, $C_2$-$C_6$ alkenyl, $C_2$-$C_6$ alkynyl, halogen, —CN, —OR, —$SR^8$, —$NR^9R^{10}$, —$C(O)NR^9R^{10}$, —$NR^8C(O)R^9$, —$NR^8C(O)NR^9R^{10}$, —$S(O)R^8$, —$S(O)_2R^8$, —$NR^8S(O)R^9$, —$NR^8S(O)_2R^9$, —$S(O)NR^9R^{10}$, —$S(O)_2NR^9R^{10}$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^3$ is $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$C(O)NR^9R^{10}$, —$NR^8C(O)R^9$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^3$ is $C_1$-$C_6$ alkyl, halogen, —CN, —$OR^8$, —$SR^8$ or —$NR^9R^{10}$. In some embodiments of a compound of Formula (I), (II), or (III), $R^3$ is —$CH_3$, halogen, —CN or —$OCH_3$. In some embodiments of a compound of Formula (I), (II), or (III), $R^3$ is H or methyl. In some embodiments of a compound of Formula (I), (II), or (III), $R^3$ is H, $C_1$-$C_6$ alkyl, halogen, —CN, or —$OR^8$.

In some embodiments of a compound of Formula (I), (II), or (III), $R^4$ is $C_1$-$C_6$ alkyl, $C_2$-$C_6$ alkenyl, $C_2$-$C_6$ alkynyl, halogen, —CN, —OR, —$SR^8$, —$NR^9R^{10}$, —$C(O)NR^9R^{10}$, —$NR^8C(O)R^9$, —$NR^8C(O)NR^9R^{10}$, —$S(O)R^8$, —$S(O)_2R$, —$NR^8S(O)R^9$, —$NR^8S(O)_2R^9$, —$S(O)NR^9R^{10}$, —$S(O)_2NR^9R^{10}$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^4$ is $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$C(O)NR^9R^{10}$, —$NR^8C(O)R^9$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^4$ is $C_1$-$C_6$ alkyl, halogen, —CN, —$OR^8$, —$SR^8$ or —$NR^9R^{10}$. In some embodiments of a compound of Formula (I), (II), or (III), $R^4$ is —$CH_3$, halogen, —CN or —$OCH_3$. In some embodiments of a compound of Formula (I), (II), or (III), $R^4$ is H or methyl. In some embodiments of a compound of Formula (I), (II), or (III), $R^4$ is H, $C_1$-$C_6$ alkyl, halogen, —CN, or —$OR^8$. In some embodiments of a compound of Formula (I), (II), or (III), $R^4$ is oxo.

In some embodiments of a compound of Formula (I), (II), or (III), $R^5$ is $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$C(O)NR^9R^{10}$, —$NR^8C(O)R^9$, —$NR^8C(O)NR^9R^{10}$, —$S(O)R^8$, —$S(O)_2R^8$, —$NR^8S(O)R^9$, —$NR^8S(O)_2R^9$, —$S(O)NR^9R^{10}$, —$S(O)_2NR^9R^{10}$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^5$ is $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$C(O)NR^9R^{10}$, —$NR^8C(O)R^9$, $C_3$-$C_6$ cycloalkyl, 3-12-membered heterocyclyl, 5- to 10-membered heteroaryl or $C_6$-$C_{14}$ aryl. In some embodiments of a compound of Formula (I), (II), or (III), $R^5$ is $C_1$-$C_6$ alkyl, halogen, —CN, —$OR^8$, —$SR^8$ or —$NR^9R^{10}$. In some embodiments of a compound of Formula (I), (II), or (III), $R^5$ is —$CH_3$, halogen, —CN or —$OCH_3$. In some embodiments of a compound of Formula (I), (II), or (III), $R^5$ is H or methyl. In some embodiments of a compound of Formula (I), (II), or (III), $R^5$ is H, $C_1$-$C_6$ alkyl, halogen, —CN, or —$OR^8$. In some embodiments of a compound of Formula (I), (II), or (III), $R^5$ is H, $C_1$-$C_6$ alkyl, halogen, —CN, or —$OR^8$. In some embodiments, $R^5$ is H. In particular embodiments of a compound of Formula (I), (II), or (III), $R^1$ is H or $C_1$-$C_6$ alkyl (such as methyl) and $R^5$ is H, $C_1$-$C_6$ alkyl, halogen, —CN, or —$OR^8$.

In some embodiments of a compound of Formula (I), (II), or (III), A is $C_6$-$C_{12}$ aryl optionally further substituted with $R^6$. In some embodiments, A is phenyl or naphthyl, optionally substituted with $R^6$. In some embodiments, A is phenyl. In some embodiments, A is naphthyl. In some embodiments, A is phenyl or naphthyl, substituted with one or more groups selected from halogen, —CN, —OR, —$SR^8$, —$NR^9R^{10}$, —$NO_2$, —$C(O)R^8$, —$C(O)OR^8$, —$C(O)NR^9R^{10}$, —$C(O)NR^8S(O)_2R^9$, —$OC(O)R^8$, —$OC(O)NR^9R^{10}$, —$NR^8C(O)R^9$, —$NR^8C(O)NR^9R^{10}$, —$S(O)R^8$, —$S(O)_2R^8$, $C_3$-$C_6$ cycloalkyl and $C_1$-$C_6$ alkyl optionally substituted by halogen. In some embodiments, A is phenyl, substituted with one or more groups selected from halogen, —CN, —OH, —$OC_1$-$C_6$ alkyl, —$NH_2$, —$NO_2$, $C_3$-$C_6$ cycloalkyl and $C_1$-$C_6$ alkyl optionally substituted by halogen. In some embodiments, A is phenyl, substituted with one or more groups selected from halogen, —OH, and $C_1$-$C_6$ alkyl.

In some embodiments of a compound of Formula (I), (II), or (III), A is 5- to 10-membered heteroaryl optionally further substituted with $R^6$. In some embodiments, A is selected from the group consisting of pyridyl, quinolinyl, isoquinolinyl, quinoxalinyl, cinnolinyl, quinazolinyl, naphthyridinyl, benzoxazolyl, benzothiazolyl, benzoimidazoyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridazinyl, pyrimidinyl, pyrazinyl, triazinyl, tetrazinyl, indolyl, isoindolyl, indazolyl, benzotriazolyl, benzofuranyl, benzoisoxazolyl, benzoxadiazolyl, benzothiophenyl, benzoisothiazolyl, benzothiadiazolyl, pyrrolopyridinyl, pyrazolopyridinyl, imidazopyridinyl, triazolopyridinyl, furopyridinyl, oxazolopyridinyl, isoxazolopyridinyl, oxadiazolopyridinyl, thienopyridinyl, thiazolopyridinyl, isothiazolopyridinyl, thiadiazolopyridinyl, thienopyridinyl, phthalazinyl, pyrazolothiazolyl, pyrazolothiazolyl and imidazothiazolyl, each optionally substituted with $R^6$. In one variation, the optional substitution with $R^6$ provides a moiety that is unsubstituted. In one variation, the optional substitution with $R^6$ provides a moiety that is substituted with 1-3 $R^6$, which may be the same or different.

In some embodiments, A is a 10-membered heteroaryl optionally further substituted with $R^6$, wherein the 10-membered heteroaryl is a 6/6-ring fused system (i.e., a ring system formed by fusing a 6-membered ring with a 6-membered ring). In some embodiments, A is a 9-membered heteroaryl, wherein the 9-membered heteroaryl is a 6/5-ring fused system (i.e., a ring system formed by fusing a 6-membered ring with a 5-membered ring). In some embodiments, the 6/5-ring fused system of A is attached to the rest of the compound via the 6-membered ring. In other embodiments, the 6/5-ring fused system of A is attached to the rest of the compound via the 5-membered ring.

In some embodiments, A is selected from the group consisting of:

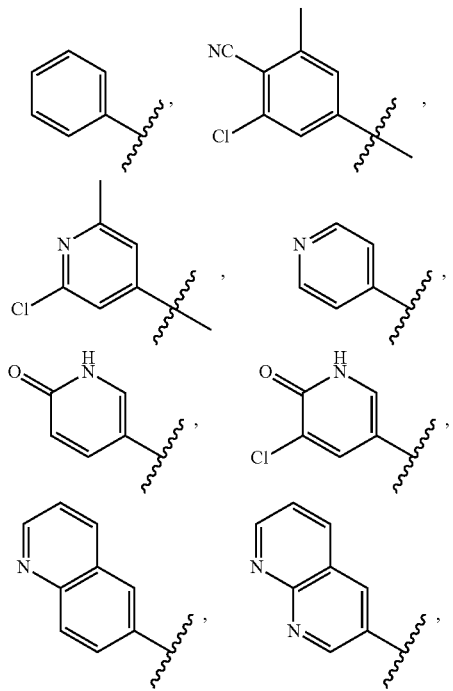

-continued
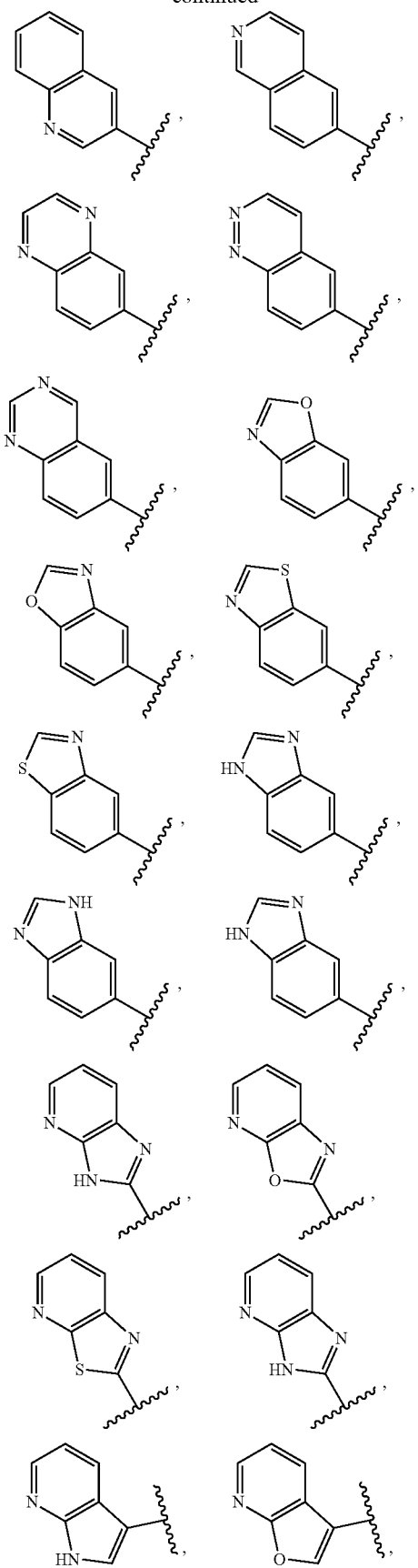
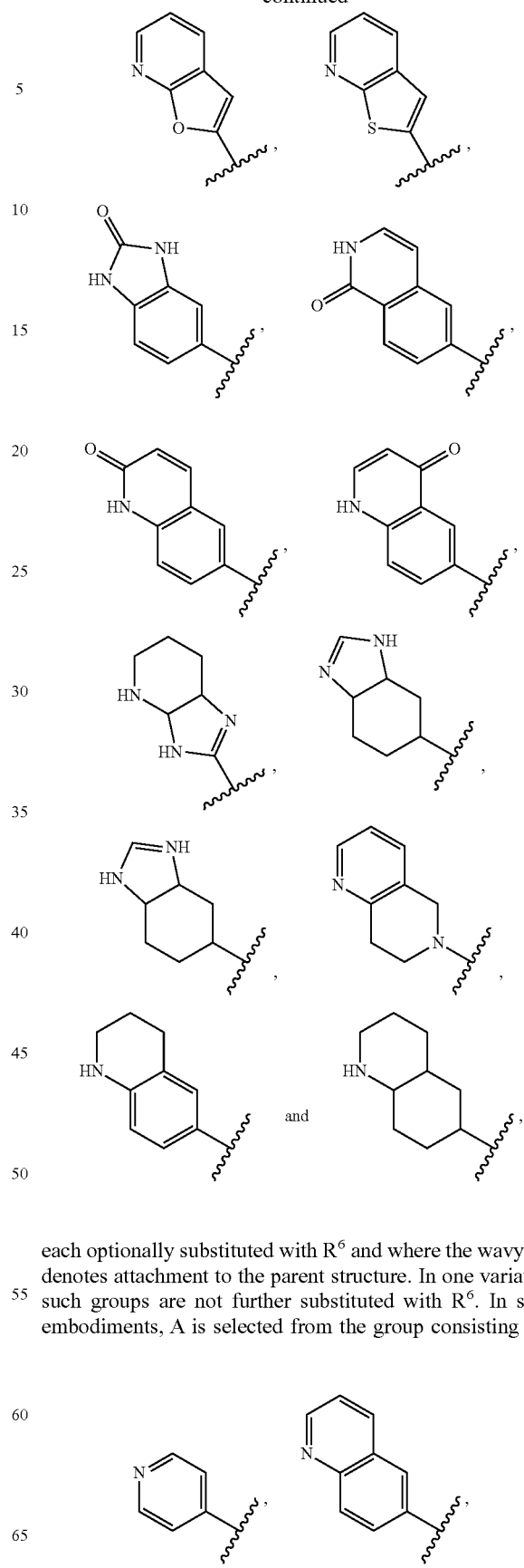
each optionally substituted with $R^6$ and where the wavy line denotes attachment to the parent structure. In one variation, such groups are not further substituted with $R^6$. In some embodiments, A is selected from the group consisting of:

-continued

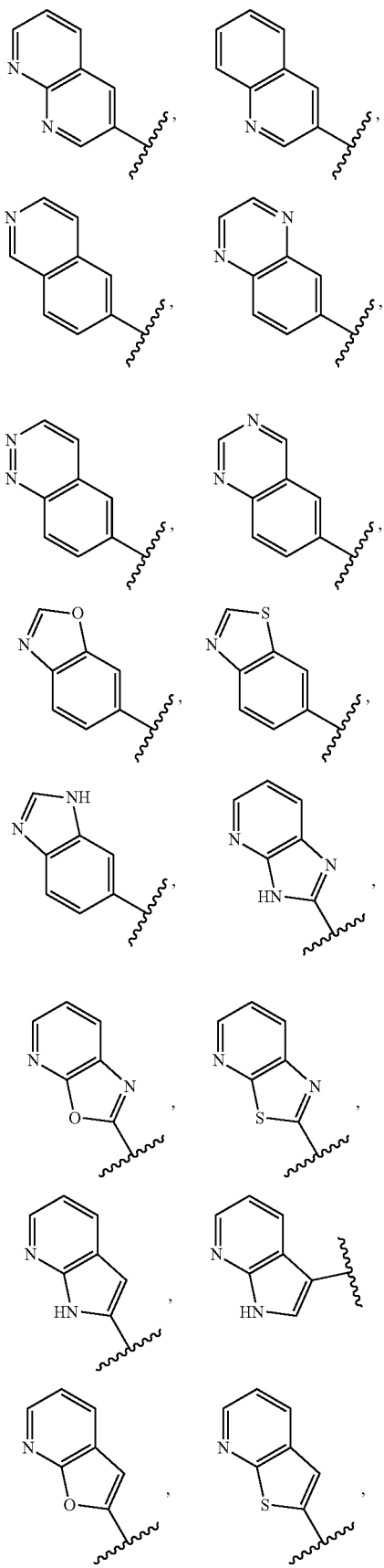

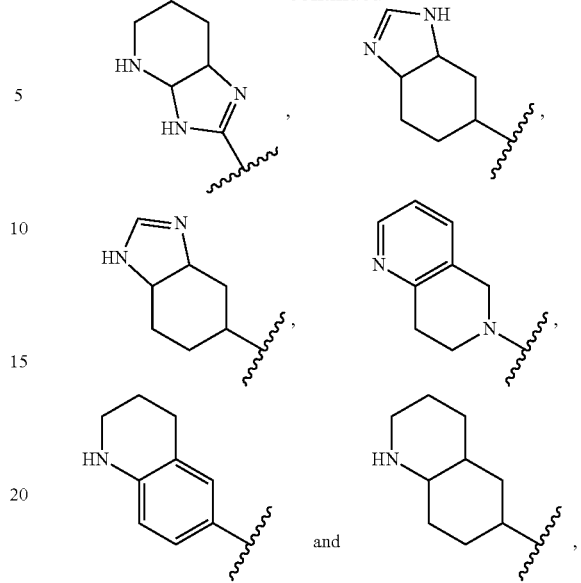

each optionally substituted with $R^6$. In one variation, such groups are not further substituted with $R^6$. In one variation, such groups are further substituted with 1-3 $R^6$, which may be the same or different. In some of these embodiments, A is 5- to 10-membered heteroaryl optionally further substituted with one or more groups selected from halogen, —CN, —$OR^8$, —$SR^8$, —$NR^9R^{10}$, —$NO_2$, —$C(O)R^8$, —$C(O)OR^8$, —$C(O)NR^9R^{10}$, —$C(O)NR^8S(O)_2R^9$, —$OC(O)R^8$, —$OC(O)NR^9R^{10}$, —$NR^8C(O)R^9$, —$NR^8C(O)NR^9R^{10}$, —$S(O)R^8$, —$S(O)_2R^8$, $C_3$-$C_6$ cycloalkyl and $C_1$-$C_6$ alkyl optionally substituted by halogen. In some embodiments, A is 5- to 10-membered heteroaryl optionally further substituted with one or more groups selected from $C_1$-$C_6$ alkyl, halogen, —CN, —OH, and —$OC_1$-$C_6$ alkyl.

In some embodiments of a compound of Formula (I), (II), or (III), A is a 9- to 10-membered carbocycle optionally further substituted with $R^6$. In some embodiments, A is a 10-membered carbocycle, wherein the 10-membered carbocycle is a 6/6-ring fused system (i.e., a ring system formed by fusing a 6-membered ring with a 6-membered ring). In some embodiments, A is a 9-membered carbocycle, wherein the 9-membered carbocycle is a 6/5-ring fused system (i.e., a ring system formed by fusing a 6-membered ring with a 5-membered ring). In some embodiments, the 6/5-ring fused system of A is attached to the rest of the compound via the 6-membered ring. In other embodiments, the 6/5-ring fused system of A is attached to the rest of the compound via the 5-membered ring. In some embodiments, A is a fully saturated 9- to 10-membered carbocycle. In some embodiments, A is a partially saturated 9- to 10-membered carbocycle. In some embodiments of a compound of Formula (I), (II), or (III), A is selected from the group consisting of decahydronaphthalenyl, octahydroindenyl, 1,2,3,4-tetrahydronaphthalenyl, and 2,3-dihydroindenyl, each optionally substituted with $R^6$. In some embodiments, A is a 9- to 10-membered carbocycle optionally further substituted with one or more groups selected from halogen, —CN, —$OR^8$, —$SR^8$, —$NR^9R^{10}$, —$NO_2$, —$C(O)R^8$, —$C(O)OR^8$, —$C(O)NR^9R^{10}$, —$C(O)NR^8S(O)_2R^9$, —$OC(O)R^8$, —$OC(O)NR^9R^{10}$, —$NR^8C(O)R^9$, —$NR^8C(O)NR^9R^{10}$, —$S(O)R^8$, —$S(O)_2R^8$, $C_3$-$C_6$ cycloalkyl and $C_1$-$C_6$ alkyl optionally substituted by halogen. In some embodiments, A is a 9- to 10-membered carbocycle optionally further substituted with one or more groups selected from $C_1$-$C_6$ alkyl, halogen, —CN, —OH, and —O$C_1$-$C_6$ alkyl.

In some embodiments, A is a 9- to 10-membered heterocycle optionally further substituted with $R^6$. In some embodiments, A is a 10-membered heterocycle optionally further substituted with $R^6$, wherein the 10-membered heterocycle is a 6/6-ring fused system (i.e., a ring system formed by fusing a 6-membered ring with a 6-membered ring). In some embodiments, A is a 9-membered heterocycle, wherein the 9-membered heterocycle is a 6/5-ring fused system (i.e., a ring system formed by fusing a 6-membered ring with a 5-membered ring). In some embodiments, the 6/5-ring fused system of A is attached to the rest of the compound via the 6-membered ring. In other embodiments, the 6/5-ring fused system of A is attached to the rest of the compound via the 5-membered ring. In some embodiments, A is a fully saturated 9- to 10-membered heterocycle. In some embodiments, A is a partially saturated 9- to 10-membered heterocycle. In some embodiments, A is selected from the group consisting of tetrahydroquinolinyl, tetrahydroisoquinolinyl, decahydroquinolinyl, decahydroisoquinolinyl, indolinyl, isoindolinyl, tetrahydronaphthyridinyl and hexahydrobenzoimidazolyl, each optionally further substituted with $R^6$. In some embodiments, A is a 9- to 10-membered heterocycle optionally further substituted with one or more groups selected from halogen, —CN, —O$R^8$, —S$R^8$, —N$R^9R^{10}$, —N$O_2$, —C(O)$R^8$, —C(O)O$R^8$, —C(O)N$R^9R^{10}$, —C(O)N$R^8$S(O)$_2R^9$, —OC(O)$R^8$, —OC(O)N$R^9R^{10}$, —N$R^8$C(O)$R^9$, —N$R^8$C(O)N$R^9R^{10}$, —S(O)$R^8$, —S(O)$_2R^8$, $C_3$-$C_6$ cycloalkyl and $C_1$-$C_6$ alkyl optionally substituted by halogen. In some embodiments, A is a 9- to 10-membered heterocycle optionally further substituted with one or more groups selected from $C_1$-$C_6$ alkyl, halogen, —CN, —OH, and —O$C_1$-$C_6$ alkyl. In some embodiments, A is selected from the group consisting of each optionally substituted with $R^6$. In some embodiments, such groups are not further substituted with $R^6$. In some embodiments, such groups are further substituted with 1-3 $R^6$, which may be the same or different. In some of these embodiments $R^6$ is independently selected from the group consisting of halogen, —CN, —O$R^8$, —S$R^8$, —N$R^9R^{10}$, —N$O_2$, —C(O)$R^8$, —C(O)O$R^8$, —C(O)N$R^9R^{10}$, —C(O)N$R^8$S(O)$_2R^9$, —OC(O)$R^8$, —OC(O)N$R^9R^{10}$, —N$R^8$C(O)$R^9$, —N$R^8$C(O)N$R^9R^{10}$, —S(O)$R^8$, —S(O)$_2R^8$, $C_3$-$C_6$ cycloalkyl and $C_1$-$C_6$ alkyl optionally substituted by halogen. In some embodiments, $R^6$ is independently selected from the group consisting of $C_1$-$C_6$ alkyl, halogen, —CN, —OH, and —O$C_1$-$C_6$ alkyl.

In some embodiments of a compound of Formula (I), (II), or (III), each $R^6$ is independently selected from the group consisting of halogen, —CN, —O$R^8$, —S$R^8$, —N$R^9R^{10}$, —N$O_2$, —C(O)$R^8$, —C(O)O$R^8$, —C(O)N$R^9R^{10}$, —C(O)N$R^8$S(O)$_2R^9$, —OC(O)$R^8$, —OC(O)N$R^9R^{10}$, —N$R^8$C(O)$R^9$, —N$R^8$C(O)N$R^9R^{10}$, —S(O)$R^8$, —S(O)$_2R^8$, $C_3$-$C_6$ cycloalkyl and $C_1$-$C_6$ alkyl optionally substituted by halogen. In some embodiments, $R^6$ is independently selected from the group consisting of $C_1$-$C_6$ alkyl, halogen, —CN, and —O$R^8$.

In some embodiments of a compound of Formula (I), (II), or (III), A is selected from the group consisting of:

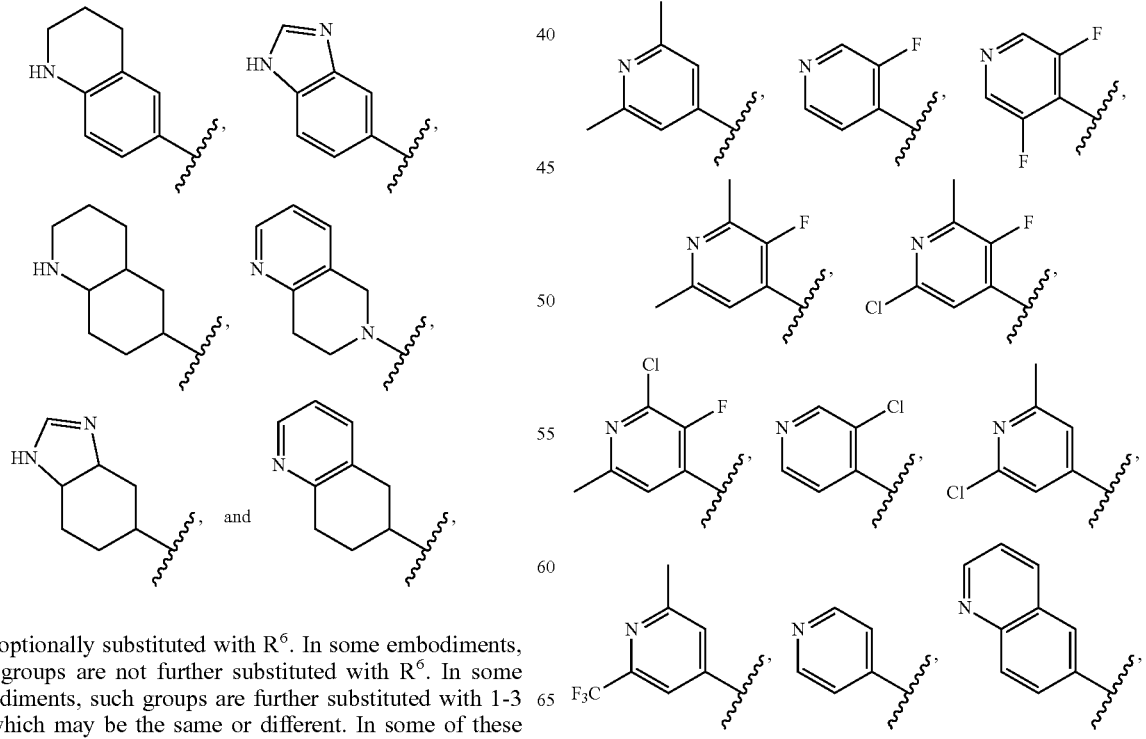

-continued
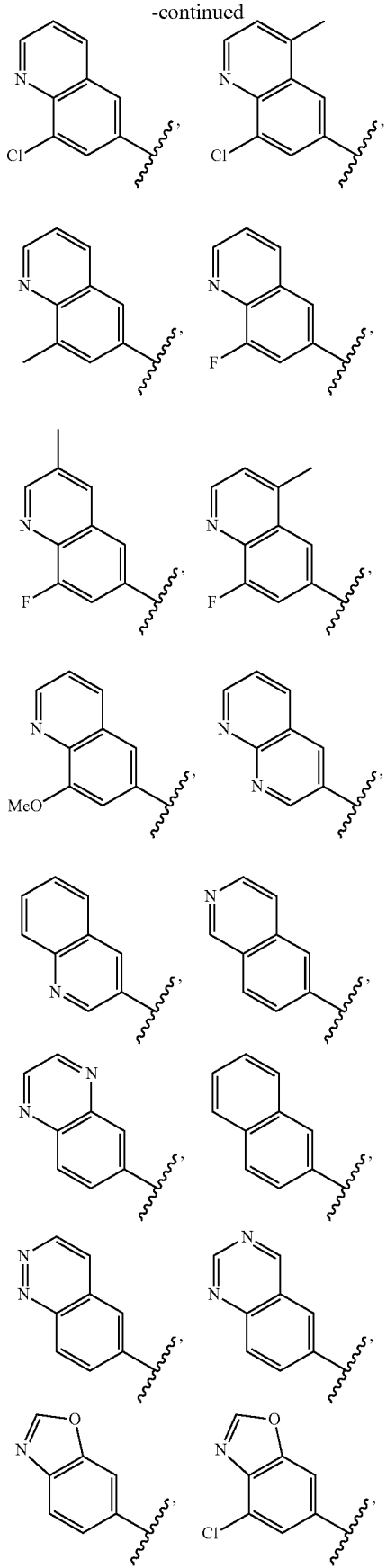
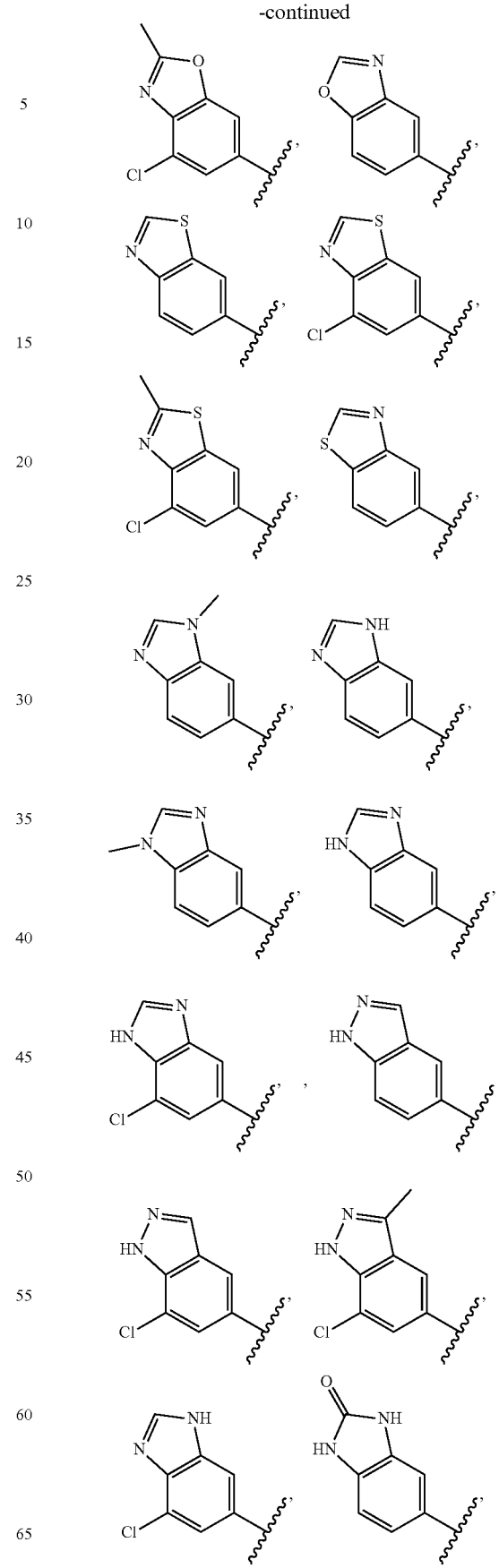

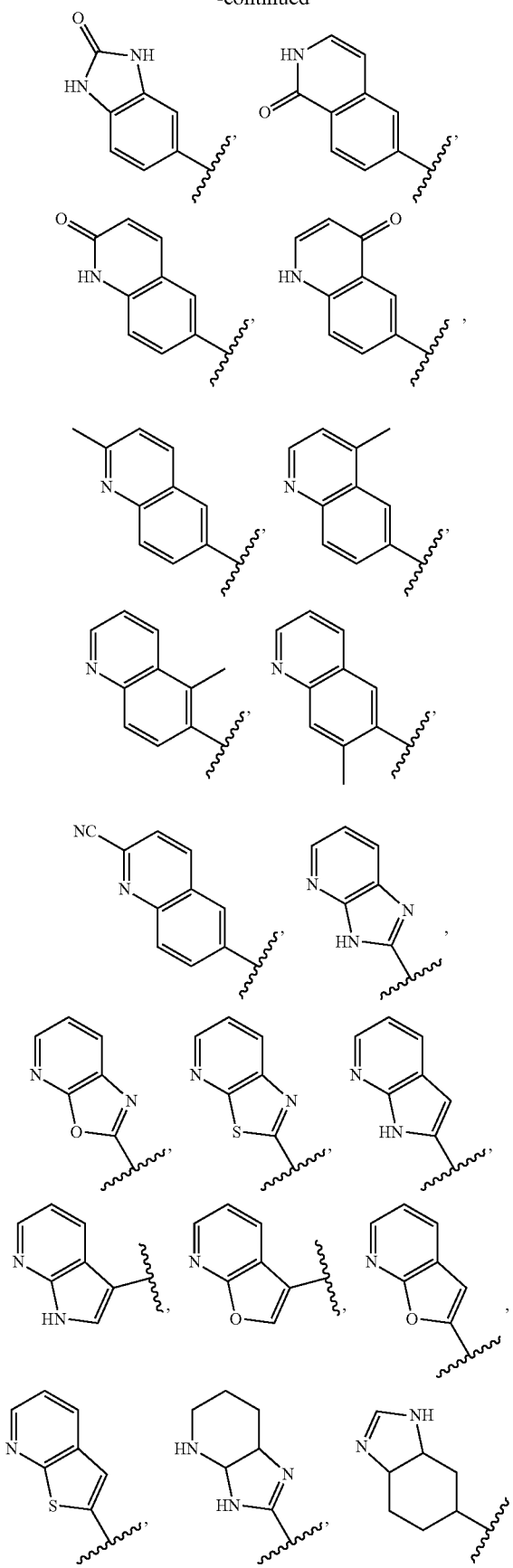
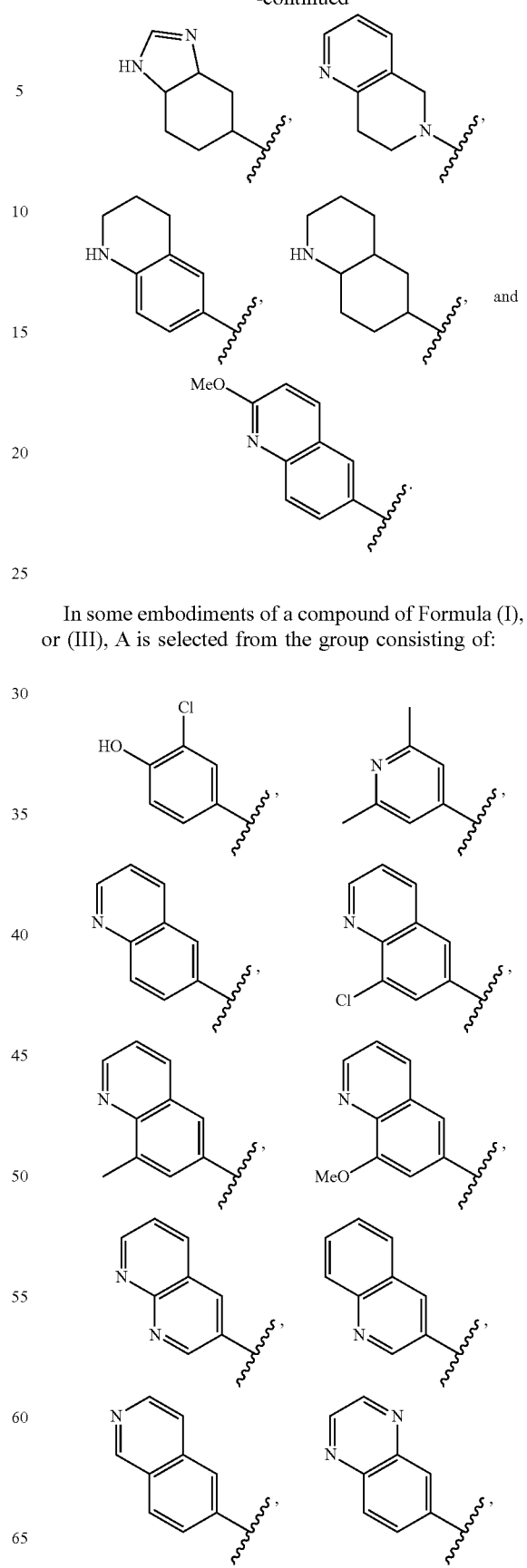
In some embodiments of a compound of Formula (I), (II), or (III), A is selected from the group consisting of:

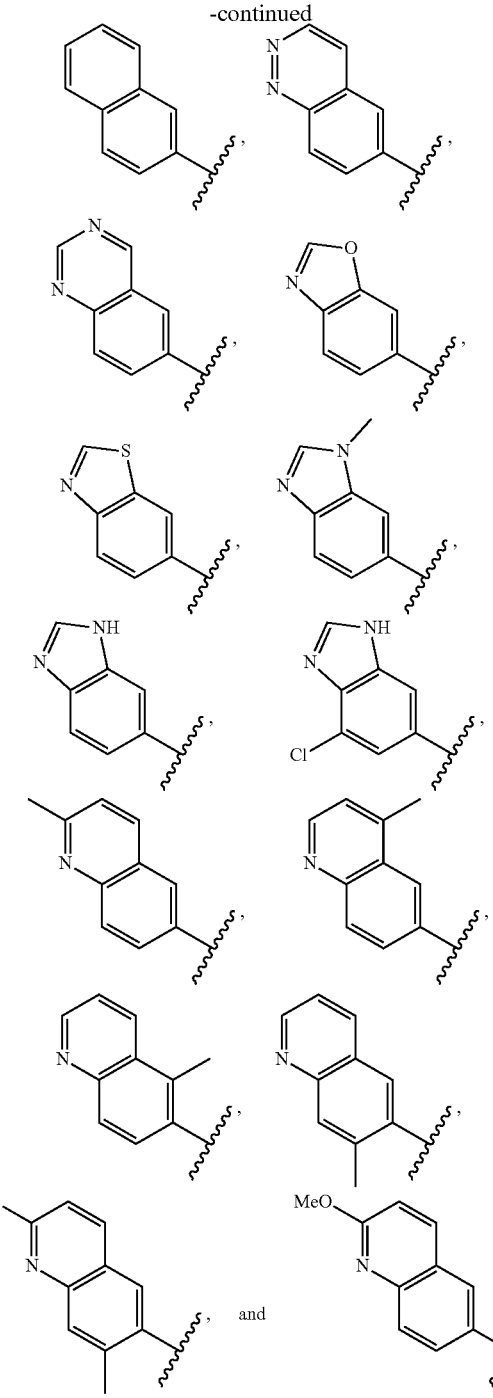
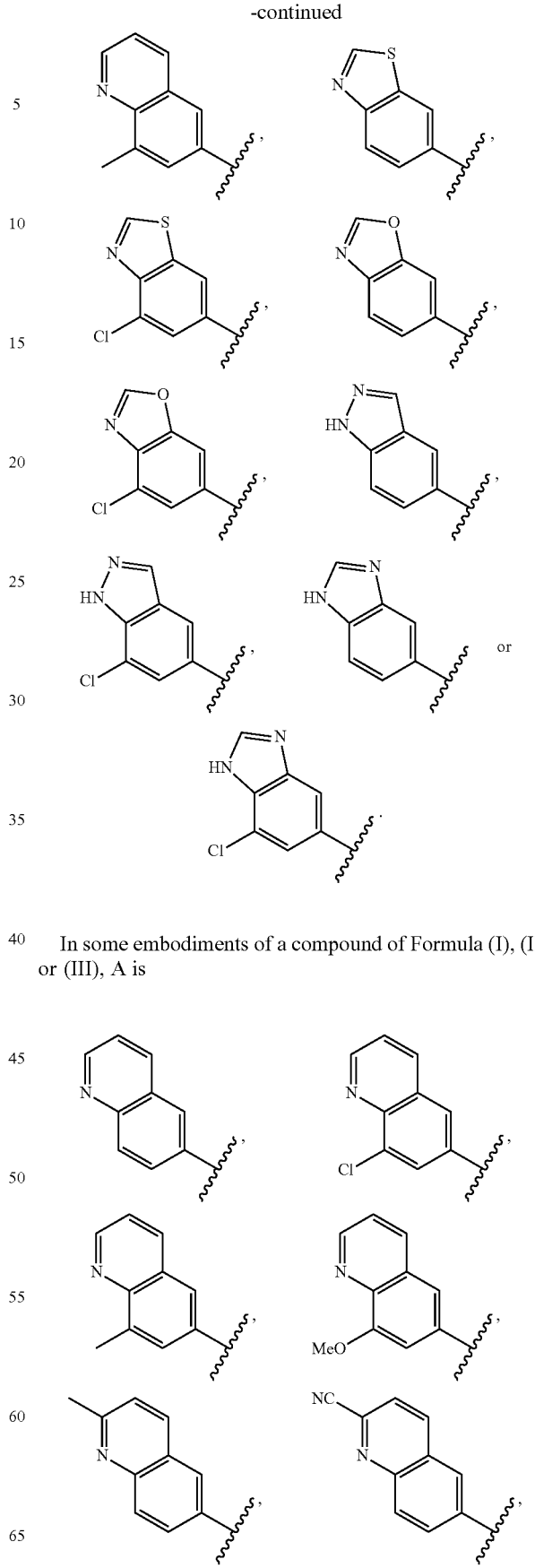
In some embodiments of a compound of Formula (I), (II), or (III), A is
In some embodiments of a compound of Formula (I), (II), or (III), A is -continued

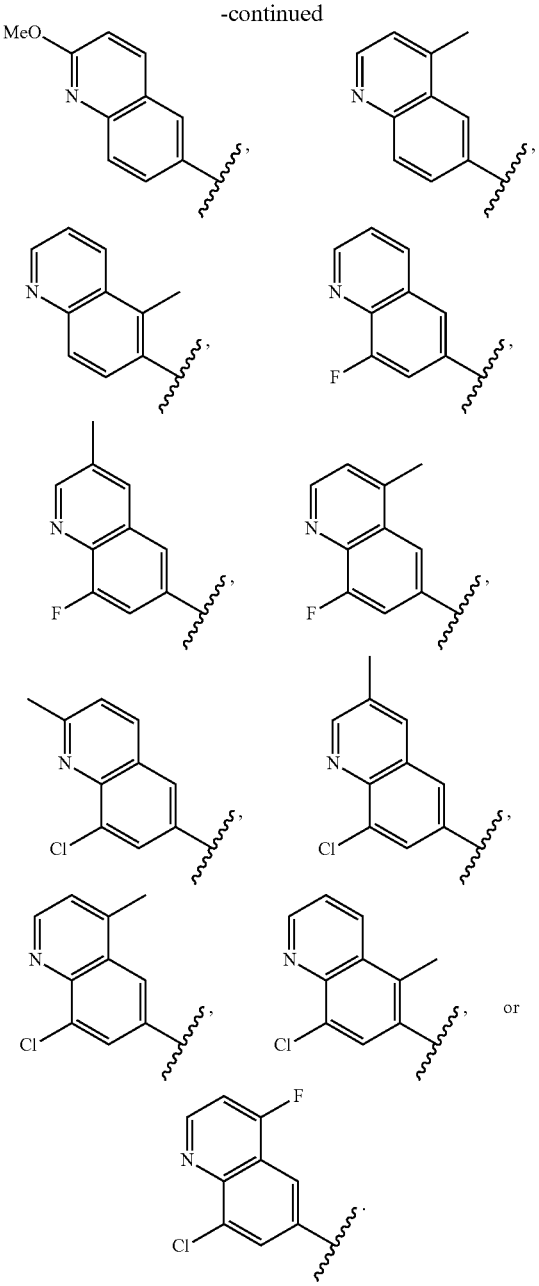

It is understood that each description of A may be combined with each description of $R^1$-$R^5$ the same as if each and every combination were specifically and individually listed. It is similarly understood that each description of A may be combined with each description of B (and further with each description of $R^1$-$R^5$) the same as if each and every combination were specifically and individually listed. For example, in one aspect, it is understood that each description of A may be combined in one aspect with a variation in which $R^1$, $R^3$, $R^5$ are each hydrogen and one of $R^2$ and $R^4$ is hydrogen and one of $R^2$ and $R^4$ is oxo. In one such variation, each description of A is combined in one aspect with a variation in which $R^1$, $R^2$, $R^3$, $R^5$ are each hydrogen and $R^4$ is oxo. In another such variation, each description of A is combined in one aspect with a variation in which $R^1$, $R^3$, $R^4$, $R^5$ are each hydrogen and $R^2$ is oxo. Such embodiments may further be combined with each description of B.

In some embodiments of a compound of Formula (I), (II), or (III), B is phenyl, optionally further substituted with $R^7$. In some embodiments, B is 5- to 6-membered heteroaryl optionally further substituted with $R^7$. In some embodiments, B is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each optionally substituted with $R^7$. In some embodiments, B is furanyl, pyridinyl, oxazoyl, or oxadiazoyl, each optionally substituted with $R^7$.

In some embodiments of a compound of Formula (I), (II), or (III), B is a 5- to 6-membered carbocycle optionally further substituted with $R^7$. In some embodiments, B is a fully saturated 5- to 6-membered carbocycle optionally further substituted with $R^7$. In some embodiments, B is cyclopentyl or cyclohexyl, optionally further substituted with $R^7$. In some embodiments, B is a 5- to 6-membered carbocycle optionally substituted with one or more groups selected from halogen, —CN, —OR$^8$, —SR$^8$, —NR$^9$R$^{10}$, —NO$_2$, —C(O)R$^8$, —C(O)OR$^8$, —C(O)NR$^9$R$^{10}$, —C(O)NR$^8$S(O)$_2$R$^9$, —OC(O)R$^8$, —OC(O)NR$^9$R$^{10}$, —NR$^8$C(O)R$^9$, —NR$^8$C(O)NR$^9$R$^{10}$, —S(O)R$^8$, —S(O)$_2$R$^8$, $C_3$-$C_6$ cycloalkyl and $C_1$-$C_6$ alkyl optionally substituted by halogen. In some embodiments, B is a 5- to 6-membered carbocycle optionally substituted with halogen.

In some embodiments of a compound of Formula (I), (II), or (III), B is a 5- to 6-membered heterocycle optionally further substituted with $R^7$. In some embodiments, B is a fully saturated 5- to 6-membered heterocycle optionally further substituted with $R^7$. In some embodiments, B is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, thiomorpholinyl optionally further substituted with $R^7$. In some embodiments, B is a 5- to 6-membered heterocycle optionally substituted with one or more groups selected from halogen, —CN, —OR$^8$, —SR$^8$, —NR$^9$R$^{10}$, —NO$_2$, —C(O)R$^8$, —C(O)OR$^8$, —C(O)NR$^9$R$^{10}$, —C(O)NR$^8$S(O)$_2$R$^9$, —OC(O)R$^8$, —OC(O)NR$^9$R$^{10}$, —NR$^8$C(O)R$^9$, —NR$^8$C(O)NR$^9$R$^{10}$, —S(O)R$^8$, —S(O)$_2$R$^8$, $C_3$-$C_6$ cycloalkyl and $C_1$-$C_6$ alkyl optionally substituted by halogen. In some embodiments, B is a 5- to 6-membered heterocycle optionally substituted with halogen.

In some embodiments of a compound of Formula (I), (II), or (III), B is a 9- to 10-membered heteroaryl optionally further substituted with $R^7$. In some embodiments, B is selected from the group consisting of pyridyl, quinolinyl, isoquinolinyl, quinoxalinyl, cinnolinyl, quinazolinyl, naphthyridinyl, benzoxazolyl, benzothiazolyl, benzoimidazoyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridazinyl, pyrimidinyl, pyrazinyl, triazinyl, tetrazinyl, indolyl, isoindolyl, indazolyl, benzotriazolyl, benzofuranyl, benzoisoxazolyl, benzoxadiazolyl, benzothiophenyl, benzoisothiazolyl, benzothiadiazolyl, pyrrolopyridinyl, pyrazolopyridinyl, imidazopyridinyl, triazolopyridinyl, furopyridinyl, oxazolopyridinyl, isoxazolopyridinyl, oxadiazolopyridinyl, thienopyridinyl, thiazolopyridinyl, isothiazolopyridinyl, thiadiazolopyridinyl, thienopyridinyl, phthalazinyl, pyrazolothiazolyl, pyrazolothiazolyl and imidazothiazolyl, each optionally substituted with $R^7$. In one aspect, such groups are unsubstituted. In another aspect, such groups are substituted with 1-3 $R^7$, which may be the same or different. In some embodiments, B is a 9- to 10-membered heteroaryl optionally substituted with one or more groups selected from halogen, —CN, —OR$^8$, —SR$^8$, —NR$^9$R$^{10}$, —NO$_2$, —C(O)R$^8$, —C(O)OR$^8$, —C(O)NR$^9$R$^{10}$, —C(O)NR$^8$S(O)$_2$R$^9$, —OC(O)R$^8$, —OC(O)NR$^9$R$^{10}$, —NR$^8$C(O)R$^9$, —NR$^8$C(O)NR$^9$R$^{10}$, —S(O)R$^8$, —S(O)$_2$R$^8$, C$_3$-C$_6$ cycloalkyl and C$_1$-C$_6$ alkyl optionally substituted by halogen. In some embodiments, B is a 9- to 10-membered heteroaryl optionally substituted with halogen.

In some embodiments of a compound of Formula (I), (II), or (III), R$^7$ is independently selected from the group consisting of halogen, —CN, —OR$^8$, —SR$^8$, —NR$^9$R$^{10}$, —NO$_2$, —C(O)R$^8$, —C(O)OR$^8$, —C(O)NR$^9$R$^{10}$, —C(O)NR$^8$S(O)$_2$R$^9$, —OC(O)R$^8$, —OC(O)NR$^9$R$^{10}$, —NR$^8$C(O)R$^9$, —NR$^8$C(O)NR$^9$R$^{10}$, —S(O)R$^8$, —S(O)$_2$R$^8$, C$_3$-C$_6$ cycloalkyl and C$_1$-C$_6$ alkyl optionally substituted by halogen. In some embodiments, R$^7$ is halogen.

In some embodiments of a compound of Formula (I), (II), or (III), B is selected from the group consisting of:

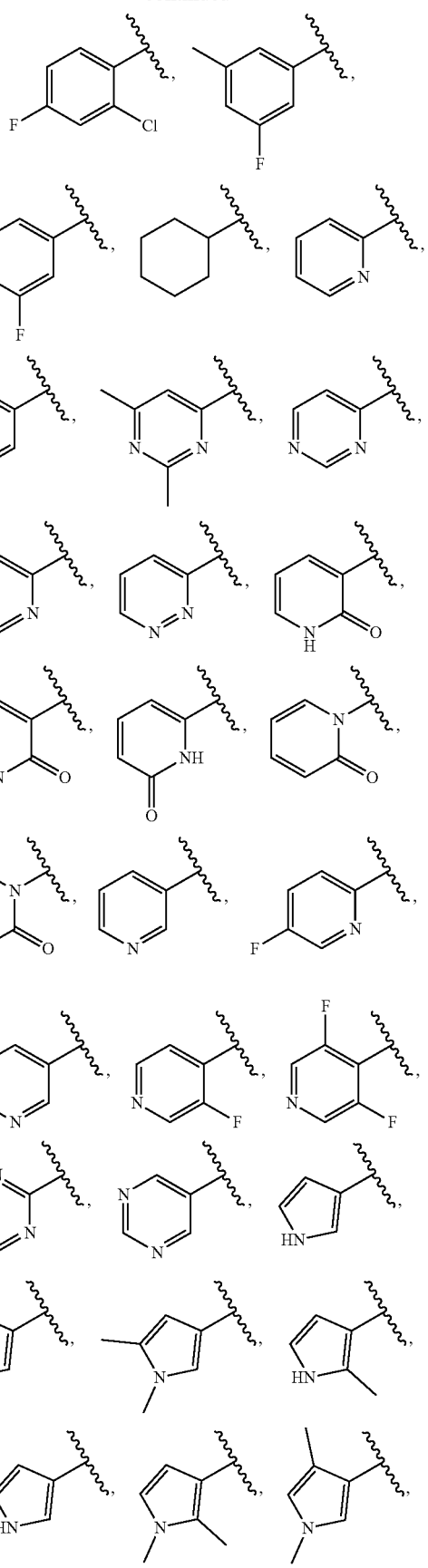

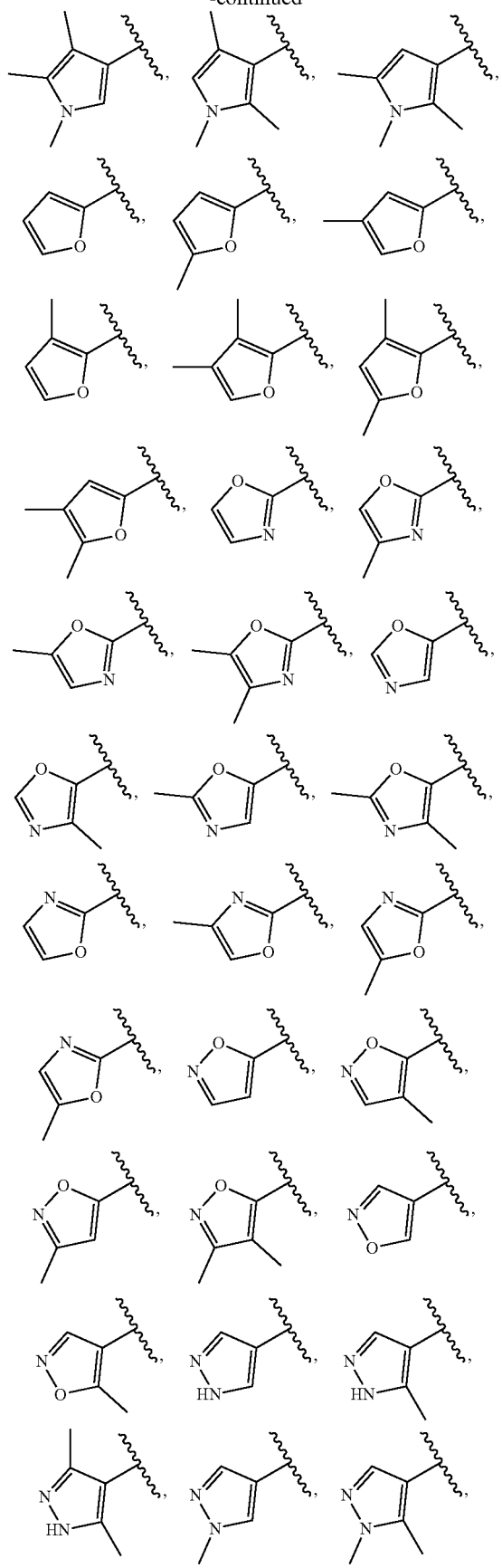
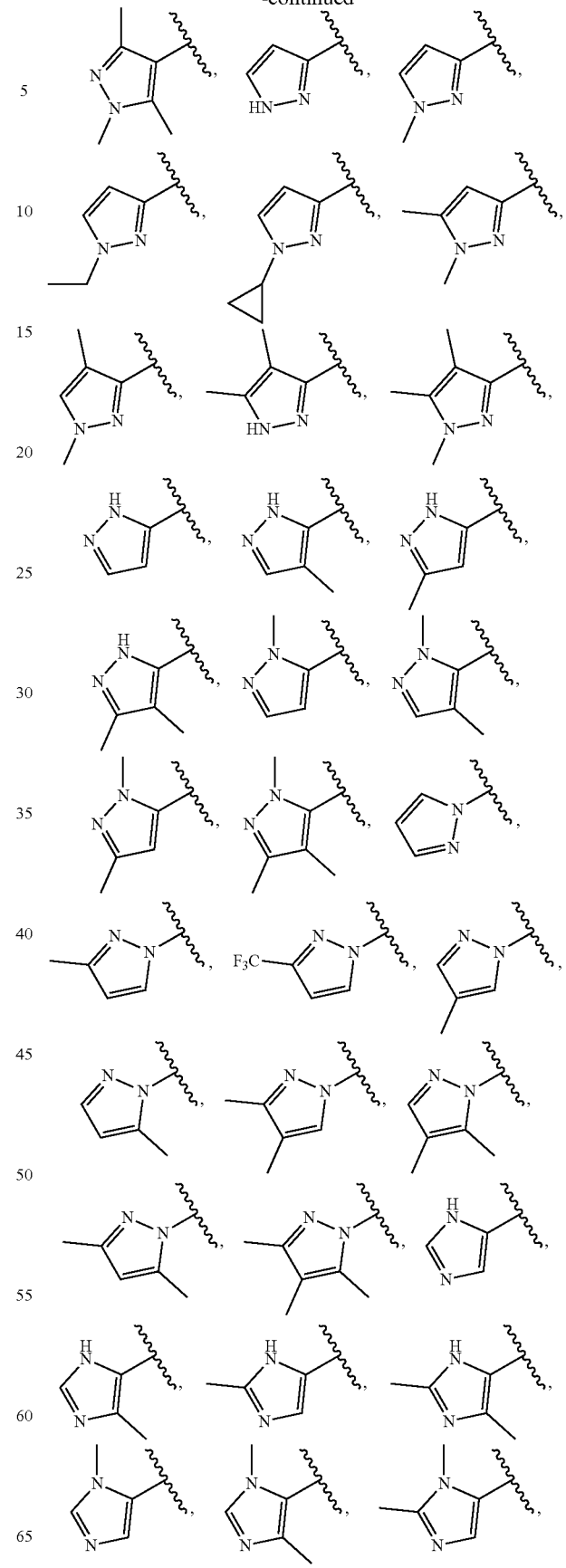

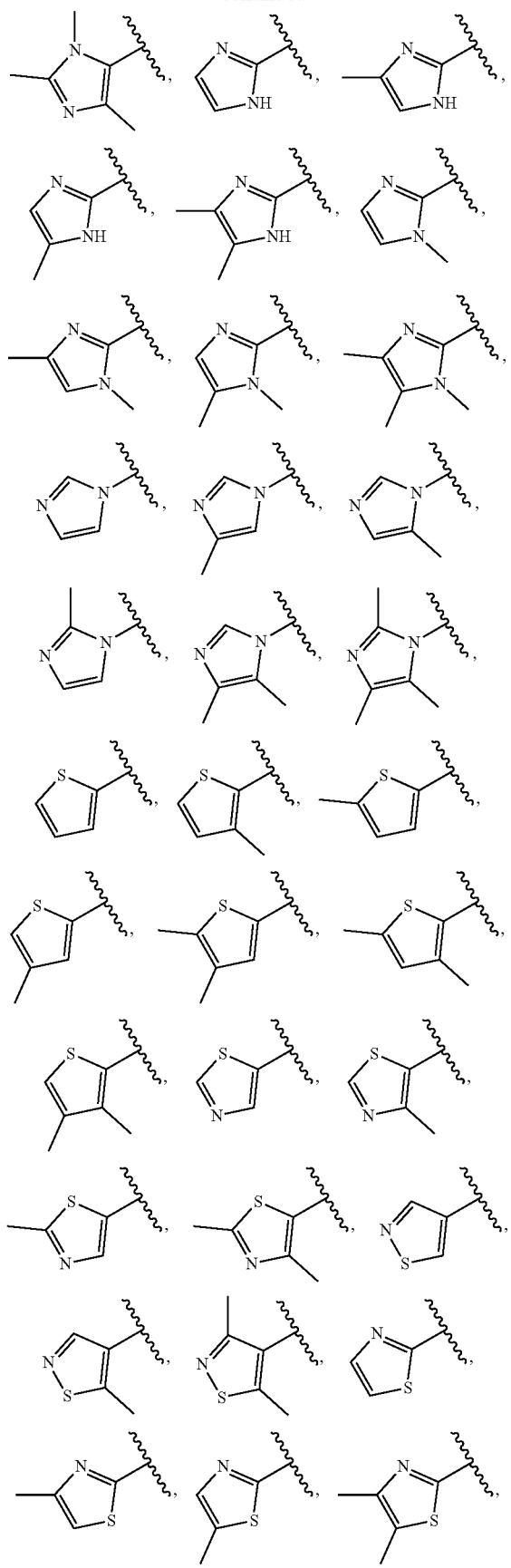
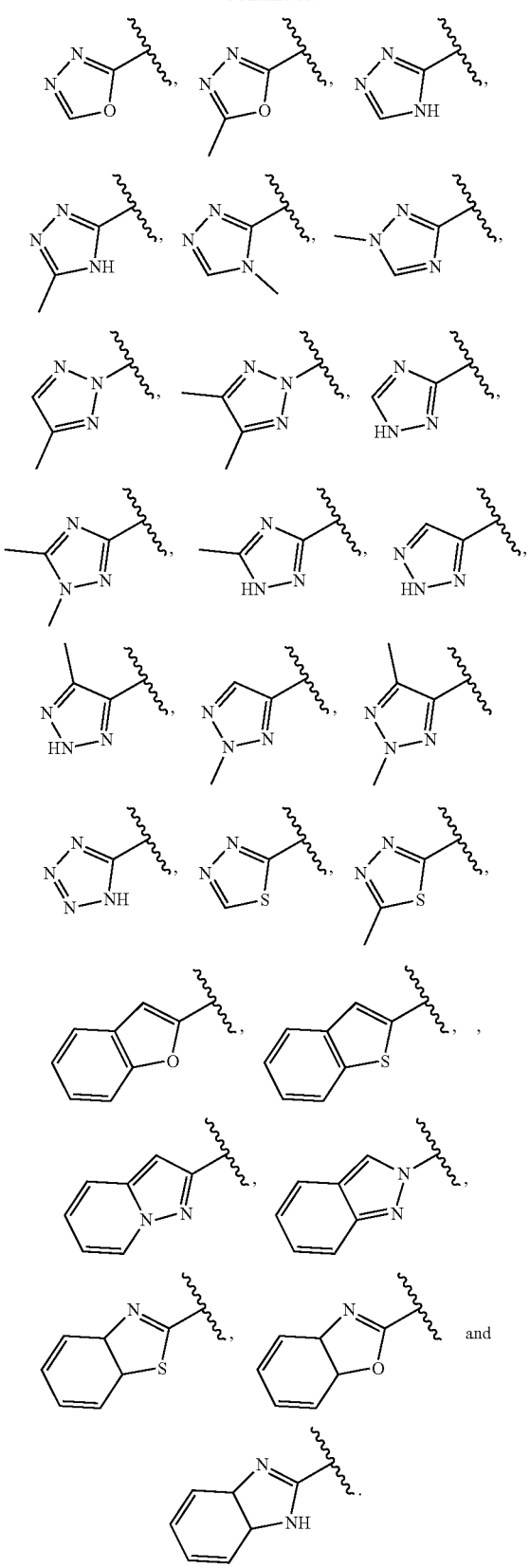
In some embodiments of a compound of Formula (I), (II), or (III), B is selected from the group consisting of:

In some embodiments of a compound of Formula (I), (II), or (III), B is selected from the group consisting of:
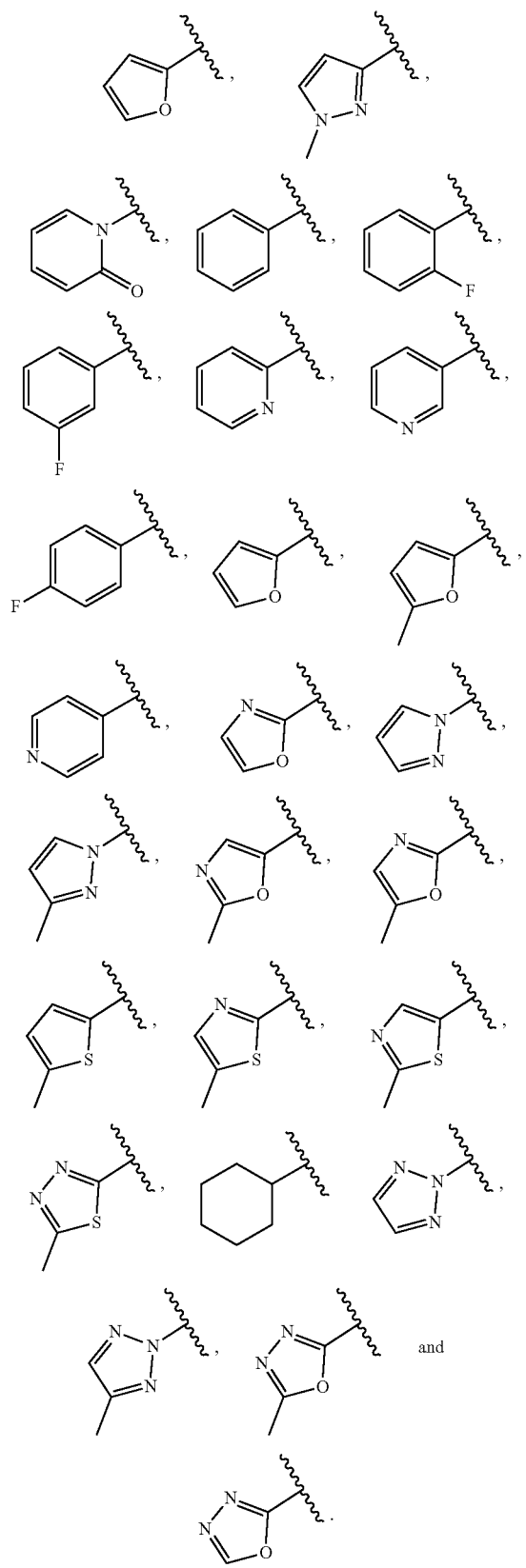
In some embodiments of a compound of Formula (I), (II), or (III), B is selected from
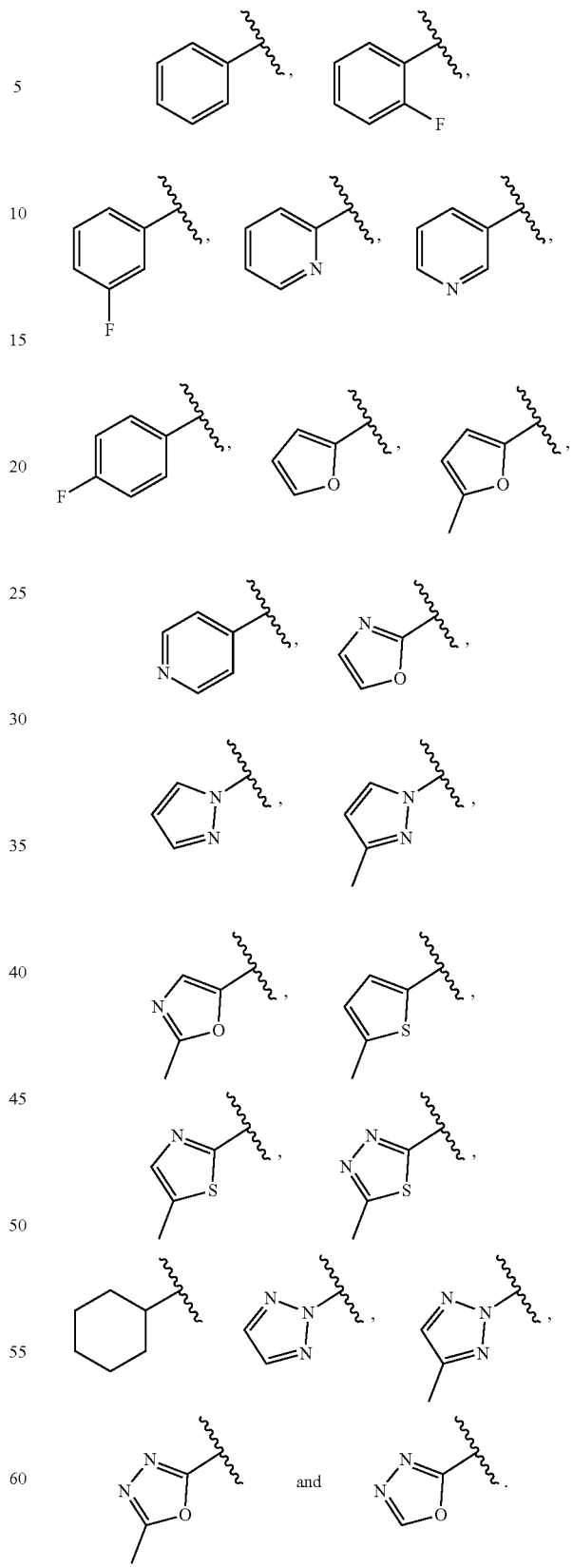

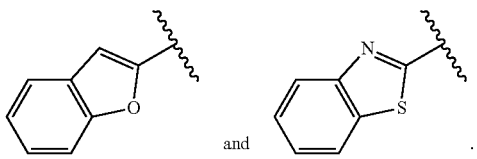 [SMILES: *c1cc2ccccc2o1 ; *c1nc2ccccc2s1]

and

In some embodiments of a compound of Formula (I), (II), or (III), A is $C_6$-$C_{12}$ aryl or 5- to 10-membered heteroaryl, each optionally further substituted with $R^6$, and B is phenyl or 5- to 6-membered heteroaryl, each optionally further substituted with $R^7$. In some embodiments, A is $C_6$-$C_{12}$ aryl, optionally further substituted with $R^6$, and B is phenyl, optionally further substituted with $R^7$. In some embodiments, A is $C_6$-$C_{12}$ aryl, optionally further substituted with $R^6$, and B is 5- to 6-membered heteroaryl, optionally further substituted with $R^7$. In some embodiments, A is 5- to 10-membered heteroaryl, optionally further substituted with $R^6$, and B is phenyl, optionally further substituted with $R^7$. In some embodiments, A is 5- to 10-membered heteroaryl, optionally further substituted with $R^6$, and B is 5- to 6-membered heteroaryl, optionally further substituted with $R^7$.

In some embodiments of a compound of Formula (I), (II), or (III), A is 9- to 10-membered carbocycle or 9- to 10-membered heterocycle, each optionally further substituted with $R^6$, and B is phenyl, 5- to 6-membered heteroaryl, 5- to 6-membered carbocycle, or 5- to 6-membered heterocycle, each optionally further substituted with $R^7$. In some embodiments, A is 9- to 10-membered carbocycle, optionally further substituted with $R^6$, and B is phenyl, optionally further substituted with $R^7$. In some embodiments, A is 9- to 10-membered carbocycle, optionally further substituted with $R^6$, and B is 5- to 6-membered heteroaryl, optionally further substituted with $R^7$. In some embodiments, A is 9- to 10-membered carbocycle, optionally further substituted with $R^6$, and B is 5- to 6-membered carbocycle, optionally further substituted with $R^7$. In some embodiments, A is 9- to 10-membered carbocycle, optionally further substituted with $R^6$, and B is 5- to 6-membered heterocycle, optionally further substituted with $R^7$.

In some embodiments of a compound of Formula (I), (II), or (III), A is $C_6$-$C_{12}$ aryl or 5- to 10-membered heteroaryl, each optionally further substituted with $R^6$, and B is 5- to 6-membered carbocycle or 5- to 6-membered heterocycle, each optionally further substituted with $R^7$. In some embodiments, A is $C_6$-$C_{12}$ aryl, optionally further substituted with $R^6$, and B is 5- to 6-membered carbocycle, optionally further substituted with $R^7$. In some embodiments, A is $C_6$-$C_{12}$ aryl, optionally further substituted with $R^6$, and B is 5- to 6-membered heterocycle, optionally further substituted with $R^7$. In some embodiments, A is 5- to 10-membered heteroaryl, optionally further substituted with $R^6$, and B is 5- to 6-membered carbocycle, optionally further substituted with $R^7$. In some embodiments, A is 5- to 10-membered heteroaryl, optionally further substituted with $R^6$, and B is 5- to 6-membered heterocycle, optionally further substituted with $R^7$. In some embodiments, when A is phenyl or pyridyl, either of which is optionally further substituted with $R^6$, B is not a saturated heterocycle.

In some embodiments of a compound of Formula (I), (II), or (III), A is $C_6$-$C_{12}$ aryl or 5- to 10-membered heteroaryl, each optionally further substituted with $R^6$, and B is 9- to 10-membered carbocycle, optionally further substituted with $R^7$. In some embodiments, A is $C_6$-$C_{12}$ aryl, optionally further substituted with $R^6$, and B is 9- to 10-membered carbocycle, optionally further substituted with $R^7$. In some embodiments, A is 5- to 10-membered heteroaryl, optionally further substituted with $R^6$, and B is 9- to 10-membered carbocycle, optionally further substituted with $R^7$.

In some embodiments of a compound of Formula (I), (II), or (III), A is

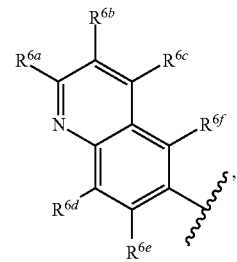

wherein $R^{6a}$, $R^{6b}$, $R^{6c}$, $R^{6d}$, $R^{6e}$, and $R^{6f}$ are each independently H, $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$NO_2$, —C=NH($OR^8$), —C(O)$R^8$, —OC(O)$R^8$, —C(O)$OR^8$, —C(O)$NR^9R^{10}$, —OC(O)$NR^9R^{10}$, —$NR^8$C(O)$R^9$, —$NR^8$C(O)$OR^9$, —$NR^8$C(O)$NR^9R^{10}$, —S(O)$R^8$, —S(O)$_2R^8$, —$NR^8$S(O)$R^9$, —C(O)$NR^8$S(O)$R^9$, —$NR^8$S(O)$_2R^9$, —C(O)$NR^8$S(O)$_2R^9$, —S(O)$NR^9R^{10}$, —S(O)$_2NR^9R^{10}$, —P(O)($OR^9$)($OR^{10}$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)$OR^8$, —($C_1$-$C_3$ alkylene)$SR^8$, —($C_1$-$C_3$ alkylene)$NR^9R^{10}$, —($C_1$-$C_3$ alkylene)$CF_3$, —($C_1$-$C_3$ alkylene)$NO_2$, —C=NH($OR^8$), —($C_1$-$C_3$ alkylene)C(O)$R^8$, —($C_1$-$C_3$ alkylene)OC(O)$R^8$, —($C_1$-$C_3$ alkylene)C(O)$OR^8$, —($C_1$-$C_3$ alkylene)C(O)$NR^9R^{10}$, —($C_1$-$C_3$ alkylene)OC(O)$NR^9R^{10}$, —($C_1$-$C_3$ alkylene)$NR^8$C(O)$R^9$, —($C_1$-$C_3$ alkylene)$NR^8$C(O)$OR^9$, —($C_1$-$C_3$ alkylene)$NR^8$C(O)$NR^9R^{10}$, —($C_1$-$C_3$ alkylene)S(O)$R^8$, —($C_1$-$C_3$ alkylene)S(O)$_2R^8$, —($C_1$-$C_3$ alkylene)$NR^8$S(O)$R^9$, —C(O)($C_1$-$C_3$ alkylene)$NR^8$S(O)$R^9$, —($C_1$-$C_3$ alkylene)$NR^8$S(O)$_2R^9$, —($C_1$-$C_3$ alkylene)C(O)$NR^8$S(O)$_2R^9$, —($C_1$-$C_3$ alkylene)S(O)$NR^9R^{10}$, —($C_1$-$C_3$ alkylene)S(O)$_2NR^9R^{10}$, —($C_1$-$C_3$ alkylene)P(O)($OR^9$)($OR^{10}$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or —($C_1$-$C_3$ alkylene)($C_6$-$C_{14}$ aryl), wherein each $R^{6a}$, $R^{6b}$, $R^{6c}$, $R^{6d}$, $R^{6e}$, and $R^{6f}$ is independently optionally substituted by halogen, oxo, —$OR^{11}$, —$NR^{11}R^{12}$, —C(O)$R^{11}$, —CN, —S(O)$R^{11}$, —S(O)$_2R^{11}$, —P(O)($OR^{11}$)($OR^{12}$), —($C_1$-$C_3$ alkylene)$OR^{11}$, —($C_1$-$C_3$ alkylene)$NR^{11}R^{12}$, —($C_1$-$C_3$ alkylene)C(O)$R^{11}$, —($C_1$-$C_3$ alkylene)S(O)$R^{11}$, —($C_1$-$C_3$ alkylene)S(O)$_2R^{11}$, —($C_1$-$C_3$ alkylene)P(O)($OR^{11}$)($OR^{12}$), $C_3$-$C_8$ cycloalkyl, or $C_1$-$C_6$ alkyl optionally substituted by oxo, —OH or halogen.

In some embodiments of a compound of Formula (I), (II), or (III), A is

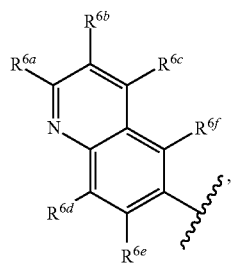

wherein $R^{6a}$, $R^{6b}$, $R^{6c}$, $R^{6d}$, $R^{6e}$, and $R^{6f}$ are each independently H, $C_1$-$C_6$ alkyl, halogen, —CN, or —$OC_1$-$C_6$ alkyl. In some embodiments, $R^{6a}$, $R^{6b}$, $R^{6c}$, $R^{6d}$, $R^{6e}$, and $R^{6f}$ are each H. In some embodiments, one of $R^{6a}$, $R^{6b}$, $R^{6c}$, $R^{6d}$, $R^{6e}$, and $R^{6f}$ is Cl, F, Br, or I. In some embodiments, one of $R^{6a}$, $R^{6b}$, $R^{6c}$, $R^{6d}$, $R^{6e}$, and $R^{6f}$ is Cl. In some embodiments, one of $R^{6a}$, $R^{6b}$, $R^{6c}$, $R^{6d}$, $R^{6e}$, and $R^{6f}$ is halogen and the others are each H. In some embodiments, one of $R^{6a}$, $R^{6b}$, $R^{6c}$, $R^{6d}$, $R^{6e}$, and $R^{6f}$ is halogen and one of $R^{6a}$, $R^{6b}$, $R^{6c}$, $R^{6d}$, $R^{6e}$, and $R^{6f}$ is $C_1$-$C_6$ alkyl. In some embodiments, one of $R^{6a}$, $R^{6b}$, $R^{6c}$, $R^{6d}$, $R^{6e}$, and $R^{6f}$ is Cl and one of $R^{6a}$, $R^{6b}$, $R^{6c}$, $R^{6d}$, $R^{6e}$, and $R^{6f}$ is methyl. In some embodiments, $R^{6a}$ is $C_1$-$C_6$ alkyl. In some embodiments, $R^{6b}$ is $C_1$-$C_6$ alkyl. In some embodiments, $R^{6c}$ is $C_1$-$C_6$ alkyl. In some embodiments, $R^{6d}$ is $C_1$-$C_6$ alkyl. In some embodiments, $R^{6e}$ is $C_1$-$C_6$ alkyl. In some embodiments, $R^{6f}$ is $C_1$-$C_6$ alkyl. In some embodiments, $R^{6a}$ is methyl, ethyl, n-propyl, isopropyl, n-butyl, isobutyl, secbutyl, or tertbutyl. In some embodiments, $R^{6b}$ is methyl, ethyl, n-propyl, isopropyl, n-butyl, isobutyl, secbutyl, or tertbutyl. In some embodiments, $R^{6c}$ is methyl, ethyl, n-propyl, isopropyl, n-butyl, isobutyl, secbutyl, or tertbutyl. In some embodiments, $R^{6d}$ is methyl, ethyl, n-propyl, isopropyl, n-butyl, isobutyl, secbutyl, or tertbutyl. In some embodiments, $R^{6e}$ is methyl, ethyl, n-propyl, isopropyl, n-butyl, isobutyl, secbutyl, or tertbutyl. In some embodiments, $R^{6f}$ is methyl, ethyl, n-propyl, isopropyl, n-butyl, isobutyl, secbutyl, or tertbutyl. In some embodiments, $R^{6a}$ is $C_1$-$C_6$ alkyl and $R^{6b}$ is halogen. In some embodiments, $R^{6a}$ is $C_1$-$C_6$ alkyl and $R^{6c}$ is halogen. In some embodiments, $R^{6a}$ is $C_1$-$C_6$ alkyl and $R^{6d}$ is halogen. In some embodiments, $R^{6a}$ is $C_1$-$C_6$ alkyl and $R^{6e}$ is halogen. In some embodiments, $R^{6a}$ is $C_1$-$C_6$ alkyl and $R^{6f}$ is halogen. In some embodiments, $R^{6b}$ is $C_1$-$C_6$ alkyl and $R^{6a}$ is halogen. In some embodiments, $R^{6b}$ is $C_1$-$C_6$ alkyl and $R^{6c}$ is halogen. In some embodiments, $R^{6b}$ is $C_1$-$C_6$ alkyl and $R^{6d}$ is halogen. In some embodiments, $R^{6b}$ is $C_1$-$C_6$ alkyl and $R^{6e}$ is halogen. In some embodiments, $R^{6b}$ is $C_1$-$C_6$ alkyl and $R^{6f}$ is halogen. In some embodiments, $R^{6c}$ is $C_1$-$C_6$ alkyl and $R^{6a}$ is halogen. In some embodiments, $R^{6c}$ is $C_1$-$C_6$ alkyl and $R^{6b}$ is halogen. In some embodiments, $R^{6c}$ is $C_1$-$C_6$ alkyl and $R^{6d}$ is halogen. In some embodiments, $R^{6c}$ is $C_1$-$C_6$ alkyl and $R^{6e}$ is halogen. In some embodiments, $R^{6c}$ is $C_1$-$C_6$ alkyl and $R^{6f}$ is halogen. In some embodiments, $R^{6d}$ is $C_1$-$C_6$ alkyl and $R^{6a}$ is halogen. In some embodiments, $R^{6d}$ is $C_1$-$C_6$ alkyl and $R^{6b}$ is halogen. In some embodiments, $R^{6d}$ is $C_1$-$C_6$ alkyl and $R^{6c}$ is halogen. In some embodiments, $R^{6d}$ is $C_1$-$C_6$ alkyl and $R^{6e}$ is halogen. In some embodiments, $R^{6d}$ is $C_1$-$C_6$ alkyl and $R^{6f}$ is halogen. In some embodiments, $R^{6e}$ is $C_1$-$C_6$ alkyl and $R^{6a}$ is halogen. In some embodiments, $R^{6e}$ is $C_1$-$C_6$ alkyl and $R^{6b}$ is halogen. In some embodiments, $R^{6e}$ is $C_1$-$C_6$ alkyl and $R^{6c}$ is halogen. In some embodiments, $R^{6e}$ is $C_1$-$C_6$ alkyl and $R^{6d}$ is halogen. In some embodiments, $R^{6e}$ is $C_1$-$C_6$ alkyl and $R^{6f}$ is halogen. In some embodiments, $R^{6f}$ is $C_1$-$C_6$ alkyl and $R^{6a}$ is halogen. In some embodiments, $R^{6f}$ is $C_1$-$C_6$ alkyl and $R^{6b}$ is halogen. In some embodiments, $R^{6f}$ is $C_1$-$C_6$ alkyl and $R^{6c}$ is halogen. In some embodiments, $R^{6f}$ is $C_1$-$C_6$ alkyl and $R^{6d}$ is halogen. In some embodiments, $R^{6f}$ is $C_1$-$C_6$ alkyl and $R^{6e}$ is halogen. In some embodiments, two of $R^{6a}$, $R^{6b}$, $R^{6c}$, $R^{6d}$, $R^{6e}$, and $R^{6f}$ are halogen. In some embodiments, two of $R^{6a}$, $R^{6b}$, $R^{6c}$, $R^{6d}$, $R^{6e}$, and $R^{6f}$ are $C_1$-$C_6$ alkyl.

In some embodiments of a compound of Formula (I), (II), or (III), A is

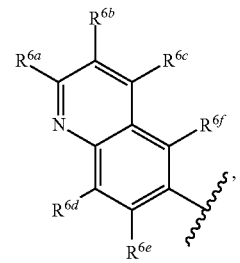

wherein one or two of $R^{6a}$, $R^{6b}$, $R^{6c}$, $R^{6d}$, $R^{6e}$, and $R^{6f}$ are independently selected from the group consisting of $C_1$-$C_6$ alkyl, halogen, —CN, and —$OC_1$-$C_6$ alkyl, and the remainder of $R^{6a}$, $R^{6b}$, $R^{6c}$, $R^{6d}$, $R^{6e}$, and $R^{6f}$ are each H; and B is phenyl, optionally substituted with $R^7$.

In some embodiments of a compound of Formula (I), (II), or (III), A is

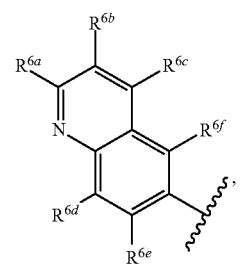

wherein one or two of $R^{6a}$, $R^{6b}$, $R^{6c}$, $R^{6d}$, $R^{6e}$, and $R^{6f}$ are independently selected from the group consisting of $C_1$-$C_6$ alkyl, halogen, —CN, and —$OC_1$-$C_6$ alkyl, and the remainder of $R^{6a}$, $R^{6b}$, $R^{6c}$, $R^{6d}$, $R^{6e}$, and $R^{6f}$ are each H; and B is a 5- to 6-membered carbocycle, optionally substituted with $R^7$.

In some embodiments of a compound of Formula (I), (II), or (III), A is

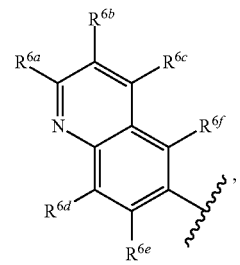

wherein one or two of $R^{6a}$, $R^{6b}$, $R^{6c}$, $R^{6d}$, $R^{6e}$, and $R^{6f}$ are independently selected from the group consisting of $C_1$-$C_6$ alkyl, halogen, —CN, and —$OC_1$-$C_6$ alkyl, and the remainder of $R^{6a}$, $R^{6b}$, $R^{6c}$, $R^{6d}$, $R^{6e}$, and $R^{6f}$ are each H; and B is a 5- to 6-membered heterocycle, optionally substituted with $R^7$.

In some embodiments of a compound of Formula (I), (II), or (III), A is

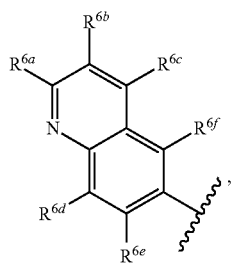

wherein one or two of $R^{6a}$, $R^{6b}$, $R^{6c}$, $R^{6d}$, $R^{6e}$, and $R^{6f}$ are independently selected from the group consisting of $C_1$-$C_6$ alkyl, halogen, —CN, and —O$C_1$-$C_6$ alkyl, and the remainder of $R^{6a}$, $R^{6b}$, $R^{6c}$, $R^{6d}$, $R^{6e}$, and $R^{6f}$ are each H; and B is a 5- to 6-membered heterocycle, optionally substituted with $R^7$.

In some embodiments of a compound of Formula (I), (II), or (III), A is

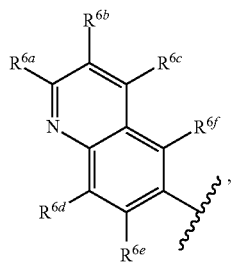

wherein one or two of $R^{6a}$, $R^{6b}$, $R^{6c}$, $R^{6d}$, $R^{6e}$, and $R^{6f}$ are independently selected from the group consisting of $C_1$-$C_6$ alkyl, halogen, —CN, and —O$C_1$-$C_6$ alkyl, and the remainder of $R^{6a}$, $R^{6b}$, $R^{6c}$, $R^{6d}$, $R^{6e}$, and $R^{6f}$ are each H; and B is a 9- to 10-membered heteroaryl, optionally substituted with $R^7$.

In some embodiments of a compound of Formula (I), (II), or (III), A is

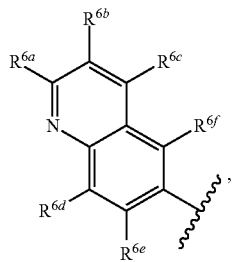

wherein one or two of $R^{6a}$, $R^{6b}$, $R^{6c}$, $R^{6d}$, $R^{6e}$, and $R^{6f}$ are independently selected from the group consisting of $C_1$-$C_6$ alkyl, halogen, —CN, and —O$C_1$-$C_6$ alkyl, and the remainder of $R^{6a}$, $R^{6b}$, $R^{6c}$, $R^{6e}$, and $R^{6f}$ are each H; and B is selected from the group consisting of:

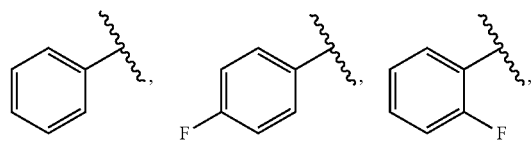

-continued

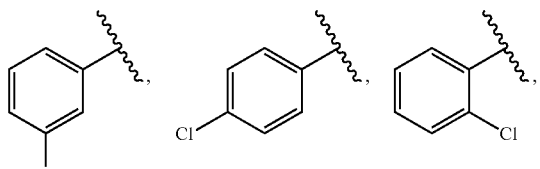

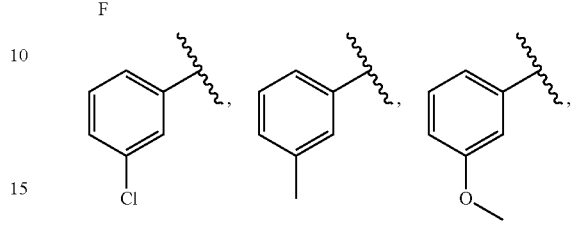

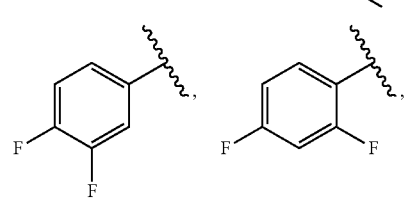

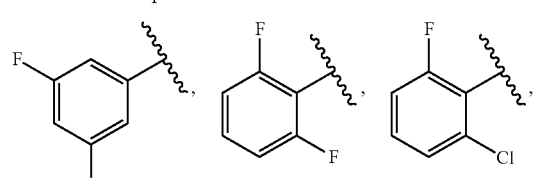

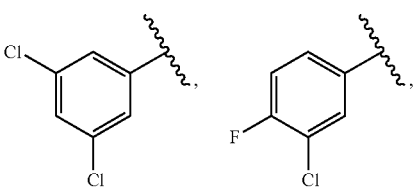

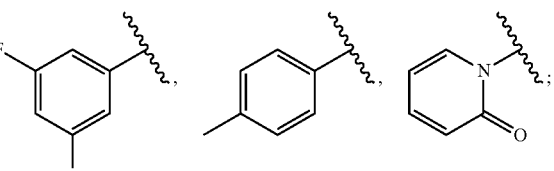

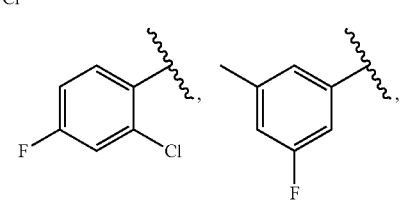

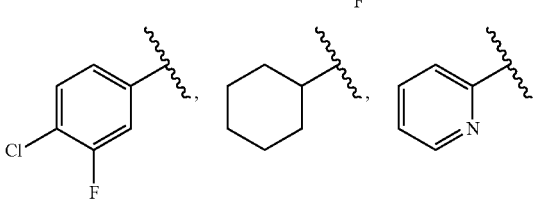

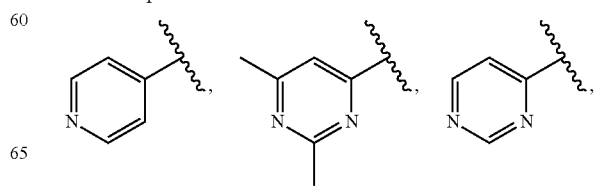

-continued
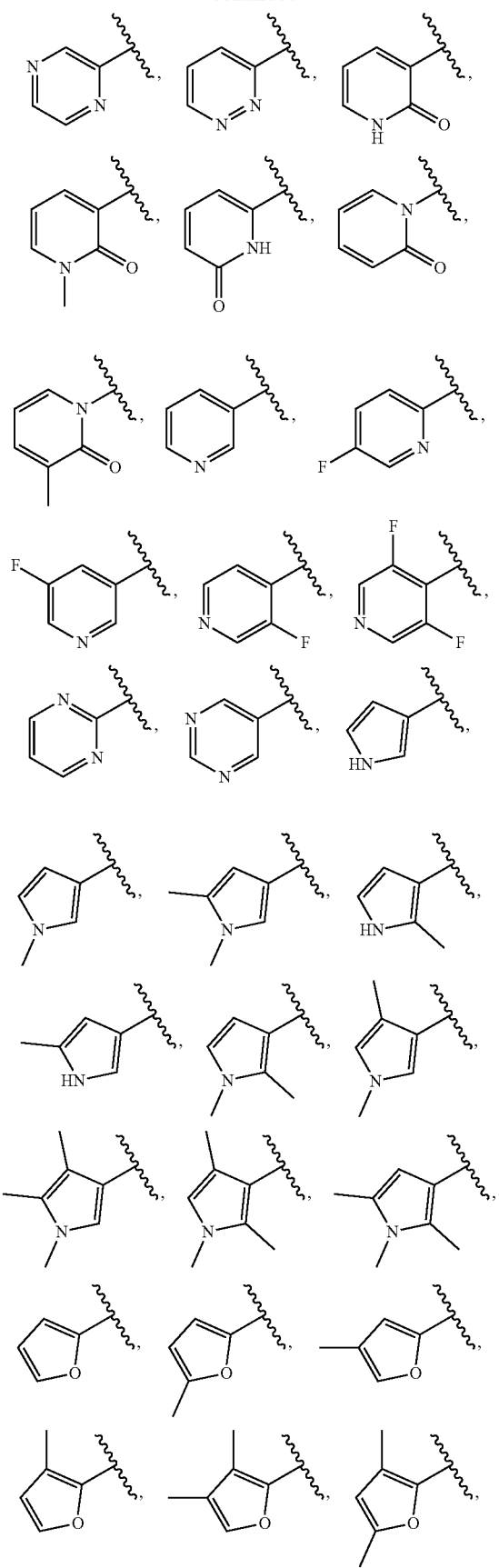
-continued
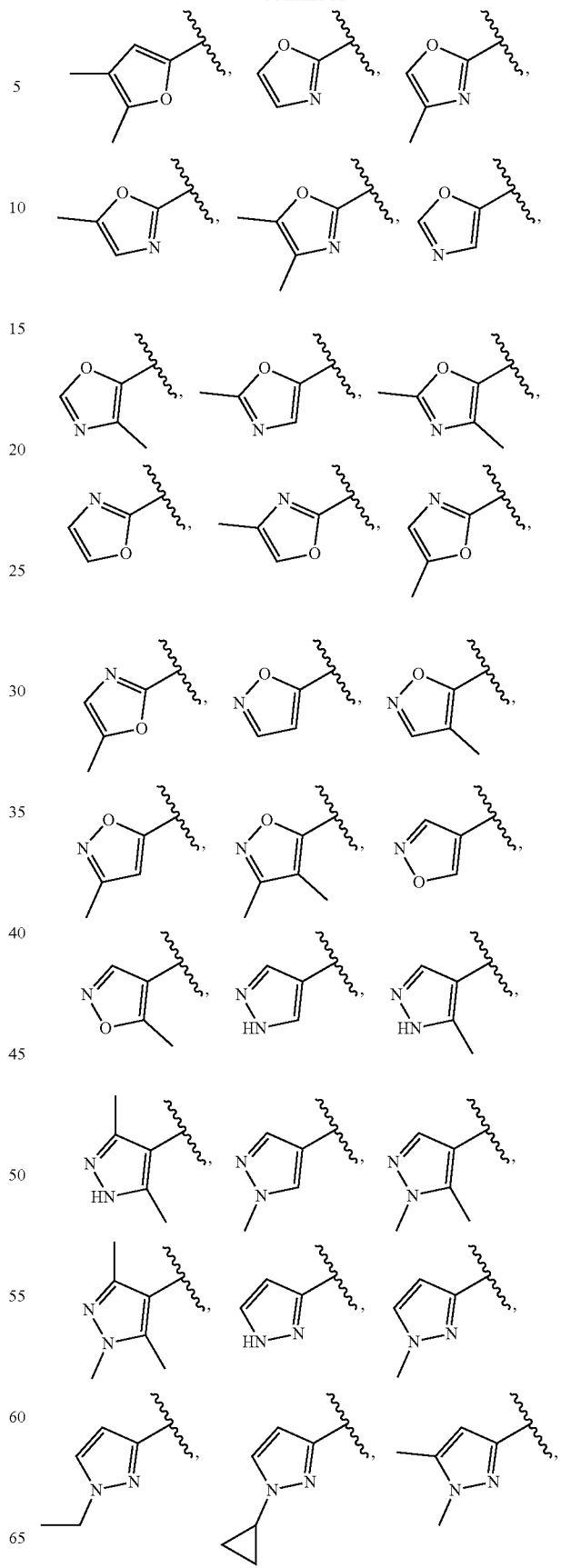

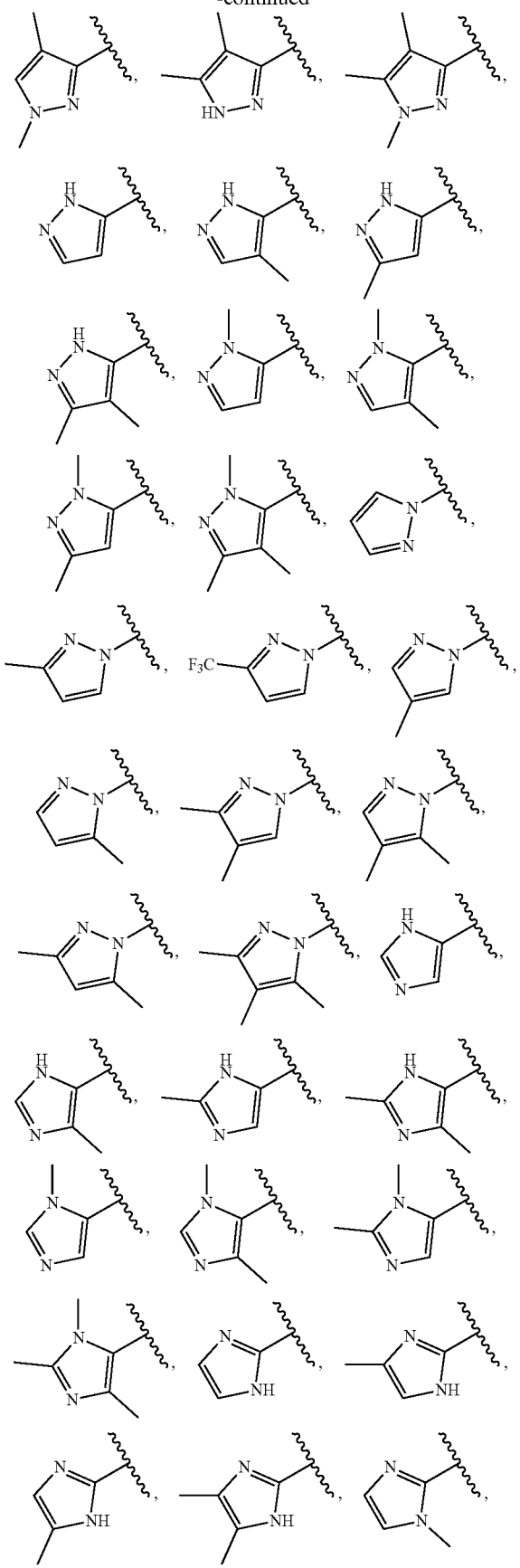
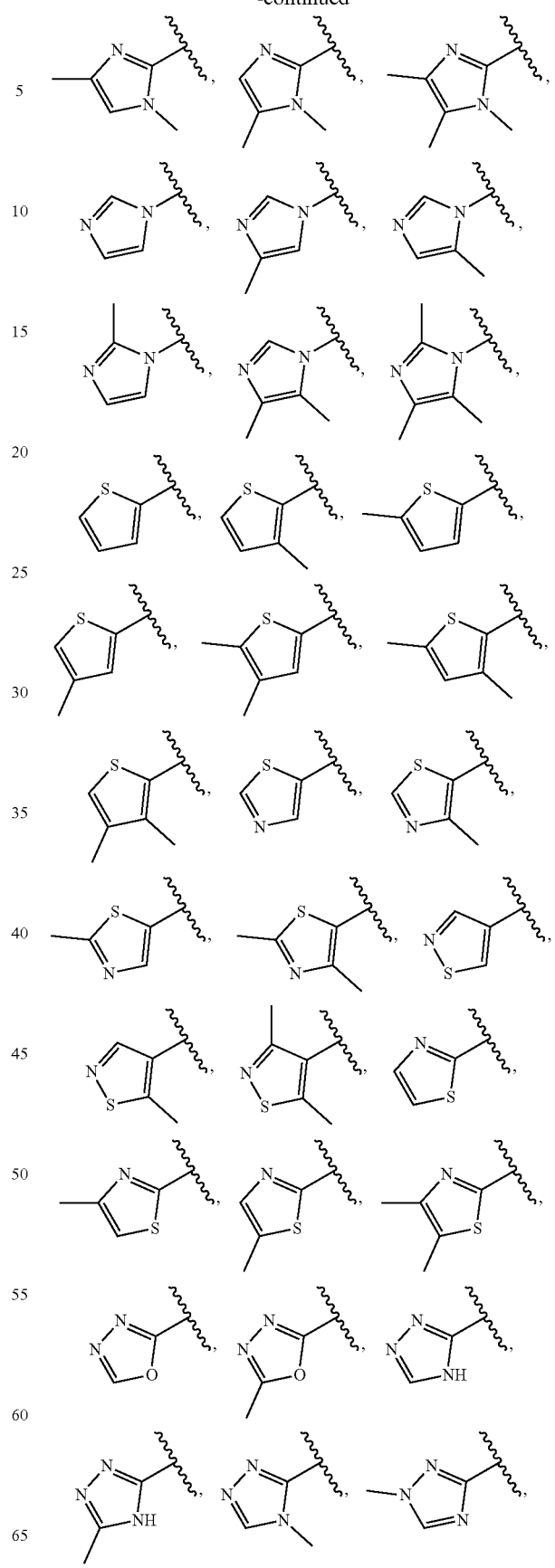

-continued

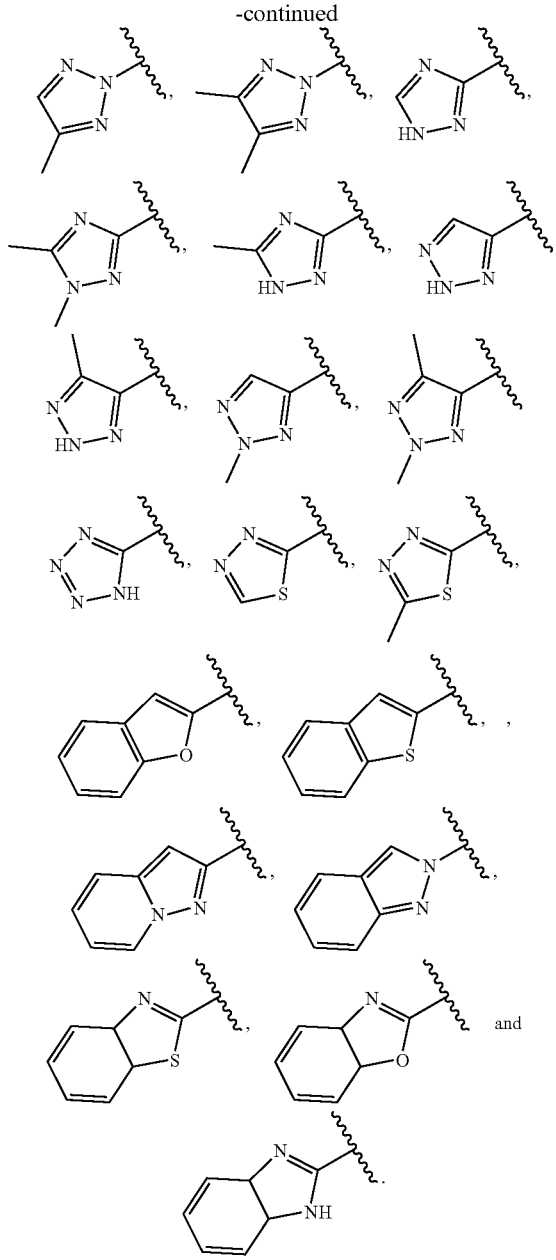

In some embodiments of a compound of Formula (I), (II), or (III), A is

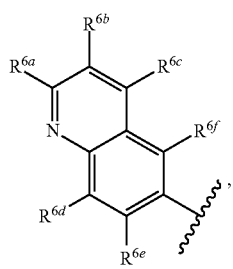

wherein one or two of $R^{6a}$, $R^{6b}$, $R^{6c}$, $R^{6d}$, $R^{6e}$, and $R^{6f}$ are independently selected from the group consisting of $C_1$-$C_6$ alkyl, halogen, —CN, and —$OC_1$-$C_6$ alkyl, and the remainder of $R^{6a}$, $R^{6b}$, $R^{6c}$, $R^{6d}$, $R^{6e}$, and $R^{6f}$ are each H; and B is selected from the group consisting of:

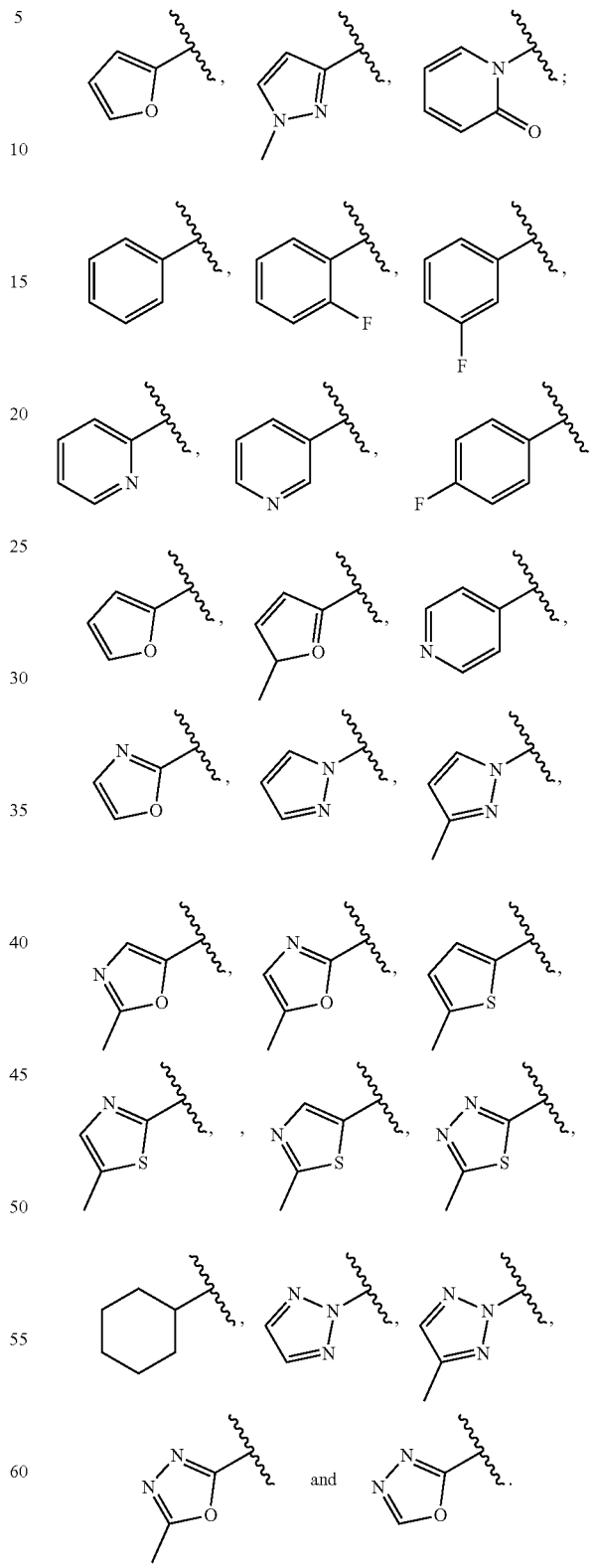

In some embodiments of a compound of Formula (I), (II), or (III), A is

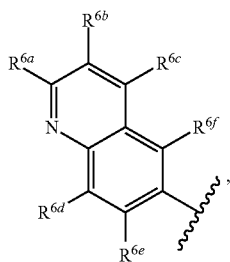

wherein one or two of $R^{6a}$, $R^{6b}$, $R^{6c}$, $R^{6d}$, $R^{6e}$, and $R^{6f}$ are independently selected from the group consisting of $C_1$-$C_6$ alkyl, halogen, —CN, and —$OC_1$-$C_6$ alkyl, and the remainder of $R^{6a}$, $R^{6b}$, $R^{6c}$, $R^{6d}$, $R^{6e}$, and $R^{6f}$ are each H; and B is selected from the group consisting of In some embodiments of a compound of Formula (I), (II), or (III), A is wherein one or two of $R^{6a}$, $R^{6b}$, $R^{6c}$, $R^{6d}$, $R^{6e}$, and $R^{6f}$ are independently selected from the group consisting of $C_1$-$C_6$ alkyl, halogen, —CN, and —$OC_1$-$C_6$ alkyl, and the remainder of $R^{6a}$, $R^{6b}$, $R^{6c}$, $R^{6d}$, $R^{6e}$, and $R^{6f}$ are each H; and B is selected from and In some embodiments of a compound of Formula (I), (II), or (III), A is wherein $R^{6b}$, $R^{6c}$, $R^{6d}$, $R^{6e}$, $R^{6f}$, and $R^{6g}$ are each independently H, $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$NO_2$, —C=NH($OR^8$), —C(O)$R^8$, —OC(O)$R^8$, —C(O)$OR^8$, —C(O)$NR^9R^{10}$, —OC(O)$NR^9R^{10}$, —$NR^8$C(O)$R^9$, —$NR^8$C(O)$OR^9$, —$NR^8$C(O)$NR^9R^{10}$, —S(O)$R^8$, —S(O)$_2R^8$, —$NR^8$S(O)$R^9$, —C(O)$NR^8$S(O)$R^9$, —$NR^8$S(O)$_2R^9$, —C(O)$NR^8$S (O)$_2$R$^9$, —S(O)NR$^9$R$^{10}$, —S(O)$_2$NR$^9$R$^{10}$, —P(O)(OR$^9$)(OR$^{10}$), C$_3$-C$_6$ cycloalkyl, 3-12-membered heterocyclyl, 5- to 10-membered heteroaryl, C$_6$-C$_{14}$ aryl, —(C$_1$-C$_3$ alkylene)CN, —(C$_1$-C$_3$ alkylene)OR$^8$, —(C$_1$-C$_3$ alkylene)SR$^8$, —(C$_1$-C$_3$ alkylene)NR$^9$R$^{10}$, —(C$_1$-C$_3$ alkylene)CF$_3$, —(C$_1$-C$_3$ alkylene)NO$_2$, —C=NH(OR$^8$), —(C$_1$-C$_3$ alkylene)C(O)R$^8$, —(C$_1$-C$_3$ alkylene)OC(O)R$^8$, —(C$_1$-C$_3$ alkylene)C(O)OR$^8$, —(C$_1$-C$_3$ alkylene)C(O)NR$^9$R$^{10}$, —(C$_1$-C$_3$ alkylene)OC(O)NR$^9$R$^{10}$, —(C$_1$-C$_3$ alkylene)NR$^8$C(O)R$^9$, —(C$_1$-C$_3$ alkylene)NR$^8$C(O)OR$^9$, —(C$_1$-C$_3$ alkylene)NR$^8$C(O)NR$^9$R$^{10}$, —(C$_1$-C$_3$ alkylene)S(O)R$^8$, —(C$_1$-C$_3$ alkylene)S(O)$_2$R$^8$, —(C$_1$-C$_3$ alkylene)NR$^8$S(O)R$^9$, —C(O)(C$_1$-C$_3$ alkylene)NR$^8$S(O)R$^9$, —(C$_1$-C$_3$ alkylene)NR$^8$S(O)$_2$R$^9$, —(C$_1$-C$_3$ alkylene)C(O)NR$^8$S(O)$_2$R$^9$, —(C$_1$-C$_3$ alkylene)S(O)NR$^9$R$^{10}$, —(C$_1$-C$_3$ alkylene)S(O)$_2$NR$^9$R$^{10}$, —(C$_1$-C$_3$ alkylene)P(O)(OR$^9$)(OR$^{10}$), —(C$_1$-C$_3$ alkylene)(C$_3$-C$_6$ cycloalkyl), —(C$_1$-C$_3$ alkylene)(3-12-membered heterocyclyl), —(C$_1$-C$_3$ alkylene)(5-10-membered heteroaryl) or —(C$_1$-C$_3$ alkylene)(C$_6$-C$_{14}$ aryl), wherein each R$^{6b}$, R$^{6c}$, R$^{6d}$, R$^{6e}$, R$^{6f}$, and R$^{6g}$ is independently optionally substituted by halogen, oxo, —OR$^{11}$, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —(C$_1$-C$_3$ alkylene)OR$^{11}$, —(C$_1$-C$_3$ alkylene)NR$^{11}$R$^{12}$, —(C$_1$-C$_3$ alkylene)C(O)R$^{11}$, —(C$_1$-C$_3$ alkylene)S(O)R$^{11}$, —(C$_1$-C$_3$ alkylene)S(O)$_2$R$^{11}$, —(C$_1$-C$_3$ alkylene)P(O)(OR$^{11}$)(OR$^{12}$), C$_3$-C$_8$ cycloalkyl, or C$_1$-C$_6$ alkyl optionally substituted by oxo, —OH or halogen.

In some embodiments of a compound of Formula (I), (II), or (III), A is

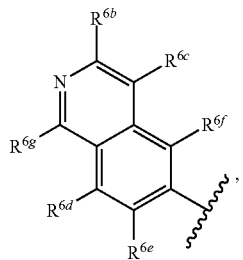

wherein R$^{6b}$, R$^{6c}$, R$^{6d}$, R$^{6e}$, R$^{6f}$, and R$^{6g}$ are each independently H, C$_1$-C$_6$ alkyl, halogen, —CN, or —OC$_1$-C$_6$ alkyl. In some embodiments, R$^{6b}$, R$^{6c}$, R$^{6d}$, R$^{6e}$, R$^{6f}$, and R$^{6g}$ are each H. In some embodiments, one of R$^{6b}$, R$^{6c}$, R$^{6d}$, R$^{6e}$, R$^{6f}$, and R$^{6g}$ is Cl, F, Br, or I. In some embodiments, one of R$^{6b}$, R$^{6c}$, R$^{6d}$, R$^{6e}$, R$^{6f}$, and R$^{6g}$ is Cl. In some embodiments, one of R$^{6b}$, R$^{6c}$, R$^{6d}$, R$^{6e}$, R$^{6f}$, and R$^{6g}$ is halogen and the others are each H. In some embodiments, one of R$^{6b}$, R$^{6c}$, R$^{6d}$, R$^{6e}$, R$^{6f}$, and R$^{6g}$ is halogen and one of R$^{6b}$, R$^{6c}$, R$^{6d}$, R$^{6e}$, R$^{6f}$, and R$^{6g}$ is C$_1$-C$_6$ alkyl. In some embodiments, one of R$^{6b}$, R$^{6c}$, R$^{6d}$, R$^{6e}$, R$^{6f}$, and R$^{6g}$ is Cl and one of R$^{6b}$, R$^{6c}$, R$^{6d}$, R$^{6e}$, R$^{6f}$ and R$^{6g}$ is methyl. In some embodiments, R$^{6g}$ is C$_1$-C$_6$ alkyl. In some embodiments, R$^{6b}$ is C$_1$-C$_6$ alkyl. In some embodiments, R$^{6c}$ is C$_1$-C$_6$ alkyl. In some embodiments, R$^{6d}$ is C$_1$-C$_6$ alkyl. In some embodiments, R$^{6e}$ is C$_1$-C$_6$ alkyl. In some embodiments, R$^{6f}$ is C$_1$-C$_6$ alkyl. In some embodiments, R$^{6g}$ is methyl, ethyl, n-propyl, isopropyl, n-butyl, isobutyl, secbutyl, or tertbutyl. In some embodiments, R$^{6b}$ is methyl, ethyl, n-propyl, isopropyl, n-butyl, isobutyl, secbutyl, or tertbutyl. In some embodiments, R$^{6c}$ is methyl, ethyl, n-propyl, isopropyl, n-butyl, isobutyl, secbutyl, or tertbutyl. In some embodiments, R$^{6d}$ is methyl, ethyl, n-propyl, isopropyl, n-butyl, isobutyl, secbutyl, or tertbutyl. In some embodiments, R$^{6e}$ is methyl, ethyl, n-propyl, isopropyl, n-butyl, isobutyl, secbutyl, or tertbutyl. In some embodiments, R$^{6f}$ is methyl, ethyl, n-propyl, isopropyl, n-butyl, isobutyl, secbutyl, or tertbutyl. In some embodiments, R$^{6g}$ is C$_1$-C$_6$ alkyl and R$^{6b}$ is halogen. In some embodiments, R$^{6g}$ is C$_1$-C$_6$ alkyl and R$^{6c}$ is halogen. In some embodiments, R$^{6g}$ is C$_1$-C$_6$ alkyl and R$^{6d}$ is halogen. In some embodiments, R$^{6g}$ is C$_1$-C$_6$ alkyl and R$^{6e}$ is halogen. In some embodiments, R$^{6g}$ is C$_1$-C$_6$ alkyl and R$^{6f}$ is halogen. In some embodiments, R$^{6b}$ is C$_1$-C$_6$ alkyl and R$^{6g}$ is halogen. In some embodiments, R$^{6b}$ is C$_1$-C$_6$ alkyl and R$^{6c}$ is halogen. In some embodiments, R$^{6b}$ is C$_1$-C$_6$ alkyl and R$^{6d}$ is halogen. In some embodiments, R$^{6b}$ is C$_1$-C$_6$ alkyl and R$^{6e}$ is halogen. In some embodiments, R$^{6b}$ is C$_1$-C$_6$ alkyl and R$^{6f}$ is halogen. In some embodiments, R$^{6c}$ is C$_1$-C$_6$ alkyl and R$^{6g}$ is halogen. In some embodiments, R$^{6c}$ is C$_1$-C$_6$ alkyl and R$^{6b}$ is halogen. In some embodiments, R$^{6c}$ is C$_1$-C$_6$ alkyl and R$^{6d}$ is halogen. In some embodiments, R$^{6c}$ is C$_1$-C$_6$ alkyl and R$^{6e}$ is halogen. In some embodiments, R$^{6c}$ is C$_1$-C$_6$ alkyl and R$^{6f}$ is halogen. In some embodiments, R$^{6d}$ is C$_1$-C$_6$ alkyl and R$^{6g}$ is halogen. In some embodiments, R$^{6d}$ is C$_1$-C$_6$ alkyl and R$^{6b}$ is halogen. In some embodiments, R$^{6d}$ is C$_1$-C$_6$ alkyl and R$^{6c}$ is halogen. In some embodiments, R$^{6d}$ is C$_1$-C$_6$ alkyl and R$^{6e}$ is halogen. In some embodiments, R$^{6d}$ is C$_1$-C$_6$ alkyl and R$^{6f}$ is halogen. In some embodiments, R$^{6e}$ is C$_1$-C$_6$ alkyl and R$^{6g}$ is halogen. In some embodiments, R$^{6e}$ is C$_1$-C$_6$ alkyl and R$^{6b}$ is halogen. In some embodiments, R$^{6e}$ is C$_1$-C$_6$ alkyl and R$^{6c}$ is halogen. In some embodiments, R$^{6e}$ is C$_1$-C$_6$ alkyl and R$^{6d}$ is halogen. In some embodiments, R$^{6e}$ is C$_1$-C$_6$ alkyl and R$^{6f}$ is halogen. In some embodiments, R$^{6f}$ is C$_1$-C$_6$ alkyl and R$^{6g}$ is halogen. In some embodiments, R$^{6f}$ is C$_1$-C$_6$ alkyl and R$^{6b}$ is halogen. In some embodiments, R$^{6f}$ is C$_1$-C$_6$ alkyl and R$^{6c}$ is halogen. In some embodiments, R$^{6f}$ is C$_1$-C$_6$ alkyl and R$^{6d}$ is halogen. In some embodiments, R$^{6f}$ is C$_1$-C$_6$ alkyl and R$^{6e}$ is halogen. In some embodiments, two of R$^{6b}$, R$^{6c}$, R$^{6d}$, R$^{6e}$, R$^{6f}$, and R$^{6g}$ are halogen. In some embodiments, two of R$^{6b}$, R$^{6c}$, R$^{6d}$, R$^{6e}$, R$^{6f}$, and R$^{6g}$ are C$_1$-C$_6$ alkyl.

In some embodiments of a compound of Formula (I), (II), or (III), A is

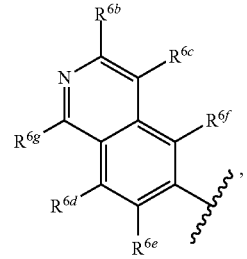

wherein one or two of R$^{6b}$, R$^{6c}$, R$^{6d}$, R$^{6e}$, R$^{6f}$, and R$^{6g}$ are independently selected from the group consisting of C$_1$-C$_6$ alkyl, halogen, —CN, and —OC$_1$-C$_6$ alkyl, and the remainder of R$^{6b}$, R$^{6c}$, R$^{6d}$, R$^{6e}$, R$^{6f}$, and R$^{6g}$ are each H; and B is phenyl, optionally substituted with R$^7$.

In some embodiments of a compound of Formula (I), (II), or (III), A is

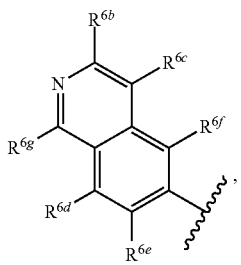

wherein one or two of $R^{6b}$, $R^{6c}$, $R^{6d}$, $R^{6e}$, $R^{6f}$, and $R^{6g}$ are independently selected from the group consisting of $C_1$-$C_6$ alkyl, halogen, —CN, and —$OC_1$-$C_6$ alkyl, and the remainder of $R^{6b}$, $R^{6c}$, $R^{6d}$, $R^{6e}$, $R^{6f}$, and $R^{6g}$ are each H; and B is a 5- to 6-membered heteroaryl, optionally substituted with $R^7$.

In some embodiments of a compound of Formula (I), (II), or (III), A is

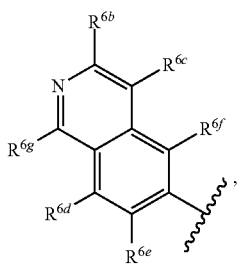

wherein one or two of $R^{6b}$, $R^{6c}$, $R^{6d}$, $R^{6e}$, $R^{6f}$, and $R^{6g}$ are independently selected from the group consisting of $C_1$-$C_6$ alkyl, halogen, —CN, and —$OC_1$-$C_6$ alkyl, and the remainder of $R^{6b}$, $R^{6c}$, $R^{6d}$, $R^{6e}$, $R^{6f}$, and $R^{6g}$ are each H; and B is a 5- to 6-membered carbocycle, optionally substituted with $R^7$.

In some embodiments of a compound of Formula (I), (II), or (III), A is

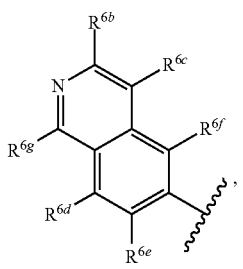

wherein one or two of $R^{6b}$, $R^{6c}$, $R^{6d}$, $R^{6e}$, $R^{6f}$, and $R^{6g}$ are independently selected from the group consisting of $C_1$-$C_6$ alkyl, halogen, —CN, and —$OC_1$-$C_6$ alkyl, and the remainder of $R^{6b}$, $R^{6c}$, $R^{6d}$, $R^{6e}$, $R^{6f}$, and $R^{6g}$ are each H; and B is a 5- to 6-membered heterocycle, optionally substituted with $R^7$.

In some embodiments of a compound of Formula (I), (II), or (III), A is

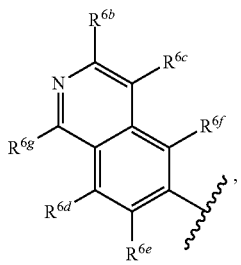

wherein one or two of $R^{6b}$, $R^{6c}$, $R^{6d}$, $R^{6e}$, $R^{6f}$, and $R^{6g}$ are independently selected from the group consisting of $C_1$-$C_6$ alkyl, halogen, —CN, and —$OC_1$-$C_6$ alkyl, and the remainder of $R^{6b}$, $R^{6c}$, $R^{6d}$, $R^{6e}$, $R^{6f}$, and $R^{6g}$ are each H; and B is a 9- to 10-membered heteroaryl, optionally substituted with $R^7$.

In some embodiments of a compound of Formula (I), (II), or (III), A is

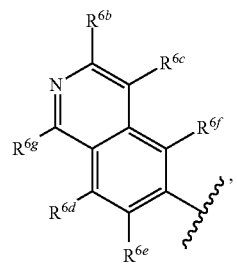

wherein one or two of $R^{6b}$, $R^{6c}$, $R^{6d}$, $R^{6e}$, $R^{6f}$, and $R^{6g}$ are independently selected from the group consisting of $C_1$-$C_6$ alkyl, halogen, —CN, and —$OC_1$-$C_6$ alkyl, and the remainder of $R^{6b}$, $R^{6c}$, $R^{6d}$, $R^{6e}$, $R^{6f}$, and $R^{6g}$ are each H; and B is selected from the group consisting of:

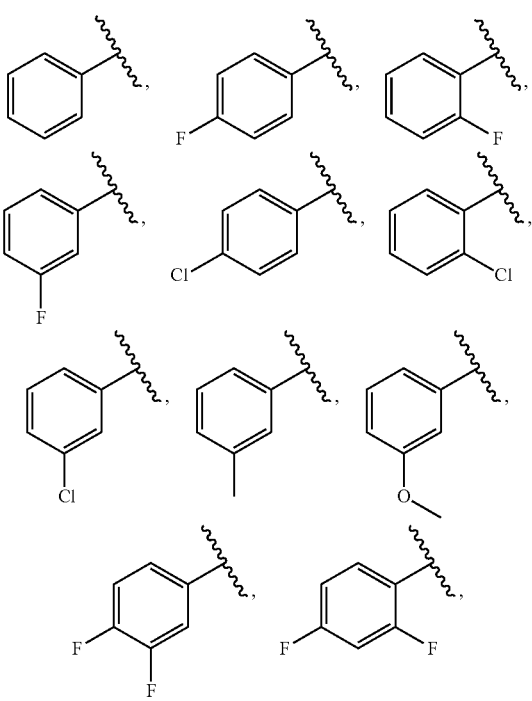

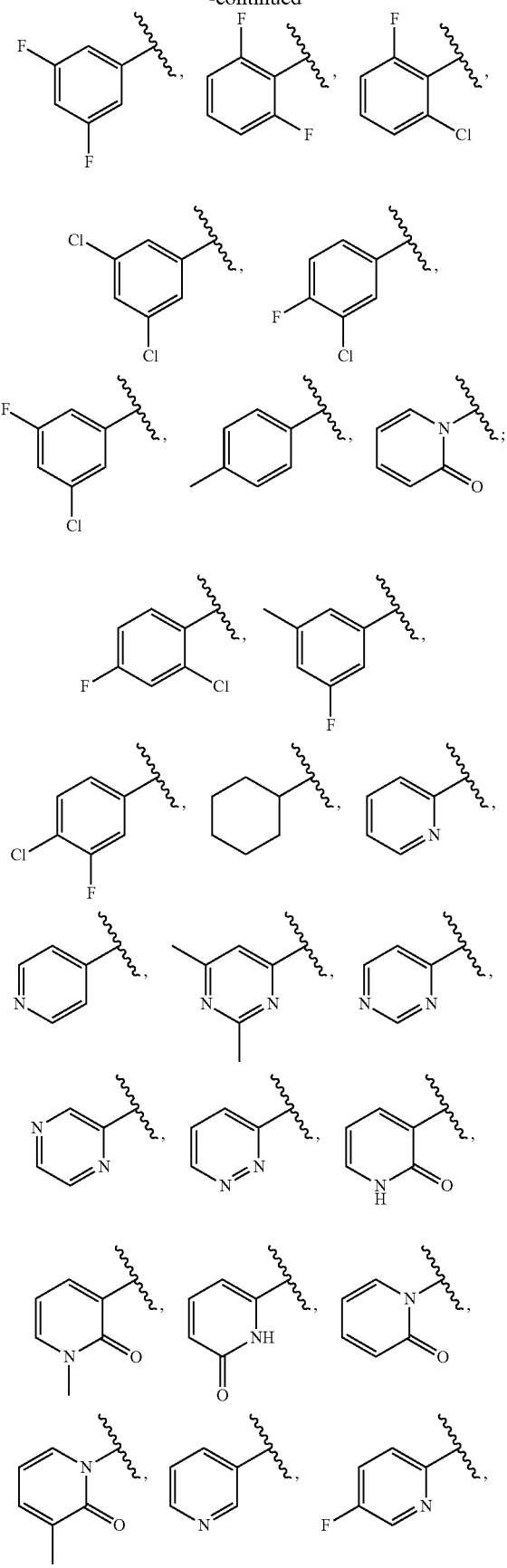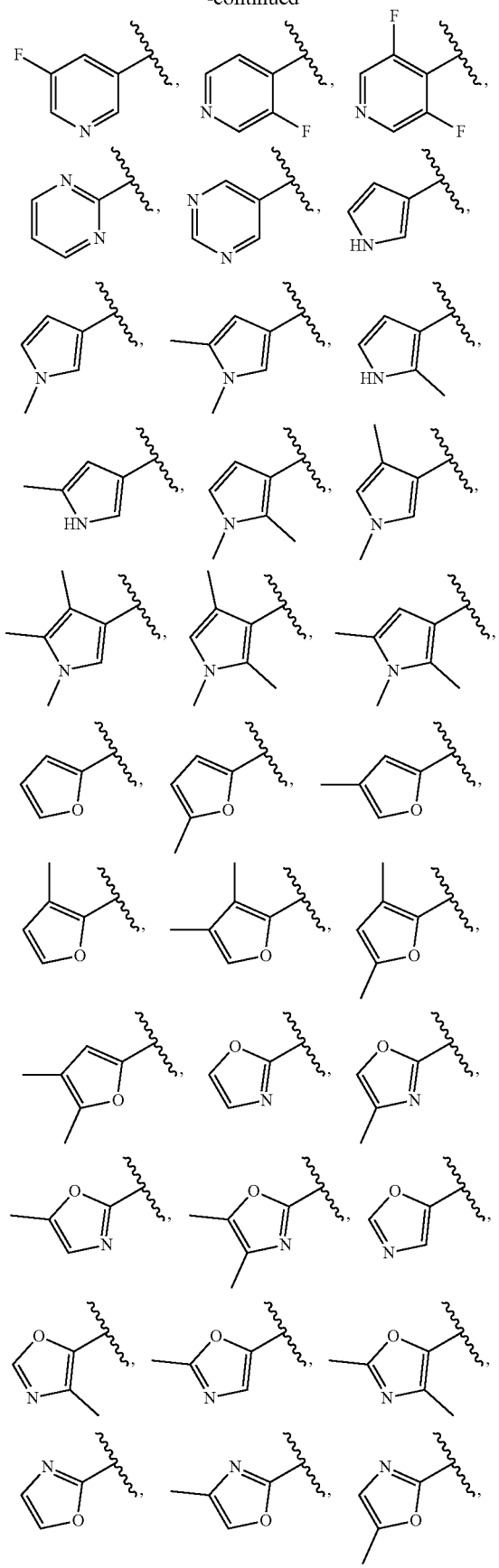

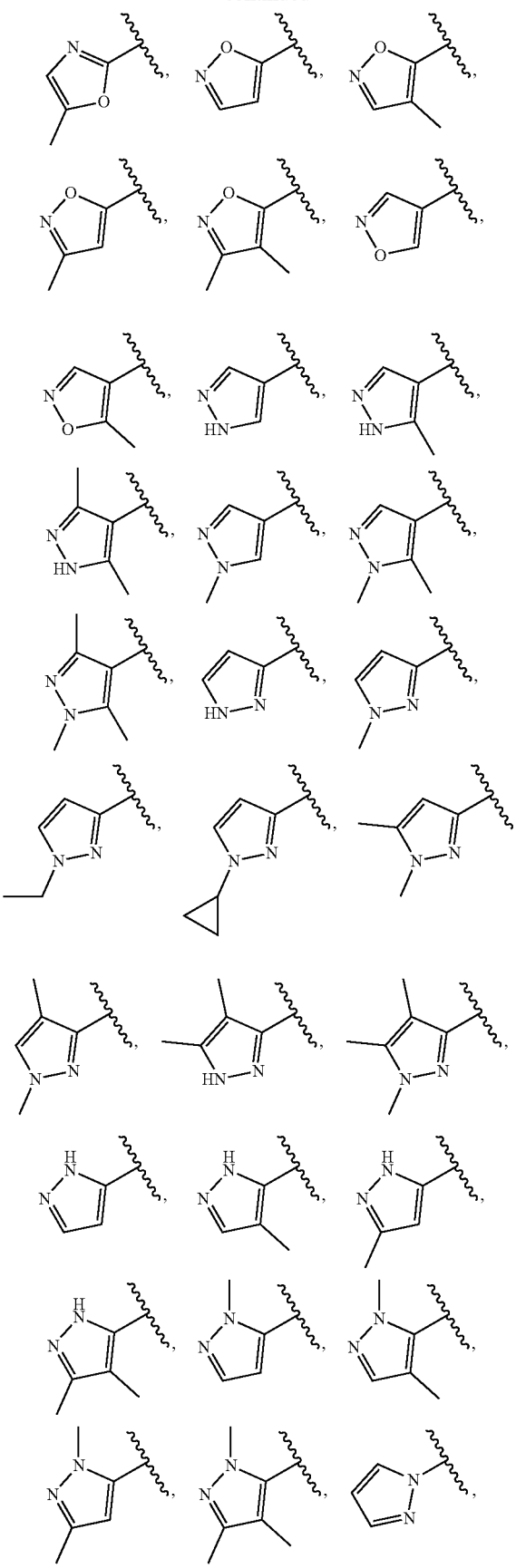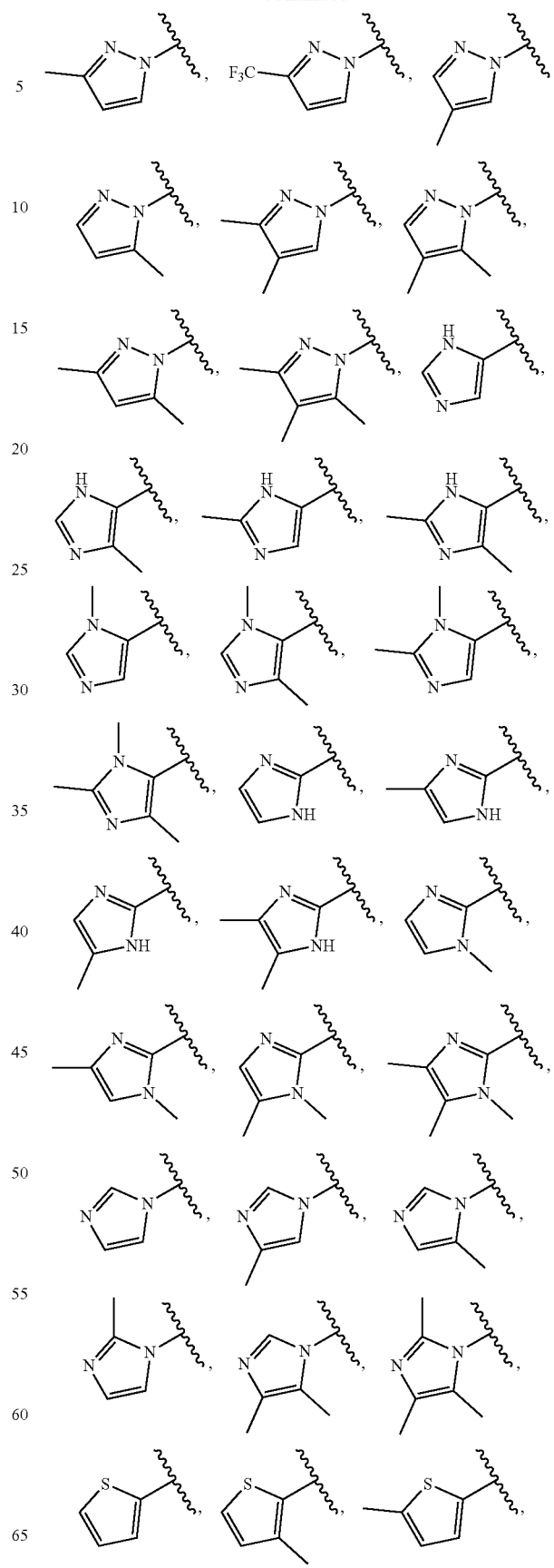

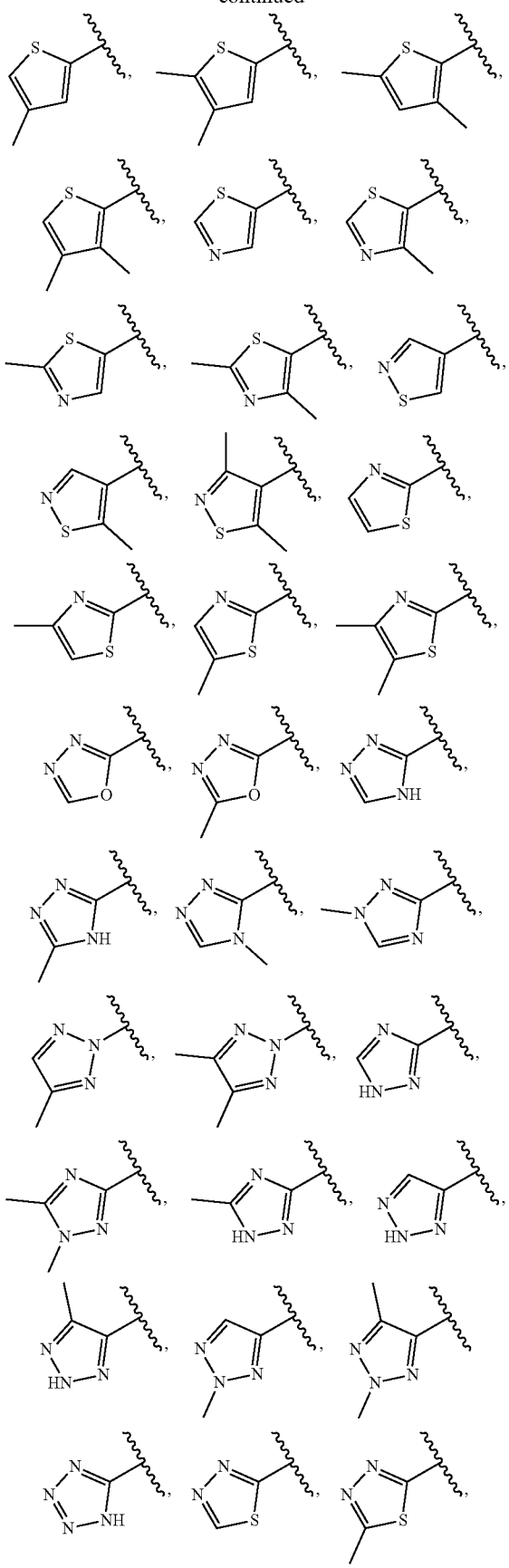
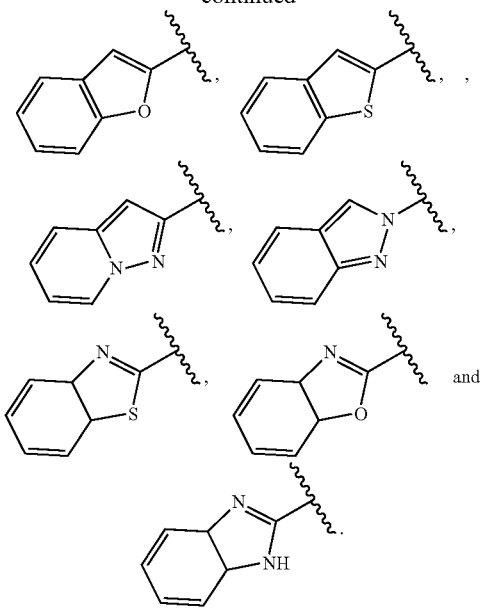
In some embodiments of a compound of Formula (I), (II), or (III), A is
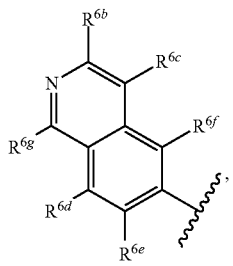
wherein one or two of $R^{6b}$, $R^{6c}$, $R^{6d}$, $R^{6e}$, $R^{6f}$, and $R^{6g}$ are independently selected from the group consisting of $C_1$-$C_6$ alkyl, halogen, —CN, and —O$C_1$-$C_6$ alkyl, and the remainder of $R^{6b}$, $R^{6c}$, $R^{6d}$, $R^{6e}$, $R^{6f}$, and $R^{6g}$ are each H; and B is selected from the group consisting of:
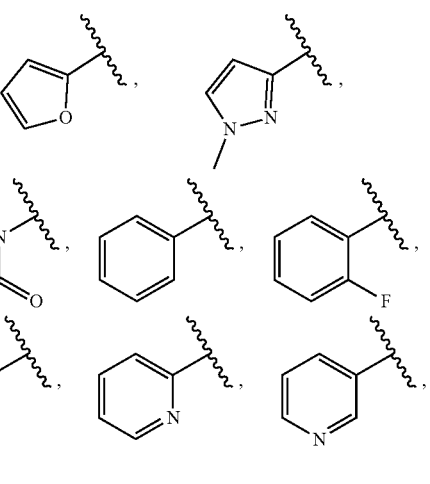

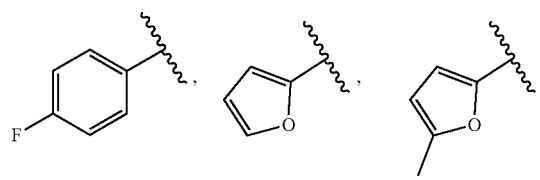
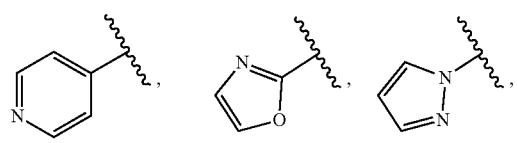
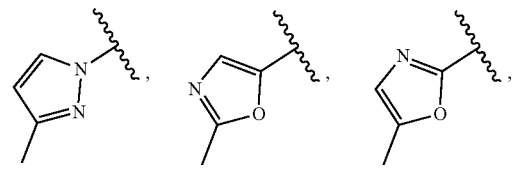
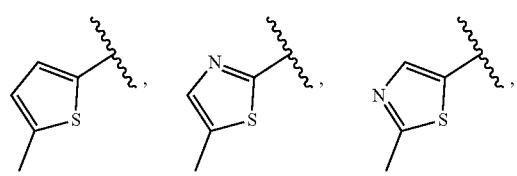
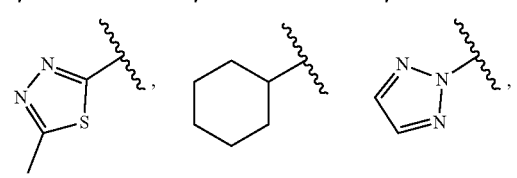
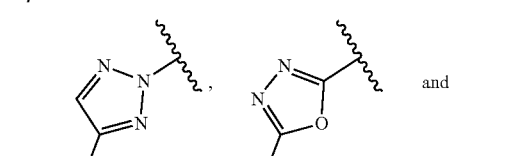
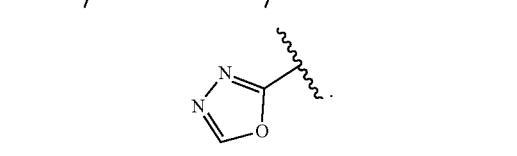
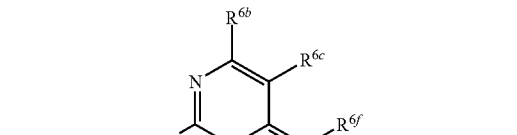

In some embodiments of a compound of Formula (I), (II), or (III), A is

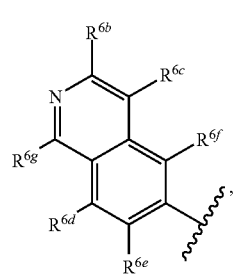

wherein one or two of $R^{6b}$, $R^{6c}$, $R^{6d}$, $R^{6e}$, $R^{6f}$, and $R^{6g}$ are independently selected from the group consisting of $C_1$-$C_6$ alkyl, halogen, —CN, and —$OC_1$-$C_6$ alkyl, and the remainder of $R^{6b}$, $R^{6c}$, $R^{6d}$, $R^{6e}$, $R^{6f}$, and $R^{6g}$ are each H; and B is selected from the group consisting of

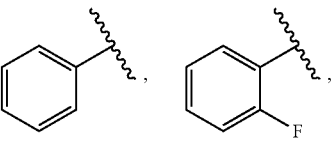
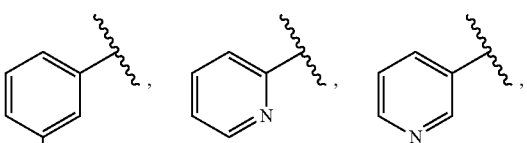
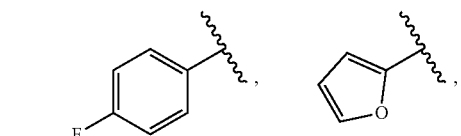
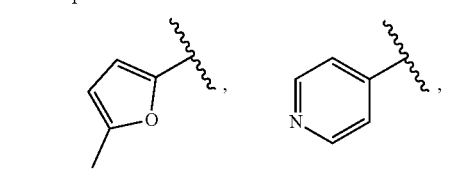
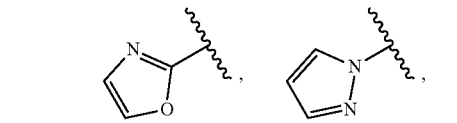
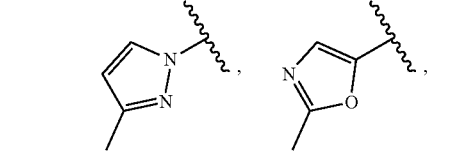
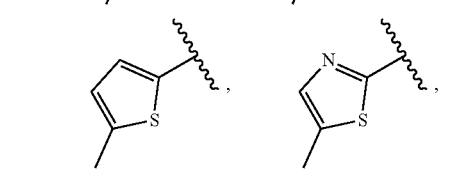
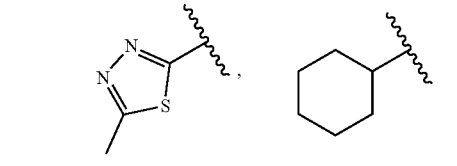
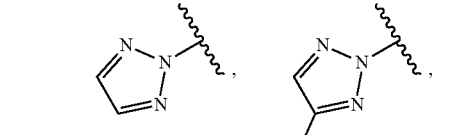
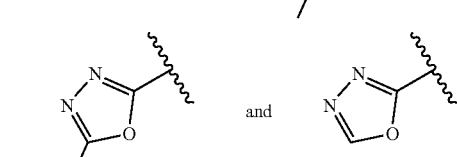

In some embodiments of a compound of Formula (I), (II), or (III), A is

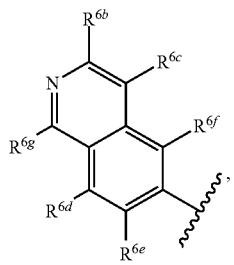

wherein one or two of $R^{6b}$, $R^{6c}$, $R^{6d}$, $R^{6e}$, $R^{6f}$, and $R^{6g}$ are independently selected from the group consisting of $C_1$-$C_6$ alkyl, halogen, —CN, and —$OC_1$-$C_6$ alkyl, and the remainder of $R^{6b}$, $R^{6c}$, $R^{6d}$, $R^{6e}$, $R^{6f}$, and $R^{6g}$ are each H; and B is selected from

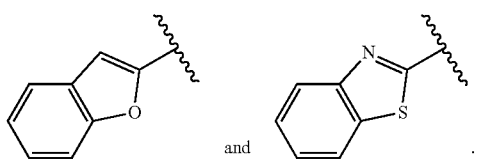 [SMILES: *c1cc2ccccc2o1 ; *c1nc2ccccc2s1]

and

In some embodiments of a compound of Formula (I), (II), or (III), A is

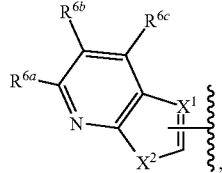

wherein $X^1$ is selected from the group consisting of N, C, and CH; $X^2$ is selected from the group consisting of NH, O, and S; and $R^{6a}$, $R^{6b}$, and $R^{6c}$ are each independently H, $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$NO_2$, —C=NH($OR^8$), —C(O)$R^8$, —OC(O)$R^8$, —C(O)$OR^8$, —C(O)$NR^9R^{10}$, —OC(O)$NR^9R^{10}$, —$NR^8$C(O)$R^9$, —$NR^8$C(O)$OR^9$, —$NR^8$C(O)$NR^9R^{10}$, —S(O)$R^8$, —S(O)$_2R^8$, —$NR^8$S(O)$R^9$, —C(O)$NR^8$S(O)$R^9$, —$NR^8$S(O)$_2R^9$, —C(O)$NR^8$S(O)$_2R^9$, —S(O)$NR^9R^{10}$, —S(O)$_2NR^9R^{10}$, —P(O)($OR^9$)($OR^{10}$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)$OR^8$, —($C_1$-$C_3$ alkylene)$SR^8$, —($C_1$-$C_3$ alkylene)$NR^9R^{10}$, —($C_1$-$C_3$ alkylene)$CF_3$, —($C_1$-$C_3$ alkylene)$NO_2$, —C=NH($OR^8$), —($C_1$-$C_3$ alkylene)C(O)$R^8$, —($C_1$-$C_3$ alkylene)OC(O)$R^8$, —($C_1$-$C_3$ alkylene)C(O)$OR^8$, —($C_1$-$C_3$ alkylene)C(O)$NR^9R^{10}$, —($C_1$-$C_3$ alkylene)OC(O)$NR^9R^{10}$, —($C_1$-$C_3$ alkylene)$NR^8$C(O)$R^9$, —($C_1$-$C_3$ alkylene)$NR^8$C(O)$OR^9$, —($C_1$-$C_3$ alkylene)$NR^8$C(O)$NR^9R^{10}$, —($C_1$-$C_3$ alkylene)S(O)$R^8$, —($C_1$-$C_3$ alkylene)S(O)$_2R^8$, —($C_1$-$C_3$ alkylene)$NR^8$S(O)$R^9$, —C(O)($C_1$-$C_3$ alkylene)$NR^8$S(O)$R^9$, —($C_1$-$C_3$ alkylene)$NR^8$S(O)$_2R^9$, —($C_1$-$C_3$ alkylene)C(O)$NR^8$S(O)$_2R^9$, —($C_1$-$C_3$ alkylene)S(O)$NR^9R^{10}$, —($C_1$-$C_3$ alkylene)S(O)$_2NR^9R^{10}$, —($C_1$-$C_3$ alkylene)P(O)($OR^9$)($OR^{10}$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or —($C_1$-$C_3$ alkylene)($C_6$-$C_{14}$ aryl), wherein each $R^{6a}$, $R^{6b}$, and $R^{6c}$ is independently optionally substituted by halogen, oxo, —OR, —$NR^{11}R^{12}$, —C(O)$R^{11}$, —CN, —S(O)$R^{11}$, —S(O)$_2R^{11}$, —P(O)($OR^{11}$)($OR^{12}$), —($C_1$-$C_3$ alkylene)$OR^{11}$, —($C_1$-$C_3$ alkylene)$NR^{11}R^{12}$, —($C_1$-$C_3$ alkylene)C(O)$R^{11}$, —($C_1$-$C_3$ alkylene)S(O)$R^{11}$, —($C_1$-$C_3$ alkylene)S(O)$_2R^{11}$, —($C_1$-$C_3$ alkylene)P(O)($OR^{11}$)($OR^{12}$), $C_3$-$C_8$ cycloalkyl, or $C_1$-$C_6$ alkyl optionally substituted by oxo, —OH or halogen.

In some embodiments of a compound of Formula (I), (II), or (III), A is

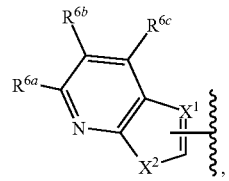

wherein $X^1$ is selected from the group consisting of N, C, and CH; $X^2$ is selected from the group consisting of NH, O, and S; and $R^{6a}$, $R^{6b}$, and $R^{6c}$ are each independently H, $C_1$-$C_6$ alkyl, halogen, —CN, or —$OC_1$-$C_6$ alkyl. In some embodiments of a compound of Formula (I), (II), or (III), A is H

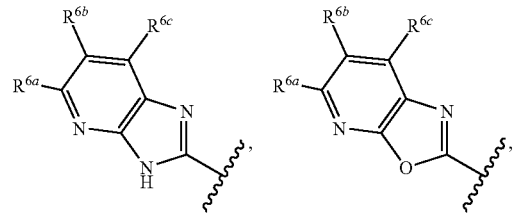

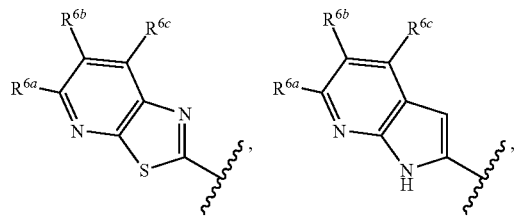

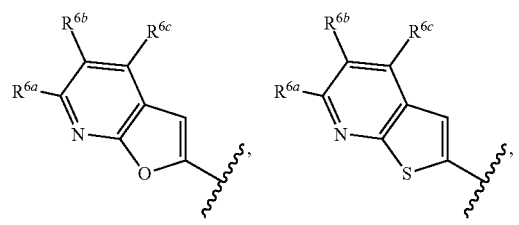

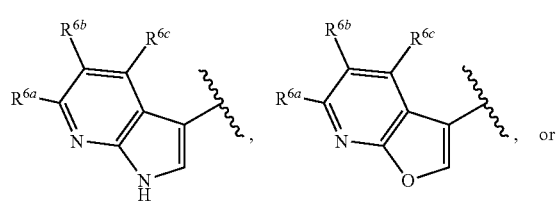

-continued

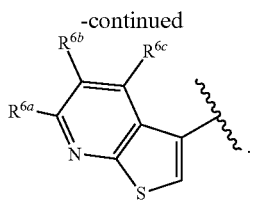

In some embodiments, $R^{6a}$, $R^{6b}$, and $R^{6c}$ are each H. In some embodiments, one of $R^{6a}$, $R^{6b}$, and $R^{6c}$ is Cl, F, Br, or I. In some embodiments, one of $R^{6a}$, $R^{6b}$, and $R^{6c}$ is Cl. In some embodiments, one of $R^{6a}$, $R^{6b}$, and $R^{6c}$ is halogen and the others are each H. In some embodiments, one of $R^{6a}$, $R^{6b}$, and $R^{6c}$ is halogen and one of $R^{6a}$, $R^{6b}$, and $R^{6c}$ is $C_1$-$C_6$ alkyl. In some embodiments, one of $R^{6a}$, $R^{6b}$, and $R^{6c}$ is Cl and one of $R^{6a}$, $R^{6b}$, and $R^{6c}$ is methyl. In some embodiments, $R^{6a}$ is $C_1$-$C_6$ alkyl. In some embodiments, $R^{6b}$ is $C_1$-$C_6$ alkyl. In some embodiments, $R^{6c}$ is $C_1$-$C_6$ alkyl. In some embodiments, $R^{6a}$ is methyl, ethyl, n-propyl, isopropyl, n-butyl, isobutyl, secbutyl, or tertbutyl. In some embodiments, $R^{6b}$ is methyl, ethyl, n-propyl, isopropyl, n-butyl, isobutyl, secbutyl, or tertbutyl. In some embodiments, $R^{6c}$ is methyl, ethyl, n-propyl, isopropyl, n-butyl, isobutyl, secbutyl, or tertbutyl. In some embodiments, $R^{6a}$ is $C_1$-$C_6$ alkyl and $R^{6b}$ is halogen. In some embodiments, $R^{6a}$ is $C_1$-$C_6$ alkyl and $R^{6c}$ is halogen. In some embodiments, $R^{6b}$ is $C_1$-$C_6$ alkyl and $R^{6a}$ is halogen. In some embodiments, $R^{6b}$ is $C_1$-$C_6$ alkyl and $R^{6c}$ is halogen. In some embodiments, $R^{6c}$ is $C_1$-$C_6$ alkyl and $R^{6a}$ is halogen. In some embodiments, $R^{6c}$ is $C_1$-$C_6$ alkyl and $R^{6b}$ is halogen. In some embodiments, two of $R^{6a}$, $R^{6b}$, and $R^{6c}$ are halogen. In some embodiments, two of $R^{6a}$, $R^{6b}$, and $R^{6c}$ are $C_1$-$C_6$ alkyl.

In some embodiments of a compound of Formula (I), (II), or (III), A is

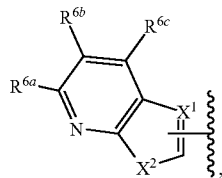

wherein one or two of $R^{6a}$, $R^{6b}$, and $R^{6c}$ are independently selected from the group consisting of $C_1$-$C_6$ alkyl, halogen, —CN, and —O$C_1$-$C_6$ alkyl, and the remainder of $R^{6a}$, $R^{6b}$, and $R^{6c}$ are each H; and B is phenyl, optionally substituted with $R^7$.

In some embodiments of a compound of Formula (I), (II), or (III), A is

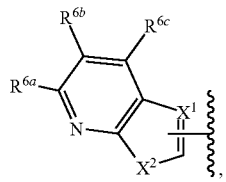

wherein one or two of $R^{6a}$, $R^{6b}$, and $R^{6c}$ are independently selected from the group consisting of $C_1$-$C_6$ alkyl, halogen, —CN, and —O$C_1$-$C_6$ alkyl, and the remainder of $R^{6a}$, $R^{6b}$, and $R^{6c}$ are each H; and B is a 5- to 6-membered heteroaryl, optionally substituted with $R^7$.

In some embodiments of a compound of Formula (I), (II), or (III), A is

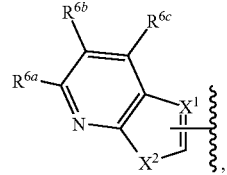

wherein one or two of $R^{6a}$, $R^{6b}$, and $R^{6c}$ are independently selected from the group consisting of $C_1$-$C_6$ alkyl, halogen, —CN, and —O$C_1$-$C_6$ alkyl, and the remainder of $R^{6a}$, $R^{6b}$, and $R^{6c}$ are each H; and B is a 5- to 6-membered carbocycle, optionally substituted with $R^7$.

In some embodiments of a compound of Formula (I), (II), or (III), A is

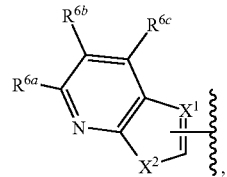

wherein one or two of $R^{6a}$, $R^{6b}$, and $R^{6c}$ are independently selected from the group consisting of $C_1$-$C_6$ alkyl, halogen, —CN, and —O$C_1$-$C_6$ alkyl, and the remainder of $R^{6a}$, $R^{6b}$, and $R^{6c}$ are each H; and B is a 5- to 6-membered heterocycle, optionally substituted with $R^7$.

In some embodiments of a compound of Formula (I), (II), or (III), A is

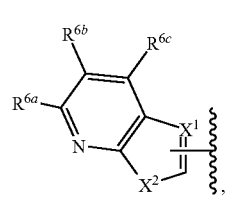

wherein one or two of $R^{6a}$, $R^{6b}$, and $R^{6c}$ are independently selected from the group consisting of $C_1$-$C_6$ alkyl, halogen, —CN, and —O$C_1$-$C_6$ alkyl, and the remainder of $R^{6a}$, $R^{6b}$, and $R^{6c}$ are each H; and B is a 9- to 10-membered heteroaryl, optionally substituted with $R^7$.

In some embodiments of a compound of Formula (I), (II), or (III), A is

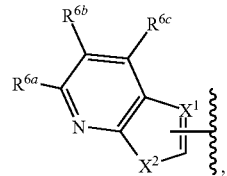

wherein one or two of $R^{6a}$, $R^{6b}$, and $R^{6c}$ are independently selected from the group consisting of $C_1$-$C_6$ alkyl, —CN, and —OC$_1$-C$_6$ alkyl, and the remainder of R$^{6a}$, R$^{6b}$, and R$^{6c}$ are each H; and B is selected from the group consisting of:
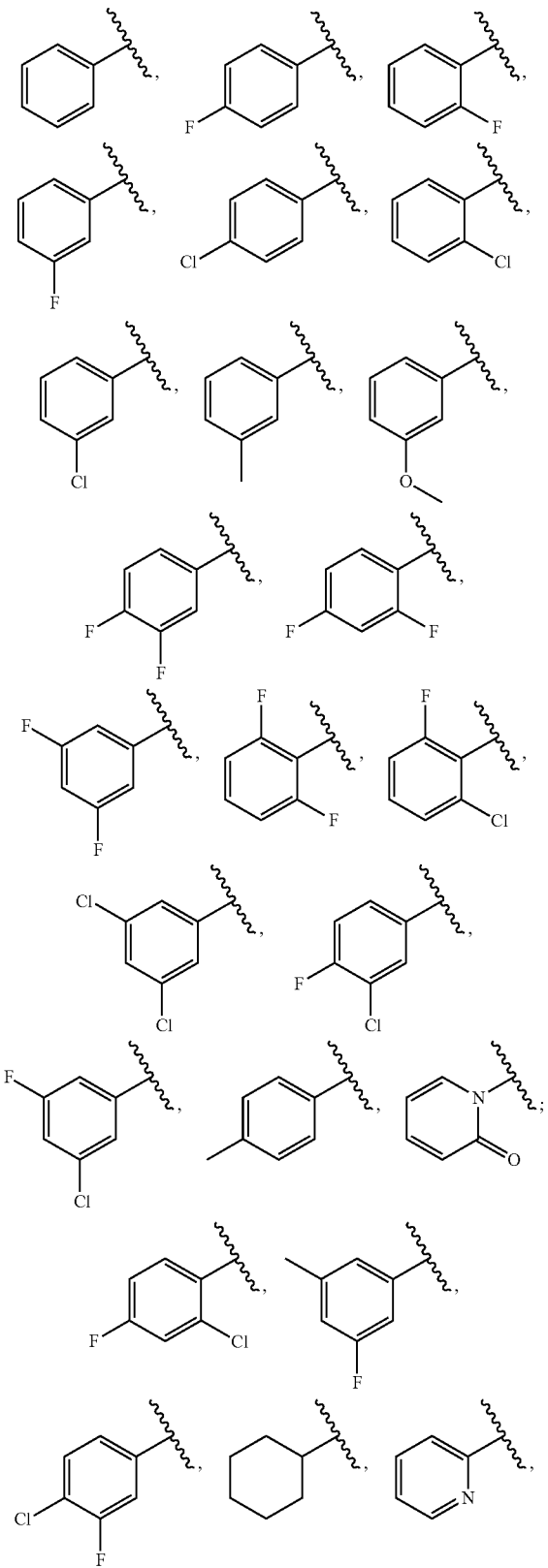
-continued
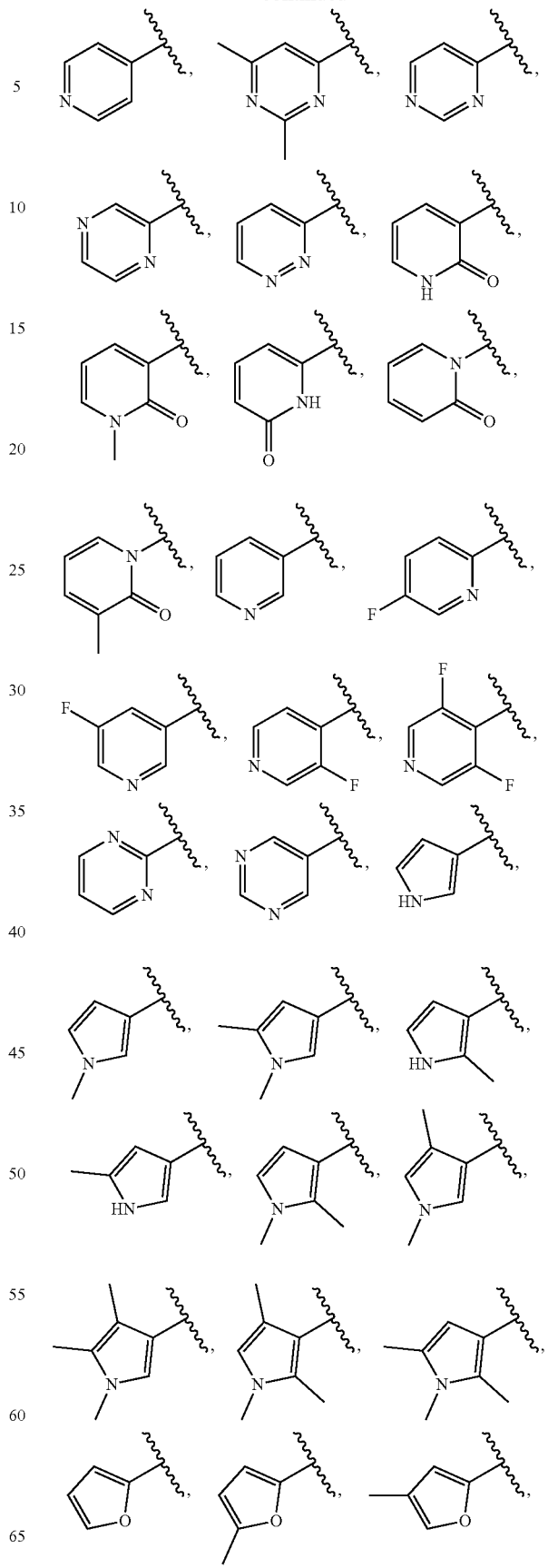

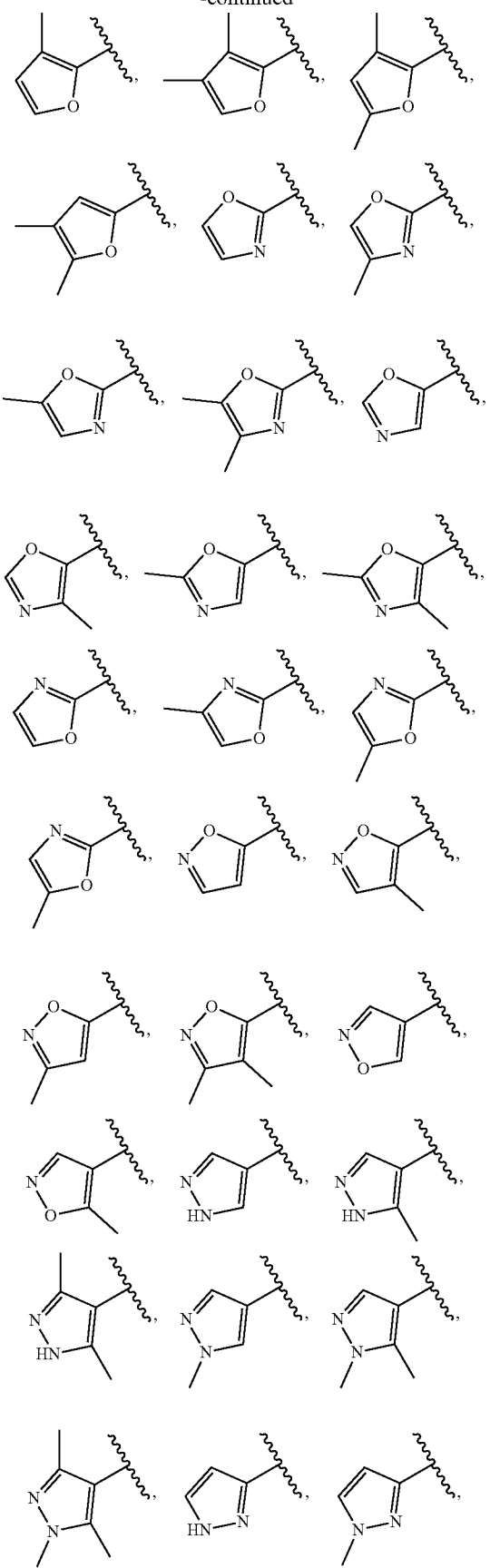
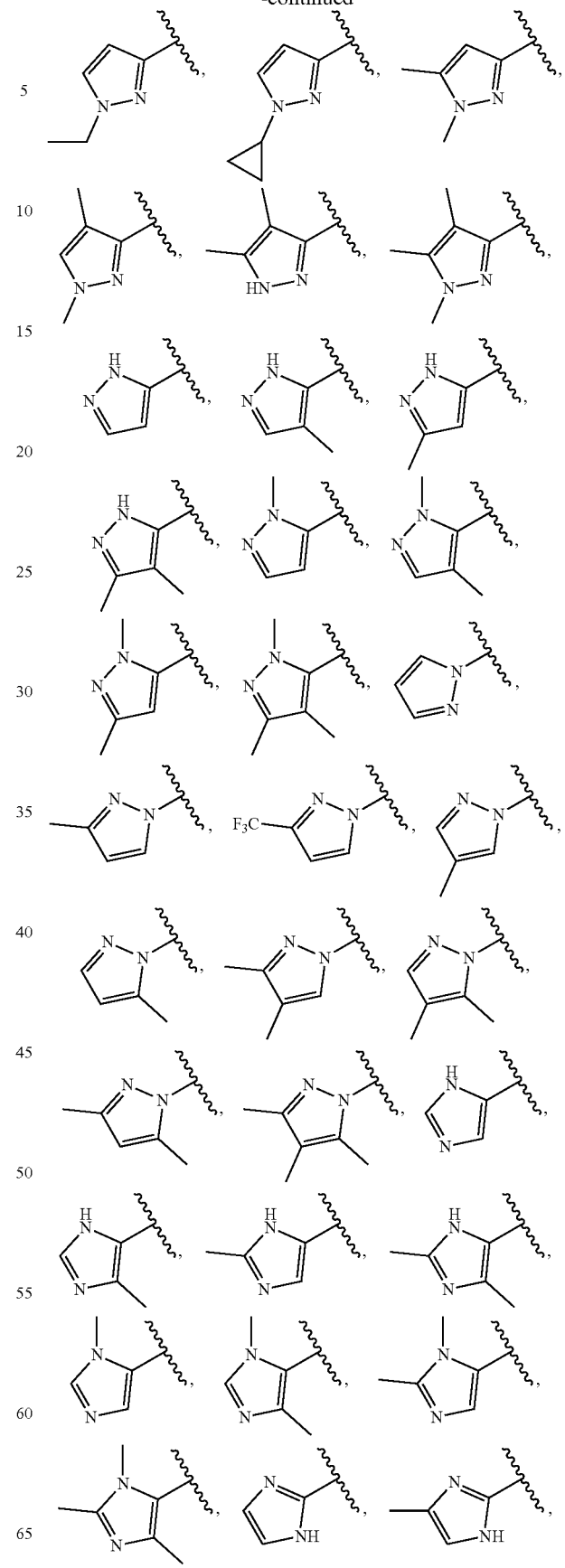

-continued
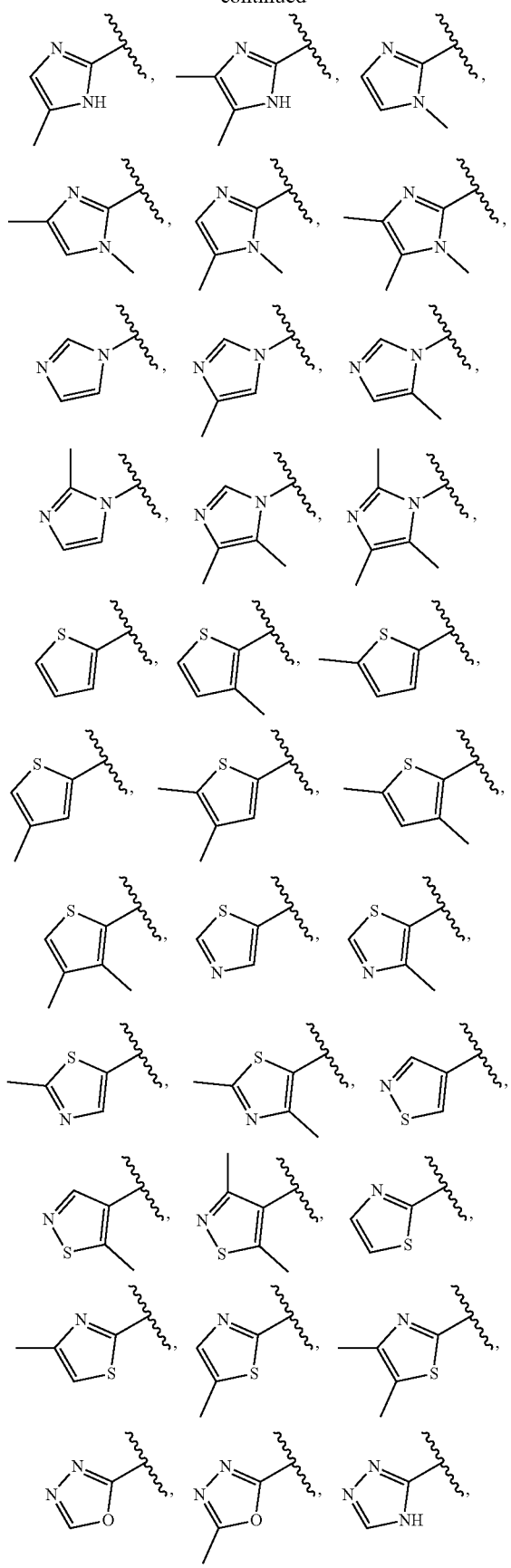
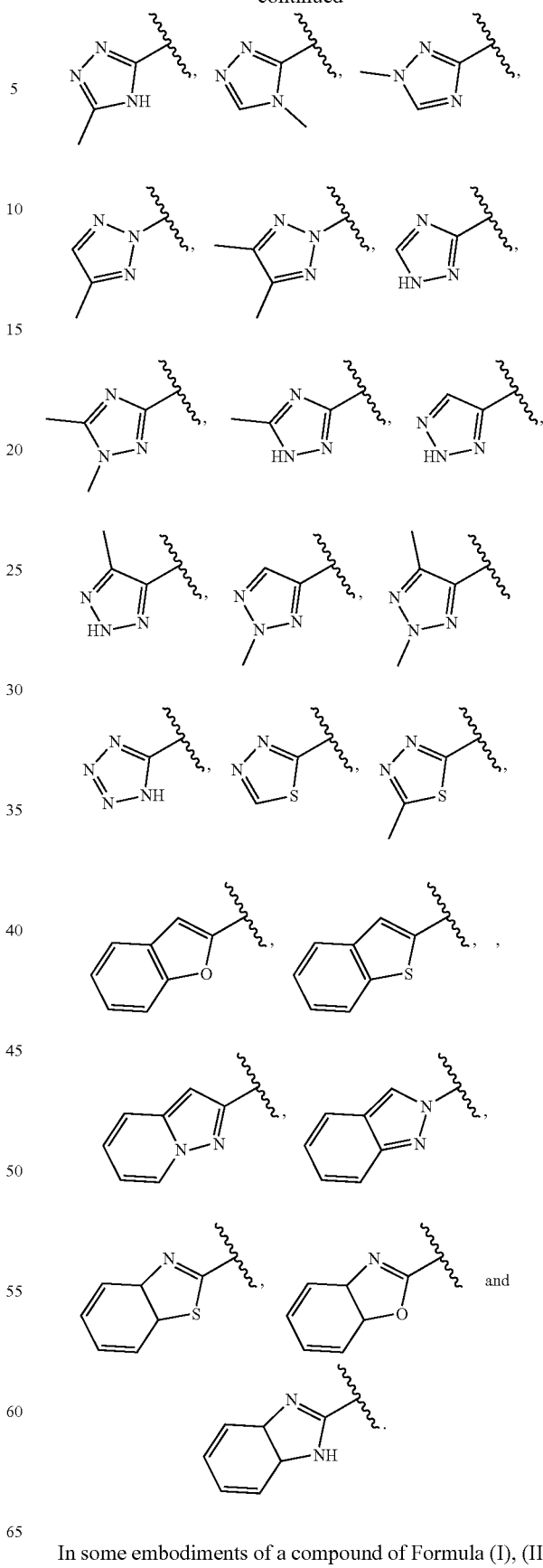
In some embodiments of a compound of Formula (I), (II), or (III), A is

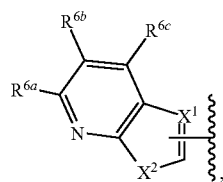

wherein one or two of $R^{6a}$, $R^{6b}$, and $R^{6c}$ are independently selected from the group consisting of $C_1$-$C_6$ alkyl, halogen, —CN, and —$OC_1$-$C_6$ alkyl, and the remainder of $R^{6a}$, $R^{6b}$, and $R^{6c}$ are each H; and B is selected from the group consisting of:

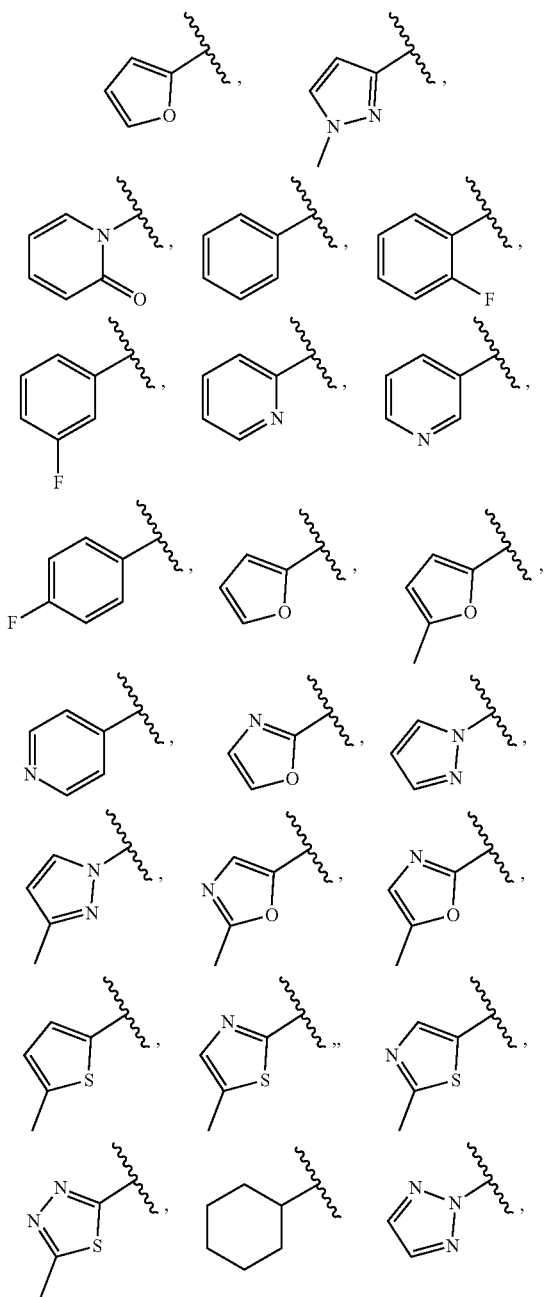

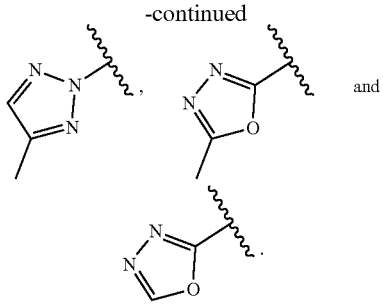

In some embodiments of a compound of Formula (I), (II), or (III), A is

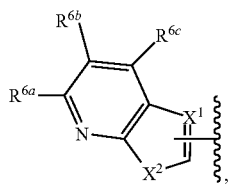

wherein one or two of $R^{6a}$, $R^{6b}$, and $R^{6c}$ are independently selected from the group consisting of $C_1$-$C_6$ alkyl, halogen, —CN, and —$OC_1$-$C_6$ alkyl, and the remainder of $R^{6a}$, $R^{6b}$, and $R^{6c}$ are each H; and B is selected from the group consisting of

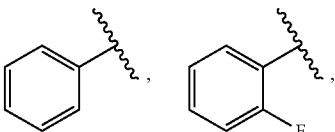

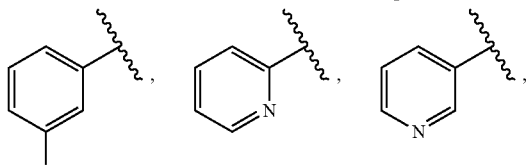

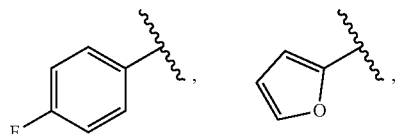

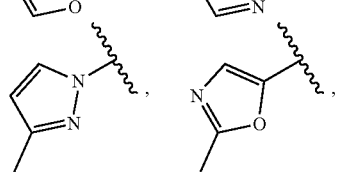

-continued

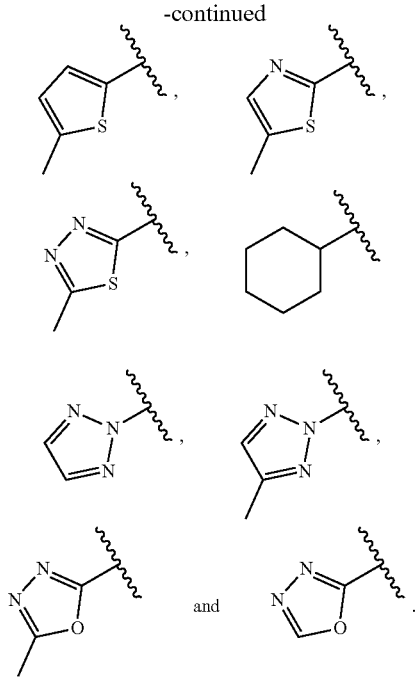

In some embodiments of a compound of Formula (I), (II), or (III), A is

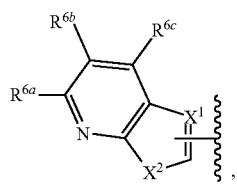

wherein one or two of $R^{6a}$, $R^{6b}$, and $R^{6c}$ are independently selected from the group consisting of $C_1$-$C_6$ alkyl, halogen, —CN, and —O$C_1$-$C_6$ alkyl, and the remainder of $R^{6a}$, $R^{6b}$, and $R^{6c}$ are each H; and B is selected from

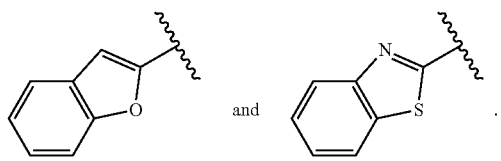 [SMILES: *c1cc2ccccc2o1 ; *c1nc2ccccc2s1]

In some embodiments of a compound of Formula (I), (II), or (III), A is

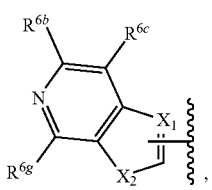

wherein $X^1$ is selected from the group consisting of N, C, and CH; $X^2$ is selected from the group consisting of NH, O, and S; and $R^{6g}$, $R^{6b}$, and $R^{6c}$ are each independently H, $C_1$-$C_6$ alkyl, $C_2$-$C_6$ alkenyl, $C_2$-$C_6$ alkynyl, halogen, —CN, —$OR^8$, —$SR^8$, —$NR^9R^{10}$, —$NO_2$, —C=NH($OR^8$), —C(O)$R^8$, —OC(O)$R^8$, —C(O)$OR^8$, —C(O)$NR^9R^{10}$, —OC(O)$NR^9R^{10}$, —$NR^8$C(O)$R^9$, —$NR^8$C(O)$OR^9$, —$NR^8$C(O)$NR^9R^{10}$, —S(O)$R^8$, —S(O)$_2R^8$, —$NR^8$S(O)$R^9$, —C(O)$NR^8$S(O)$R^9$, —$NR^8$S(O)$_2R^9$, —C(O)$NR^8$S(O)$_2R^9$, —S(O)$NR^9R^{10}$, —S(O)$_2NR^9R^{10}$, —P(O)($OR^9$)($OR^{10}$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)$OR^8$, —($C_1$-$C_3$ alkylene)$SR^8$, —($C_1$-$C_3$ alkylene)$NR^9R^{10}$, —($C_1$-$C_3$ alkylene)$CF_3$, —($C_1$-$C_3$ alkylene)$NO_2$, —C=NH($OR^8$), —($C_1$-$C_3$ alkylene)C(O)$R^8$, —($C_1$-$C_3$ alkylene)OC(O)$R^8$, —($C_1$-$C_3$ alkylene)C(O)$OR^8$, —($C_1$-$C_3$ alkylene)C(O)$NR^9R^{10}$, —($C_1$-$C_3$ alkylene)OC(O)$NR^9R^{10}$, —($C_1$-$C_3$ alkylene)$NR^8$C(O)$R^9$, —($C_1$-$C_3$ alkylene)$NR^8$C(O)$OR^9$, —($C_1$-$C_3$ alkylene)$NR^8$C(O)$NR^9R^{10}$, —($C_1$-$C_3$ alkylene)S(O)$R^8$, —($C_1$-$C_3$ alkylene)S(O)$_2R^8$, —($C_1$-$C_3$ alkylene)$NR^8$S(O)$R^9$, —C(O)($C_1$-$C_3$ alkylene)$NR^8$S(O)$R^9$, —($C_1$-$C_3$ alkylene)$NR^8$S(O)$_2R^9$, —($C_1$-$C_3$ alkylene)C(O)$NR^8$S(O)$_2R^9$, —($C_1$-$C_3$ alkylene)S(O)$NR^9R^{10}$, —($C_1$-$C_3$ alkylene)S(O)$_2NR^9R^{10}$, —($C_1$-$C_3$ alkylene)P(O)($OR^9$)($OR^{10}$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or —($C_1$-$C_3$ alkylene)($C_6$-$C_{14}$ aryl), wherein each $R^{6g}$, $R^{6b}$, and $R^{6c}$ is independently optionally substituted by halogen, oxo, —$OR^{11}$, —$NR^{11}R^{12}$, —C(O)$R^{11}$, —CN, —S(O)$R^{11}$, —S(O)$_2R^{11}$, —P(O)($OR^{11}$)($OR^{12}$), —($C_1$-$C_3$ alkylene)$OR^{11}$, —($C_1$-$C_3$ alkylene)$NR^{11}R^{12}$, —($C_1$-$C_3$ alkylene)C(O)$R^{11}$, —($C_1$-$C_3$ alkylene)S(O)$R^{11}$, —($C_1$-$C_3$ alkylene)S(O)$_2R^{11}$, —($C_1$-$C_3$ alkylene)P(O)(OR)($OR^{12}$), $C_3$-$C_8$ cycloalkyl, or $C_1$-$C_6$ alkyl optionally substituted by oxo, —OH or halogen.

In some embodiments of a compound of Formula (I), (II), or (III), A is

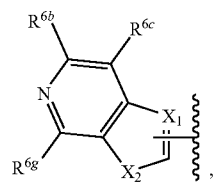

wherein $X^1$ is selected from the group consisting of N, C, and CH; $X^2$ is selected from the group consisting of NH, O, and S; and $R^{6g}$, $R^{6b}$, and $R^{6c}$ are each independently H, $C_1$-$C_6$ alkyl, halogen, —CN, or —O$C_1$-$C_6$ alkyl. In some embodiments of a compound of Formula (I), (II), or (III), A is

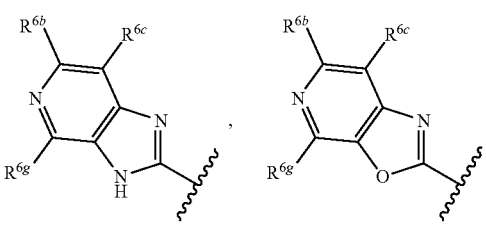

-continued

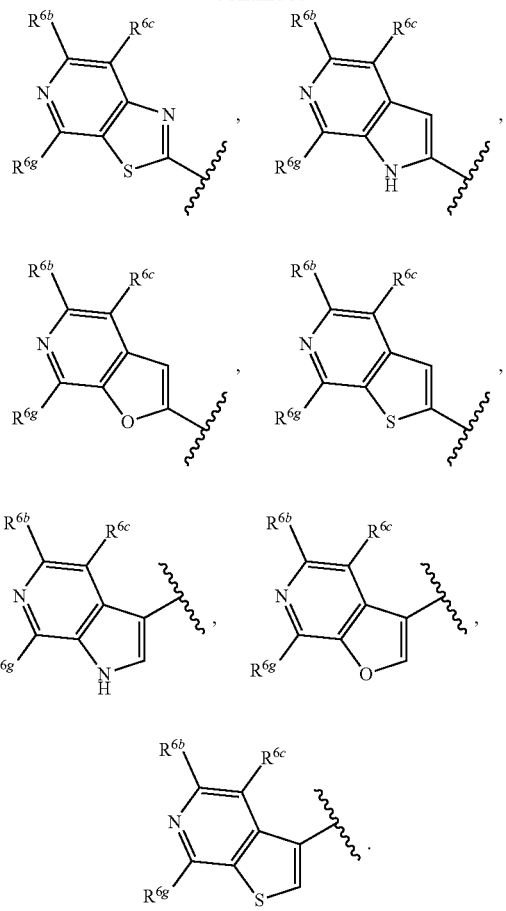

In some embodiments, $R^{6g}$, $R^{6b}$, and $R^{6c}$ are each H. In some embodiments, one of $R^{6g}$, $R^{6b}$, and $R^{6c}$ is Cl, F, Br, or I. In some embodiments, one of $R^{6g}$, $R^{6b}$, and $R^{6c}$ is Cl. In some embodiments, one of $R^{6g}$, $R^{6b}$, and $R^{6c}$ is halogen and the others are each H. In some embodiments, one of $R^{6g}$, $R^{6b}$, and $R^{6c}$ is halogen and one of $R^{6g}$, $R^{6b}$, and $R^{6c}$ is $C_1$-$C_6$ alkyl. In some embodiments, one of $R^{6g}$, $R^{6b}$, and $R^{6c}$ is Cl and one of $R^{6g}$, $R^{6b}$, and $R^{6c}$ is methyl. In some embodiments, $R^{6g}$ is $C_1$-$C_6$ alkyl. In some embodiments, $R^{6b}$ is $C_1$-$C_6$ alkyl. In some embodiments, $R^{6c}$ is $C_1$-$C_6$ alkyl. In some embodiments, $R^{6g}$ is methyl, ethyl, n-propyl, isopropyl, n-butyl, isobutyl, secbutyl, or tertbutyl. In some embodiments, $R^{6b}$ is methyl, ethyl, n-propyl, isopropyl, n-butyl, isobutyl, secbutyl, or tertbutyl. In some embodiments, $R^{6c}$ is methyl, ethyl, n-propyl, isopropyl, n-butyl, isobutyl, secbutyl, or tertbutyl. In some embodiments, $R^{6g}$ is $C_1$-$C_6$ alkyl and $R^{6b}$ is halogen. In some embodiments, $R^{6g}$ is $C_1$-$C_6$ alkyl and $R^{6c}$ is halogen. In some embodiments, $R^{6b}$ is $C_1$-$C_6$ alkyl and $R^{6g}$ is halogen. In some embodiments, $R^{6b}$ is $C_1$-$C_6$ alkyl and $R^{6c}$ is halogen. In some embodiments, $R^{6c}$ is $C_1$-$C_6$ alkyl and $R^{6g}$ is halogen. In some embodiments, $R^{6c}$ is $C_1$-$C_6$ alkyl and $R^{6b}$ is halogen. In some embodiments, two of $R^{6g}$, $R^{6b}$, and $R^{6c}$ are halogen. In some embodiments, two of $R^{6g}$, $R^{6b}$, and $R^{6c}$ are $C_1$-$C_6$ alkyl.

In some embodiments of a compound of Formula (I), (II), or (III), A is

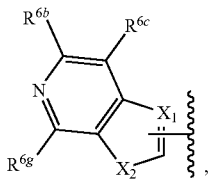

wherein one or two of $R^{6b}$, and $R^{6c}$ are independently selected from the group consisting of $C_1$-$C_6$ alkyl, halogen, —CN, and —$OC_1$-$C_6$ alkyl, and the remainder of $R^{6g}$, $R^{6b}$, and $R^{6c}$ are each H; and B is phenyl, optionally substituted with $R^7$.

In some embodiments of a compound of Formula (I), (II), or (III), A is

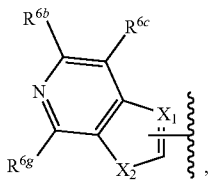

wherein one or two of $R^{6g}$, $R^{6b}$, and $R^{6c}$ are independently selected from the group consisting of $C_1$-$C_6$ alkyl, halogen, —CN, and —$OC_1$-$C_6$ alkyl, and the remainder of $R^{6g}$, $R^{6b}$, and $R^{6c}$ are each H; and B is a 5- to 6-membered carbocycle, optionally substituted with $R^7$.

In some embodiments of a compound of Formula (I), (II), or (III), A is

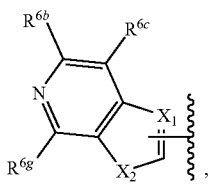

wherein one or two of $R^{6g}$, $R^{6b}$, and $R^{6c}$ are independently selected from the group consisting of $C_1$-$C_6$ alkyl, halogen, —CN, and —$OC_1$-$C_6$ alkyl, and the remainder of $R^{6g}$, $R^{6b}$, and $R^{6c}$ are each H; and B is a 5- to 6-membered heterocycle, optionally substituted with $R^7$.

In some embodiments of a compound of Formula (I), (II), or (III), A is

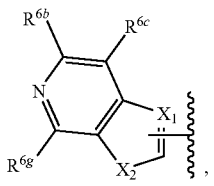

wherein one or two of $R^{6g}$, $R^{6b}$, and $R^{6c}$ are independently selected from the group consisting of $C_1$-$C_6$ alkyl, halogen, —CN, and —$OC_1$-$C_6$ alkyl, and the remainder of $R^{6g}$, $R^{6b}$, and $R^{6c}$ are each H; and B is a 9- to 10-membered heteroaryl, optionally substituted with $R^7$.

In some embodiments of a compound of Formula (I), (II), or (III), A is

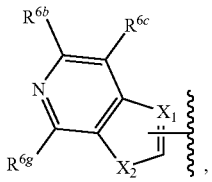

wherein one or two of R$^{6g}$, R$^{6b}$, and R$^{6c}$ are independently selected from the group consisting of C$_1$-C$_6$ alkyl, halogen, —CN, and —OC$_1$-C$_6$ alkyl, and the remainder of R$^{6g}$, R$^{6b}$, and R$^{6c}$ are each H; and B is a 9- to 10-membered heteroaryl, optionally substituted with R$^7$.

In some embodiments of a compound of Formula (I), (II), or (III), A is

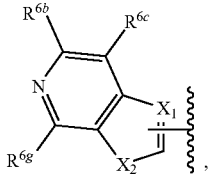

wherein one or two of R$^{6g}$, R$^{6b}$, and R$^{6c}$ are independently selected from the group consisting of C$_1$-C$_6$ alkyl, halogen, —CN, and —OC$_1$-C$_6$ alkyl, and the remainder of R$^{6g}$, R$^{6b}$, and R$^{6c}$ are each H; and B is selected from the group consisting of:

-continued

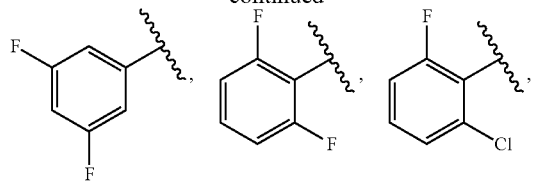
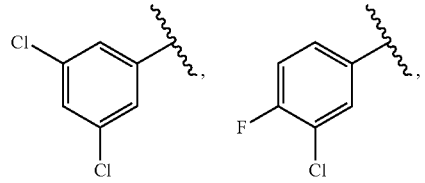
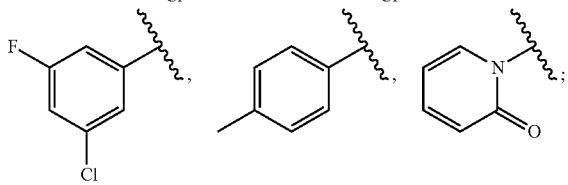
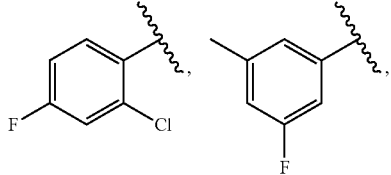
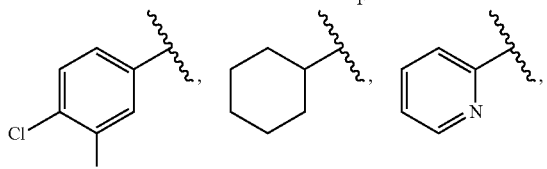
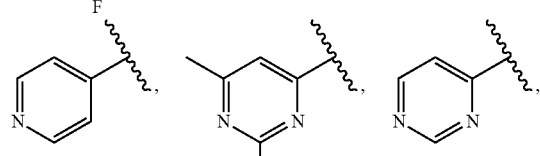
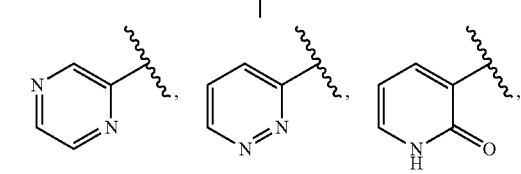
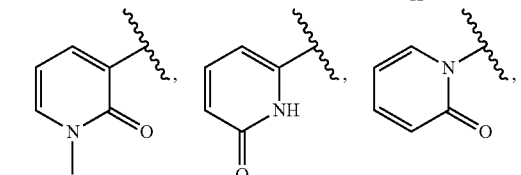
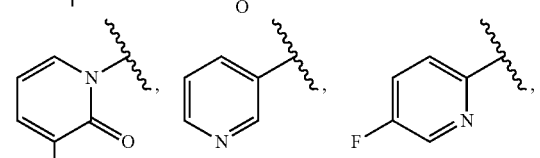
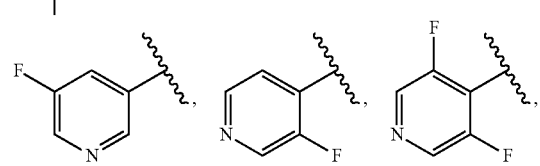

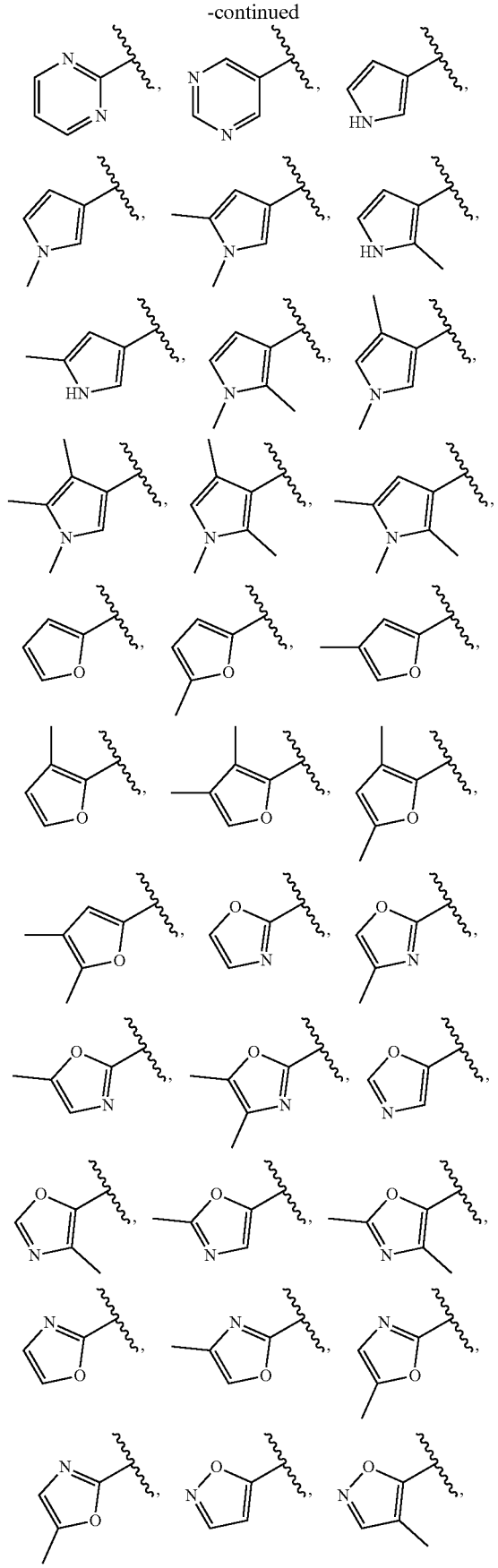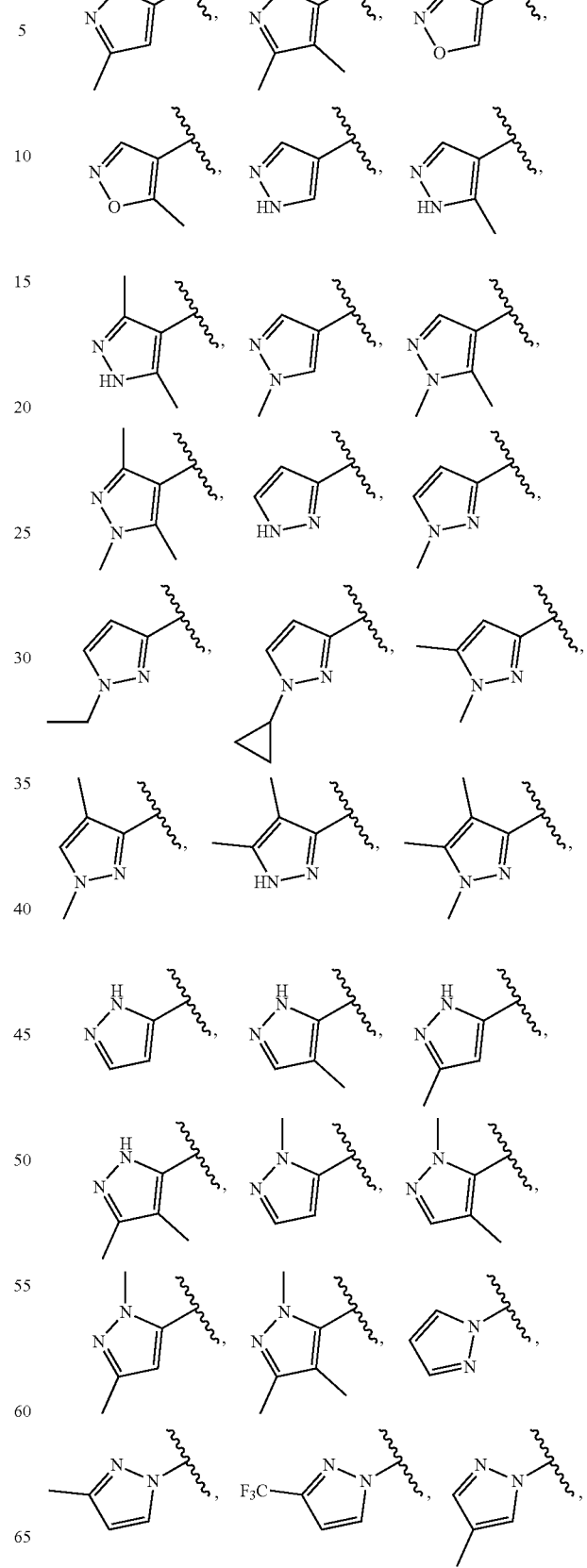

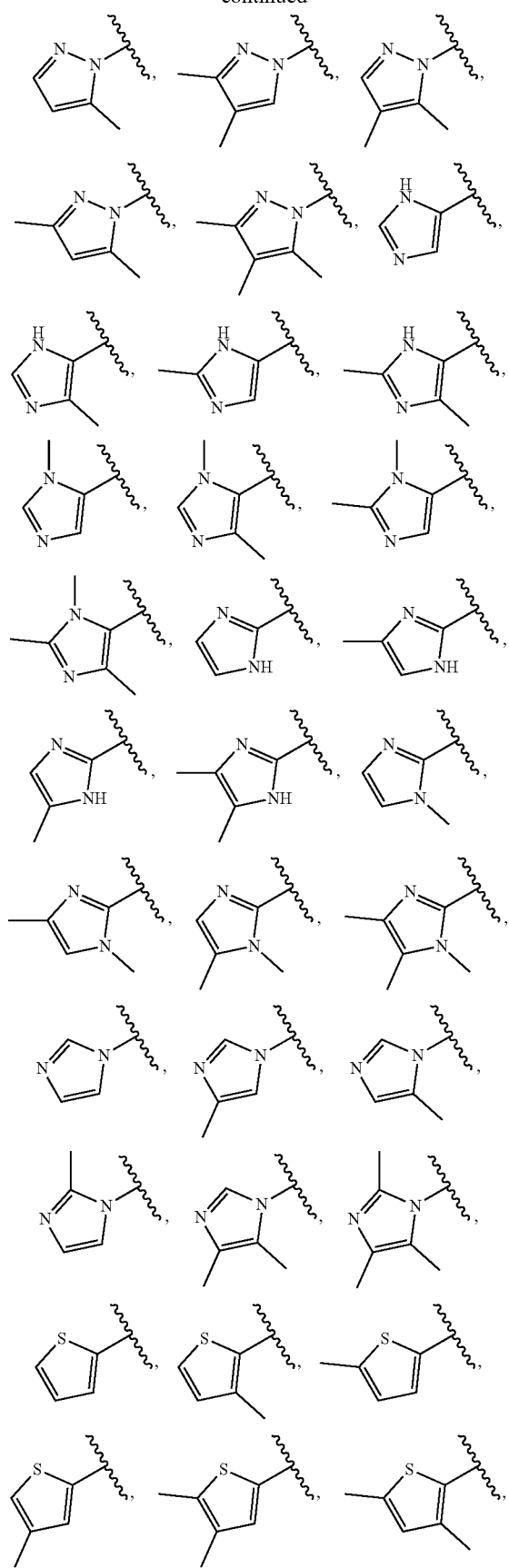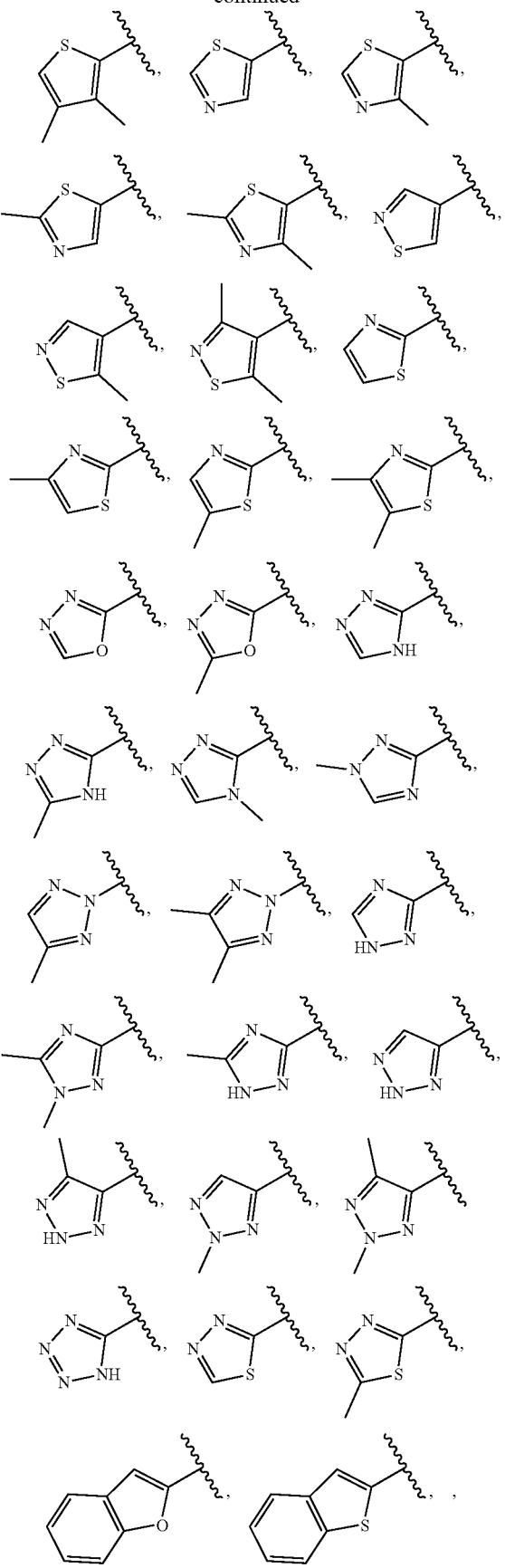

-continued

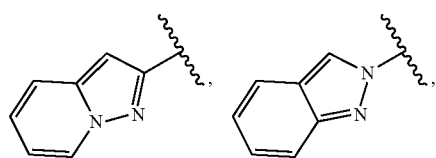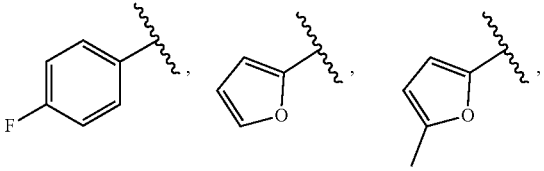

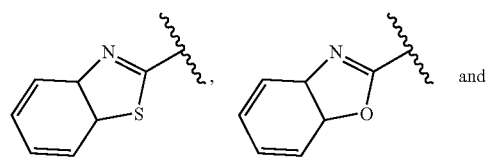 and

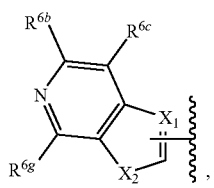

In some embodiments of a compound of Formula (I), (II), or (III), A is

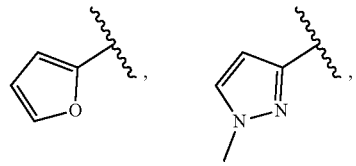

wherein one or two of $R^{6g}$, $R^{6b}$, and $R^{6c}$ are independently selected from the group consisting of $C_1$-$C_6$ alkyl, halogen, —CN, and —O$C_1$-$C_6$ alkyl, and the remainder of $R^{6g}$, $R^{6b}$, and $R^{6c}$ are each H; and B is selected from the group consisting of:

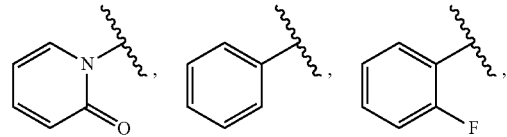

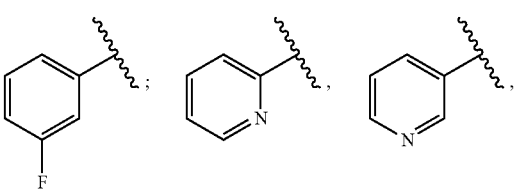

-continued

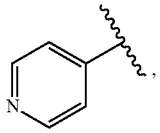, 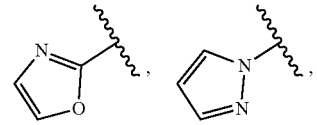

, 

, 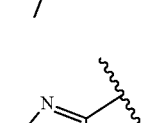, 

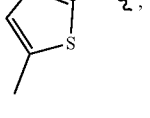, 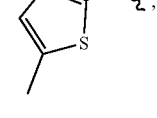, 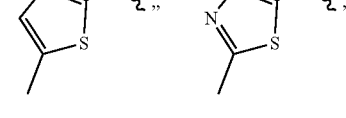

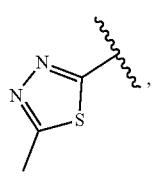, 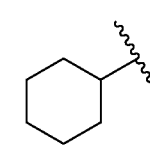, 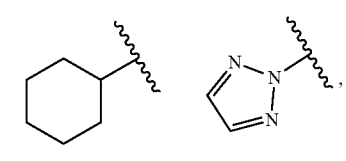

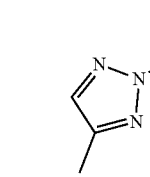, 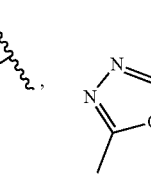, 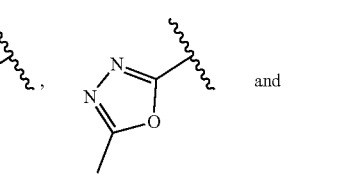

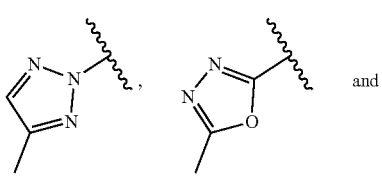 and

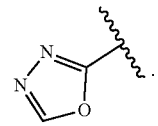

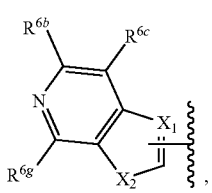.

In some embodiments of a compound of Formula (I), (II), or (III), A is wherein one or two of $R^{6g}$, $R^{6b}$, and $R^{6c}$ are independently selected from the group consisting of $C_1$-$C_6$ alkyl, halogen, —CN, and —O$C_1$-$C_6$ alkyl, and the remainder of $R^{6g}$, $R^{6b}$, and $R^{6c}$ are each H; and B is selected from the group consisting of

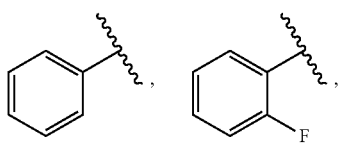

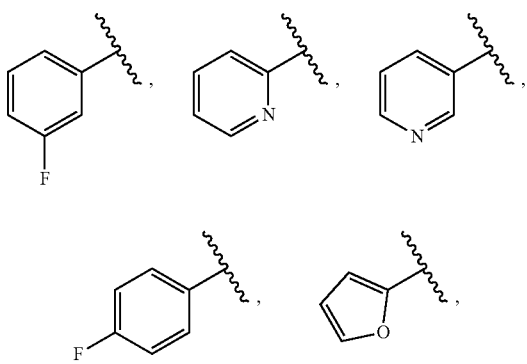

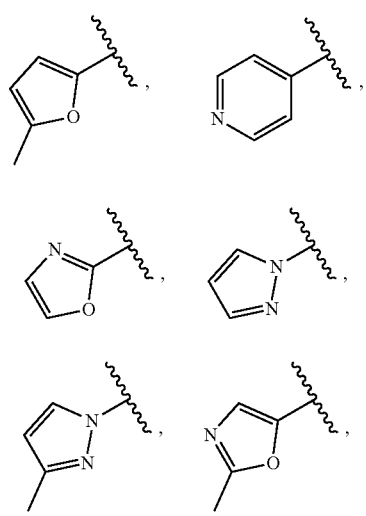

-continued

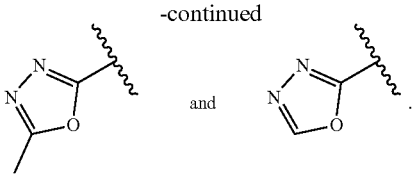

In some embodiments of a compound of Formula (I), (II), or (III), A is

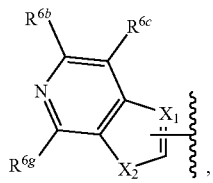

wherein one or two of $R^{6g}$, $R^{6b}$, and $R^{6c}$ are independently selected from the group consisting of $C_1$-$C_6$ alkyl, halogen, —CN, and —$OC_1$-$C_6$ alkyl, and the remainder of $R^{6g}$, $R^{6b}$, and $R^{6c}$ are each H; and B is selected from

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Table 1. It is understood that individual enantiomers and diastereomers if not depicted are embraced herein and their corresponding structures can be readily determined therefrom.

TABLE 1

| Compound No. | Compound |
|---|---|
| 1.1 | 6-(3-chloro-4-hydroxyphenyl)-7-phenyl-1,8-naphthyridin-2(1H)-one |
| 1.2 | 6-(3-chloro-4-hydroxyphenyl)-7-phenyl-1,8-naphthyridin-4(1H)-one |
| 1.3 | 6-(2,6-dimethylpyridin-4-yl)-7-phenyl-1,8-naphthyridin-4(1H)-one |
| 1.4 | 7-phenyl-6-(quinolin-6-yl)-1,8-naphthyridin-2(1H)-one |
| 1.5 | 7-phenyl-6-(quinolin-6-yl)-1,8-naphthyridin-4(1H)-one |

TABLE 1-continued

| Compound No. | Compound |
|---|---|
| 1.6 | |
| 1.7 | |
| 1.8 | |
| 1.9 | |
| 1.10 | |

TABLE 1-continued

| Compound No. | Compound |
|---|---|
| 1.11 | |
| 1.12 | |
| 1.13 | |
| 1.14 | |
| 1.15 | |

TABLE 1-continued
| Compound No. | Compound |
|---|---|
| 1.16 | 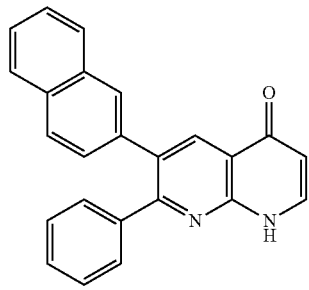 [SMILES: O=c1cc[nH]c2nc(-c3ccccc3)c(-c3ccc4ccccc4c3)cc12] |
| 1.17 | 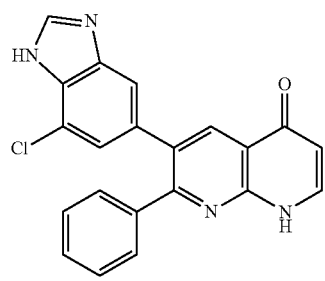 [SMILES: O=c1cc[nH]c2nc(-c3ccccc3)c(-c3cc(Cl)c4[nH]cnc4c3)cc12] |
| 1.18 | 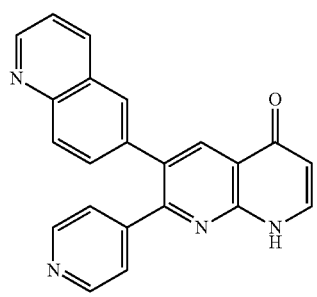 [SMILES: O=c1cc[nH]c2nc(-c3ccncc3)c(-c3ccc4ncccc4c3)cc12] |
| 1.19 | 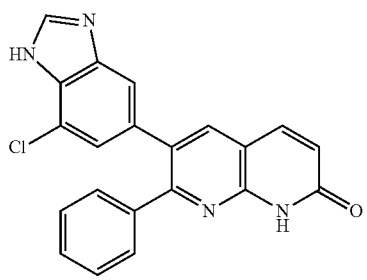 [SMILES: O=c1ccc2cc(-c3cc(Cl)c4[nH]cnc4c3)c(-c3ccccc3)nc2[nH]1] |
| 1.20 | 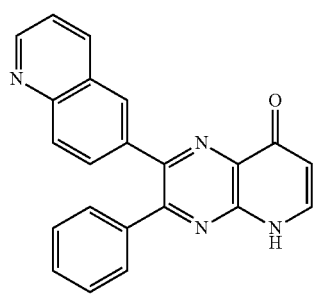 [SMILES: O=c1cc[nH]c2nc(-c3ccccc3)c(-c3ccc4ncccc4c3)nc12] |

TABLE 1-continued

| Compound No. | Compound |
|---|---|
| 1.21 | (benzoxazol-5-yl substituted 2-phenyl-1,8-naphthyridin-4(1H)-one) |
| 1.22 | (1-methyl-1H-benzimidazol-5-yl substituted 2-phenyl-1,8-naphthyridin-4(1H)-one) |
| 1.23 | (8-methylquinolin-6-yl substituted 2-phenyl-1,8-naphthyridin-4(1H)-one) |
| 1.24 | (benzothiazol-6-yl substituted 2-phenyl-1,8-naphthyridin-4(1H)-one) |
| 1.25 | (quinolin-6-yl substituted 2-(5-methylfuran-2-yl)-1,8-naphthyridin-4(1H)-one) |

TABLE 1-continued
| Compound No. | Compound |
|---|---|
| 1.26 | 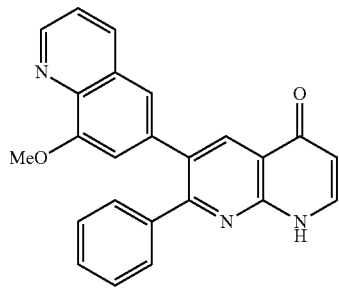 [SMILES: COc1cc(-c2cc3c(=O)cc[nH]c3nc2-c2ccccc2)cc2cccnc12] |
| 1.27 | 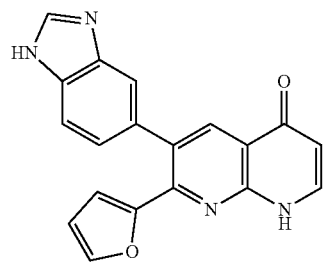 [SMILES: O=c1cc[nH]c2nc(-c3ccco3)c(-c3ccc4[nH]cnc4c3)cc12] |
| 1.28 | 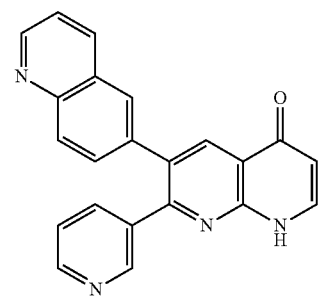 [SMILES: O=c1cc[nH]c2nc(-c3cccnc3)c(-c3ccc4ncccc4c3)cc12] |
| 1.29 | 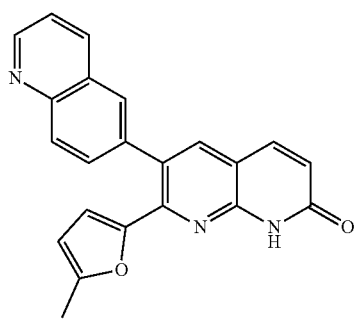 [SMILES: Cc1ccc(-c2nc3[nH]c(=O)ccc3cc2-c2ccc3ncccc3c2)o1] |
| 1.30 | 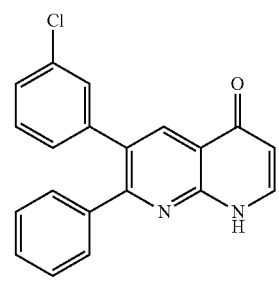 [SMILES: O=c1cc[nH]c2nc(-c3ccccc3)c(-c3cccc(Cl)c3)cc12] |

TABLE 1-continued
| Compound No. | Compound |
|---|---|
| 1.31 | 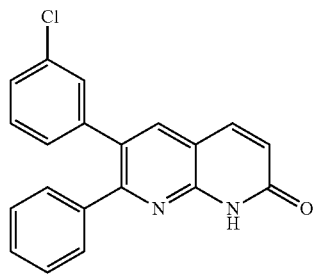 [SMILES: O=c1ccc2cc(-c3cccc(Cl)c3)c(-c3ccccc3)nc2[nH]1] |
| 1.32 | 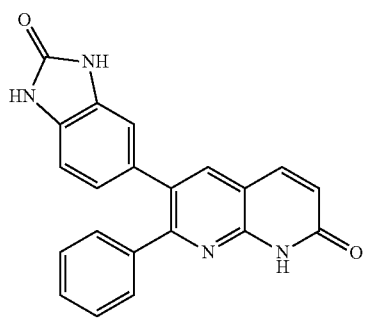 [SMILES: O=c1ccc2cc(-c3ccc4[nH]c(=O)[nH]c4c3)c(-c3ccccc3)nc2[nH]1] |
| 1.33 | 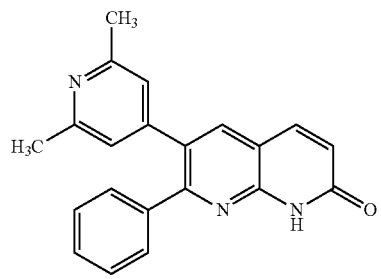 [SMILES: Cc1cc(-c2cc3ccc(=O)[nH]c3nc2-c2ccccc2)cc(C)n1] |
| 1.34 | 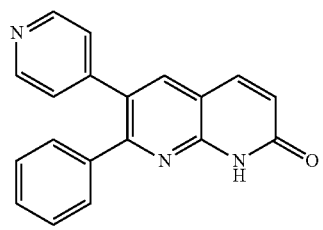 [SMILES: O=c1ccc2cc(-c3ccncc3)c(-c3ccccc3)nc2[nH]1] |
| 1.35 | 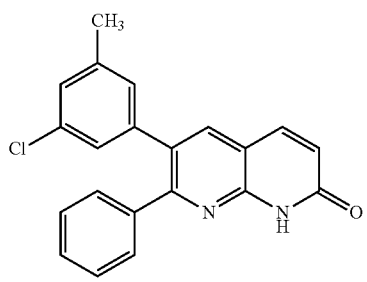 [SMILES: Cc1cc(Cl)cc(-c2cc3ccc(=O)[nH]c3nc2-c2ccccc2)c1] |

TABLE 1-continued
| Compound No. | Compound |
|---|---|
| 1.36 | 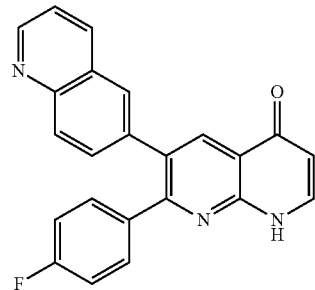 [SMILES: O=c1cc[nH]c2nc(-c3ccc(F)cc3)c(-c3ccc4ncccc4c3)cc12] |
| 1.37 | 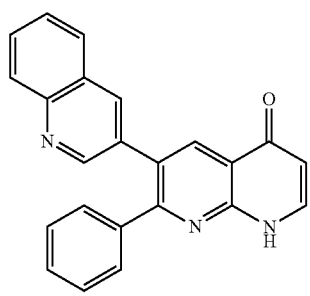 [SMILES: O=c1cc[nH]c2nc(-c3ccccc3)c(-c3cnc4ccccc4c3)cc12] |
| 1.38 | 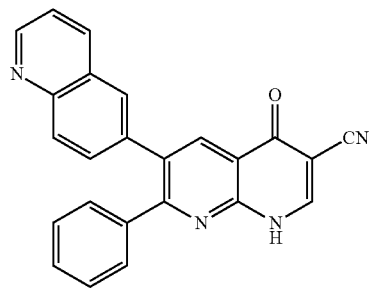 [SMILES: N#Cc1c[nH]c2nc(-c3ccccc3)c(-c3ccc4ncccc4c3)cc2c1=O] |
| 1.39 | 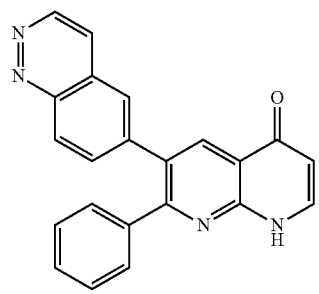 [SMILES: O=c1cc[nH]c2nc(-c3ccccc3)c(-c3ccc4nnccc4c3)cc12] |
| 1.40 | 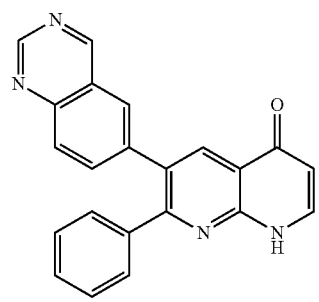 [SMILES: O=c1cc[nH]c2nc(-c3ccccc3)c(-c3ccc4ncncc4c3)cc12] |

TABLE 1-continued

| Compound No. | Compound |
|---|---|
| 1.41 | (structure: 3-(quinolin-6-yl)-2-(oxazol-2-yl)-1,8-naphthyridin-4(1H)-one) |
| 1.42 | (structure: 3-(quinolin-6-yl)-2-(1,3,4-oxadiazol-2-yl)-1,8-naphthyridin-4(1H)-one) |
| 1.43 | (structure: 3-(benzo[d]oxazol-6-yl)-2-phenyl-1,8-naphthyridin-4(1H)-one) |
| 1.44 | (structure: 3-(1-methyl-1H-benzo[d]imidazol-6-yl)-2-phenyl-1,8-naphthyridin-4(1H)-one) |
| 1.45 | (structure: 2-methyl-7-phenyl-6-(quinolin-6-yl)-1,8-naphthyridin-4(1H)-one) |

TABLE 1-continued
| Compound No. | Compound |
|---|---|
| 1.46 | 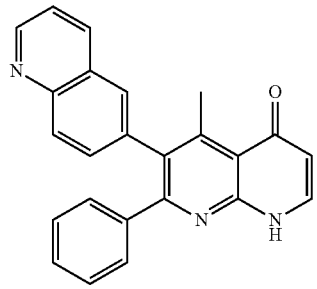 [SMILES: Cc1c(-c2ccc3ncccc3c2)c(-c2ccccc2)nc2[nH]ccc(=O)c12] |
| 1.47 | 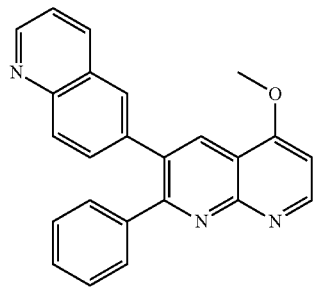 [SMILES: COc1ccnc2nc(-c3ccccc3)c(-c3ccc4ncccc4c3)cc12] |
| 1.48 | 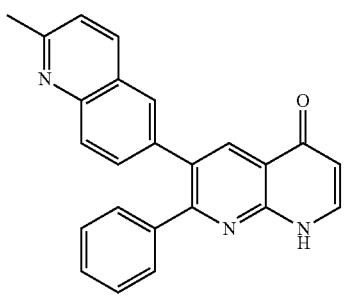 [SMILES: Cc1ccc2cc(-c3cc4c(=O)cc[nH]c4nc3-c3ccccc3)ccc2n1] |
| 1.49 | 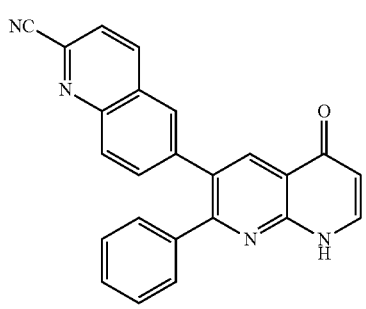 [SMILES: N#Cc1ccc2cc(-c3cc4c(=O)cc[nH]c4nc3-c3ccccc3)ccc2n1] |
| 1.50 | 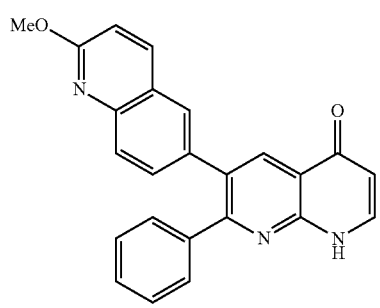 [SMILES: COc1ccc2cc(-c3cc4c(=O)cc[nH]c4nc3-c3ccccc3)ccc2n1] |

TABLE 1-continued

| Compound No. | Compound |
|---|---|
| 1.51 | |
| 1.52 | |
| 1.53 | |
| 1.54 | |
| 1.55 | |

TABLE 1-continued
| Compound No. | Compound |
|---|---|
| 1.56 | 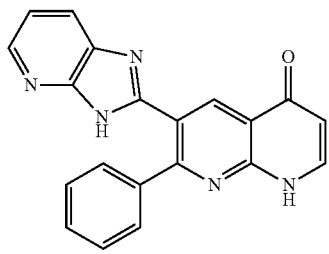 [SMILES: O=c1cc[nH]c2nc(-c3ccccc3)c(-c3nc4cccnc4[nH]3)cc12] |
| 1.57 | 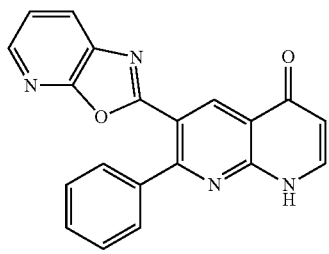 [SMILES: O=c1cc[nH]c2nc(-c3ccccc3)c(-c3nc4cccnc4o3)cc12] |
| 1.58 | 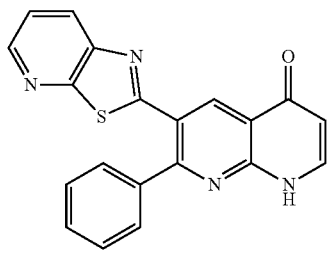 [SMILES: O=c1cc[nH]c2nc(-c3ccccc3)c(-c3nc4cccnc4s3)cc12] |
| 1.59 | 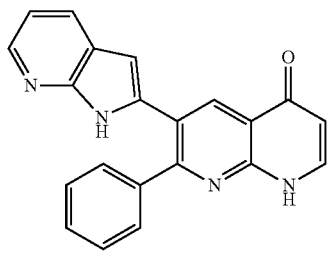 [SMILES: O=c1cc[nH]c2nc(-c3ccccc3)c(-c3cc4cccnc4[nH]3)cc12] |
| 1.60 | 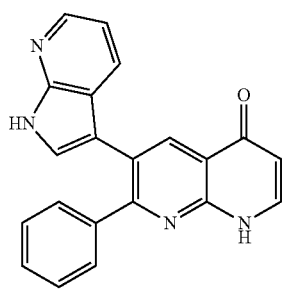 [SMILES: O=c1cc[nH]c2nc(-c3ccccc3)c(-c3c[nH]c4ncccc34)cc12] |

TABLE 1-continued
| Compound No. | Compound |
|---|---|
| 1.61 | 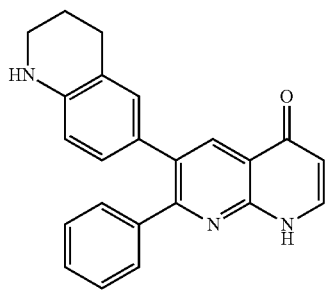 [SMILES: O=c1cc[nH]c2nc(-c3ccccc3)c(-c3ccc4c(c3)CCCN4)cc12] |
| 1.62 | 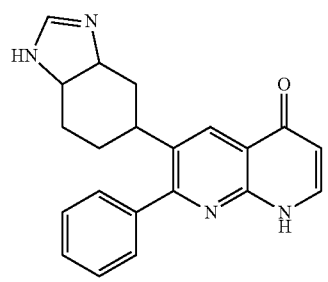 [SMILES: O=c1cc[nH]c2nc(-c3ccccc3)c(C3CCC4NC=NC4C3)cc12] |
| 1.63 | 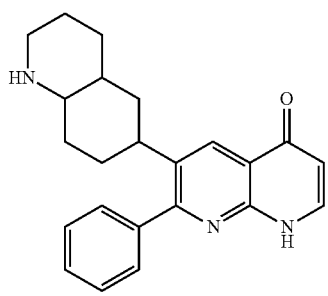 [SMILES: O=c1cc[nH]c2nc(-c3ccccc3)c(C3CCC4NCCCC4C3)cc12] |
| 1.64 | 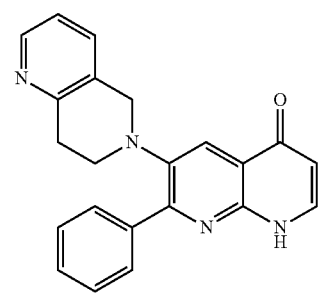 [SMILES: O=c1cc[nH]c2nc(-c3ccccc3)c(N3CCc4ncccc4C3)cc12] |
| 1.65 | 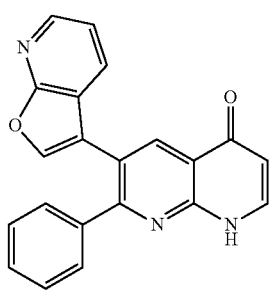 [SMILES: O=c1cc[nH]c2nc(-c3ccccc3)c(-c3coc4ncccc34)cc12] |

TABLE 1-continued
| Compound No. | Compound |
|---|---|
| 1.66 | 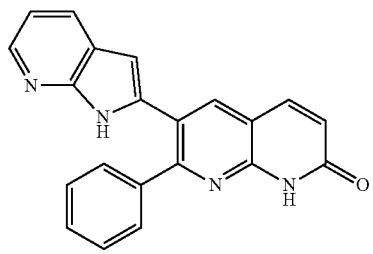 [SMILES: O=c1ccc2cc(-c3cc4cccnc4[nH]3)c(-c3ccccc3)nc2[nH]1] |
| 1.67 | 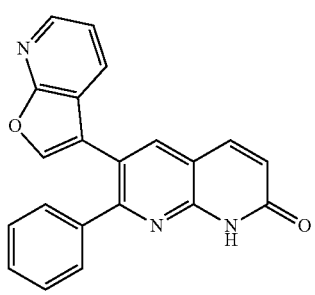 [SMILES: O=c1ccc2cc(-c3coc4ncccc34)c(-c3ccccc3)nc2[nH]1] |
| 1.68 | 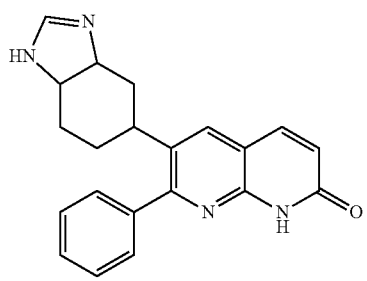 [SMILES: O=c1ccc2cc(C3CCC4NC=NC4C3)c(-c3ccccc3)nc2[nH]1] |
| 1.69 | 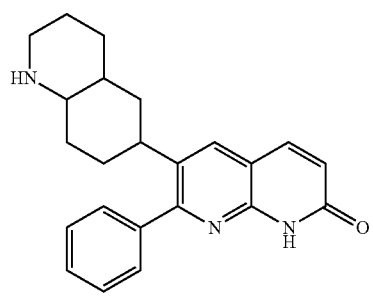 [SMILES: O=c1ccc2cc(C3CCC4NCCCC4C3)c(-c3ccccc3)nc2[nH]1] |
| 1.70 | 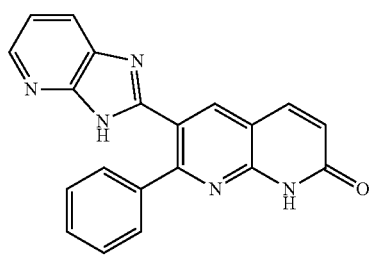 [SMILES: O=c1ccc2cc(-c3nc4cccnc4[nH]3)c(-c3ccccc3)nc2[nH]1] |

119 120
TABLE 1-continued
| Compound No. | Compound |
|---|---|
| 1.71 | 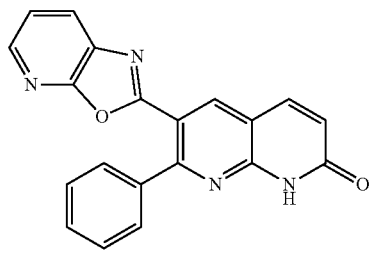 [SMILES: O=c1ccc2cc(-c3nc4cccnc4o3)c(-c3ccccc3)nc2[nH]1] |
| 1.72 | 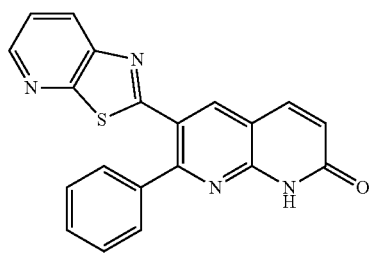 [SMILES: O=c1ccc2cc(-c3nc4cccnc4s3)c(-c3ccccc3)nc2[nH]1] |
| 1.73 | 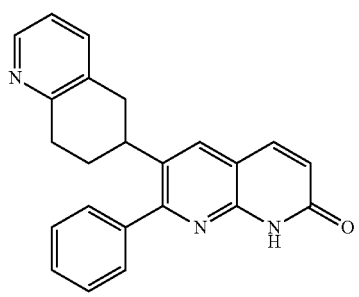 [SMILES: O=c1ccc2cc(C3CCc4ncccc4C3)c(-c3ccccc3)nc2[nH]1] |
| 1.74 | 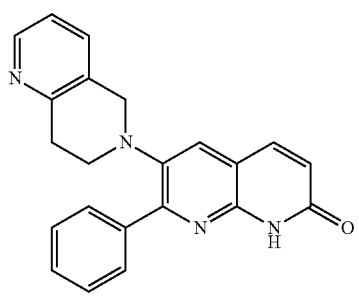 [SMILES: O=c1ccc2cc(N3CCc4ncccc4C3)c(-c3ccccc3)nc2[nH]1] |
| 1.75 | 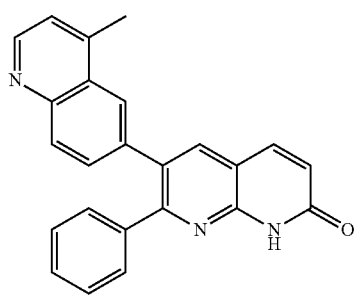 [SMILES: Cc1ccnc2ccc(-c3cc4ccc(=O)[nH]c4nc3-c3ccccc3)cc12] |

TABLE 1-continued
| Compound No. | Compound |
|---|---|
| 1.76 | 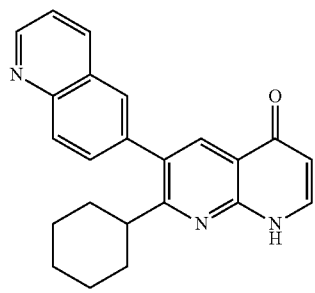 [SMILES: O=c1cc[nH]c2nc(C3CCCCC3)c(-c3ccc4ncccc4c3)cc12] |
| 1.77 | 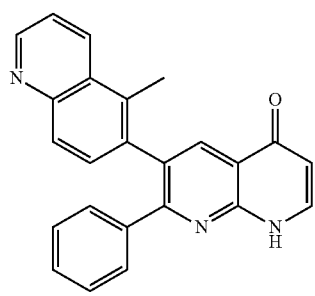 [SMILES: Cc1c(-c2cc3c(=O)cc[nH]c3nc2-c2ccccc2)ccc2ncccc12] |
| 1.78 | 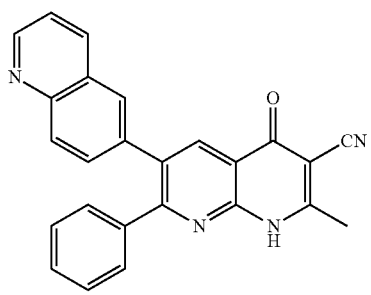 [SMILES: Cc1[nH]c2nc(-c3ccccc3)c(-c3ccc4ncccc4c3)cc2c(=O)c1C#N] |
| 1.79 | 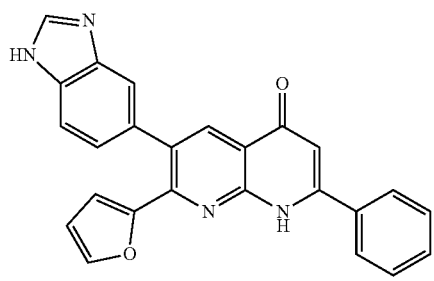 [SMILES: O=c1cc(-c2ccccc2)[nH]c2nc(-c3ccco3)c(-c3ccc4[nH]cnc4c3)cc12] |
| 1.80 | 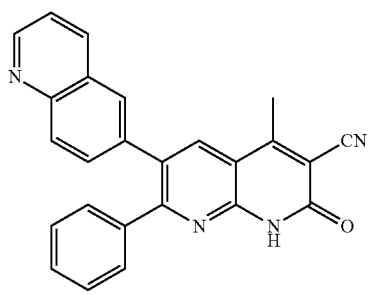 [SMILES: Cc1c(C#N)c(=O)[nH]c2nc(-c3ccccc3)c(-c3ccc4ncccc4c3)cc12] |

TABLE 1-continued
| Compound No. | Compound |
|---|---|
| 1.81 | 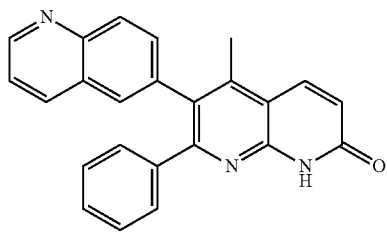 [SMILES: Cc1c(-c2ccc3ncccc3c2)c(-c2ccccc2)nc2[nH]c(=O)ccc12] |
| 1.82 | 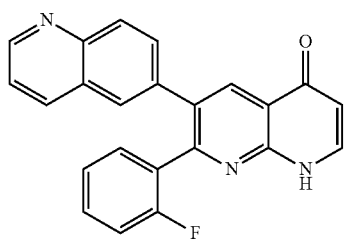 [SMILES: O=c1cc[nH]c2nc(-c3ccccc3F)c(-c3ccc4ncccc4c3)cc12] |
| 1.83 | 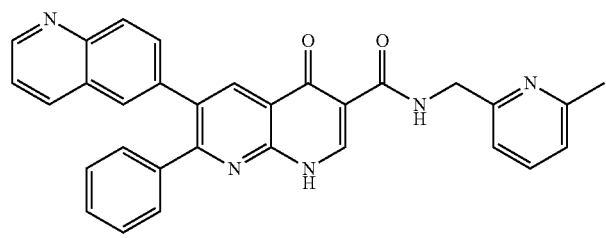 [SMILES: Cc1cccc(CNC(=O)c2c[nH]c3nc(-c4ccccc4)c(-c4ccc5ncccc5c4)cc3c2=O)n1] |
| 1.84 | 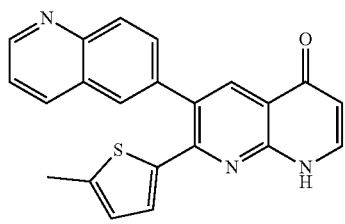 [SMILES: Cc1ccc(-c2nc3[nH]ccc(=O)c3cc2-c2ccc3ncccc3c2)s1] |
| 1.85 | 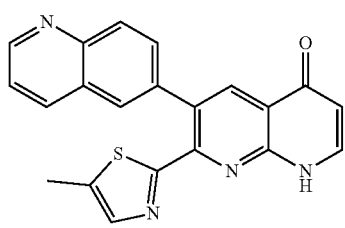 [SMILES: Cc1cnc(-c2nc3[nH]ccc(=O)c3cc2-c2ccc3ncccc3c2)s1] |
| 1.86 | 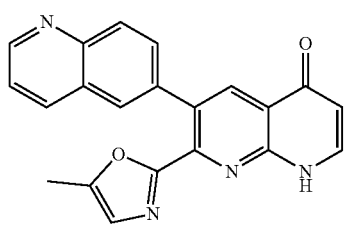 [SMILES: Cc1cnc(-c2nc3[nH]ccc(=O)c3cc2-c2ccc3ncccc3c2)o1] |

TABLE 1-continued
| Compound No. | Compound |
|---|---|
| 1.87 | 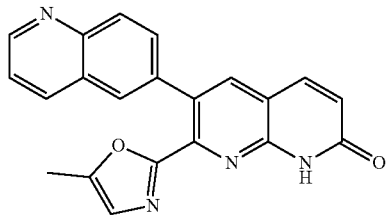 [SMILES: Cc1cnc(-c2nc3[nH]c(=O)ccc3cc2-c2ccc3ncccc3c2)o1] |
| 1.88 | 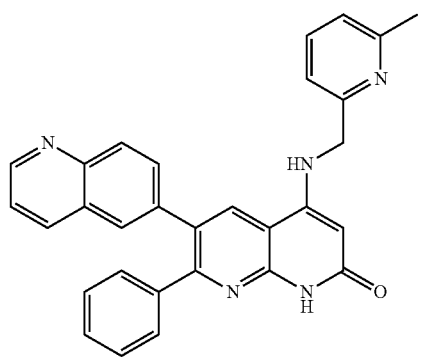 [SMILES: Cc1cccc(CNc2cc(=O)[nH]c3nc(-c4ccccc4)c(-c4ccc5ncccc5c4)cc23)n1] |
| 1.89 | 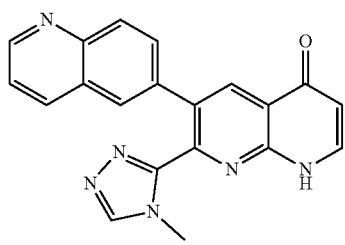 [SMILES: Cn1cnnc1-c1nc2[nH]ccc(=O)c2cc1-c1ccc2ncccc2c1] |
| 1.90 | 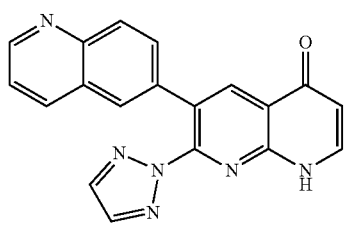 [SMILES: O=c1cc[nH]c2nc(-n3nccn3)c(-c3ccc4ncccc4c3)cc12] |
| 1.91 | 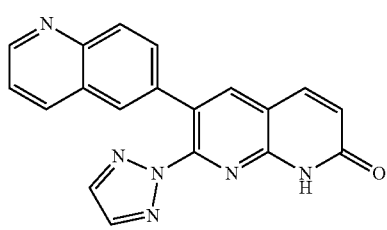 [SMILES: O=c1ccc2cc(-c3ccc4ncccc4c3)c(-n3nccn3)nc2[nH]1] |
| 1.92 | 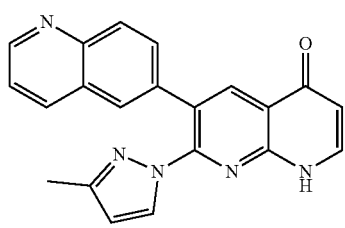 [SMILES: Cc1ccn(-c2nc3[nH]ccc(=O)c3cc2-c2ccc3ncccc3c2)n1] |

TABLE 1-continued
| Compound No. | Compound |
|---|---|
| 1.93 | 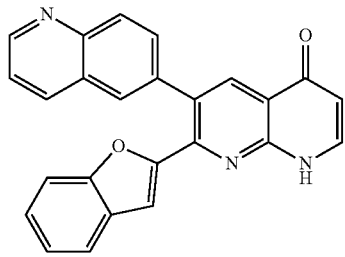 [SMILES: O=c1cc[nH]c2nc(-c3cc4ccccc4o3)c(-c3ccc4ncccc4c3)cc12] |
| 1.94 | 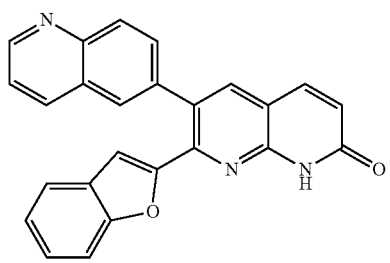 [SMILES: O=c1ccc2cc(-c3ccc4ncccc4c3)c(-c3cc4ccccc4o3)nc2[nH]1] |
| 1.95 | 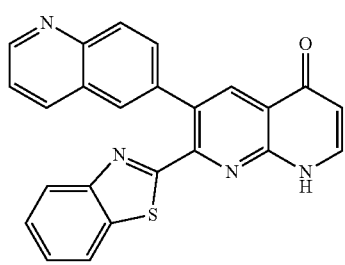 [SMILES: O=c1cc[nH]c2nc(-c3nc4ccccc4s3)c(-c3ccc4ncccc4c3)cc12] |
| 1.96 | 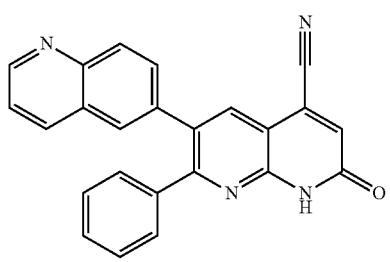 [SMILES: N#Cc1cc(=O)[nH]c2nc(-c3ccccc3)c(-c3ccc4ncccc4c3)cc12] |
| 1.97 | 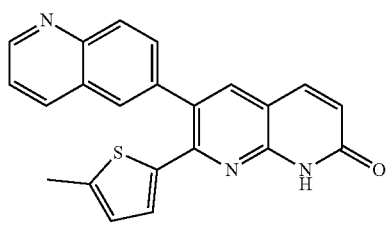 [SMILES: Cc1ccc(-c2nc3[nH]c(=O)ccc3cc2-c2ccc3ncccc3c2)s1] |
| 1.98 | 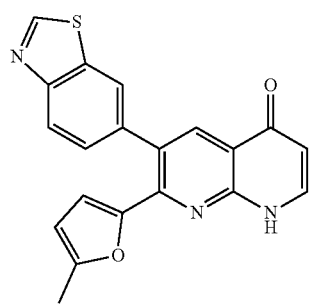 [SMILES: Cc1ccc(-c2nc3[nH]ccc(=O)c3cc2-c2ccc3ncsc3c2)o1] |

TABLE 1-continued

| Compound No. | Compound |
|---|---|
| 1.99 | |
| 1.100 | |
| 1.101 | |
| 1.102 | |
| 1.103 | |

US 10,793,561 B2
TABLE 1-continued
| Compound No. | Compound |
|---|---|
| 1.104 | 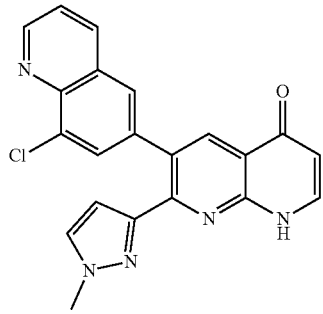 [SMILES: Cn1ccc(-c2nc3[nH]ccc(=O)c3cc2-c2cc(Cl)c3ncccc3c2)n1] |
| 1.105 | 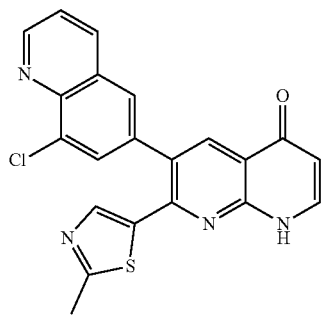 [SMILES: Cc1ncc(-c2nc3[nH]ccc(=O)c3cc2-c2cc(Cl)c3ncccc3c2)s1] |
| 1.106 | 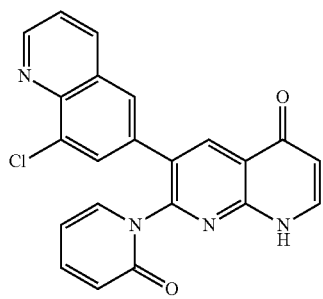 [SMILES: O=c1cc[nH]c2nc(-n3ccccc3=O)c(-c3cc(Cl)c4ncccc4c3)cc12] |
| 1.107 | 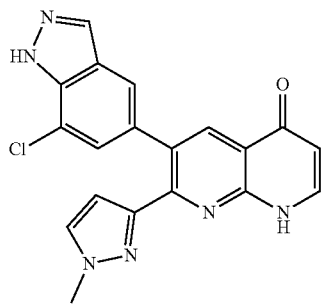 [SMILES: Cn1ccc(-c2nc3[nH]ccc(=O)c3cc2-c2cc(Cl)c3[nH]ncc3c2)n1] |
| 1.108 | 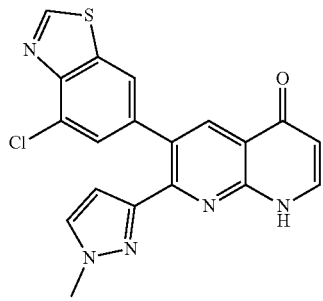 |

TABLE 1-continued
| Compound No. | Compound |
|---|---|
| 1.109 | 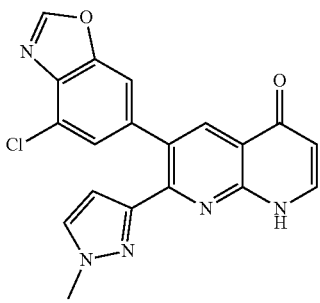 |
| 1.110 | 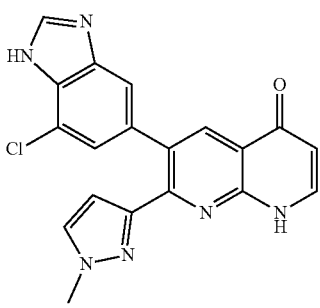 [SMILES: Cn1ccc(-c2nc3[nH]ccc(=O)c3cc2-c2cc(Cl)c3[nH]cnc3c2)n1] |
| 1.111 | 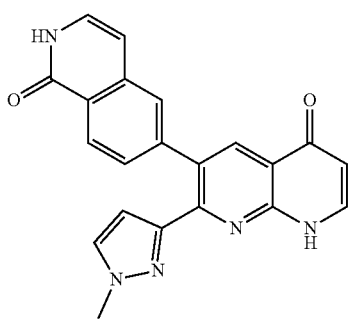 [SMILES: Cn1ccc(-c2nc3[nH]ccc(=O)c3cc2-c2ccc3c(=O)[nH]ccc3c2)n1] |
| 1.112 | 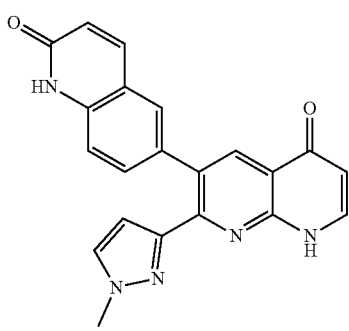 [SMILES: Cn1ccc(-c2nc3[nH]ccc(=O)c3cc2-c2ccc3[nH]c(=O)ccc3c2)n1] |
| 1.113 | 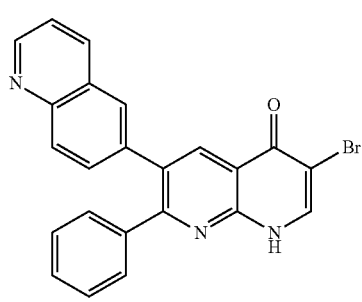 [SMILES: O=c1c(Br)c[nH]c2nc(-c3ccccc3)c(-c3ccc4ncccc4c3)cc12] |

TABLE 1-continued
| Compound No. | Compound |
|---|---|
| 1.114 | 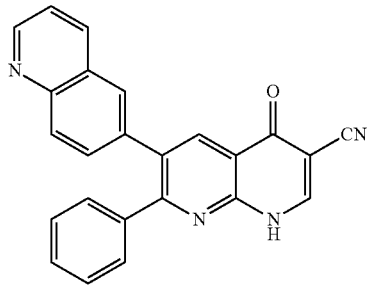 [SMILES: N#Cc1c[nH]c2nc(-c3ccccc3)c(-c3ccc4ncccc4c3)cc2c1=O] |
| 1.115 | 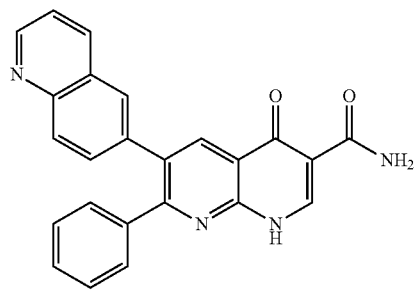 [SMILES: NC(=O)c1c[nH]c2nc(-c3ccccc3)c(-c3ccc4ncccc4c3)cc2c1=O] |
| 1.116 | 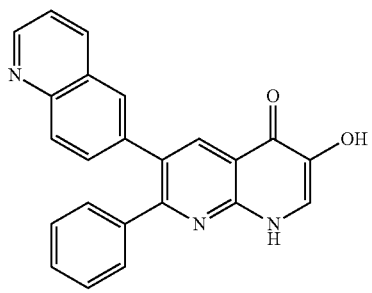 |
| 1.117 | 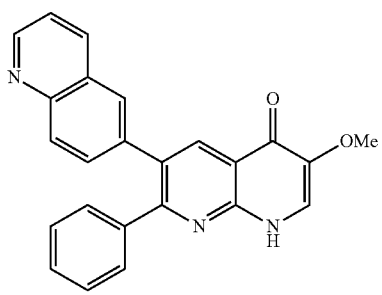 [SMILES: COc1c[nH]c2nc(-c3ccccc3)c(-c3ccc4ncccc4c3)cc2c1=O] |
| 1.118 | 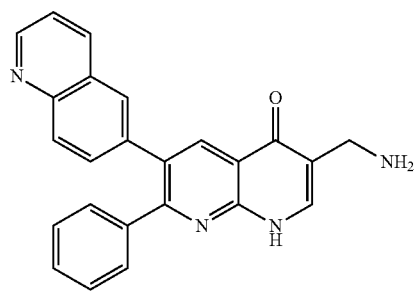 [SMILES: NCc1c[nH]c2nc(-c3ccccc3)c(-c3ccc4ncccc4c3)cc2c1=O] |

TABLE 1-continued
| Compound No. | Compound |
|---|---|
| 1.119 | 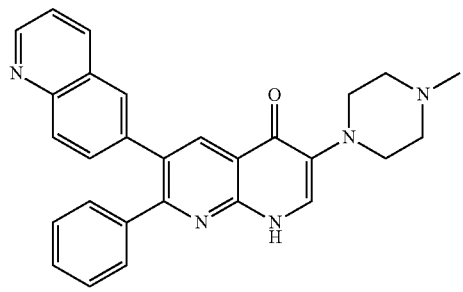 [SMILES: CN1CCN(c2c[nH]c3nc(-c4ccccc4)c(-c4ccc5ncccc5c4)cc3c2=O)CC1] |
| 1.120 | 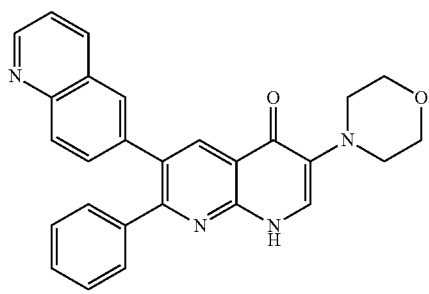 [SMILES: O=c1c(N2CCOCC2)c[nH]c2nc(-c3ccccc3)c(-c3ccc4ncccc4c3)cc12] |
| 1.121 | 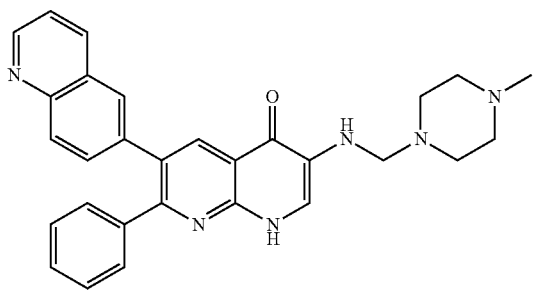 [SMILES: CN1CCN(CNc2c[nH]c3nc(-c4ccccc4)c(-c4ccc5ncccc5c4)cc3c2=O)CC1] |
| 1.122 | 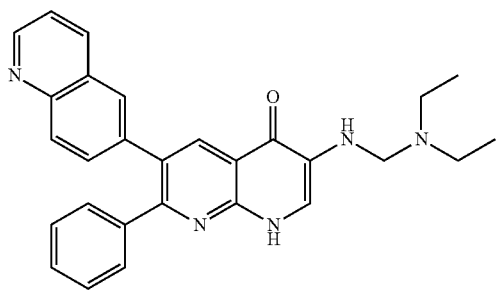 [SMILES: CCN(CC)CNc1c[nH]c2nc(-c3ccccc3)c(-c3ccc4ncccc4c3)cc2c1=O] |
| 1.123 | 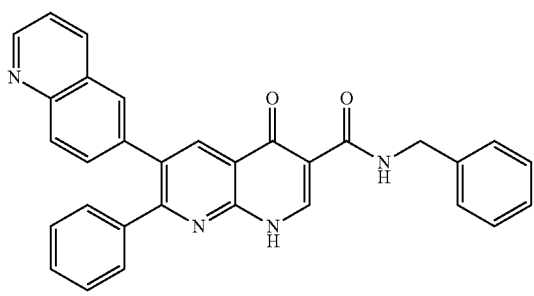 [SMILES: O=C(NCc1ccccc1)c1c[nH]c2nc(-c3ccccc3)c(-c3ccc4ncccc4c3)cc2c1=O] |

US 10,793,561 B2
TABLE 1-continued
| Compound No. | Compound |
|---|---|
| 1.124 | 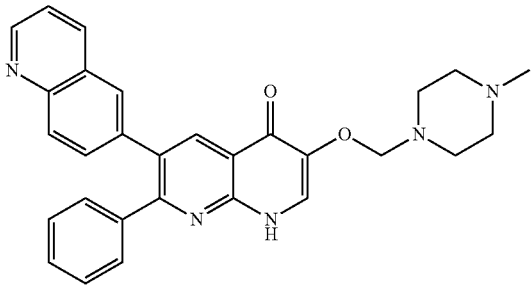 |
| 1.125 | 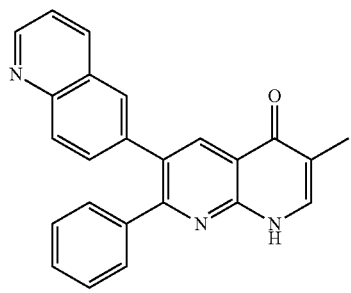 [SMILES: Cc1c[nH]c2nc(-c3ccccc3)c(-c3ccc4ncccc4c3)cc2c1=O] |
| 1.126 | 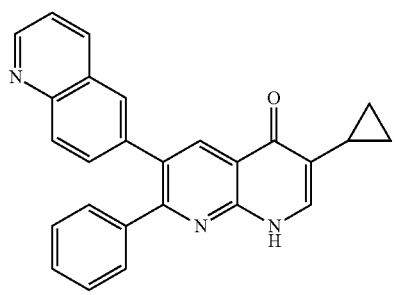 [SMILES: O=c1c(C2CC2)c[nH]c2nc(-c3ccccc3)c(-c3ccc4ncccc4c3)cc12] |
| 1.127 | 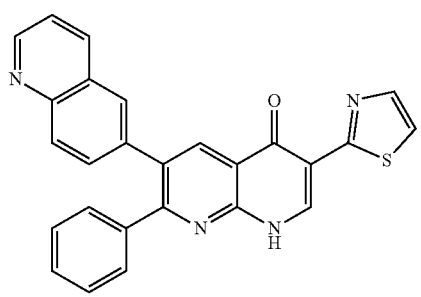 [SMILES: O=c1c(-c2nccs2)c[nH]c2nc(-c3ccccc3)c(-c3ccc4ncccc4c3)cc12] |
| 1.128 | 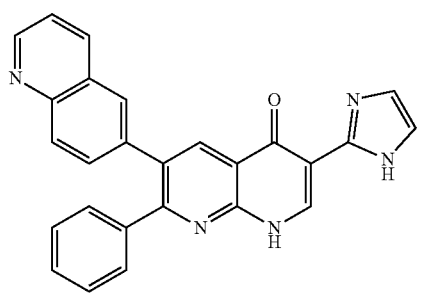 [SMILES: O=c1c(-c2ncc[nH]2)c[nH]c2nc(-c3ccccc3)c(-c3ccc4ncccc4c3)cc12] |

TABLE 1-continued
| Compound No. | Compound |
|---|---|
| 1.129 | 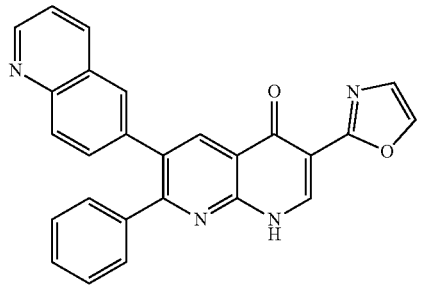 [SMILES: O=c1c(-c2ncco2)c[nH]c2nc(-c3ccccc3)c(-c3ccc4ncccc4c3)cc12] |
| 1.130 | 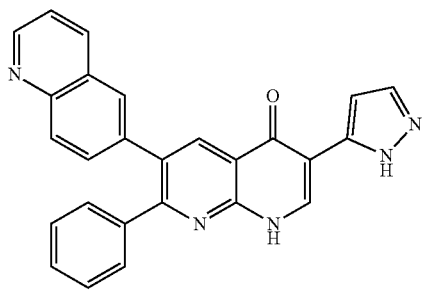 [SMILES: O=c1c(-c2ccn[nH]2)c[nH]c2nc(-c3ccccc3)c(-c3ccc4ncccc4c3)cc12] |
| 1.131 | 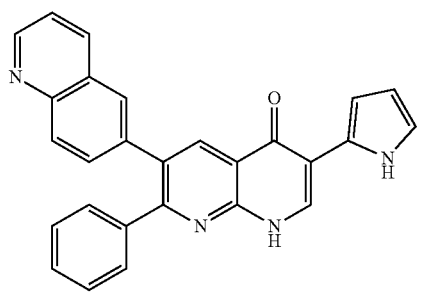 [SMILES: O=c1c(-c2ccc[nH]2)c[nH]c2nc(-c3ccccc3)c(-c3ccc4ncccc4c3)cc12] |
| 1.132 | 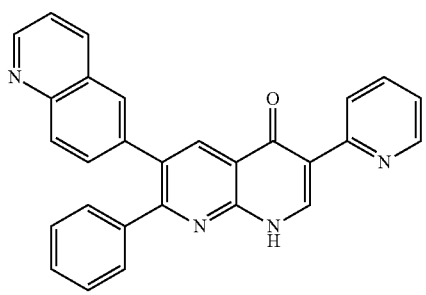 [SMILES: O=c1c(-c2ccccn2)c[nH]c2nc(-c3ccccc3)c(-c3ccc4ncccc4c3)cc12] |
| 1.133 | 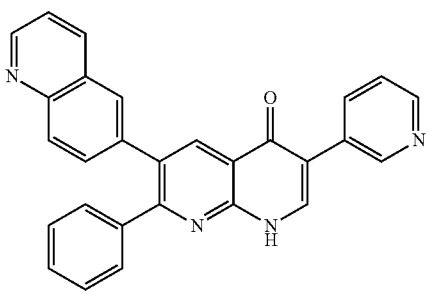 [SMILES: O=c1c(-c2cccnc2)c[nH]c2nc(-c3ccccc3)c(-c3ccc4ncccc4c3)cc12] |

TABLE 1-continued
| Compound No. | Compound |
|---|---|
| 1.134 | 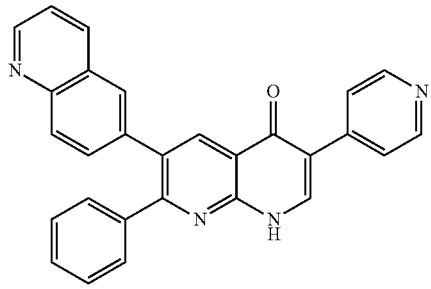 [SMILES: O=c1c(-c2ccncc2)c[nH]c2nc(-c3ccccc3)c(-c3ccc4ncccc4c3)cc12] |
| 1.135 | 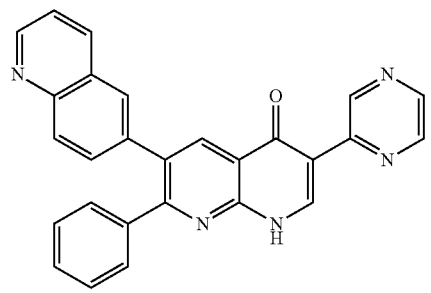 |
| 1.136 | 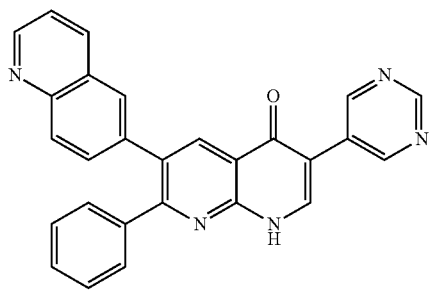 [SMILES: O=c1c(-c2cncnc2)c[nH]c2nc(-c3ccccc3)c(-c3ccc4ncccc4c3)cc12] |
| 1.137 | 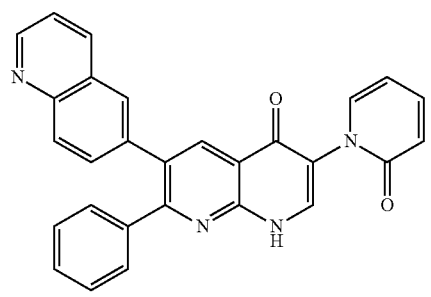 [SMILES: O=c1c(-n2ccccc2=O)c[nH]c2nc(-c3ccccc3)c(-c3ccc4ncccc4c3)cc12] |
| 1.138 | 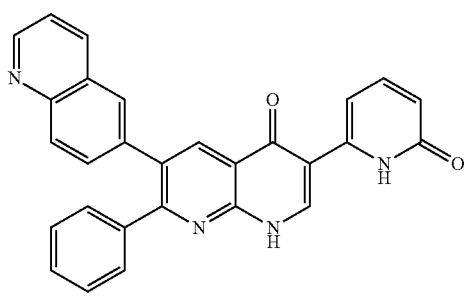 [SMILES: O=c1cccc(-c2c[nH]c3nc(-c4ccccc4)c(-c4ccc5ncccc5c4)cc3c2=O)[nH]1] |

TABLE 1-continued
| Compound No. | Compound |
|---|---|
| 1.139 | 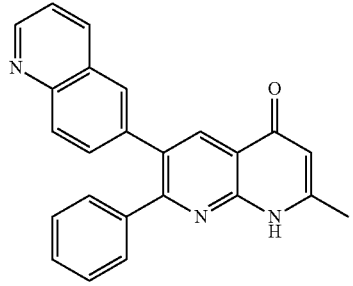 [SMILES: Cc1cc(=O)c2cc(-c3ccc4ncccc4c3)c(-c3ccccc3)nc2[nH]1] |
| 1.140 | 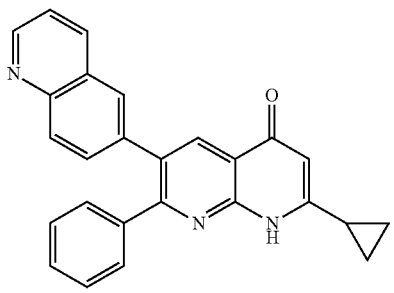 [SMILES: O=c1cc(C2CC2)[nH]c2nc(-c3ccccc3)c(-c3ccc4ncccc4c3)cc12] |
| 1.141 | 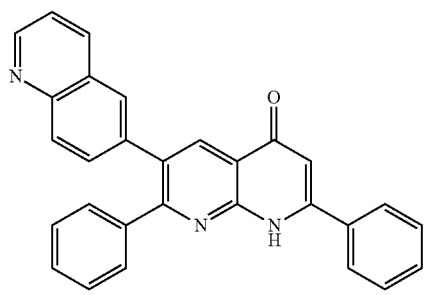 [SMILES: O=c1cc(-c2ccccc2)[nH]c2nc(-c3ccccc3)c(-c3ccc4ncccc4c3)cc12] |
| 1.142 | 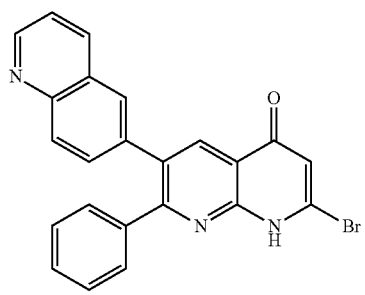 [SMILES: O=c1cc(Br)[nH]c2nc(-c3ccccc3)c(-c3ccc4ncccc4c3)cc12] |
| 1.143 | 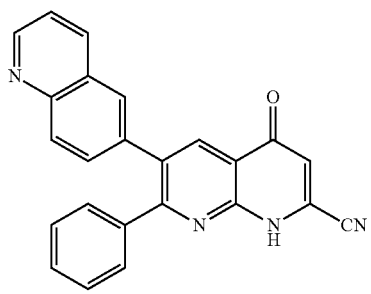 [SMILES: N#Cc1cc(=O)c2cc(-c3ccc4ncccc4c3)c(-c3ccccc3)nc2[nH]1] |

TABLE 1-continued
| Compound No. | Compound |
|---|---|
| 1.144 | 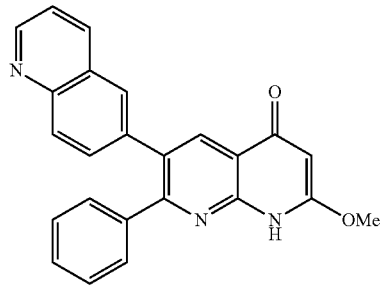 [SMILES: COc1cc(=O)c2cc(-c3ccc4ncccc4c3)c(-c3ccccc3)nc2[nH]1] |
| 1.145 | 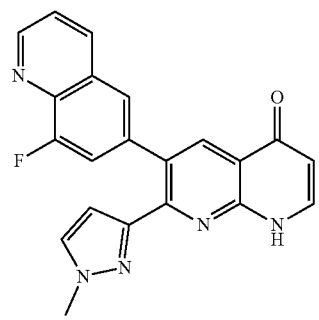 [SMILES: Cn1ccc(-c2nc3[nH]ccc(=O)c3cc2-c2cc(F)c3ncccc3c2)n1] |
| 1.146 | 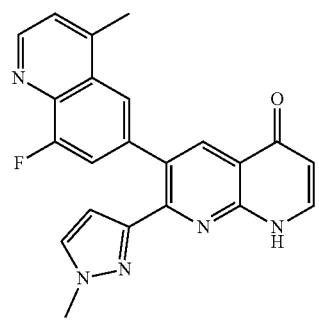 [SMILES: Cc1ccnc2c(F)cc(-c3cc4c(=O)cc[nH]c4nc3-c3ccn(C)n3)cc12] |
| 1.147 | 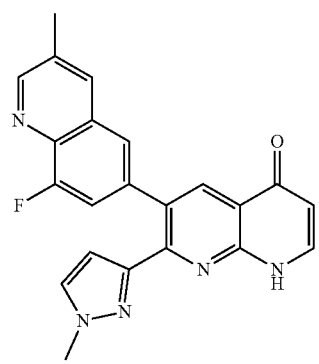 [SMILES: Cc1cnc2c(F)cc(-c3cc4c(=O)cc[nH]c4nc3-c3ccn(C)n3)cc2c1] |

TABLE 1-continued
| Compound No. | Compound |
|---|---|
| 1.148 | 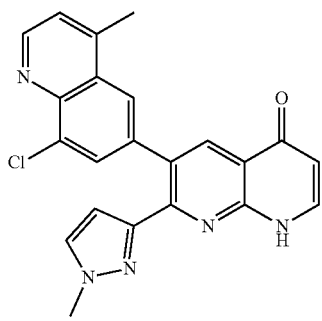 [SMILES: Cc1ccnc2c(Cl)cc(-c3cc4c(=O)cc[nH]c4nc3-c3ccn(C)n3)cc12] |
| 1.149 | 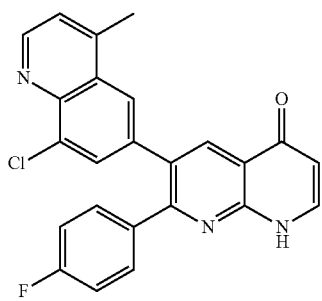 [SMILES: Cc1ccnc2c(Cl)cc(-c3cc4c(=O)cc[nH]c4nc3-c3ccc(F)cc3)cc12] |
| 1.150 | 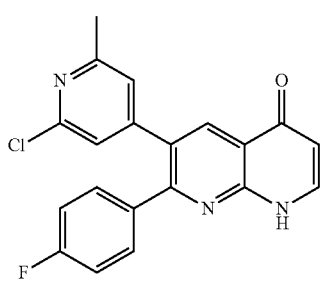 [SMILES: Cc1cc(-c2cc3c(=O)cc[nH]c3nc2-c2ccc(F)cc2)cc(Cl)n1] |
| 1.151 | 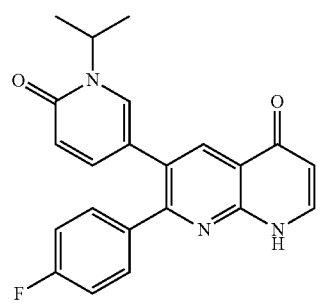 [SMILES: CC(C)n1cc(-c2cc3c(=O)cc[nH]c3nc2-c2ccc(F)cc2)ccc1=O] |
| 1.152 | 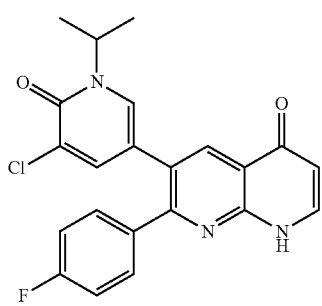 [SMILES: CC(C)n1cc(-c2cc3c(=O)cc[nH]c3nc2-c2ccc(F)cc2)cc(Cl)c1=O] |

TABLE 1-continued
| Compound No. | Compound |
|---|---|
| 1.153 | 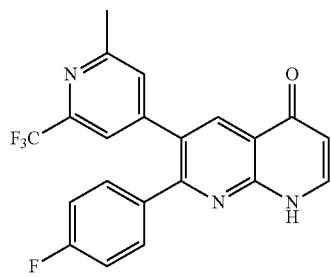 [SMILES: Cc1cc(-c2cc3c(=O)cc[nH]c3nc2-c2ccc(F)cc2)cc(C(F)(F)F)n1] |
| 1.154 | 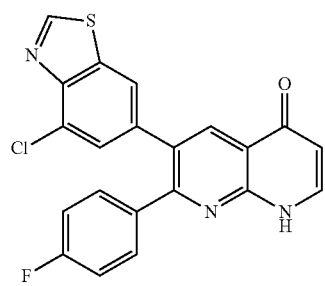 [SMILES: O=c1cc[nH]c2nc(-c3ccc(F)cc3)c(-c3cc(Cl)c4ncsc4c3)cc12] |
| 1.155 | 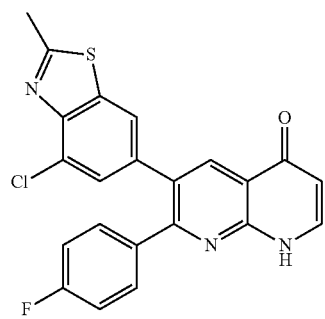 [SMILES: Cc1nc2c(Cl)cc(-c3cc4c(=O)cc[nH]c4nc3-c3ccc(F)cc3)cc2s1] |
| 1.156 | 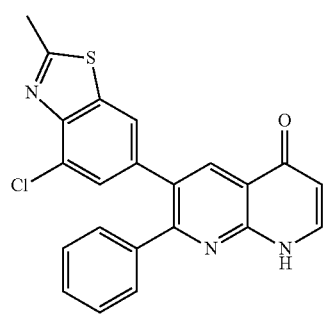 [SMILES: Cc1nc2c(Cl)cc(-c3cc4c(=O)cc[nH]c4nc3-c3ccccc3)cc2s1] |
| 1.157 | 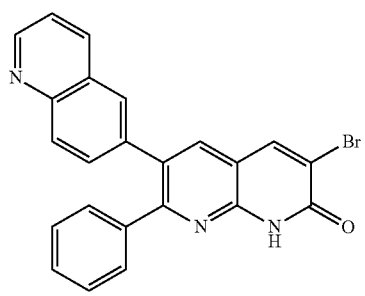 [SMILES: O=c1[nH]c2nc(-c3ccccc3)c(-c3ccc4ncccc4c3)cc2cc1Br] |

TABLE 1-continued
| Compound No. | Compound |
|---|---|
| 1.158 | 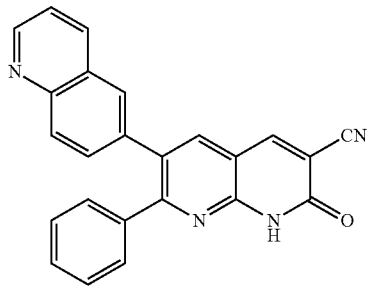 [SMILES: N#Cc1cc2cc(-c3ccc4ncccc4c3)c(-c3ccccc3)nc2[nH]c1=O] |
| 1.159 | 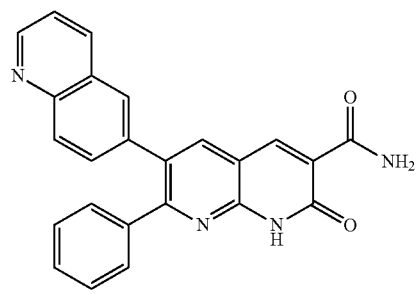 [SMILES: NC(=O)c1cc2cc(-c3ccc4ncccc4c3)c(-c3ccccc3)nc2[nH]c1=O] |
| 1.160 | 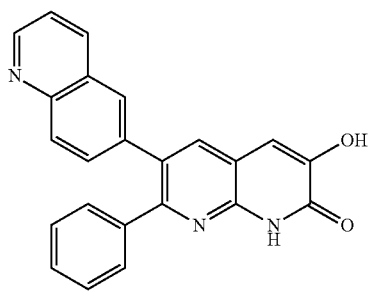 |
| 1.161 | 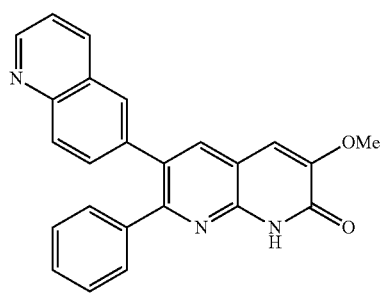 [SMILES: COc1cc2cc(-c3ccc4ncccc4c3)c(-c3ccccc3)nc2[nH]c1=O] |
| 1.162 | 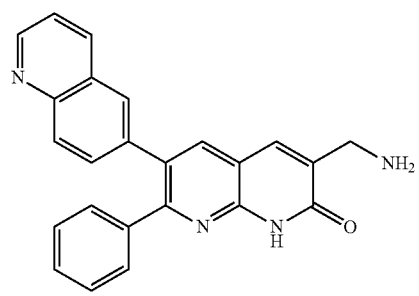 [SMILES: NCc1cc2cc(-c3ccc4ncccc4c3)c(-c3ccccc3)nc2[nH]c1=O] |

TABLE 1-continued
| Compound No. | Compound |
|---|---|
| 1.163 | 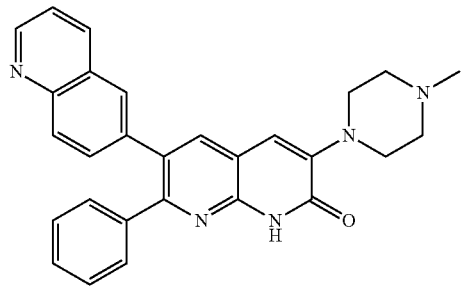 [SMILES: CN1CCN(c2cc3cc(-c4ccc5ncccc5c4)c(-c4ccccc4)nc3[nH]c2=O)CC1] |
| 1.164 | 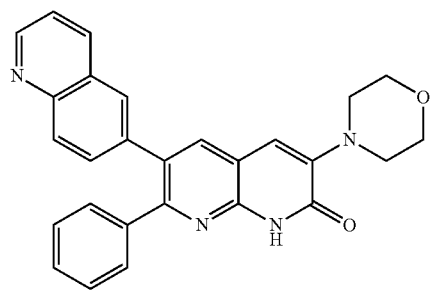 [SMILES: O=c1[nH]c2nc(-c3ccccc3)c(-c3ccc4ncccc4c3)cc2cc1N1CCOCC1] |
| 1.165 | 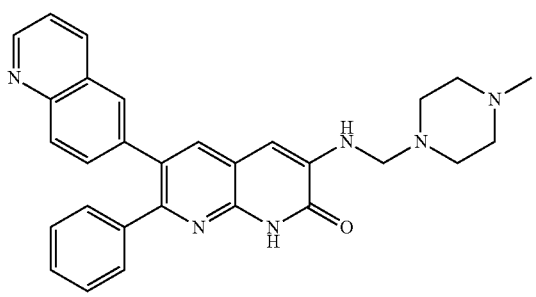 [SMILES: CN1CCN(CNc2cc3cc(-c4ccc5ncccc5c4)c(-c4ccccc4)nc3[nH]c2=O)CC1] |
| 1.166 | 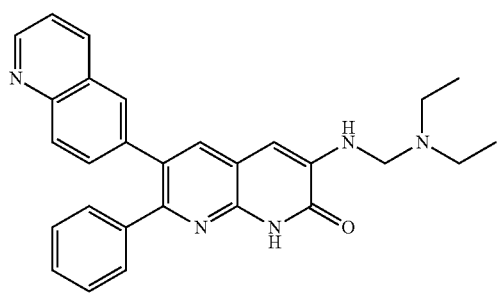 [SMILES: CCN(CC)CNc1cc2cc(-c3ccc4ncccc4c3)c(-c3ccccc3)nc2[nH]c1=O] |
| 1.167 | 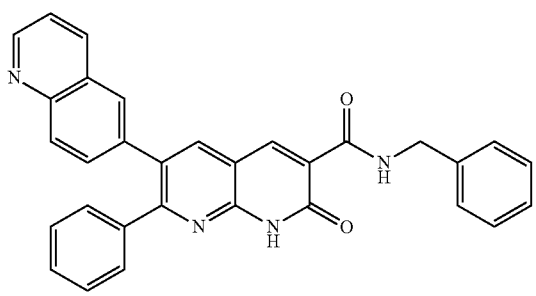 [SMILES: O=C(NCc1ccccc1)c1cc2cc(-c3ccc4ncccc4c3)c(-c3ccccc3)nc2[nH]c1=O] |

TABLE 1-continued
| Compound No. | Compound |
|---|---|
| 1.168 | 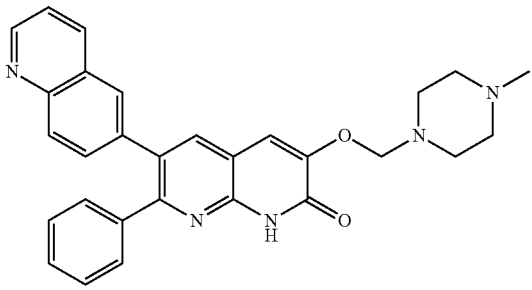 [SMILES: CN1CCN(COc2cc3cc(-c4ccc5ncccc5c4)c(-c4ccccc4)nc3[nH]c2=O)CC1] |
| 1.169 | 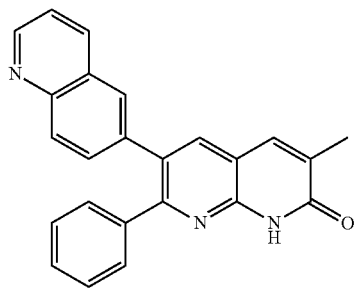 [SMILES: Cc1cc2cc(-c3ccc4ncccc4c3)c(-c3ccccc3)nc2[nH]c1=O] |
| 1.170 | 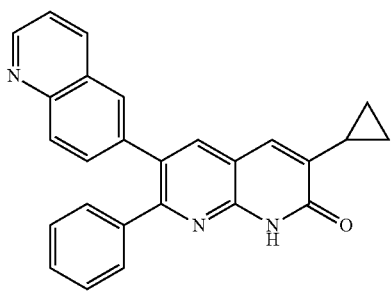 [SMILES: O=c1[nH]c2nc(-c3ccccc3)c(-c3ccc4ncccc4c3)cc2cc1C1CC1] |
| 1.171 | 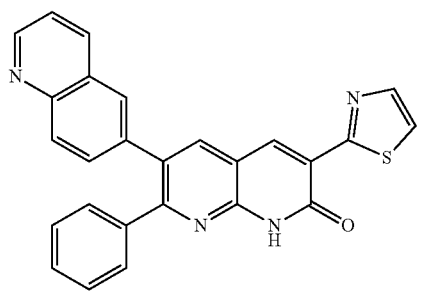 [SMILES: O=c1[nH]c2nc(-c3ccccc3)c(-c3ccc4ncccc4c3)cc2cc1-c1nccs1] |
| 1.172 | 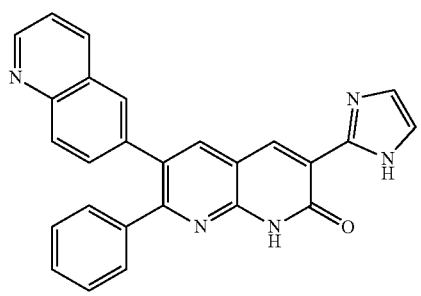 [SMILES: O=c1[nH]c2nc(-c3ccccc3)c(-c3ccc4ncccc4c3)cc2cc1-c1ncc[nH]1] |

TABLE 1-continued
| Compound No. | Compound |
|---|---|
| 1.173 | 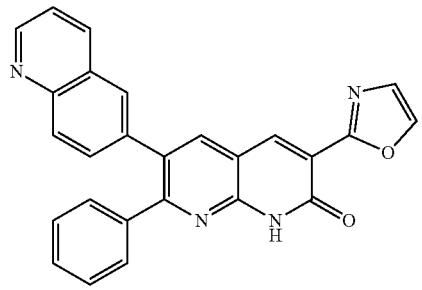 [SMILES: O=c1[nH]c2nc(-c3ccccc3)c(-c3ccc4ncccc4c3)cc2cc1-c1ncco1] |
| 1.174 | 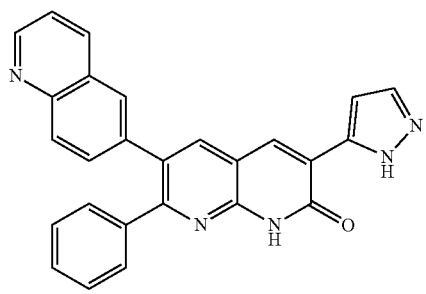 [SMILES: O=c1[nH]c2nc(-c3ccccc3)c(-c3ccc4ncccc4c3)cc2cc1-c1ccn[nH]1] |
| 1.175 | 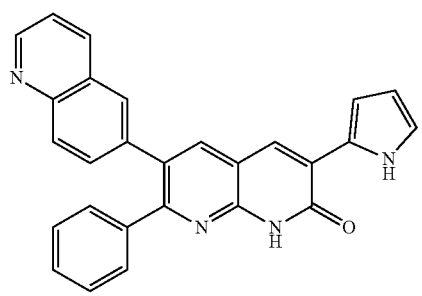 [SMILES: O=c1[nH]c2nc(-c3ccccc3)c(-c3ccc4ncccc4c3)cc2cc1-c1ccc[nH]1] |
| 1.176 | 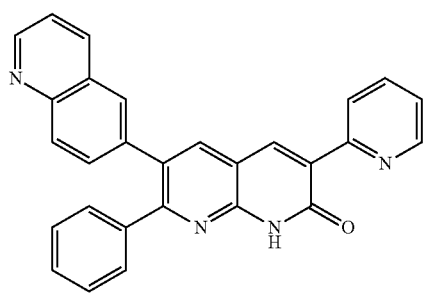 |
| 1.177 | 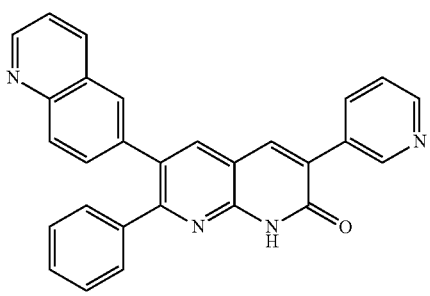 [SMILES: O=c1[nH]c2nc(-c3ccccc3)c(-c3ccc4ncccc4c3)cc2cc1-c1cccnc1] |

TABLE 1-continued
| Compound No. | Compound |
|---|---|
| 1.178 | 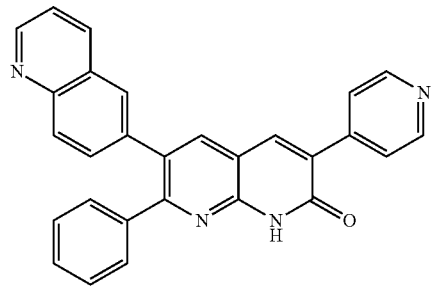 [SMILES: O=c1[nH]c2nc(-c3ccccc3)c(-c3ccc4ncccc4c3)cc2cc1-c1ccncc1] |
| 1.179 | 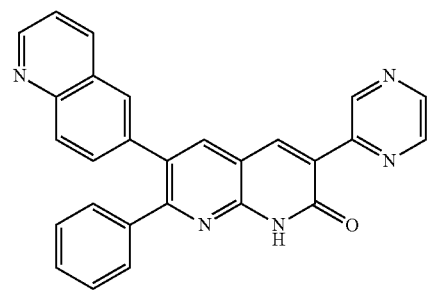 [SMILES: O=c1[nH]c2nc(-c3ccccc3)c(-c3ccc4ncccc4c3)cc2cc1-c1cnccn1] |
| 1.180 | 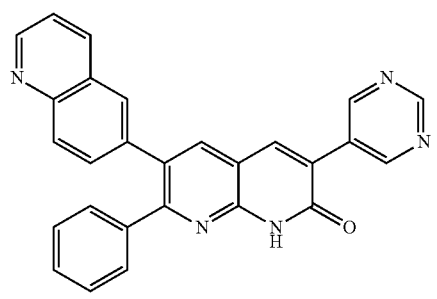 [SMILES: O=c1[nH]c2nc(-c3ccccc3)c(-c3ccc4ncccc4c3)cc2cc1-c1cncnc1] |
| 1.181 | 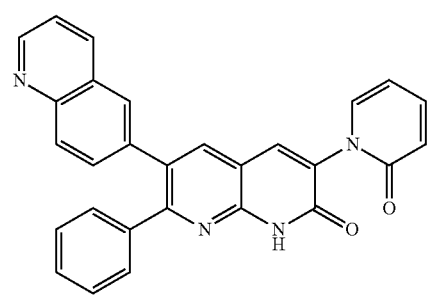 [SMILES: O=c1[nH]c2nc(-c3ccccc3)c(-c3ccc4ncccc4c3)cc2cc1-n1ccccc1=O] |
| 1.182 | 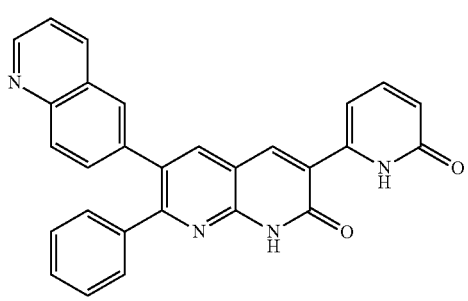 [SMILES: O=c1cccc(-c2cc3cc(-c4ccc5ncccc5c4)c(-c4ccccc4)nc3[nH]c2=O)[nH]1] |

TABLE 1-continued
| Compound No. | Compound |
|---|---|
| 1.183 | 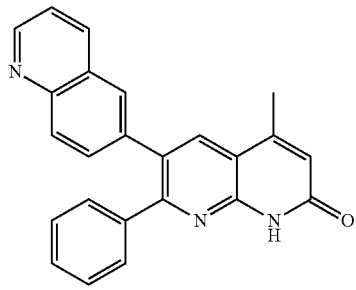 [SMILES: Cc1cc(=O)[nH]c2nc(-c3ccccc3)c(-c3ccc4ncccc4c3)cc12] |
| 1.184 | 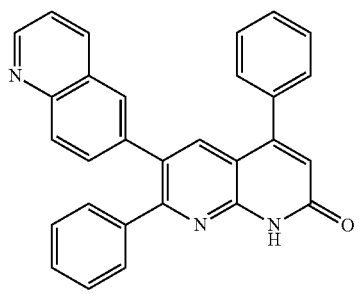 [SMILES: O=c1cc(-c2ccccc2)c2cc(-c3ccc4ncccc4c3)c(-c3ccccc3)nc2[nH]1] |
| 1.185 | 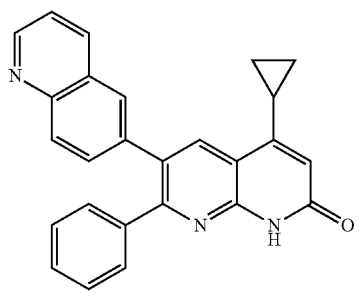 [SMILES: O=c1cc(C2CC2)c2cc(-c3ccc4ncccc4c3)c(-c3ccccc3)nc2[nH]1] |
| 1.186 | 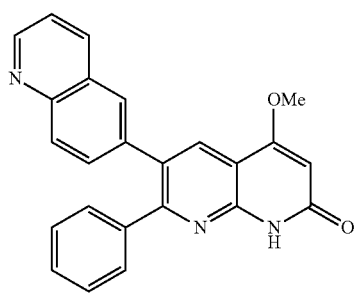 |
| 1.187 | 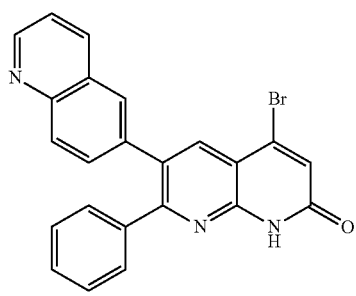 [SMILES: O=c1cc(Br)c2cc(-c3ccc4ncccc4c3)c(-c3ccccc3)nc2[nH]1] |

TABLE 1-continued
| Compound No. | Compound |
|---|---|
| 1.188 | 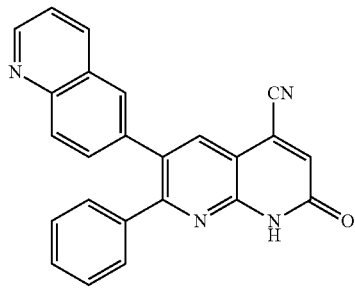 [SMILES: N#Cc1cc(=O)[nH]c2nc(-c3ccccc3)c(-c3ccc4ncccc4c3)cc12] |
| 1.189 | 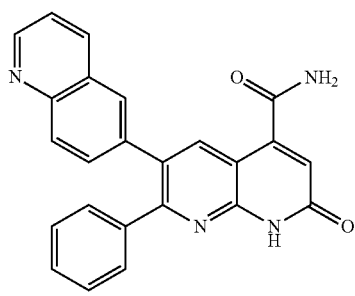 [SMILES: NC(=O)c1cc(=O)[nH]c2nc(-c3ccccc3)c(-c3ccc4ncccc4c3)cc12] |
| 1.190 | 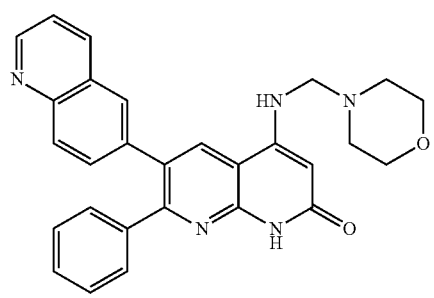 [SMILES: O=c1cc(NCN2CCOCC2)c2cc(-c3ccc4ncccc4c3)c(-c3ccccc3)nc2[nH]1] |
| 1.191 | 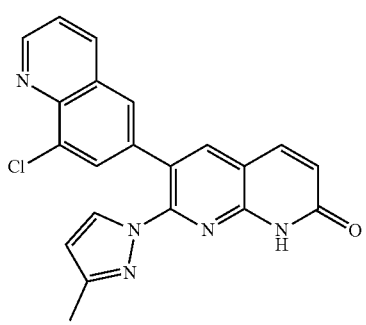 [SMILES: Cc1ccn(-c2nc3[nH]c(=O)ccc3cc2-c2cc(Cl)c3ncccc3c2)n1] |
| 1.192 | 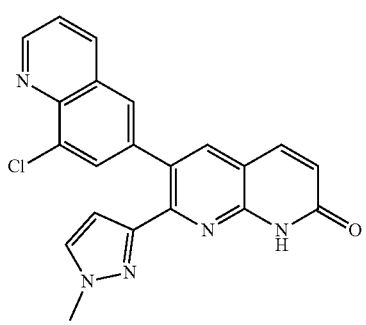 [SMILES: Cn1ccc(-c2nc3[nH]c(=O)ccc3cc2-c2cc(Cl)c3ncccc3c2)n1] |

TABLE 1-continued
| Compound No. | Compound |
|---|---|
| 1.193 | 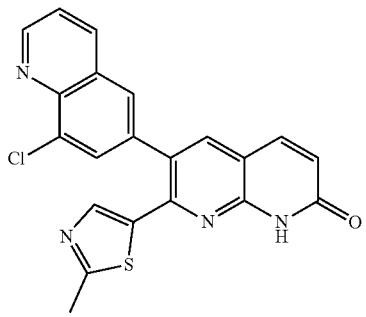 [SMILES: Cc1ncc(-c2nc3[nH]c(=O)ccc3cc2-c2cc(Cl)c3ncccc3c2)s1] |
| 1.194 | 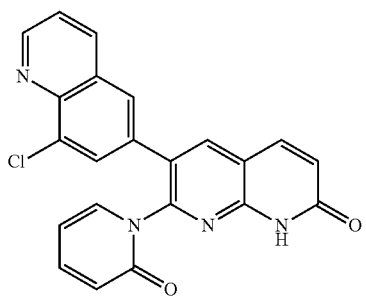 [SMILES: O=c1ccc2cc(-c3cc(Cl)c4ncccc4c3)c(-n3ccccc3=O)nc2[nH]1] |
| 1.195 | 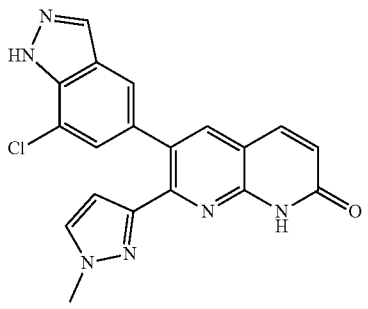 [SMILES: Cn1ccc(-c2nc3[nH]c(=O)ccc3cc2-c2cc(Cl)c3[nH]ncc3c2)n1] |
| 1.196 | 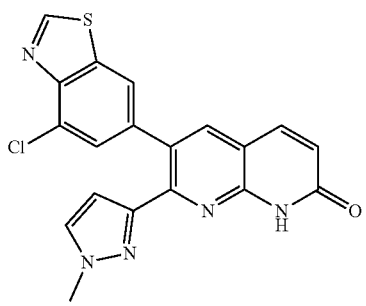 |
| 1.197 | 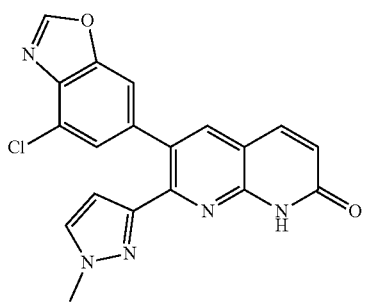 [SMILES: Cn1ccc(-c2nc3[nH]c(=O)ccc3cc2-c2cc(Cl)c3ncoc3c2)n1] |

TABLE 1-continued
| Compound No. | Compound |
|---|---|
| 1.198 | 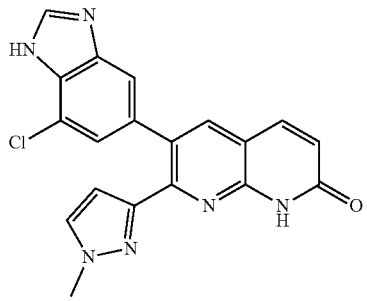 [SMILES: Cn1ccc(-c2nc3[nH]c(=O)ccc3cc2-c2cc(Cl)c3[nH]cnc3c2)n1] |
| 1.199 | 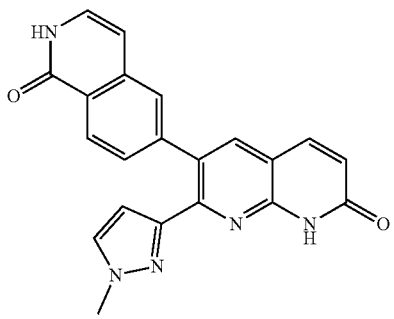 [SMILES: Cn1ccc(-c2nc3[nH]c(=O)ccc3cc2-c2ccc3c(=O)[nH]ccc3c2)n1] |
| 1.200 | 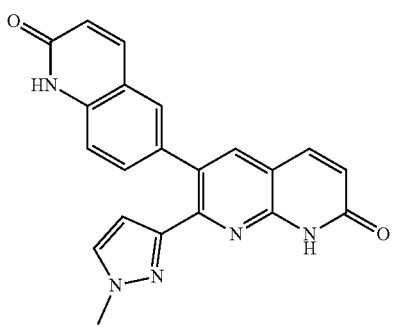 [SMILES: Cn1ccc(-c2nc3[nH]c(=O)ccc3cc2-c2ccc3[nH]c(=O)ccc3c2)n1] |
| 1.201 | 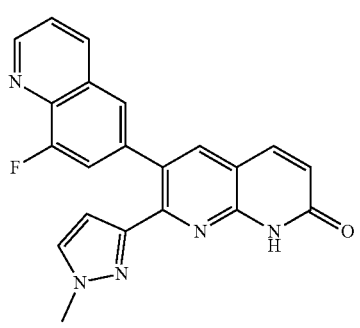 [SMILES: Cn1ccc(-c2nc3[nH]c(=O)ccc3cc2-c2cc(F)c3ncccc3c2)n1] |
| 1.202 | 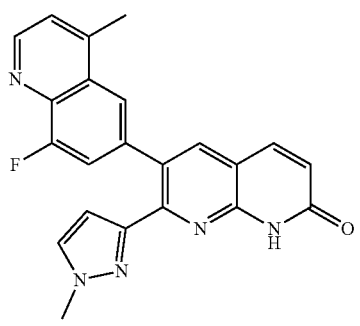 [SMILES: Cc1ccnc2c(F)cc(-c3cc4ccc(=O)[nH]c4nc3-c3ccn(C)n3)cc12] |

TABLE 1-continued
| Compound No. | Compound |
|---|---|
| 1.203 | 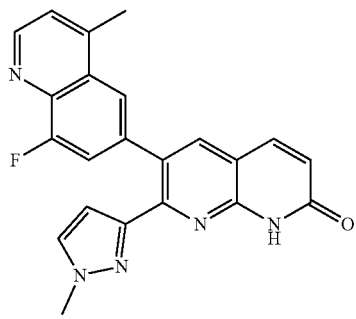 [SMILES: Cc1ccnc2c(F)cc(-c3cc4ccc(=O)[nH]c4nc3-c3ccn(C)n3)cc12] |
| 1.204 | 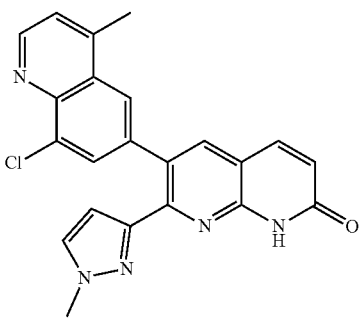 [SMILES: Cc1ccnc2c(Cl)cc(-c3cc4ccc(=O)[nH]c4nc3-c3ccn(C)n3)cc12] |
| 1.205 | 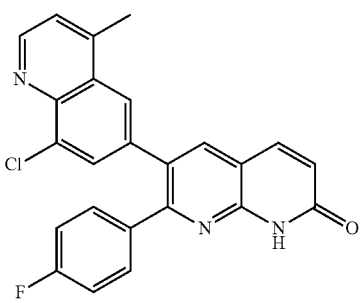 [SMILES: Cc1ccnc2c(Cl)cc(-c3cc4ccc(=O)[nH]c4nc3-c3ccc(F)cc3)cc12] |
| 1.206 | 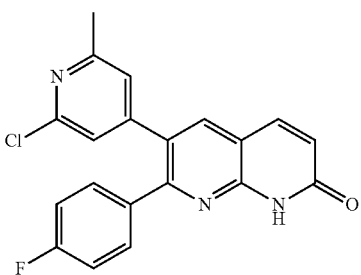 [SMILES: Cc1cc(-c2cc3ccc(=O)[nH]c3nc2-c2ccc(F)cc2)cc(Cl)n1] |
| 1.207 | 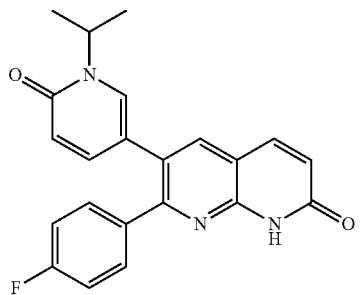 [SMILES: CC(C)n1cc(-c2cc3ccc(=O)[nH]c3nc2-c2ccc(F)cc2)ccc1=O] |

TABLE 1-continued
| Compound No. | Compound |
|---|---|
| 1.208 | 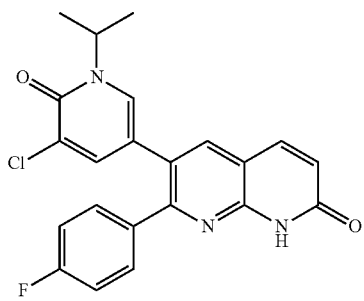 [SMILES: CC(C)n1cc(-c2cc3ccc(=O)[nH]c3nc2-c2ccc(F)cc2)cc(Cl)c1=O] |
| 1.209 | 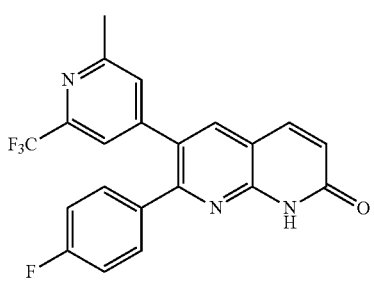 [SMILES: Cc1cc(-c2cc3ccc(=O)[nH]c3nc2-c2ccc(F)cc2)cc(C(F)(F)F)n1] |
| 1.210 | 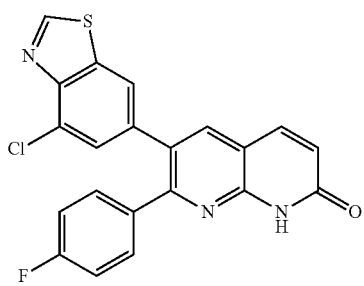 [SMILES: O=c1ccc2cc(-c3cc(Cl)c4ncsc4c3)c(-c3ccc(F)cc3)nc2[nH]1] |
| 1.211 | 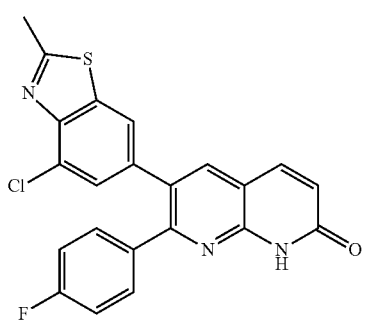 [SMILES: Cc1nc2c(Cl)cc(-c3cc4ccc(=O)[nH]c4nc3-c3ccc(F)cc3)cc2s1] |
| 1.212 | 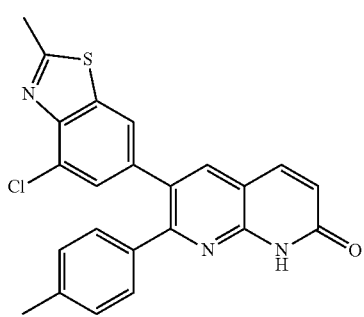 [SMILES: Cc1ccc(-c2nc3[nH]c(=O)ccc3cc2-c2cc(Cl)c3nc(C)sc3c2)cc1] |

TABLE 1-continued

| Compound No. | Compound |
|---|---|
| 1.213 | (structure) |
| 1.214 | (structure) |
| 1.215 | (structure) |
| 1.216 | (structure) |
| 1.217 | (structure) |

TABLE 1-continued

| Compound No. | Compound |
|---|---|
| 1.218 | |
| 1.219 | |
| 1.220 | |
| 1.221 | |
| 1.222 | |

TABLE 1-continued
| Compound No. | Compound |
|---|---|
| 1.223 | 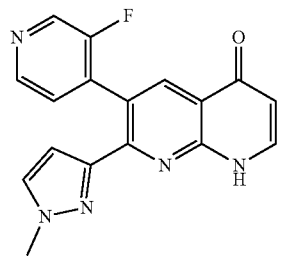 [SMILES: Cn1ccc(-c2nc3[nH]ccc(=O)c3cc2-c2ccncc2F)n1] |
| 1.224 | 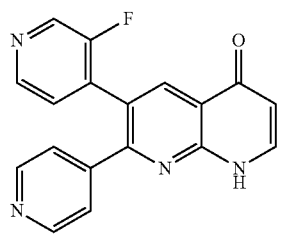 [SMILES: O=c1cc[nH]c2nc(-c3ccncc3)c(-c3ccncc3F)cc12] |
| 1.225 | 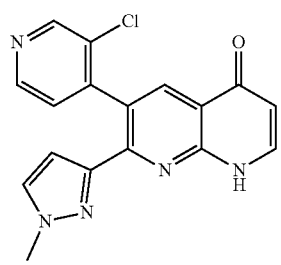 [SMILES: Cn1ccc(-c2nc3[nH]ccc(=O)c3cc2-c2ccncc2Cl)n1] |
| 1.226 | 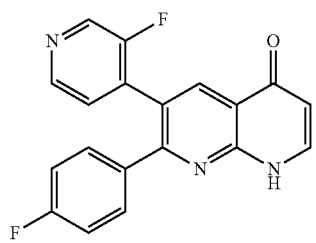 [SMILES: O=c1cc[nH]c2nc(-c3ccc(F)cc3)c(-c3ccncc3F)cc12] |
| 1.227 | 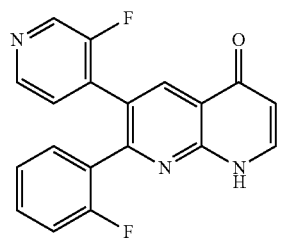 |
| 1.228 | 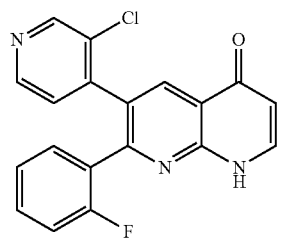 [SMILES: O=c1cc[nH]c2nc(-c3ccccc3F)c(-c3ccncc3Cl)cc12] |

TABLE 1-continued
| Compound No. | Compound |
|---|---|
| 1.229 | 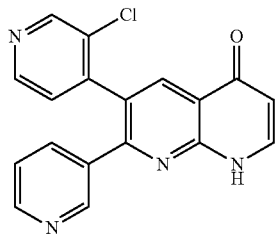 [SMILES: O=c1cc[nH]c2nc(-c3cccnc3)c(-c3ccncc3Cl)cc12] |
| 1.230 | 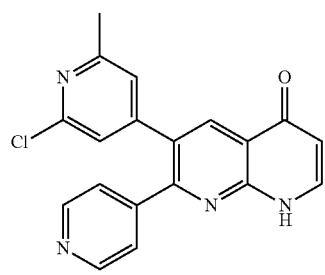 [SMILES: Cc1cc(-c2cc3c(=O)cc[nH]c3nc2-c2ccncc2)cc(Cl)n1] |
| 1.231 | 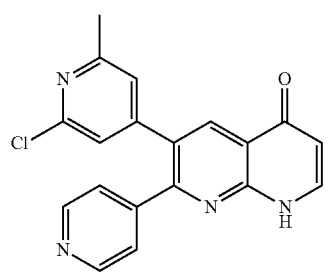 [SMILES: Cc1cc(-c2cc3c(=O)cc[nH]c3nc2-c2ccncc2)cc(Cl)n1] |
| 1.232 | 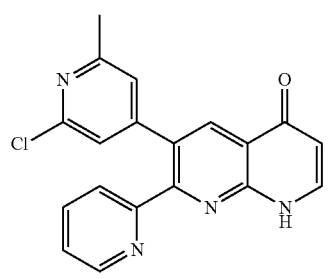 [SMILES: Cc1cc(-c2cc3c(=O)cc[nH]c3nc2-c2ccccn2)cc(Cl)n1] |
| 1.233 | 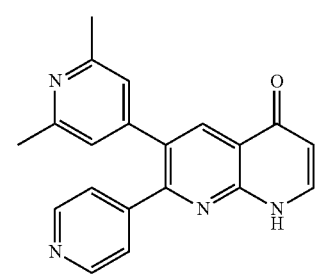 |

TABLE 1-continued
| Compound No. | Compound |
|---|---|
| 1.234 | 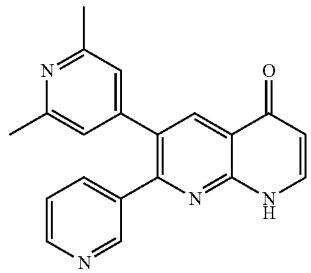 [SMILES: Cc1cc(-c2cc3c(=O)cc[nH]c3nc2-c2cccnc2)cc(C)n1] |
| 1.235 | 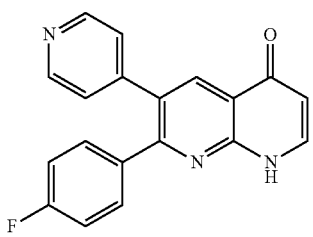 [SMILES: O=c1cc[nH]c2nc(-c3ccc(F)cc3)c(-c3ccncc3)cc12] |
| 1.236 | 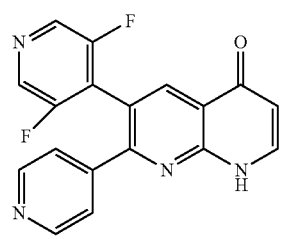 [SMILES: O=c1cc[nH]c2nc(-c3ccncc3)c(-c3c(F)cncc3F)cc12] |
| 1.237 | 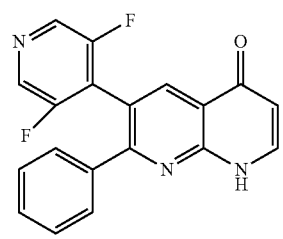 [SMILES: O=c1cc[nH]c2nc(-c3ccccc3)c(-c3c(F)cncc3F)cc12] |
| 1.238 | 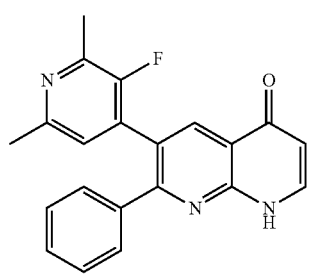 [SMILES: Cc1cc(-c2cc3c(=O)cc[nH]c3nc2-c2ccccc2)c(F)c(C)n1] |
| 1.239 | 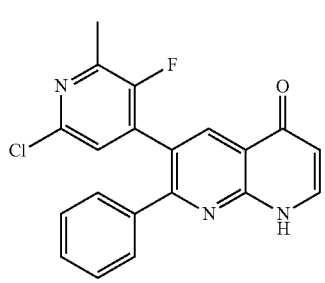 [SMILES: Cc1nc(Cl)cc(-c2cc3c(=O)cc[nH]c3nc2-c2ccccc2)c1F] |

TABLE 1-continued
| Compound No. | Compound |
|---|---|
| 1.240 | 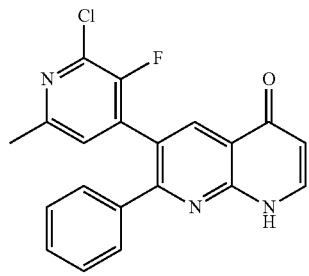 [SMILES: Cc1cc(-c2cc3c(=O)cc[nH]c3nc2-c2ccccc2)c(F)c(Cl)n1] |
| 1.241 | 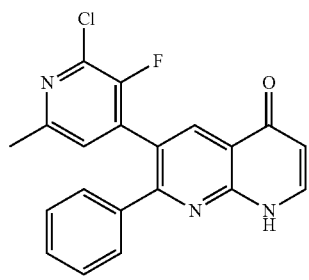 [SMILES: Cc1cc(-c2cc3c(=O)cc[nH]c3nc2-c2ccccc2)c(F)c(Cl)n1] |
| 1.242 | 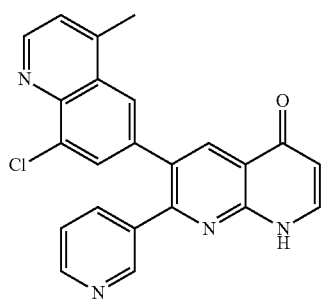 [SMILES: Cc1ccnc2c(Cl)cc(-c3cc4c(=O)cc[nH]c4nc3-c3cccnc3)cc12] |
| 1.243 | 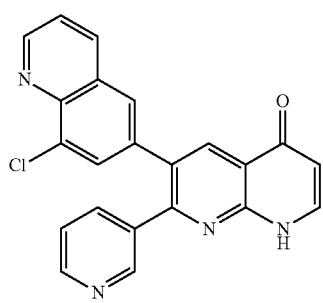 [SMILES: O=c1cc[nH]c2nc(-c3cccnc3)c(-c3cc(Cl)c4ncccc4c3)cc12] |
| 1.244 | 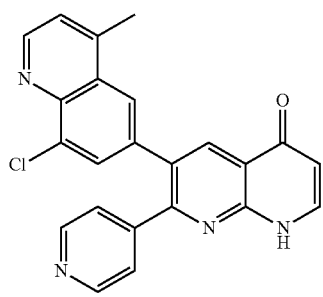 |

TABLE 1-continued
| Compound No. | Compound |
|---|---|
| 1.245 | 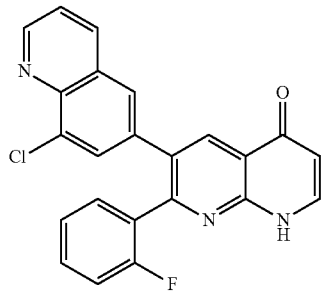 [SMILES: O=c1cc[nH]c2nc(-c3ccccc3F)c(-c3cc(Cl)c4ncccc4c3)cc12] |
| 1.246 | 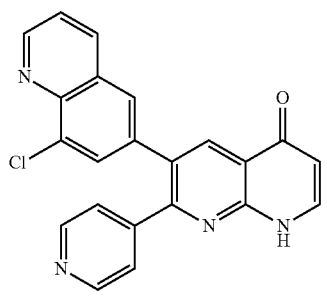 [SMILES: O=c1cc[nH]c2nc(-c3ccncc3)c(-c3cc(Cl)c4ncccc4c3)cc12] |
| 1.247 | 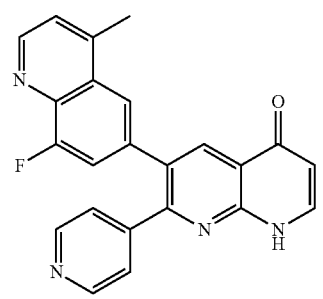 [SMILES: Cc1ccnc2c(F)cc(-c3cc4c(=O)cc[nH]c4nc3-c3ccncc3)cc12] |
| 1.248 | 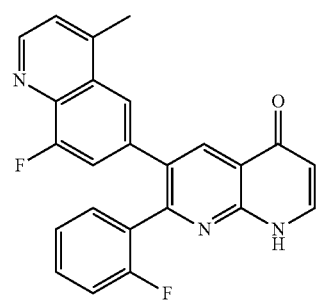 [SMILES: Cc1ccnc2c(F)cc(-c3cc4c(=O)cc[nH]c4nc3-c3ccccc3F)cc12] |
| 1.249 | 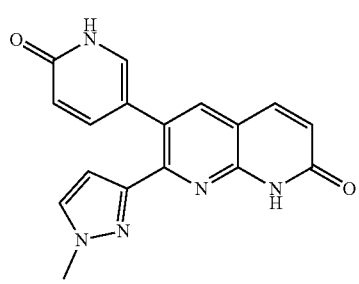 [SMILES: Cn1ccc(-c2nc3[nH]c(=O)ccc3cc2-c2ccc(=O)[nH]c2)n1] |

TABLE 1-continued

| Compound No. | Compound |
|---|---|
| 1.250 | (3-(pyridin-4-yl)-2-(1-methyl-1H-pyrazol-3-yl)-1,8-naphthyridin-2(1H)-one) |
| 1.251 | (3-(pyridin-4-yl)-2-(pyridin-4-yl)-1,8-naphthyridin-2(1H)-one) |
| 1.252 | (3-(3-fluoropyridin-4-yl)-2-(1-methyl-1H-pyrazol-3-yl)-1,8-naphthyridin-2(1H)-one) |
| 1.253 | (3-(3-fluoropyridin-4-yl)-2-(pyridin-3-yl)-1,8-naphthyridin-2(1H)-one) |
| 1.254 | (3-(3-chloropyridin-4-yl)-2-(1-methyl-1H-pyrazol-3-yl)-1,8-naphthyridin-2(1H)-one) |
| 1.255 | (3-(3-fluoropyridin-4-yl)-2-(4-fluorophenyl)-1,8-naphthyridin-2(1H)-one) |

TABLE 1-continued
| Compound No. | Compound |
|---|---|
| 1.256 | 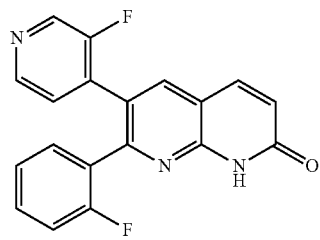 [SMILES: O=c1ccc2cc(-c3ccncc3F)c(-c3ccccc3F)nc2[nH]1] |
| 1.257 | 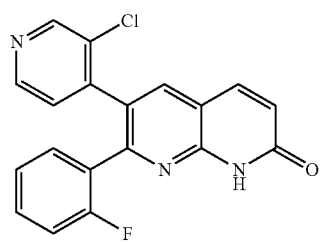 [SMILES: O=c1ccc2cc(-c3ccncc3Cl)c(-c3ccccc3F)nc2[nH]1] |
| 1.258 | 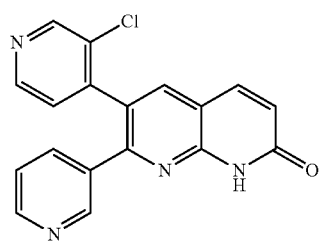 [SMILES: O=c1ccc2cc(-c3ccncc3Cl)c(-c3cccnc3)nc2[nH]1] |
| 1.259 | 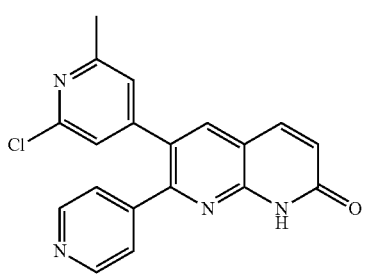 [SMILES: Cc1cc(-c2cc3ccc(=O)[nH]c3nc2-c2ccncc2)cc(Cl)n1] |
| 1.260 | 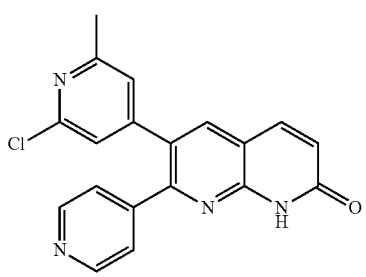 [SMILES: Cc1cc(-c2cc3ccc(=O)[nH]c3nc2-c2ccncc2)cc(Cl)n1] |
| 1.261 | 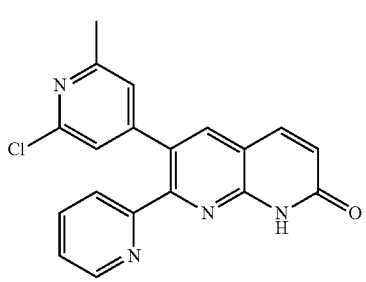 [SMILES: Cc1cc(-c2cc3ccc(=O)[nH]c3nc2-c2ccccn2)cc(Cl)n1] |

TABLE 1-continued
| Compound No. | Compound |
|---|---|
| 1.262 | 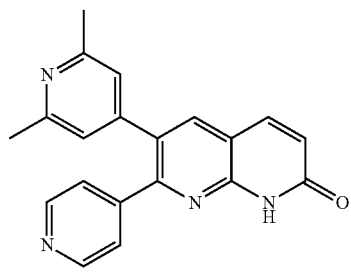 [SMILES: Cc1cc(-c2cc3ccc(=O)[nH]c3nc2-c2ccncc2)cc(C)n1] |
| 1.263 | 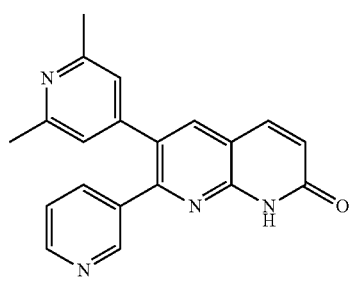 [SMILES: Cc1cc(-c2cc3ccc(=O)[nH]c3nc2-c2cccnc2)cc(C)n1] |
| 1.264 | 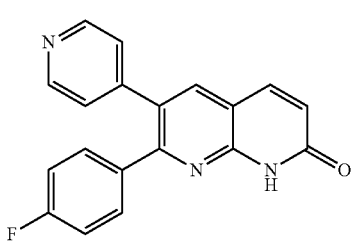 [SMILES: O=c1ccc2cc(-c3ccncc3)c(-c3ccc(F)cc3)nc2[nH]1] |
| 1.265 | 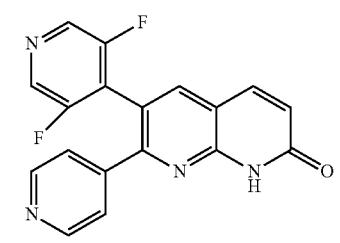 |
| 1.266 | 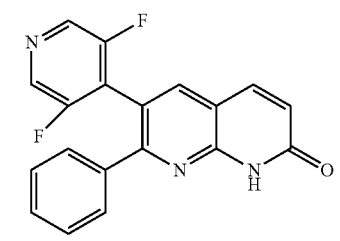 [SMILES: O=c1ccc2cc(-c3c(F)cncc3F)c(-c3ccccc3)nc2[nH]1] |
| 1.267 | 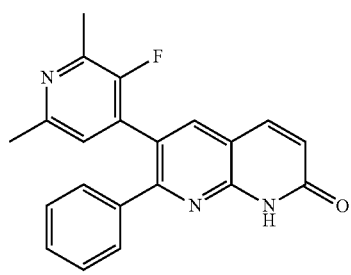 [SMILES: Cc1cc(-c2cc3ccc(=O)[nH]c3nc2-c2ccccc2)c(F)c(C)n1] |

TABLE 1-continued
| Compound No. | Compound |
|---|---|
| 1.268 | 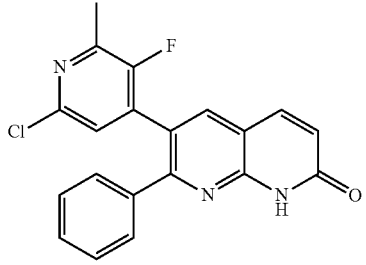 [SMILES: Cc1nc(Cl)cc(-c2cc3ccc(=O)[nH]c3nc2-c2ccccc2)c1F] |
| 1.269 | 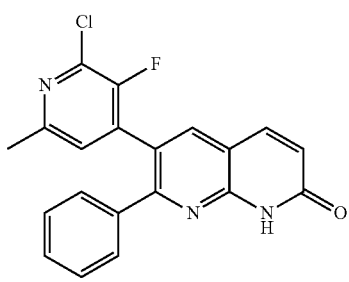 [SMILES: Cc1cc(-c2cc3ccc(=O)[nH]c3nc2-c2ccccc2)c(F)c(Cl)n1] |
| 1.270 | 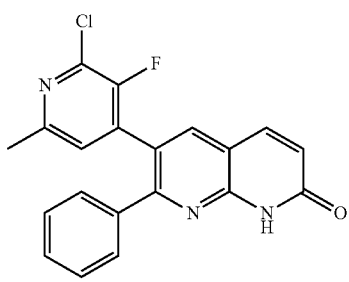 [SMILES: Cc1cc(-c2cc3ccc(=O)[nH]c3nc2-c2ccccc2)c(F)c(Cl)n1] |
| 1.271 | 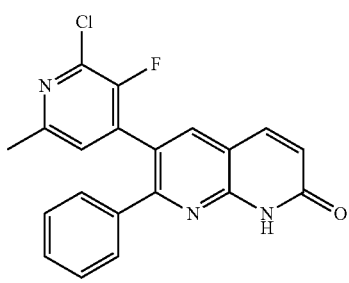 [SMILES: Cc1cc(-c2cc3ccc(=O)[nH]c3nc2-c2ccccc2)c(F)c(Cl)n1] |
| 1.272 | 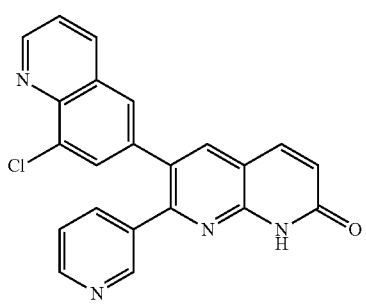 [SMILES: O=c1ccc2cc(-c3cc(Cl)c4ncccc4c3)c(-c3cccnc3)nc2[nH]1] |

TABLE 1-continued
| Compound No. | Compound |
|---|---|
| 1.273 | 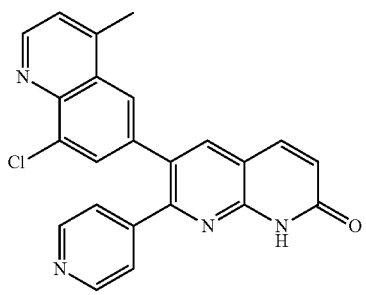 |
| 1.274 | 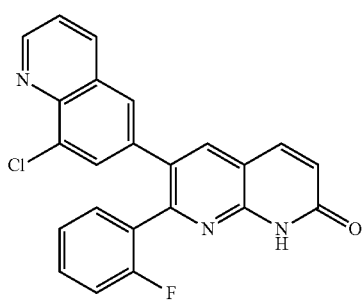 [SMILES: O=c1ccc2cc(-c3cc(Cl)c4ncccc4c3)c(-c3ccccc3F)nc2[nH]1] |
| 1.275 | 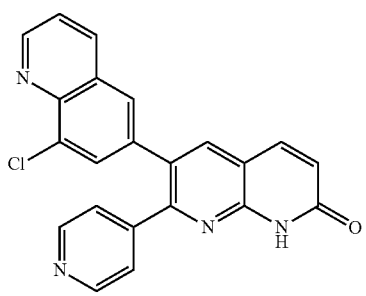 |
| 1.276 | 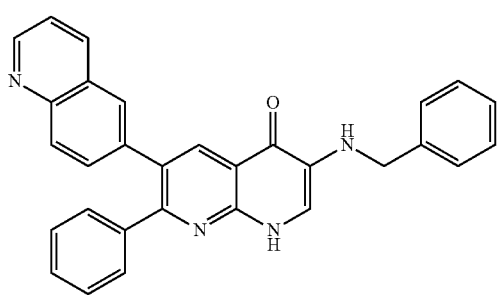 [SMILES: O=c1c(NCc2ccccc2)c[nH]c2nc(-c3ccccc3)c(-c3ccc4ncccc4c3)cc12] |
| 1.277 | 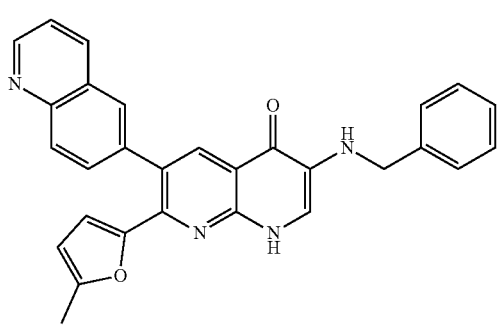 [SMILES: Cc1ccc(-c2nc3[nH]cc(NCc4ccccc4)c(=O)c3cc2-c2ccc3ncccc3c2)o1] |

TABLE 1-continued
| Compound No. | Compound |
|---|---|
| 1.278 | 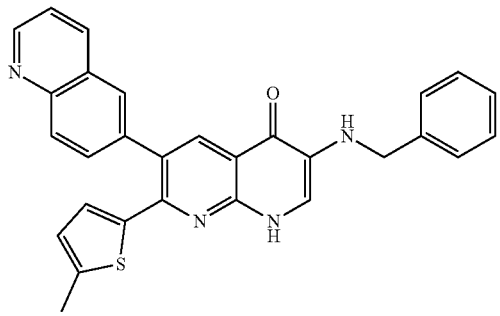 |
| 1.279 | 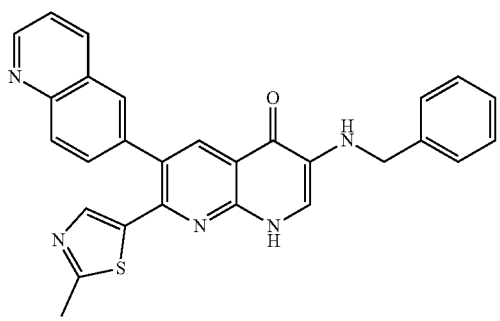 [SMILES: Cc1ncc(-c2nc3[nH]cc(NCc4ccccc4)c(=O)c3cc2-c2ccc3ncccc3c2)s1] |
| 1.280 | 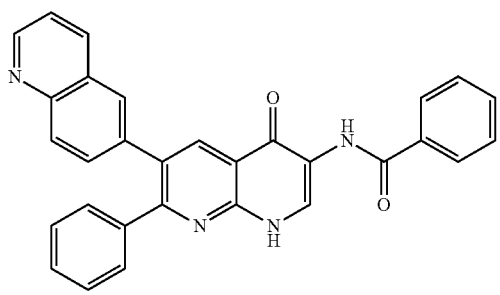 [SMILES: O=C(Nc1c[nH]c2nc(-c3ccccc3)c(-c3ccc4ncccc4c3)cc2c1=O)c1ccccc1] |
| 1.281 | 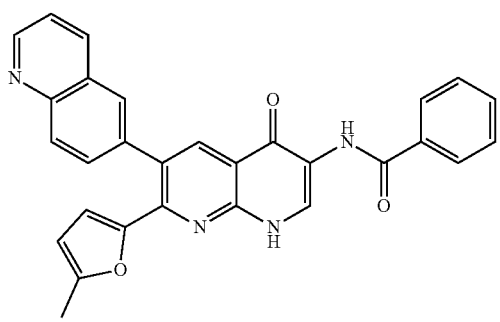 [SMILES: Cc1ccc(-c2nc3[nH]cc(NC(=O)c4ccccc4)c(=O)c3cc2-c2ccc3ncccc3c2)o1] |
| 1.282 | 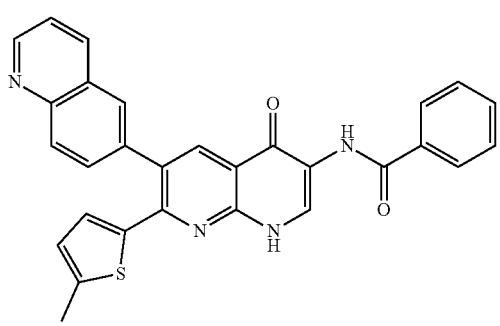 [SMILES: Cc1ccc(-c2nc3[nH]cc(NC(=O)c4ccccc4)c(=O)c3cc2-c2ccc3ncccc3c2)s1] |

TABLE 1-continued
| Compound No. | Compound |
|---|---|
| 1.283 | 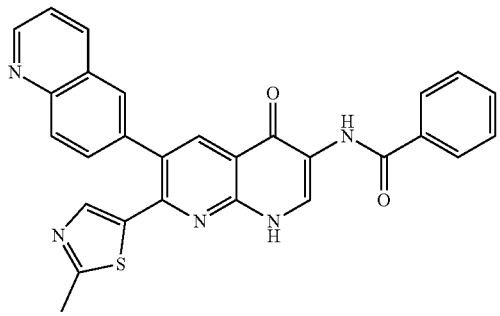 [SMILES: Cc1ncc(-c2nc3[nH]cc(NC(=O)c4ccccc4)c(=O)c3cc2-c2ccc3ncccc3c2)s1] |
| 1.284 | 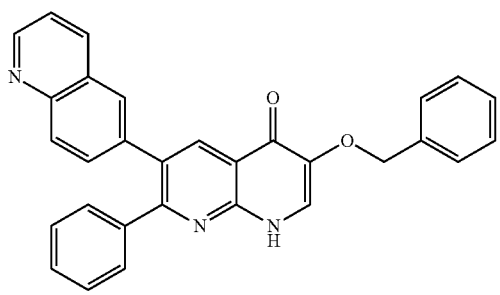 [SMILES: O=c1c(OCc2ccccc2)c[nH]c2nc(-c3ccccc3)c(-c3ccc4ncccc4c3)cc12] |
| 1.285 | 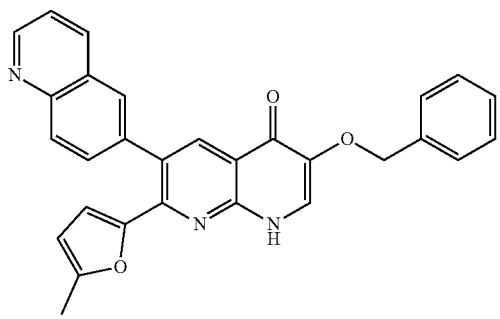 [SMILES: Cc1ccc(-c2nc3[nH]cc(OCc4ccccc4)c(=O)c3cc2-c2ccc3ncccc3c2)o1] |
| 1.286 | 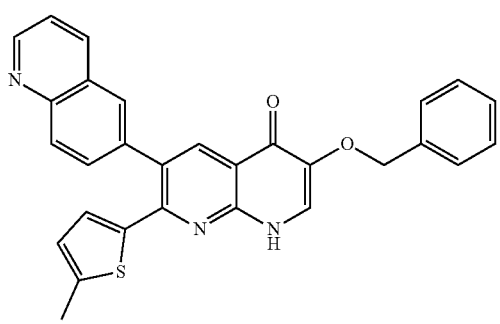 |
| 1.287 | 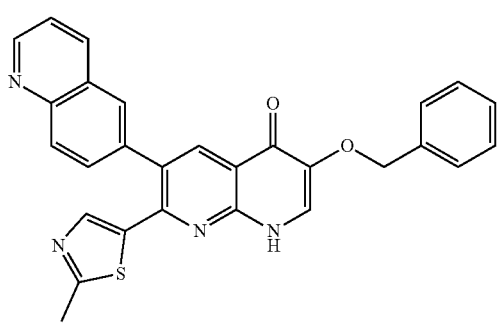 [SMILES: Cc1ncc(-c2nc3[nH]cc(OCc4ccccc4)c(=O)c3cc2-c2ccc3ncccc3c2)s1] |

TABLE 1-continued
| Compound No. | Compound |
|---|---|
| 1.288 | 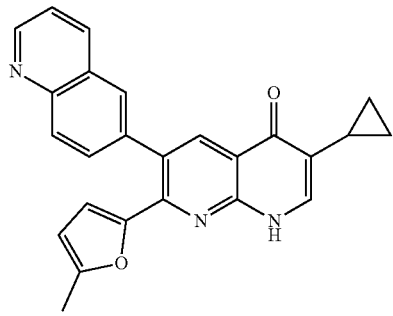 [SMILES: Cc1ccc(-c2nc3[nH]cc(C4CC4)c(=O)c3cc2-c2ccc3ncccc3c2)o1] |
| 1.289 | 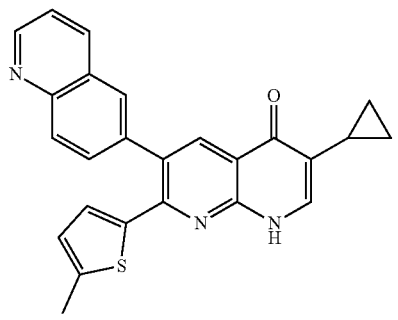 [SMILES: Cc1ccc(-c2nc3[nH]cc(C4CC4)c(=O)c3cc2-c2ccc3ncccc3c2)s1] |
| 1.290 | 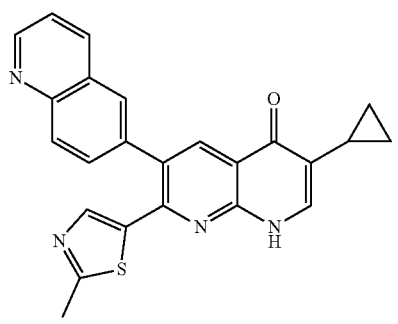 [SMILES: Cc1ncc(-c2nc3[nH]cc(C4CC4)c(=O)c3cc2-c2ccc3ncccc3c2)s1] |
| 1.291 | 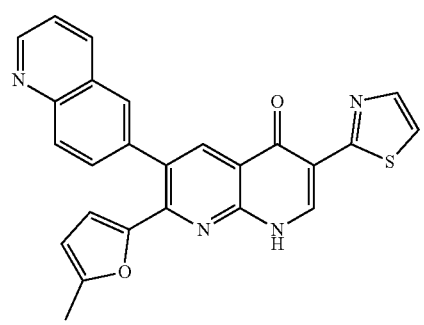 [SMILES: Cc1ccc(-c2nc3[nH]cc(-c4nccs4)c(=O)c3cc2-c2ccc3ncccc3c2)o1] |
| 1.292 | 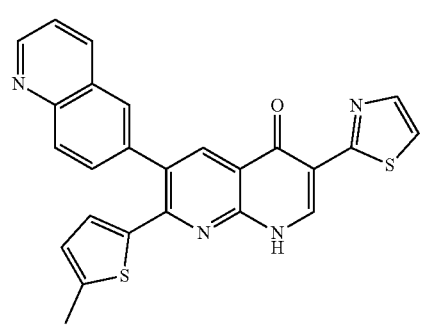 |

TABLE 1-continued
| Compound No. | Compound |
|---|---|
| 1.293 | 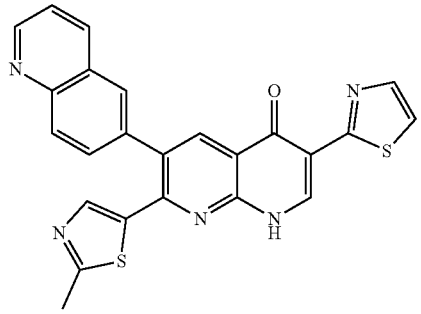 [SMILES: Cc1ncc(-c2nc3[nH]cc(-c4nccs4)c(=O)c3cc2-c2ccc3ncccc3c2)s1] |
| 1.294 | 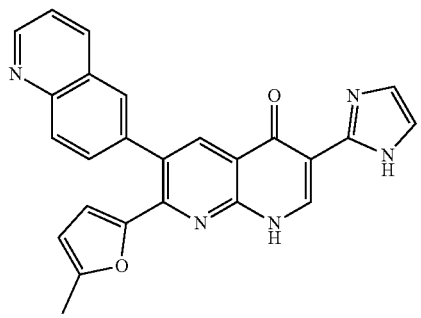 [SMILES: Cc1ccc(-c2nc3[nH]cc(-c4ncc[nH]4)c(=O)c3cc2-c2ccc3ncccc3c2)o1] |
| 1.295 | 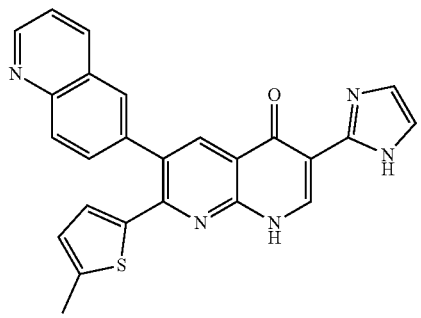 |
| 1.296 | 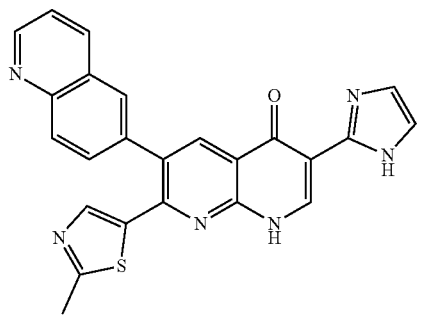 [SMILES: Cc1ncc(-c2nc3[nH]cc(-c4ncc[nH]4)c(=O)c3cc2-c2ccc3ncccc3c2)s1] |
| 1.297 | 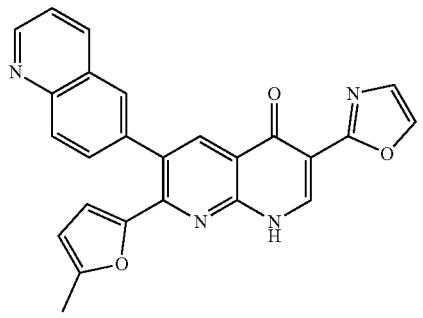 |

TABLE 1-continued

| Compound No. | Compound |
|---|---|
| 1.298 | |
| 1.299 | |
| 1.300 | |
| 1.301 | |
| 1.302 | |

TABLE 1-continued
| Compound No. | Compound |
|---|---|
| 1.303 | 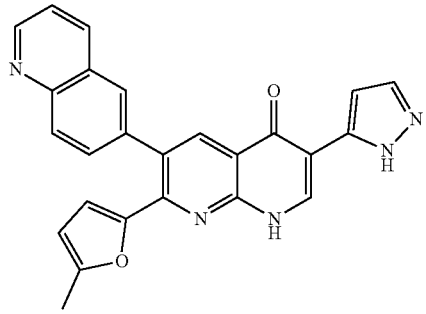 [SMILES: Cc1ccc(-c2nc3[nH]cc(-c4ccn[nH]4)c(=O)c3cc2-c2ccc3ncccc3c2)o1] |
| 1.304 | 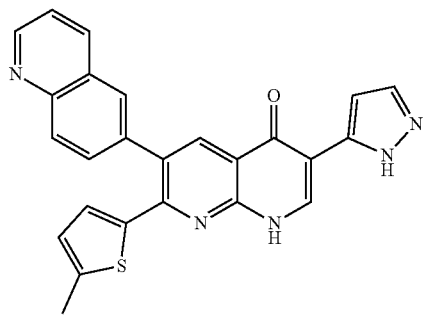 [SMILES: Cc1ccc(-c2nc3[nH]cc(-c4ccn[nH]4)c(=O)c3cc2-c2ccc3ncccc3c2)s1] |
| 1.305 | 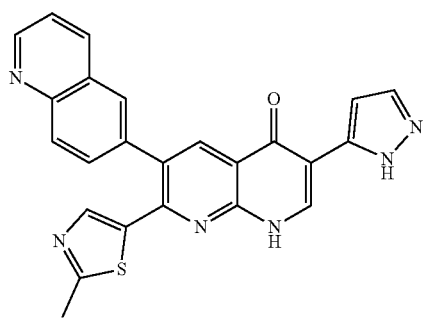 [SMILES: Cc1ncc(-c2nc3[nH]cc(-c4ccn[nH]4)c(=O)c3cc2-c2ccc3ncccc3c2)s1] |
| 1.306 | 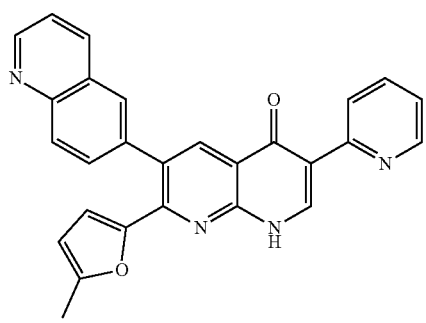 [SMILES: Cc1ccc(-c2nc3[nH]cc(-c4ccccn4)c(=O)c3cc2-c2ccc3ncccc3c2)o1] |
| 1.307 | 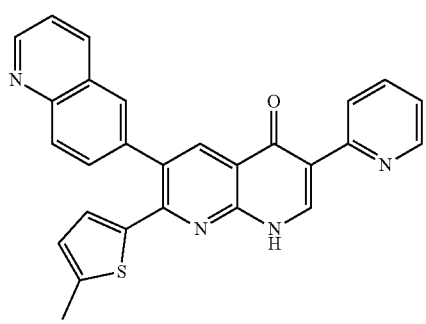 [SMILES: Cc1ccc(-c2nc3[nH]cc(-c4ccccn4)c(=O)c3cc2-c2ccc3ncccc3c2)s1] |

TABLE 1-continued

| Compound No. | Compound |
|---|---|
| 1.308 | |
| 1.309 | |
| 1.310 | |
| 1.311 | |
| 1.312 | |

TABLE 1-continued
| Compound No. | Compound |
|---|---|
| 1.313 | 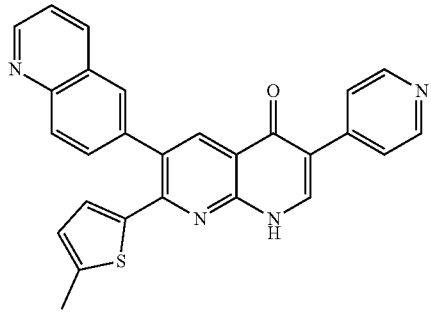 [SMILES: Cc1ccc(-c2nc3[nH]cc(-c4ccncc4)c(=O)c3cc2-c2ccc3ncccc3c2)s1] |
| 1.314 | 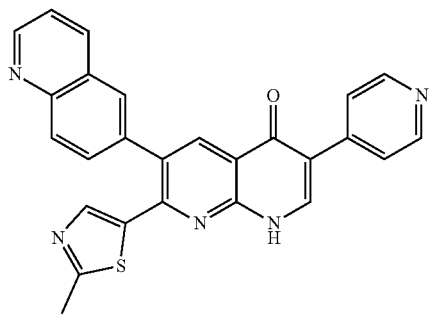 [SMILES: Cc1ncc(-c2nc3[nH]cc(-c4ccncc4)c(=O)c3cc2-c2ccc3ncccc3c2)s1] |
| 1.315 | 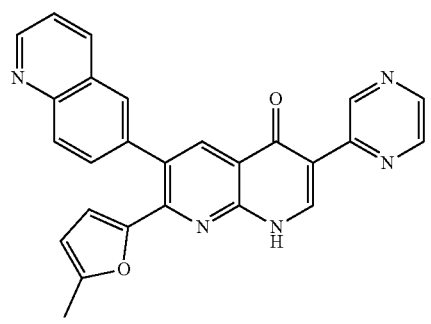 [SMILES: Cc1ccc(-c2nc3[nH]cc(-c4cnccn4)c(=O)c3cc2-c2ccc3ncccc3c2)o1] |
| 1.316 | 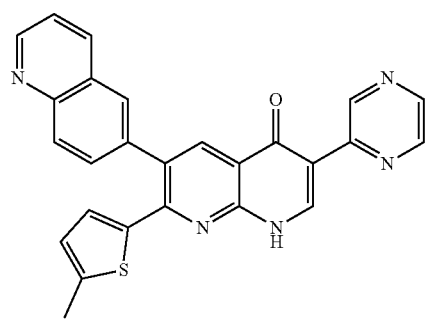 [SMILES: Cc1ccc(-c2nc3[nH]cc(-c4cnccn4)c(=O)c3cc2-c2ccc3ncccc3c2)s1] |
| 1.317 | 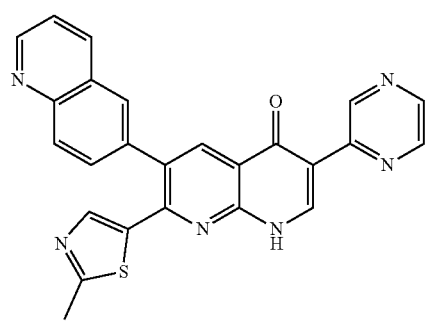 [SMILES: Cc1ncc(-c2nc3[nH]cc(-c4cnccn4)c(=O)c3cc2-c2ccc3ncccc3c2)s1] |

TABLE 1-continued
| Compound No. | Compound |
|---|---|
| 1.318 | 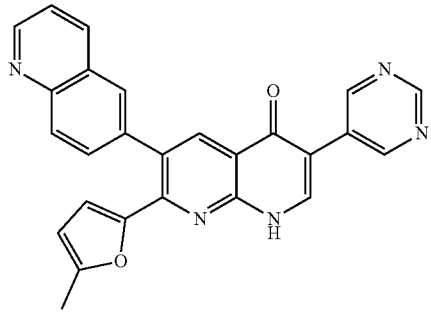 [SMILES: Cc1ccc(-c2nc3[nH]cc(-c4cncnc4)c(=O)c3cc2-c2ccc3ncccc3c2)o1] |
| 1.319 | 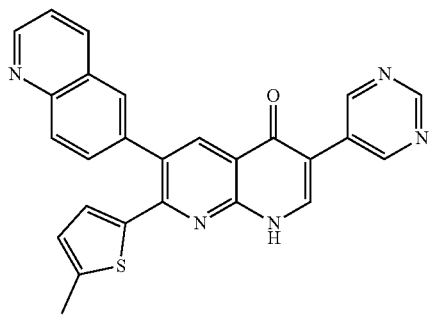 [SMILES: Cc1ccc(-c2nc3[nH]cc(-c4cncnc4)c(=O)c3cc2-c2ccc3ncccc3c2)s1] |
| 1.320 | 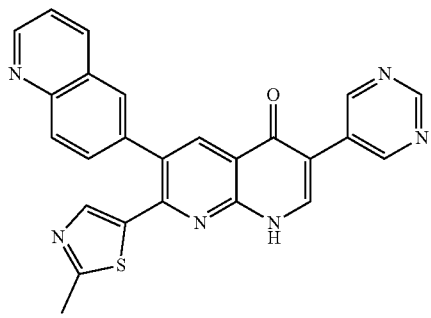 [SMILES: Cc1ncc(-c2nc3[nH]cc(-c4cncnc4)c(=O)c3cc2-c2ccc3ncccc3c2)s1] |
| 1.321 | 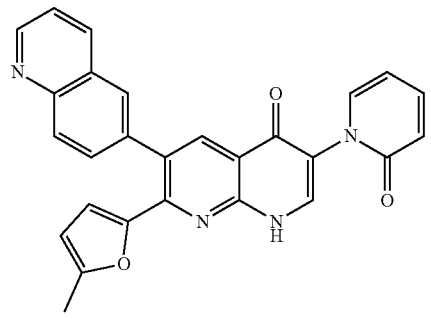 [SMILES: Cc1ccc(-c2nc3[nH]cc(-n4ccccc4=O)c(=O)c3cc2-c2ccc3ncccc3c2)o1] |
| 1.322 | 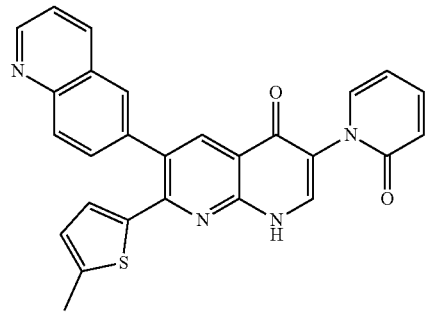 [SMILES: Cc1ccc(-c2nc3[nH]cc(-n4ccccc4=O)c(=O)c3cc2-c2ccc3ncccc3c2)s1] |

TABLE 1-continued
| Compound No. | Compound |
|---|---|
| 1.323 | 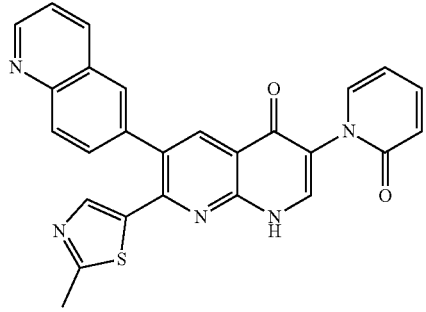 [SMILES: Cc1ncc(-c2nc3[nH]cc(-n4ccccc4=O)c(=O)c3cc2-c2ccc3ncccc3c2)s1] |
| 1.324 | 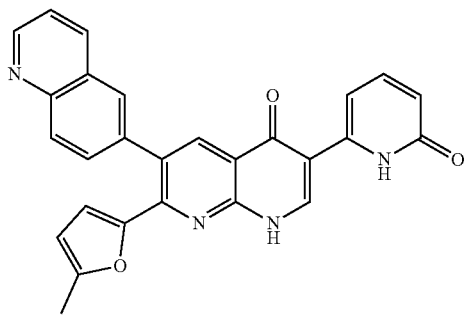 [SMILES: Cc1ccc(-c2nc3[nH]cc(-c4cccc(=O)[nH]4)c(=O)c3cc2-c2ccc3ncccc3c2)o1] |
| 1.325 | 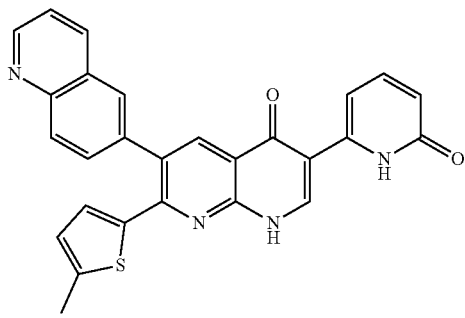 [SMILES: Cc1ccc(-c2nc3[nH]cc(-c4cccc(=O)[nH]4)c(=O)c3cc2-c2ccc3ncccc3c2)s1] |
| 1.326 | 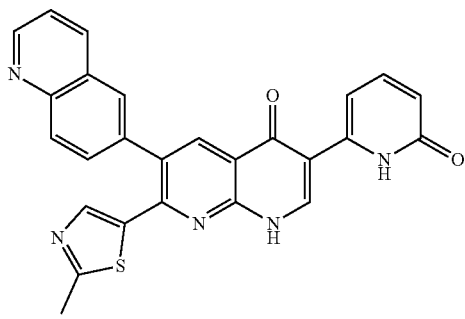 [SMILES: Cc1ncc(-c2nc3[nH]cc(-c4cccc(=O)[nH]4)c(=O)c3cc2-c2ccc3ncccc3c2)s1] |
| 1.327 | 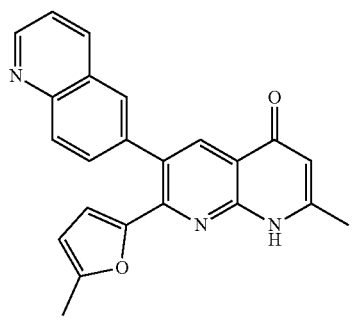 [SMILES: Cc1cc(=O)c2cc(-c3ccc4ncccc4c3)c(-c3ccc(C)o3)nc2[nH]1] |

TABLE 1-continued
| Compound No. | Compound |
|---|---|
| 1.328 | 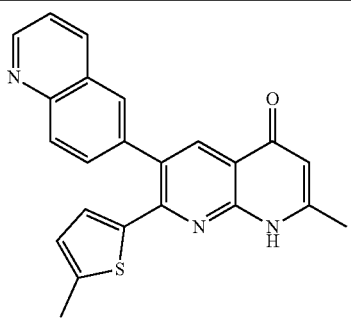 |
| 1.329 | 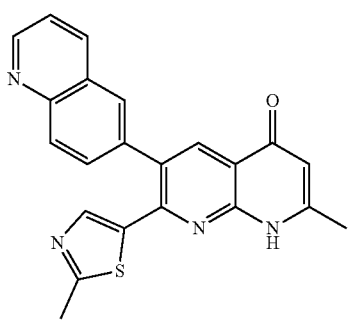 [SMILES: Cc1cc(=O)c2cc(-c3ccc4ncccc4c3)c(-c3cnc(C)s3)nc2[nH]1] |
| 1.330 | 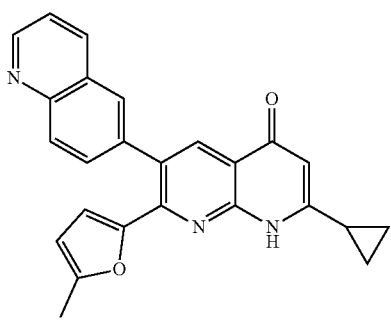 [SMILES: Cc1ccc(-c2nc3[nH]c(C4CC4)cc(=O)c3cc2-c2ccc3ncccc3c2)o1] |
| 1.331 | 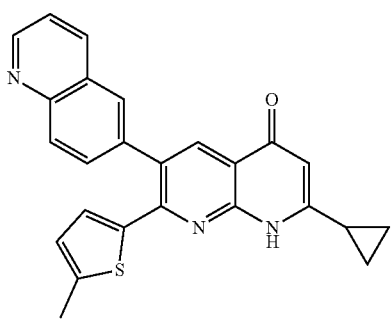 [SMILES: Cc1ccc(-c2nc3[nH]c(C4CC4)cc(=O)c3cc2-c2ccc3ncccc3c2)s1] |
| 1.332 | 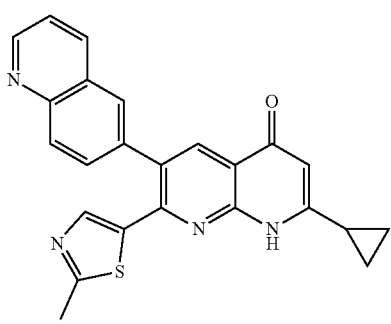 [SMILES: Cc1ncc(-c2nc3[nH]c(C4CC4)cc(=O)c3cc2-c2ccc3ncccc3c2)s1] |

TABLE 1-continued

| Compound No. | Compound |
|---|---|
| 1.333 | |
| 1.334 | |
| 1.335 | |
| 1.336 | |
| 1.337 | |

TABLE 1-continued

| Compound No. | Compound |
|---|---|
| 1.338 | ![structure] |
| 1.339 | ![structure] |
| 1.340 | ![structure] |
| 1.341 | ![structure] |
| 1.342 | ![structure] |

TABLE 1-continued

| Compound No. | Compound |
|---|---|
| 1.343 | |
| 1.344 | |
| 1.345 | |
| 1.346 | |
| 1.347 | |

TABLE 1-continued
| Compound No. | Compound |
|---|---|
| 1.348 | 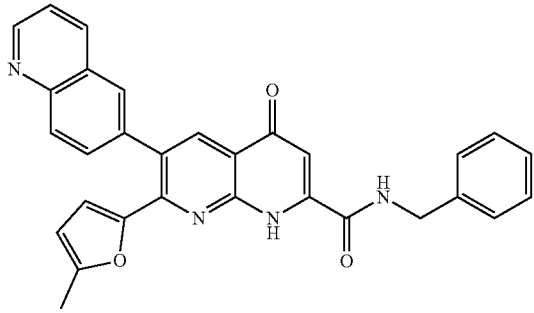 [SMILES: Cc1ccc(-c2nc3[nH]c(C(=O)NCc4ccccc4)cc(=O)c3cc2-c2ccc3ncccc3c2)o1] |
| 1.349 | 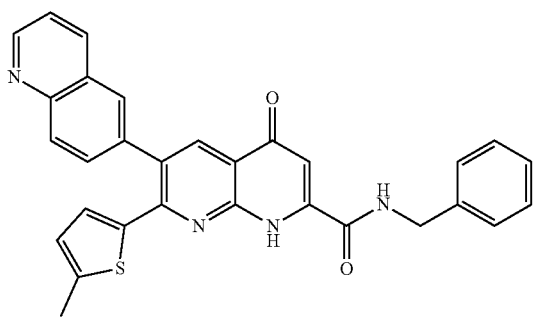 |
| 1.350 | 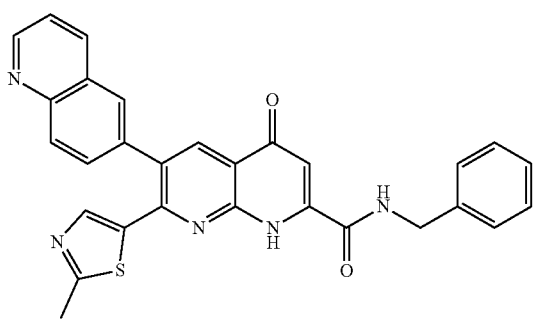 [SMILES: Cc1ncc(-c2nc3[nH]c(C(=O)NCc4ccccc4)cc(=O)c3cc2-c2ccc3ncccc3c2)s1] |
| 1.351 | 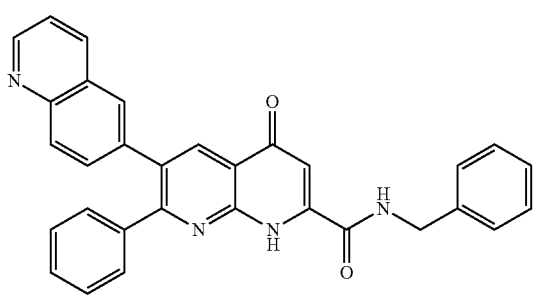 [SMILES: O=C(NCc1ccccc1)c1cc(=O)c2cc(-c3ccc4ncccc4c3)c(-c3ccccc3)nc2[nH]1] |
| 1.352 | 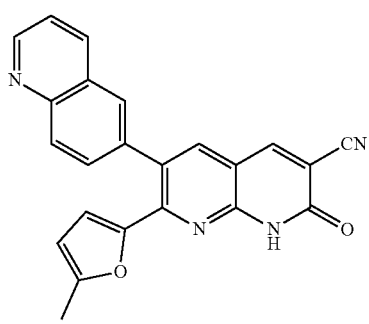 [SMILES: Cc1ccc(-c2nc3[nH]c(=O)c(C#N)cc3cc2-c2ccc3ncccc3c2)o1] |

TABLE 1-continued

| Compound No. | Compound |
|---|---|
| 1.353 | (quinolin-6-yl substituted 1,8-naphthyridin-2(1H)-one with 3-cyano and 7-(5-methylthiophen-2-yl)) |
| 1.354 | (quinolin-6-yl substituted 1,8-naphthyridin-2(1H)-one with 3-cyano and 7-(2-methylthiazol-5-yl)) |
| 1.355 | (quinolin-6-yl substituted 1,8-naphthyridin-2(1H)-one-3-carboxamide with 7-(5-methylfuran-2-yl)) |
| 1.356 | (quinolin-6-yl substituted 1,8-naphthyridin-2(1H)-one-3-carboxamide with 7-(5-methylthiophen-2-yl)) |
| 1.357 | (quinolin-6-yl substituted 1,8-naphthyridin-2(1H)-one-3-carboxamide with 7-(2-methylthiazol-5-yl)) |

TABLE 1-continued
| Compound No. | Compound |
|---|---|
| 1.358 | 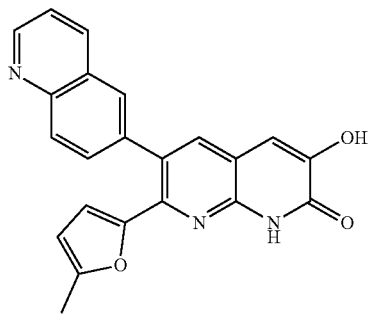 |
| 1.359 | 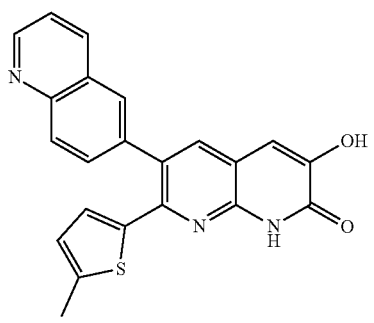 [SMILES: Cc1ccc(-c2nc3[nH]c(=O)c(C#N)cc3cc2-c2ccc3ncccc3c2)s1] |
| 1.360 | 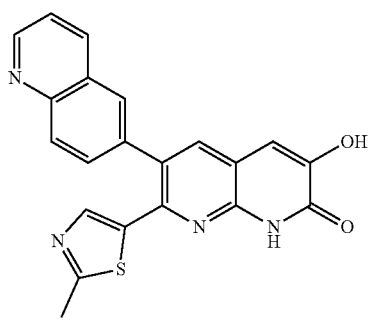 [SMILES: Cc1ncc(-c2nc3[nH]c(=O)c(O)cc3cc2-c2ccc3ncccc3c2)s1] |
| 1.361 | 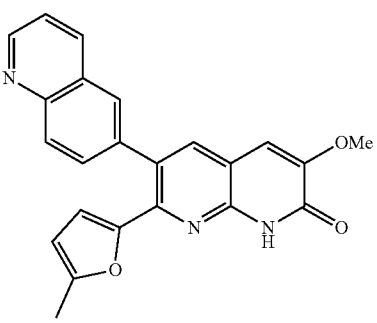 [SMILES: COc1cc2cc(-c3ccc4ncccc4c3)c(-c3ccc(C)o3)nc2[nH]c1=O] |
| 1.362 | 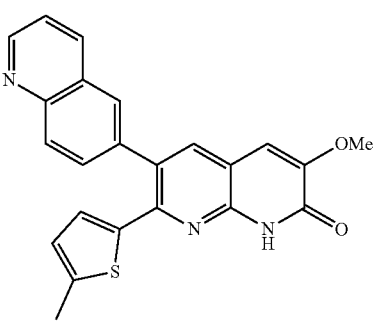 [SMILES: COc1cc2cc(-c3ccc4ncccc4c3)c(-c3ccc(C)s3)nc2[nH]c1=O] |

TABLE 1-continued
| Compound No. | Compound |
|---|---|
| 1.363 | 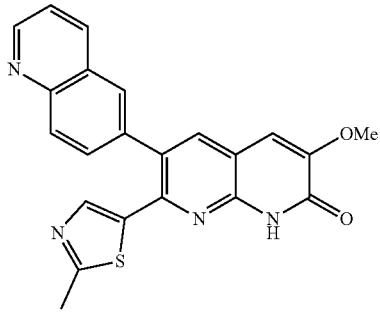 [SMILES: COc1cc2cc(-c3ccc4ncccc4c3)c(-c3cnc(C)s3)nc2[nH]c1=O] |
| 1.364 | 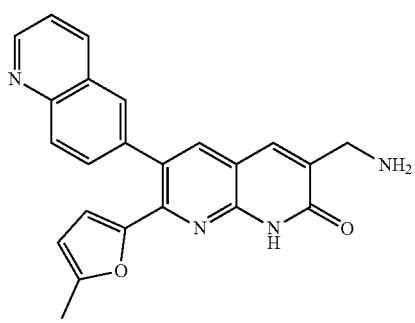 [SMILES: Cc1ccc(-c2nc3[nH]c(=O)c(CN)cc3cc2-c2ccc3ncccc3c2)o1] |
| 1.365 | 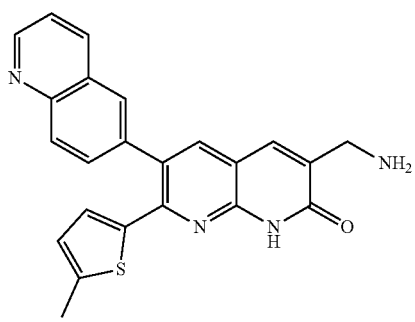 [SMILES: Cc1ccc(-c2nc3[nH]c(=O)c(CN)cc3cc2-c2ccc3ncccc3c2)s1] |
| 1.366 | 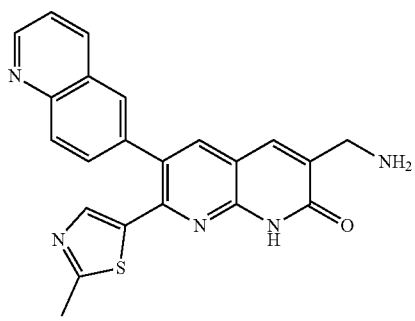 [SMILES: Cc1ncc(-c2nc3[nH]c(=O)c(CN)cc3cc2-c2ccc3ncccc3c2)s1] |
| 1.367 | 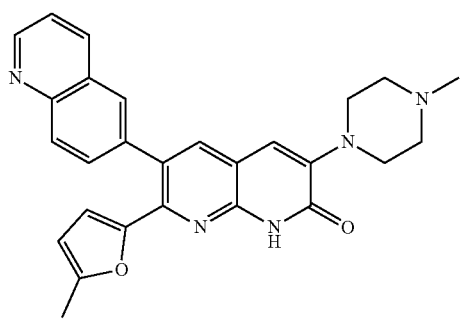 |

TABLE 1-continued
| Compound No. | Compound |
|---|---|
| 1.368 | 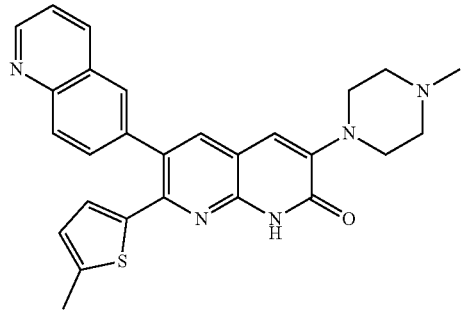 [SMILES: Cc1ccc(-c2nc3[nH]c(=O)c(N4CCN(C)CC4)cc3cc2-c2ccc3ncccc3c2)o1] |
| 1.369 | 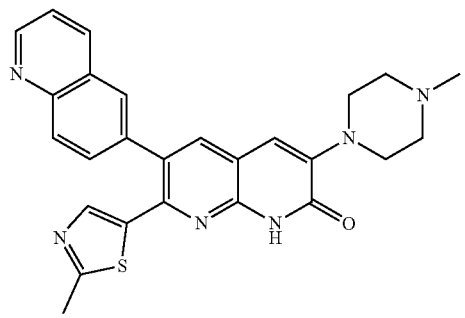 [SMILES: Cc1ncc(-c2nc3[nH]c(=O)c(N4CCN(C)CC4)cc3cc2-c2ccc3ncccc3c2)s1] |
| 1.370 | 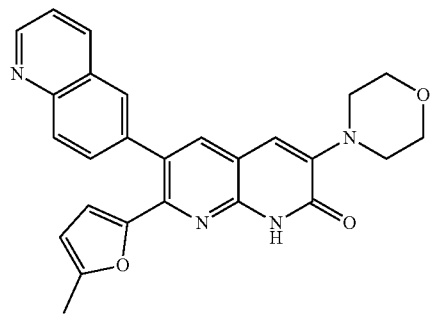 [SMILES: Cc1ccc(-c2nc3[nH]c(=O)c(N4CCOCC4)cc3cc2-c2ccc3ncccc3c2)o1] |
| 1.371 | 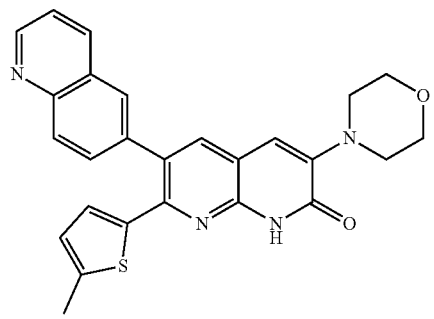 [SMILES: Cc1ccc(-c2nc3[nH]c(=O)c(N4CCOCC4)cc3cc2-c2ccc3ncccc3c2)s1] |
| 1.372 | 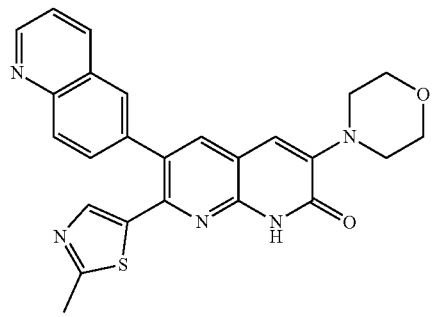 [SMILES: Cc1ncc(-c2nc3[nH]c(=O)c(N4CCOCC4)cc3cc2-c2ccc3ncccc3c2)s1] |

TABLE 1-continued

| Compound No. | Compound |
|---|---|
| 1.373 | |
| 1.374 | |
| 1.375 | |
| 1.376 | |
| 1.377 | |

TABLE 1-continued
| Compound No. | Compound |
| --- | --- |
| 1.378 | 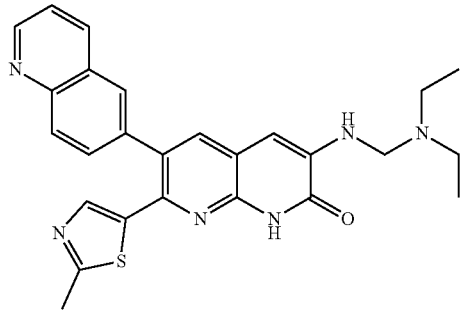 [SMILES: CCN(CC)CNc1cc2cc(-c3ccc4ncccc4c3)c(-c3cnc(C)s3)nc2[nH]c1=O] |
| 1.379 | 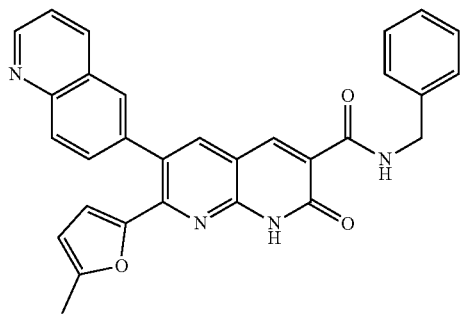 [SMILES: Cc1ccc(-c2nc3[nH]c(=O)c(C(=O)NCc4ccccc4)cc3cc2-c2ccc3ncccc3c2)o1] |
| 1.380 | 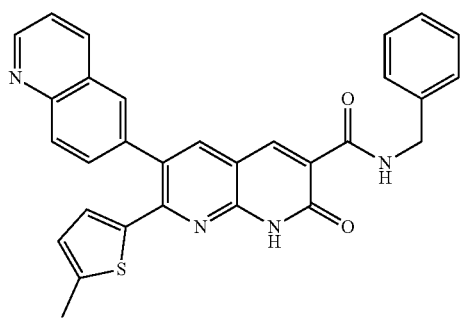 |
| 1.381 | 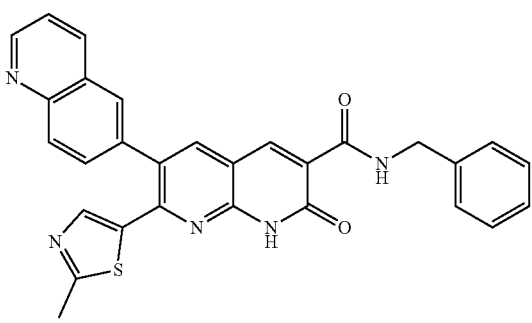 [SMILES: Cc1ncc(-c2nc3[nH]c(=O)c(C(=O)NCc4ccccc4)cc3cc2-c2ccc3ncccc3c2)s1] |
| 1.382 | 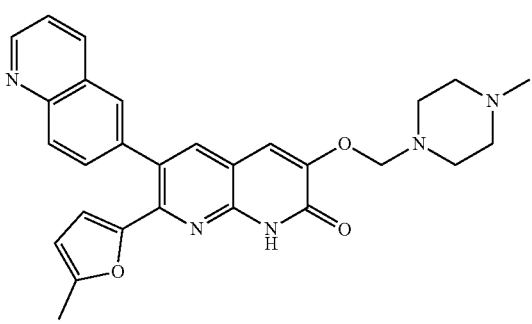 [SMILES: Cc1ccc(-c2nc3[nH]c(=O)c(OCN4CCN(C)CC4)cc3cc2-c2ccc3ncccc3c2)o1] |

TABLE 1-continued
| Compound No. | Compound |
|---|---|
| 1.383 | 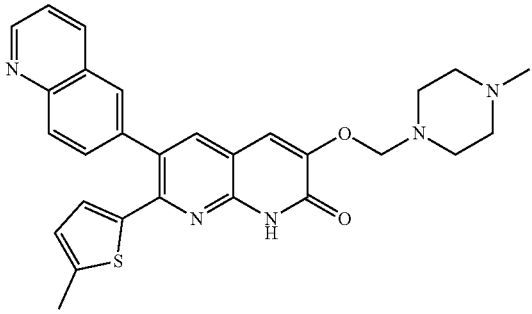 [SMILES: Cc1ccc(-c2nc3[nH]c(=O)c(OCN4CCN(C)CC4)cc3cc2-c2ccc3ncccc3c2)s1] |
| 1.384 | 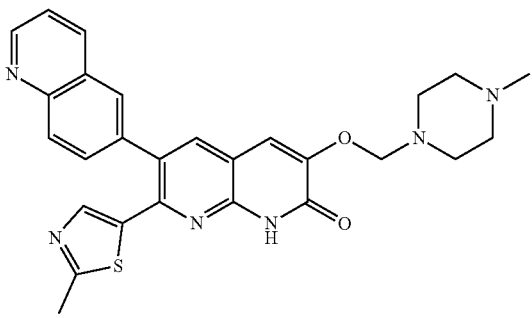 [SMILES: Cc1ncc(-c2nc3[nH]c(=O)c(OCN4CCN(C)CC4)cc3cc2-c2ccc3ncccc3c2)s1] |
| 1.385 | 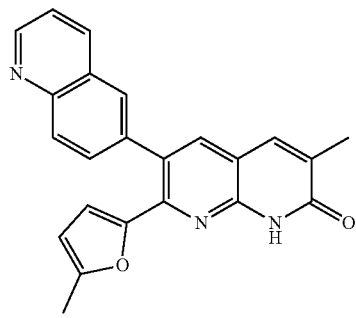 [SMILES: Cc1ccc(-c2nc3[nH]c(=O)c(C)cc3cc2-c2ccc3ncccc3c2)o1] |
| 1.386 | 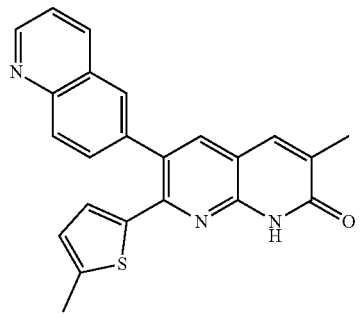 [SMILES: Cc1ccc(-c2nc3[nH]c(=O)c(C)cc3cc2-c2ccc3ncccc3c2)s1] |
| 1.387 | 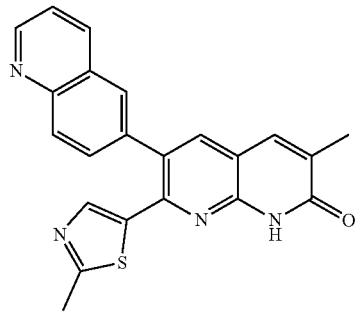 [SMILES: Cc1ncc(-c2nc3[nH]c(=O)c(C)cc3cc2-c2ccc3ncccc3c2)s1] |

TABLE 1-continued
| Compound No. | Compound |
|---|---|
| 1.388 | 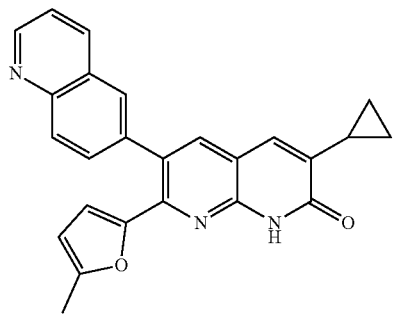 [SMILES: Cc1ccc(-c2nc3[nH]c(=O)c(C4CC4)cc3cc2-c2ccc3ncccc3c2)o1] |
| 1.389 | 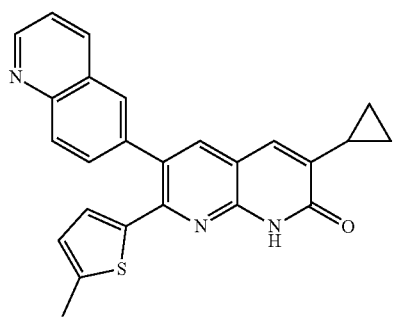 [SMILES: Cc1ccc(-c2nc3[nH]c(=O)c(C4CC4)cc3cc2-c2ccc3ncccc3c2)s1] |
| 1.390 | 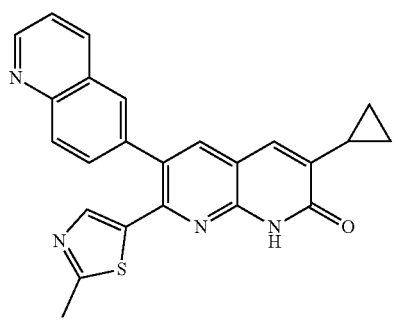 [SMILES: Cc1ncc(-c2nc3[nH]c(=O)c(C4CC4)cc3cc2-c2ccc3ncccc3c2)s1] |
| 1.391 | 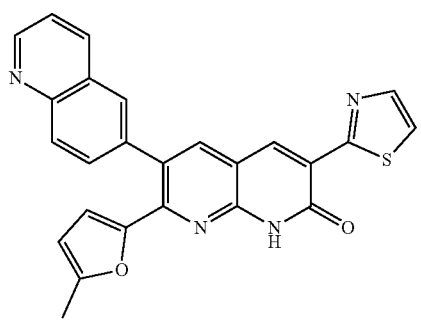 [SMILES: Cc1ccc(-c2nc3[nH]c(=O)c(-c4nccs4)cc3cc2-c2ccc3ncccc3c2)o1] |
| 1.392 | 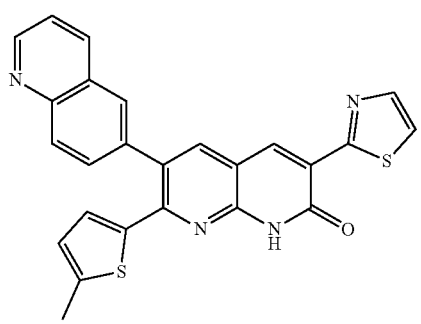 [SMILES: Cc1ccc(-c2nc3[nH]c(=O)c(-c4nccs4)cc3cc2-c2ccc3ncccc3c2)s1] |

TABLE 1-continued
| Compound No. | Compound |
|---|---|
| 1.393 | 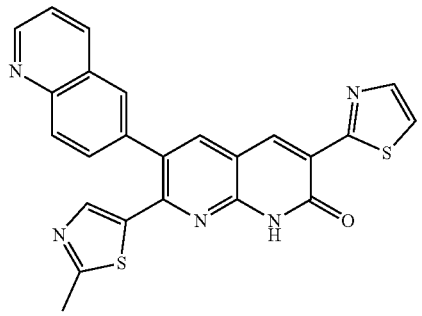 [SMILES: Cc1ncc(-c2nc3[nH]c(=O)c(-c4nccs4)cc3cc2-c2ccc3ncccc3c2)s1] |
| 1.394 | 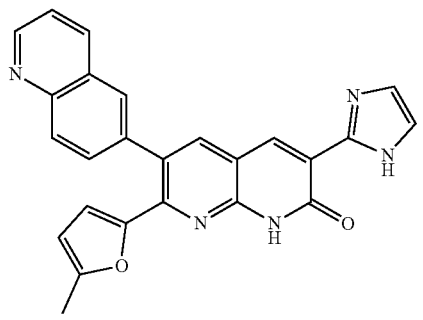 [SMILES: Cc1ccc(-c2nc3[nH]c(=O)c(-c4ncc[nH]4)cc3cc2-c2ccc3ncccc3c2)o1] |
| 1.395 | 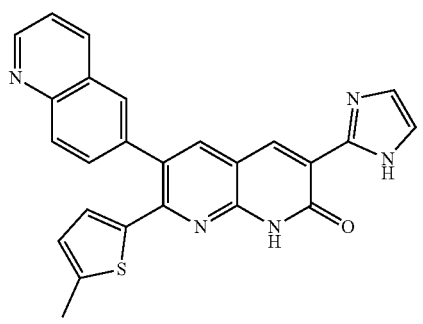 [SMILES: Cc1ccc(-c2nc3[nH]c(=O)c(-c4ncc[nH]4)cc3cc2-c2ccc3ncccc3c2)s1] |
| 1.396 | 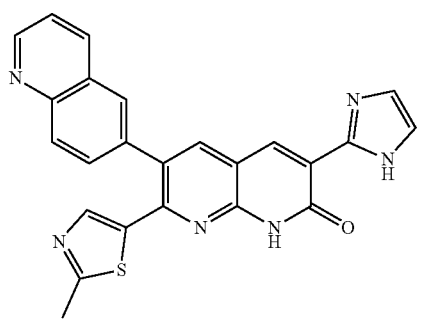 [SMILES: Cc1ncc(-c2nc3[nH]c(=O)c(-c4ncc[nH]4)cc3cc2-c2ccc3ncccc3c2)s1] |
| 1.397 | 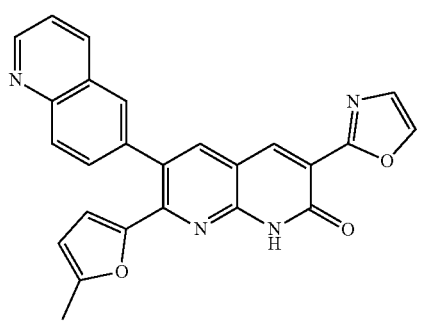 [SMILES: Cc1ccc(-c2nc3[nH]c(=O)c(-c4ncco4)cc3cc2-c2ccc3ncccc3c2)o1] |

US 10,793,561 B2
TABLE 1-continued
| Compound No. | Compound |
|---|---|
| 1.398 | 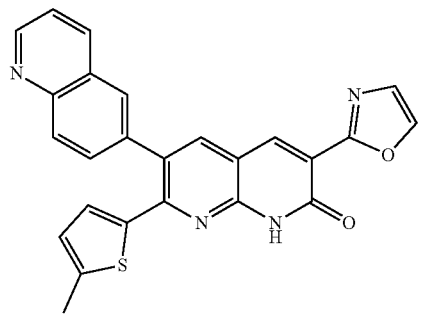 |
| 1.399 | 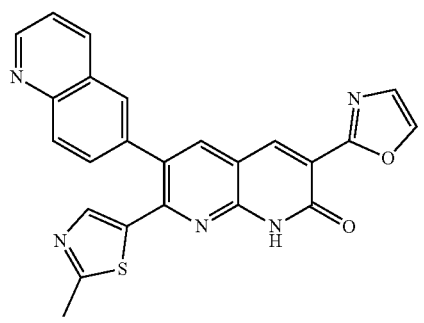 [SMILES: Cc1ncc(-c2nc3[nH]c(=O)c(-c4ncco4)cc3cc2-c2ccc3ncccc3c2)s1] |
| 1.400 | 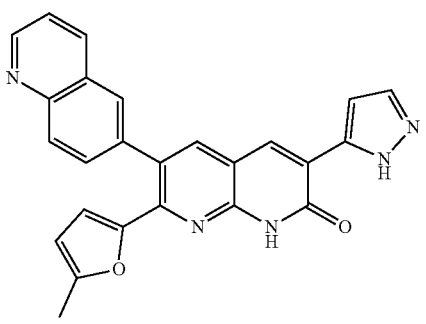 [SMILES: Cc1ccc(-c2nc3[nH]c(=O)c(-c4ccn[nH]4)cc3cc2-c2ccc3ncccc3c2)o1] |
| 1.401 | 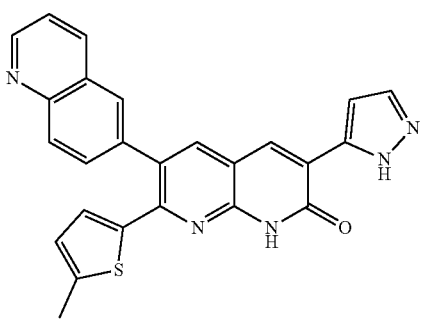 [SMILES: Cc1ccc(-c2nc3[nH]c(=O)c(-c4ccn[nH]4)cc3cc2-c2ccc3ncccc3c2)s1] |
| 1.402 | 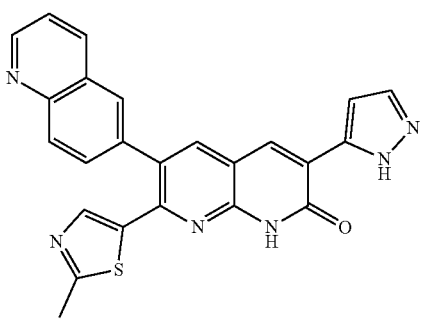 [SMILES: Cc1ncc(-c2nc3[nH]c(=O)c(-c4ccn[nH]4)cc3cc2-c2ccc3ncccc3c2)s1] |

TABLE 1-continued
| Compound No. | Compound |
|---|---|
| 1.403 | 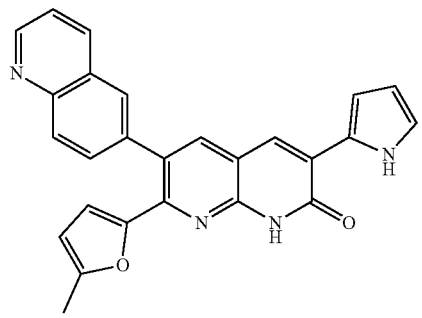 [SMILES: Cc1ccc(-c2nc3[nH]c(=O)c(-c4ccc[nH]4)cc3cc2-c2ccc3ncccc3c2)o1] |
| 1.404 | 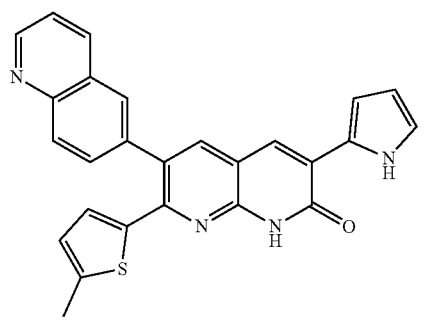 [SMILES: Cc1ccc(-c2nc3[nH]c(=O)c(-c4ccc[nH]4)cc3cc2-c2ccc3ncccc3c2)s1] |
| 1.405 | 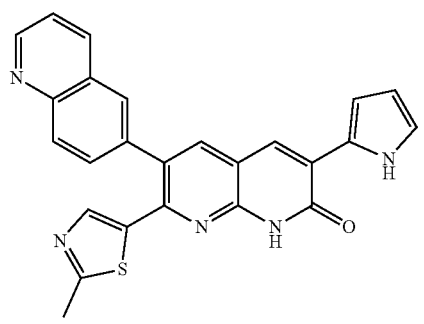 [SMILES: Cc1ncc(-c2nc3[nH]c(=O)c(-c4ccc[nH]4)cc3cc2-c2ccc3ncccc3c2)s1] |
| 1.406 | 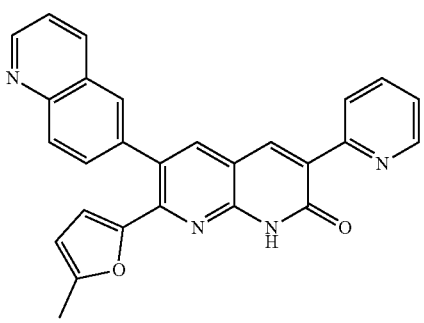 |
| 1.407 | 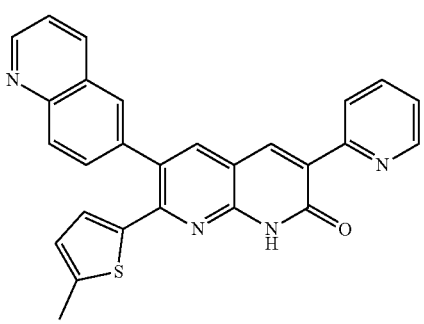 [SMILES: Cc1ccc(-c2nc3[nH]c(=O)c(-c4ccccn4)cc3cc2-c2ccc3ncccc3c2)s1] |

TABLE 1-continued
| Compound No. | Compound |
|---|---|
| 1.408 | 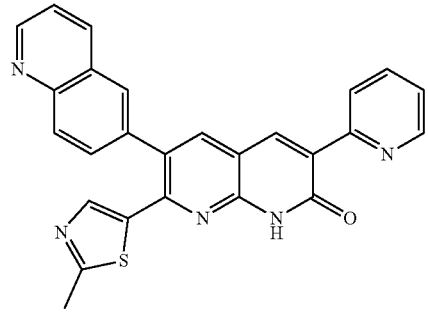 [SMILES: Cc1ncc(-c2nc3[nH]c(=O)c(-c4ccccn4)cc3cc2-c2ccc3ncccc3c2)s1] |
| 1.409 | 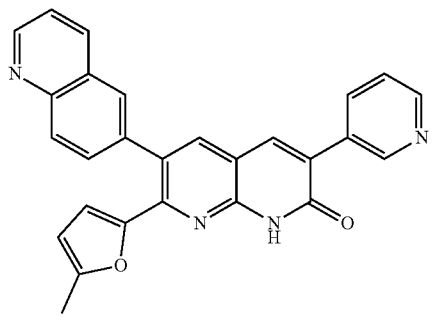 |
| 1.410 | 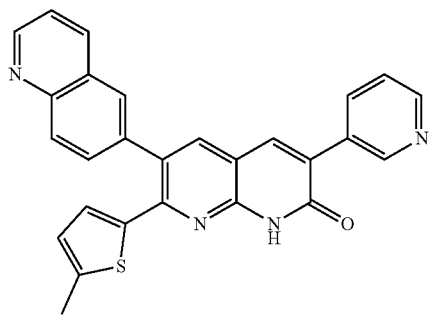 [SMILES: Cc1ccc(-c2nc3[nH]c(=O)c(-c4cccnc4)cc3cc2-c2ccc3ncccc3c2)s1] |
| 1.411 | 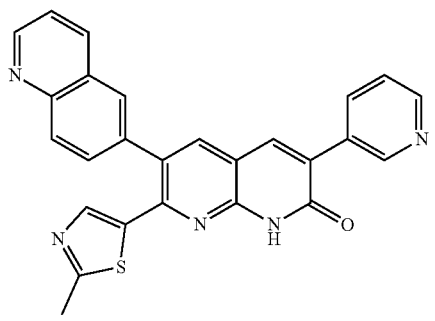 [SMILES: Cc1ncc(-c2nc3[nH]c(=O)c(-c4cccnc4)cc3cc2-c2ccc3ncccc3c2)s1] |

TABLE 1-continued
| Compound No. | Compound |
|---|---|
| 1.412 | 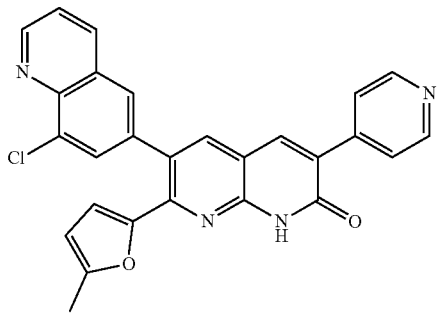 [SMILES: Cc1ccc(-c2nc3[nH]c(=O)c(-c4ccncc4)cc3cc2-c2cc(Cl)c3ncccc3c2)o1] |
| 1.413 | 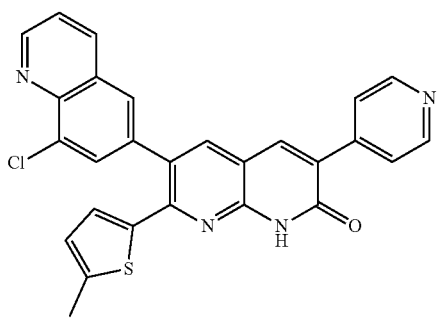 [SMILES: Cc1ccc(-c2nc3[nH]c(=O)c(-c4ccncc4)cc3cc2-c2cc(Cl)c3ncccc3c2)s1] |
| 1.414 | 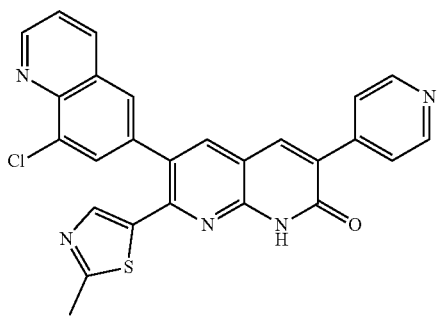 [SMILES: Cc1ncc(-c2nc3[nH]c(=O)c(-c4ccncc4)cc3cc2-c2cc(Cl)c3ncccc3c2)s1] |
| 1.415 | 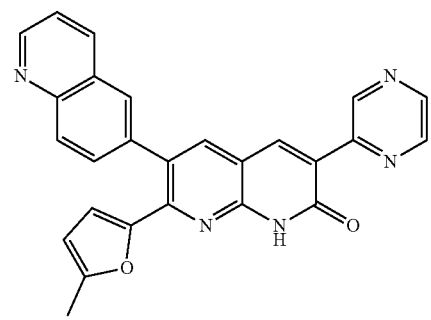 [SMILES: Cc1ccc(-c2nc3[nH]c(=O)c(-c4cnccn4)cc3cc2-c2ccc3ncccc3c2)o1] |

US 10,793,561 B2
TABLE 1-continued
| Compound No. | Compound |
|---|---|
| 1.416 | 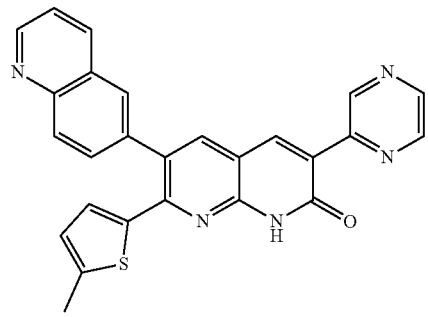 [SMILES: Cc1ccc(-c2nc3[nH]c(=O)c(-c4cnccn4)cc3cc2-c2ccc3ncccc3c2)s1] |
| 1.417 | 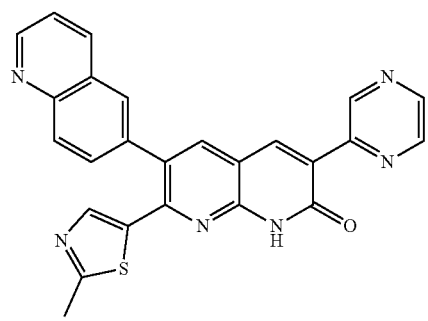 [SMILES: Cc1ncc(-c2nc3[nH]c(=O)c(-c4cnccn4)cc3cc2-c2ccc3ncccc3c2)s1] |
| 1.418 | 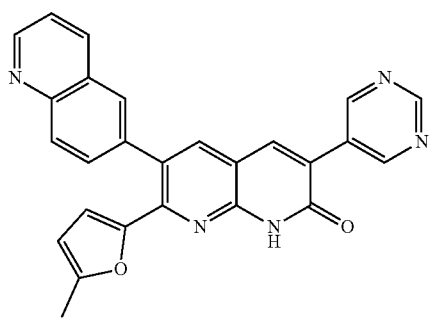 [SMILES: Cc1ccc(-c2nc3[nH]c(=O)c(-c4cncnc4)cc3cc2-c2ccc3ncccc3c2)o1] |
| 1.419 | 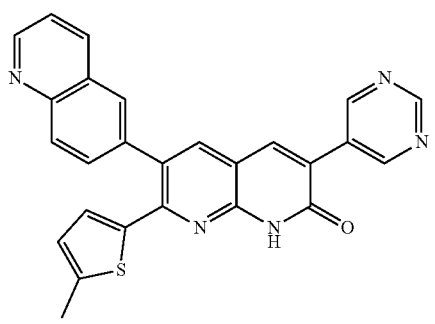 [SMILES: Cc1ccc(-c2nc3[nH]c(=O)c(-c4cncnc4)cc3cc2-c2ccc3ncccc3c2)s1] |

257 258
TABLE 1-continued
| Compound No. | Compound |
|---|---|
| 1.420 | 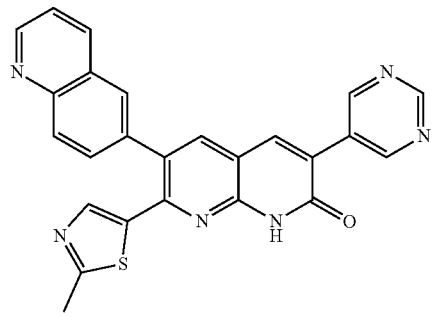 [SMILES: Cc1ncc(-c2nc3[nH]c(=O)c(-c4cncnc4)cc3cc2-c2ccc3ncccc3c2)s1] |
| 1.421 | 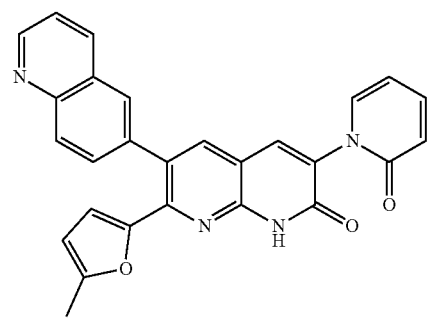 [SMILES: Cc1ccc(-c2nc3[nH]c(=O)c(-n4ccccc4=O)cc3cc2-c2ccc3ncccc3c2)o1] |
| 1.422 | 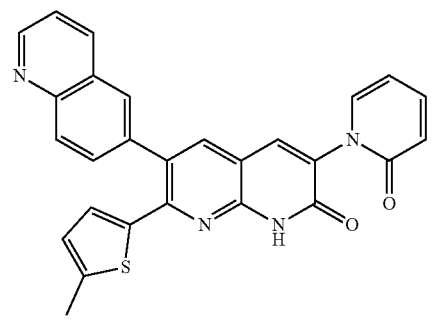 [SMILES: Cc1ncc(-c2nc3[nH]c(=O)c(-n4ccccc4=O)cc3cc2-c2ccc3ncccc3c2)s1] |
| 1.423 | 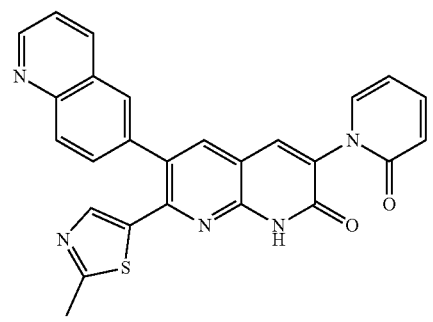 |

TABLE 1-continued
| Compound No. | Compound |
|---|---|
| 1.424 | 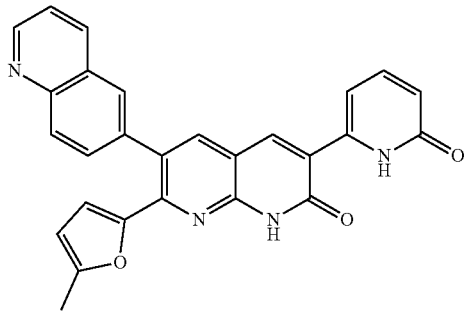 [SMILES: Cc1ccc(-c2nc3[nH]c(=O)c(-c4cccc(=O)[nH]4)cc3cc2-c2ccc3ncccc3c2)o1] |
| 1.425 | 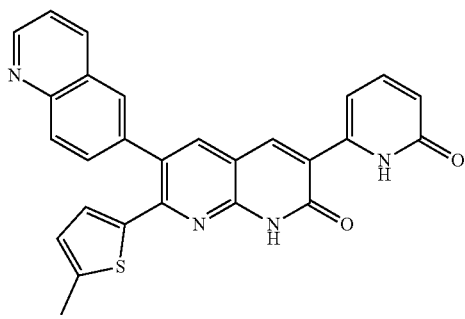 |
| 1.426 | 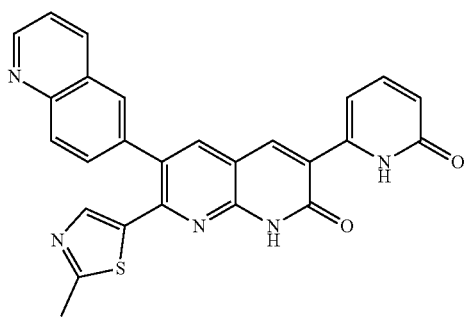 [SMILES: Cc1ncc(-c2nc3[nH]c(=O)c(-c4cccc(=O)[nH]4)cc3cc2-c2ccc3ncccc3c2)s1] |
| 1.427 | 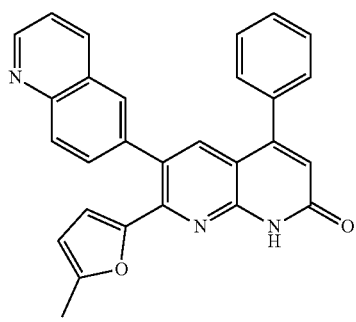 [SMILES: Cc1ccc(-c2nc3[nH]c(=O)cc(-c4ccccc4)c3cc2-c2ccc3ncccc3c2)o1] |
| 1.428 | 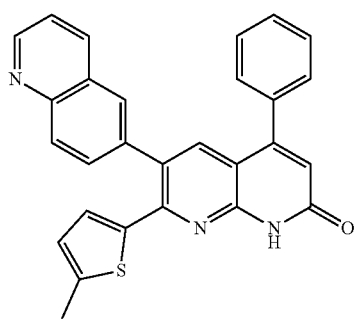 [SMILES: Cc1ccc(-c2nc3[nH]c(=O)cc(-c4ccccc4)c3cc2-c2ccc3ncccc3c2)s1] |

TABLE 1-continued
| Compound No. | Compound |
|---|---|
| 1.429 | 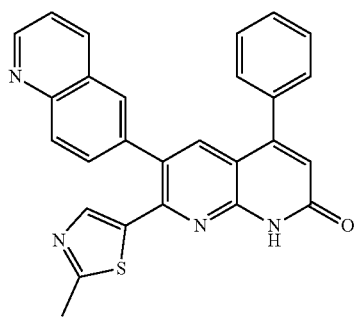 [SMILES: Cc1ncc(-c2nc3[nH]c(=O)cc(-c4ccccc4)c3cc2-c2ccc3ncccc3c2)s1] |
| 1.430 | 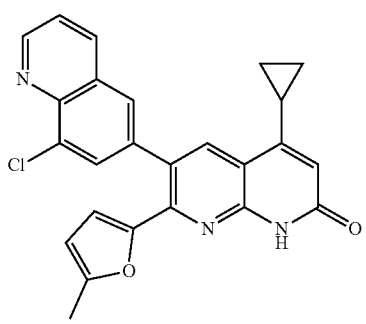 [SMILES: Cc1ccc(-c2nc3[nH]c(=O)cc(C4CC4)c3cc2-c2cc(Cl)c3ncccc3c2)o1] |
| 1.431 | 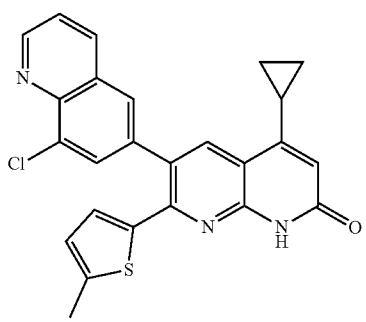 [SMILES: Cc1ccc(-c2nc3[nH]c(=O)cc(C4CC4)c3cc2-c2cc(Cl)c3ncccc3c2)s1] |
| 1.432 | 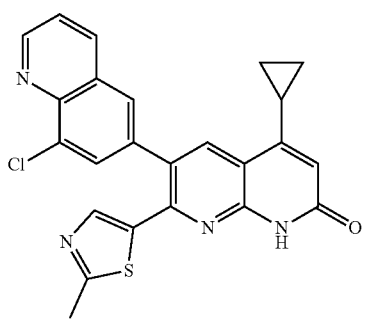 [SMILES: Cc1ncc(-c2nc3[nH]c(=O)cc(C4CC4)c3cc2-c2cc(Cl)c3ncccc3c2)s1] |
| 1.433 | 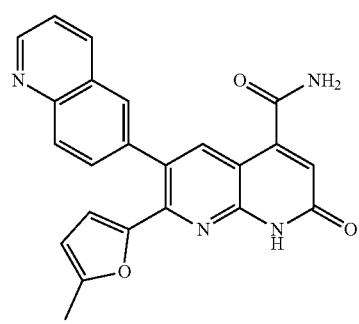 [SMILES: Cc1ccc(-c2nc3[nH]c(=O)cc(C(N)=O)c3cc2-c2ccc3ncccc3c2)o1] |

TABLE 1-continued

| Compound No. | Compound |
|---|---|
| 1.434 | |
| 1.435 | |
| 1.436 | |
| 1.437 | |
| 1.438 | |

TABLE 1-continued
| Compound No. | Compound |
|---|---|
| 1.439 | 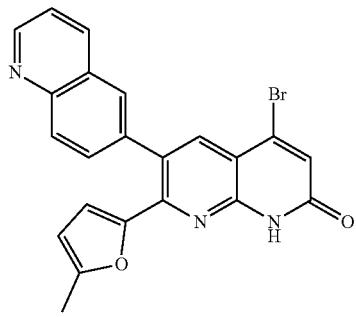 [SMILES: Cc1ccc(-c2nc3[nH]c(=O)cc(Br)c3cc2-c2ccc3ncccc3c2)o1] |
| 1.440 | 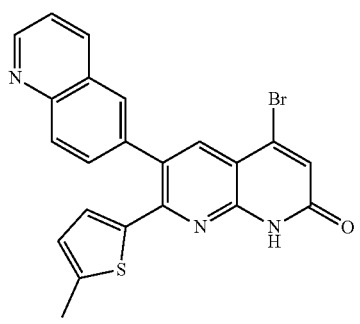 [SMILES: Cc1ccc(-c2nc3[nH]c(=O)cc(Br)c3cc2-c2ccc3ncccc3c2)s1] |
| 1.441 | 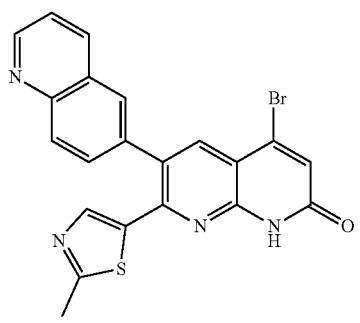 [SMILES: Cc1ncc(-c2nc3[nH]c(=O)cc(Br)c3cc2-c2ccc3ncccc3c2)s1] |
| 1.442 | 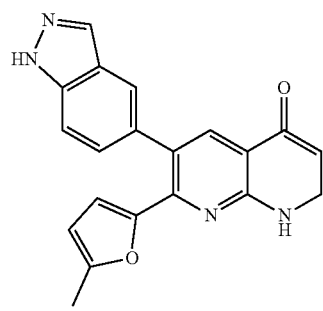 |
| 1.443 | 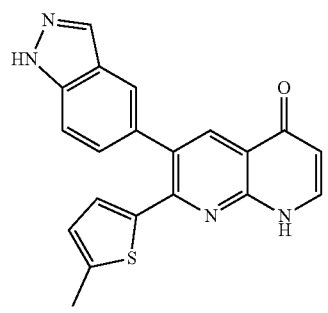 [SMILES: Cc1ccc(-c2nc3[nH]ccc(=O)c3cc2-c2ccc3[nH]ncc3c2)s1] |

TABLE 1-continued
| Compound No. | Compound |
|---|---|
| 1.444 | 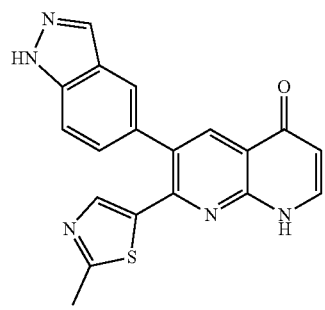 [SMILES: Cc1ncc(-c2nc3[nH]ccc(=O)c3cc2-c2ccc3[nH]ncc3c2)s1] |
| 1.445 | 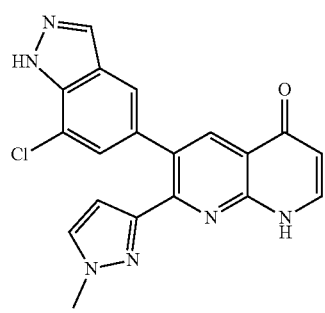 [SMILES: Cn1ccc(-c2nc3[nH]ccc(=O)c3cc2-c2cc(Cl)c3[nH]ncc3c2)n1] |
| 1.446 | 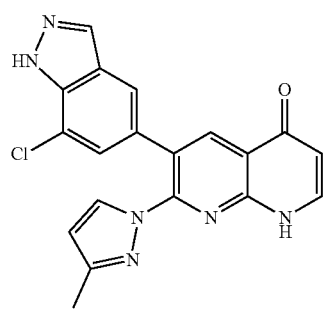 [SMILES: Cc1ccn(-c2nc3[nH]ccc(=O)c3cc2-c2cc(Cl)c3[nH]ncc3c2)n1] |
| 1.447 | 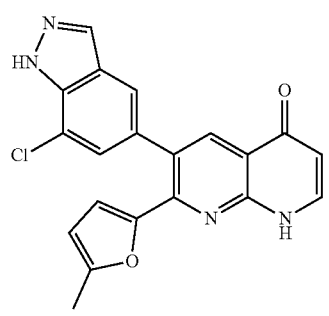 [SMILES: Cc1ccc(-c2nc3[nH]ccc(=O)c3cc2-c2cc(Cl)c3[nH]ncc3c2)o1] |
| 1.448 | 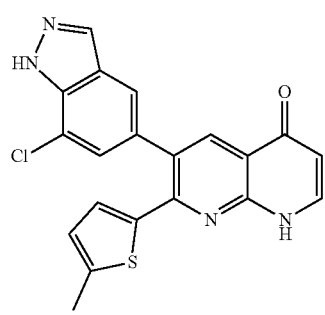 [SMILES: Cc1ccc(-c2nc3[nH]ccc(=O)c3cc2-c2cc(Cl)c3[nH]ncc3c2)s1] |

TABLE 1-continued
| Compound No. | Compound |
|---|---|
| 1.449 | 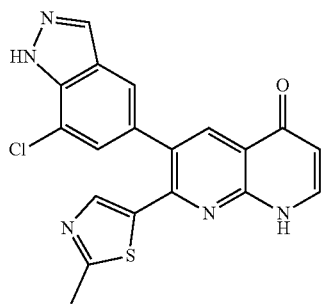 [SMILES: Cc1ncc(-c2nc3[nH]ccc(=O)c3cc2-c2cc(Cl)c3[nH]ncc3c2)s1] |
| 1.450 | 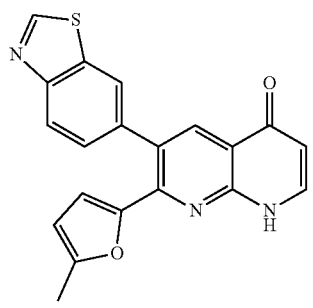 [SMILES: Cc1ccc(-c2nc3[nH]ccc(=O)c3cc2-c2ccc3ncsc3c2)o1] |
| 1.451 | 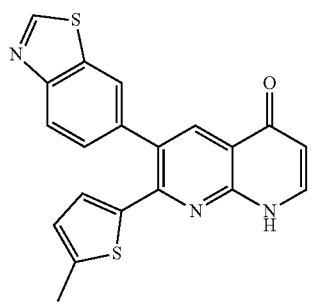 [SMILES: Cc1ccc(-c2nc3[nH]ccc(=O)c3cc2-c2ccc3ncsc3c2)s1] |
| 1.452 | 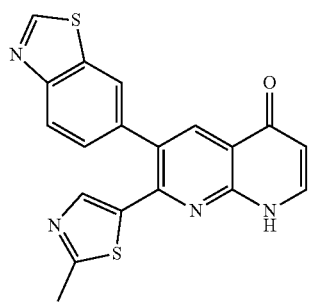 [SMILES: Cc1ncc(-c2nc3[nH]ccc(=O)c3cc2-c2ccc3ncsc3c2)s1] |
| 1.453 | 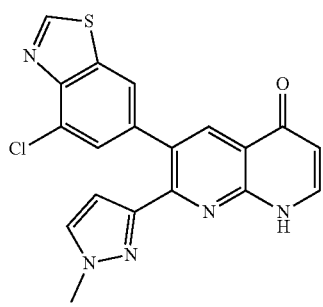 [SMILES: Cn1ccc(-c2nc3[nH]ccc(=O)c3cc2-c2cc(Cl)c3ncsc3c2)n1] |

TABLE 1-continued

| Compound No. | Compound |
|---|---|
| 1.454 | |
| 1.455 | |
| 1.456 | |
| 1.457 | |
| 1.458 | |

TABLE 1-continued

| Compound No. | Compound |
|---|---|
| 1.459 | |
| 1.460 | |
| 1.461 | |
| 1.462 | |
| 1.463 | |

TABLE 1-continued
| Compound No. | Compound |
|---|---|
| 1.464 | 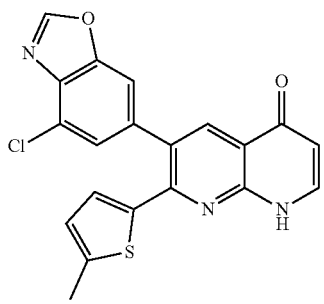 [SMILES: Cc1ccc(-c2nc3[nH]ccc(=O)c3cc2-c2cc(Cl)c3ncsc3c2)s1] |
| 1.465 | 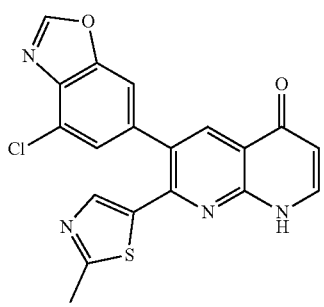 [SMILES: Cc1ncc(-c2nc3[nH]ccc(=O)c3cc2-c2cc(Cl)c3ncoc3c2)s1] |
| 1.466 | 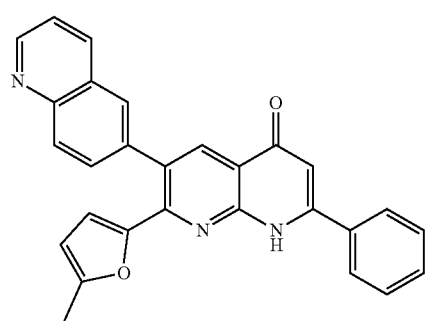 [SMILES: Cc1ccc(-c2nc3[nH]c(-c4ccccc4)cc(=O)c3cc2-c2ccc3ncccc3c2)o1] |
| 1.467 | 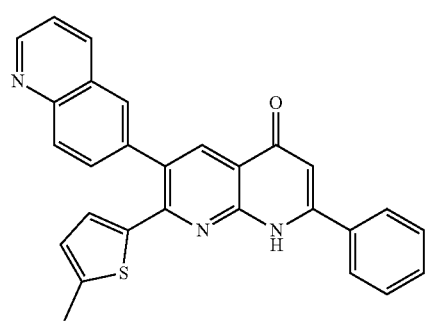 |
| 1.468 | 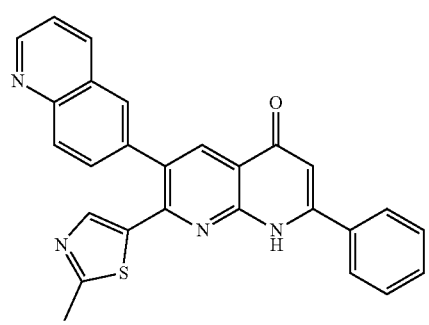 [SMILES: Cc1ncc(-c2nc3[nH]c(-c4ccccc4)cc(=O)c3cc2-c2ccc3ncccc3c2)s1] |

TABLE 1-continued
| Compound No. | Compound |
|---|---|
| 1.469 | 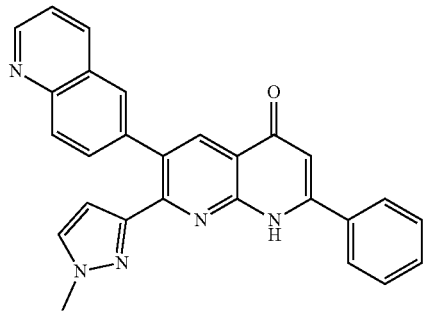 [SMILES: Cn1ccc(-c2nc3[nH]c(-c4ccccc4)cc(=O)c3cc2-c2ccc3ncccc3c2)n1] |
| 1.470 | 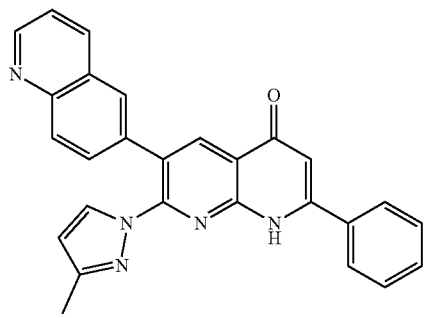 [SMILES: Cc1ccn(-c2nc3[nH]c(-c4ccccc4)cc(=O)c3cc2-c2ccc3ncccc3c2)n1] |
| 1.471 | 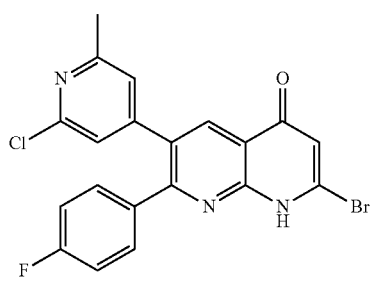 [SMILES: Cc1cc(-c2cc3c(=O)cc(Br)[nH]c3nc2-c2ccc(F)cc2)cc(Cl)n1] |
| 1.472 | 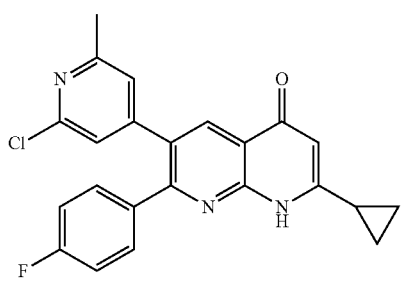 [SMILES: Cc1cc(-c2cc3c(=O)cc(C4CC4)[nH]c3nc2-c2ccc(F)cc2)cc(Cl)n1] |
| 1.473 | 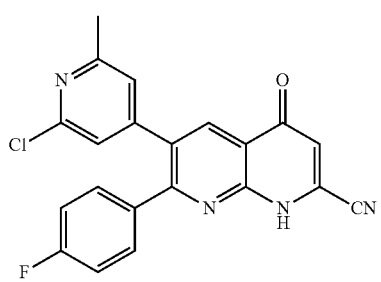 [SMILES: Cc1cc(-c2cc3c(=O)cc(C#N)[nH]c3nc2-c2ccc(F)cc2)cc(Cl)n1] |

279 280
TABLE 1-continued
| Compound No. | Compound |
|---|---|
| 1.474 | 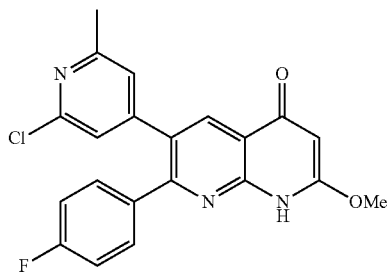 [SMILES: COc1cc(=O)c2cc(-c3cc(C)nc(Cl)c3)c(-c3ccc(F)cc3)nc2[nH]1] |
| 1.475 | 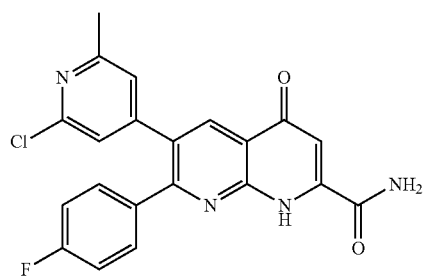 [SMILES: Cc1cc(-c2cc3c(=O)cc(C(N)=O)[nH]c3nc2-c2ccc(F)cc2)cc(Cl)n1] |
| 1.476 | 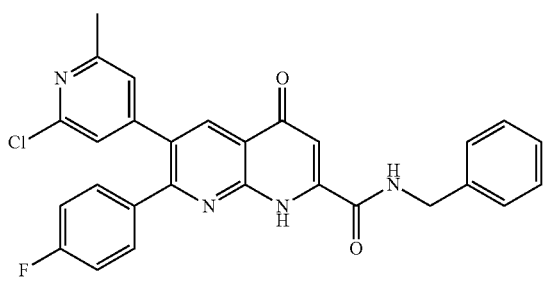 [SMILES: Cc1cc(-c2cc3c(=O)cc(C(=O)NCc4ccccc4)[nH]c3nc2-c2ccc(F)cc2)cc(Cl)n1] |
| 1.477 | 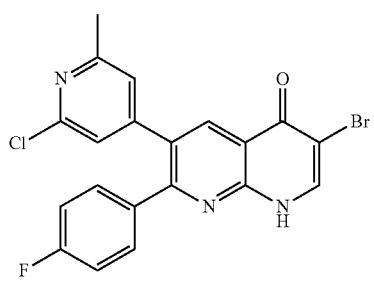 [SMILES: Cc1cc(-c2cc3c(=O)c(Br)c[nH]c3nc2-c2ccc(F)cc2)cc(Cl)n1] |
| 1.478 | 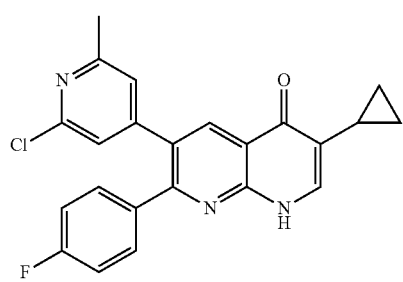 [SMILES: Cc1cc(-c2cc3c(=O)c(C4CC4)c[nH]c3nc2-c2ccc(F)cc2)cc(Cl)n1] |

TABLE 1-continued
| Compound No. | Compound |
|---|---|
| 1.479 | 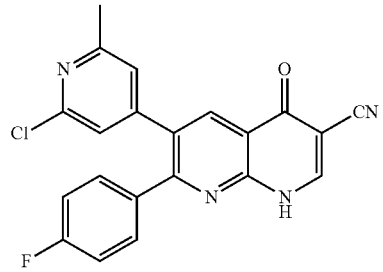 [SMILES: Cc1cc(-c2cc3c(=O)c(C#N)c[nH]c3nc2-c2ccc(F)cc2)cc(Cl)n1] |
| 1.480 | 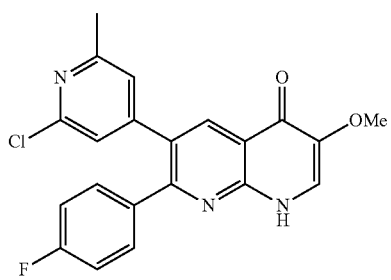 [SMILES: COc1c[nH]c2nc(-c3ccc(F)cc3)c(-c3cc(C)nc(Cl)c3)cc2c1=O] |
| 1.481 | 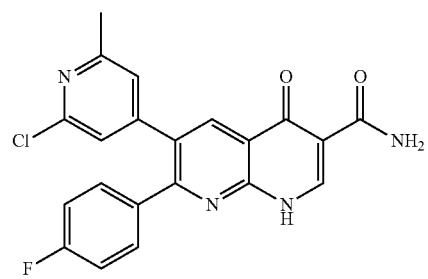 [SMILES: Cc1cc(-c2cc3c(=O)c(C(N)=O)c[nH]c3nc2-c2ccc(F)cc2)cc(Cl)n1] |
| 1.482 | 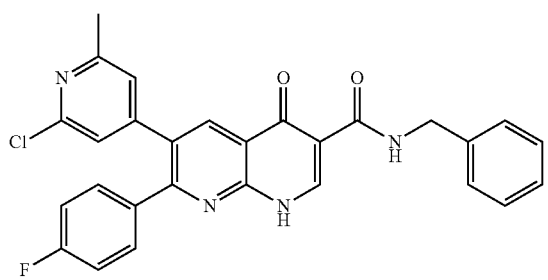 [SMILES: Cc1cc(-c2cc3c(=O)c(C(=O)NCc4ccccc4)c[nH]c3nc2-c2ccc(F)cc2)cc(Cl)n1] |
| 1.483 | 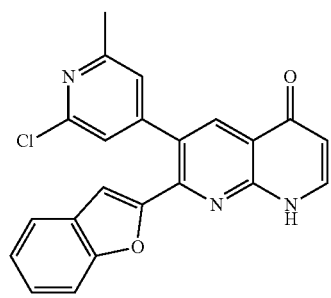 [SMILES: Cc1cc(-c2cc3c(=O)cc[nH]c3nc2-c2cc3ccccc3o2)cc(Cl)n1] |

TABLE 1-continued
| Compound No. | Compound |
|---|---|
| 1.484 | 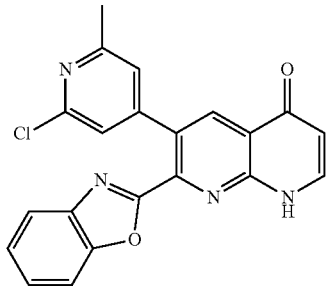 [SMILES: Cc1cc(-c2cc3c(=O)cc[nH]c3nc2-c2nc3ccccc3o2)cc(Cl)n1] |
| 1.485 | 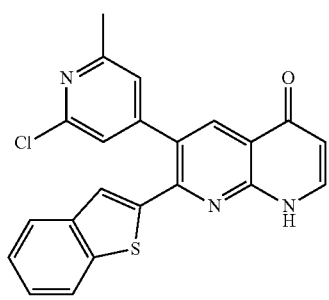 |
| 1.486 | 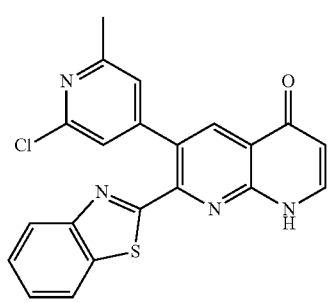 |
| 1.487 | 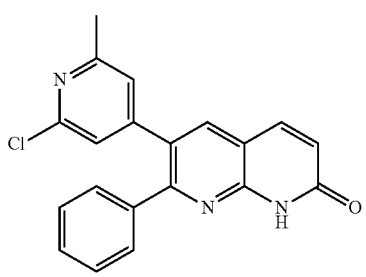 |
| 1.488 | 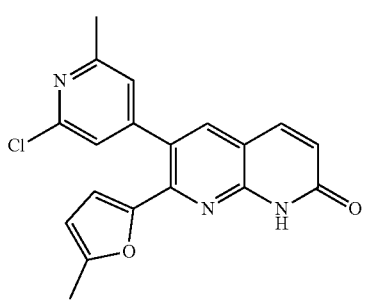 [SMILES: Cc1cc(-c2cc3ccc(=O)[nH]c3nc2-c2ccc(C)o2)cc(Cl)n1] |

TABLE 1-continued
| Compound No. | Compound |
|---|---|
| 1.489 | 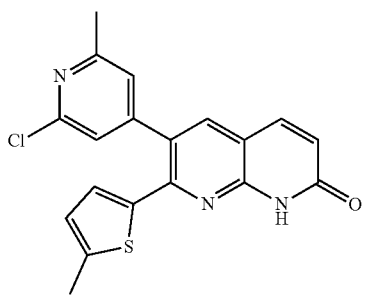 [SMILES: Cc1cc(-c2cc3ccc(=O)[nH]c3nc2-c2ccc(C)s2)cc(Cl)n1] |
| 1.490 | 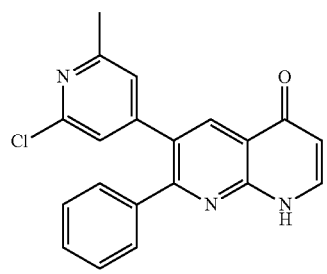 [SMILES: Cc1cc(-c2cc3c(=O)cc[nH]c3nc2-c2ccccc2)cc(Cl)n1] |
| 1.491 | 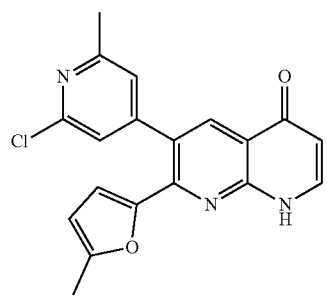 [SMILES: Cc1cc(-c2cc3c(=O)cc[nH]c3nc2-c2ccc(C)o2)cc(Cl)n1] |
| 1.492 | 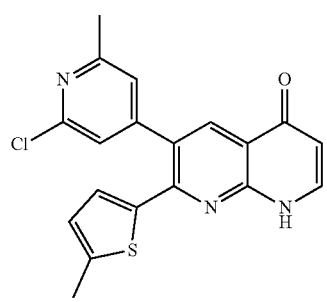 [SMILES: Cc1cc(-c2cc3c(=O)cc[nH]c3nc2-c2ccc(C)s2)cc(Cl)n1] |
| 1.493 | 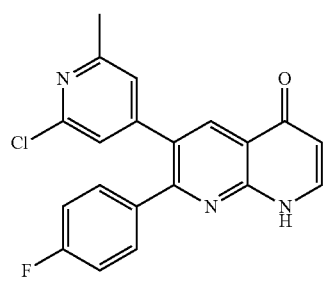 [SMILES: Cc1cc(-c2cc3c(=O)cc[nH]c3nc2-c2ccc(F)cc2)cc(Cl)n1] |

TABLE 1-continued
| Compound No. | Compound |
|---|---|
| 1.494 | 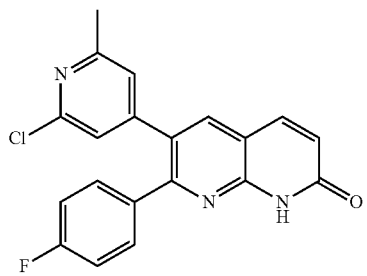 [SMILES: Cc1cc(-c2cc3ccc(=O)[nH]c3nc2-c2ccc(F)cc2)cc(Cl)n1] |
| 1.495 | 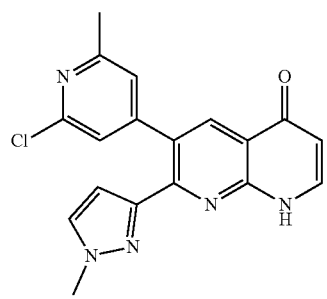 [SMILES: Cc1cc(-c2cc3c(=O)cc[nH]c3nc2-c2ccn(C)n2)cc(Cl)n1] |
| 1.496 | 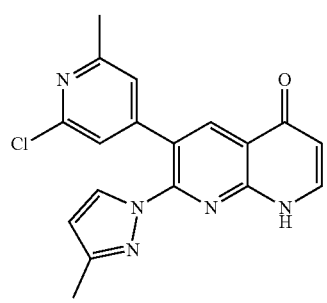 [SMILES: Cc1cc(-c2cc3c(=O)cc[nH]c3nc2-n2ccc(C)n2)cc(Cl)n1] |
| 1.497 | 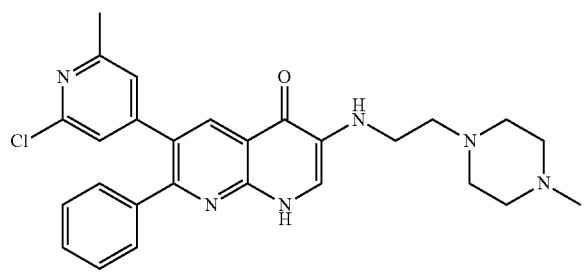 [SMILES: Cc1cc(-c2cc3c(=O)c(NCCN4CCN(C)CC4)c[nH]c3nc2-c2ccccc2)cc(Cl)n1] |
| 1.498 | 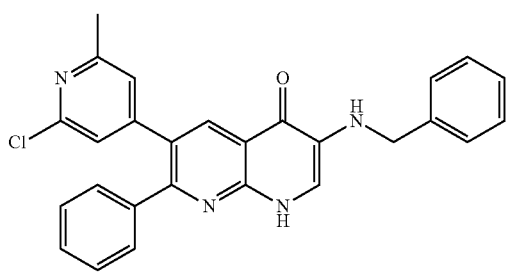 [SMILES: Cc1cc(-c2cc3c(=O)c(NCc4ccccc4)c[nH]c3nc2-c2ccccc2)cc(Cl)n1] |

TABLE 1-continued
| Compound No. | Compound |
|---|---|
| 1.499 | 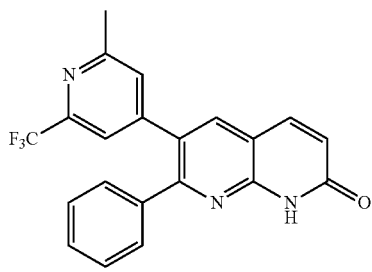 [SMILES: Cc1cc(-c2cc3ccc(=O)[nH]c3nc2-c2ccccc2)cc(C(F)(F)F)n1] |
| 1.500 | 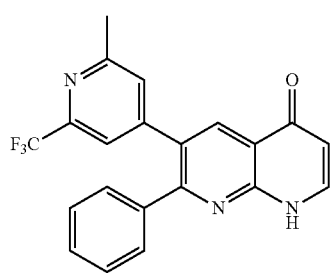 [SMILES: Cc1cc(-c2cc3c(=O)cc[nH]c3nc2-c2ccccc2)cc(C(F)(F)F)n1] |
| 1.501 | 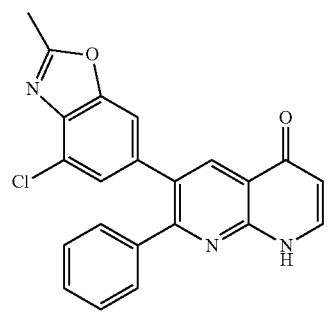 [SMILES: Cc1nc2c(Cl)cc(-c3cc4c(=O)cc[nH]c4nc3-c3ccccc3)cc2o1] |
| 1.502 | 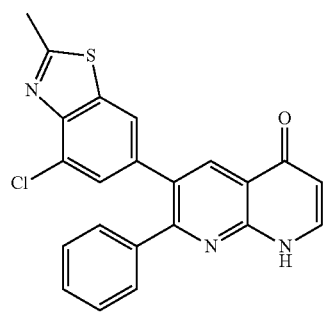 [SMILES: Cc1nc2c(Cl)cc(-c3cc4c(=O)cc[nH]c4nc3-c3ccccc3)cc2s1] |
| 1.503 | 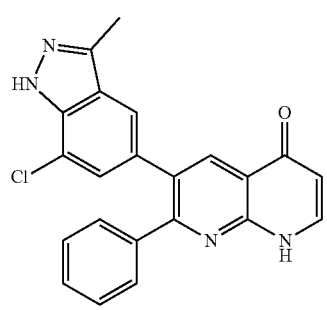 [SMILES: Cc1n[nH]c2c(Cl)cc(-c3cc4c(=O)cc[nH]c4nc3-c3ccccc3)cc12] |

TABLE 1-continued
| Compound No. | Compound |
|---|---|
| 1.504 | 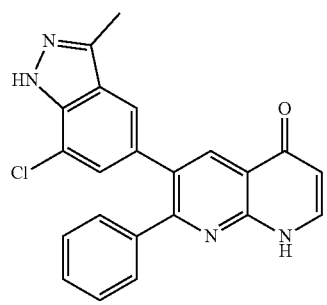 [SMILES: Cc1n[nH]c2c(Cl)cc(-c3cc4c(=O)cc[nH]c4nc3-c3ccccc3)cc12] |
| 1.505 | 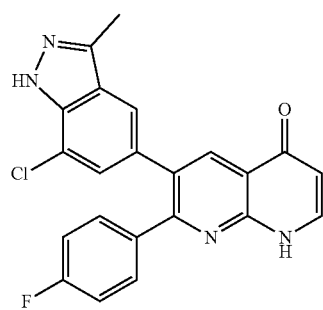 [SMILES: Cc1n[nH]c2c(Cl)cc(-c3cc4c(=O)cc[nH]c4nc3-c3ccc(F)cc3)cc12] |
| 1.506 | 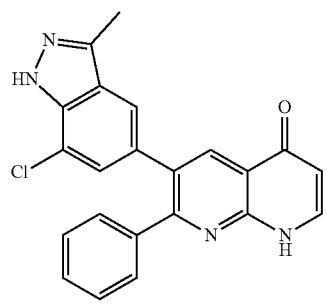 [SMILES: Cc1n[nH]c2c(Cl)cc(-c3cc4c(=O)cc[nH]c4nc3-c3ccccc3)cc12] |
| 1.507 | 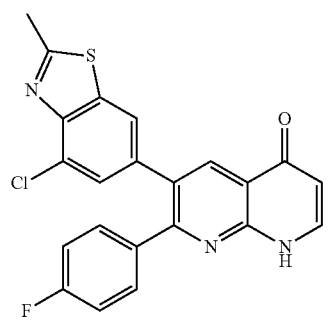 [SMILES: Cc1nc2c(Cl)cc(-c3cc4c(=O)cc[nH]c4nc3-c3ccc(F)cc3)cc2s1] |
| 1.508 | 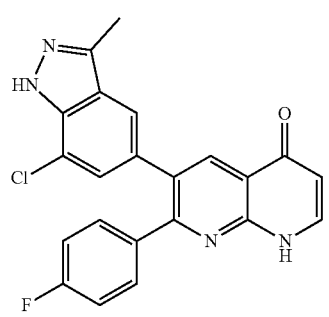 [SMILES: Cc1n[nH]c2c(Cl)cc(-c3cc4c(=O)cc[nH]c4nc3-c3ccc(F)cc3)cc12] |

TABLE 1-continued
| Compound No. | Compound |
|---|---|
| 1.509 | 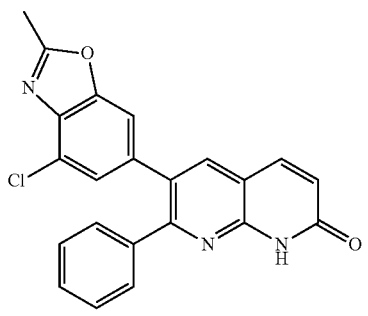 [SMILES: Cc1nc2c(Cl)cc(-c3cc4ccc(=O)[nH]c4nc3-c3ccccc3)cc2o1] |
| 1.510 | 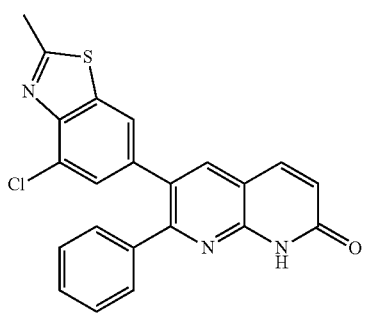 |
| 1.511 | 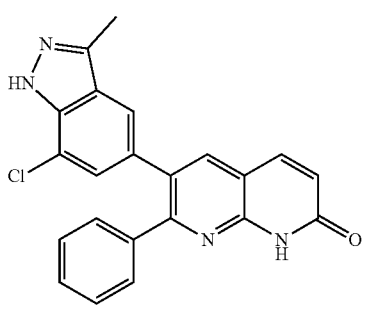 [SMILES: Cc1n[nH]c2c(Cl)cc(-c3cc4ccc(=O)[nH]c4nc3-c3ccccc3)cc12] |
| 1.512 | 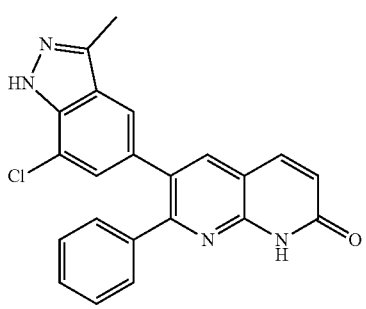 [SMILES: Cc1n[nH]c2c(Cl)cc(-c3cc4ccc(=O)[nH]c4nc3-c3ccccc3)cc12] |
| 1.513 | 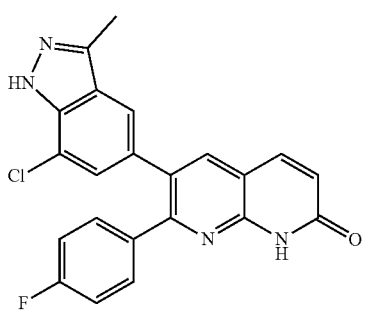 [SMILES: Cc1n[nH]c2c(Cl)cc(-c3cc4ccc(=O)[nH]c4nc3-c3ccc(F)cc3)cc12] |

TABLE 1-continued
| Compound No. | Compound |
|---|---|
| 1.514 | 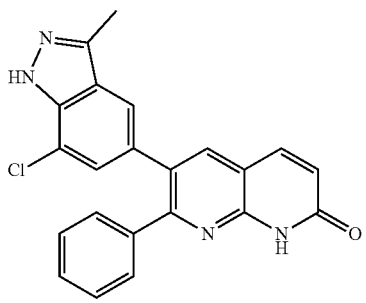 [SMILES: Cc1n[nH]c2c(Cl)cc(-c3cc4ccc(=O)[nH]c4nc3-c3ccccc3)cc12] |
| 1.515 | 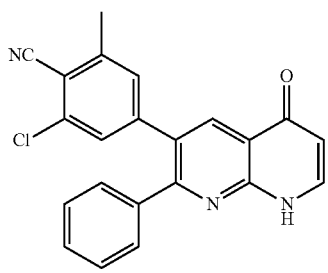 [SMILES: Cc1cc(-c2cc3c(=O)cc[nH]c3nc2-c2ccccc2)cc(Cl)c1C#N] |
| 1.516 | 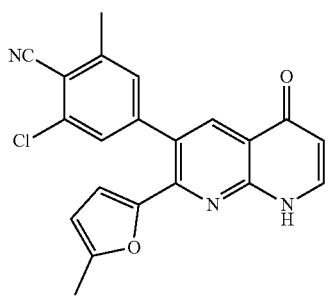 [SMILES: Cc1ccc(-c2nc3[nH]ccc(=O)c3cc2-c2cc(C)c(C#N)c(Cl)c2)o1] |
| 1.517 | 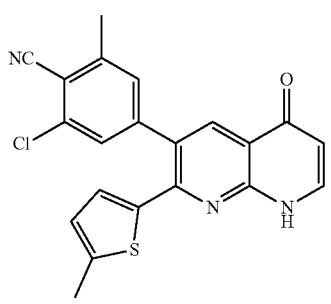 [SMILES: Cc1ccc(-c2nc3[nH]ccc(=O)c3cc2-c2cc(C)c(C#N)c(Cl)c2)s1] |
| 1.518 | 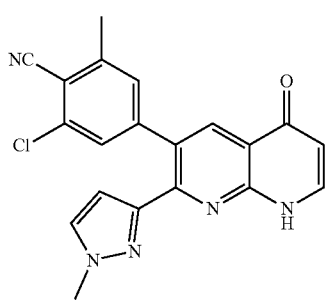 [SMILES: Cc1cc(-c2cc3c(=O)cc[nH]c3nc2-c2ccn(C)n2)cc(Cl)c1C#N] |

TABLE 1-continued
| Compound No. | Compound |
|---|---|
| 1.519 | 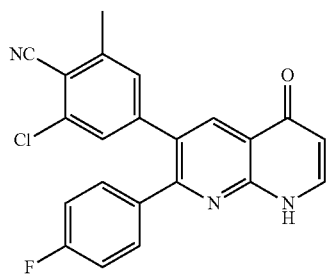 [SMILES: Cc1cc(-c2cc3c(=O)cc[nH]c3nc2-c2ccc(F)cc2)cc(Cl)c1C#N] |
| 1.520 | 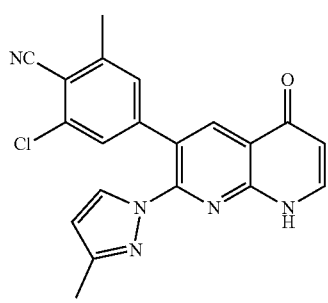 [SMILES: Cc1ccn(-c2nc3[nH]ccc(=O)c3cc2-c2cc(C)c(C#N)c(Cl)c2)n1] |
| 1.521 | 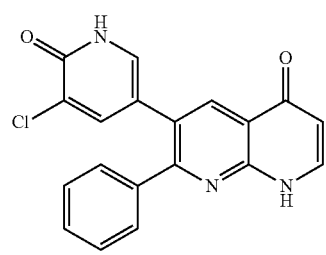 [SMILES: O=c1[nH]cc(-c2cc3c(=O)cc[nH]c3nc2-c2ccccc2)cc1Cl] |
| 1.522 | 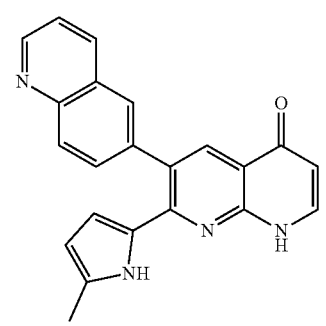 [SMILES: Cc1ccc(-c2nc3[nH]ccc(=O)c3cc2-c2ccc3ncccc3c2)[nH]1] |
| 1.523 | 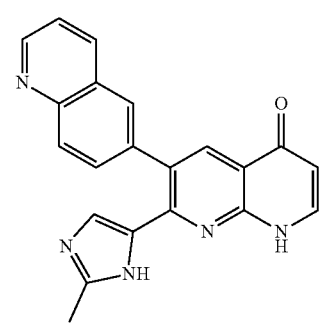 [SMILES: Cc1ncc(-c2nc3[nH]ccc(=O)c3cc2-c2ccc3ncccc3c2)[nH]1] |

TABLE 1-continued
| Compound No. | Compound |
|---|---|
| 1.524 | 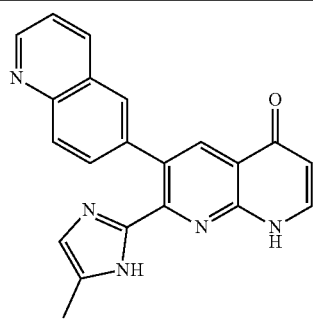 |
| 1.525 | 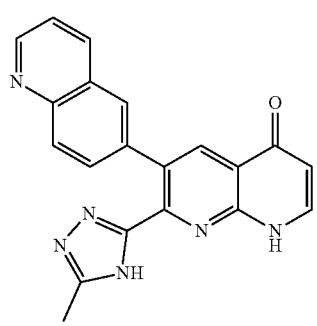 [SMILES: Cc1nnc(-c2nc3[nH]ccc(=O)c3cc2-c2ccc3ncccc3c2)[nH]1] |
| 1.526 | 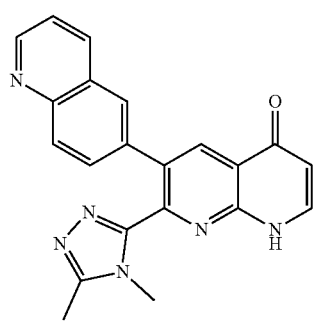 [SMILES: Cc1nnc(-c2nc3[nH]ccc(=O)c3cc2-c2ccc3ncccc3c2)n1C] |
| 1.527 | 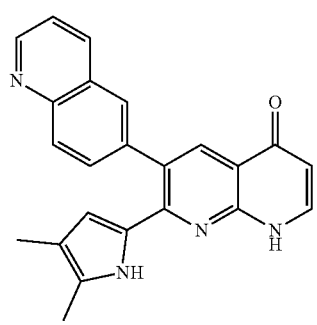 [SMILES: Cc1cc(-c2nc3[nH]ccc(=O)c3cc2-c2ccc3ncccc3c2)[nH]c1C] |
| 1.528 | 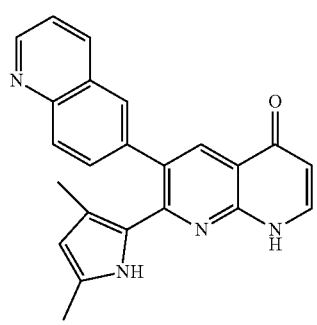 [SMILES: Cc1cc(C)c(-c2nc3[nH]ccc(=O)c3cc2-c2ccc3ncccc3c2)[nH]1] |

TABLE 1-continued
| Compound No. | Compound |
|---|---|
| 1.529 | 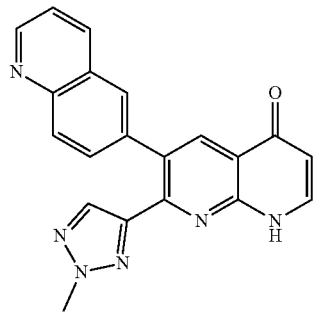 [SMILES: Cn1ncc(-c2nc3[nH]ccc(=O)c3cc2-c2ccc3ncccc3c2)n1] |
| 1.530 | 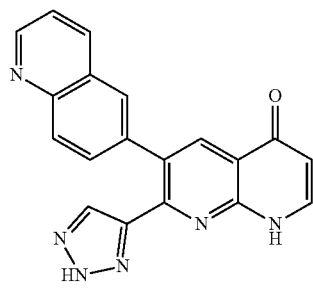 [SMILES: O=c1cc[nH]c2nc(-c3cn[nH]n3)c(-c3ccc4ncccc4c3)cc12] |
| 1.531 | 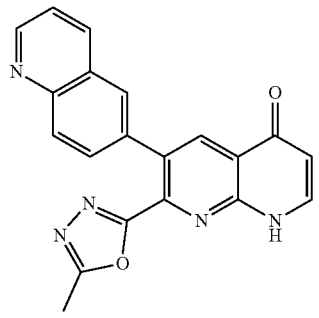 [SMILES: Cc1nnc(-c2nc3[nH]ccc(=O)c3cc2-c2ccc3ncccc3c2)o1] |
| 1.532 | 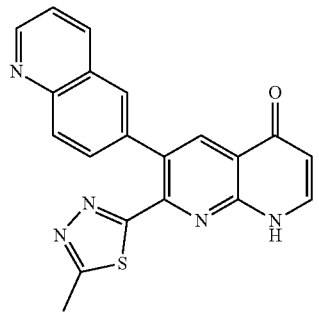 [SMILES: Cc1nnc(-c2nc3[nH]ccc(=O)c3cc2-c2ccc3ncccc3c2)s1] |
| 1.533 | 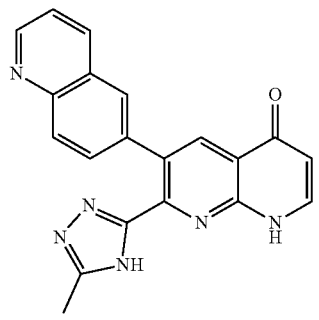 [SMILES: Cc1nnc(-c2nc3[nH]ccc(=O)c3cc2-c2ccc3ncccc3c2)[nH]1] |

TABLE 1-continued
| Compound No. | Compound |
|---|---|
| 1.534 | 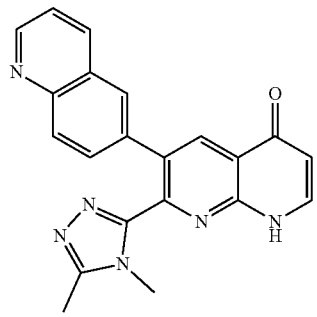 [SMILES: Cc1nnc(-c2nc3[nH]ccc(=O)c3cc2-c2ccc3ncccc3c2)n1C] |
| 1.535 | 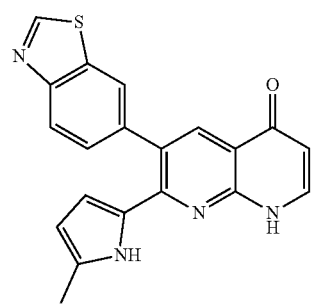 [SMILES: Cc1ccc(-c2nc3[nH]ccc(=O)c3cc2-c2ccc3ncsc3c2)[nH]1] |
| 1.536 | 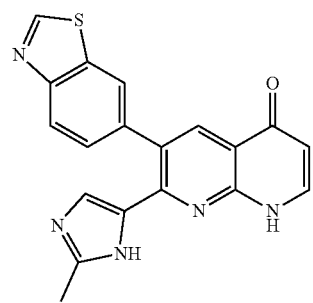 [SMILES: Cc1ncc(-c2nc3[nH]ccc(=O)c3cc2-c2ccc3ncsc3c2)[nH]1] |
| 1.537 | 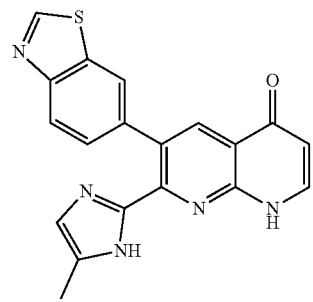 [SMILES: Cc1cnc(-c2nc3[nH]ccc(=O)c3cc2-c2ccc3ncsc3c2)[nH]1] |
| 1.538 | 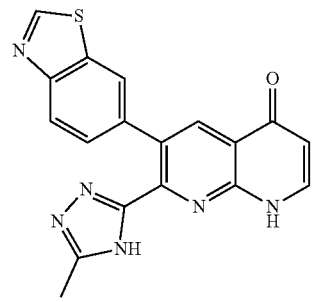 [SMILES: Cc1nnc(-c2nc3[nH]ccc(=O)c3cc2-c2ccc3ncsc3c2)[nH]1] |

TABLE 1-continued
| Compound No. | Compound |
|---|---|
| 1.539 | 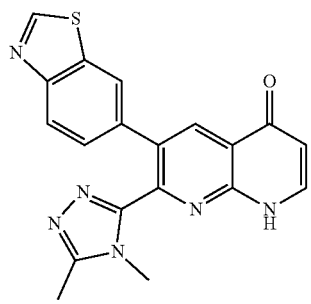 [SMILES: Cc1nnc(-c2nc3[nH]ccc(=O)c3cc2-c2ccc3ncsc3c2)n1C] |
| 1.540 | 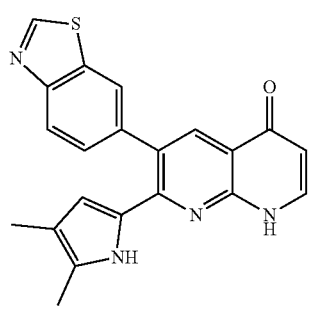 [SMILES: Cc1cc(-c2nc3[nH]ccc(=O)c3cc2-c2ccc3ncsc3c2)[nH]c1C] |
| 1.541 | 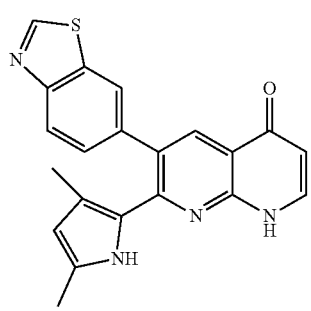 [SMILES: Cc1cc(C)c(-c2nc3[nH]ccc(=O)c3cc2-c2ccc3ncsc3c2)[nH]1] |
| 1.542 | 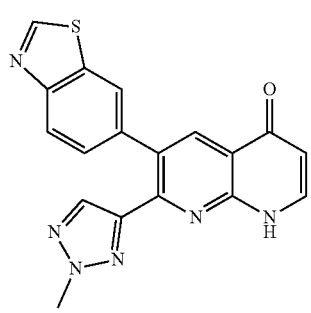 [SMILES: Cn1ncc(-c2nc3[nH]ccc(=O)c3cc2-c2ccc3ncsc3c2)n1] |
| 1.543 | 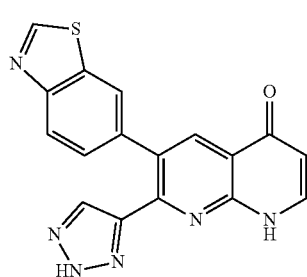 [SMILES: O=c1cc[nH]c2nc(-c3cn[nH]n3)c(-c3ccc4ncsc4c3)cc12] |

TABLE 1-continued
| Compound No. | Compound |
|---|---|
| 1.544 | 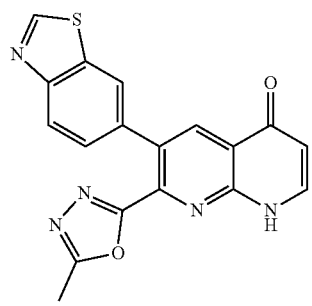 [SMILES: Cc1nnc(-c2nc3[nH]ccc(=O)c3cc2-c2ccc3ncsc3c2)o1] |
| 1.545 | 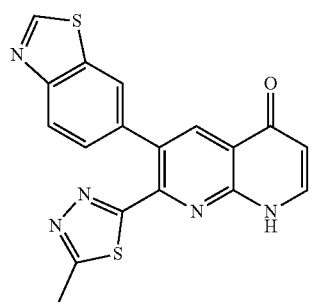 [SMILES: Cc1nnc(-c2nc3[nH]ccc(=O)c3cc2-c2ccc3ncsc3c2)s1] |
| 1.546 | 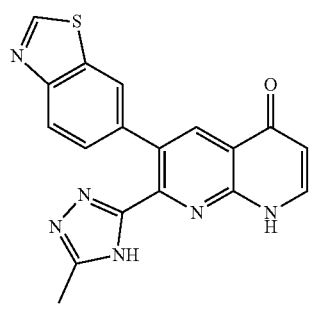 [SMILES: Cc1nnc(-c2nc3[nH]ccc(=O)c3cc2-c2ccc3ncsc3c2)[nH]1] |
| 1.547 | 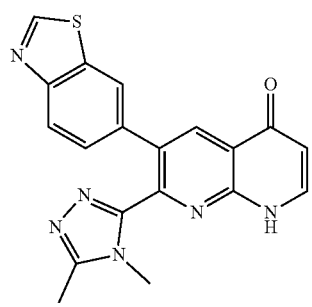 [SMILES: Cc1nnc(-c2nc3[nH]ccc(=O)c3cc2-c2ccc3ncsc3c2)n1C] |
| 1.548 | 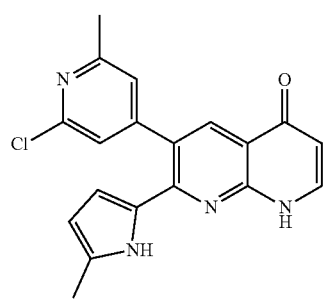 [SMILES: Cc1cc(-c2cc3c(=O)cc[nH]c3nc2-c2ccc(C)[nH]2)cc(Cl)n1] |

TABLE 1-continued
| Compound No. | Compound |
|---|---|
| 1.549 | 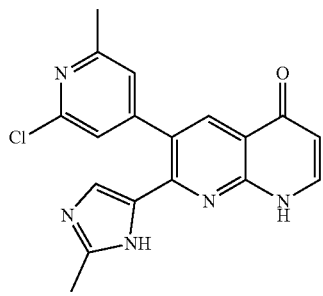 [SMILES: Cc1cc(-c2cc3c(=O)cc[nH]c3nc2-c2cnc(C)[nH]2)cc(Cl)n1] |
| 1.550 | 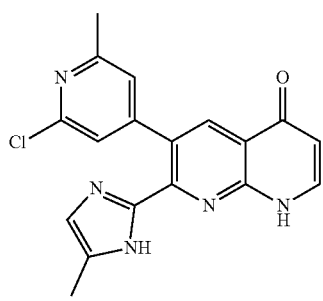 [SMILES: Cc1cc(-c2cc3c(=O)cc[nH]c3nc2-c2ncc(C)[nH]2)cc(Cl)n1] |
| 1.551 | 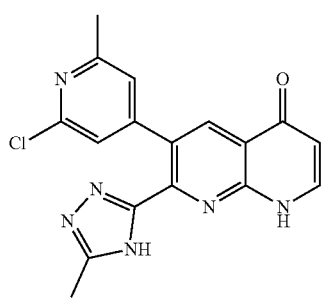 [SMILES: Cc1cc(-c2cc3c(=O)cc[nH]c3nc2-c2nnc(C)[nH]2)cc(Cl)n1] |
| 1.552 | 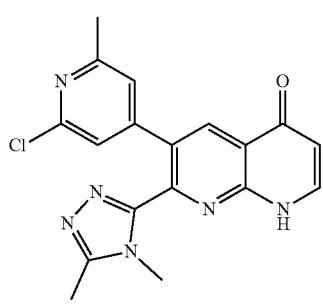 [SMILES: Cc1cc(-c2cc3c(=O)cc[nH]c3nc2-c2nnc(C)n2C)cc(Cl)n1] |
| 1.553 | 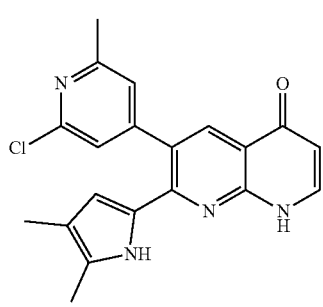 [SMILES: Cc1cc(-c2cc3c(=O)cc[nH]c3nc2-c2cc(C)c(C)[nH]2)cc(Cl)n1] |

US 10,793,561 B2
311
312
TABLE 1-continued
| Compound No. | Compound |
|---|---|
| 1.554 | 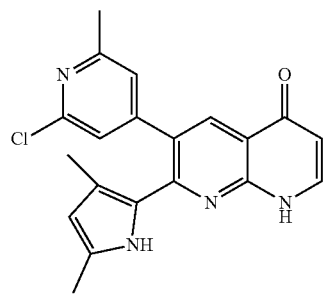 [SMILES: Cc1cc(-c2cc3c(=O)cc[nH]c3nc2-c2[nH]c(C)cc2C)cc(Cl)n1] |
| 1.555 | 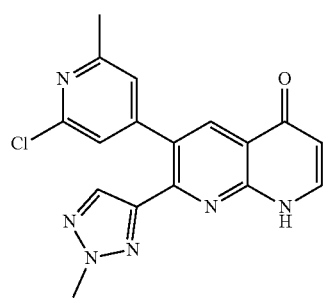 [SMILES: Cc1cc(-c2cc3c(=O)cc[nH]c3nc2-c2cnn(C)n2)cc(Cl)n1] |
| 1.556 | 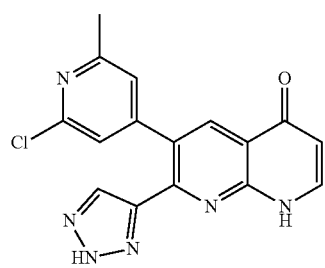 [SMILES: Cc1cc(-c2cc3c(=O)cc[nH]c3nc2-c2cn[nH]n2)cc(Cl)n1] |
| 1.557 | 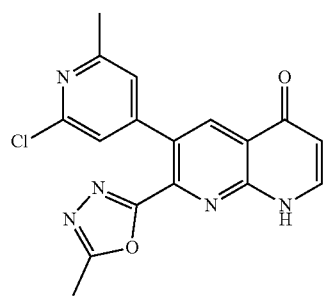 [SMILES: Cc1cc(-c2cc3c(=O)cc[nH]c3nc2-c2nnc(C)o2)cc(Cl)n1] |
| 1.558 | 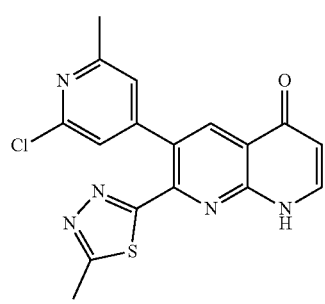 [SMILES: Cc1cc(-c2cc3c(=O)cc[nH]c3nc2-c2nnc(C)s2)cc(Cl)n1] |

TABLE 1-continued
| Compound No. | Compound |
|---|---|
| 1.559 | 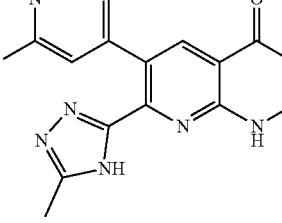 |
| 1.560 | 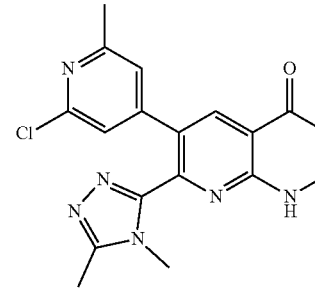 |
| 1.561 | 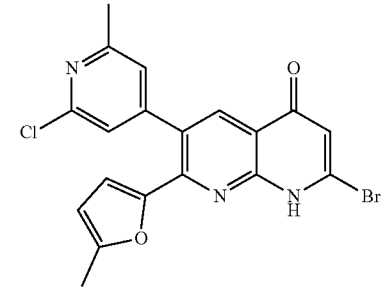 [SMILES: Cc1cc(-c2cc3c(=O)cc(Br)[nH]c3nc2-c2ccc(C)o2)cc(Cl)n1] |
| 1.562 | 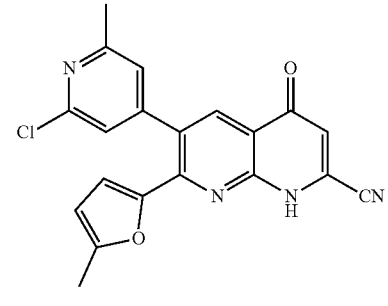 [SMILES: Cc1cc(-c2cc3c(=O)cc(C#N)[nH]c3nc2-c2ccc(C)o2)cc(Cl)n1] |
| 1.563 | 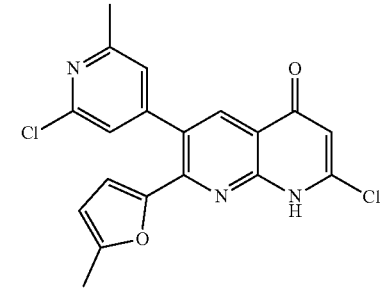 |

TABLE 1-continued

| Compound No. | Compound |
|---|---|
| 1.564 | |
| 1.565 | |
| 1.566 | |
| 1.567 | |
| 1.568 | |

TABLE 1-continued

| Compound No. | Compound |
|---|---|
| 1.569 | |
| 1.570 | |
| 1.571 | |
| 1.572 | |
| 1.573 | |

TABLE 1-continued
| Compound No. | Compound |
|---|---|
| 1.574 | 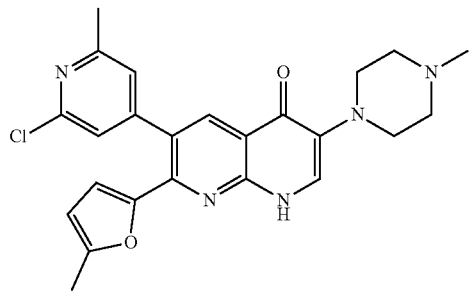 [SMILES: Cc1cc(-c2cc3c(=O)c(N4CCN(C)CC4)c[nH]c3nc2-c2ccc(C)o2)cc(Cl)n1] |
| 1.575 | 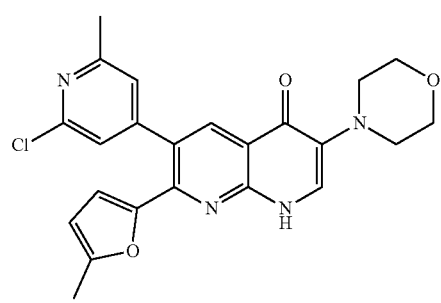 [SMILES: Cc1cc(-c2cc3c(=O)c(N4CCOCC4)c[nH]c3nc2-c2ccc(C)o2)cc(Cl)n1] |
| 1.576 | 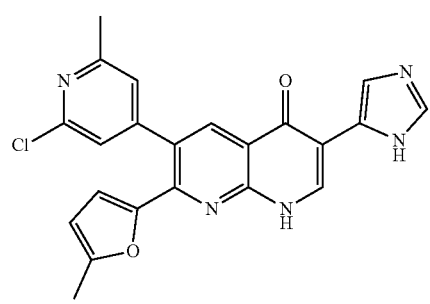 [SMILES: Cc1cc(-c2cc3c(=O)c(-c4cnc[nH]4)c[nH]c3nc2-c2ccc(C)o2)cc(Cl)n1] |
| 1.577 | 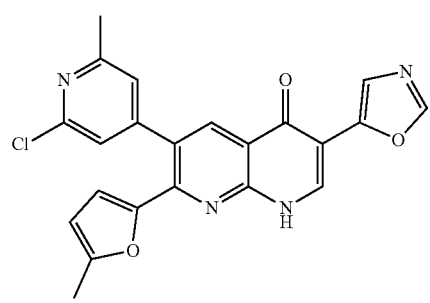 [SMILES: Cc1cc(-c2cc3c(=O)c(-c4cnco4)c[nH]c3nc2-c2ccc(C)o2)cc(Cl)n1] |
| 1.578 | 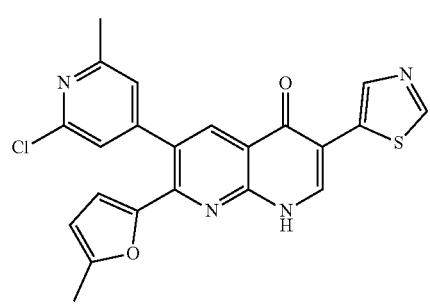 [SMILES: Cc1cc(-c2cc3c(=O)c(-c4cncs4)c[nH]c3nc2-c2ccc(C)o2)cc(Cl)n1] |

TABLE 1-continued
| Compound No. | Compound |
|---|---|
| 1.579 | 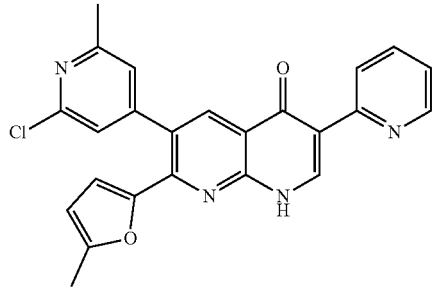 [SMILES: Cc1cc(-c2cc3c(=O)c(-c4ccccn4)c[nH]c3nc2-c2ccc(C)o2)cc(Cl)n1] |
| 1.580 | 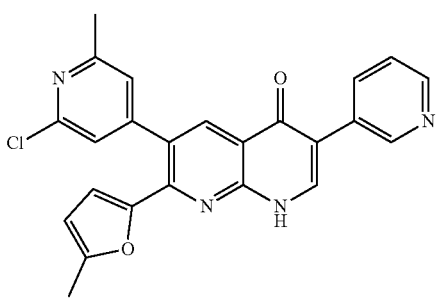 [SMILES: Cc1cc(-c2cc3c(=O)c(-c4cccnc4)c[nH]c3nc2-c2ccc(C)o2)cc(Cl)n1] |
| 1.581 | 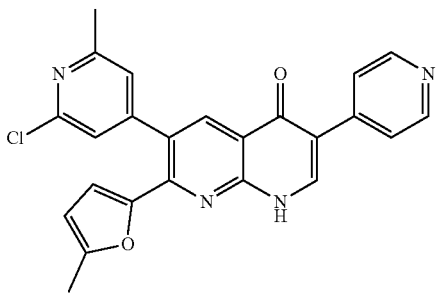 [SMILES: Cc1cc(-c2cc3c(=O)c(-c4ccncc4)c[nH]c3nc2-c2ccc(C)o2)cc(Cl)n1] |
| 1.582 | 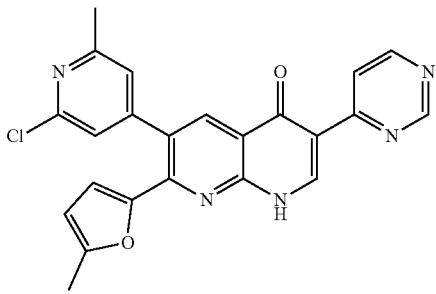 [SMILES: Cc1cc(-c2cc3c(=O)c(-c4ccncn4)c[nH]c3nc2-c2ccc(C)o2)cc(Cl)n1] |
| 1.583 | 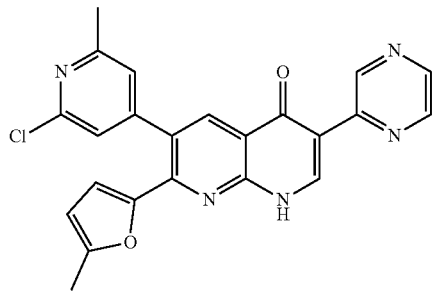 [SMILES: Cc1cc(-c2cc3c(=O)c(-c4cnccn4)c[nH]c3nc2-c2ccc(C)o2)cc(Cl)n1] |

US 10,793,561 B2
323
TABLE 1-continued
324
| Compound No. | Compound |
|---|---|
| 1.584 | 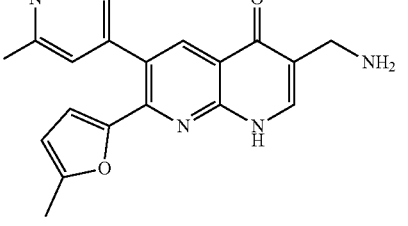 |
| 1.585 | 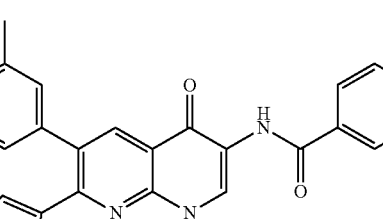 |
| 1.586 | 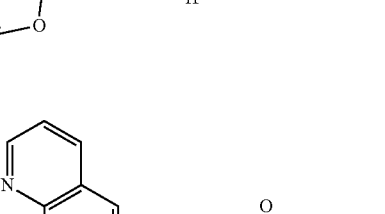 |
| 1.587 | 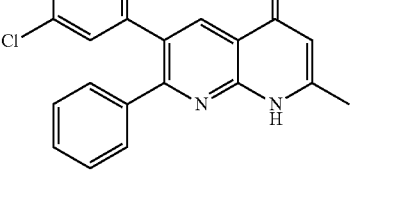 |
| 1.588 | 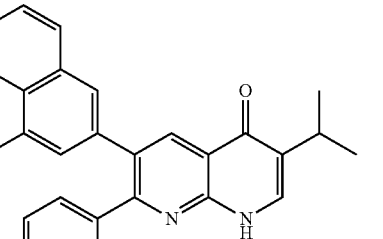 |

TABLE 1-continued
| Compound No. | Compound |
|---|---|
| 1.589 | 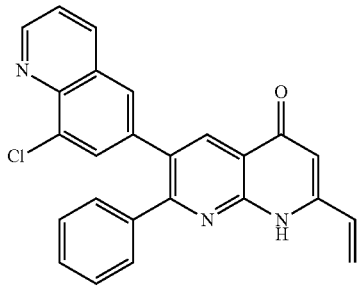 [SMILES: C=Cc1cc(=O)c2cc(-c3cc(Cl)c4ncccc4c3)c(-c3ccccc3)nc2[nH]1] |
| 1.590 | 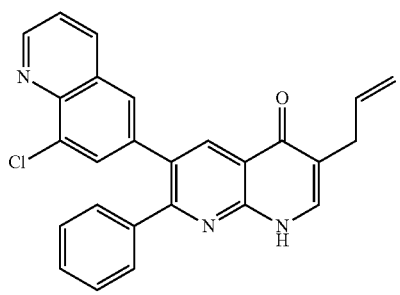 [SMILES: C=CCc1c[nH]c2nc(-c3ccccc3)c(-c3cc(Cl)c4ncccc4c3)cc2c1=O] |
| 1.591 | 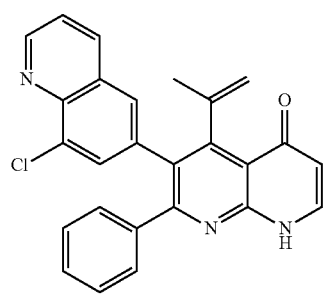 [SMILES: C=C(C)c1c(-c2cc(Cl)c3ncccc3c2)c(-c2ccccc2)nc2[nH]ccc(=O)c12] |
| 1.592 | 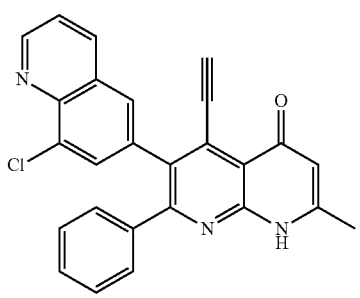 [SMILES: C#Cc1c(-c2cc(Cl)c3ncccc3c2)c(-c2ccccc2)nc2[nH]c(C)cc(=O)c12] |
| 1.593 | 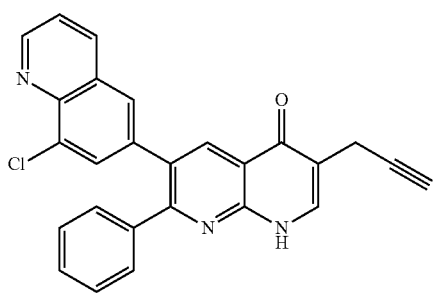 [SMILES: C#CCc1c[nH]c2nc(-c3ccccc3)c(-c3cc(Cl)c4ncccc4c3)cc2c1=O] |

US 10,793,561 B2
TABLE 1-continued
| Compound No. | Compound |
|---|---|
| 1.594 | 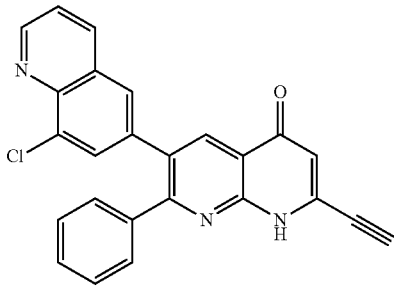 [SMILES: C#Cc1cc(=O)c2cc(-c3cc(Cl)c4ncccc4c3)c(-c3ccccc3)nc2[nH]1] |
| 1.595 | 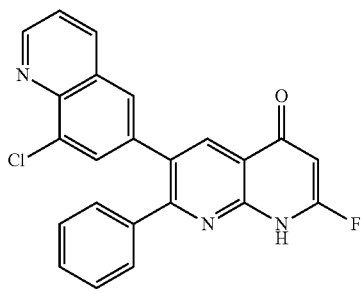 [SMILES: O=c1cc(F)[nH]c2nc(-c3ccccc3)c(-c3cc(Cl)c4ncccc4c3)cc12] |
| 1.596 | 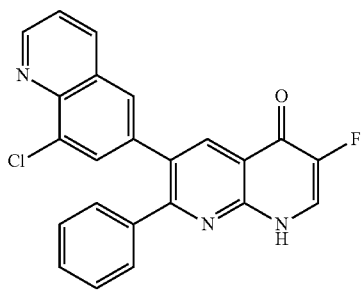 [SMILES: O=c1c(F)c[nH]c2nc(-c3ccccc3)c(-c3cc(Cl)c4ncccc4c3)cc12] |
| 1.597 | 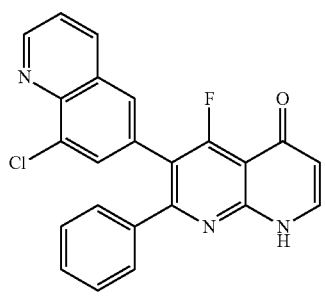 [SMILES: O=c1cc[nH]c2nc(-c3ccccc3)c(-c3cc(Cl)c4ncccc4c3)c(F)c12] |
| 1.598 | 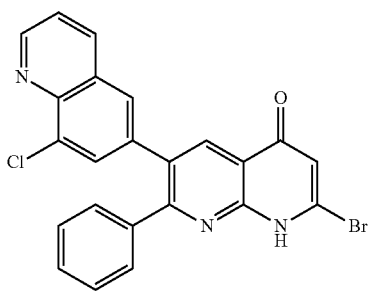 [SMILES: O=c1cc(Br)[nH]c2nc(-c3ccccc3)c(-c3cc(Cl)c4ncccc4c3)cc12] |

TABLE 1-continued
| Compound No. | Compound |
|---|---|
| 1.599 | 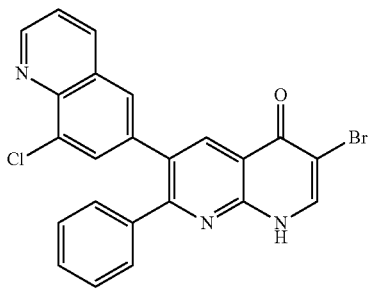 [SMILES: O=c1c(Br)c[nH]c2nc(-c3ccccc3)c(-c3cc(Cl)c4ncccc4c3)cc12] |
| 1.600 | 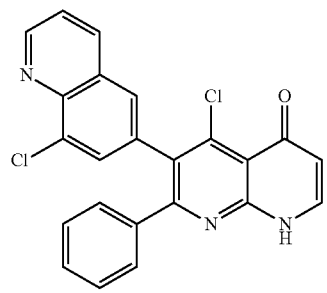 [SMILES: O=c1cc[nH]c2nc(-c3ccccc3)c(-c3cc(Cl)c4ncccc4c3)c(Cl)c12] |
| 1.601 | 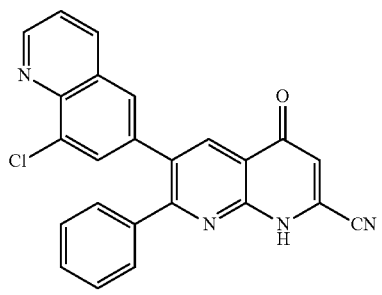 [SMILES: N#Cc1cc(=O)c2cc(-c3cc(Cl)c4ncccc4c3)c(-c3ccccc3)nc2[nH]1] |
| 1.602 | 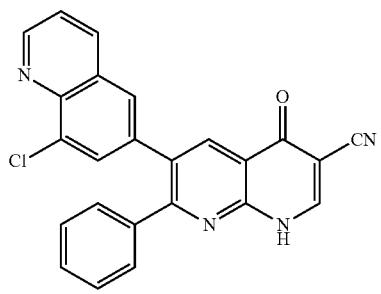 [SMILES: N#Cc1c[nH]c2nc(-c3ccccc3)c(-c3cc(Cl)c4ncccc4c3)cc2c1=O] |
| 1.603 | 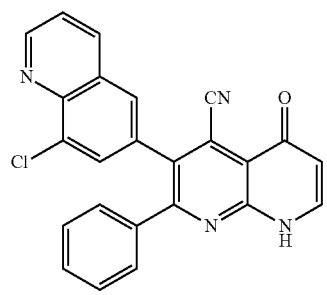 [SMILES: N#Cc1c(-c2cc(Cl)c3ncccc3c2)c(-c2ccccc2)nc2[nH]ccc(=O)c12] |

TABLE 1-continued
| Compound No. | Compound |
|---|---|
| 1.604 | 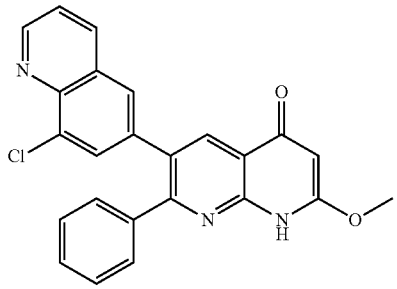 [SMILES: COc1cc(=O)c2cc(-c3cc(Cl)c4ncccc4c3)c(-c3ccccc3)nc2[nH]1] |
| 1.605 | 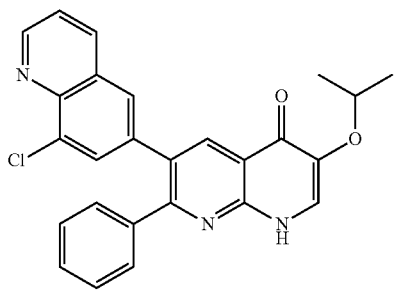 [SMILES: CC(C)Oc1c[nH]c2nc(-c3ccccc3)c(-c3cc(Cl)c4ncccc4c3)cc2c1=O] |
| 1.606 | 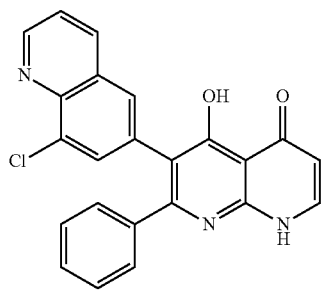 [SMILES: O=c1cc[nH]c2nc(-c3ccccc3)c(-c3cc(Cl)c4ncccc4c3)c(O)c12] |
| 1.607 | 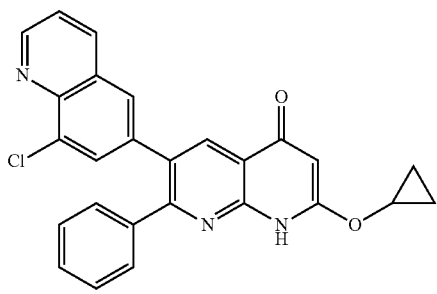 [SMILES: O=c1cc(OC2CC2)[nH]c2nc(-c3ccccc3)c(-c3cc(Cl)c4ncccc4c3)cc12] |
| 1.608 | 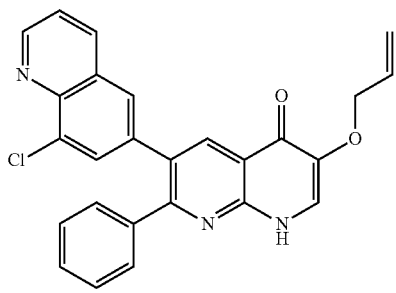 [SMILES: C=CCOc1c[nH]c2nc(-c3ccccc3)c(-c3cc(Cl)c4ncccc4c3)cc2c1=O] |

TABLE 1-continued

| Compound No. | Compound |
|---|---|
| 1.609 | |
| 1.610 | |
| 1.611 | |
| 1.612 | |
| 1.613 | |

TABLE 1-continued
| Compound No. | Compound |
|---|---|
| 1.614 | 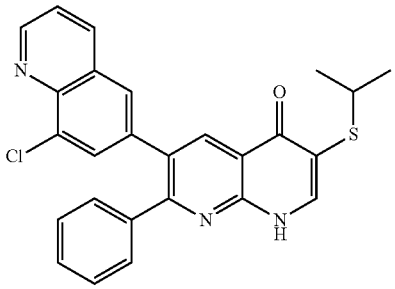 |
| 1.615 | 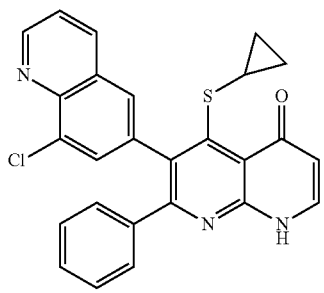 [SMILES: O=c1cc[nH]c2nc(-c3ccccc3)c(-c3cc(Cl)c4ncccc4c3)c(SC3CC3)c12] |
| 1.616 | 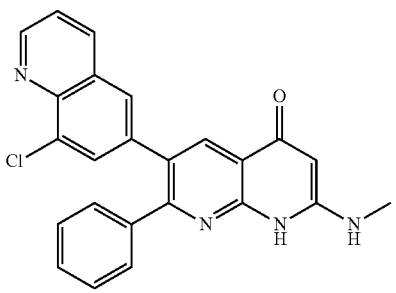 [SMILES: CNc1cc(=O)c2cc(-c3cc(Cl)c4ncccc4c3)c(-c3ccccc3)nc2[nH]1] |
| 1.617 | 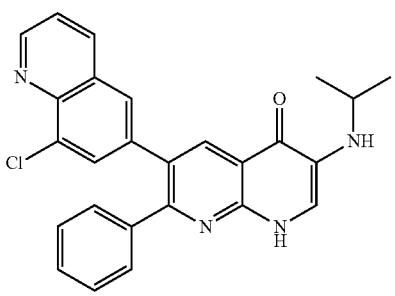 [SMILES: CC(C)Nc1c[nH]c2nc(-c3ccccc3)c(-c3cc(Cl)c4ncccc4c3)cc2c1=O] |
| 1.618 | 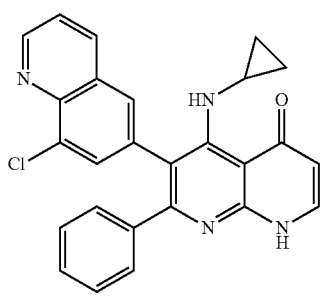 [SMILES: O=c1cc[nH]c2nc(-c3ccccc3)c(-c3cc(Cl)c4ncccc4c3)c(NC3CC3)c12] |

US 10,793,561 B2
337                                                                 338
TABLE 1-continued
| Compound No. | Compound |
|---|---|
| 1.619 | 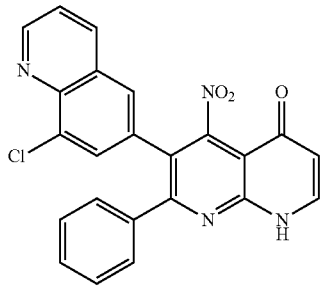 [SMILES: O=c1cc[nH]c2nc(-c3ccccc3)c(-c3cc(Cl)c4ncccc4c3)c([N+](=O)[O-])c12] |
| 1.620 | 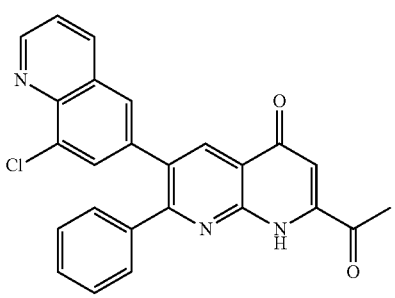 [SMILES: CC(=O)c1cc(=O)c2cc(-c3cc(Cl)c4ncccc4c3)c(-c3ccccc3)nc2[nH]1] |
| 1.621 | 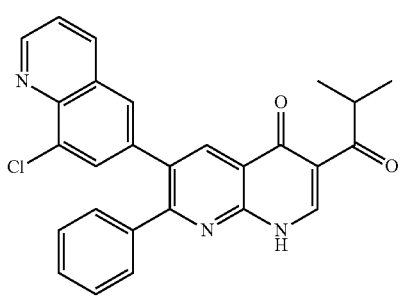 [SMILES: CC(C)C(=O)c1c[nH]c2nc(-c3ccccc3)c(-c3cc(Cl)c4ncccc4c3)cc2c1=O] |
| 1.622 | 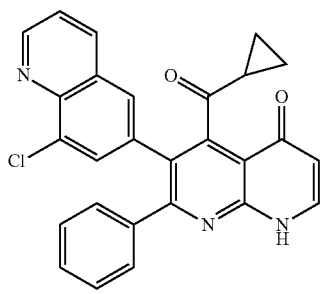 [SMILES: O=C(c1c(-c2cc(Cl)c3ncccc3c2)c(-c2ccccc2)nc2[nH]ccc(=O)c12)C1CC1] |
| 1.623 | 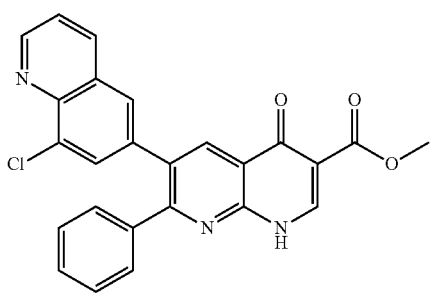 [SMILES: COC(=O)c1c[nH]c2nc(-c3ccccc3)c(-c3cc(Cl)c4ncccc4c3)cc2c1=O] |

TABLE 1-continued
| Compound No. | Compound |
|---|---|
| 1.624 | 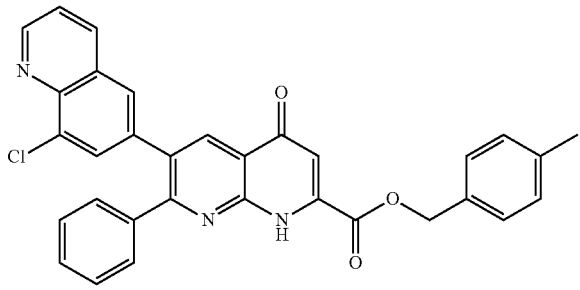 [SMILES: Cc1ccc(COC(=O)c2cc(=O)c3cc(-c4cc(Cl)c5ncccc5c4)c(-c4ccccc4)nc3[nH]2)cc1] |
| 1.625 | 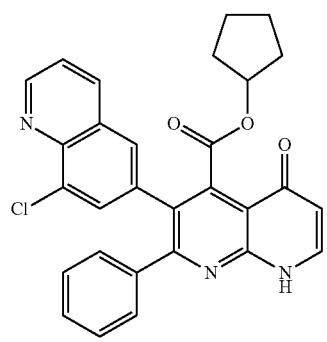 |
| 1.626 | 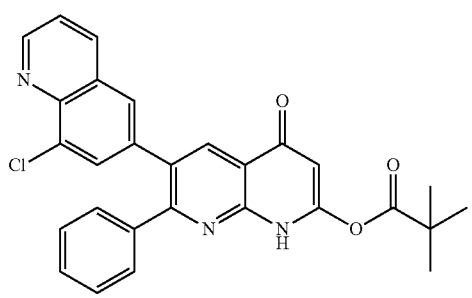 [SMILES: CC(C)(C)C(=O)Oc1cc(=O)c2cc(-c3cc(Cl)c4ncccc4c3)c(-c3ccccc3)nc2[nH]1] |
| 1.627 | 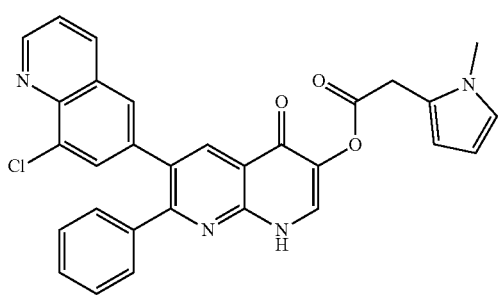 [SMILES: Cn1cccc1CC(=O)Oc1c[nH]c2nc(-c3ccccc3)c(-c3cc(Cl)c4ncccc4c3)cc2c1=O] |
| 1.628 | 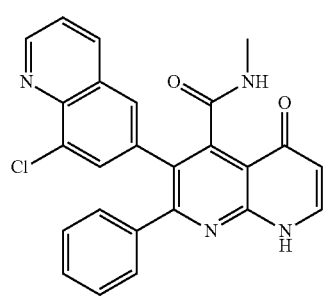 |

TABLE 1-continued
| Compound No. | Compound |
|---|---|
| 1.629 | 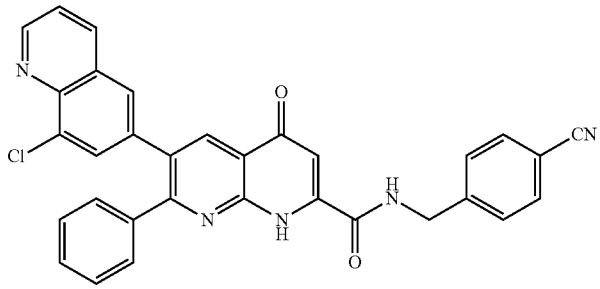 [SMILES: N#Cc1ccc(CNC(=O)c2cc(=O)c3cc(-c4cc(Cl)c5ncccc5c4)c(-c4ccccc4)nc3[nH]2)cc1] |
| 1.630 | 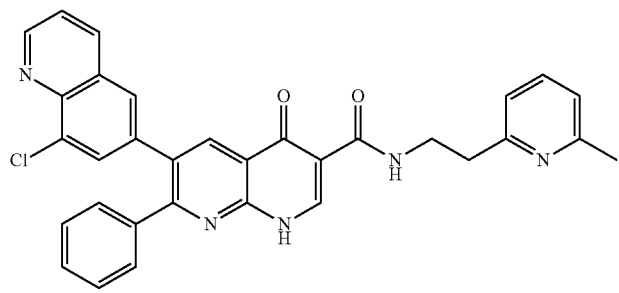 [SMILES: Cc1cccc(CCNC(=O)c2c[nH]c3nc(-c4ccccc4)c(-c4cc(Cl)c5ncccc5c4)cc3c2=O)n1] |
| 1.631 | 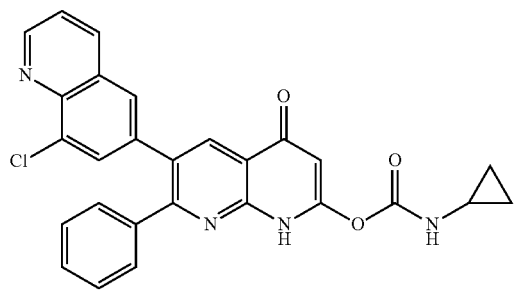 [SMILES: O=C(NC1CC1)Oc1cc(=O)c2cc(-c3cc(Cl)c4ncccc4c3)c(-c3ccccc3)nc2[nH]1] |
| 1.632 | 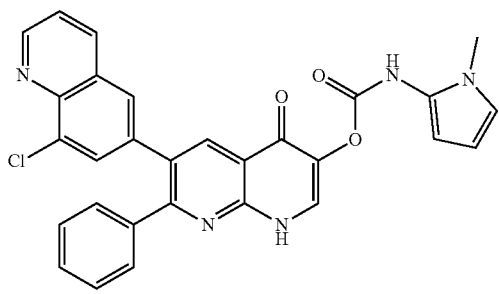 [SMILES: Cn1cccc1NC(=O)Oc1c[nH]c2nc(-c3ccccc3)c(-c3cc(Cl)c4ncccc4c3)cc2c1=O] |
| 1.633 | 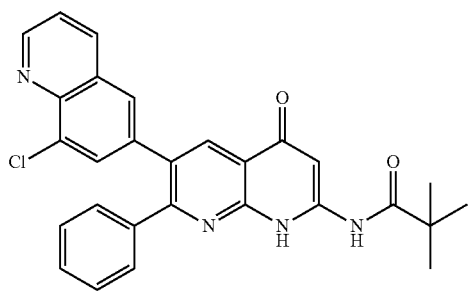 [SMILES: CC(C)(C)C(=O)Nc1cc(=O)c2cc(-c3cc(Cl)c4ncccc4c3)c(-c3ccccc3)nc2[nH]1] |

TABLE 1-continued
| Compound No. | Compound |
|---|---|
| 1.634 | 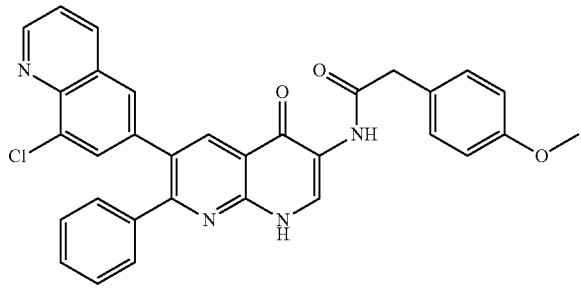 [SMILES: COc1ccc(CC(=O)Nc2c[nH]c3nc(-c4ccccc4)c(-c4cc(Cl)c5ncccc5c4)cc3c2=O)cc1] |
| 1.635 | 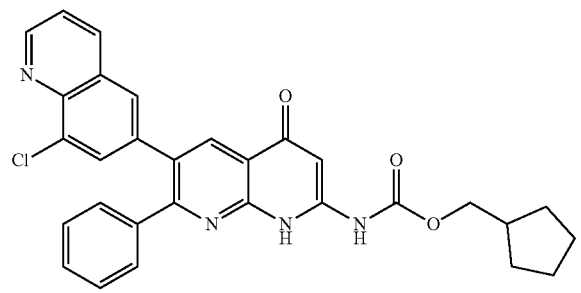 [SMILES: O=C(Nc1cc(=O)c2cc(-c3cc(Cl)c4ncccc4c3)c(-c3ccccc3)nc2[nH]1)OCC1CCCC1] |
| 1.636 | 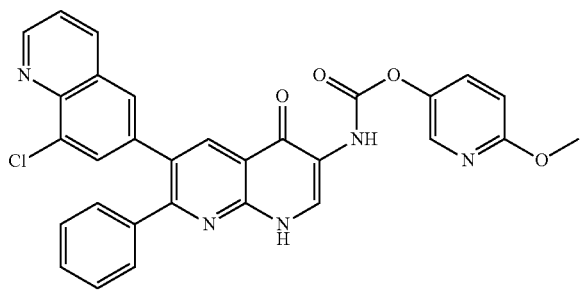 [SMILES: COc1ccc(OC(=O)Nc2c[nH]c3nc(-c4ccccc4)c(-c4cc(Cl)c5ncccc5c4)cc3c2=O)cn1] |
| 1.637 | 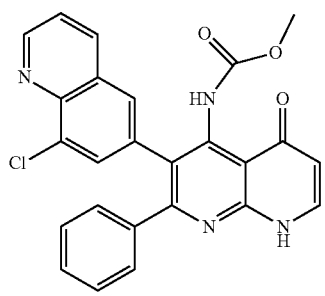 [SMILES: COC(=O)Nc1c(-c2cc(Cl)c3ncccc3c2)c(-c2ccccc2)nc2[nH]ccc(=O)c12] |
| 1.638 | 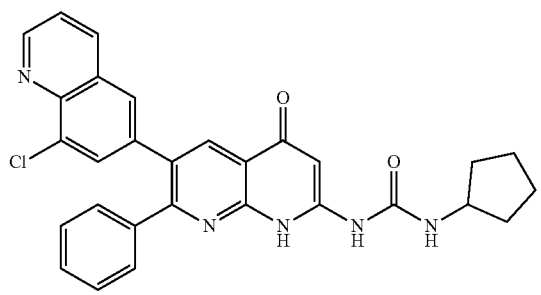 [SMILES: O=C(Nc1cc(=O)c2cc(-c3cc(Cl)c4ncccc4c3)c(-c3ccccc3)nc2[nH]1)NC1CCCC1] |

TABLE 1-continued
| Compound No. | Compound |
|---|---|
| 1.639 | 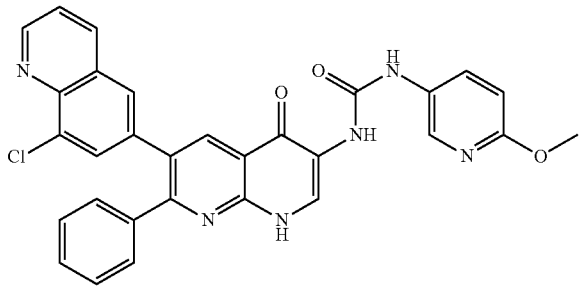 [SMILES: COc1ccc(NC(=O)Nc2c[nH]c3nc(-c4ccccc4)c(-c4cc(Cl)c5ncccc5c4)cc3c2=O)cn1] |
| 1.640 | 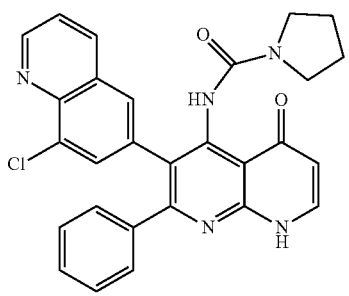 [SMILES: O=C(Nc1c(-c2cc(Cl)c3ncccc3c2)c(-c2ccccc2)nc2[nH]ccc(=O)c12)N1CCCC1] |
| 1.641 | 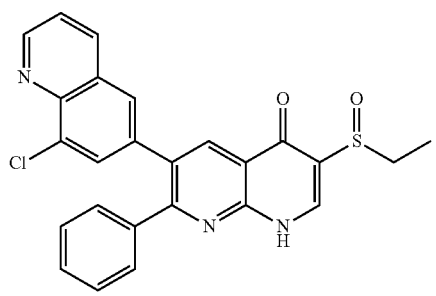 [SMILES: CCS(=O)c1c[nH]c2nc(-c3ccccc3)c(-c3cc(Cl)c4ncccc4c3)cc2c1=O] |
| 1.642 | 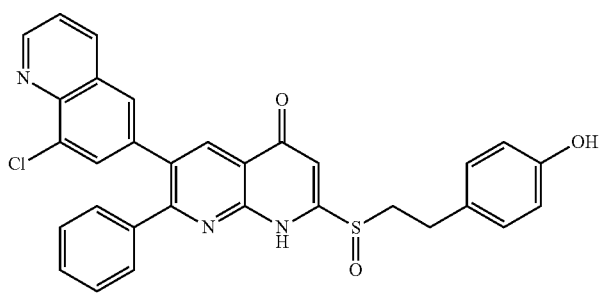 [SMILES: O=c1cc(S(=O)CCc2ccc(O)cc2)[nH]c2nc(-c3ccccc3)c(-c3cc(Cl)c4ncccc4c3)cc12] |
| 1.643 | 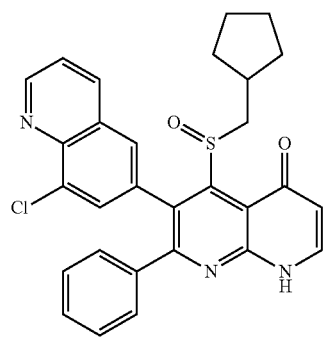 [SMILES: O=c1cc[nH]c2nc(-c3ccccc3)c(-c3cc(Cl)c4ncccc4c3)c(S(=O)CC3CCCC3)c12] |

TABLE 1-continued
| Compound No. | Compound |
|---|---|
| 1.644 | 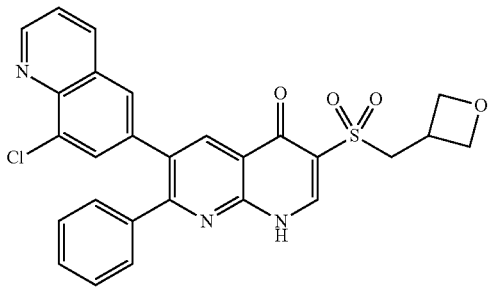 [SMILES: O=c1c(S(=O)(=O)CC2COC2)c[nH]c2nc(-c3ccccc3)c(-c3cc(Cl)c4ncccc4c3)cc12] |
| 1.645 | 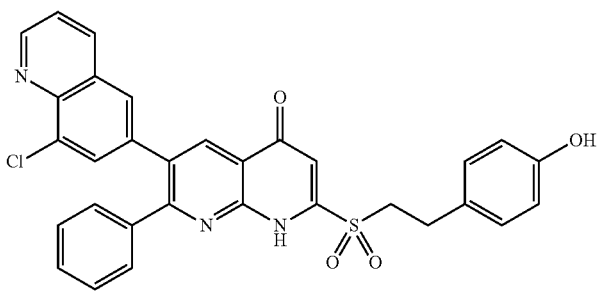 [SMILES: O=c1cc(S(=O)(=O)CCc2ccc(O)cc2)[nH]c2nc(-c3ccccc3)c(-c3cc(Cl)c4ncccc4c3)cc12] |
| 1.646 | 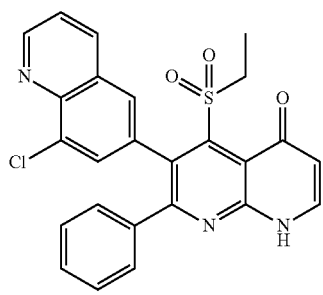 [SMILES: CCS(=O)(=O)c1c(-c2cc(Cl)c3ncccc3c2)c(-c2ccccc2)nc2[nH]ccc(=O)c12] |
| 1.647 | 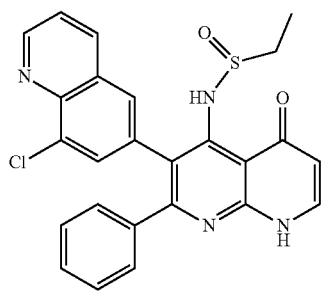 [SMILES: CCS(=O)Nc1c(-c2cc(Cl)c3ncccc3c2)c(-c2ccccc2)nc2[nH]ccc(=O)c12] |
| 1.648 | 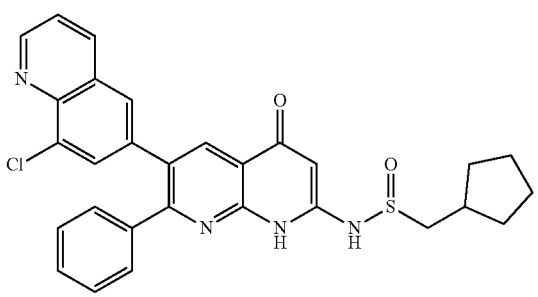 [SMILES: O=c1cc(NS(=O)CC2CCCC2)[nH]c2nc(-c3ccccc3)c(-c3cc(Cl)c4ncccc4c3)cc12] |

TABLE 1-continued

| Compound No. | Compound |
|---|---|
| 1.649 | |
| 1.650 | |
| 1.651 | |
| 1.652 | |
| 1.653 | |

TABLE 1-continued
| Compound No. | Compound |
|---|---|
| 1.654 | 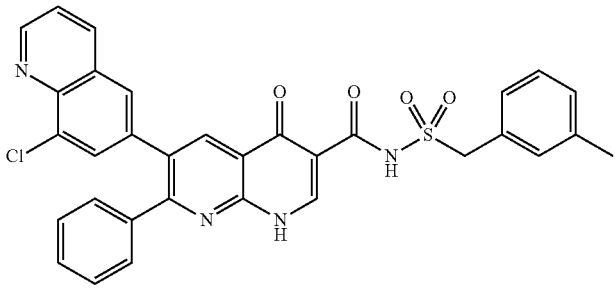 [SMILES: Cc1cccc(CS(=O)(=O)NC(=O)c2c[nH]c3nc(-c4ccccc4)c(-c4cc(Cl)c5ncccc5c4)cc3c2=O)c1] |
| 1.655 | 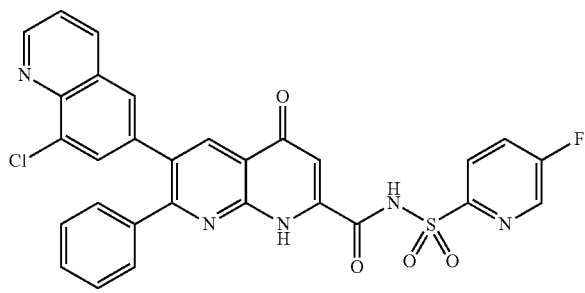 [SMILES: O=C(NS(=O)(=O)c1ccc(F)cn1)c1cc(=O)c2cc(-c3cc(Cl)c4ncccc4c3)c(-c3ccccc3)nc2[nH]1] |
| 1.656 | 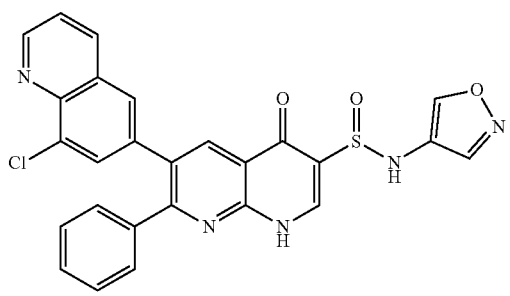 [SMILES: O=c1c(S(=O)Nc2cnoc2)c[nH]c2nc(-c3ccccc3)c(-c3cc(Cl)c4ncccc4c3)cc12] |
| 1.657 | 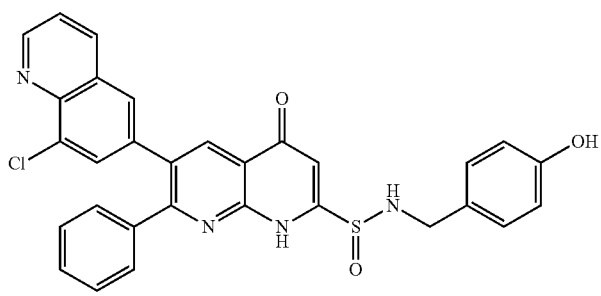 [SMILES: O=c1cc(S(=O)NCc2ccc(O)cc2)[nH]c2nc(-c3ccccc3)c(-c3cc(Cl)c4ncccc4c3)cc12] |
| 1.658 | 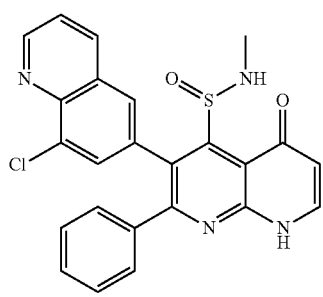 [SMILES: CNS(=O)c1c(-c2cc(Cl)c3ncccc3c2)c(-c2ccccc2)nc2[nH]ccc(=O)c12] |

TABLE 1-continued
| Compound No. | Compound |
|---|---|
| 1.659 | 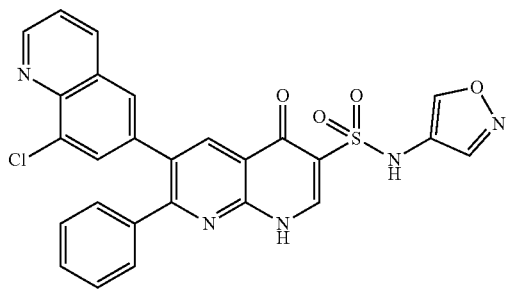 [SMILES: O=c1c(S(=O)(=O)Nc2cnoc2)c[nH]c2nc(-c3ccccc3)c(-c3cc(Cl)c4ncccc4c3)cc12] |
| 1.660 | 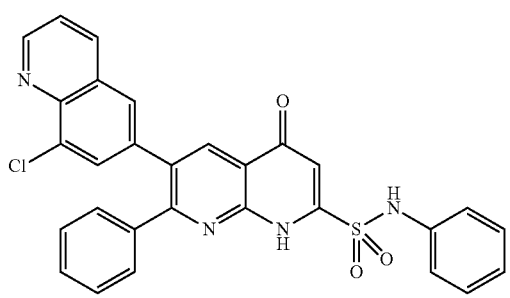 [SMILES: O=c1cc(S(=O)(=O)Nc2ccccc2)[nH]c2nc(-c3ccccc3)c(-c3cc(Cl)c4ncccc4c3)cc12] |
| 1.661 | 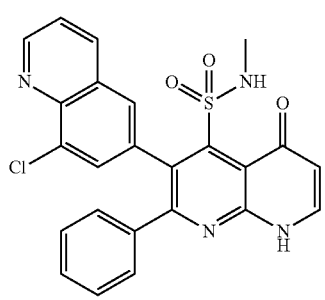 [SMILES: CNS(=O)(=O)c1c(-c2cc(Cl)c3ncccc3c2)c(-c2ccccc2)nc2[nH]ccc(=O)c12] |
| 1.662 | 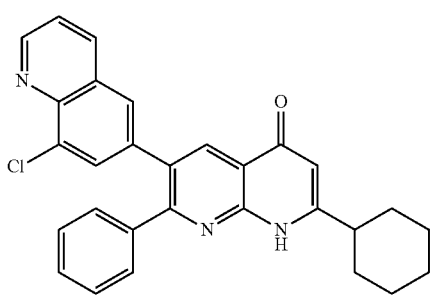 [SMILES: O=c1cc(C2CCCCC2)[nH]c2nc(-c3ccccc3)c(-c3cc(Cl)c4ncccc4c3)cc12] |
| 1.663 | 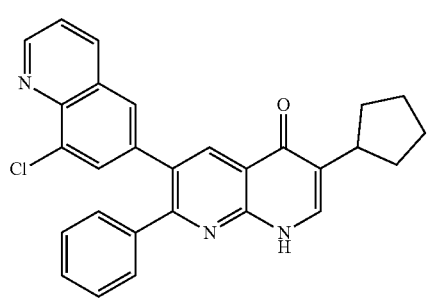 [SMILES: O=c1c(C2CCCC2)c[nH]c2nc(-c3ccccc3)c(-c3cc(Cl)c4ncccc4c3)cc12] |

TABLE 1-continued
| Compound No. | Compound |
|---|---|
| 1.664 | 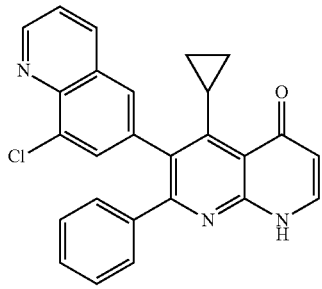 [SMILES: O=c1cc[nH]c2nc(-c3ccccc3)c(-c3cc(Cl)c4ncccc4c3)c(C3CC3)c12] |
| 1.665 | 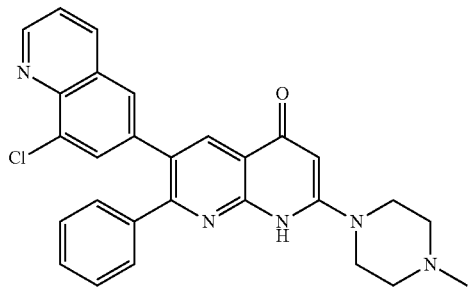 [SMILES: CN1CCN(c2cc(=O)c3cc(-c4cc(Cl)c5ncccc5c4)c(-c4ccccc4)nc3[nH]2)CC1] |
| 1.666 | 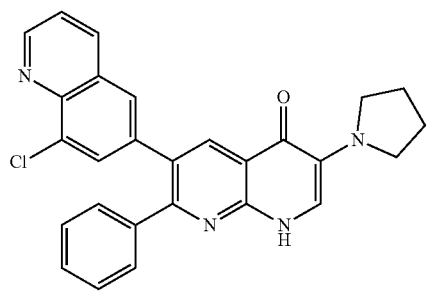 [SMILES: O=c1c(N2CCCC2)c[nH]c2nc(-c3ccccc3)c(-c3cc(Cl)c4ncccc4c3)cc12] |
| 1.667 | 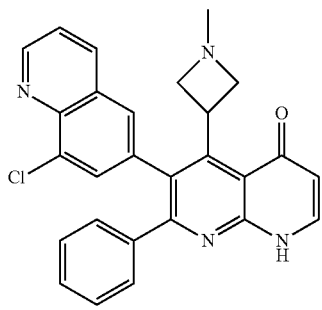 [SMILES: CN1CC(c2c(-c3cc(Cl)c4ncccc4c3)c(-c3ccccc3)nc3[nH]ccc(=O)c23)C1] |
| 1.668 | 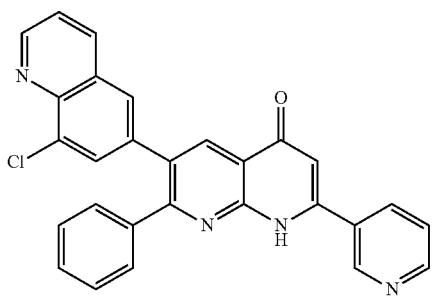 [SMILES: O=c1cc(-c2cccnc2)[nH]c2nc(-c3ccccc3)c(-c3cc(Cl)c4ncccc4c3)cc12] |

TABLE 1-continued
| Compound No. | Compound |
|---|---|
| 1.669 | 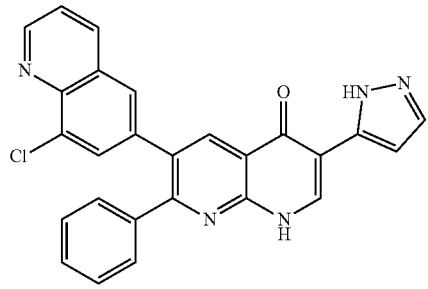 [SMILES: O=c1c(-c2ccn[nH]2)c[nH]c2nc(-c3ccccc3)c(-c3cc(Cl)c4ncccc4c3)cc12] |
| 1.670 | 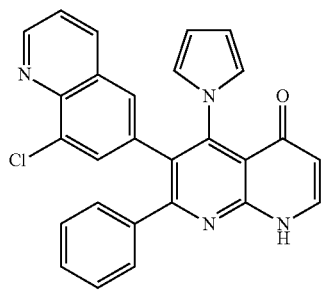 [SMILES: O=c1cc[nH]c2nc(-c3ccccc3)c(-c3cc(Cl)c4ncccc4c3)c(-n3cccc3)c12] |
| 1.671 | 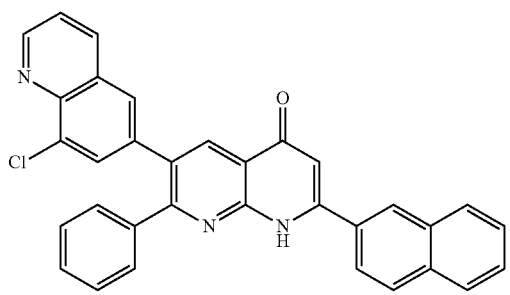 [SMILES: O=c1cc(-c2ccc3ccccc3c2)[nH]c2nc(-c3ccccc3)c(-c3cc(Cl)c4ncccc4c3)cc12] |
| 1.672 | 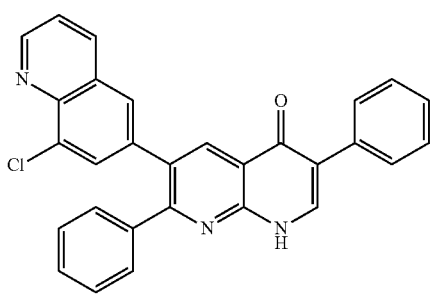 [SMILES: O=c1c(-c2ccccc2)c[nH]c2nc(-c3ccccc3)c(-c3cc(Cl)c4ncccc4c3)cc12] |
| 1.673 | 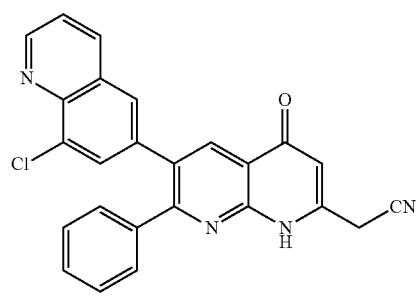 [SMILES: N#CCc1cc(=O)c2cc(-c3cc(Cl)c4ncccc4c3)c(-c3ccccc3)nc2[nH]1] |

TABLE 1-continued
| Compound No. | Compound |
|---|---|
| 1.674 | 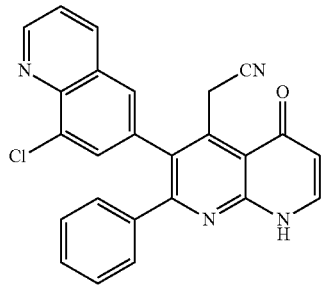 [SMILES: N#CCc1c(-c2cc(Cl)c3ncccc3c2)c(-c2ccccc2)nc2[nH]ccc(=O)c12] |
| 1.675 | 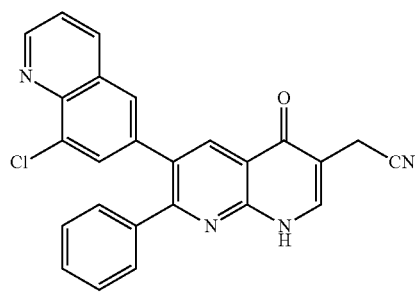 [SMILES: N#CCc1c[nH]c2nc(-c3ccccc3)c(-c3cc(Cl)c4ncccc4c3)cc2c1=O] |
| 1.676 | 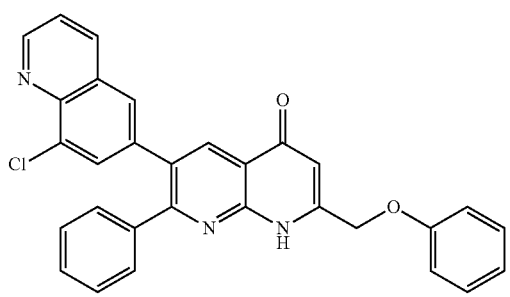 [SMILES: O=c1cc(COc2ccccc2)[nH]c2nc(-c3ccccc3)c(-c3cc(Cl)c4ncccc4c3)cc12] |
| 1.677 | 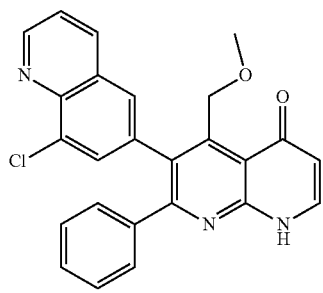 [SMILES: COCc1c(-c2cc(Cl)c3ncccc3c2)c(-c2ccccc2)nc2[nH]ccc(=O)c12] |
| 1.678 | 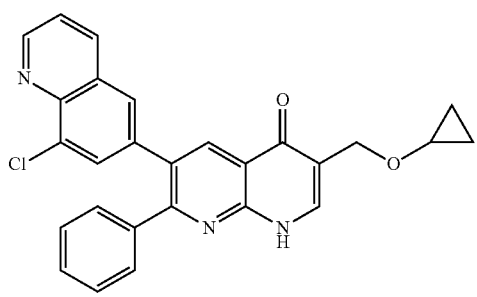 [SMILES: O=c1c(COC2CC2)c[nH]c2nc(-c3ccccc3)c(-c3cc(Cl)c4ncccc4c3)cc12] |

TABLE 1-continued
| Compound No. | Compound |
|---|---|
| 1.679 | 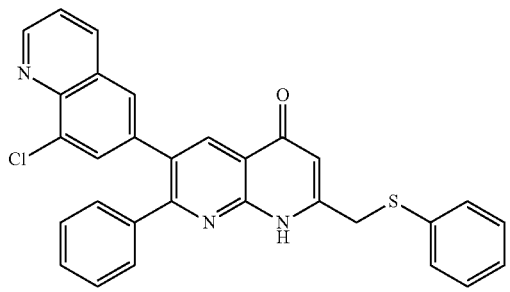 [SMILES: O=c1cc(CSc2ccccc2)[nH]c2nc(-c3ccccc3)c(-c3cc(Cl)c4ncccc4c3)cc12] |
| 1.680 | 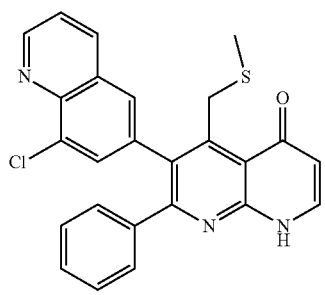 [SMILES: CSCc1c(-c2cc(Cl)c3ncccc3c2)c(-c2ccccc2)nc2[nH]ccc(=O)c12] |
| 1.681 | 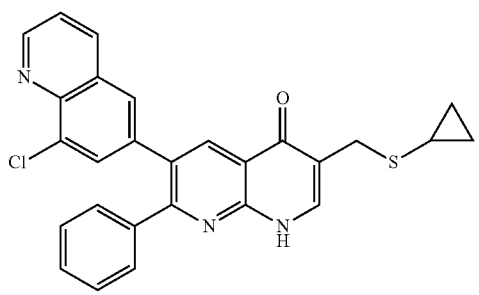 [SMILES: O=c1c(CSC2CC2)c[nH]c2nc(-c3ccccc3)c(-c3cc(Cl)c4ncccc4c3)cc12] |
| 1.682 | 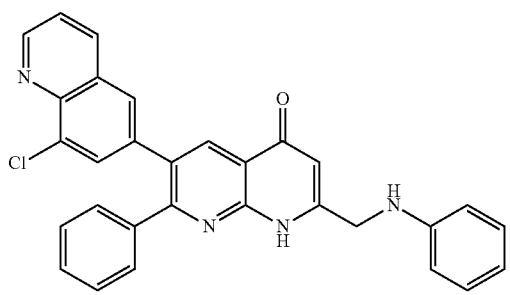 [SMILES: O=c1cc(CNc2ccccc2)[nH]c2nc(-c3ccccc3)c(-c3cc(Cl)c4ncccc4c3)cc12] |
| 1.683 | 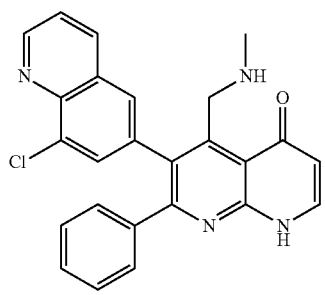 [SMILES: CNCc1c(-c2cc(Cl)c3ncccc3c2)c(-c2ccccc2)nc2[nH]ccc(=O)c12] |

TABLE 1-continued
| Compound No. | Compound |
|---|---|
| 1.684 | 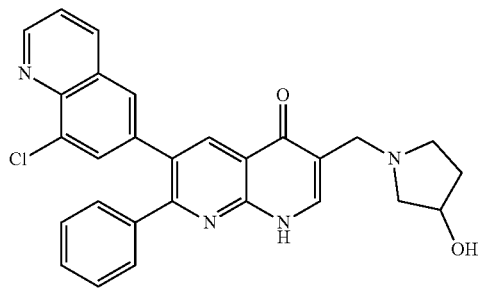 [SMILES: O=c1c(CN2CCC(O)C2)c[nH]c2nc(-c3ccccc3)c(-c3cc(Cl)c4ncccc4c3)cc12] |
| 1.685 | 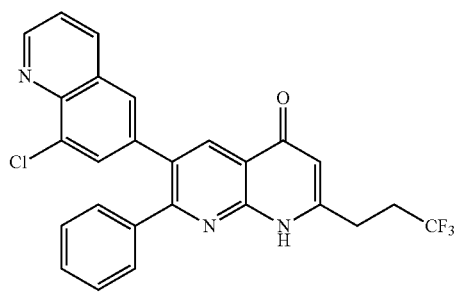 [SMILES: O=c1cc(CCC(F)(F)F)[nH]c2nc(-c3ccccc3)c(-c3cc(Cl)c4ncccc4c3)cc12] |
| 1.686 | 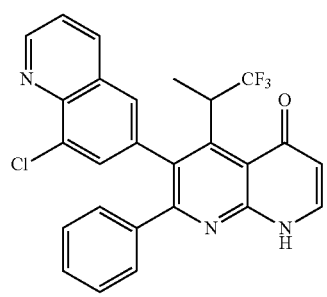 [SMILES: CC(c1c(-c2cc(Cl)c3ncccc3c2)c(-c2ccccc2)nc2[nH]ccc(=O)c12)C(F)(F)F] |
| 1.687 | 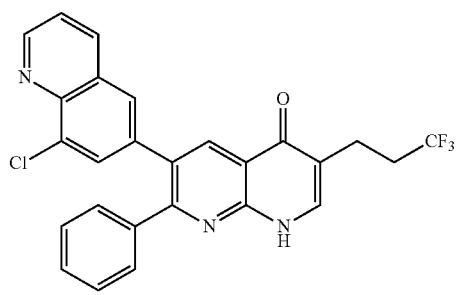 [SMILES: O=c1c(CCC(F)(F)F)c[nH]c2nc(-c3ccccc3)c(-c3cc(Cl)c4ncccc4c3)cc12] |
| 1.688 | 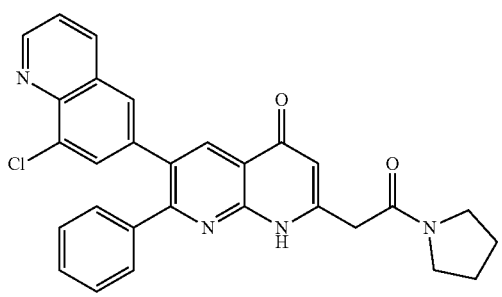 [SMILES: O=C(Cc1cc(=O)c2cc(-c3cc(Cl)c4ncccc4c3)c(-c3ccccc3)nc2[nH]1)N1CCCC1] |

TABLE 1-continued
| Compound No. | Compound |
|---|---|
| 1.689 | 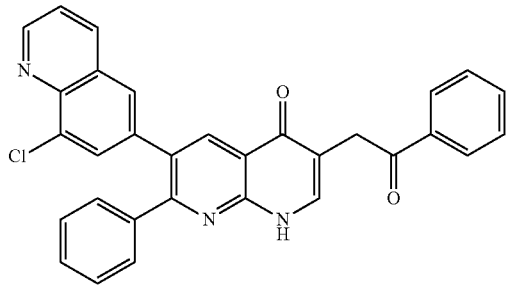 |
| 1.690 | 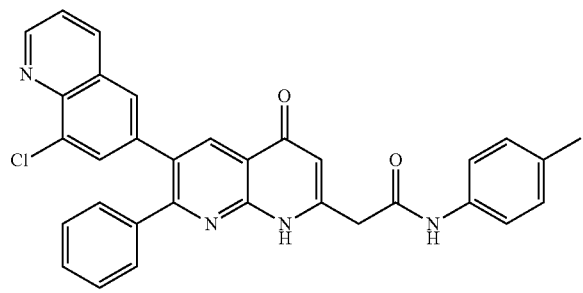 [SMILES: Cc1ccc(NC(=O)Cc2cc(=O)c3cc(-c4cc(Cl)c5ncccc5c4)c(-c4ccccc4)nc3[nH]2)cc1] |
| 1.691 | 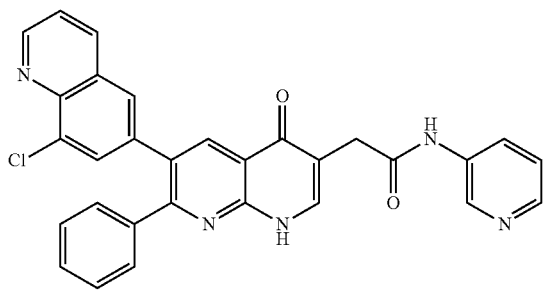 [SMILES: O=C(Cc1c[nH]c2nc(-c3ccccc3)c(-c3cc(Cl)c4ncccc4c3)cc2c1=O)Nc1cccnc1] |
| 1.692 | 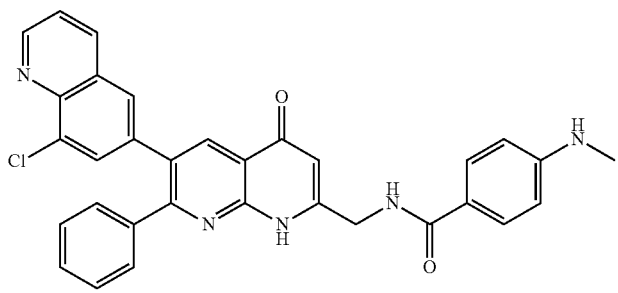 [SMILES: CNc1ccc(C(=O)NCc2cc(=O)c3cc(-c4cc(Cl)c5ncccc5c4)c(-c4ccccc4)nc3[nH]2)cc1] |
| 1.693 | 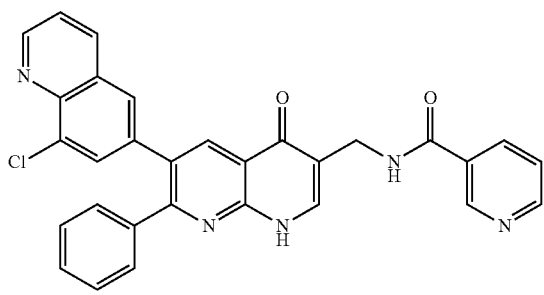 [SMILES: O=C(NCc1c[nH]c2nc(-c3ccccc3)c(-c3cc(Cl)c4ncccc4c3)cc2c1=O)c1cccnc1] |

TABLE 1-continued
| Compound No. | Compound |
|---|---|
| 1.694 | 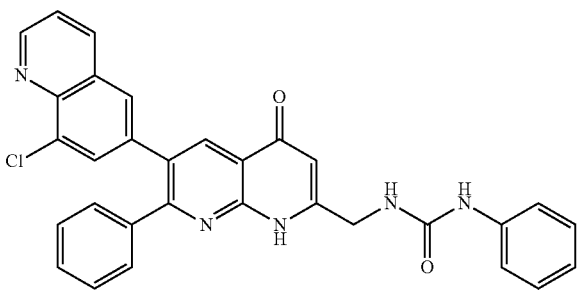 [SMILES: O=C(NCc1cc(=O)c2cc(-c3cc(Cl)c4ncccc4c3)c(-c3ccccc3)nc2[nH]1)Nc1ccccc1] |
| 1.695 | 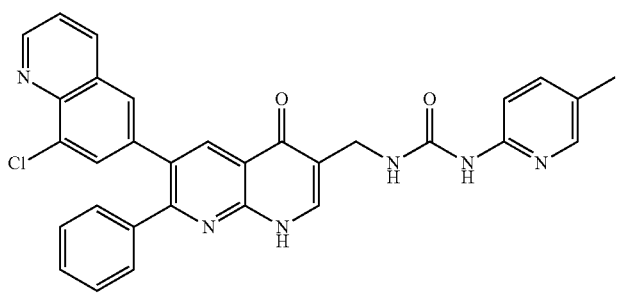 [SMILES: Cc1ccc(NC(=O)NCc2c[nH]c3nc(-c4ccccc4)c(-c4cc(Cl)c5ncccc5c4)cc3c2=O)nc1] |
| 1.696 | 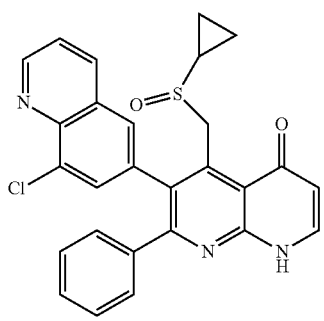 [SMILES: O=c1cc[nH]c2nc(-c3ccccc3)c(-c3cc(Cl)c4ncccc4c3)c(CS(=O)C3CC3)c12] |
| 1.697 | 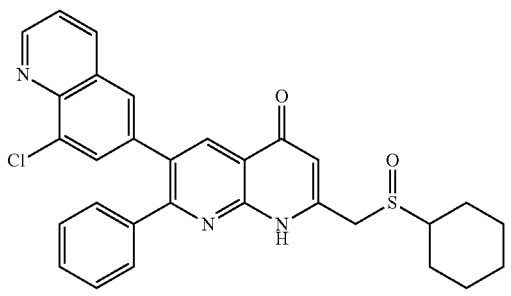 [SMILES: O=c1cc(CS(=O)C2CCCCC2)[nH]c2nc(-c3ccccc3)c(-c3cc(Cl)c4ncccc4c3)cc12] |
| 1.698 | 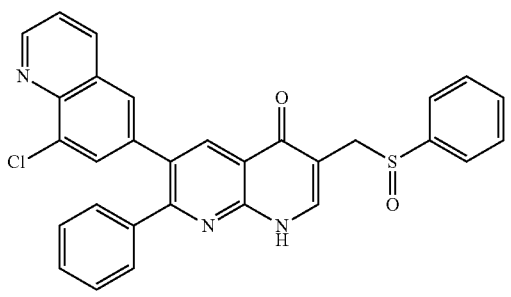 [SMILES: O=c1c(CS(=O)c2ccccc2)c[nH]c2nc(-c3ccccc3)c(-c3cc(Cl)c4ncccc4c3)cc12] |

TABLE 1-continued
| Compound No. | Compound |
|---|---|
| 1.699 | 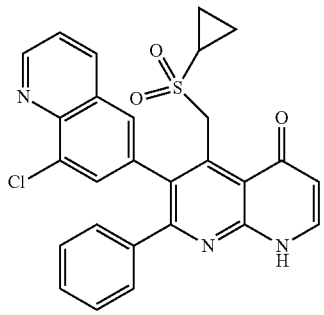 [SMILES: O=c1cc[nH]c2nc(-c3ccccc3)c(-c3cc(Cl)c4ncccc4c3)c(CS(=O)(=O)C3CC3)c12] |
| 1.700 | 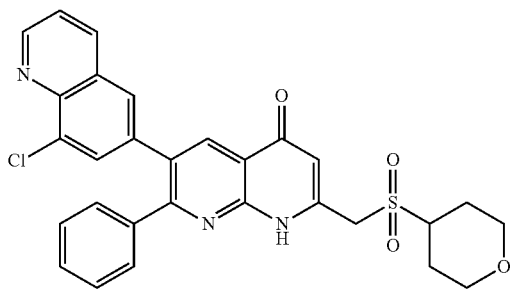 [SMILES: O=c1cc(CS(=O)(=O)C2CCOCC2)[nH]c2nc(-c3ccccc3)c(-c3cc(Cl)c4ncccc4c3)cc12] |
| 1.701 | 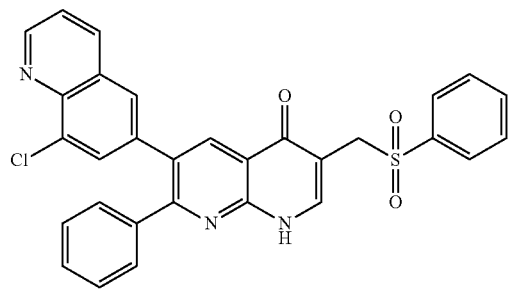 [SMILES: O=c1c(CS(=O)(=O)c2ccccc2)c[nH]c2nc(-c3ccccc3)c(-c3cc(Cl)c4ncccc4c3)cc12] |
| 1.702 | 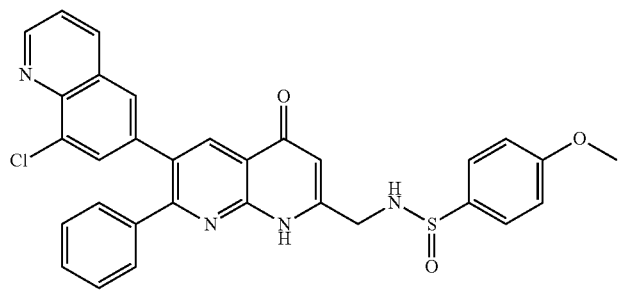 [SMILES: COc1ccc(S(=O)NCc2cc(=O)c3cc(-c4cc(Cl)c5ncccc5c4)c(-c4ccccc4)nc3[nH]2)cc1] |
| 1.703 | 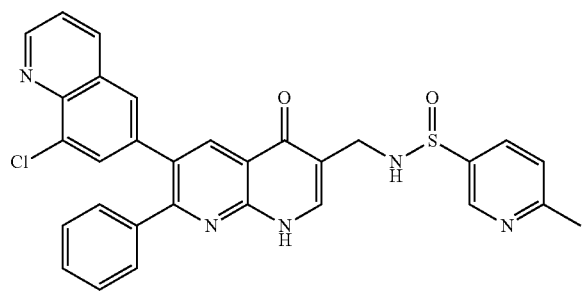 [SMILES: Cc1ccc(S(=O)NCc2c[nH]c3nc(-c4ccccc4)c(-c4cc(Cl)c5ncccc5c4)cc3c2=O)cn1] |

TABLE 1-continued
| Compound No. | Compound |
|---|---|
| 1.704 | 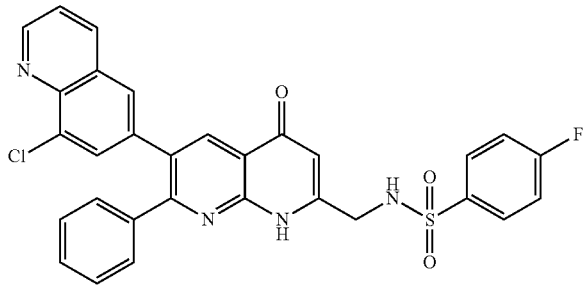 [SMILES: O=c1cc(CNS(=O)(=O)c2ccc(F)cc2)[nH]c2nc(-c3ccccc3)c(-c3cc(Cl)c4ncccc4c3)cc12] |
| 1.705 | 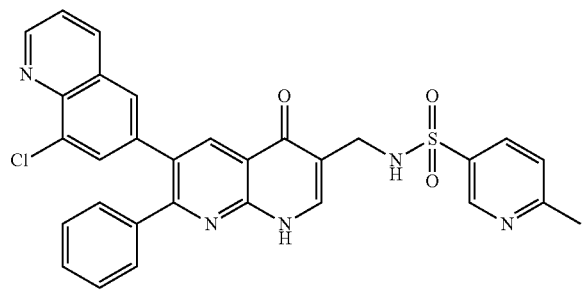 [SMILES: Cc1ccc(S(=O)(=O)NCc2c[nH]c3nc(-c4ccccc4)c(-c4cc(Cl)c5ncccc5c4)cc3c2=O)cn1] |
| 1.706 | 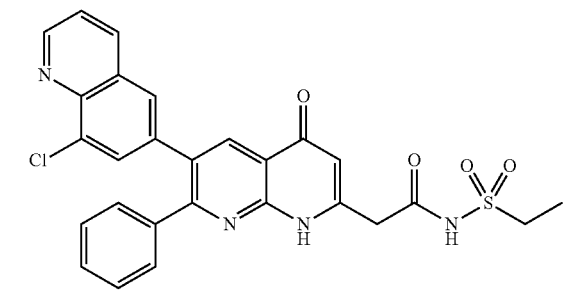 [SMILES: CCS(=O)(=O)NC(=O)Cc1cc(=O)c2cc(-c3cc(Cl)c4ncccc4c3)c(-c3ccccc3)nc2[nH]1] |
| 1.707 | 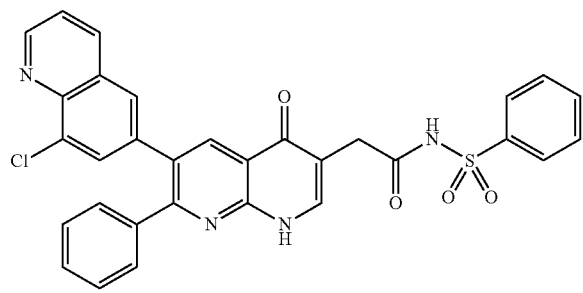 [SMILES: O=C(Cc1c[nH]c2nc(-c3ccccc3)c(-c3cc(Cl)c4ncccc4c3)cc2c1=O)NS(=O)(=O)c1ccccc1] |
| 1.708 | 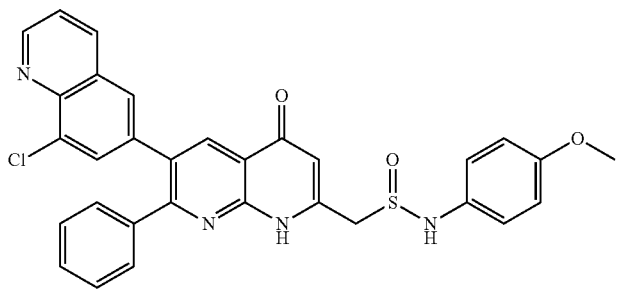 [SMILES: COc1ccc(NS(=O)Cc2cc(=O)c3cc(-c4cc(Cl)c5ncccc5c4)c(-c4ccccc4)nc3[nH]2)cc1] |

TABLE 1-continued
| Compound No. | Compound |
|---|---|
| 1.709 | 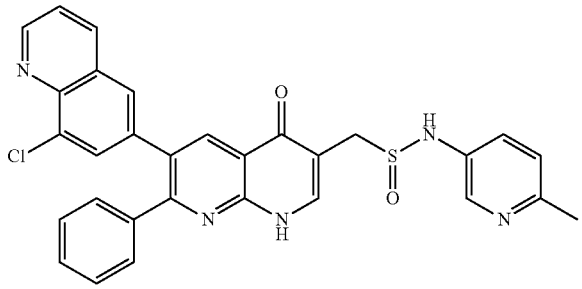 [SMILES: Cc1ccc(NS(=O)Cc2c[nH]c3nc(-c4ccccc4)c(-c4cc(Cl)c5ncccc5c4)cc3c2=O)cn1] |
| 1.710 | 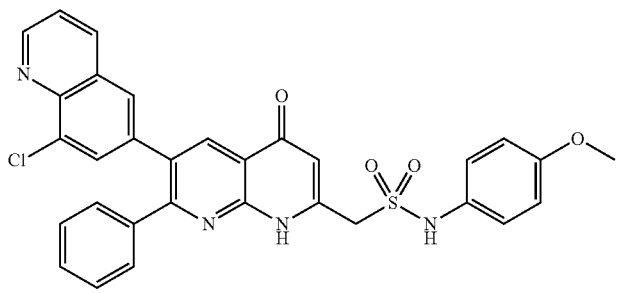 [SMILES: COc1ccc(NS(=O)(=O)Cc2cc(=O)c3cc(-c4cc(Cl)c5ncccc5c4)c(-c4ccccc4)nc3[nH]2)cc1] |
| 1.711 | 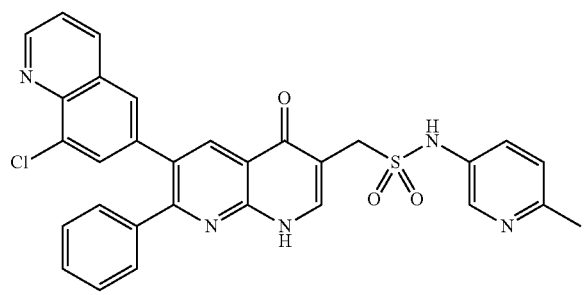 [SMILES: Cc1ccc(NS(=O)(=O)Cc2c[nH]c3nc(-c4ccccc4)c(-c4cc(Cl)c5ncccc5c4)cc3c2=O)cn1] |
| 1.712 | 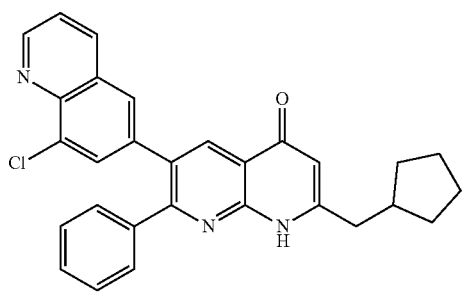 [SMILES: O=c1cc(CC2CCCC2)[nH]c2nc(-c3ccccc3)c(-c3cc(Cl)c4ncccc4c3)cc12] |
| 1.713 | 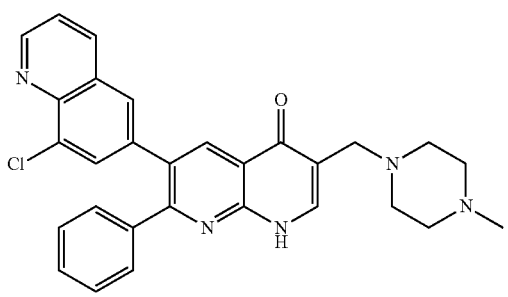 [SMILES: CN1CCN(Cc2c[nH]c3nc(-c4ccccc4)c(-c4cc(Cl)c5ncccc5c4)cc3c2=O)CC1] |

TABLE 1-continued
| Compound No. | Compound |
|---|---|
| 1.714 | 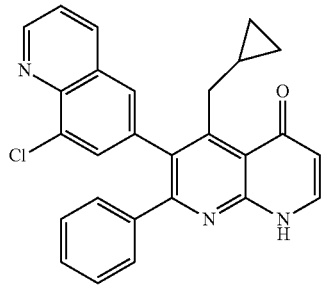 [SMILES: O=c1cc[nH]c2nc(-c3ccccc3)c(-c3cc(Cl)c4ncccc4c3)c(CC3CC3)c12] |
| 1.715 | 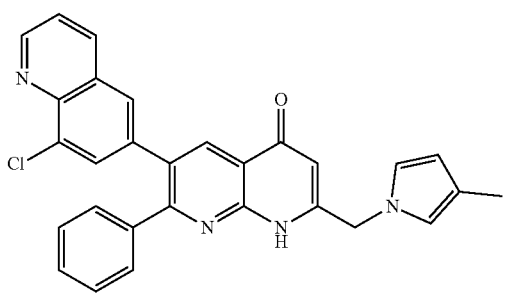 [SMILES: Cc1ccn(Cc2cc(=O)c3cc(-c4cc(Cl)c5ncccc5c4)c(-c4ccccc4)nc3[nH]2)c1] |
| 1.716 | 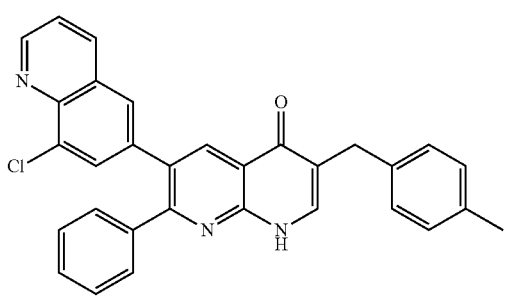 [SMILES: Cc1ccc(Cc2c[nH]c3nc(-c4ccccc4)c(-c4cc(Cl)c5ncccc5c4)cc3c2=O)cc1] |
| 1.717 | 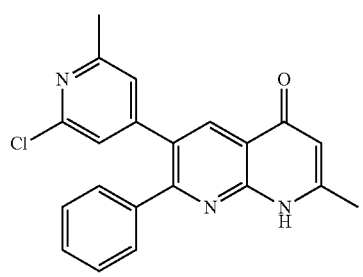 [SMILES: Cc1cc(-c2cc3c(=O)cc(C)[nH]c3nc2-c2ccccc2)cc(Cl)n1] |
| 1.718 | 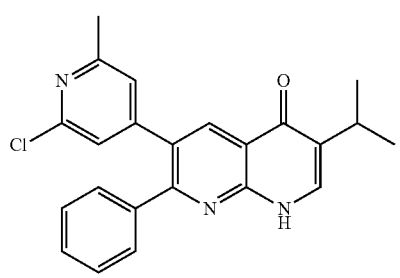 [SMILES: Cc1cc(-c2cc3c(=O)c(C(C)C)c[nH]c3nc2-c2ccccc2)cc(Cl)n1] |

TABLE 1-continued
| Compound No. | Compound |
|---|---|
| 1.719 | 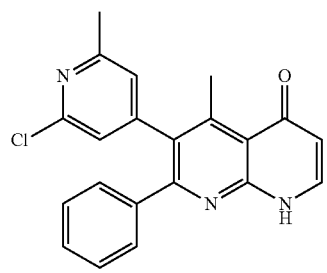 [SMILES: Cc1cc(-c2c(-c3ccccc3)nc3[nH]ccc(=O)c3c2C)cc(Cl)n1] |
| 1.720 | 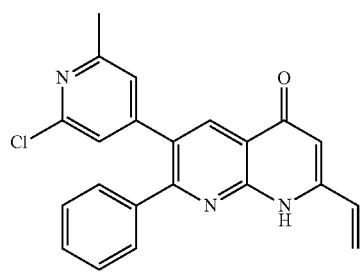 [SMILES: C=Cc1cc(=O)c2cc(-c3cc(C)nc(Cl)c3)c(-c3ccccc3)nc2[nH]1] |
| 1.721 | 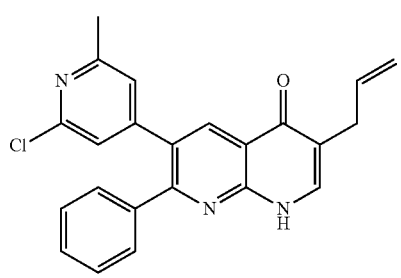 [SMILES: C=CCc1c[nH]c2nc(-c3ccccc3)c(-c3cc(C)nc(Cl)c3)cc2c1=O] |
| 1.722 | 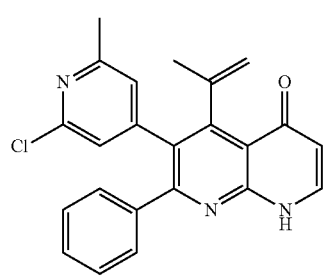 [SMILES: C=C(C)c1c(-c2cc(C)nc(Cl)c2)c(-c2ccccc2)nc2[nH]ccc(=O)c12] |
| 1.723 | 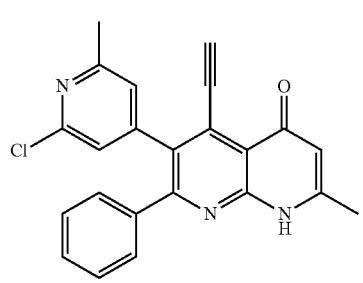 [SMILES: C#Cc1c(-c2cc(C)nc(Cl)c2)c(-c2ccccc2)nc2[nH]c(C)cc(=O)c12] |

TABLE 1-continued
| Compound No. | Compound |
|---|---|
| 1.724 | 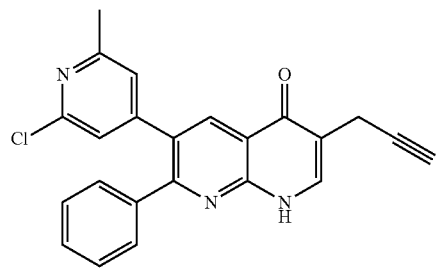 [SMILES: C#CCc1c[nH]c2nc(-c3ccccc3)c(-c3cc(C)nc(Cl)c3)cc2c1=O] |
| 1.725 | 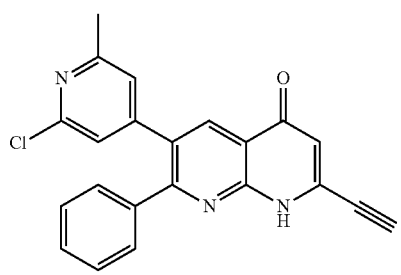 [SMILES: C#Cc1cc(=O)c2cc(-c3cc(C)nc(Cl)c3)c(-c3ccccc3)nc2[nH]1] |
| 1.726 | 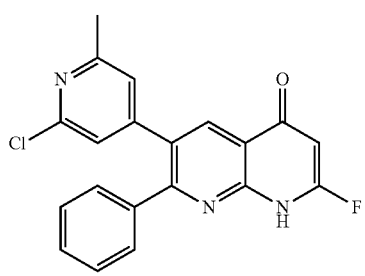 [SMILES: Cc1cc(-c2cc3c(=O)cc(F)[nH]c3nc2-c2ccccc2)cc(Cl)n1] |
| 1.727 | 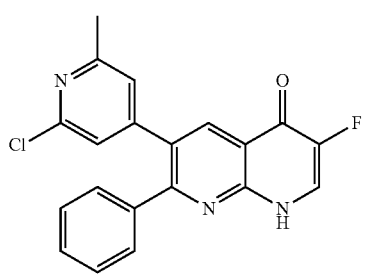 [SMILES: Cc1cc(-c2cc3c(=O)c(F)c[nH]c3nc2-c2ccccc2)cc(Cl)n1] |
| 1.728 | 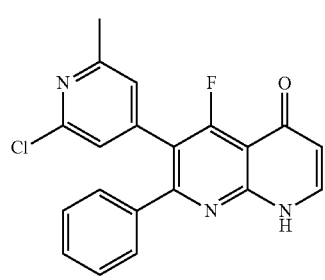 |

TABLE 1-continued
| Compound No. | Compound |
|---|---|
| 1.729 | 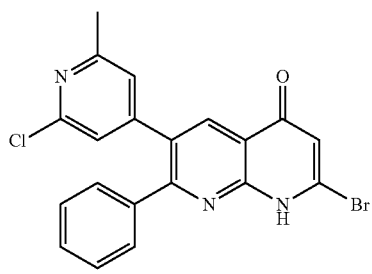 [SMILES: Cc1cc(-c2cc3c(=O)cc(Br)[nH]c3nc2-c2ccccc2)cc(Cl)n1] |
| 1.730 | 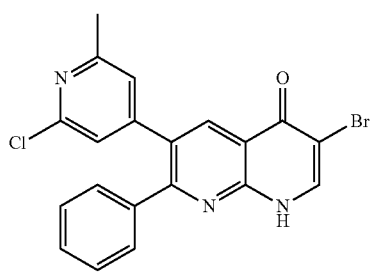 [SMILES: Cc1cc(-c2cc3c(=O)c(Br)c[nH]c3nc2-c2ccccc2)cc(Cl)n1] |
| 1.731 | 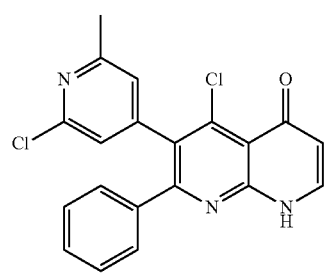 |
| 1.732 | 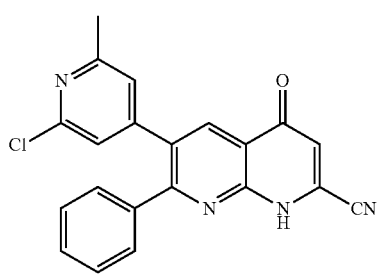 [SMILES: Cc1cc(-c2cc3c(=O)cc(C#N)[nH]c3nc2-c2ccccc2)cc(Cl)n1] |
| 1.733 | 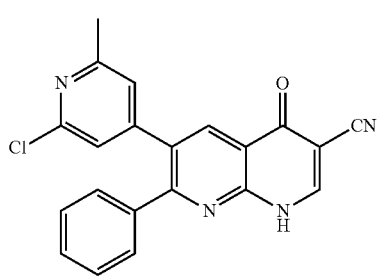 [SMILES: Cc1cc(-c2cc3c(=O)c(C#N)c[nH]c3nc2-c2ccccc2)cc(Cl)n1] |

TABLE 1-continued
| Compound No. | Compound |
|---|---|
| 1.734 | 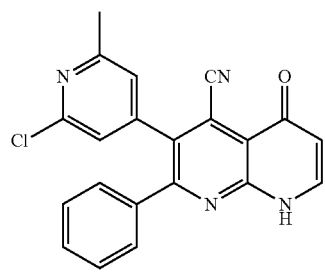 |
| 1.735 | 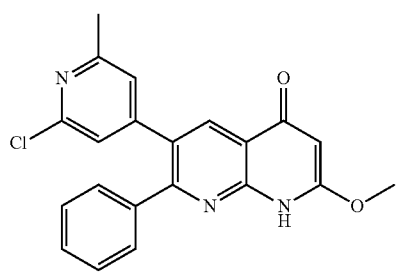 |
| 1.736 | 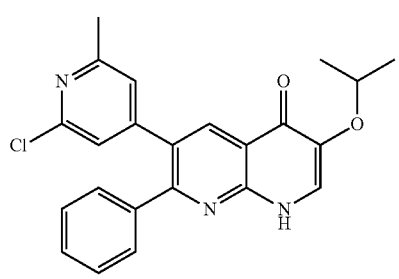 |
| 1.737 | 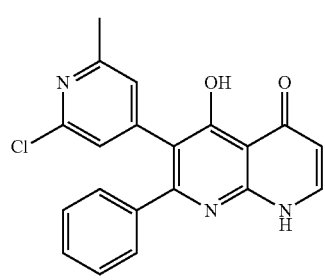 |
| 1.738 | 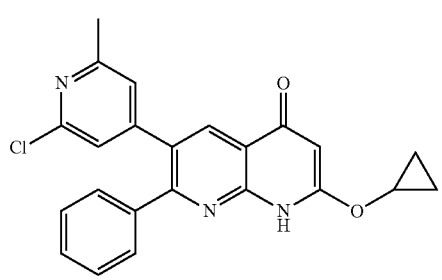 [SMILES: Cc1cc(-c2cc3c(=O)cc(OC4CC4)[nH]c3nc2-c2ccccc2)cc(Cl)n1] |

TABLE 1-continued
| Compound No. | Compound |
|---|---|
| 1.739 | 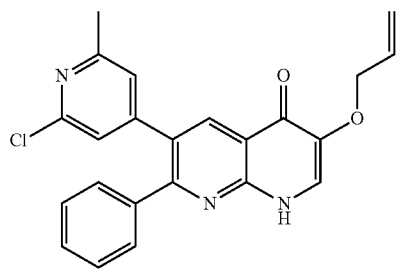 [SMILES: C=CCOc1c[nH]c2nc(-c3ccccc3)c(-c3cc(C)nc(Cl)c3)cc2c1=O] |
| 1.740 | 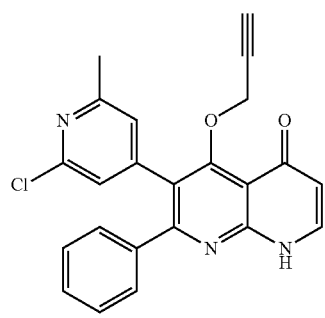 [SMILES: C#CCOc1c(-c2cc(C)nc(Cl)c2)c(-c2ccccc2)nc2[nH]ccc(=O)c12] |
| 1.741 | 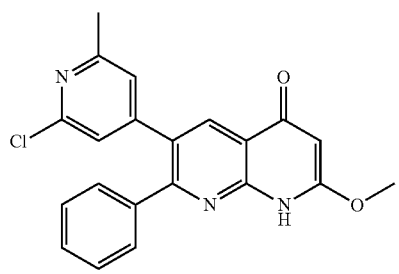 [SMILES: COc1cc(=O)c2cc(-c3cc(C)nc(Cl)c3)c(-c3ccccc3)nc2[nH]1] |
| 1.742 | 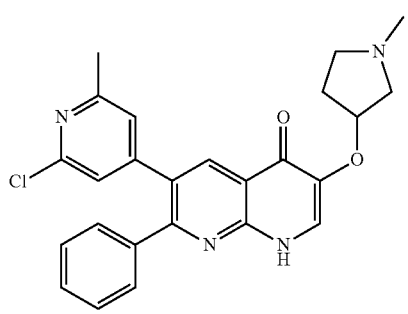 [SMILES: Cc1cc(-c2cc3c(=O)c(OC4CCN(C)C4)c[nH]c3nc2-c2ccccc2)cc(Cl)n1] |
| 1.743 | 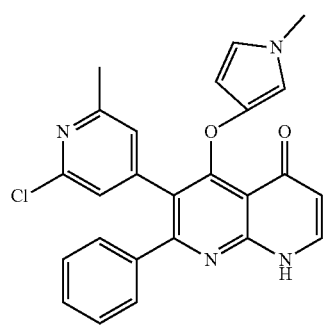 [SMILES: Cc1cc(-c2c(-c3ccccc3)nc3[nH]ccc(=O)c3c2Oc2ccn(C)c2)cc(Cl)n1] |

TABLE 1-continued
| Compound No. | Compound |
|---|---|
| 1.744 | 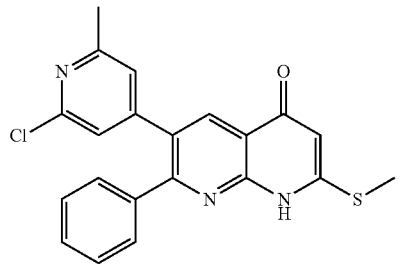 [SMILES: CSc1cc(=O)c2cc(-c3cc(C)nc(Cl)c3)c(-c3ccccc3)nc2[nH]1] |
| 1.745 | 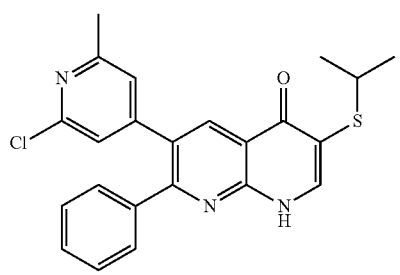 [SMILES: Cc1cc(-c2cc3c(=O)c(SC(C)C)c[nH]c3nc2-c2ccccc2)cc(Cl)n1] |
| 1.746 | 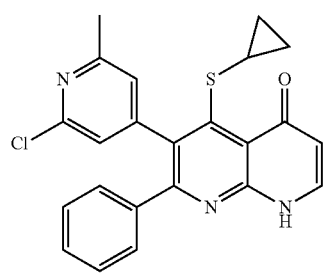 [SMILES: Cc1cc(-c2c(-c3ccccc3)nc3[nH]ccc(=O)c3c2SC2CC2)cc(Cl)n1] |
| 1.747 | 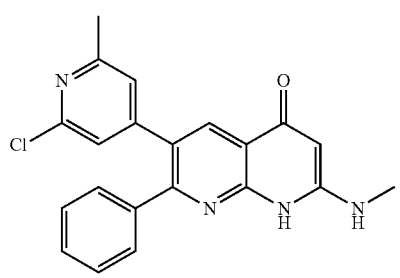 [SMILES: CNc1cc(=O)c2cc(-c3cc(C)nc(Cl)c3)c(-c3ccccc3)nc2[nH]1] |
| 1.748 | 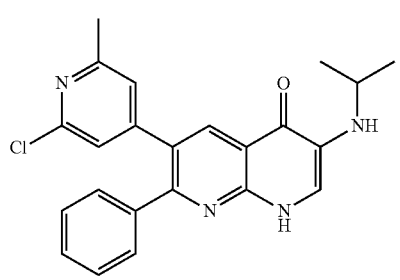 [SMILES: Cc1cc(-c2cc3c(=O)c(NC(C)C)c[nH]c3nc2-c2ccccc2)cc(Cl)n1] |

TABLE 1-continued
| Compound No. | Compound |
|---|---|
| 1.749 | 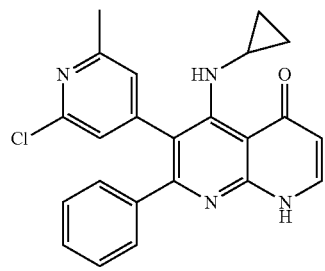 [SMILES: Cc1cc(-c2c(-c3ccccc3)nc3[nH]ccc(=O)c3c2NC2CC2)cc(Cl)n1] |
| 1.750 | 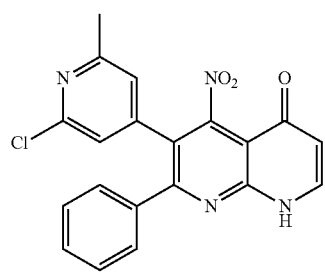 [SMILES: Cc1cc(-c2c(-c3ccccc3)nc3[nH]ccc(=O)c3c2[N+](=O)[O-])cc(Cl)n1] |
| 1.751 | 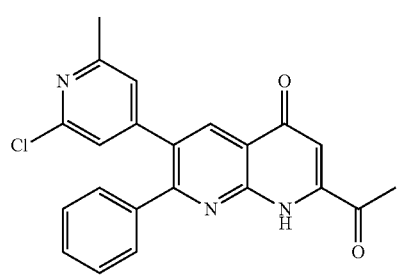 [SMILES: CC(=O)c1cc(=O)c2cc(-c3cc(C)nc(Cl)c3)c(-c3ccccc3)nc2[nH]1] |
| 1.752 | 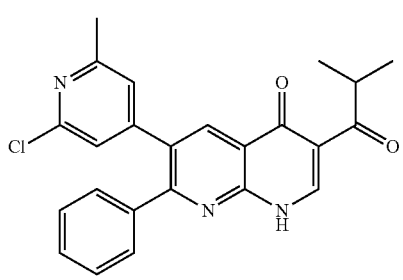 [SMILES: Cc1cc(-c2cc3c(=O)c(C(=O)C(C)C)c[nH]c3nc2-c2ccccc2)cc(Cl)n1] |
| 1.753 | 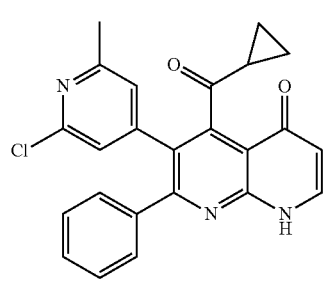 [SMILES: Cc1cc(-c2c(-c3ccccc3)nc3[nH]ccc(=O)c3c2C(=O)C2CC2)cc(Cl)n1] | ously
TABLE 1-continued
| Compound No. | Compound |
|---|---|
| 1.754 | 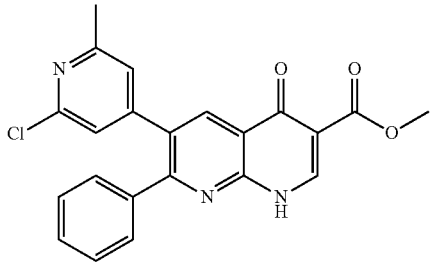 [SMILES: COC(=O)c1c[nH]c2nc(-c3ccccc3)c(-c3cc(C)nc(Cl)c3)cc2c1=O] |
| 1.755 | 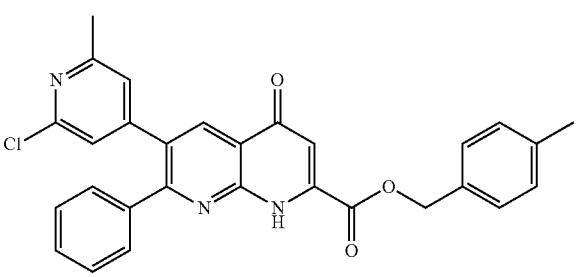 [SMILES: Cc1ccc(COC(=O)c2cc(=O)c3cc(-c4cc(C)nc(Cl)c4)c(-c4ccccc4)nc3[nH]2)cc1] |
| 1.756 | 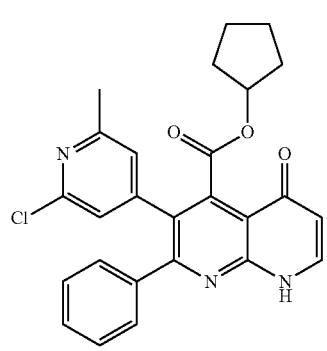 [SMILES: Cc1cc(-c2c(-c3ccccc3)nc3[nH]ccc(=O)c3c2C(=O)OC2CCCC2)cc(Cl)n1] |
| 1.757 | 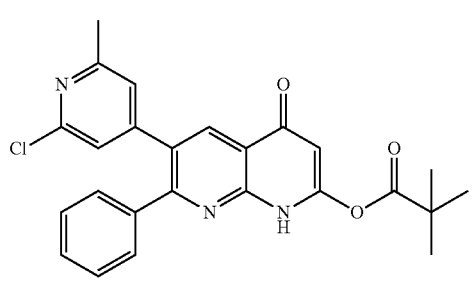 [SMILES: Cc1cc(-c2cc3c(=O)cc(OC(=O)C(C)(C)C)[nH]c3nc2-c2ccccc2)cc(Cl)n1] |
| 1.758 | 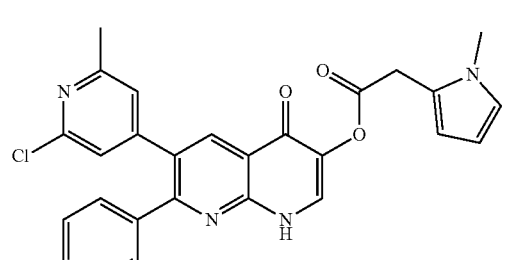 |

TABLE 1-continued
| Compound No. | Compound |
|---|---|
| 1.759 | 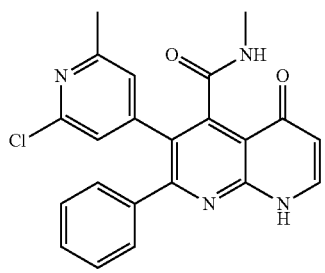 |
| 1.760 | 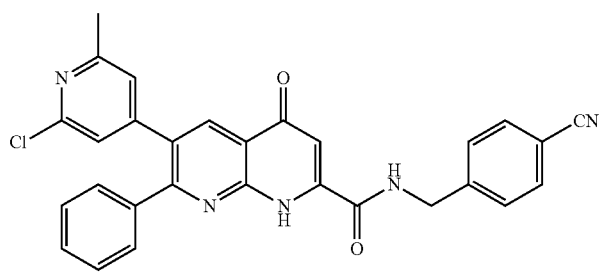 [SMILES: Cc1cc(-c2cc3c(=O)cc(C(=O)NCc4ccc(C#N)cc4)[nH]c3nc2-c2ccccc2)cc(Cl)n1] |
| 1.761 | 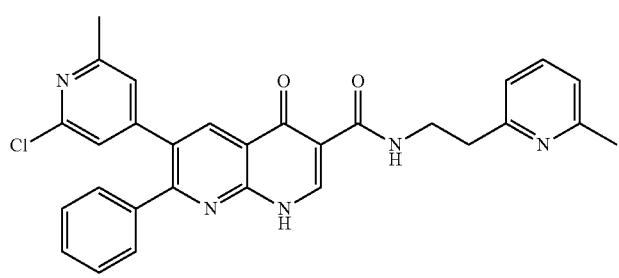 [SMILES: Cc1cc(-c2cc3c(=O)c(C(=O)NCCc4cccc(C)n4)c[nH]c3nc2-c2ccccc2)cc(Cl)n1] |
| 1.762 | 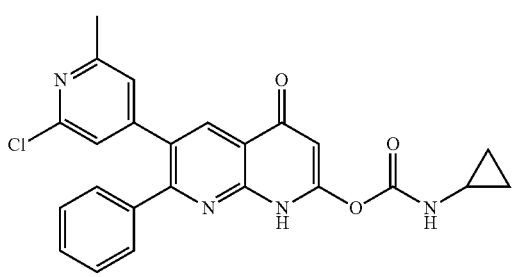 [SMILES: Cc1cc(-c2cc3c(=O)cc(OC(=O)NC4CC4)[nH]c3nc2-c2ccccc2)cc(Cl)n1] |
| 1.763 | 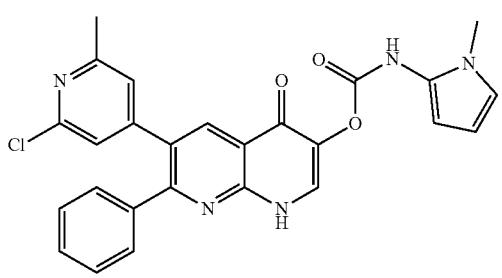 [SMILES: Cc1cc(-c2cc3c(=O)c(OC(=O)Nc4cccn4C)c[nH]c3nc2-c2ccccc2)cc(Cl)n1] |

TABLE 1-continued
| Compound No. | Compound |
|---|---|
| 1.764 | 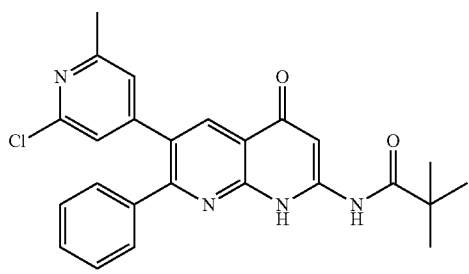 [SMILES: Cc1cc(-c2cc3c(=O)cc(NC(=O)C(C)(C)C)[nH]c3nc2-c2ccccc2)cc(Cl)n1] |
| 1.765 | 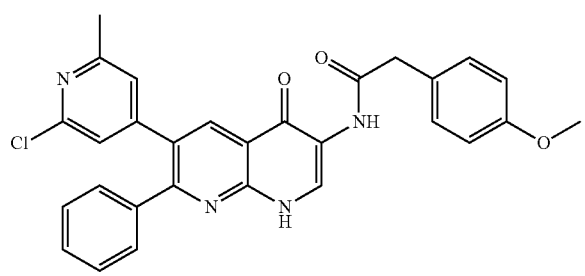 [SMILES: COc1ccc(CC(=O)Nc2c[nH]c3nc(-c4ccccc4)c(-c4cc(C)nc(Cl)c4)cc3c2=O)cc1] |
| 1.766 | 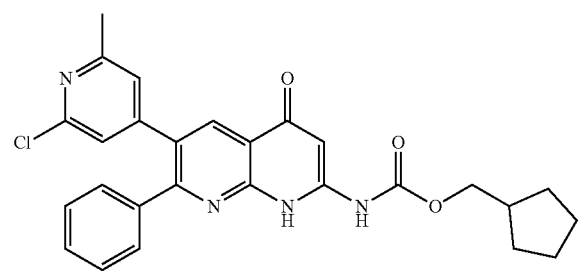 [SMILES: Cc1cc(-c2cc3c(=O)cc(NC(=O)OCC4CCCC4)[nH]c3nc2-c2ccccc2)cc(Cl)n1] |
| 1.767 | 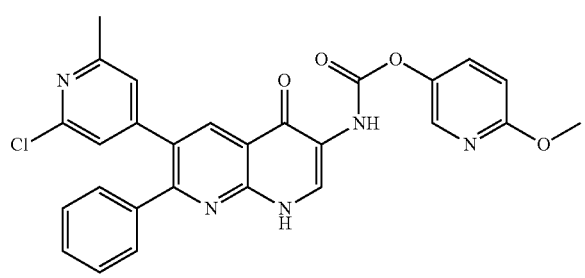 [SMILES: COc1ccc(OC(=O)Nc2c[nH]c3nc(-c4ccccc4)c(-c4cc(C)nc(Cl)c4)cc3c2=O)cn1] |
| 1.768 | 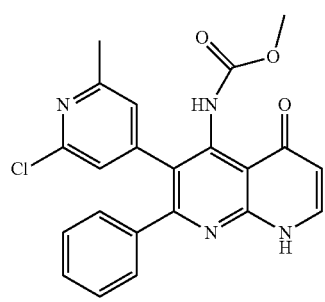 [SMILES: COC(=O)Nc1c(-c2cc(C)nc(Cl)c2)c(-c2ccccc2)nc2[nH]ccc(=O)c12] |

TABLE 1-continued
| Compound No. | Compound |
|---|---|
| 1.769 | 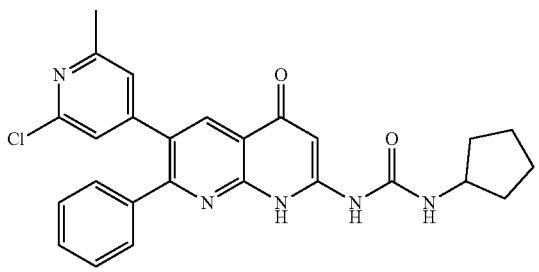 [SMILES: Cc1cc(-c2cc3c(=O)cc(NC(=O)NC4CCCC4)[nH]c3nc2-c2ccccc2)cc(Cl)n1] |
| 1.770 | 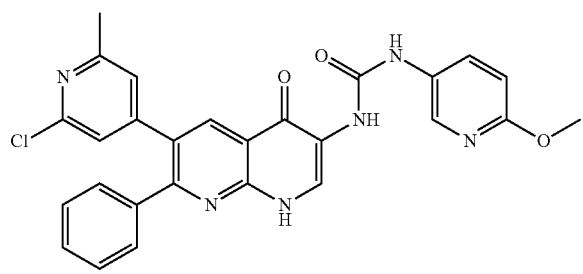 [SMILES: COc1ccc(NC(=O)Nc2c[nH]c3nc(-c4ccccc4)c(-c4cc(C)nc(Cl)c4)cc3c2=O)cn1] |
| 1.771 | 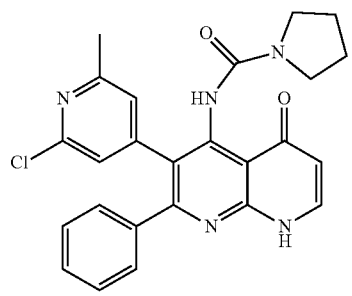 [SMILES: Cc1cc(-c2c(-c3ccccc3)nc3[nH]ccc(=O)c3c2NC(=O)N2CCCC2)cc(Cl)n1] |
| 1.772 | 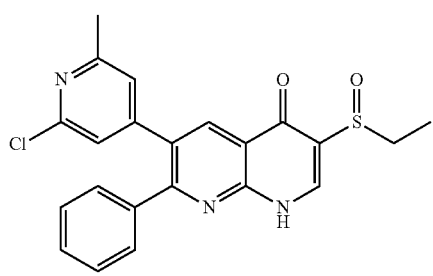 [SMILES: CCS(=O)c1c[nH]c2nc(-c3ccccc3)c(-c3cc(C)nc(Cl)c3)cc2c1=O] |
| 1.773 | 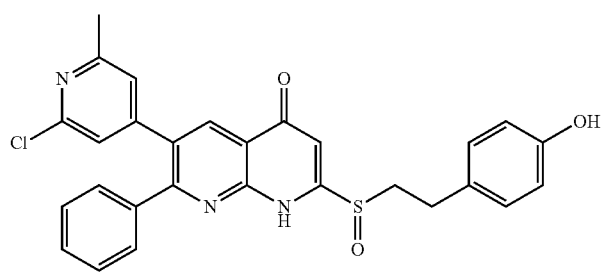 [SMILES: Cc1cc(-c2cc3c(=O)cc(S(=O)CCc4ccc(O)cc4)[nH]c3nc2-c2ccccc2)cc(Cl)n1] |

399
400
TABLE 1-continued
| Compound No. | Compound |
|---|---|
| 1.774 | 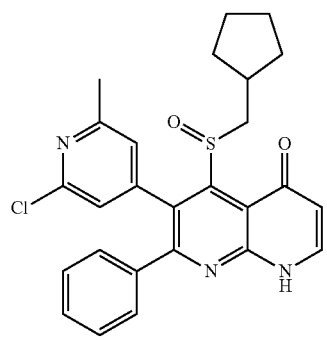 [SMILES: Cc1cc(-c2c(-c3ccccc3)nc3[nH]ccc(=O)c3c2S(=O)CC2CCCC2)cc(Cl)n1] |
| 1.775 | 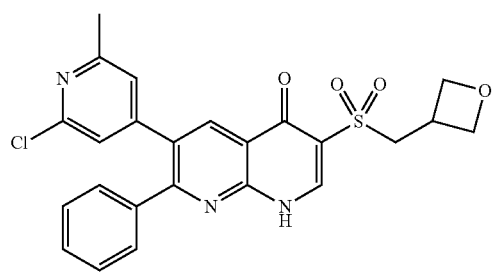 [SMILES: Cc1cc(-c2cc3c(=O)c(S(=O)(=O)CC4COC4)c[nH]c3nc2-c2ccccc2)cc(Cl)n1] |
| 1.776 | 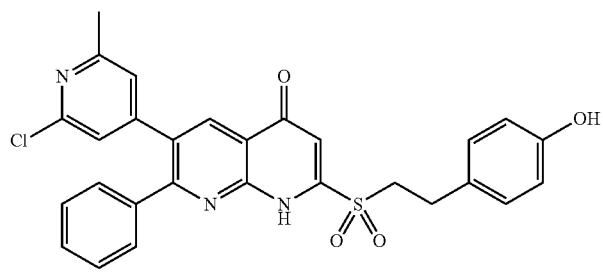 [SMILES: Cc1cc(-c2cc3c(=O)cc(S(=O)(=O)CCc4ccc(O)cc4)[nH]c3nc2-c2ccccc2)cc(Cl)n1] |
| 1.777 | 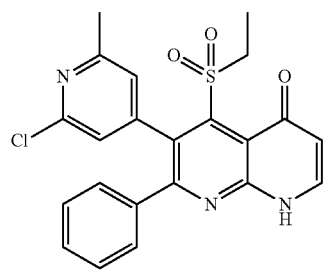 [SMILES: CCS(=O)(=O)c1c(-c2cc(C)nc(Cl)c2)c(-c2ccccc2)nc2[nH]ccc(=O)c12] |
| 1.778 | 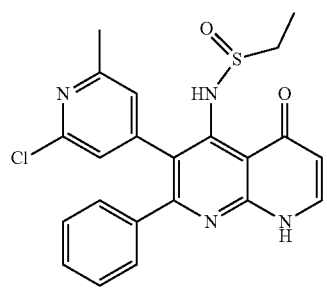 [SMILES: CCS(=O)Nc1c(-c2cc(C)nc(Cl)c2)c(-c2ccccc2)nc2[nH]ccc(=O)c12] |

TABLE 1-continued
| Compound No. | Compound |
|---|---|
| 1.779 | 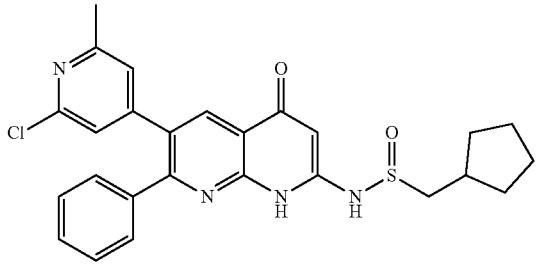 [SMILES: Cc1cc(-c2cc3c(=O)cc(NS(=O)CC4CCCC4)[nH]c3nc2-c2ccccc2)cc(Cl)n1] |
| 1.780 | 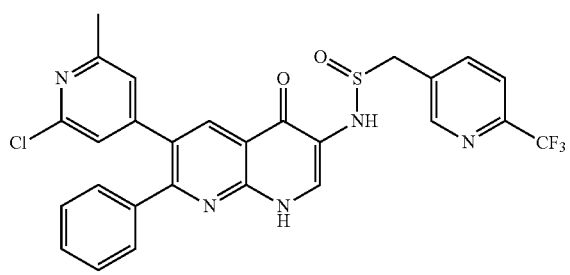 [SMILES: Cc1cc(-c2cc3c(=O)c(NS(=O)Cc4ccc(C(F)(F)F)nc4)c[nH]c3nc2-c2ccccc2)cc(Cl)n1] |
| 1.781 | 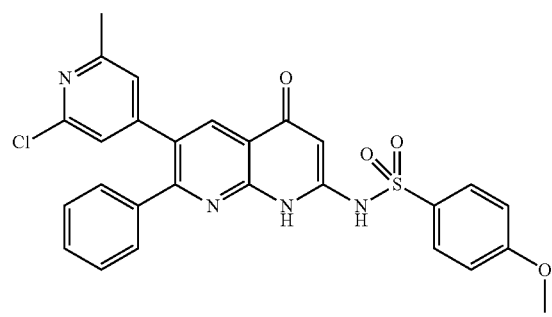 [SMILES: COc1ccc(S(=O)(=O)Nc2cc(=O)c3cc(-c4cc(C)nc(Cl)c4)c(-c4ccccc4)nc3[nH]2)cc1] |
| 1.782 | 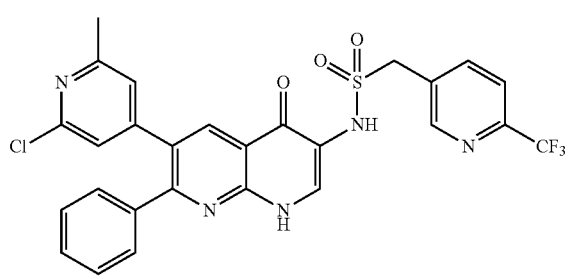 [SMILES: Cc1cc(-c2cc3c(=O)c(NS(=O)(=O)Cc4ccc(C(F)(F)F)nc4)c[nH]c3nc2-c2ccccc2)cc(Cl)n1] |
| 1.783 | 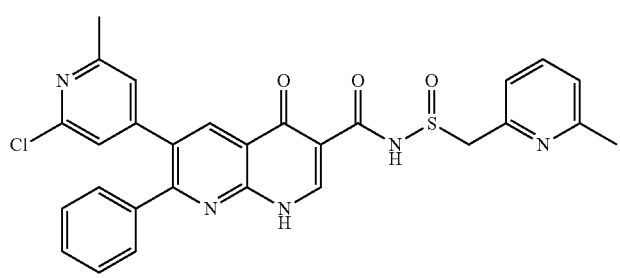 [SMILES: Cc1cc(-c2cc3c(=O)c(C(=O)NS(=O)Cc4cccc(C)n4)c[nH]c3nc2-c2ccccc2)cc(Cl)n1] |

TABLE 1-continued
| Compound No. | Compound |
|---|---|
| 1.784 | 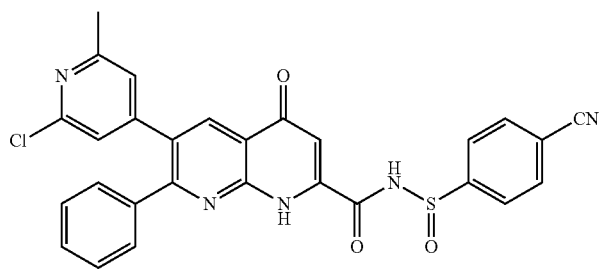 [SMILES: Cc1cc(-c2cc3c(=O)cc(C(=O)NS(=O)c4ccc(C#N)cc4)[nH]c3nc2-c2ccccc2)cc(Cl)n1] |
| 1.785 | 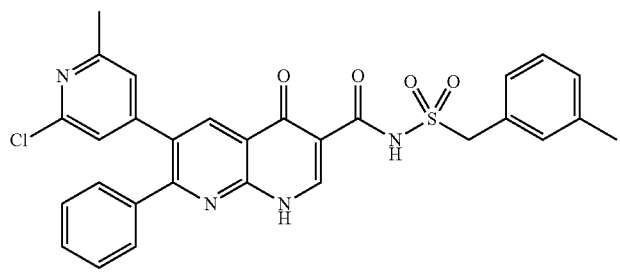 [SMILES: Cc1cccc(CS(=O)(=O)NC(=O)c2c[nH]c3nc(-c4ccccc4)c(-c4cc(C)nc(Cl)c4)cc3c2=O)c1] |
| 1.786 | 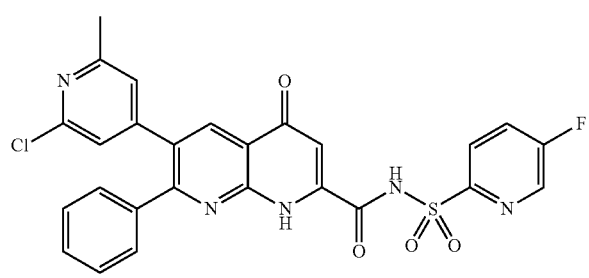 [SMILES: Cc1cc(-c2cc3c(=O)cc(C(=O)NS(=O)(=O)c4ccc(F)cn4)[nH]c3nc2-c2ccccc2)cc(Cl)n1] |
| 1.787 | 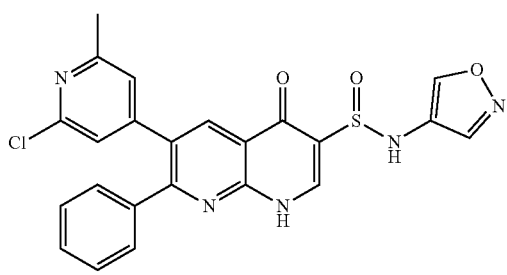 [SMILES: Cc1cc(-c2cc3c(=O)c(S(=O)Nc4cnoc4)c[nH]c3nc2-c2ccccc2)cc(Cl)n1] |
| 1.788 | 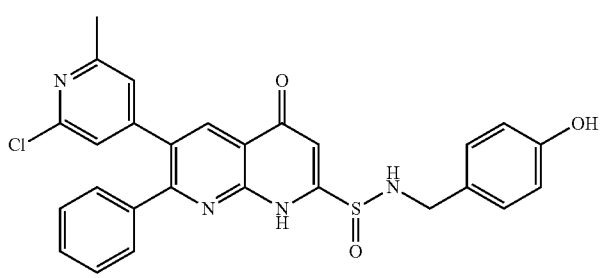 [SMILES: Cc1cc(-c2cc3c(=O)cc(S(=O)NCc4ccc(O)cc4)[nH]c3nc2-c2ccccc2)cc(Cl)n1] |

TABLE 1-continued
| Compound No. | Compound |
|---|---|
| 1.789 | 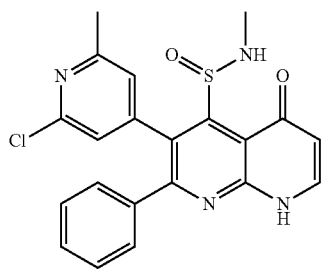 [SMILES: CNS(=O)c1c(-c2cc(C)nc(Cl)c2)c(-c2ccccc2)nc2[nH]ccc(=O)c12] |
| 1.790 | 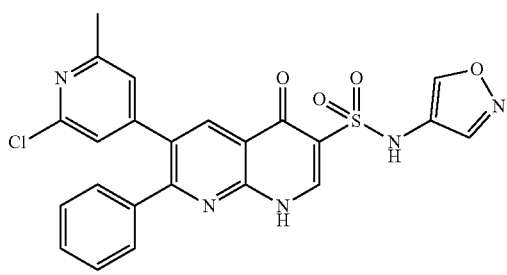 [SMILES: Cc1cc(-c2cc3c(=O)c(S(=O)(=O)Nc4cnoc4)c[nH]c3nc2-c2ccccc2)cc(Cl)n1] |
| 1.791 | 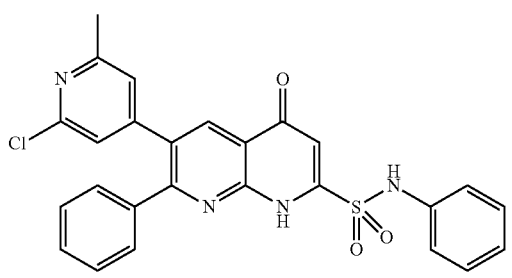 [SMILES: Cc1cc(-c2cc3c(=O)cc(S(=O)(=O)Nc4ccccc4)[nH]c3nc2-c2ccccc2)cc(Cl)n1] |
| 1.792 | 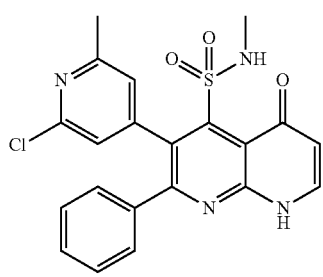 [SMILES: CNS(=O)(=O)c1c(-c2cc(C)nc(Cl)c2)c(-c2ccccc2)nc2[nH]ccc(=O)c12] |
| 1.793 | 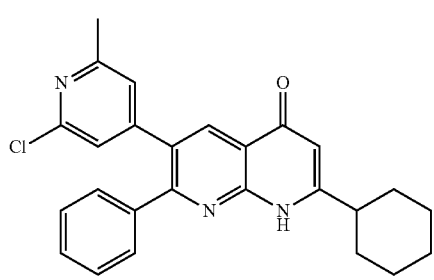 [SMILES: Cc1cc(-c2cc3c(=O)cc(C4CCCCC4)[nH]c3nc2-c2ccccc2)cc(Cl)n1] |

TABLE 1-continued
| Compound No. | Compound |
|---|---|
| 1.794 | 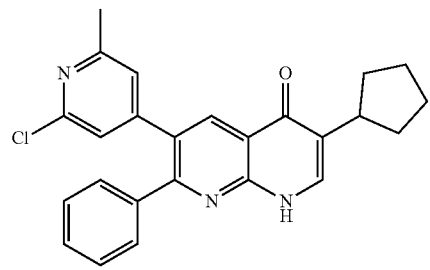 [SMILES: Cc1cc(-c2cc3c(=O)c(C4CCCC4)c[nH]c3nc2-c2ccccc2)cc(Cl)n1] |
| 1.795 | 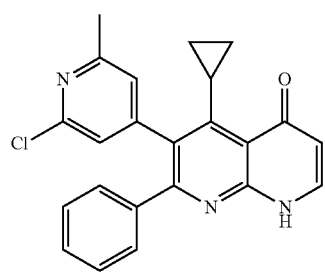 [SMILES: Cc1cc(-c2c(-c3ccccc3)nc3[nH]ccc(=O)c3c2C2CC2)cc(Cl)n1] |
| 1.796 | 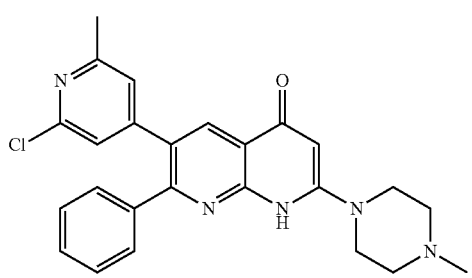 [SMILES: Cc1cc(-c2cc3c(=O)cc(N4CCN(C)CC4)[nH]c3nc2-c2ccccc2)cc(Cl)n1] |
| 1.797 | 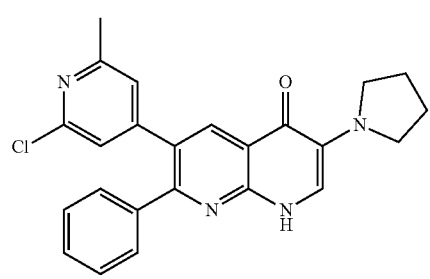 [SMILES: Cc1cc(-c2cc3c(=O)c(N4CCCC4)c[nH]c3nc2-c2ccccc2)cc(Cl)n1] |
| 1.798 | 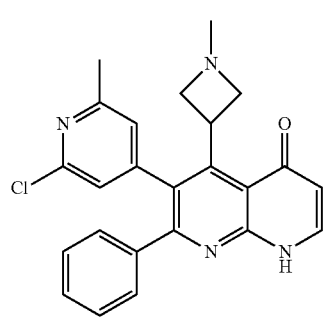 [SMILES: Cc1cc(-c2c(-c3ccccc3)nc3[nH]ccc(=O)c3c2C2CN(C)C2)cc(Cl)n1] |

TABLE 1-continued
| Compound No. | Compound |
|---|---|
| 1.799 | 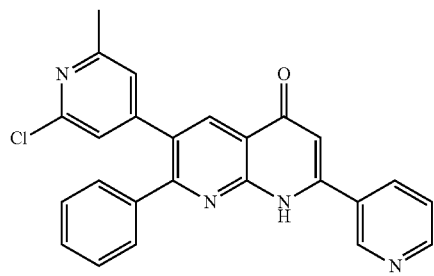 [SMILES: Cc1cc(-c2cc3c(=O)cc(-c4cccnc4)[nH]c3nc2-c2ccccc2)cc(Cl)n1] |
| 1.800 | 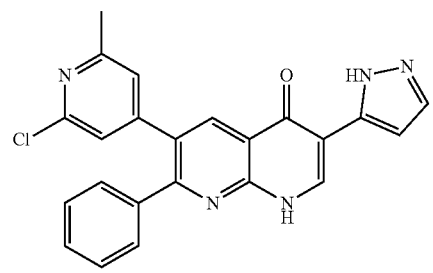 [SMILES: Cc1cc(-c2cc3c(=O)c(-c4ccn[nH]4)c[nH]c3nc2-c2ccccc2)cc(Cl)n1] |
| 1.801 | 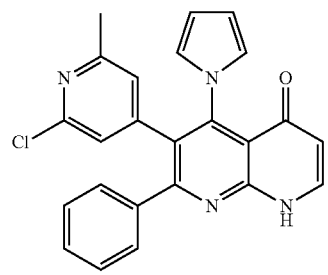 [SMILES: Cc1cc(-c2c(-c3ccccc3)nc3[nH]ccc(=O)c3c2-n2cccc2)cc(Cl)n1] |
| 1.802 | 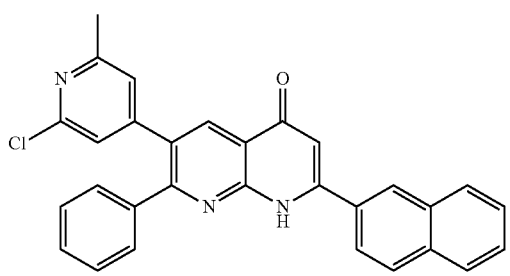 [SMILES: Cc1cc(-c2cc3c(=O)cc(-c4ccc5ccccc5c4)[nH]c3nc2-c2ccccc2)cc(Cl)n1] |
| 1.803 | 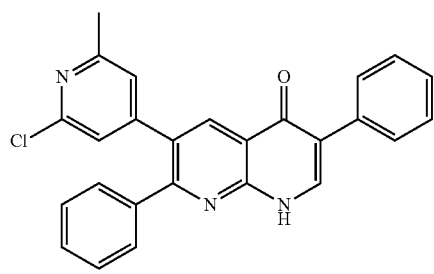 [SMILES: Cc1cc(-c2cc3c(=O)c(-c4ccccc4)c[nH]c3nc2-c2ccccc2)cc(Cl)n1] |

TABLE 1-continued
| Compound No. | Compound |
|---|---|
| 1.804 | 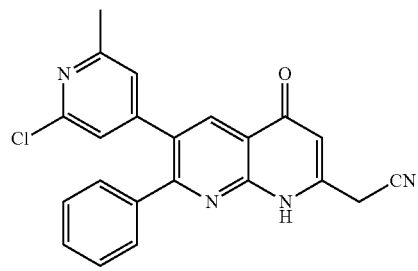 [SMILES: Cc1cc(-c2cc3c(=O)cc(CC#N)[nH]c3nc2-c2ccccc2)cc(Cl)n1] |
| 1.805 | 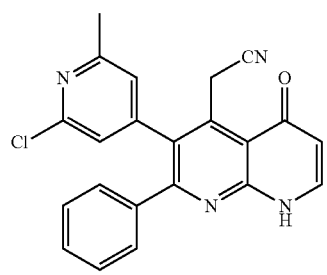 [SMILES: Cc1cc(-c2c(-c3ccccc3)nc3[nH]ccc(=O)c3c2CC#N)cc(Cl)n1] |
| 1.806 | 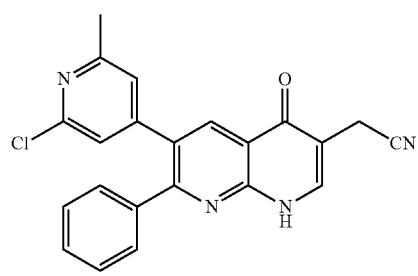 [SMILES: Cc1cc(-c2cc3c(=O)c(CC#N)c[nH]c3nc2-c2ccccc2)cc(Cl)n1] |
| 1.807 | 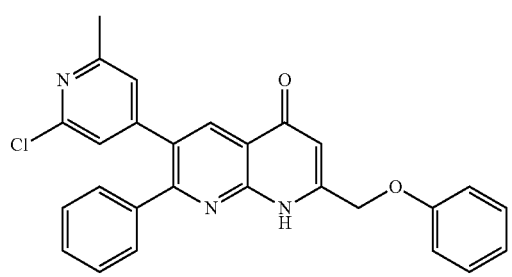 [SMILES: Cc1cc(-c2cc3c(=O)cc(COc4ccccc4)[nH]c3nc2-c2ccccc2)cc(Cl)n1] |
| 1.808 | 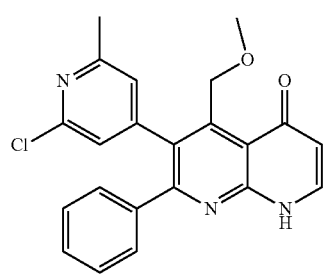 [SMILES: COCc1c(-c2cc(C)nc(Cl)c2)c(-c2ccccc2)nc2[nH]ccc(=O)c12] |

TABLE 1-continued
| Compound No. | Compound |
|---|---|
| 1.809 | 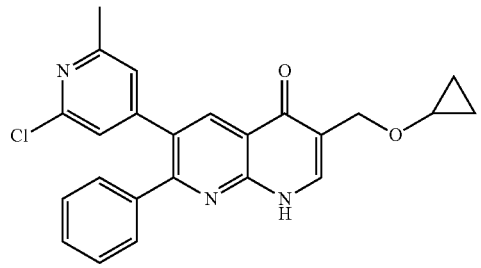 [SMILES: Cc1cc(-c2cc3c(=O)c(COC4CC4)c[nH]c3nc2-c2ccccc2)cc(Cl)n1] |
| 1.810 | 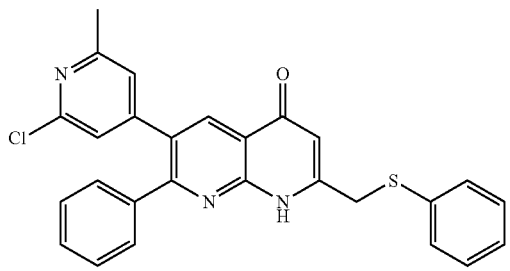 [SMILES: Cc1cc(-c2cc3c(=O)cc(CSc4ccccc4)[nH]c3nc2-c2ccccc2)cc(Cl)n1] |
| 1.811 | 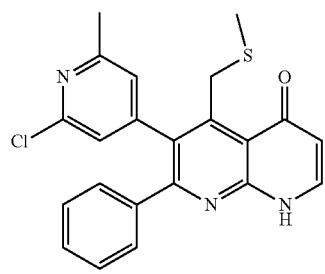 [SMILES: CSCc1c(-c2cc(C)nc(Cl)c2)c(-c2ccccc2)nc2[nH]ccc(=O)c12] |
| 1.812 | 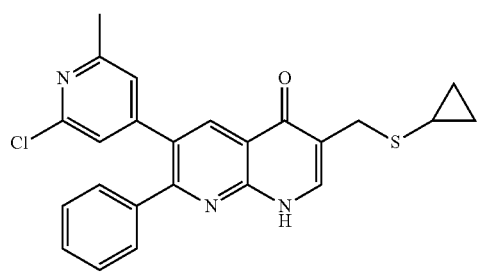 [SMILES: Cc1cc(-c2cc3c(=O)c(CSC4CC4)c[nH]c3nc2-c2ccccc2)cc(Cl)n1] |
| 1.813 | 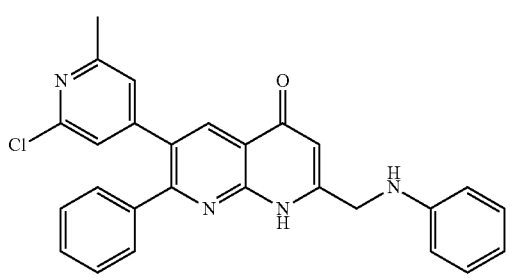 [SMILES: Cc1cc(-c2cc3c(=O)cc(CNc4ccccc4)[nH]c3nc2-c2ccccc2)cc(Cl)n1] |

TABLE 1-continued
| Compound No. | Compound |
|---|---|
| 1.814 | 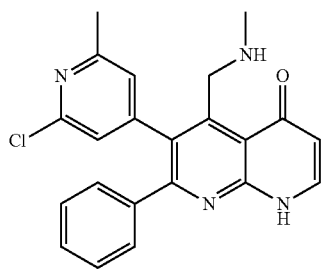 [SMILES: CNCc1c(-c2cc(C)nc(Cl)c2)c(-c2ccccc2)nc2[nH]ccc(=O)c12] |
| 1.815 | 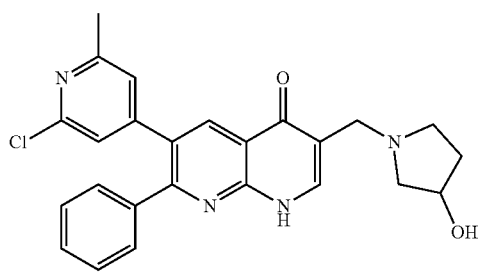 [SMILES: Cc1cc(-c2cc3c(=O)c(CN4CCC(O)C4)c[nH]c3nc2-c2ccccc2)cc(Cl)n1] |
| 1.816 | 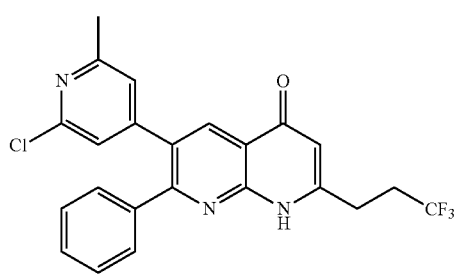 [SMILES: Cc1cc(-c2cc3c(=O)cc(CCC(F)(F)F)[nH]c3nc2-c2ccccc2)cc(Cl)n1] |
| 1.817 | 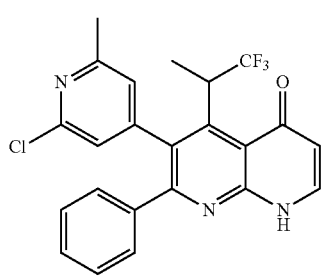 [SMILES: Cc1cc(-c2c(-c3ccccc3)nc3[nH]ccc(=O)c3c2C(C)C(F)(F)F)cc(Cl)n1] |
| 1.818 | 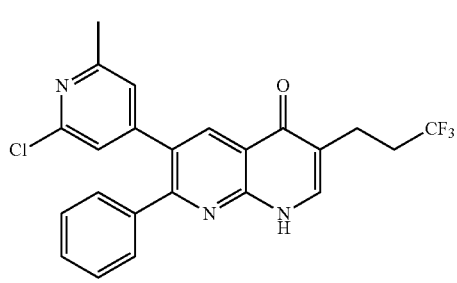 [SMILES: Cc1cc(-c2cc3c(=O)c(CCC(F)(F)F)c[nH]c3nc2-c2ccccc2)cc(Cl)n1] |

TABLE 1-continued
| Compound No. | Compound |
|---|---|
| 1.819 | 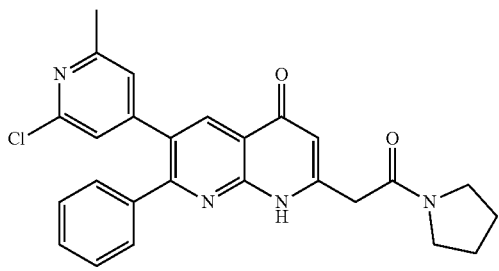 [SMILES: Cc1cc(-c2cc3c(=O)cc(CC(=O)N4CCCC4)[nH]c3nc2-c2ccccc2)cc(Cl)n1] |
| 1.820 | 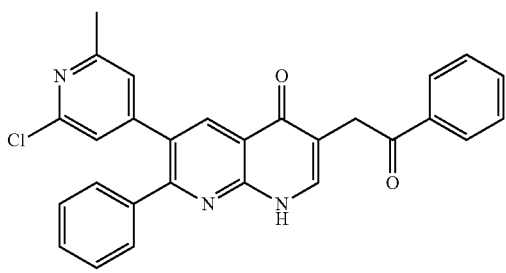 [SMILES: Cc1cc(-c2cc3c(=O)c(CC(=O)c4ccccc4)c[nH]c3nc2-c2ccccc2)cc(Cl)n1] |
| 1.821 | 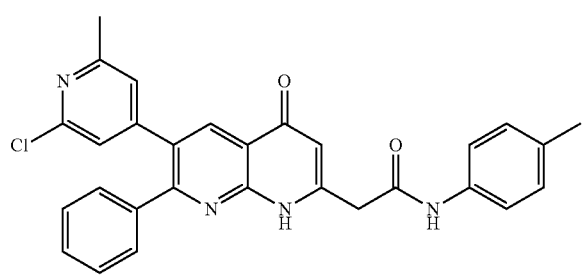 [SMILES: Cc1ccc(NC(=O)Cc2cc(=O)c3cc(-c4cc(C)nc(Cl)c4)c(-c4ccccc4)nc3[nH]2)cc1] |
| 1.822 | 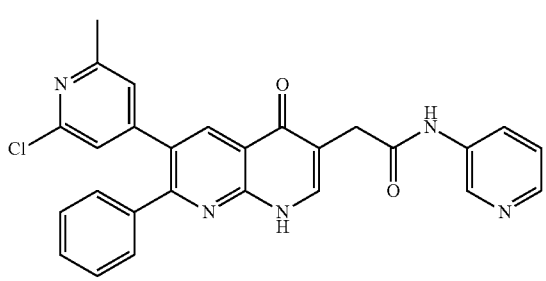 [SMILES: Cc1cc(-c2cc3c(=O)c(CC(=O)Nc4cccnc4)c[nH]c3nc2-c2ccccc2)cc(Cl)n1] |
| 1.823 | 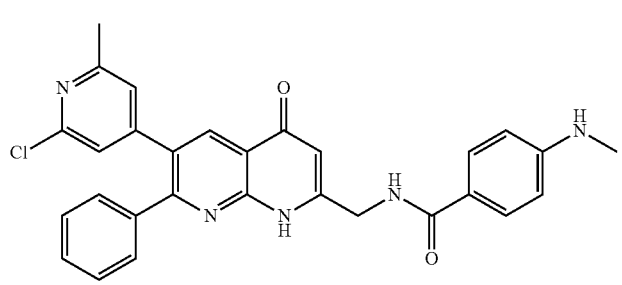 [SMILES: CNc1ccc(C(=O)NCc2cc(=O)c3cc(-c4cc(C)nc(Cl)c4)c(-c4ccccc4)nc3[nH]2)cc1] |

TABLE 1-continued
| Compound No. | Compound |
|---|---|
| 1.824 | 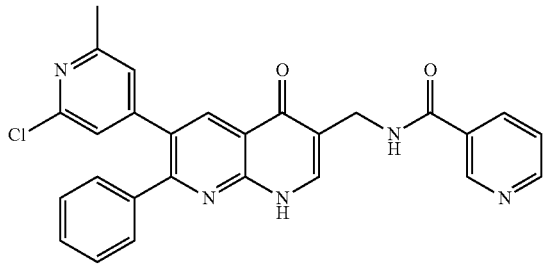 [SMILES: Cc1cc(-c2cc3c(=O)c(CNC(=O)c4cccnc4)c[nH]c3nc2-c2ccccc2)cc(Cl)n1] |
| 1.825 | 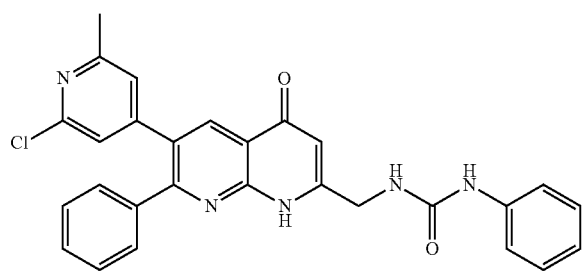 [SMILES: Cc1cc(-c2cc3c(=O)cc(CNC(=O)Nc4ccccc4)[nH]c3nc2-c2ccccc2)cc(Cl)n1] |
| 1.826 | 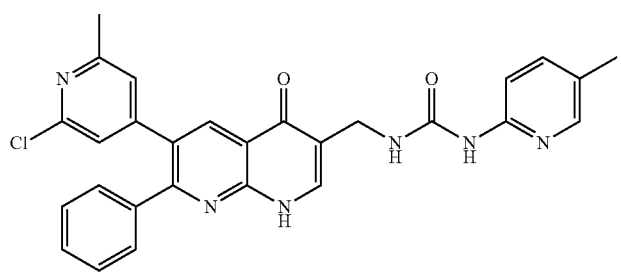 [SMILES: Cc1ccc(NC(=O)NCc2c[nH]c3nc(-c4ccccc4)c(-c4cc(C)nc(Cl)c4)cc3c2=O)nc1] |
| 1.827 | 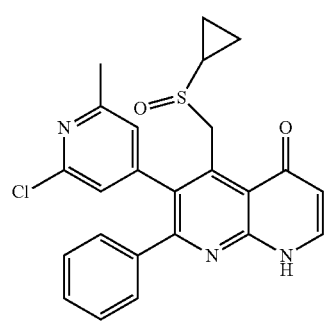 [SMILES: Cc1cc(-c2c(-c3ccccc3)nc3[nH]ccc(=O)c3c2CS(=O)C2CC2)cc(Cl)n1] |
| 1.828 | 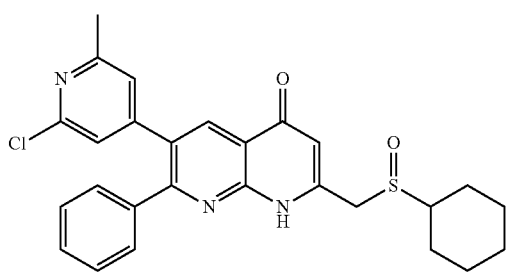 [SMILES: Cc1cc(-c2cc3c(=O)cc(CS(=O)C4CCCCC4)[nH]c3nc2-c2ccccc2)cc(Cl)n1] |

TABLE 1-continued
| Compound No. | Compound |
|---|---|
| 1.829 | 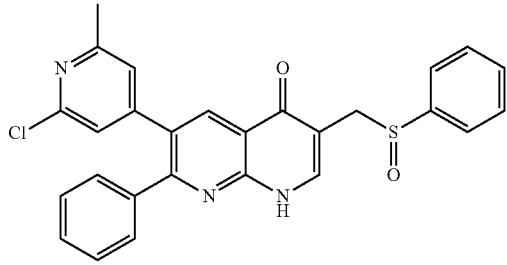 [SMILES: Cc1cc(-c2cc3c(=O)c(CS(=O)c4ccccc4)c[nH]c3nc2-c2ccccc2)cc(Cl)n1] |
| 1.830 | 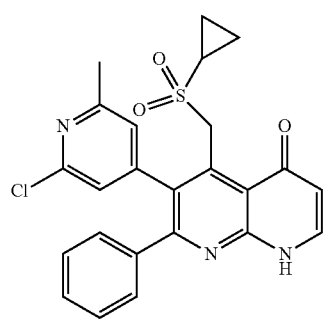 [SMILES: Cc1cc(-c2c(-c3ccccc3)nc3[nH]ccc(=O)c3c2CS(=O)(=O)C2CC2)cc(Cl)n1] |
| 1.831 | 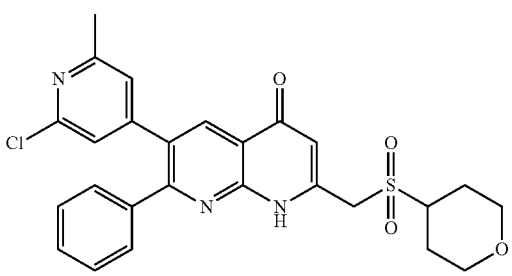 [SMILES: Cc1cc(-c2cc3c(=O)cc(CS(=O)(=O)C4CCOCC4)[nH]c3nc2-c2ccccc2)cc(Cl)n1] |
| 1.832 | 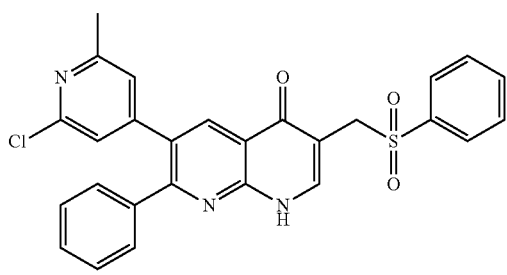 [SMILES: Cc1cc(-c2cc3c(=O)c(CS(=O)(=O)c4ccccc4)c[nH]c3nc2-c2ccccc2)cc(Cl)n1] |
| 1.833 | 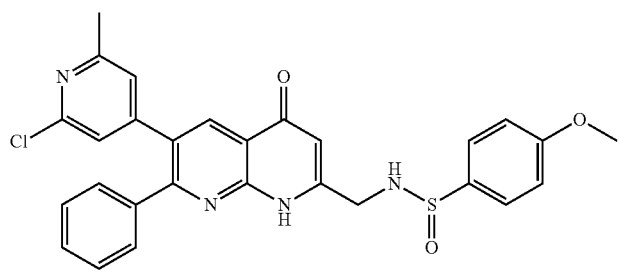 [SMILES: COc1ccc(S(=O)NCc2cc(=O)c3cc(-c4cc(C)nc(Cl)c4)c(-c4ccccc4)nc3[nH]2)cc1] |

TABLE 1-continued
| Compound No. | Compound |
|---|---|
| 1.834 | 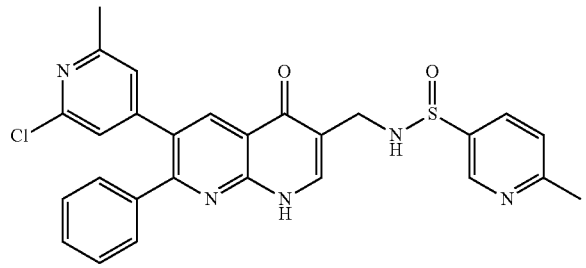 [SMILES: Cc1ccc(S(=O)NCc2c[nH]c3nc(-c4ccccc4)c(-c4cc(C)nc(Cl)c4)cc3c2=O)cn1] |
| 1.835 | 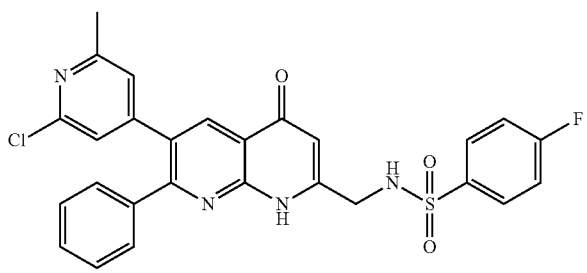 [SMILES: Cc1cc(-c2cc3c(=O)cc(CNS(=O)(=O)c4ccc(F)cc4)[nH]c3nc2-c2ccccc2)cc(Cl)n1] |
| 1.836 | 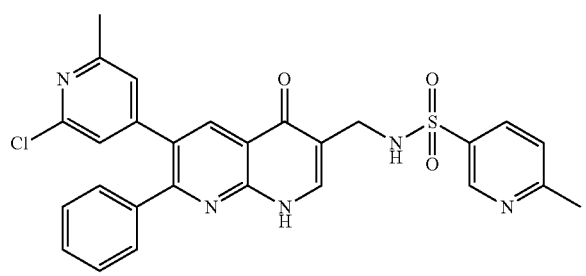 [SMILES: Cc1ccc(S(=O)(=O)NCc2c[nH]c3nc(-c4ccccc4)c(-c4cc(C)nc(Cl)c4)cc3c2=O)cn1] |
| 1.837 | 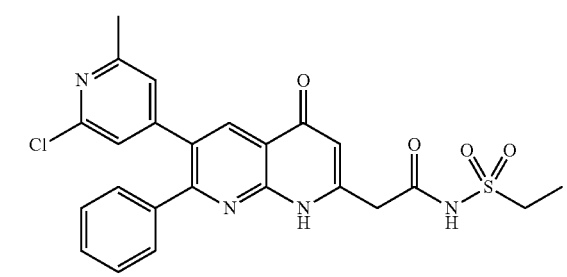 [SMILES: CCS(=O)(=O)NC(=O)Cc1cc(=O)c2cc(-c3cc(C)nc(Cl)c3)c(-c3ccccc3)nc2[nH]1] |
| 1.838 | 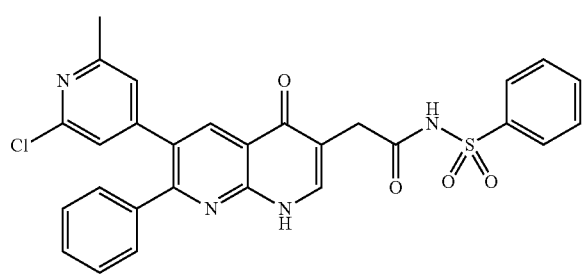 [SMILES: Cc1cc(-c2cc3c(=O)c(CC(=O)NS(=O)(=O)c4ccccc4)c[nH]c3nc2-c2ccccc2)cc(Cl)n1] |

TABLE 1-continued

| Compound No. | Compound |
|---|---|
| 1.839 | |
| 1.840 | |
| 1.841 | |
| 1.842 | |
| 1.843 | |

TABLE 1-continued

| Compound No. | Compound |
|---|---|
| 1.844 | |
| 1.845 | |
| 1.846 | |
| 1.847 | |
| 1.848 | |

TABLE 1-continued
| Compound No. | Compound |
|---|---|
| 1.849 | 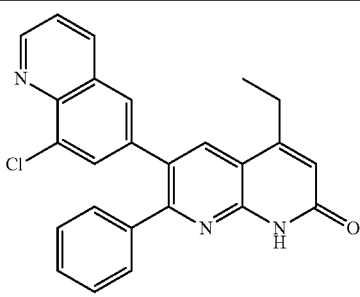 |
| 1.850 | 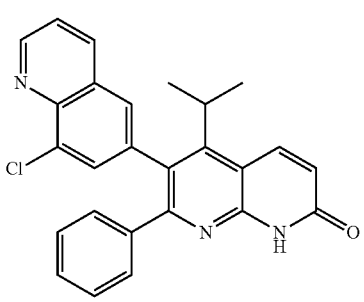 [SMILES: CC(C)c1c(-c2cc(Cl)c3ncccc3c2)c(-c2ccccc2)nc2[nH]c(=O)ccc12] |
| 1.851 | 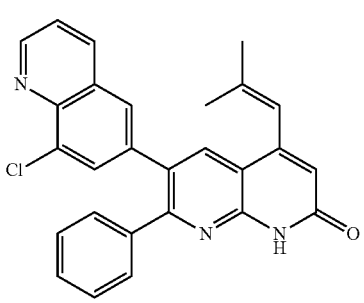 [SMILES: CC(C)=Cc1cc(=O)[nH]c2nc(-c3ccccc3)c(-c3cc(Cl)c4ncccc4c3)cc12] |
| 1.852 | 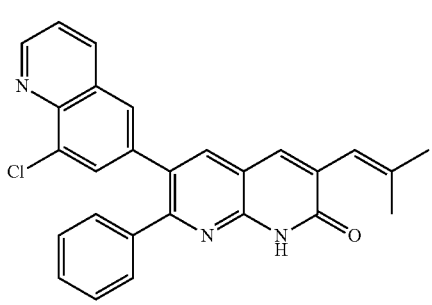 [SMILES: CC(C)=Cc1cc2cc(-c3cc(Cl)c4ncccc4c3)c(-c3ccccc3)nc2[nH]c1=O] |
| 1.853 | 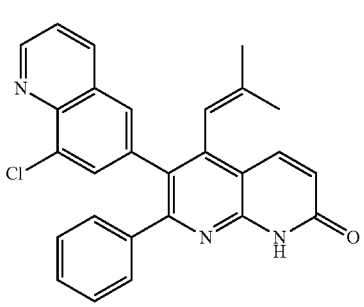 [SMILES: CC(C)=Cc1c(-c2cc(Cl)c3ncccc3c2)c(-c2ccccc2)nc2[nH]c(=O)ccc12] |

TABLE 1-continued
| Compound No. | Compound |
|---|---|
| 1.854 | 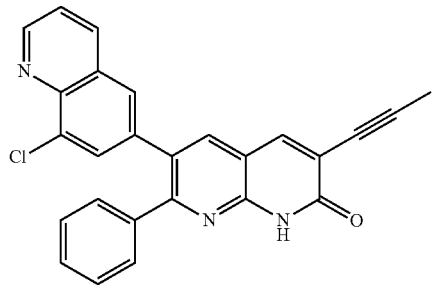 [SMILES: CC#Cc1cc2cc(-c3cc(Cl)c4ncccc4c3)c(-c3ccccc3)nc2[nH]c1=O] |
| 1.855 | 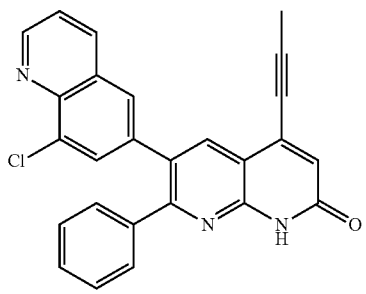 [SMILES: CC#Cc1cc(=O)[nH]c2nc(-c3ccccc3)c(-c3cc(Cl)c4ncccc4c3)cc12] |
| 1.856 | 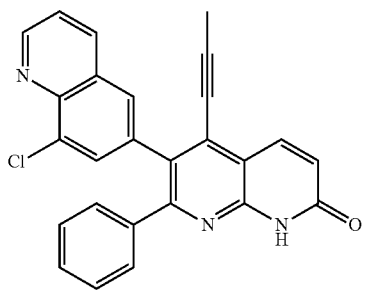 [SMILES: CC#Cc1c(-c2cc(Cl)c3ncccc3c2)c(-c2ccccc2)nc2[nH]c(=O)ccc12] |
| 1.857 | 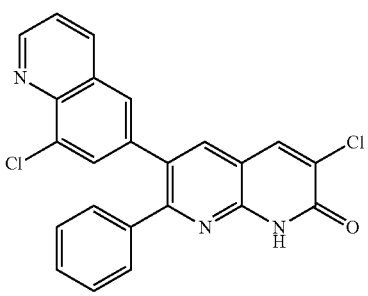 [SMILES: O=c1[nH]c2nc(-c3ccccc3)c(-c3cc(Cl)c4ncccc4c3)cc2cc1Cl] |
| 1.858 | 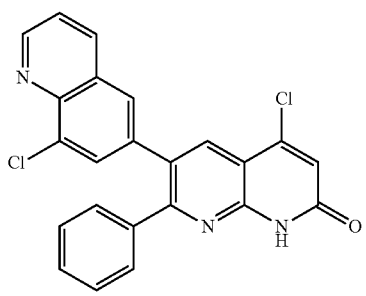 [SMILES: O=c1cc(Cl)c2cc(-c3cc(Cl)c4ncccc4c3)c(-c3ccccc3)nc2[nH]1] |

TABLE 1-continued
| Compound No. | Compound |
|---|---|
| 1.859 | 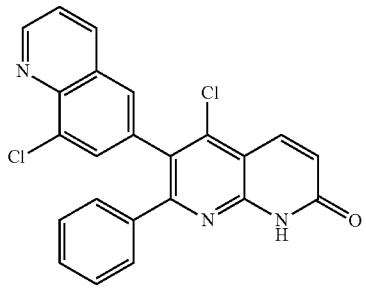 [SMILES: O=c1ccc2c(Cl)c(-c3cc(Cl)c4ncccc4c3)c(-c3ccccc3)nc2[nH]1] |
| 1.860 | 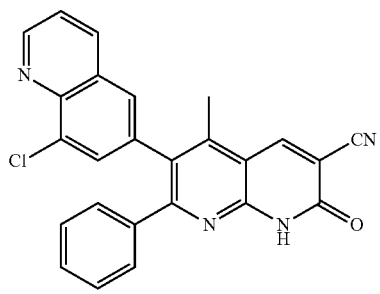 [SMILES: Cc1c(-c2cc(Cl)c3ncccc3c2)c(-c2ccccc2)nc2[nH]c(=O)c(C#N)cc12] |
| 1.861 | 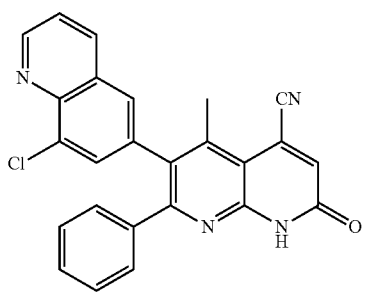 [SMILES: Cc1c(-c2cc(Cl)c3ncccc3c2)c(-c2ccccc2)nc2[nH]c(=O)cc(C#N)c12] |
| 1.862 | 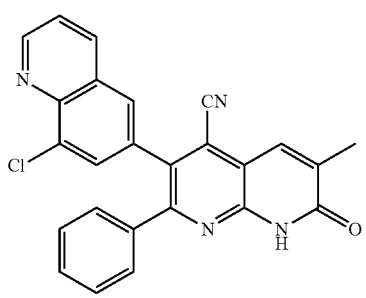 [SMILES: Cc1cc2c(C#N)c(-c3cc(Cl)c4ncccc4c3)c(-c3ccccc3)nc2[nH]c1=O] |
| 1.863 | 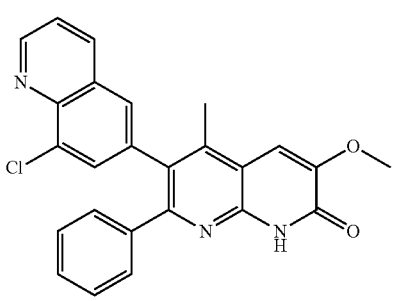 [SMILES: COc1cc2c(C)c(-c3cc(Cl)c4ncccc4c3)c(-c3ccccc3)nc2[nH]c1=O] |

TABLE 1-continued
| Compound No. | Compound |
|---|---|
| 1.864 | 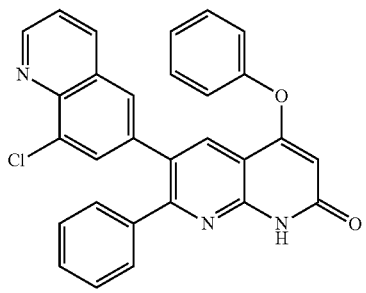 [SMILES: O=c1cc(Oc2ccccc2)c2cc(-c3cc(Cl)c4ncccc4c3)c(-c3ccccc3)nc2[nH]1] |
| 1.865 | 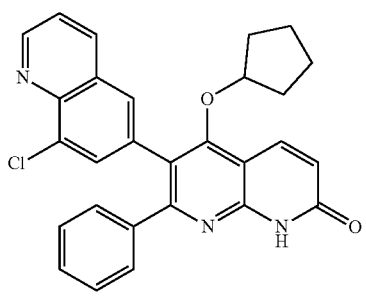 [SMILES: O=c1ccc2c(OC3CCCC3)c(-c3cc(Cl)c4ncccc4c3)c(-c3ccccc3)nc2[nH]1] |
| 1.866 | 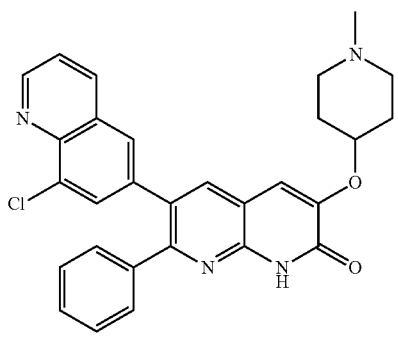 [SMILES: CN1CCC(Oc2cc3cc(-c4cc(Cl)c5ncccc5c4)c(-c4ccccc4)nc3[nH]c2=O)CC1] |
| 1.867 | 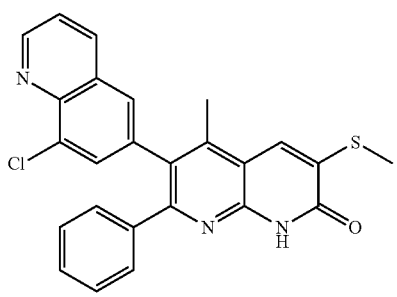 [SMILES: CSc1cc2c(C)c(-c3cc(Cl)c4ncccc4c3)c(-c3ccccc3)nc2[nH]c1=O] |
| 1.868 | 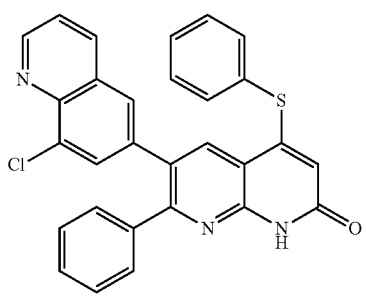 [SMILES: O=c1cc(Sc2ccccc2)c2cc(-c3cc(Cl)c4ncccc4c3)c(-c3ccccc3)nc2[nH]1] |

US 10,793,561 B2
TABLE 1-continued
| Compound No. | Compound |
|---|---|
| 1.869 | 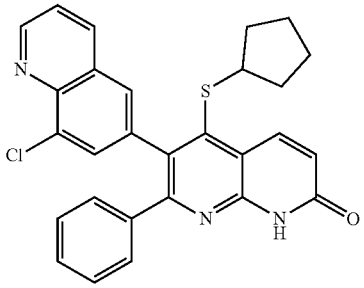 [SMILES: O=c1ccc2c(SC3CCCC3)c(-c3cc(Cl)c4ncccc4c3)c(-c3ccccc3)nc2[nH]1] |
| 1.870 | 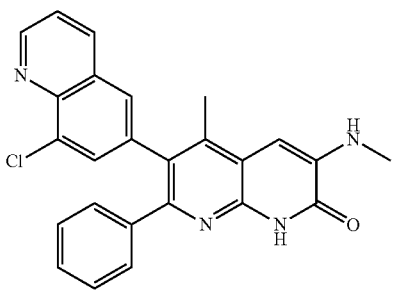 [SMILES: CNc1cc2c(C)c(-c3cc(Cl)c4ncccc4c3)c(-c3ccccc3)nc2[nH]c1=O] |
| 1.871 | 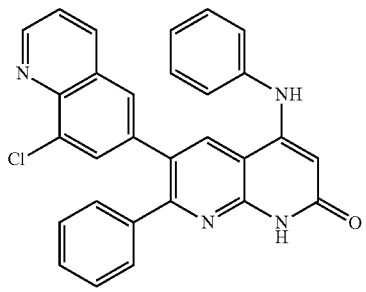 [SMILES: O=c1cc(Nc2ccccc2)c2cc(-c3cc(Cl)c4ncccc4c3)c(-c3ccccc3)nc2[nH]1] |
| 1.872 | 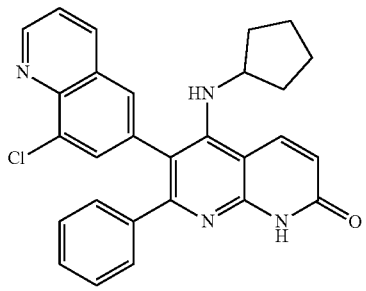 [SMILES: O=c1ccc2c(NC3CCCC3)c(-c3cc(Cl)c4ncccc4c3)c(-c3ccccc3)nc2[nH]1] |
| 1.873 | 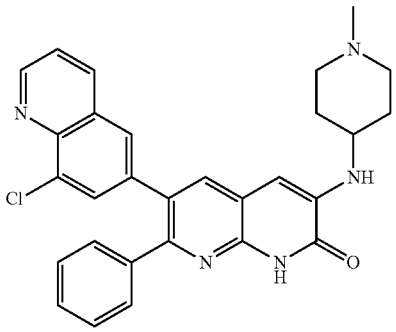 [SMILES: CN1CCC(Nc2cc3cc(-c4cc(Cl)c5ncccc5c4)c(-c4ccccc4)nc3[nH]c2=O)CC1] |

TABLE 1-continued

| Compound No. | Compound |
|---|---|
| 1.874 | |
| 1.875 | |
| 1.876 | |
| 1.877 | |
| 1.878 | |

441
442
TABLE 1-continued
| Compound No. | Compound |
|---|---|
| 1.879 | 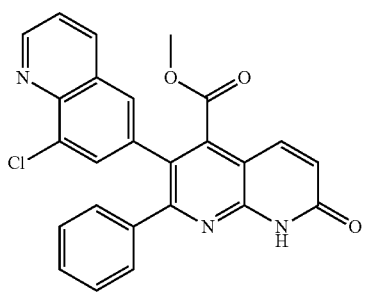 [SMILES: COC(=O)c1c(-c2cc(Cl)c3ncccc3c2)c(-c2ccccc2)nc2[nH]c(=O)ccc12] |
| 1.880 | 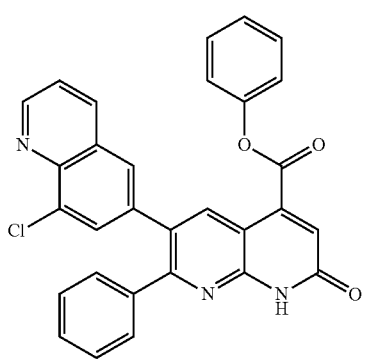 [SMILES: O=C(Oc1ccccc1)c1cc(=O)[nH]c2nc(-c3ccccc3)c(-c3cc(Cl)c4ncccc4c3)cc12] |
| 1.881 | 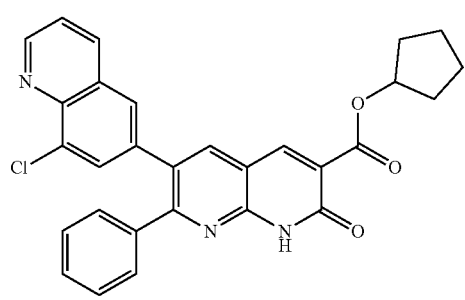 [SMILES: O=C(OC1CCCC1)c1cc2cc(-c3cc(Cl)c4ncccc4c3)c(-c3ccccc3)nc2[nH]c1=O] |
| 1.882 | 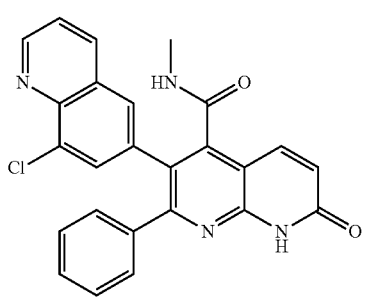 [SMILES: CNC(=O)c1c(-c2cc(Cl)c3ncccc3c2)c(-c2ccccc2)nc2[nH]c(=O)ccc12] |
| 1.883 | 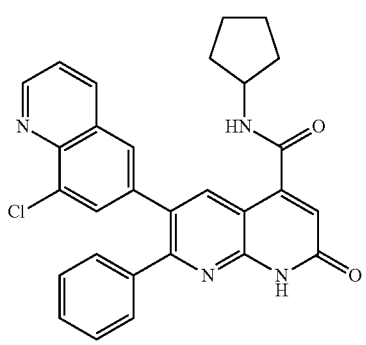 [SMILES: O=C(NC1CCCC1)c1cc(=O)[nH]c2nc(-c3ccccc3)c(-c3cc(Cl)c4ncccc4c3)cc12] |

TABLE 1-continued
| Compound No. | Compound |
|---|---|
| 1.884 | 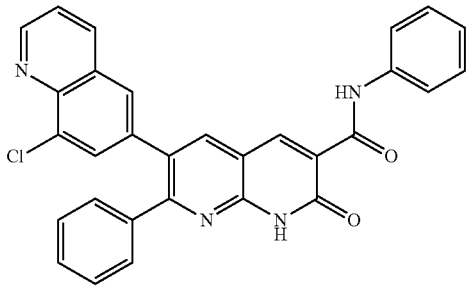 [SMILES: O=C(Nc1ccccc1)c1cc2cc(-c3cc(Cl)c4ncccc4c3)c(-c3ccccc3)nc2[nH]c1=O] |
| 1.885 | 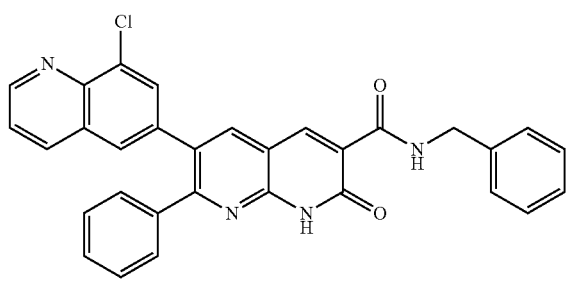 [SMILES: O=C(NCc1ccccc1)c1cc2cc(-c3cc(Cl)c4ncccc4c3)c(-c3ccccc3)nc2[nH]c1=O] |
| 1.886 | 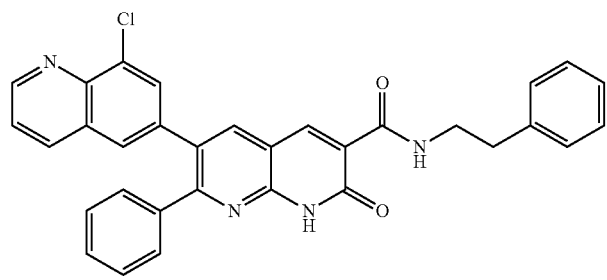 [SMILES: O=C(NCCc1ccccc1)c1cc2cc(-c3cc(Cl)c4ncccc4c3)c(-c3ccccc3)nc2[nH]c1=O] |
| 1.887 | 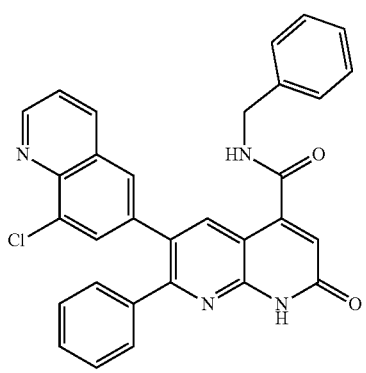 [SMILES: O=C(NCc1ccccc1)c1cc(=O)[nH]c2nc(-c3ccccc3)c(-c3cc(Cl)c4ncccc4c3)cc12] |
| 1.888 | 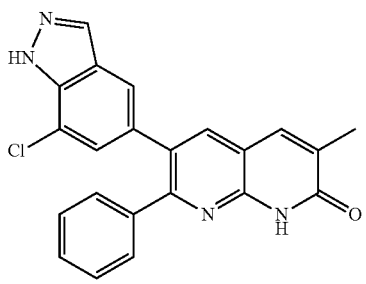 [SMILES: Cc1cc2cc(-c3cc(Cl)c4[nH]ncc4c3)c(-c3ccccc3)nc2[nH]c1=O] |

TABLE 1-continued
| Compound No. | Compound |
|---|---|
| 1.889 | 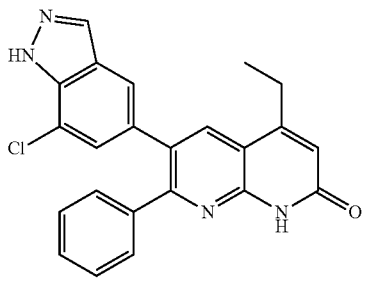 [SMILES: CCc1cc(=O)[nH]c2nc(-c3ccccc3)c(-c3cc(Cl)c4[nH]ncc4c3)cc12] |
| 1.890 | 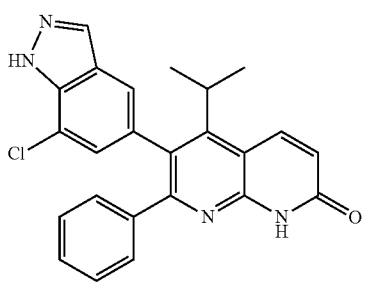 [SMILES: CC(C)c1c(-c2cc(Cl)c3[nH]ncc3c2)c(-c2ccccc2)nc2[nH]c(=O)ccc12] |
| 1.891 | 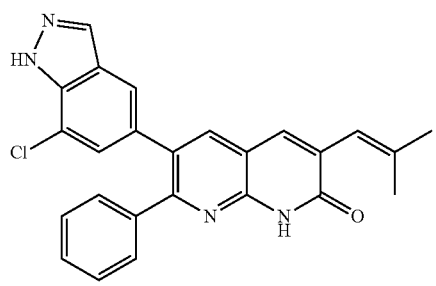 [SMILES: CC(C)=Cc1cc2cc(-c3cc(Cl)c4[nH]ncc4c3)c(-c3ccccc3)nc2[nH]c1=O] |
| 1.892 | 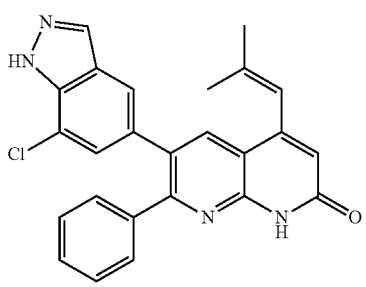 [SMILES: CC(C)=Cc1cc(=O)[nH]c2nc(-c3ccccc3)c(-c3cc(Cl)c4[nH]ncc4c3)cc12] |
| 1.893 | 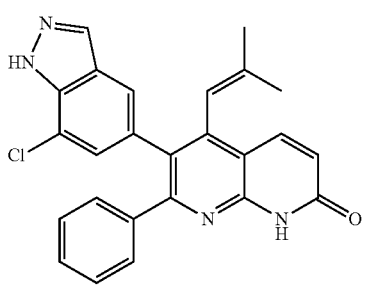 [SMILES: CC(C)=Cc1c(-c2cc(Cl)c3[nH]ncc3c2)c(-c2ccccc2)nc2[nH]c(=O)ccc12] |

TABLE 1-continued

| Compound No. | Compound |
|---|---|
| 1.894 | |
| 1.895 | |
| 1.896 | |
| 1.897 | |
| 1.898 | |

TABLE 1-continued

| Compound No. | Compound |
|---|---|
| 1.899 | |
| 1.900 | |
| 1.901 | |
| 1.902 | |
| 1.903 | |

TABLE 1-continued
| Compound No. | Compound |
|---|---|
| 1.904 | 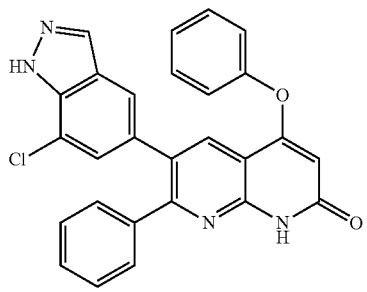 [SMILES: O=c1cc(Oc2ccccc2)c2cc(-c3cc(Cl)c4[nH]ncc4c3)c(-c3ccccc3)nc2[nH]1] |
| 1.905 | 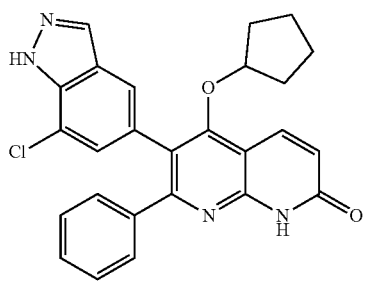 [SMILES: O=c1ccc2c(OC3CCCC3)c(-c3cc(Cl)c4[nH]ncc4c3)c(-c3ccccc3)nc2[nH]1] |
| 1.906 | 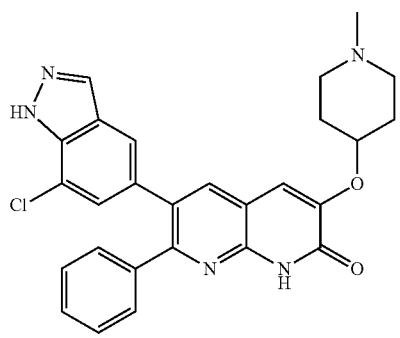 [SMILES: CN1CCC(Oc2cc3cc(-c4cc(Cl)c5[nH]ncc5c4)c(-c4ccccc4)nc3[nH]c2=O)CC1] |
| 1.907 | 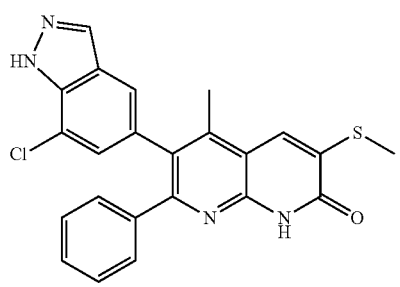 [SMILES: CSc1cc2c(C)c(-c3cc(Cl)c4[nH]ncc4c3)c(-c3ccccc3)nc2[nH]c1=O] |
| 1.908 | 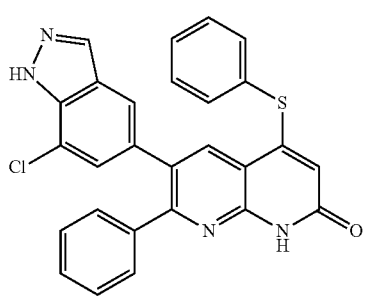 [SMILES: O=c1cc(Sc2ccccc2)c2cc(-c3cc(Cl)c4[nH]ncc4c3)c(-c3ccccc3)nc2[nH]1] |

TABLE 1-continued
| Compound No. | Compound |
|---|---|
| 1.909 | 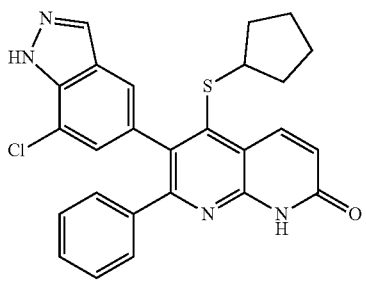 [SMILES: O=c1ccc2c(SC3CCCC3)c(-c3cc(Cl)c4[nH]ncc4c3)c(-c3ccccc3)nc2[nH]1] |
| 1.910 | 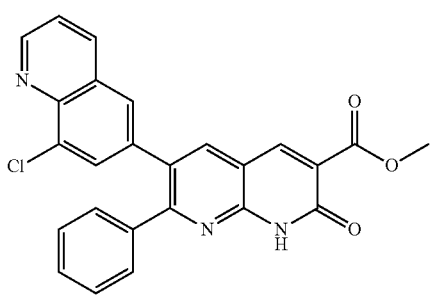 [SMILES: COC(=O)c1cc2cc(-c3cc(Cl)c4ncccc4c3)c(-c3ccccc3)nc2[nH]c1=O] |
| 1.911 | 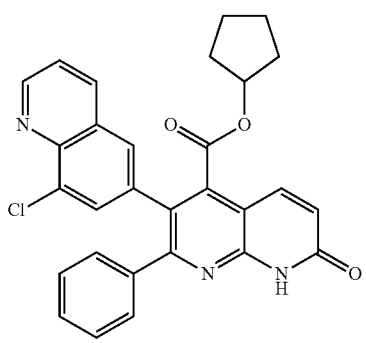 [SMILES: O=C(OC1CCCC1)c1c(-c2cc(Cl)c3ncccc3c2)c(-c2ccccc2)nc2[nH]c(=O)ccc12] |
| 1.912 | 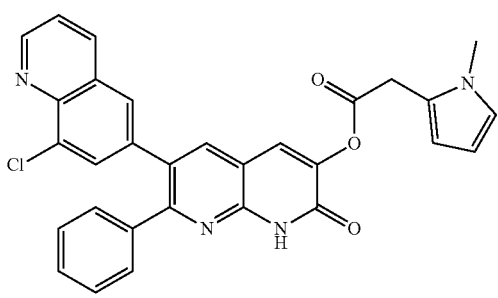 [SMILES: Cn1cccc1CC(=O)Oc1cc2cc(-c3cc(Cl)c4ncccc4c3)c(-c3ccccc3)nc2[nH]c1=O] |
| 1.913 | 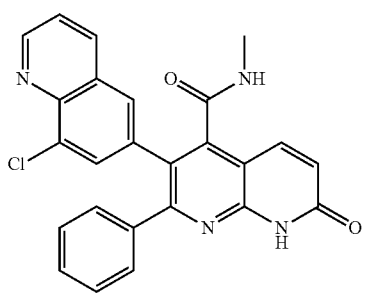 [SMILES: CNC(=O)c1c(-c2cc(Cl)c3ncccc3c2)c(-c2ccccc2)nc2[nH]c(=O)ccc12] |

TABLE 1-continued
| Compound No. | Compound |
|---|---|
| 1.914 | 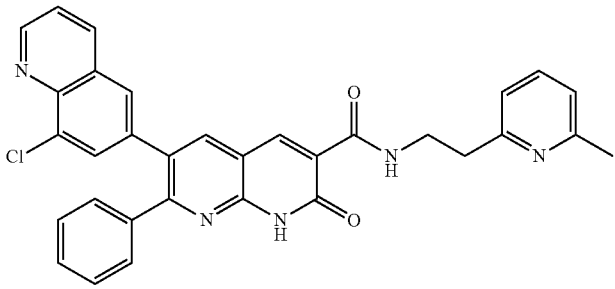 [SMILES: Cc1cccc(CCNC(=O)c2cc3cc(-c4cc(Cl)c5ncccc5c4)c(-c4ccccc4)nc3[nH]c2=O)n1] |
| 1.915 | 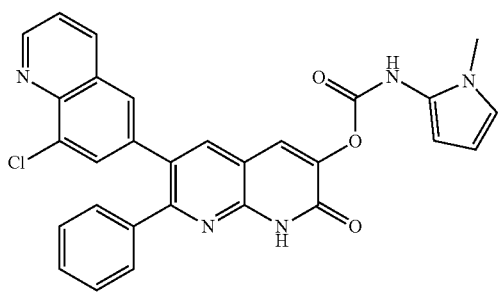 [SMILES: Cn1cccc1NC(=O)Oc1cc2cc(-c3cc(Cl)c4ncccc4c3)c(-c3ccccc3)nc2[nH]c1=O] |
| 1.916 | 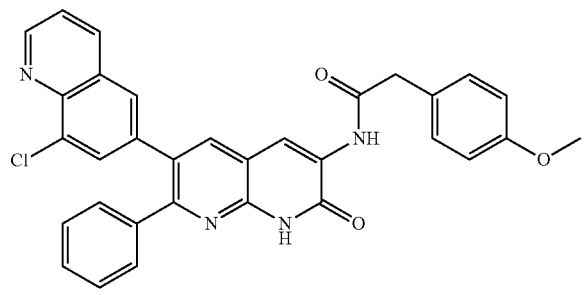 [SMILES: COc1ccc(CC(=O)Nc2cc3cc(-c4cc(Cl)c5ncccc5c4)c(-c4ccccc4)nc3[nH]c2=O)cc1] |
| 1.917 | 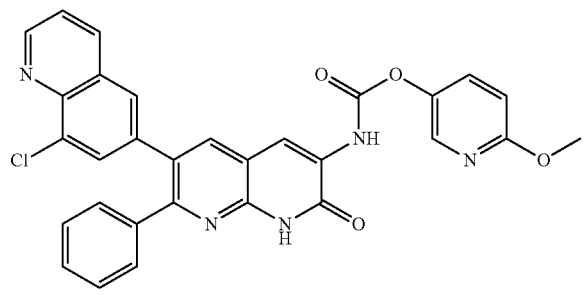 [SMILES: COc1ccc(OC(=O)Nc2cc3cc(-c4cc(Cl)c5ncccc5c4)c(-c4ccccc4)nc3[nH]c2=O)cn1] |
| 1.918 | 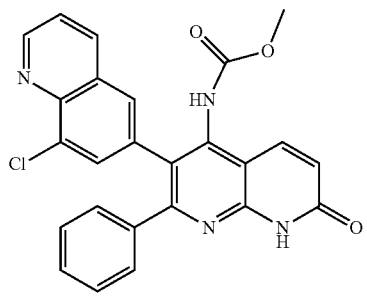 [SMILES: COC(=O)Nc1c(-c2cc(Cl)c3ncccc3c2)c(-c2ccccc2)nc2[nH]c(=O)ccc12] |

TABLE 1-continued
| Compound No. | Compound |
|---|---|
| 1.919 | 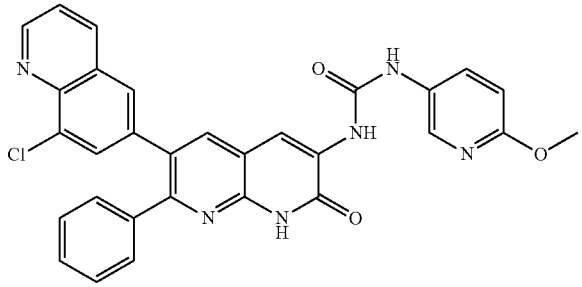 [SMILES: COc1ccc(NC(=O)Nc2cc3cc(-c4cc(Cl)c5ncccc5c4)c(-c4ccccc4)nc3[nH]c2=O)cn1] |
| 1.920 | 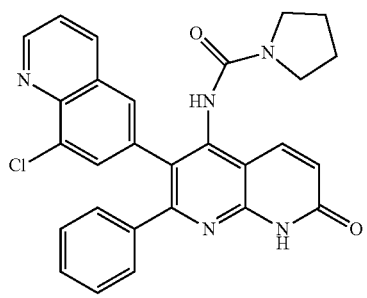 [SMILES: O=C(Nc1c(-c2cc(Cl)c3ncccc3c2)c(-c2ccccc2)nc2[nH]c(=O)ccc12)N1CCCC1] |
| 1.921 | 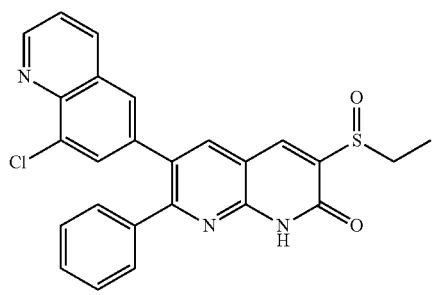 [SMILES: CCS(=O)c1cc2cc(-c3cc(Cl)c4ncccc4c3)c(-c3ccccc3)nc2[nH]c1=O] |
| 1.922 | 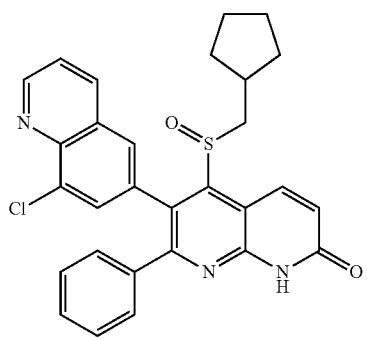 [SMILES: O=c1ccc2c(S(=O)CC3CCCC3)c(-c3cc(Cl)c4ncccc4c3)c(-c3ccccc3)nc2[nH]1] |
| 1.923 | 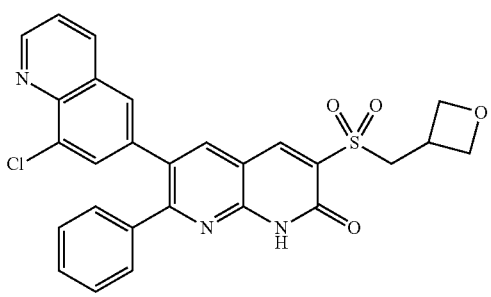 [SMILES: O=c1[nH]c2nc(-c3ccccc3)c(-c3cc(Cl)c4ncccc4c3)cc2cc1S(=O)(=O)CC1COC1] |

TABLE 1-continued
| Compound No. | Compound |
|---|---|
| 1.924 | 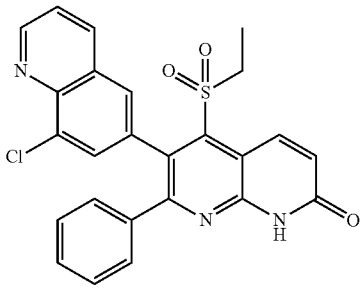 [SMILES: CCS(=O)(=O)c1c(-c2cc(Cl)c3ncccc3c2)c(-c2ccccc2)nc2[nH]c(=O)ccc12] |
| 1.925 | 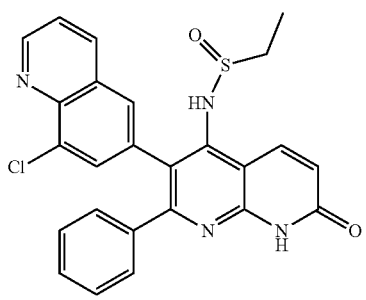 [SMILES: CCS(=O)Nc1c(-c2cc(Cl)c3ncccc3c2)c(-c2ccccc2)nc2[nH]c(=O)ccc12] |
| 1.926 | 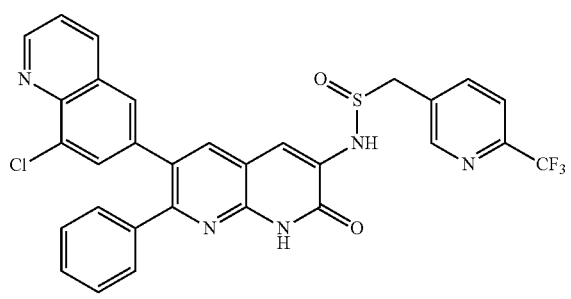 [SMILES: O=c1[nH]c2nc(-c3ccccc3)c(-c3cc(Cl)c4ncccc4c3)cc2cc1NS(=O)Cc1ccc(C(F)(F)F)nc1] |
| 1.927 | 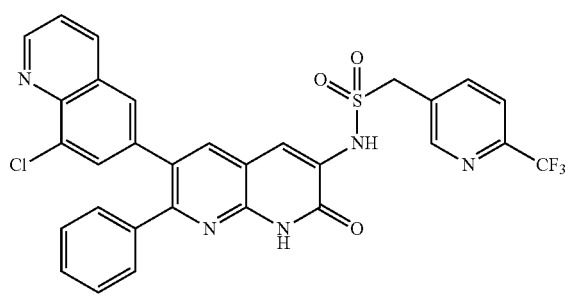 [SMILES: O=c1[nH]c2nc(-c3ccccc3)c(-c3cc(Cl)c4ncccc4c3)cc2cc1NS(=O)(=O)Cc1ccc(C(F)(F)F)nc1] |
| 1.928 | 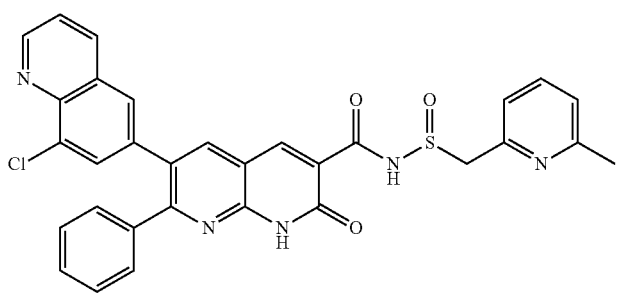 [SMILES: Cc1cccc(CS(=O)NC(=O)c2cc3cc(-c4cc(Cl)c5ncccc5c4)c(-c4ccccc4)nc3[nH]c2=O)n1] |

TABLE 1-continued
| Compound No. | Compound |
|---|---|
| 1.929 | 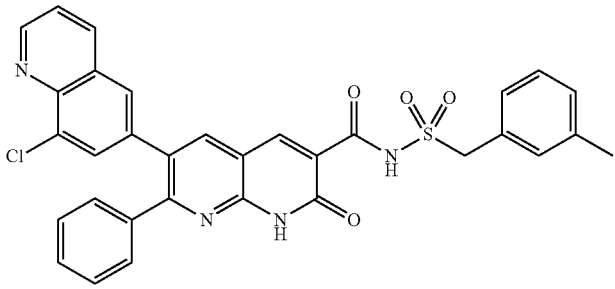 [SMILES: Cc1cccc(CS(=O)(=O)NC(=O)c2cc3cc(-c4cc(Cl)c5ncccc5c4)c(-c4ccccc4)nc3[nH]c2=O)c1] |
| 1.930 | 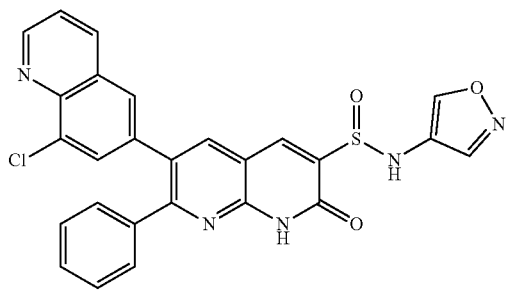 [SMILES: O=c1[nH]c2nc(-c3ccccc3)c(-c3cc(Cl)c4ncccc4c3)cc2cc1S(=O)Nc1cnoc1] |
| 1.931 | 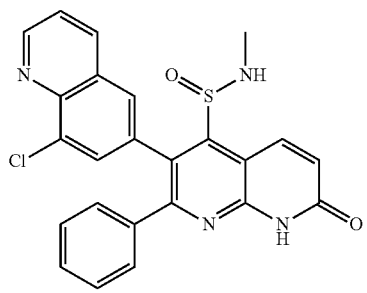 [SMILES: CNS(=O)c1c(-c2cc(Cl)c3ncccc3c2)c(-c2ccccc2)nc2[nH]c(=O)ccc12] |
| 1.932 | 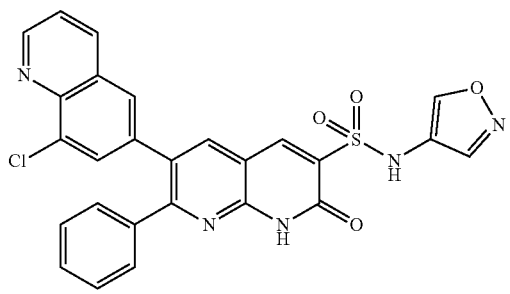 [SMILES: O=c1[nH]c2nc(-c3ccccc3)c(-c3cc(Cl)c4ncccc4c3)cc2cc1S(=O)(=O)Nc1cnoc1] |
| 1.933 | 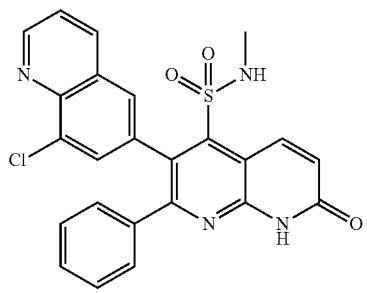 [SMILES: CNS(=O)(=O)c1c(-c2cc(Cl)c3ncccc3c2)c(-c2ccccc2)nc2[nH]c(=O)ccc12] |

TABLE 1-continued
| Compound No. | Compound |
|---|---|
| 1.934 | 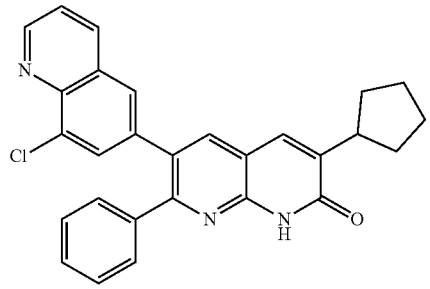 [SMILES: O=c1[nH]c2nc(-c3ccccc3)c(-c3cc(Cl)c4ncccc4c3)cc2cc1C1CCCC1] |
| 1.935 | 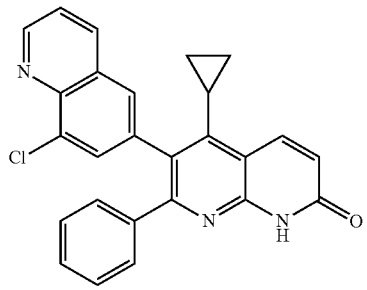 [SMILES: O=c1ccc2c(C3CC3)c(-c3cc(Cl)c4ncccc4c3)c(-c3ccccc3)nc2[nH]1] |
| 1.936 | 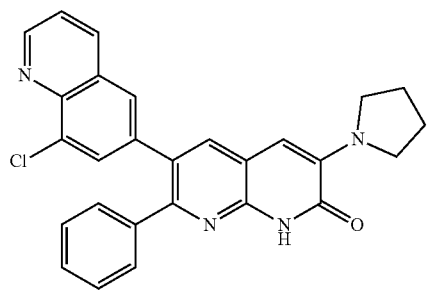 [SMILES: O=c1[nH]c2nc(-c3ccccc3)c(-c3cc(Cl)c4ncccc4c3)cc2cc1N1CCCC1] |
| 1.937 | 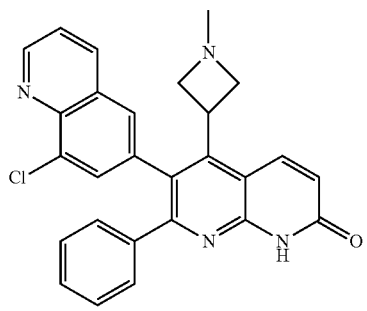 [SMILES: CN1CC(c2c(-c3cc(Cl)c4ncccc4c3)c(-c3ccccc3)nc3[nH]c(=O)ccc23)C1] |
| 1.938 | 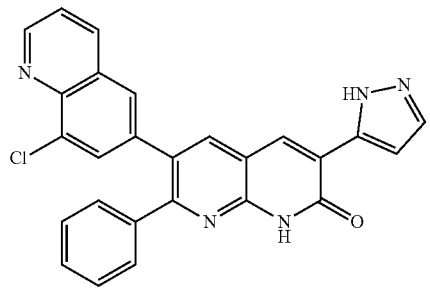 [SMILES: O=c1[nH]c2nc(-c3ccccc3)c(-c3cc(Cl)c4ncccc4c3)cc2cc1-c1ccn[nH]1] |

TABLE 1-continued
| Compound No. | Compound |
|---|---|
| 1.939 | 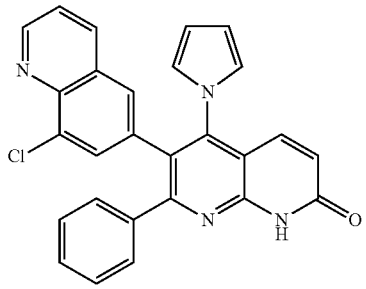 [SMILES: O=c1ccc2c(-n3cccc3)c(-c3cc(Cl)c4ncccc4c3)c(-c3ccccc3)nc2[nH]1] |
| 1.940 | 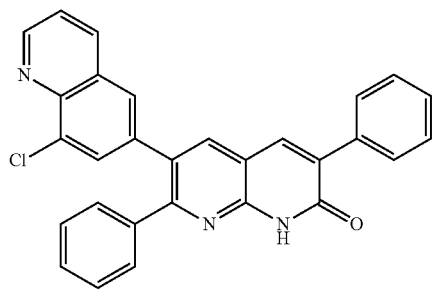 [SMILES: O=c1[nH]c2nc(-c3ccccc3)c(-c3cc(Cl)c4ncccc4c3)cc2cc1-c1ccccc1] |
| 1.941 | 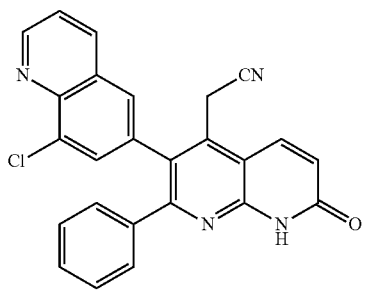 [SMILES: N#CCc1c(-c2cc(Cl)c3ncccc3c2)c(-c2ccccc2)nc2[nH]c(=O)ccc12] |
| 1.942 | 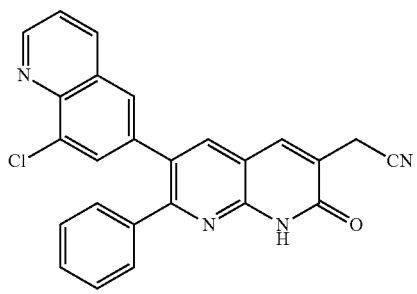 [SMILES: N#CCc1cc2cc(-c3cc(Cl)c4ncccc4c3)c(-c3ccccc3)nc2[nH]c1=O] |
| 1.943 | 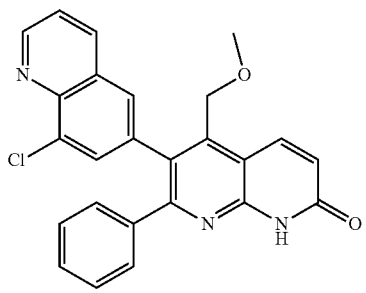 [SMILES: COCc1c(-c2cc(Cl)c3ncccc3c2)c(-c2ccccc2)nc2[nH]c(=O)ccc12] |

TABLE 1-continued
| Compound No. | Compound |
|---|---|
| 1.944 | 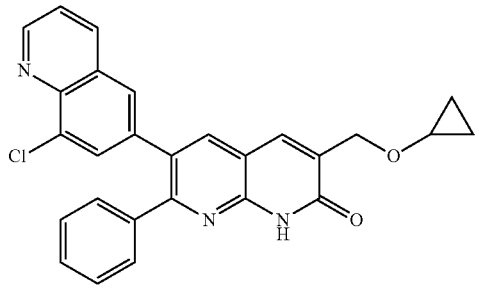 [SMILES: O=c1[nH]c2nc(-c3ccccc3)c(-c3cc(Cl)c4ncccc4c3)cc2cc1COC1CC1] |
| 1.945 | 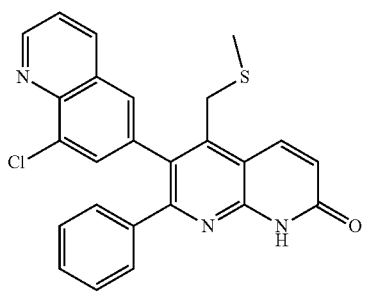 [SMILES: CSCc1c(-c2cc(Cl)c3ncccc3c2)c(-c2ccccc2)nc2[nH]c(=O)ccc12] |
| 1.946 | 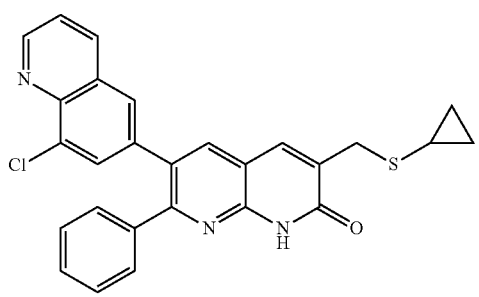 [SMILES: O=c1[nH]c2nc(-c3ccccc3)c(-c3cc(Cl)c4ncccc4c3)cc2cc1CSC1CC1] |
| 1.947 | 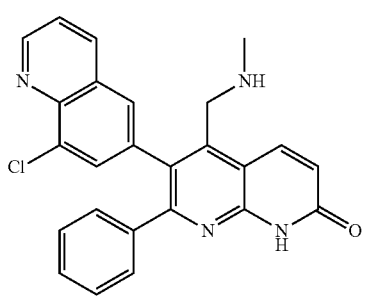 [SMILES: CNCc1c(-c2cc(Cl)c3ncccc3c2)c(-c2ccccc2)nc2[nH]c(=O)ccc12] |
| 1.948 | 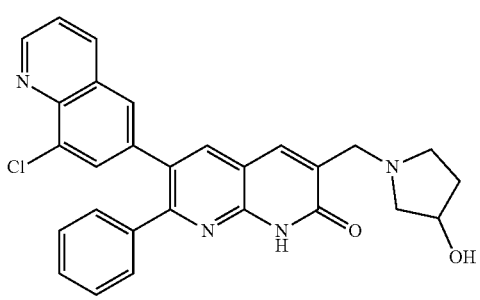 [SMILES: O=c1[nH]c2nc(-c3ccccc3)c(-c3cc(Cl)c4ncccc4c3)cc2cc1CN1CCC(O)C1] |

TABLE 1-continued
| Compound No. | Compound |
|---|---|
| 1.949 | 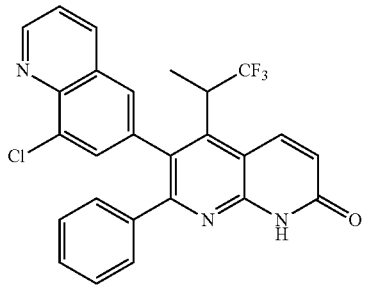 |
| 1.950 | 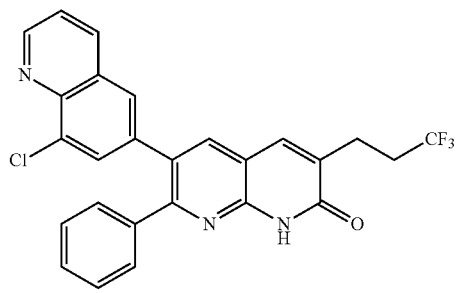 [SMILES: O=c1[nH]c2nc(-c3ccccc3)c(-c3cc(Cl)c4ncccc4c3)cc2cc1CCC(F)(F)F] |
| 1.951 | 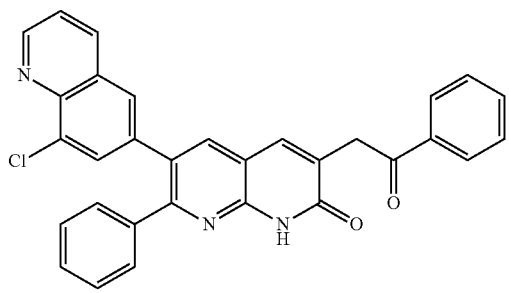 [SMILES: O=C(Cc1cc2cc(-c3cc(Cl)c4ncccc4c3)c(-c3ccccc3)nc2[nH]c1=O)c1ccccc1] |
| 1.952 | 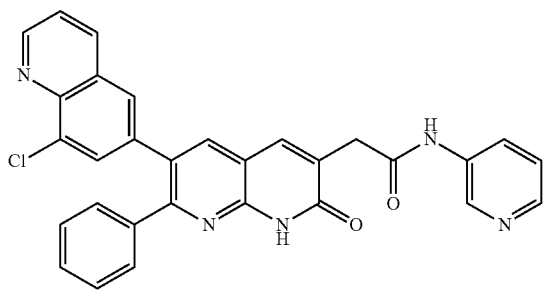 [SMILES: O=C(Cc1cc2cc(-c3cc(Cl)c4ncccc4c3)c(-c3ccccc3)nc2[nH]c1=O)Nc1cccnc1] |
| 1.953 | 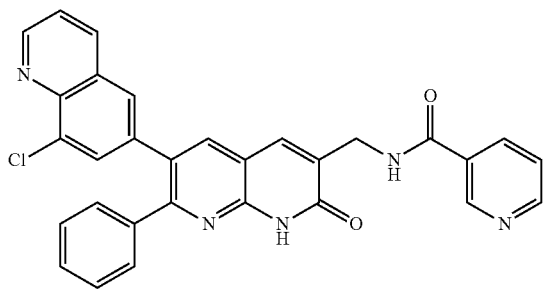 [SMILES: O=C(NCc1cc2cc(-c3cc(Cl)c4ncccc4c3)c(-c3ccccc3)nc2[nH]c1=O)c1cccnc1] |

TABLE 1-continued
| Compound No. | Compound |
|---|---|
| 1.954 | 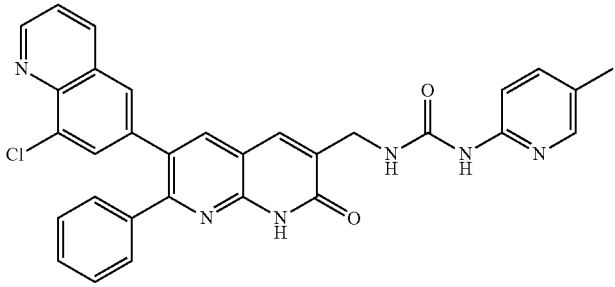 [SMILES: Cc1ccc(NC(=O)NCc2cc3cc(-c4cc(Cl)c5ncccc5c4)c(-c4ccccc4)nc3[nH]c2=O)nc1] |
| 1.955 | 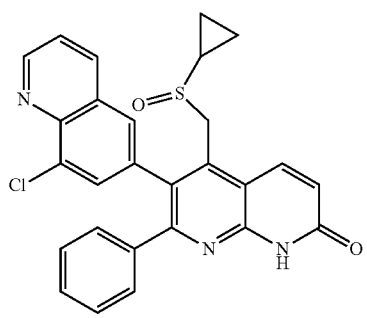 [SMILES: O=c1ccc2c(CS(=O)C3CC3)c(-c3cc(Cl)c4ncccc4c3)c(-c3ccccc3)nc2[nH]1] |
| 1.956 | 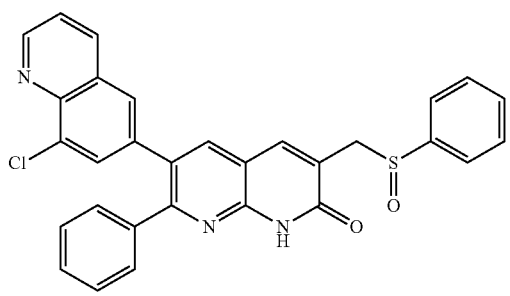 [SMILES: O=c1[nH]c2nc(-c3ccccc3)c(-c3cc(Cl)c4ncccc4c3)cc2cc1CS(=O)c1ccccc1] |
| 1.957 | 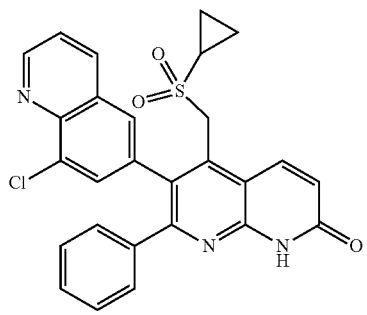 [SMILES: O=c1ccc2c(CS(=O)(=O)C3CC3)c(-c3cc(Cl)c4ncccc4c3)c(-c3ccccc3)nc2[nH]1] |
| 1.958 | 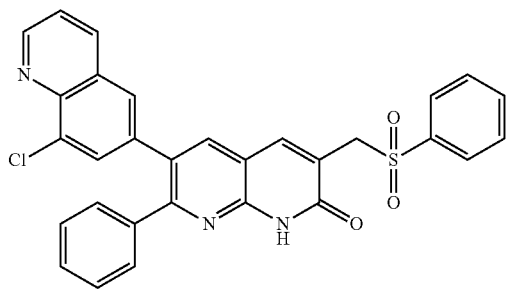 [SMILES: O=c1[nH]c2nc(-c3ccccc3)c(-c3cc(Cl)c4ncccc4c3)cc2cc1CS(=O)(=O)c1ccccc1] |

TABLE 1-continued

| Compound No. | Compound |
| --- | --- |
| 1.959 | |
| 1.960 | |
| 1.961 | |
| 1.962 | |
| 1.963 | |

475
476
TABLE 1-continued
| Compound No. | Compound |
|---|---|
| 1.964 | 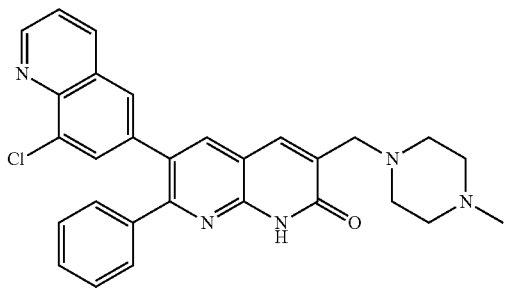 [SMILES: CN1CCN(Cc2cc3cc(-c4cc(Cl)c5ncccc5c4)c(-c4ccccc4)nc3[nH]c2=O)CC1] |
| 1.965 | 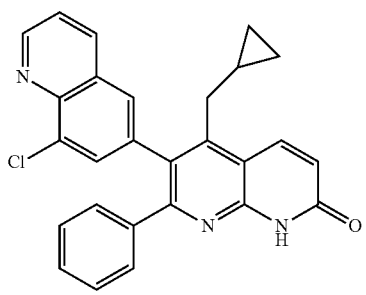 [SMILES: O=c1ccc2c(CC3CC3)c(-c3cc(Cl)c4ncccc4c3)c(-c3ccccc3)nc2[nH]1] |
| 1.966 | 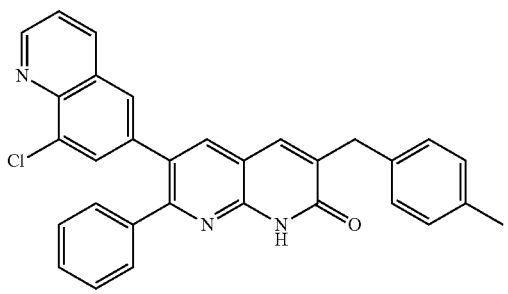 [SMILES: Cc1ccc(Cc2cc3cc(-c4cc(Cl)c5ncccc5c4)c(-c4ccccc4)nc3[nH]c2=O)cc1] |
| 1.967 | 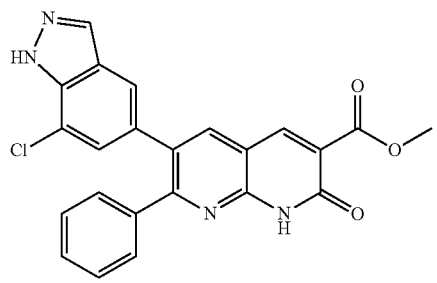 [SMILES: COC(=O)c1cc2cc(-c3cc(Cl)c4[nH]ncc4c3)c(-c3ccccc3)nc2[nH]c1=O] |
| 1.968 | 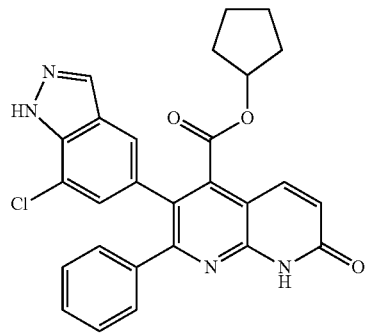 [SMILES: O=C(OC1CCCC1)c1c(-c2cc(Cl)c3[nH]ncc3c2)c(-c2ccccc2)nc2[nH]c(=O)ccc12] |

TABLE 1-continued
| Compound No. | Compound |
|---|---|
| 1.969 | 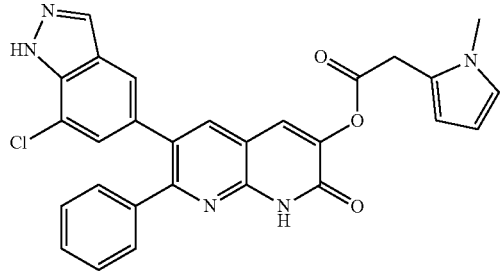 [SMILES: Cn1cccc1CC(=O)Oc1cc2cc(-c3cc(Cl)c4[nH]ncc4c3)c(-c3ccccc3)nc2[nH]c1=O] |
| 1.970 | 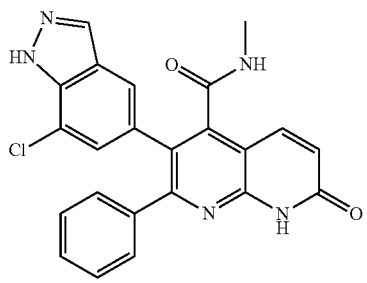 [SMILES: CNC(=O)c1c(-c2cc(Cl)c3[nH]ncc3c2)c(-c2ccccc2)nc2[nH]c(=O)ccc12] |
| 1.971 | 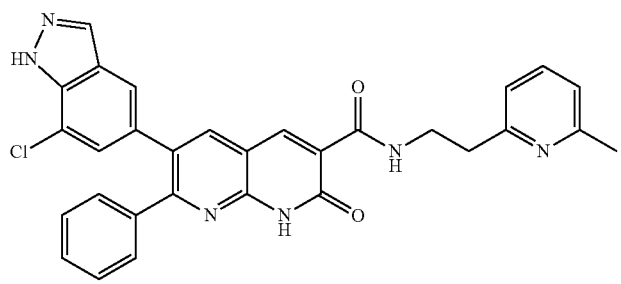 [SMILES: Cc1cccc(CCNC(=O)c2cc3cc(-c4cc(Cl)c5[nH]ncc5c4)c(-c4ccccc4)nc3[nH]c2=O)n1] |
| 1.972 | 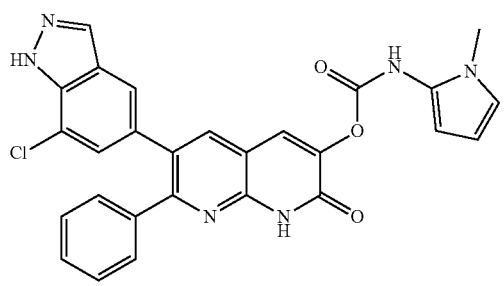 [SMILES: Cn1cccc1NC(=O)Oc1cc2cc(-c3cc(Cl)c4[nH]ncc4c3)c(-c3ccccc3)nc2[nH]c1=O] |
| 1.973 | 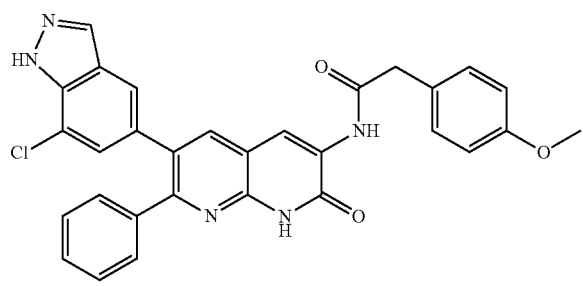 [SMILES: COc1ccc(CC(=O)Nc2cc3cc(-c4cc(Cl)c5[nH]ncc5c4)c(-c4ccccc4)nc3[nH]c2=O)cc1] |

TABLE 1-continued
| Compound No. | Compound |
|---|---|
| 1.974 | 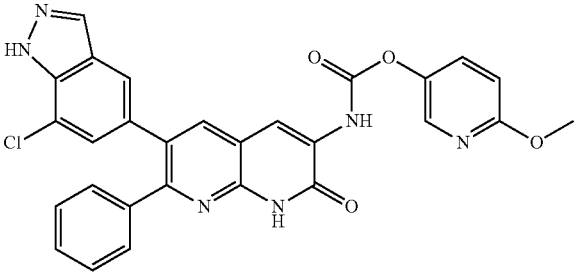 [SMILES: COc1ccc(OC(=O)Nc2cc3cc(-c4cc(Cl)c5[nH]ncc5c4)c(-c4ccccc4)nc3[nH]c2=O)cn1] |
| 1.975 | 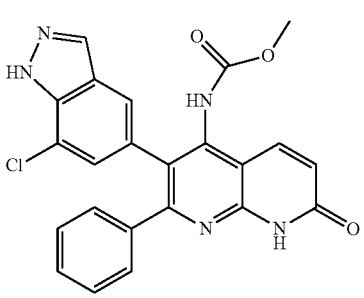 [SMILES: COC(=O)Nc1c(-c2cc(Cl)c3[nH]ncc3c2)c(-c2ccccc2)nc2[nH]c(=O)ccc12] |
| 1.976 | 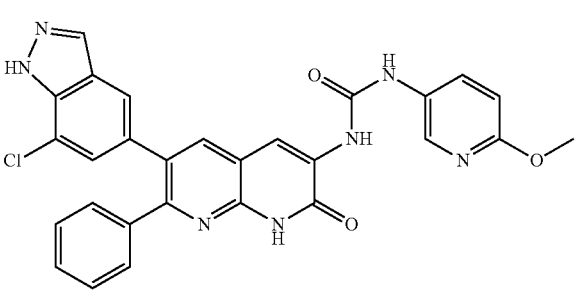 [SMILES: COc1ccc(NC(=O)Nc2cc3cc(-c4cc(Cl)c5[nH]ncc5c4)c(-c4ccccc4)nc3[nH]c2=O)cn1] |
| 1.977 | 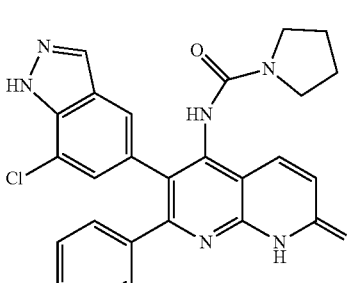 |
| 1.978 | 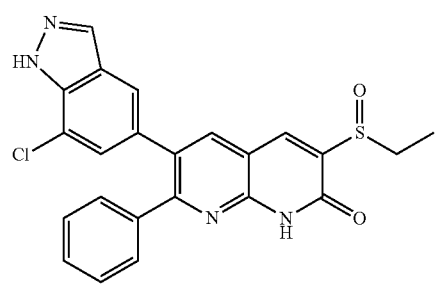 [SMILES: CCS(=O)c1cc2cc(-c3cc(Cl)c4[nH]ncc4c3)c(-c3ccccc3)nc2[nH]c1=O] |

TABLE 1-continued

| Compound No. | Compound |
|---|---|
| 1.979 | |
| 1.980 | |
| 1.981 | |
| 1.982 | |
| 1.983 | |

TABLE 1-continued

| Compound No. | Compound |
|---|---|
| 1.984 | |
| 1.985 | |
| 1.986 | |
| 1.987 | |
| 1.988 | |

TABLE 1-continued
| Compound No. | Compound |
|---|---|
| 1.989 | 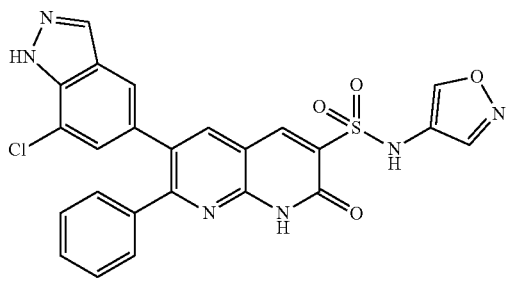 [SMILES: O=c1[nH]c2nc(-c3ccccc3)c(-c3cc(Cl)c4[nH]ncc4c3)cc2cc1S(=O)(=O)Nc1cnoc1] |
| 1.990 | 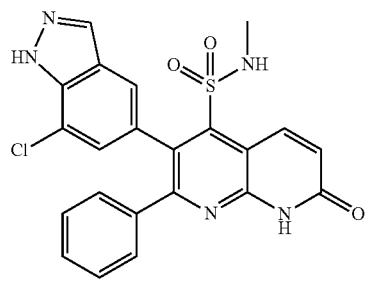 [SMILES: CNS(=O)(=O)c1c(-c2cc(Cl)c3[nH]ncc3c2)c(-c2ccccc2)nc2[nH]c(=O)ccc12] |
| 1.991 | 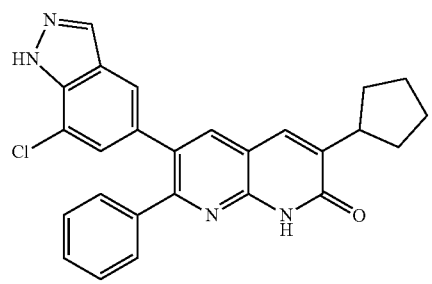 [SMILES: O=c1[nH]c2nc(-c3ccccc3)c(-c3cc(Cl)c4[nH]ncc4c3)cc2cc1C1CCCC1] |
| 1.992 | 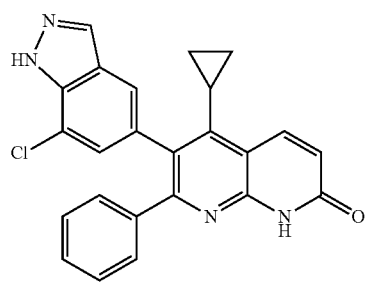 [SMILES: O=c1ccc2c(C3CC3)c(-c3cc(Cl)c4[nH]ncc4c3)c(-c3ccccc3)nc2[nH]1] |
| 1.993 | 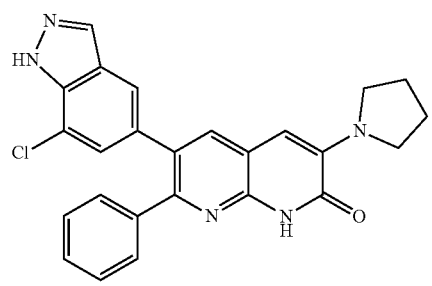 [SMILES: O=c1[nH]c2nc(-c3ccccc3)c(-c3cc(Cl)c4[nH]ncc4c3)cc2cc1N1CCCC1] |

TABLE 1-continued

| Compound No. | Compound |
|---|---|
| 1.994 | |
| 1.995 | |
| 1.996 | |
| 1.997 | |
| 1.998 | |

TABLE 1-continued

| Compound No. | Compound |
|---|---|
| 1.999 | |
| 2.000 | |
| 2.001 | |
| 2.002 | |
| 2.003 | |

TABLE 1-continued
| Compound No. | Compound |
|---|---|
| 2.004 | 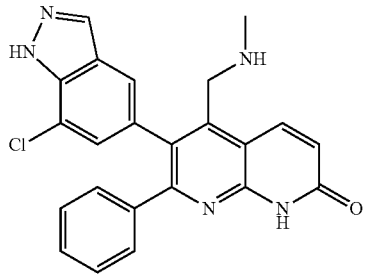 [SMILES: CNCc1c(-c2cc(Cl)c3[nH]ncc3c2)c(-c2ccccc2)nc2[nH]c(=O)ccc12] |
| 2.005 | 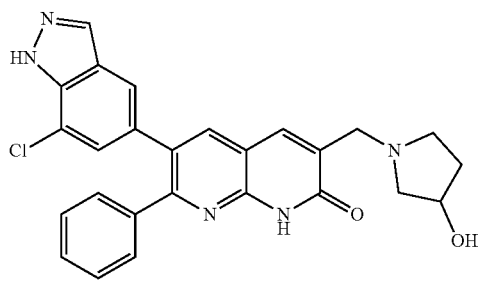 [SMILES: O=c1[nH]c2nc(-c3ccccc3)c(-c3cc(Cl)c4[nH]ncc4c3)cc2cc1CN1CCC(O)C1] |
| 2.006 | 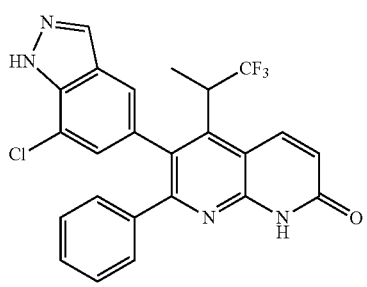 |
| 2.007 | 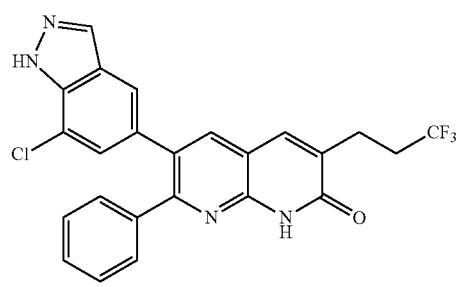 [SMILES: O=c1[nH]c2nc(-c3ccccc3)c(-c3cc(Cl)c4[nH]ncc4c3)cc2cc1CCC(F)(F)F] |
| 2.008 | 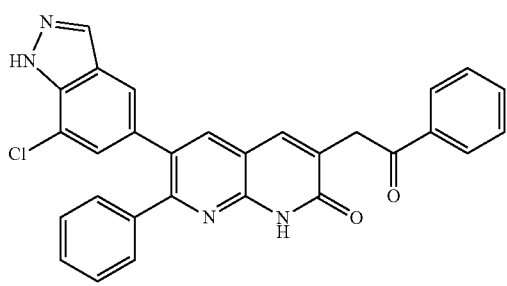 [SMILES: O=C(Cc1cc2cc(-c3cc(Cl)c4[nH]ncc4c3)c(-c3ccccc3)nc2[nH]c1=O)c1ccccc1] |

TABLE 1-continued

| Compound No. | Compound |
|---|---|
| 2.009 | |
| 2.010 | |
| 2.011 | |
| 2.012 | |
| 2.013 | |

TABLE 1-continued
| Compound No. | Compound |
|---|---|
| 2.014 | 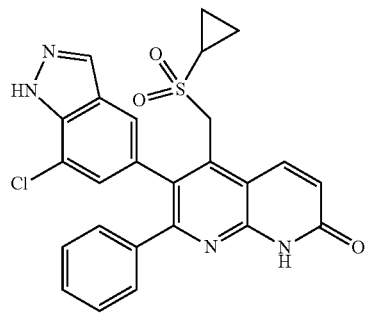 [SMILES: O=c1ccc2c(CS(=O)(=O)C3CC3)c(-c3cc(Cl)c4[nH]ncc4c3)c(-c3ccccc3)nc2[nH]1] |
| 2.015 | 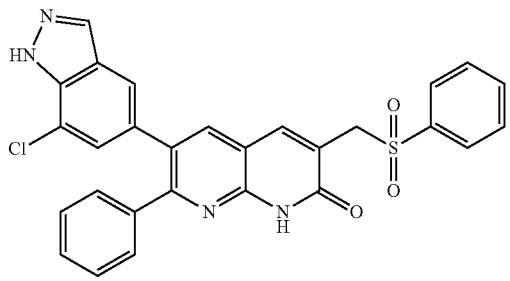 [SMILES: O=c1[nH]c2nc(-c3ccccc3)c(-c3cc(Cl)c4[nH]ncc4c3)cc2cc1CS(=O)(=O)c1ccccc1] |
| 2.016 | 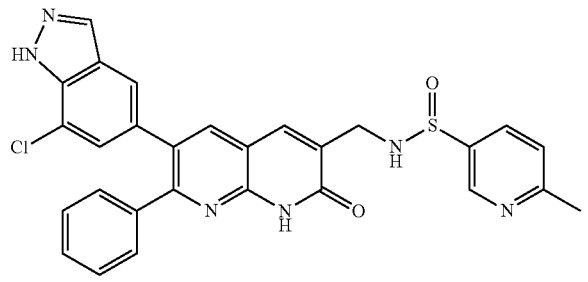 [SMILES: Cc1ccc(S(=O)NCc2cc3cc(-c4cc(Cl)c5[nH]ncc5c4)c(-c4ccccc4)nc3[nH]c2=O)cn1] |
| 2.017 | 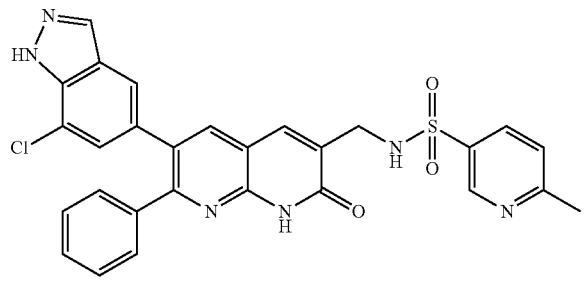 [SMILES: Cc1ccc(S(=O)(=O)NCc2cc3cc(-c4cc(Cl)c5[nH]ncc5c4)c(-c4ccccc4)nc3[nH]c2=O)cn1] |
| 2.018 | 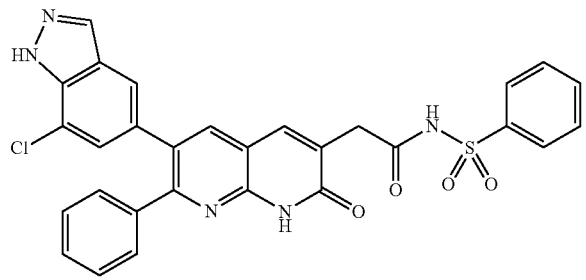 [SMILES: O=C(Cc1cc2cc(-c3cc(Cl)c4[nH]ncc4c3)c(-c3ccccc3)nc2[nH]c1=O)NS(=O)(=O)c1ccccc1] |

TABLE 1-continued

| Compound No. | Compound |
|---|---|
| 2.019 | |
| 2.020 | |
| 2.021 | |
| 2.022 | |
| 2.023 | |

TABLE 1-continued
| Compound No. | Compound |
|---|---|
| 2.024 | 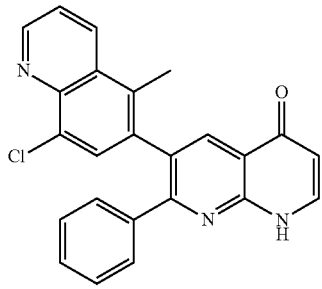 [SMILES: Cc1c(-c2cc3c(=O)cc[nH]c3nc2-c2ccccc2)cc(Cl)c2ncccc12] |
| 2.025 | 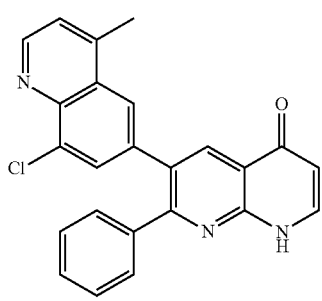 [SMILES: Cc1ccnc2c(Cl)cc(-c3cc4c(=O)cc[nH]c4nc3-c3ccccc3)cc12] |
| 2.026 | 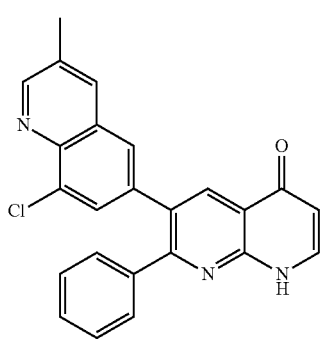 [SMILES: Cc1cnc2c(Cl)cc(-c3cc4c(=O)cc[nH]c4nc3-c3ccccc3)cc2c1] |
| 2.027 | 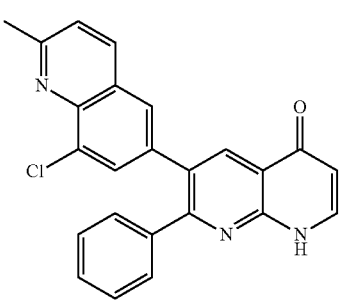 [SMILES: Cc1ccc2cc(-c3cc4c(=O)cc[nH]c4nc3-c3ccccc3)cc(Cl)c2n1] |
| 2.028 | 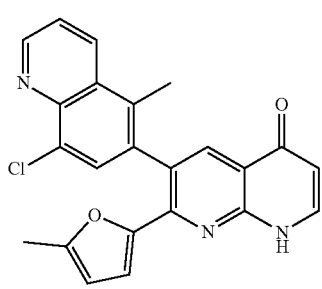 [SMILES: Cc1ccc(-c2nc3[nH]ccc(=O)c3cc2-c2cc(Cl)c3ncccc3c2C)o1] |

TABLE 1-continued
| Compound No. | Compound |
|---|---|
| 2.029 | 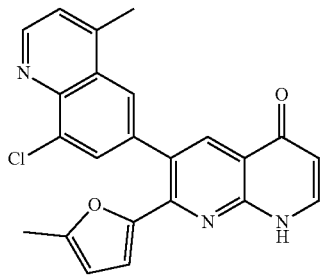 [SMILES: Cc1ccc(-c2nc3[nH]ccc(=O)c3cc2-c2cc(Cl)c3nccc(C)c3c2)o1] |
| 2.030 | 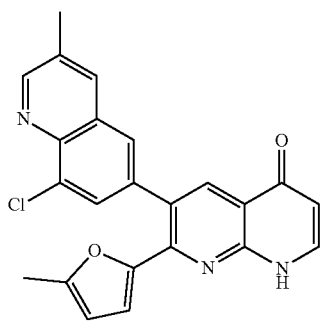 [SMILES: Cc1cnc2c(Cl)cc(-c3cc4c(=O)cc[nH]c4nc3-c3ccc(C)o3)cc2c1] |
| 2.031 | 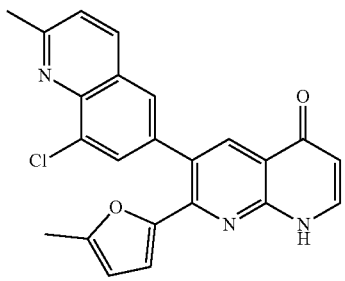 [SMILES: Cc1ccc2cc(-c3cc4c(=O)cc[nH]c4nc3-c3ccc(C)o3)cc(Cl)c2n1] |
| 2.032 | 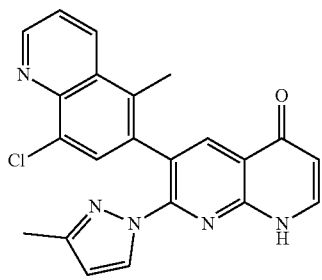 [SMILES: Cc1ccn(-c2nc3[nH]ccc(=O)c3cc2-c2cc(Cl)c3ncccc3c2C)n1] |
| 2.033 | 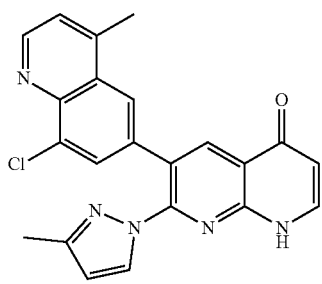 [SMILES: Cc1ccn(-c2nc3[nH]ccc(=O)c3cc2-c2cc(Cl)c3nccc(C)c3c2)n1] |

TABLE 1-continued

| Compound No. | Compound |
|---|---|
| 2.034 | |
| 2.035 | |
| 2.036 | |
| 2.037 | |
| 2.038 | |

TABLE 1-continued
| Compound No. | Compound |
|---|---|
| 2.039 | 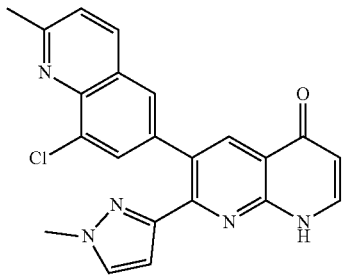 [SMILES: Cc1ccc2cc(-c3cc4c(=O)cc[nH]c4nc3-c3ccn(C)n3)cc(Cl)c2n1] |
| 2.040 | 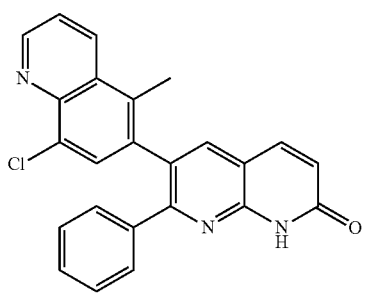 [SMILES: Cc1c(-c2cc3ccc(=O)[nH]c3nc2-c2ccccc2)cc(Cl)c2ncccc12] |
| 2.041 | 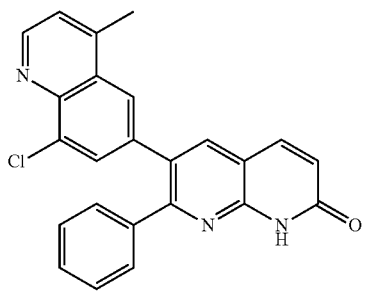 [SMILES: Cc1ccnc2c(Cl)cc(-c3cc4ccc(=O)[nH]c4nc3-c3ccccc3)cc12] |
| 2.042 | 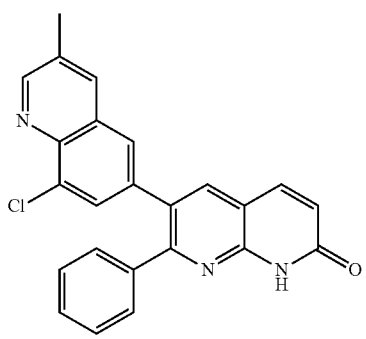 [SMILES: Cc1cnc2c(Cl)cc(-c3cc4ccc(=O)[nH]c4nc3-c3ccccc3)cc2c1] |
| 2.043 | 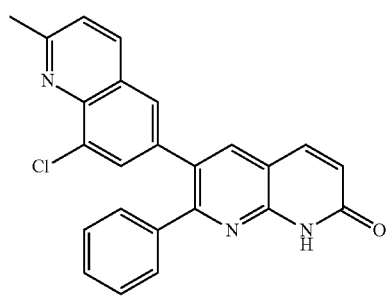 [SMILES: Cc1ccc2cc(-c3cc4ccc(=O)[nH]c4nc3-c3ccccc3)cc(Cl)c2n1] |

In some embodiments, provided herein are compounds described in Table 1, or a tautomer or isomer thereof, or a pharmaceutically acceptable salt of any of the foregoing, and uses thereof.

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. The structure or name is intended to embrace all possible isomers of a compound depicted.

Additionally, the structure or name is intended to embrace tautomeric forms of the compounds described herein. For example, when $R^1$ is hydrogen, the tautomer of Formula (II) is Formula (IIa):

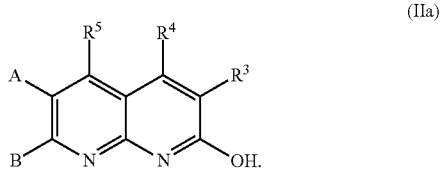

(IIa)

Similarly, when $R^1$ is hydrogen, the tautomer of Formula (III) is Formula (IIIa):

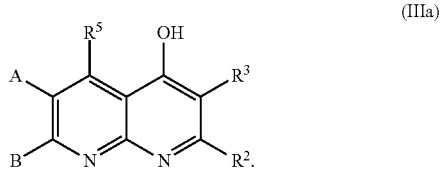

(IIIa)

All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2H$, $^3H$, $^{11}C$, $^{13}C$, $^{14}C$ $^{13}N$, $^{15}O$, $^{17}O$, $^{32}P$, $^{35}S$, $^{18}F$, $^{36}Cl$. Certain isotope labeled compounds (e.g. $^3H$ and $^{14}C$) are useful in compound or substrate tissue distribution study. Incorporation of heavier isotopes such as deuterium ($^2H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate In some embodiments, compounds of the formula (I) may be synthesized according to Scheme 1, 2, 3, 4, or 5.

SCHEME 1

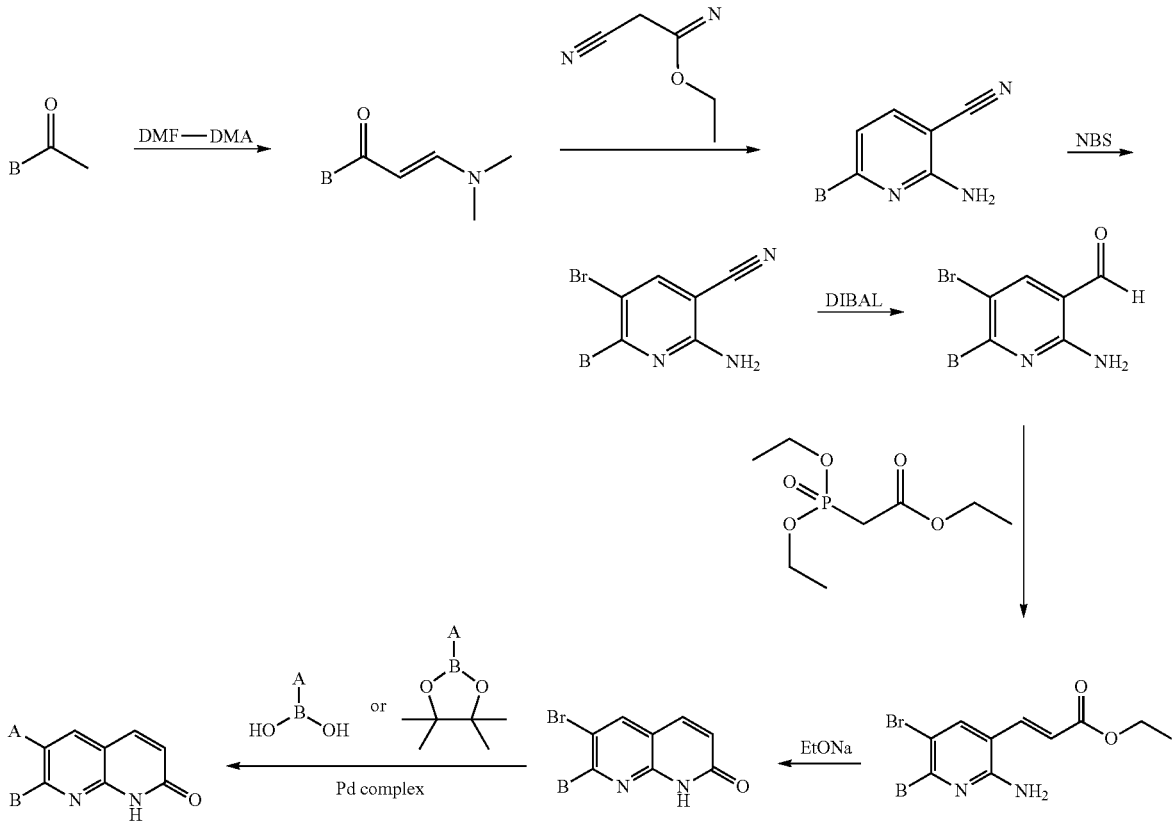

wherein A and B are as defined for formula (I), or any variation thereof detailed herein. It is understood that modifications of Scheme 1 can be made, such as further substitution of the structures depicted. Particular examples are provided in the Example section below.

Scheme 2

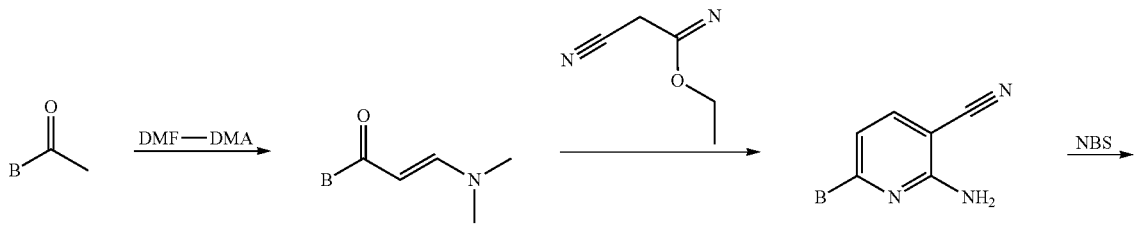

-continued
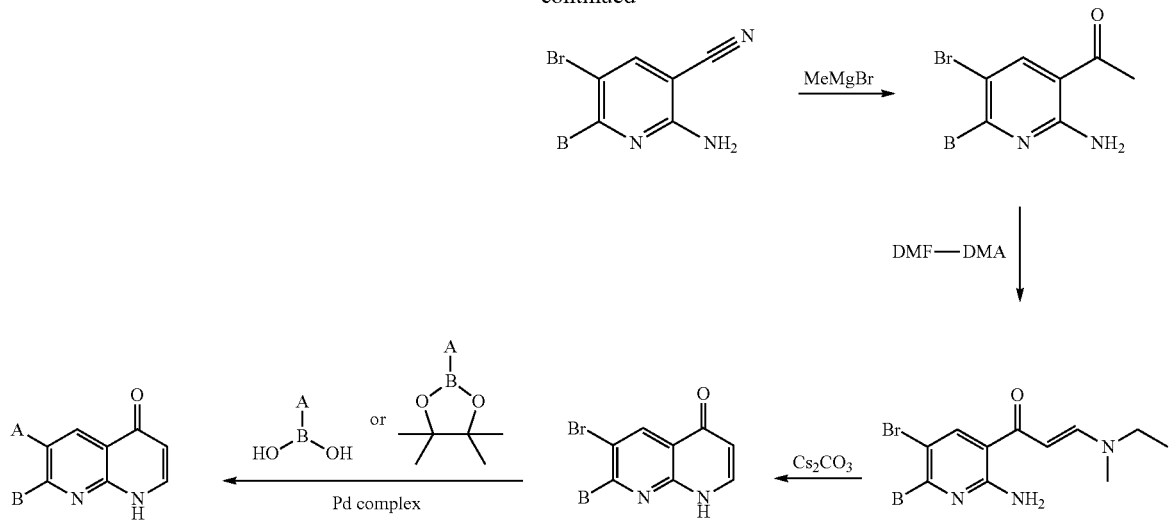
wherein A and B are as defined for formula (I), or any variation thereof detailed herein. It is understood that modifications of Scheme 2 can be made, such as further substitution of the structures depicted. Particular examples are provided in the Example section below.
Scheme 3
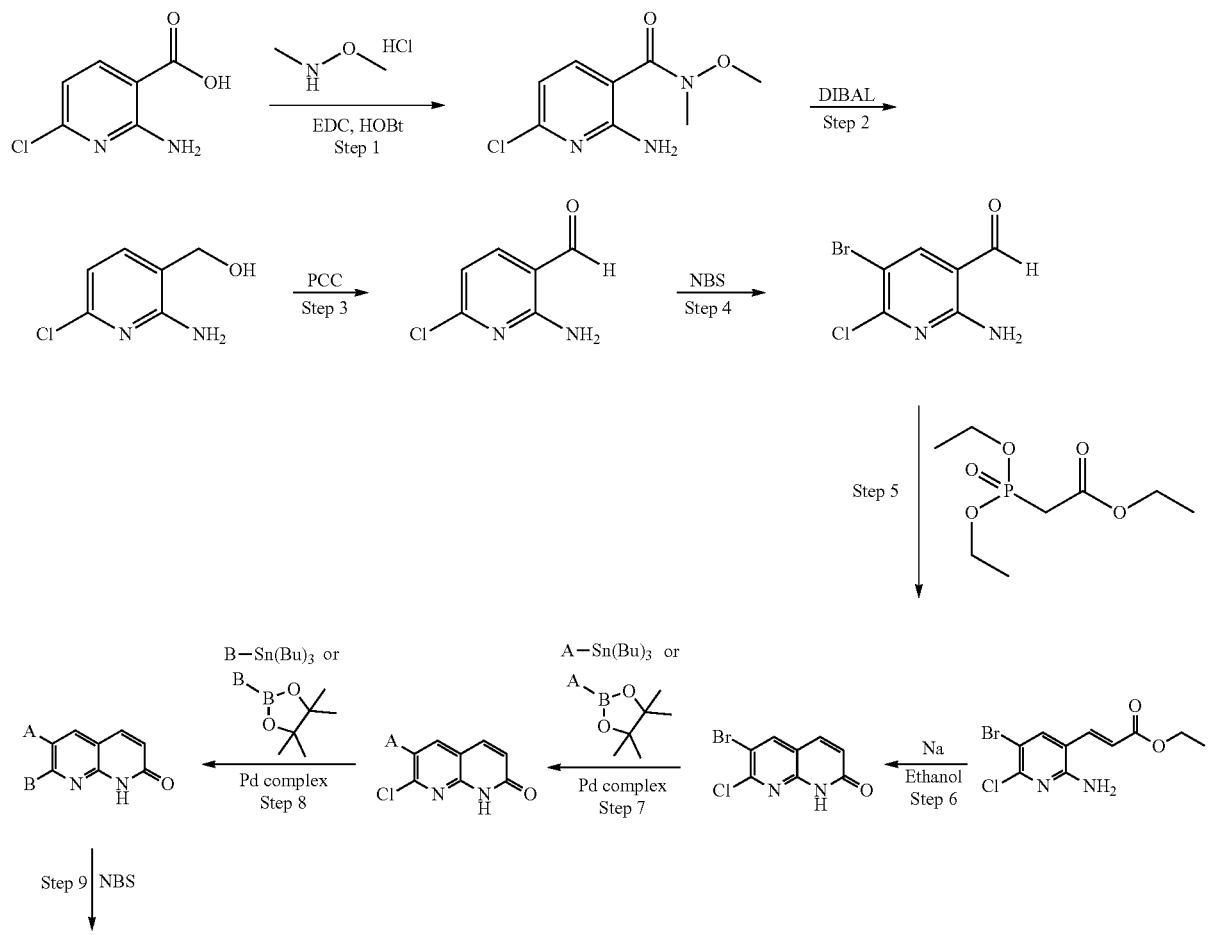

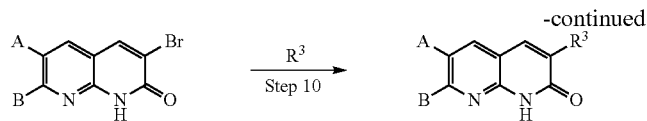
wherein A B and R³ are as defined for formula (I), or any variation thereof detailed herein. It is understood that modifications of Scheme 3 can be made, such as further substitution of the structures depicted. Particular examples are provided in the Example section below.
Scheme 4
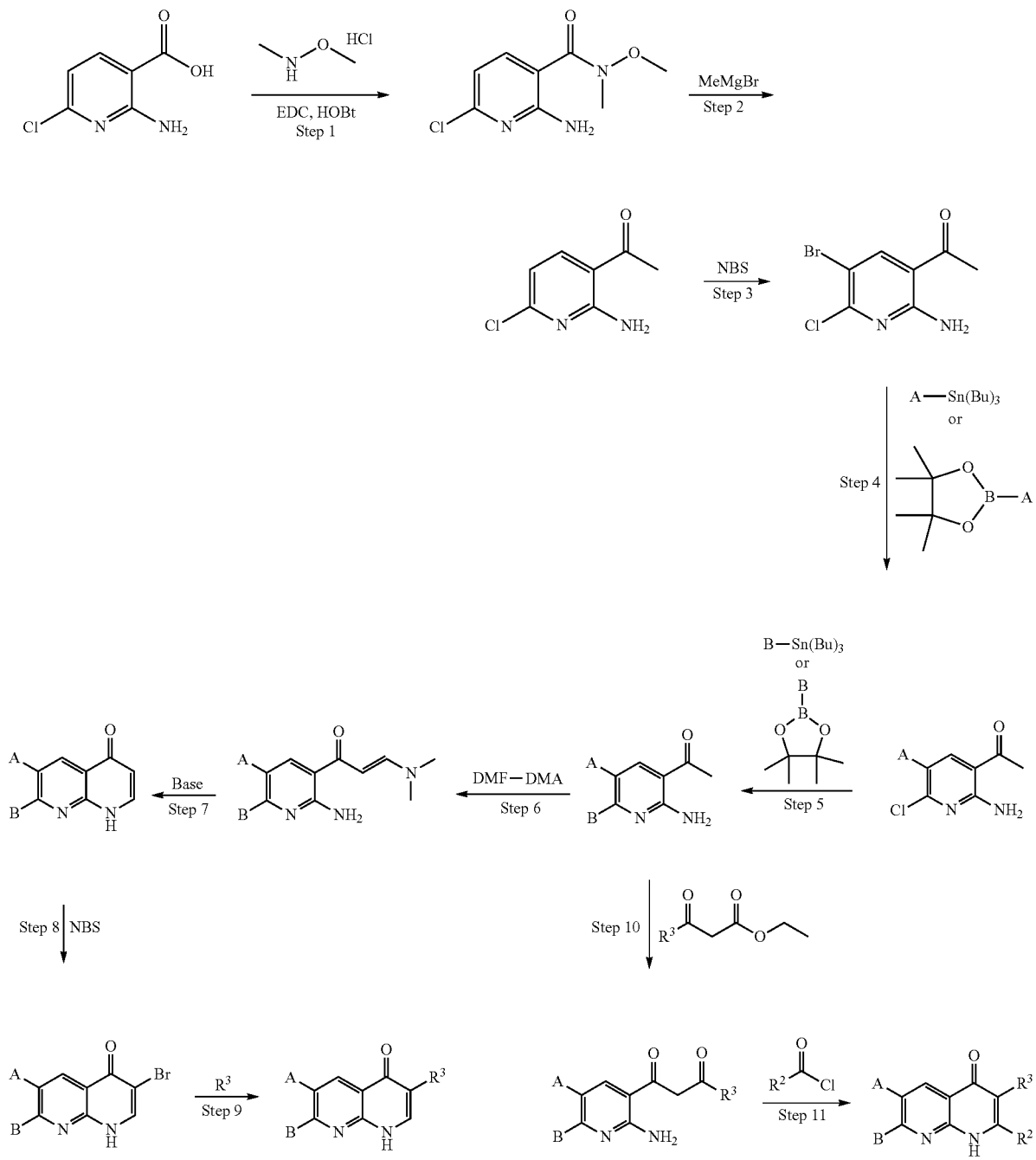

wherein A, B, R² and R³ are as defined for formula (I), or any variation thereof detailed herein. It is understood that modifications of Scheme 4 can be made, such as further substitution of the structures depicted. Particular examples are provided in the Example section below.

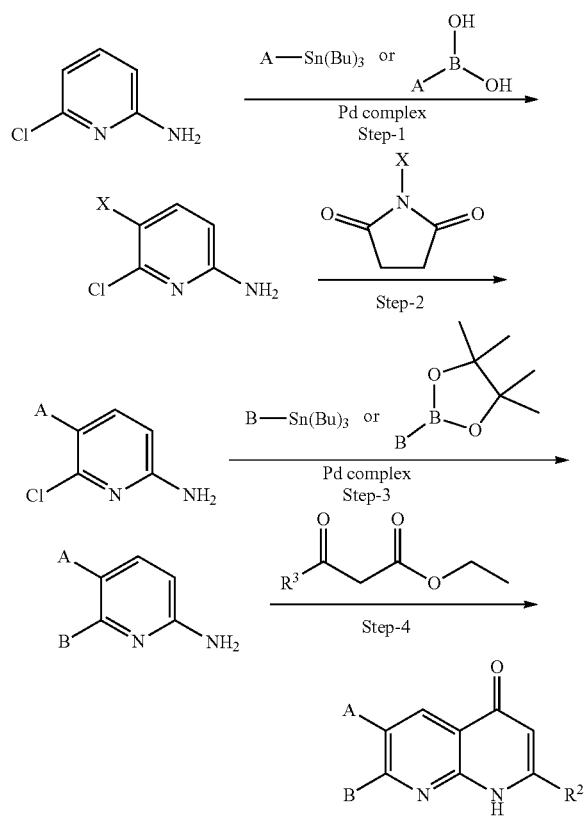

Scheme 5 wherein A, B and R² are as defined for formula (I), or any variation thereof detailed herein. It is understood that modifications of Scheme 4 can be made, such as further substitution of the structures depicted. Particular examples are provided in the Example section below. It is understood that General Synthetic Scheme 1, Scheme 2, Scheme 3, Scheme 4, Scheme 5 and present synthetic routes involving steps clearly familiar to those skilled in the art, wherein the substituents described in compounds of formula (I) herein can be varied with a choice of appropriate starting materials and reagents utilized in the steps presented. Pharmaceutical Compositions and Formulations Pharmaceutical compositions of any of the compounds detailed herein are embraced by this disclosure. Thus, the present disclosure includes pharmaceutical compositions comprising a compound as detailed herein or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20<sup>th</sup> ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease in an individual comprising administering an effective amount of a compound of formula (I) or any embodiment, variation or aspect thereof (collectively, a compound of formula (I) or the present compounds or the compounds detailed or described herein) or a pharmaceutically acceptable salt thereof, to the individual. In some embodiments, provided herein is a method of treating a disease mediated by a G protein coupled receptor signaling pathway in an individual comprising administering an effective amount of a compound of formula (I), or a pharmaceutically acceptable salt thereof, to the individual. In some embodiments, the disease is mediated by a class A G protein coupled receptor. In some embodiments, the disease is mediated by a class B G protein coupled receptor. In some embodiments, the disease is mediated by a class C G protein coupled receptor. In some embodiments, the G protein coupled receptor is a purinergic G protein receptor. In some embodiments, the G protein coupled receptor is an adenosine receptor, such as any of the $A_1$, $A_{2A}$, $A_{2B}$, and $A_3$ receptors.

The present compounds or salts thereof are believed to be effective for treating a variety of diseases and disorders. For example, in some embodiments, the present compositions may be used to treat a proliferative disease, such as cancer. In some embodiments the cancer is a solid tumor. In some embodiments the cancer is any of adult and pediatric oncology, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In some embodiments, the present compounds or salts thereof are used in treatment of tumors which produce high levels of ATP and/or adenosine. For example, in some embodiments the extracellular concentration of adenosine is 10-20 times higher in the tumor compared to adjacent tissue. In some embodiments, the present compounds or salts thereof are used in treatment of tumors that express high levels of an ectonucleotidase. In some embodiments, the ectonucleotidase is CD39. In some embodiments, the ectonucleotidase is CD73.

Also provided herein is a method of enhancing an immune response in an individual in need thereof comprising administering an effective amount of a compound of formula (I), or a pharmaceutically acceptable salt thereof, to the individual. Adenosine receptors are known to play an immunosuppressive role in cancer biology. High levels of adenosine present in the tumor microenvironment bind to adenosine receptors on immune cells to provide an immunosuppressive microenvironment. Specifically, binding of adenosine to the $A_{2A}$ receptor provides an immunosuppressive signal that inhibits T cell proliferation, cytokine production and cytotoxicity. The $A_{2A}$ receptor signaling has been implicated in adenosine-mediated inhibition of NK cell cytotoxicity, NKT cell cytokine production and CD40L upregulation. Therefore, use of an $A_{2A}$ receptor antagonist, such as those provided herein, may reverse the immunosuppressive effect of adenosine on immune cells. In some embodiments, the immune response is enhanced by a compound of formula (I) or a salt thereof enhancing activity of natural killer (NK) cells. In some embodiments, the present compounds or salts thereof increase NK cell-meditated cytotoxicity. In some embodiments, the immune response is enhanced by enhancing the activity of $CD8^+$ T cells. In some embodiments, the present compounds or salts thereof cause an inflammatory response in the tumor microenvironment.

The present disclosure further provides a method of increasing the activity of a natural killer cell in an individual comprising administering an effective amount of a compound of formula (I), or a pharmaceutically acceptable salt thereof, to the individual. In some of these embodiments, the present compounds or salts thereof increase NK cell-meditated cytotoxicity. In some embodiments, a compound of formula (I) or a salt thereof increases the number of NK cells.

A compound of formula (I) or a salt thereof may be useful for modulating the activity of G protein receptor coupled signaling pathway proteins. In some embodiments, a compound of formula (I) or a salt thereof activates a G protein receptor coupled signaling pathway protein (i.e. is an agonist of a G protein receptor). In some embodiments, a compound of formula (I) or a salt thereof inhibits a G protein receptor coupled signaling pathway protein (i.e., is a G protein receptor antagonist). In some embodiments, a compound of formula (I) or a salt thereof is an adenosine receptor antagonist. In some embodiments, a compound of formula (I) or a salt thereof is an antagonist of any of the $A_1$, $A_{2A}$, $A_{2B}$, and $A_3$ receptors.

Accordingly, also provided herein is a method of modulating the activity of an $A_{2A}$ receptor in an individual comprising administering an effective amount of a compound of formula (I), or a pharmaceutically acceptable salt thereof to an individual. In some embodiments a compound of formula (I) or a salt thereof is an $A_{2A}$ receptor antagonist. In some embodiments, a compound of formula (I) or a salt thereof reduces $A_{2A}$ receptor signaling by at least 10%, 20%, 30%, 40%, 50%, 60%, 70%, 80%, 90%, 91%, 92%, 93%, 94%, 95%, 96%, 97%, 98%, or 99%. In some embodiments, a compound of formula (I) or a salt thereof reduces $A_{2A}$ receptor signaling by 40-99%, 50-99%, 60-99%, 70-99%, 80-99%, 90-99%, or 95-99%. In some of these embodiments, a compound of formula (I) or a salt thereof binds to the $A_{2A}$ receptor with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 10 nM, less than 1 nM or less than 100 pM. In some embodiments, [compound x] binds to the $A_{2A}$ receptor with an $IC_{50}$ of 500 nM to 100 pM, 400 nM to 100 pM, 300 nM to 100 pM, 200 nM to 100 pM, or 100 nM to 100 pM.

Also provided herein is a method of modulating the activity of an $A_{2B}$ receptor in an individual comprising administering an effective amount of a compound of formula (I), or a pharmaceutically acceptable salt thereof to an individual. In some embodiments a compound of formula (I) or a salt thereof is an $A_{2B}$ receptor antagonist. In some embodiments, a compound of formula (I) or a salt thereof reduces $A_{2B}$ receptor signaling by at least 10%, 20%, 30%, 40%, 50%, 60%, 70%, 80%, 90%, 91%, 92%, 93%, 94%, 95%, 96%, 97%, 98%, or 99%. In some embodiments, a compound of formula (I) or a salt thereof reduces $A_{2B}$ receptor signaling by 40-99%, 50-99%, 60-99%, 70-99%, 80-99%, 90-99%, or 95-99%. In some of these embodiments, a compound of formula (I) or a salt thereof binds to the $A_{2B}$ receptor with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 10 nM, less than 1 nM or less than 100 pM. In some embodiments, a compound of formula (I) or a salt thereof binds to the $A_{2B}$ receptor with an $IC_{50}$ of 500 nM to 100 pM, 400 nM to 100 pM, 300 nM to 100 pM, 200 nM to 100 pM, or 100 nM to 100 pM.

Also provided herein is a method of modulating the activity of an $A_3$ receptor in an individual comprising administering an effective amount of a compound of formula (I), or a pharmaceutically acceptable salt thereof to an individual. In some embodiments a compound of formula (I) or a salt thereof is an $A_3$ receptor antagonist. In some embodiments, a compound of formula (I) or a salt thereof reduces $A_3$ receptor signaling by at least 10%, 20%, 30%, 40%, 50%, 60%, 70%, 80%, 90%, 91%, 92%, 93%, 94%, 95%, 96%, 97%, 98%, or 99%. In some embodiments, a compound of formula (I) or a salt thereof reduces $A_3$ receptor signaling by 40-99%, 50-99%, 60-99%, 70-99%, 80-99%, 90-99%, or 95-99%. In some of these embodiments, a compound of formula (I) or a salt thereof binds to the $A_3$ receptor with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 10 nM, less than 1 nM or less than 100 pM. In some embodiments, a compound of formula (I) or a salt thereof binds to the $A_3$ receptor with an $IC_{50}$ of 500 nM to 100 pM, 400 nM to 100 pM, 300 nM to 100 pM, 200 nM to 100 pM, or 100 nM to 100 pM.

In some embodiments, the present invention comprises a method of inhibiting tumor metastasis in an individual in need thereof comprising administering a compound of formula (I), or a pharmaceutically acceptable salt thereof, to the individual. In some embodiments, the metastasis is to the lung, liver, lymph node, bone, adrenal gland, brain, peritoneum, muscle, or vagina. In some embodiments, a compound of formula (I) or a salt thereof inhibits metastasis of melanoma cells. In some embodiments, the present disclosure includes a method of delaying tumor metastasis comprising administering a compound of formula (I), or a pharmaceutically acceptable salt thereof, to the individual. In some of these embodiments, the time to metastatic is delayed by 1 month, 2 months 3 months, 4 months, 5 months, 6 months, 12 months, or more, upon treatment with the compounds of the present invention.

In some embodiments, a compound of formula (I) or a salt thereof is used to treat an individual having a proliferative disease, such as cancer as described herein. In some embodiments, the individual is at risk of developing a proliferative disease, such as cancer. In some of these embodiments, the individual is determined to be at risk of developing cancer based upon one or more risk factors. In some of these embodiments, the risk factor is a family history and/or gene associated with cancer. In some embodiments, the individual has a cancer that expresses a high level of a nucleotide metabolizing enzyme. In some embodiments, the nucleotide metabolizing enzyme is a nucleotidase, such as CD73 (ecto-5'-nucleotidase, Ecto5'NTase). In some of these embodiments, the individual has a cancer that expresses a high level of a nucleotidase, such as CD73. In any of these embodiments, the nucleotide metabolizing enzyme is an ecto-nucleotidase. In some embodiments, the ecto-nucleotidase degrades adenosine monophosphate. In some embodiments, the nucleotide metabolizing enzyme is CD39 (ecto-nucleoside triphosphate diphosphohydrolase 1, E-NTPDase1). In some of these embodiments, the individual has a cancer that expresses a high level of CD39. In some embodiments, the individual has a cancer that expresses a high level of an adenosine receptor, such as the $A_{2A}$ receptor.

Combination Therapy

As provided herein, the presently disclosed compounds or a salt thereof may activate the immune system by modulating the activity of a G protein coupled receptor signaling pathway, for example acting as an $A_{2A}$ receptor antagonist, which results in significant anti-tumor effects. Accordingly, the present compounds or a salt thereof may be used in combination with other anti-cancer agents to enhance tumor immunotherapy. In some embodiments, provided herein is a method of treating a disease mediated by a G protein coupled receptor signaling pathway in an individual comprising administering an effective amount of a compound of formula (I), or a pharmaceutically acceptable salt thereof, and an additional therapeutic agent to the individual. In some embodiments, the disease mediated by a G protein coupled receptor signaling pathway is a proliferative disease such as cancer.

In some embodiments, the additional therapeutic agent is a cancer immunotherapy. In some embodiments, the additional therapeutic agent is an immunostimulatory agent. In some embodiments, the additional therapeutic agent targets a checkpoint protein. In some embodiments, the additional therapeutic agent is effective to stimulate, enhance or improve an immune response against a tumor.

In another aspect, provided herein is a combination therapy in which a compound of formula (I) is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of formula (I) or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. As another example, provided is a method for stimulating an immune response in a subject comprising administering to the subject a compound of formula (I) or a salt thereof and one or more immunostimulatory antibodies or immunotherapy like Chimeric antigen receptor (CAR) T-cell therapy; immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of formula (I) or a salt thereof and an anti-PD-1 antibody. In another embodiment, the subject is administered a compound of formula (I) or a salt thereof and an anti-PD-L1 antibody. In yet another embodiment, the subject is administered a compound of formula (I) or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody). In another embodiment, the subject is administered a compound of formula (I) or a salt thereof and CAR T-cells (genetically modified T cells).

In one embodiment, the present disclosure provides a method for treating a proliferative disease (e.g., cancer), comprising administering a compound of formula (I) or a salt thereof and an anti-PD-1 antibody to a subject. In further embodiments, a compound of formula (I) or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of formula (I) or a salt thereof and a subtherapeutic dose of anti-PD-1 antibody to a subject. In certain embodiments, the subject is human. In certain embodiments, the anti-PD-1 antibody is a human sequence monoclonal antibody In one embodiment, the present invention provides a method for treating a hyperproliferative disease (e.g., cancer), comprising administering a compound of formula (I) or a salt thereof and an anti-PD-L1 antibody to a subject. In further embodiments, a compound of formula (I) or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of formula (I) or a salt thereof and a subtherapeutic dose of anti-PD-L1 antibody to a subject. In certain embodiments, the subject is human. In certain embodiments, the anti-PD-L1 antibody is a human sequence monoclonal antibody.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of formula (I) or a salt thereof can be administered sequentially, such as anti-CTLA-4 antibody being administered first and a compound of formula (I) or a salt thereof second, or a compound of formula (I) or a salt thereof being administered first and anti-CTLA-4 antibody second. Additionally or alternatively, an anti-PD-1 antibody and a compound of formula (I) or a salt thereof can be administered sequentially, such as anti-PD-1 antibody being administered first and a compound of formula (I) or a salt thereof second, or a compound of formula (I) or a salt thereof being administered first and anti-PD-1 antibody second. Additionally or alternatively, an anti-PD-L1 antibody and a compound of formula (I) or a salt thereof can be administered sequentially, such as anti-PD-L1 antibody being administered first and a compound of formula (I) or a salt thereof second, or a compound of formula (I) or a salt thereof being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof.

Optionally, the combination of a compound of formula (I) or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

A compound of formula (I) or a salt thereof can also be further combined with standard cancer treatments. For example, a compound of formula (I) or a salt thereof can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). Other combination therapies with a compound of formula (I) or a salt thereof include radiation, surgery, or hormone deprivation. Angiogenesis inhibitors can also be combined with a compound of formula (I) or a salt thereof. Inhibition of angiogenesis leads to tumor cell death, which can be a source of tumor antigen fed into host antigen presentation pathways.

In another example, a compound of formula (I) or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of formula (I) or a salt thereof. In an exemplary embodiment, a treatment of a hyperproliferative disease (e.g., a cancer tumor) can include an anti-cancer antibody in combination with a compound of formula (I) or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of formula (I) or a salt thereof.

In some embodiments, a compound of formula (I) or a salt thereof can be combined with an anti-CD73 therapy, such as an anti-CD73 antibody.

In some embodiments, a compound of formula (I) or a salt thereof can be combined with an anti-CD39 therapy, such as an anti-CD39 antibody.

In yet further embodiments, a compound of formula (I) or a salt thereof is administered in combination another G protein receptor antagonist, such as an adenosine $A_1$ and/or $A_3$ antagonist.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits

The present disclosure further provides kits for carrying out the methods of the invention, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Synthetic Examples

Example S1. Synthesis of 6-(3-chloro-4-hydroxyphenyl)-7-phenyl-1H-1,8-naphthyridin-2-one (Compound No. 1.1)

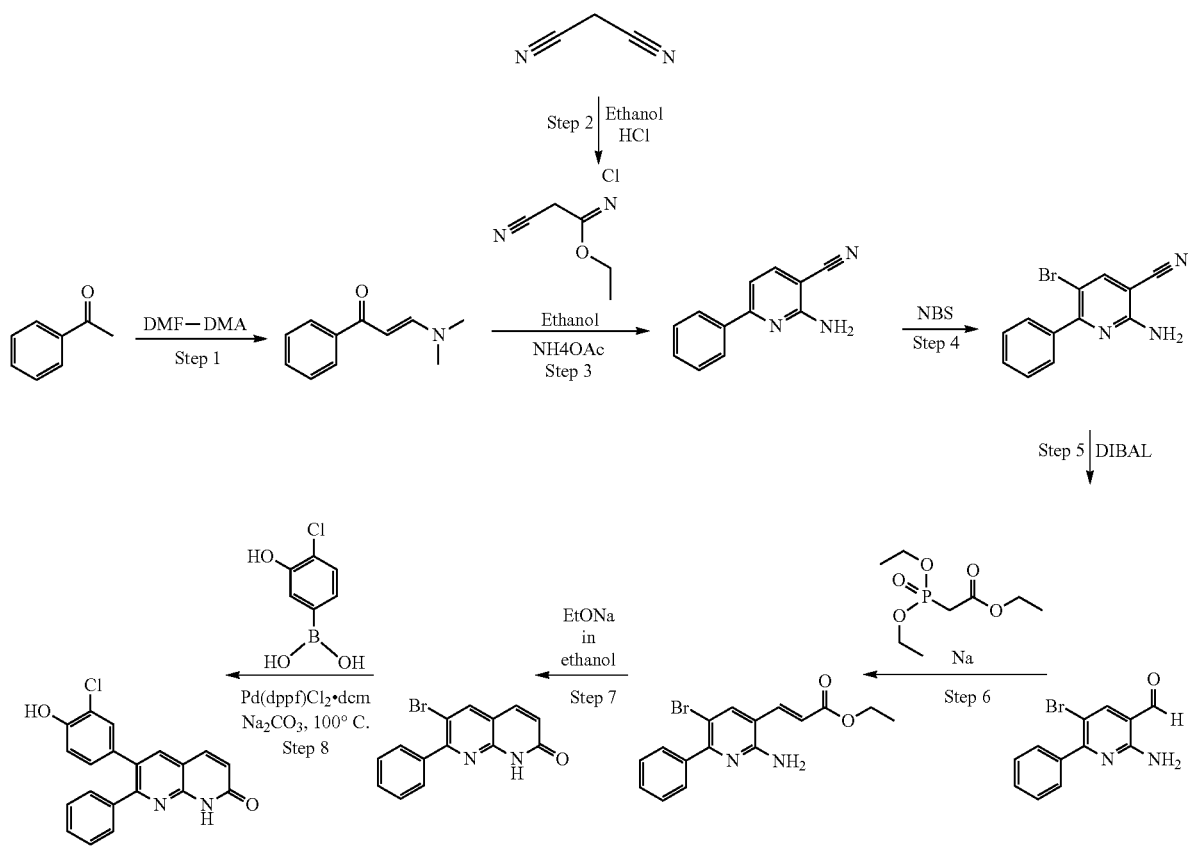

Step 1: Synthesis of (E)-3-(dimethylamino)-1-phenylprop-2-en-1-one

A mixture of DMF.DMA (21.9 g, 300 mmol, 3.6 equiv) and acetophenone (10.0 g, 1.0 equiv, 83 mmol) was heated at 100° C. for 16 h. The reaction mixture was then cooled to RT and diluted with cold water. The yellow precipitates were filtered under vacuum and washed with excess water followed by hexane. The yellow solid (6 g) was used as such for next step without further purification. LCMS: 176 [M+1]$^+$

Step 2: Synthesis of ethyl 2-cyanoacetimidate

To a solution of malononitrile (10 g, 151.52 mmol) in diethyl ether (60 mL) was cooled to 0° C. To this reaction mixture was ethanol (7.0 g, 151.52 mmol, 1 equiv) added 2M HCl in diethyl ether (40 mL) and the reaction mixture was allowed to stir at 10° C. for 16 h. The precipitates formed were filtered and the solid was washed with ether and dried to give the desired product (6 g, 36%).

Step 3: Synthesis of 2-amino-6-phenylnicotinonitrile

To a solution of (E)-3-(dimethylamino)-1-phenyl-prop-2-en-1-one (3.0 g, 18.18 mmol) in ethanol (100 mL) was added ethyl 2-cyanoethanimidate hydrochloride (3.2 g, 1.2 equiv, 21.82 mmol) and ammonium acetate (14 g, 181.8 mmol, 10 equiv) and the reaction mixture was allowed to stir at 85° C. for 16 h. Progress of the reaction was monitored by $^1$H NMR. Reaction mixture was cooled to RT, diluted with cold water (250 mL) and the solid was filtered. The solid was washed with hexane and dried under vacuum to afford 2.9 g (78%) of desired product.

LCMS: 196 [M+1]$^+$

Step 4: Synthesis of 2-amino-5-bromo-6-phenylnicotinonitrile

To a stirred solution of 2-amino-6-phenyl-pyridine-3-carbonitrile (2.80 g, 14.36 mmol, 1.0 equiv) in DMF (40 mL) was added NBS portion wise (2.56 g, 14.36 mmol, 1.0 equiv). The resulting solution was poured over ice to get the precipitates which were filtered under vacuum, washed with excess water and vacuum dried to get the desired product (3 g) which was used as such for next step without further purification.

LCMS: 274 [M+1]$^+$

Step 5: Synthesis of 2-amino-5-bromo-6-phenylnicotinaldehyde

To a stirred solution of 2-amino-5-bromo-6-phenyl-pyridine-3-carbonitrile (1.0 g, 3.64 mmol, 1.0 equiv) in THF (30 mL) was added 1M solution of DIBAL-H in toluene (12.7 mL, 12.7 mmol, 3.5 eq) and the reaction mixture was allowed to stir at 0° C. for 45 min. Progress of the reaction was monitored by TLC and ¹H NMR. To the reaction mixture was added 2M HCl in water (16 mL) dropwise at 0° C. and the reaction mixture was allowed to stir at the same temperature for 10 min. The reaction mixture was basified with saturated sodium carbonate solution (20 mL) and extracted with ethyl acetate (3×75 mL). Combined organic layers were washed (brine), dried (anhydrous Na$_2$SO$_4$) and concentrated under vacuum to get the yellow solid (0.98 g) which was used as such for next step without further purification.

LCMS: 277 [M+1]$^+$

Step 6: Synthesis of ethyl (E)-3-(2-amino-5-bromo-6-phenylpyridin-3-yl)acrylate

To a solution of ethyl 2-diethoxyphosphorylacetate (0.98 g, 4.38 mmol, 1.0 equiv) in THF was added NaH (0.174 g, 4.38 mmol, 1.1 equiv) at 0° C. To this mixture was added 2-amino-5-bromo-6-phenyl-pyridine-3-carbaldehyde (1.10 g, 3.97 mmol, 1.0 equiv). Progress of the reaction was monitored by TLC. The reaction mixture was quenched by adding cold water and extracted by using ethyl acetate. The combined organic layers were washed (brine), dried (anhydrous Na$_2$SO$_4$) and concentrated under vacuum to get the desired product as yellow solid (0.210 g) which was used as such for next step without further purification.

LCMS: 347 [M+1]$^+$

Step 7 Synthesis of 6-bromo-7-phenyl-1,8-naphthyridin-2(1H)-one

Sodium metal (0.106 g, 4.0 equiv, 4.6 mmol) was added to ethanol (2 mL) at 0° C. The resulting mixture was stirred at this temperature for 15 min. Solution of (E)-3-(2-amino-5-bromo-6-phenyl-3-pyridyl)prop-2-enoate (0.400 g, 1.15 mmol, 1.0 equiv) in ethanol (3 mL) was added to the above reaction mixture at 0° C. and the resulting reaction mixture was heated at 80° C. for 16 h. The reaction mixture was cooled to RT and neutralized by adding dilute HCl. The resulting precipitates were filtered, washed with excess water followed by washing with hexane and vacuum dried to get the desired product which was purified by normal phase silica gel flash chromatography to get the desired product (0.300 g).

LCMS: 301 [M+1]$^+$

Step 8: Synthesis of 6-(3-chloro-4-hydroxyphenyl)-7-phenyl-1,8-naphthyridin-2(1H)-one To a stirred solution of 6-bromo-7-phenyl-1H-1,8-naphthyridin-2-one (0.140 g, 0.46 mmol, 1.0 eq) and (4-chloro-3-hydroxy-phenyl)boronic acid (0.104 g, 0.60 mmol, 1.3 eq) in dioxane (3 mL) was added 2M aq. Na$_2$CO$_3$ (0.107 g, 1.0 mmol, 2.2 eq, 0.5 mL). The reaction was purged with N$_2$ for 5 min. Following this Pd(dppf)Cl$_2$.DCM (0.018 g, 5 mol %) was added and N$_2$ was purged again for 5 minute. The reaction was then heated at 100° C. for 2 h. The reaction was allowed to cool to RT and extracted using ethyl acetate (2×30 mL). The combined organic layers were washed (brine), dried (anhydrous Na$_2$SO$_4$) and concentrated under vacuum to get the solid which was purified by supercritical fluid chromatography to get the desired product (0.020 g, 16%).

LCMS: 349 [M+1]$^+$

¹H NMR (400 MHz, DMSO-d$_6$) δ 12.21 (br. s., 1H), 10.26 (s, 1H), 8.16 (s, 1H), 7.98 (d, J=9.78 Hz, 1H), 7.33 (s, 5H), 7.19 (s, 1H), 6.86 (q, J=8.64 Hz, 2H), 6.60 (d, J=10.27 Hz, 1H).

Example S2. Synthesis of 6-(3-chloro-4-hydroxyphenyl)-7-phenyl-1H-1,8-naphthyridin-4-one (Compound No. 1.2)

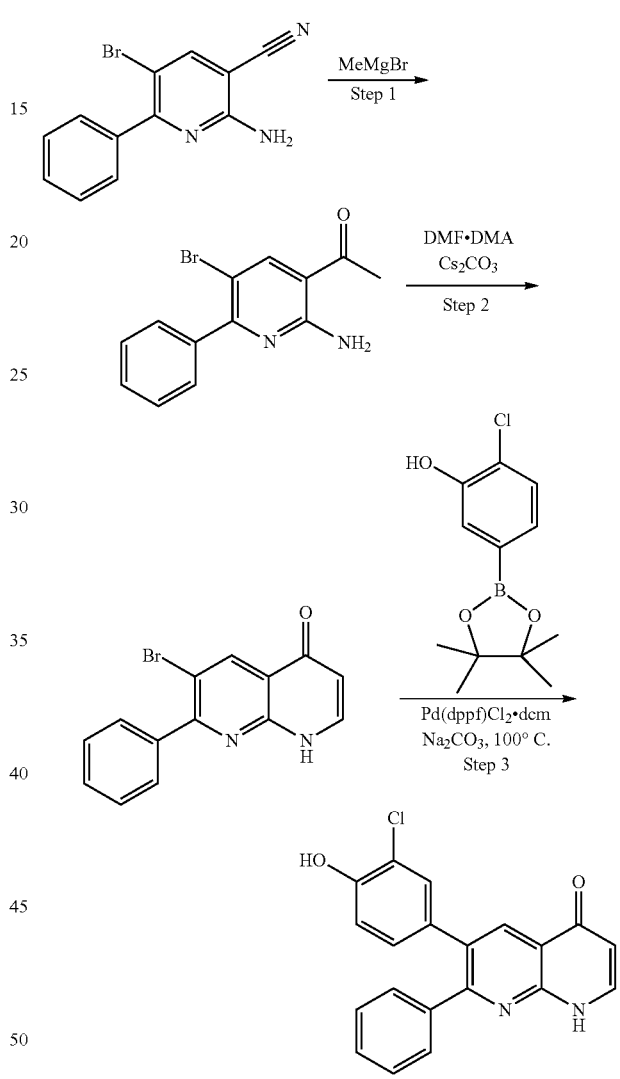

Step 1: Synthesis of 1-(2-amino-5-bromo-6-phenyl-3-pyridyl)ethanone

To a stirred solution of 2-amino-5-bromo-6-phenyl-pyridine-3-carbonitrile (2.0 g, 7.30 mmol, 1.0 eq) in THF (60 mL) was added 3M MeMgBr in diethyl ether (11.0 g, 146.9 mmol, 20.0 equiv) at 0° C. The resulting reaction mixture was stirred at 50° C. for 16 h. Reaction mixture was then cooled to 0° C. and quenched by adding dilute HCl. The acidic reaction mixture was neutralized by using aq. sodium bicarbonate solution and extracted by using ethyl acetate (2×75 mL). The combined organic layers were washed (brine), dried (anhydrous Na$_2$SO$_4$) and concentrated under vacuum to get the light green solid (2.0 g, 94%) which was used as such for next step without further purification

LCMS: 291 [M+1]+

Step 2: Synthesis of
6-bromo-7-phenyl-1H-1,8-naphthyridin-4-one

To a solution of 1-(2-amino-5-bromo-6-phenyl-3-pyridyl)ethanone (2.0 g, 6.89 mmol, 1.0 eq) in DMF (10 mL) was added DMF-DMA (1.5 g, 20.68 mmol, 3.0 equiv). The reaction mixture was warmed to 100° C. After stirring for 3 h, $Cs_2CO_3$ (4.5 g, 13.78 mmol, 2.0 equiv) was added and the reaction was stirred for 16 h at 100° C. The reaction mixture was cooled to 0° C. and diluted with cold water. The resulting precipitates were filtered, washed with excess water and vacuum dried. The solid obtained was purified by normal phase silica gel flash chromatography to get the yellow solid (0.250 g, 12%)

LCMS: 301 [M+1]+

Step 3: Synthesis of 6-(3-chloro-4-hydroxy-phenyl)-7-phenyl-1H-1,8-naphthyridin-4-one To a stirred solution of 6-bromo-7-phenyl-1H-1,8-naphthyridin-4-one (0.120 g, 0.40 mmol, 1.0 eq) and 2-chloro-5-(4,4,5,5-tetramethyl-1,3,2-dioxaborolan-2-yl)phenol (0.127 g, 0.50 mmol, 1.25 eq) in dioxane (5 mL) was added 0.4 mL 2M aq. $Na_2CO_3$ (0.084 g, 0.8 mmol, 2.0 eq) under $N_2$. The reaction was purged with $N_2$ for 5 min. Following this Pd(dppf)$Cl_2$·DCM (0.016 g, 5 mol %) was added and $N_2$ was purged again for another 5 min. The reaction was then heated at 100° C. for 4 h. The reaction was allowed to cool to RT and extracted using ethyl acetate (2×30 mL). The combined organic layers were washed (brine), dried (anhydrous $Na_2SO_4$) and concentrated under vacuum to get the solid which was purified by supercritical fluid chromatography to get the desired product (0.017 g, 12%).

LCMS: 349 [M+1]+

$^1$H NMR (400 MHz, DMSO-$d_6$) δ 12.39 (br. s., 1H), 10.30 (br. s., 1H), 8.32 (s, 1H), 7.99 (br. s., 1H), 7.37 (d, J=2.93 Hz, 5H), 7.18 (d, J=1.96 Hz, 1H), 6.92-7.00 (m, 1H), 6.88 (d, J=8.31 Hz, 1H), 6.16 (d, J=7.34 Hz, 1H).

Example S3. Synthesis of 6-(2,6-dimethylpyridin-4-yl)-7-phenyl-1,8-naphthyridin-4(1H)-one (Compound No. 1.3)

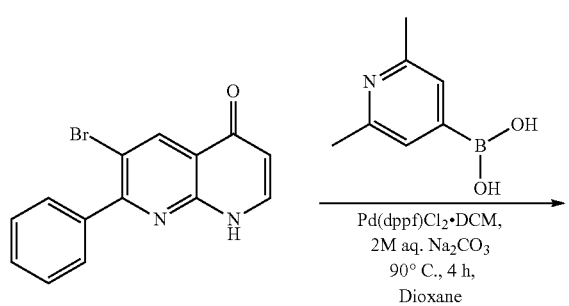

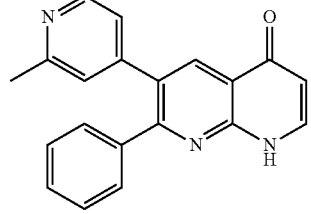

To a stirred solution of (2,6-dimethylpyridin-4-yl)boronic acid (0.73 g, 0.48 mmol, 1.2 equiv) and 6-bromo-7-phenyl-1,8-naphthyridin-4(1H)-one (0.073 g, 0.40 mmol, 1.0 equiv) in dioxane (2 mL) was added $Na_2CO_3$ (0.085 g, 0.80 mmol, 2.0 equiv) and water 0.8 mL. The reaction was purged with $N_2$ for 5 min. To this reaction mixture was added Pd(dppf)$Cl_2$·DCM (0.016 g, 5 mol %) and $N_2$ was re-purged for another 5 min. The reaction mixture was heated at 90° C. for 4 h. The reaction mixture was allowed to cool to RT and extracted using ethyl acetate (2×35 mL). The combined organic layers were washed (brine), dried (anhydrous $Na_2SO_4$) and concentrated under vacuum to get the solid residue which was purified by reverse phase column chromatography to get the desired product as off white solid (0.030 g, 22%).

LCMS: 328 [M+1]+

$^1$H NMR (400 MHz, DMSO-$d_6$) δ 12.37 (d, J=5.38 Hz, 1H), 8.39 (s, 1H), 7.93-8.05 (m, 1H), 7.27-7.47 (m, 5H), 6.89 (s, 2H), 6.15 (d, J=7.34 Hz, 1H), 2.33 (s, 6H).

Example S4. Synthesis of 7-phenyl-6-(quinolin-6-yl)-1,8-naphthyridin-2(1H)-one (Compound No. 1.4)

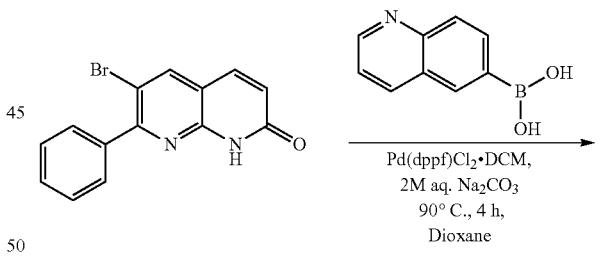

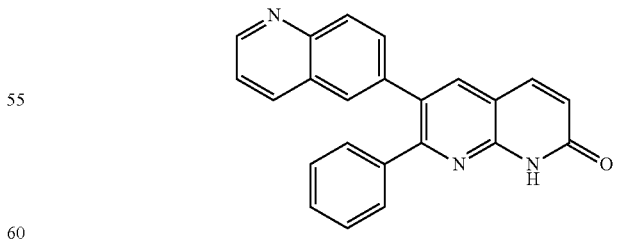

To a stirred solution of quinolin-6-ylboronic acid (0.83 g, 0.48 mmol, 1.2 equiv) and 6-bromo-7-phenyl-1,8-naphthyridin-2(1H)-one (0.120 g, 0.40 mmol, 1.0 equiv) in dioxane (4 mL) was added 2M aqueous $Na_2CO_3$ (0.084 g, 0.80 mmol, 2.0 equiv, 0.4 mL). The reaction was purged with $N_2$ for 5 min. To this reaction mixture was added Pd(dppf)

Cl$_2$.DCM (0.016 g, 5 mol %) and N$_2$ was purged again for another 5 min. The reaction mixture was heated at 90° C. for 4 h. The reaction mixture was allowed to cool to RT and extracted using ethyl acetate (2×35 mL). The combined organic layers were washed (brine), dried (anhydrous Na$_2$SO$_4$) and concentrated under vacuum to get the solid residue which was purified by reverse phase column chromatography to get the desired product as off white solid (0.020 g, 14%).

LCMS: 350 [M+1]$^+$ $^1$H NMR (400 MHz, DMSO-d$_6$): δ 12.32 (br. s., 1H), 9.01 (d, J=2.93 Hz, 1H), 8.54 (d, J=7.83 Hz, 1H), 7.99-8.18 (m, 2H), 7.93 (d, J=8.80 Hz, 1H), 7.70 (dd, J=4.65, 8.07 Hz, 1H), 7.52 (dd, J=1.47, 8.80 Hz, 1H), 7.17-7.41 (m, 5H), 6.65 (d, J=9.78 Hz, 1H).

Example S5. Synthesis of 7-phenyl-6-(quinolin-6-yl)-1,8-naphthyridin-4(1H)-one (Compound No. 1.5)

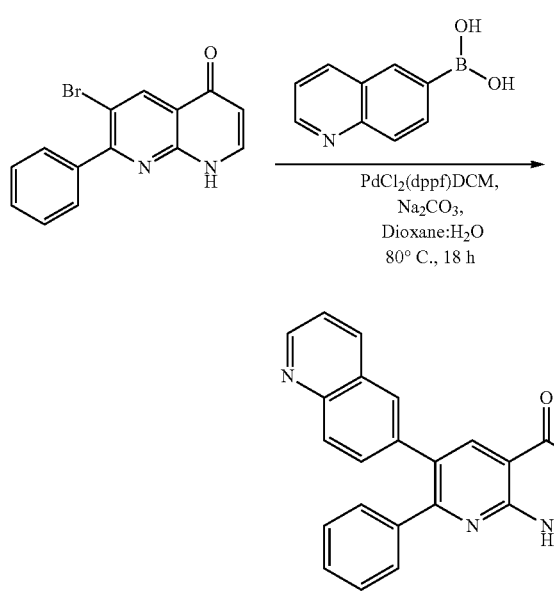

To a solution of 6-bromo-7-phenyl-1,8-naphthyridin-4 (1H)-one (100 mg, 0.33 mmol, 1 eq.) in 1,4 dioxane (8 mL): water (2 mL) was added quinolin-6-ylboronic acid (68 mg, 0.39 mmol, 1.1 eq.), Na$_2$CO$_3$ (70 mg, 0.66 mmol, 2 eq.), PdCl$_2$(dppf).DCM complex (6 mg, 0.008 mmol, 0.025 eq.). The reaction mixture was deoxygenated using N$_2$ atmosphere and the reaction mixture was heated at 80° C. for 18 h. The reaction was monitored by $^1$H NMR and LCMS. The reaction mixture was diluted with water (50 mL) and extracted using ethyl acetate (2×50 mL). The separated organic layer was dried over sodium sulfate and concentrated under reduced pressure. The crude product was purified by reverse phase column chromatography to afford (8 mg, 8%) as desired product (8 mg, 8%).

LCMS: 350 [M+1]$^+$ $^1$H NMR (400 MHz, DMSO-d$_6$) δ 6.18 (d, 1H), 7.30-7.40 (m, 3H), 7.40 (d, 3H), 7.58 (m, 1H), 7.82 (d, 1H), 8.00 (d, 1H), 8.02 (s, 1H), 8.48 (d, 1H), 8.50 (s, 1H), 8.90 (s, 1H).

Example S6. Synthesis of 6-(1H-benzo[d]imidazol-5-yl)-7-phenyl-1,8-naphthyridin-2(1H)-one (Compound No. 1.6)

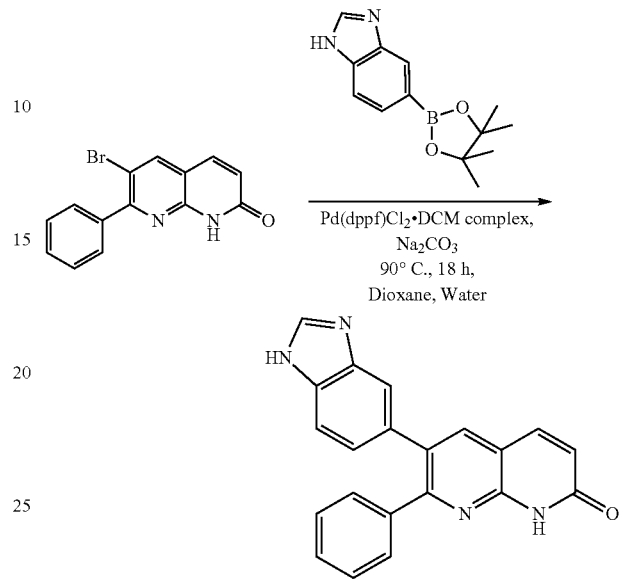

To a stirred solution of 5-(4,4,5,5-tetramethyl-1,3,2-dioxaborolan-2-yl)-1H-benzo[d]imidazole (0.117 g, 0.48 mmol, 1.2 equiv) and 6-bromo-7-phenyl-1,8-naphthyridin-2(1H)-one (0.120 g, 0.40 mmol, 1.0 equiv) in dioxane (3 mL) was added Na$_2$CO$_3$ (0.085 g, 0.80 mmol, 2.0 equiv) and 1 mL water. The reaction was purged with N$_2$ for 5 min. To this reaction mixture was added Pd(dppf)Cl$_2$.DCM complex (0.017 g, 5 mol %) and N$_2$ was purged again for 5 more min. The reaction mixture was heated at 90° C. for 18 h. The reaction mixture was allowed to cool to RT and extracted using ethyl acetate (2×35 mL). The combined organic layers were washed (brine), dried (anhydrous Na$_2$SO$_4$) and concentrated under vacuum to get the solid residue which was purified by reverse phase column chromatography to get the desired product as off white solid (0.015 g, 9%).

LCMS: 339 [M+1]$^+$ $^1$H NMR (400 MHz, DMSO-d$_6$) δ $^1$H NMR (400 MHz, DMSO-d$_6$) 8.14-8.26 (m, 2H), 8.01 (d, J=9.21 Hz, 1H), 7.46 (br. s., 2H), 7.34 (d, J=7.45 Hz, 2H), 7.17-7.30 (m, 3H), 6.97 (d, J=7.89 Hz, 1H), 6.61 (d, J=9.21 Hz, 1H)

Example S7. Synthesis of 6-(1H-benzo[d]imidazol-5-yl)-7-phenyl-1,8-naphthyridin-4(1H)-one (Compound No. 1.7)

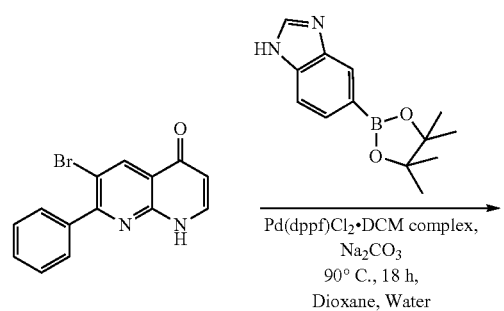

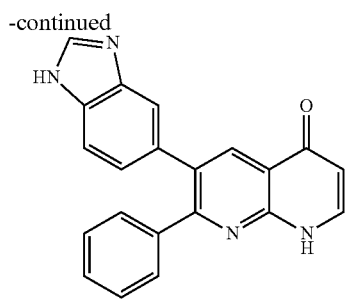

To a stirred solution of 5-(4,4,5,5-tetramethyl-1,3,2-dioxaborolan-2-yl)-1H-benzo[d]imidazole (0.117 g, 0.48 mmol, 1.2 equiv) and 6-bromo-7-phenyl-1,8-naphthyridin-4(1H)-one (0.120 g, 0.40 mmol, 1.0 equiv) in dioxane (3 mL) was added Na$_2$CO$_3$ (0.085 g, 0.80 mmol, 2.0 equiv) and 1 mL water. The reaction was purged with N$_2$ for 5 min. To this reaction mixture was added Pd(dppf)Cl$_2$.DCM complex (0.017 g, 5 mol %) and N$_2$ was purged again for another 5 min. The reaction mixture was heated at 90° C. for 18 h. The reaction mixture was allowed to cool to RT and extracted using ethyl acetate (2×35 mL). The combined organic layers were washed (brine), dried (anhydrous Na$_2$SO$_4$) and concentrated under vacuum to get the solid residue which was purified by reverse phase column chromatography to get the desired product as off white solid (0.010 g, 6%).

LCMS: 339 [M+1]$^+$ $^1$H NMR (400 MHz, DMSO-d$_6$) δ 12.47 (br. s., 1H), 12.28 (br. s., 1H), 8.38 (s, 1H), 8.21 (s, 1H), 7.98 (d, J=7.45 Hz, 1H), 7.46 (br. s., 2H), 7.38 (d, J=7.02 Hz, 2H), 7.19-7.34 (m, 3H), 7.02 (br. s., 1H), 6.13 (d, J=7.45 Hz, 1H)

Example S8. Synthesis of 1-methyl-7-phenyl-6-(quinolin-6-yl)-1,8-naphthyridin-4(1H)-one (Compound No. 1.8)

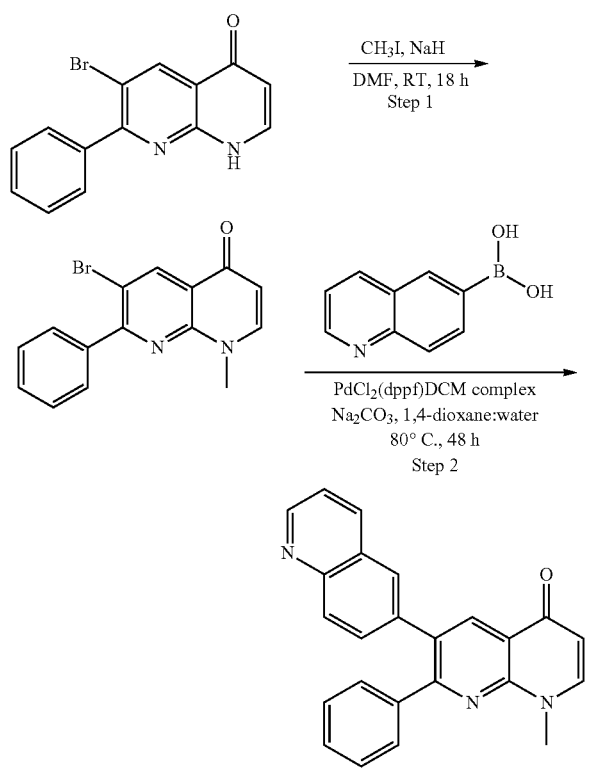

Step 1: Synthesis of 6-bromo-1-methyl-7-phenyl-1,8-naphthyridin-4(1H)-one

To a solution of 6-bromo-7-phenyl-1,8-naphthyridin-4 (1H)-one (150 mg, 0.5 mmol, 1.00 eq.) in DMF (3 mL) was added NaH (30 mg, 0.75 mmol, 1.5 eq) at 0° C. After 10 min methyl iodide (85 mg, 0.6 mmol, 1.2 eq) was added at same temperature, The reaction mixture was stirred at room temperature for 18 h. The reaction mixture was diluted with ice cold water (20 mL) and extracted with ethyl acetate (2×20 ml). The combined organic layer was wash with water (5×20 mL). The organic layer was dried over sodium sulfate and concentrated under reduced pressure to afford the desired product (140 mg, 87%).

LCMS: 316 [M+1]$^+$

Step 2: Synthesis of 1-methyl-7-phenyl-6-(quinolin-6-yl)-1,8-naphthyridin-4(1H)-one To a solution of 6-bromo-1-methyl-7-phenyl-1,8-naphthyridin-4(1H)-one (140 mg, 0.44 mmol, 1 eq.) in 1,4 dioxane (8 mL): water (2 mL) was added quinolin-6-yl boronic acid (84 mg, 0.49 mmol, 1.1 eq.), Na$_2$CO$_3$ (94 mg, 0.89 mmol, 2 eq.), and PdCl$_2$(dppf).DCM complex (18 mg, 0.022 mmol, 0.05 eq). The reaction mixture was deoxygenated using N$_2$ atmosphere followed by heating at 80° C. for 48 h. The reaction was monitored by TLC and LCMS. The reaction mixture was diluted with water (30 mL) and extracted using ethyl acetate (2×50 mL). The separated organic layer was dried over sodium sulfate and concentrated under reduced pressure. The crude product was purified by reverse phase column chromatography to afford the desired product (25 mg, 15%).

LCMS: 364 [M+1]$^+$ $^1$H NMR (400 MHz, DMSO) δ 3.90 (s, 3H), 6.20 (d, 1H), 7.20-7.60 (m, 7H), 7.82 (d, 1H), 8.03 (s, 1H) 8.20 (d, 1H), 8.38 (d, 1H), 8.58 (s, 1H), 8.90 (d, 1H).

Example S9. Synthesis of 6-(isoquinolin-6-yl)-7-phenyl-1,8-naphthyridin-4(1H)-one (Compound No. 1.9)

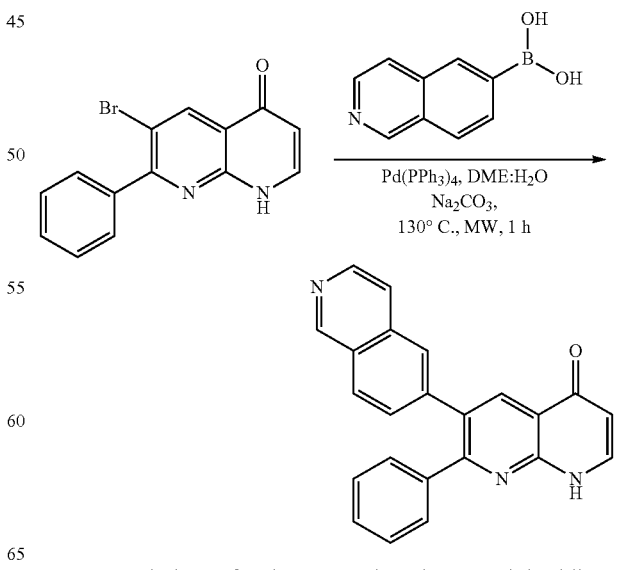

To a solution of 6-bromo-7-phenyl-1,8-naphthyridin-4 (1H)-one (100 mg, 0.33 mmol, 1 eq.) in DME (8 mL): water (2 mL) was added isoquinolin-6-ylboronic acid (63 mg, 0.36 mmol, 1.1 eq.), Na$_2$CO$_3$ (70 mg, 0.66 mmol, 2 eq.), Pd(PPh$_3$)$_4$(11 mg, 0.011 mmol, 0.03 eq). The reaction mixture was deoxygenated using N$_2$ atmosphere and the reaction mixture was heated at 130° C. for 1 h under microwave irradiation. The reaction was monitored by NMR and LCMS. The reaction mixture was diluted with water (30 mL) and extracted using ethyl acetate (2×50 mL). The separated organic layer was dried over sodium sulfate and concentrated under reduced pressure. The crude product was purified by reverse phase column chromatography to afford the desired product as a TFA salt (8 mg, 11%).

LCMS: 350 [M+1]$^+$ $^1$H NMR (400 MHz, DMSO) δ 6.20 (d, 1H), 7.30-7.42 (m, 5H), 7.50 (d, 1H), 8.02 (d, 1H), 8.18 (d, H), 8.22 (s, 1H), 8.58 (s, 1H), 8.60 (d, 1H), 9.50 (s, 1H), 12.42 (bs, 1H).

Example S10. Synthesis of 7-phenyl-6-(quinoxalin-6-yl)-1,8-naphthyridin-2(1H)-one (Compound No. 1.10)

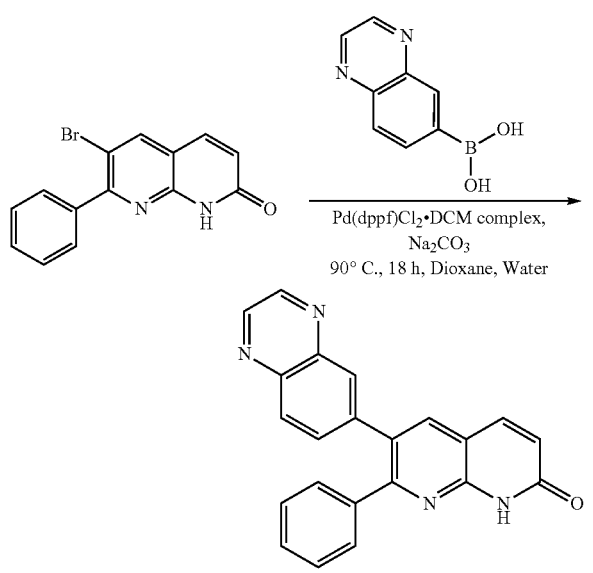

To a stirred solution of quinoxalin-6-ylboronic acid (0.84 g, 0.48 mmol, 1.2 equiv) and 6-bromo-7-phenyl-1,8-naphthyridin-2(1H)-one (0.120 g, 0.40 mmol, 1.0 equiv) in dioxane (3 mL) was added Na$_2$CO$_3$ (0.085 g, 0.80 mmol, 2.0 equiv) and 1 mL water. The reaction was purged with N$_2$ for 5 min. To this reaction mixture was added Pd(dppf)Cl$_2$.DCM complex (0.017 g, 5 mol %) and N$_2$ was purged again for 5 more min. The reaction mixture was heated at 90° C. for 18 h. The reaction mixture was allowed to cool to RT and extracted using ethyl acetate (2×35 mL). The combined organic layers were washed (brine), dried (anhydrous Na$_2$SO$_4$) and concentrated under vacuum to get the solid residue which was purified by reversed phase column chromatography to get the desired product as off white solid (0.006 g, 4%).

LCMS: 351 [M+1]$^+$ $^1$H NMR (400 MHz, DMSO-d$_6$)$^1$H NMR (400 MHz, DMSO-d$_6$) 8.84-8.93 (m, 2H), 8.31 (s, 1H), 8.02-8.14 (m, 2H), 7.91-8.00 (m, 1H), 7.56-7.67 (m, 2H), 7.44 (d, J=7.02 Hz, 2H), 7.17-7.34 (m, 3H), 6.73 (d, J=9.21 Hz, 1H).

Example S11. Synthesis of 2-phenyl-[3,3'-bi(1,8-naphthyridin)]-5(8H)-one (Compound No. 1.11)

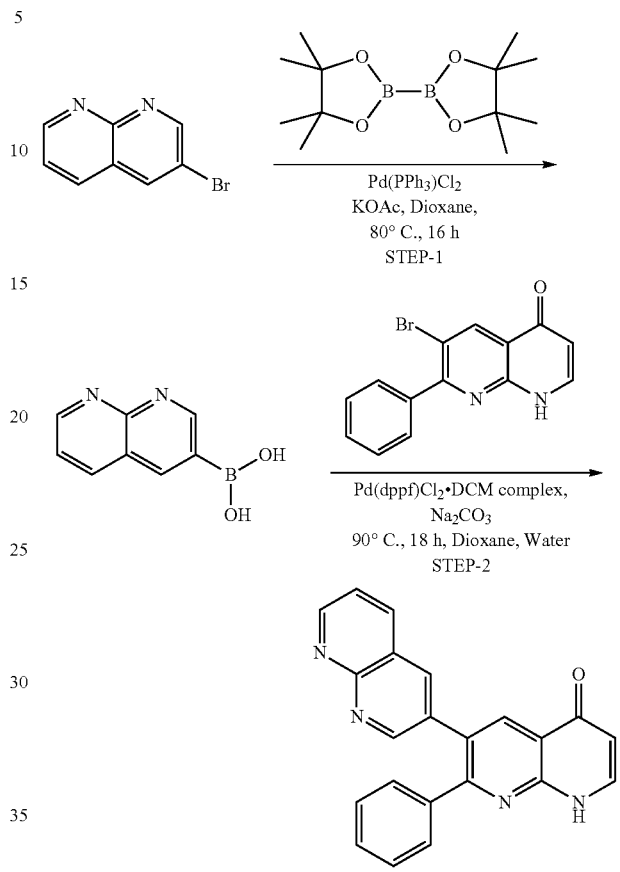

Step 1: Synthesis of (1,8-naphthyridin-3-yl)boronic acid

To a solution of 3-bromo-1,8-naphthyridine (0.160 g, 0.76 mmol, 1 eq.) in 1,4-dioxane (3 mL) was added 5-(4,4,5,5-bis(pinacolato)diboron (0.289 mg, 1.14 mmol, 1.5 eq.), KOAc (0.224 g, 2.28 mmol, 3 eq.), and Pd(PPh$_3$)Cl$_2$ complex (0.026 g, 0.038 mmol, 0.05 eq.). The reaction mixture was deoxygenated with N$_2$ allowed stir at 80° C. for 16 h. The reaction mixture was cooled to RT and filtered through Celite. The filtrate was concentrated (0.120 g, 90%) and used for next step without further purification.

LCMS: 175 [M+1]$^+$

Step 2: Synthesis of 2-phenyl-[3,3'-bi(1,8-naphthyridin)]-5(8H)-one

To a stirred solution of (1,8-naphthyridin-3-yl)boronic acid (0.068 g, 0.39 mmol, 1.2 equiv) and 6-bromo-7-phenyl-1,8-naphthyridin-4(1H)-one (0.100 g, 0.33 mmol, 1.0 equiv) in dioxane (3 mL) was added Na$_2$CO$_3$ (0.069 g, 0.66 mmol, 2.0 equiv) and 1 mL water. The reaction was purged with N$_2$ for 5 min. To this reaction mixture was added Pd(dppf)Cl$_2$.DCM complex (0.014 g, 5 mol %) and N$_2$ was purged again for another 5 min. The reaction mixture was heated at 90° C. for 18 h. The reaction mixture was allowed to cool to RT and extracted using ethyl acetate (2×35 mL). The combined organic layers were washed (brine), dried (anhydrous Na$_2$SO$_4$) and concentrated under vacuum to get the solid residue which was purified by reversed phase column chromatography to get the desired product as off white solid (0.040 g, 29%).

LCMS: 351 [M+1]$^+$ $^1$H NMR (400 MHz, DMSO-d$_6$) δ 12.52 (br. s., 1H), 9.14 (br. s., 1H), 8.70 (d, J=5.26 Hz, 2H), 8.48-8.67 (m, 2H), 8.05 (d, J=7.45 Hz, 1H), 7.78 (d, J=3.95 Hz, 1H), 7.24-7.48 (m, 4H), 6.21 (d, J=7.89 Hz, 1H)

Example S12. Synthesis of 6-(8-chloroquinolin-6-yl)-7-phenyl-1,8-naphthyridin-2 (1H)-one (Compound No. 1.12)

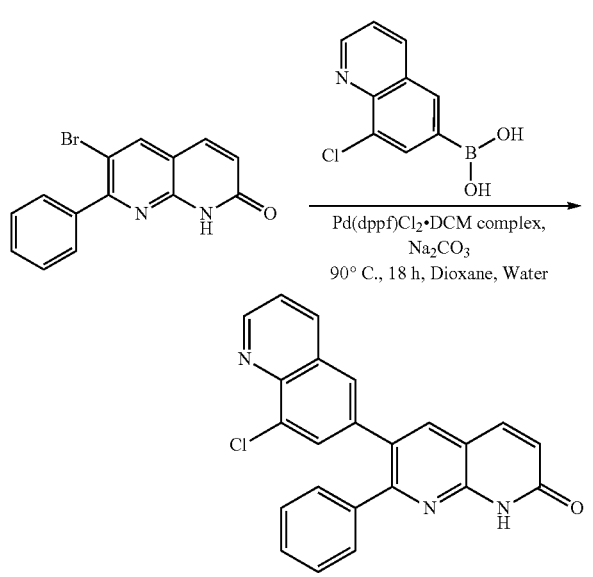

To a stirred solution of (8-chloroquinolin-6-yl)boronic acid (0.083 g, 0.40 mmol, 1.2 equiv) and 6-bromo-7-phenyl-1,8-naphthyridin-2(1H)-one (0.100 g, 0.33 mmol, 1.0 equiv) in dioxane (3 mL) was added Na$_2$CO$_3$ (0.070 g, 0.66 mmol, 2.0 equiv) and 1 mL water. The reaction was purged with N$_2$ for 5 min. To this reaction mixture was added Pd(dppf)Cl$_2$.DCM complex (0.014 g, 5 mol %) and N$_2$ was purged again for another 5 min. The reaction mixture was heated at 90° C. for 18 h. The reaction mixture was allowed to cool to RT and extracted using ethyl acetate (2×35 mL). The combined organic layers were washed (brine), dried (anhydrous Na$_2$SO$_4$) and concentrated under vacuum to get the solid residue which was purified by reversed phase column chromatography to get the desired product as off white solid (0.013 g, 10%).

LCMS: 384 [M+1]$^+$ $^1$H NMR (400 MHz, DMSO-d$_6$) δ$^1$H NMR (400 MHz, DMSO-d$_6$) 12.34 (br. s., 1H), 9.01 (d, J=3.07 Hz, 1H), 8.30-8.46 (m, 2H), 8.03 (d, J=9.21 Hz, 1H), 7.94 (s, 1H), 7.57-7.73 (m, 2H), 7.23-7.45 (m, 5H), 6.66 (d, J=9.65 Hz, 1H)

Example S13. Synthesis of 6-(8-chloroquinolin-6-yl)-7-phenyl-1,8-naphthyridin-4(1H)-one (Compound No. 1.13)

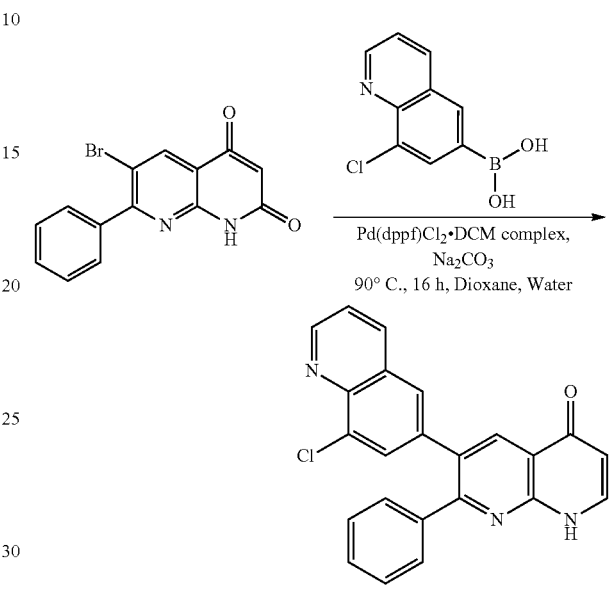

To a stirred solution of 6-bromo-7-phenyl-1,8-naphthyridin-4(1H)-one (0.100 g, 0.33 mmol, 1.0 equiv) and (8-chloroquinolin-6-yl)boronic acid (0.083 g, 0.40 mmol, 1.2 equiv) in dioxane (3 mL) was added Na$_2$CO$_3$ (0.070 g, 0.66 mmol, 2.0 equiv) and 1 mL water. The reaction was purged with N$_2$ for 5 min. To this reaction mixture was added Pd(dppf)Cl$_2$.DCM complex (0.014 g, 5 mol %) and N$_2$ was purged again for another 5 min. The reaction mixture was heated at 90° C. for 16 h. The reaction mixture was allowed to cool to RT and extracted using ethyl acetate (2×35 mL). The combined organic layers were washed (brine), dried (anhydrous Na$_2$SO$_4$) and concentrated under vacuum to get the solid residue which was purified by reversed phase column chromatography to get the desired product as off white solid (0.010 g, 10%).

LCMS: 384 [M+1]$^+$ $^1$H NMR (400 MHz, DMSO-d$_6$) δ 9.01 (d, J=2.63 Hz, 1H), 8.55 (s, 1H), 8.43 (d, J=7.02 Hz, 1H), 7.97-8.11 (m, 2H), 7.66 (dd, J=4.38, 8.33 Hz, 1H), 7.59 (d, J=1.75 Hz, 1H), 7.28-7.45 (m, 5H), 6.18 (d, J=7.45 Hz, 1H)

Example S14. Synthesis of 7-(furan-2-yl)-6-(quinolin-6-yl)-1,8-naphthyridin-4(1H)-one (Compound No. 1.14)

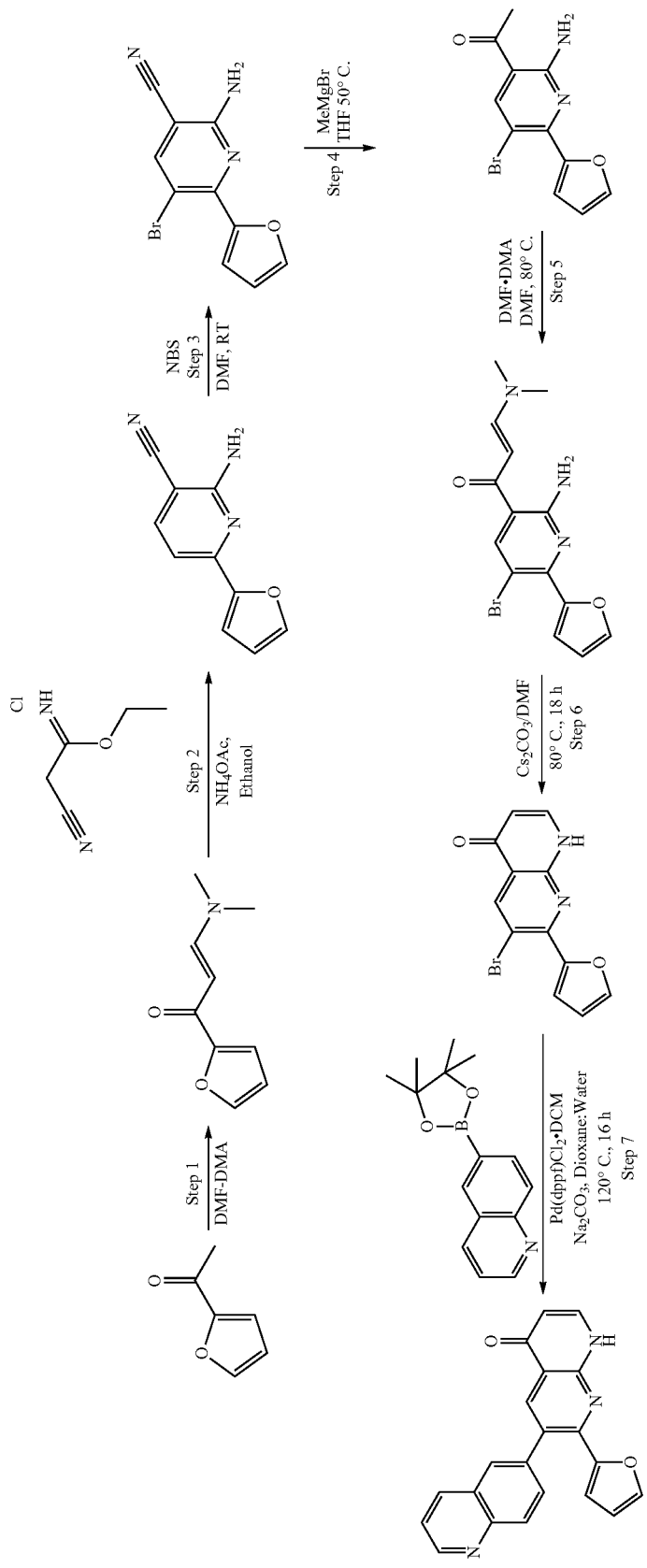

Step 1: Synthesis of 3-(dimethylamino)-1-(furan-2-yl)prop-2-en-1-one

A mixture of DMF.DMA (21.9 g, 297.17 mmol, 3.6 eq) and 1-(furan-2-yl)ethanone (10.0 g, 90.81 mmol, 1.0 eq,) was heated at 100° C. for 16 h. The reaction mixture was then cooled to RT and diluted with cold water. The yellow precipitates were filtered under vacuum and washed with excess water followed by hexane. The yellow solid (13.4 g, 88%) was used as such for next step without further purification.

LCMS: 166 [M+1]$^+$

Step 2: Synthesis of 2-amino-6-(furan-2-yl)nicotinonitrile

To a solution of 3-(dimethylamino)-1-(furan-2-yl)prop-2-en-1-one (9.0 g, 54.54 mmol. 1.00 eq) in ethanol (200 mL) was added ethyl 2-cyanoethanimidate hydrochloride (9.68 g, 1.2 eq, 65.45 mmol) and ammonium acetate (48.50 g, 54.5 mmol, 10 eq). The reaction mixture was allowed to stir at 85° C. for 16 h. Progress of the reaction was monitored by LCMS. Reaction mixture was cooled to RT, diluted with cold water (250 mL) and the solid was filtered. The solid was washed with hexane and dried under vacuum to afford the desired product (5.7 g, 57%).

LCMS: 186 [M+1]$^+$

Step 3: Synthesis of 2-amino-5-bromo-6-(furan-2-yl)nicotinonitrile

To a stirred solution of 2-amino-6-(furan-2-yl)nicotinonitrile (3.0 g 16.21 mmol, 1.0 equiv) in DMF (120 mL) was added NBS portion wise (2.88 g, 16.21 mmol, 1.0 equiv). The reaction mixture was allowed to stir at RT. The progress of the reaction was monitored by TLC. After completion of the reaction the reaction mixture was poured over ice to get the precipitates which were filtered under vacuum, washed with excess water and vacuum dried to get the desired product (2.2 g, 52%) which was used as such for next step without further purification.

LCMS: 264 [M+1]$^+$

Step 4: Synthesis of 1-(2-amino-5-bromo-6-(furan-2-yl)pyridin-3-yl)ethanone

To a stirred solution of 2-amino-5-bromo-6-(furan-2-yl)nicotinonitrile (1.6 g, 6.08 mmol, 1.0 eq) in THF (60 mL) was added 3M MeMgBr in diethyl ether (40.0 mL, 121.6 mmol, 20.0 equiv) at 0° C. The resulting reaction mixture was stirred at 50° C. for 16 h. Reaction mixture was then cooled to 0° C. and quenched by adding dilute HCl. The acidic reaction mixture was neutralized by using aq. sodium bicarbonate solution and extracted by using ethyl acetate (2×75 mL). The combined organic layers were washed (brine), dried (anhydrous Na$_2$SO$_4$) and concentrated under vacuum to get the light green solid (1.1 g, 64%). which was used as such for next step without further purification

LCMS: 281 [M+1]$^+$

Step 5: Synthesis of 1-(2-amino-5-bromo-6-(furan-2-yl)pyridin-3-yl)-3-(dimethylamino)prop-2-en-1-one To a solution of 1-(2-amino-5-bromo-6-(furan-2-yl)pyridin-3-yl)ethanone (1.0 g, 3.58 mmol, 1.0 eq) in 1,4-dioxane (10 mL) was added DMF.DMA (0.52 mL 3.94 mmol, 1.1 equiv). The reaction mixture was warmed to 100° C. for 3 h. The reaction solvent was evaporated under reduced pressure to afford the desired product (800 mg, 61%).

LCMS: 336 [M+1]$^+$

Step 6: Synthesis of 6-bromo-7-(furan-2-yl)-1,8-naphthyridin-4(1H)-one

To a stirred solution of 1-(2-amino-5-bromo-6-(furan-2-yl)pyridin-3-yl)-3-(dimethylamino)prop-2-en-1-one (1.0 g, 2.98 mmol, 1.0 eq) in DMF (10.0 mL) was added Cs$_2$CO$_3$ (1.94 g, 2.0 eq, 5.97 mmol) and allowed to stir at 100° C. for 16 h. Progress of reaction was monitored by TLC. The reaction mixture was diluted with ice cold water and the resulting precipitates were filtered and vacuum dried to get the desired product (0.400 g, 50%).

LCMS: 291[M+1]$^+$

Step 7: Synthesis of 7-(furan-2-yl)-6-(quinolin-6-yl)-1,8-naphthyridin-4(1H)-one To a stirred solution of 6-bromo-7-(furan-2-yl)-1,8-naphthyridin-4(1H)-one (0.100 g, 0.34 mmol, 1.0 eq), quinoline (0.072 g, 0.41 mmol, 1.2 eq) in dioxane (5 mL) was added 0.4 mL 2M aq. Na$_2$CO$_3$ (0.073 g, 0.68 mmol, 2.0 eq) under N$_2$. The reaction was purged with N$_2$ for 5 min. Following this Pd(dppf)Cl$_2$.DCM (0.014 g, 5 mol %) was added and N$_2$ was purged again for another 5 min. The reaction was then heated at 100° C. for 16 h. The reaction was allowed to cool to RT and extracted using ethyl acetate (2×30 mL). The combined organic layers were washed (brine), dried (anhydrous Na$_2$SO$_4$) and concentrated under vacuum to get the solid which was purified by supercritical fluid chromatography to get the desired product (0.018 g, 15%).

LCMS: 340 [M+1]$^+$ $^1$H NMR (400 MHz, DMSO-d$_6$) δ 12.42 (s, 1H), 8.98 (d, J=2.63 Hz, 1H), 8.46 (d, J=8.77 Hz, 1H), 8.35 (s, 1H), 7.91-8.15 (m, 3H), 7.55-7.76 (m, 3H), 6.44-6.54 (m, 1H), 6.31 (d, J=3.07 Hz, 1H), 6.14 (d, J=7.45 Hz, 1H).

Example S15. Synthesis of 7-phenyl-6-(quinoxalin-6-yl)-1,8-naphthyridin-4(1H)-one (Compound No. 1.15)

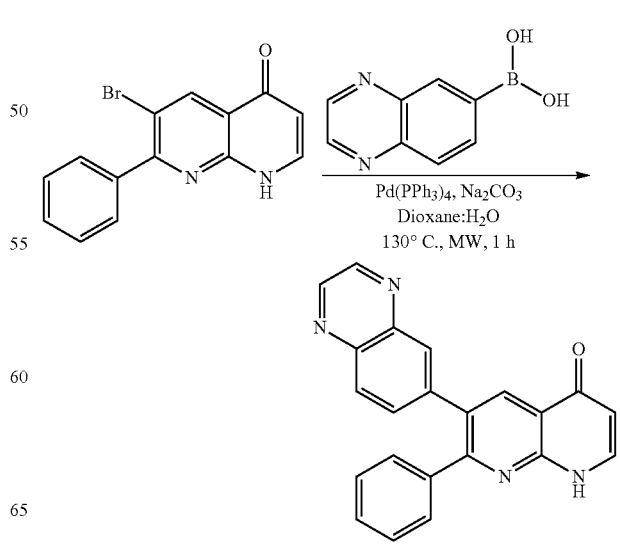

To a solution of 6-bromo-7-phenyl-1,8-naphthyridin-4 (1H)-one (100 mg, 0.33 mmol, 1 eq.) in DME (8 mL): water (2 mL) was added quinoxalin-6-ylboronic acid (63 mg, 0.36 mmol, 1.1 eq.), Na$_2$CO$_3$ (70 mg, 0.66 mmol, 2 eq.), Pd(PPh$_3$)$_4$(11 mg, 0.008 mmol, 0.025 eq.). The reaction mixture was deoxygenated using N$_2$ atmosphere and the reaction mixture was heated at 130° C. for 1 h under microwave irradiation. The reaction was monitored by LCMS. The reaction mixture was diluted with water (20 mL) and extracted using ethyl acetate (2×20 mL). The separated organic layer was dried over anhydrous sodium sulfate and concentrated under reduced pressure. The crude product was purified by reverse phase column chromatography to afford the desired product (15 mg, 13%).

LCMS: 351 [M+1]$^+$ $^1$H NMR (400 MHz, DMSO-d$_6$) δ 6.20 (d, 1H), 7.30 (m, 3H), 7.40 (d, 2H), 7.60 (d, 1H), 8.00 (m, 3H), 8.58 (s, 1H), 8.88 (s, 2H).

Example S16. Synthesis of 6-(naphthalen-2-yl)-7-phenyl-1,8-naphthyridin-4(1H)-one. (Compound No. 1.16)

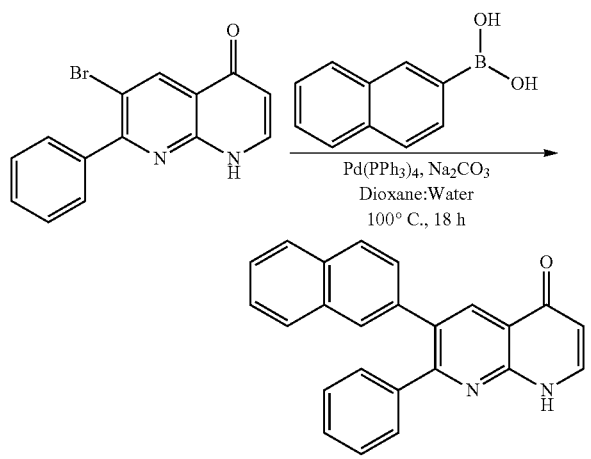

To a solution of 6-bromo-7-phenyl-1,8-naphthyridin-4 (1H)-one (100 mg, 0.33 mmol, 1 eq.) in dioxane (8 mL): water (2 mL) was added naphthalen-2-ylboronic acid (62 mg, 0.36 mmol, 1.1 eq.), Na$_2$CO$_3$ (70 mg, 0.66 mmol, 2 eq.), Pd(PPh$_3$)$_4$(13 mg, 0.008 mmol, 0.05 eq.). The reaction mixture was deoxygenated using N$_2$ atmosphere and the reaction mixture was heated at 100° C. for 18 h. The reaction was monitored by LCMS. The reaction mixture was diluted with water (20 mL) and extracted using ethyl acetate (2×20 mL). The separated organic layer was dried over anhydrous sodium sulfate and concentrated under reduced pressure. The crude product was purified by reverse phase column chromatography to afford the desired product (12 mg, 9%).

LCMS: 349 [M+1]$^+$ $^1$H NMR (400 MHz, DMSO-d$_6$) δ 6.18 (d, 1H), 7.18 (d, 1H), 7.30 (m, 3H), 7.40 (d, 2H), 7.52 (d, 2H), 7.78 (d, 1H), 7.90 (t, 2H), 8.00 (m, 2H), 8.50 (s, 1H).

Example S17. Synthesis of 6-(7-chloro-1H-benzo [d]imidazol-5-yl)-7-phenyl-1,8-naphthyridin-4(1H)-one (Compound No. 1.17)

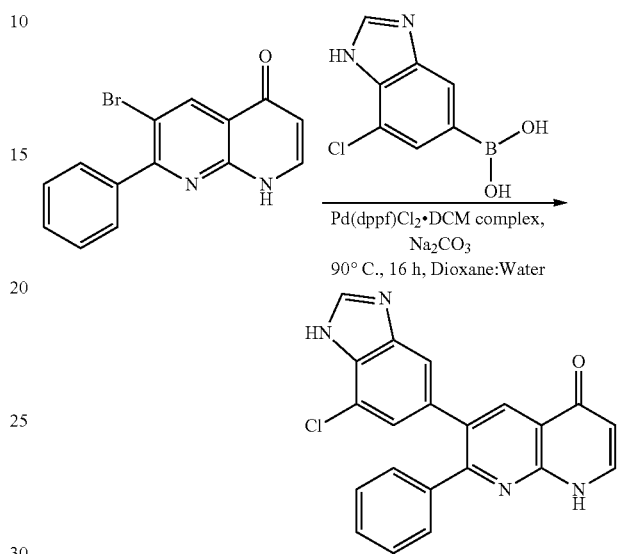

To a stirred solution of 6-bromo-7-phenyl-1,8-naphthyridin-4(1H)-one (0.100 g, 0.33 mmol, 1.0 equiv) and (7-chloro-1H-benzo[d]imidazol-5-yl)boronic acid (0.108 g, 0.39 mmol, 1.2 equiv) in dioxane (3 mL) was added Na$_2$CO$_3$ (0.069 g, 0.66 mmol, 2.0 equiv) and 1 mL water. The reaction was purged with N$_2$ for 5 min. To this reaction mixture was added Pd(dppf)Cl$_2$.DCM complex (0.014 g, 5 mol %) and N$_2$ was purged again for another 5 min. The reaction mixture was heated at 90° C. for 16 h. The reaction mixture was allowed to cool to RT and extracted using ethyl acetate (2×35 mL). The combined organic layers were washed (brine), dried (anhydrous Na$_2$SO$_4$) and concentrated under vacuum to get the solid residue which was purified by reversed phase column chromatography to get the desired product as off white solid (0.008 g, 7%).

LCMS: 373 [M+1]$^+$ $^1$H NMR (400 MHz, DMSO-d$_6$) δ 8.40 (s, 1H), 8.30 (s, 1H), 8.00 (d, J=7.45 Hz, 1H), 7.25-7.44 (m, 6H), 7.10 (br. s., 1H), 6.15 (d, J=7.89 Hz, 1H)

Example S18. Synthesis of 7-(pyridin-4-yl)-6-(quinolin-6-yl)-1,8-naphthyridin-4(1H)-one (Compound No. 1.18)

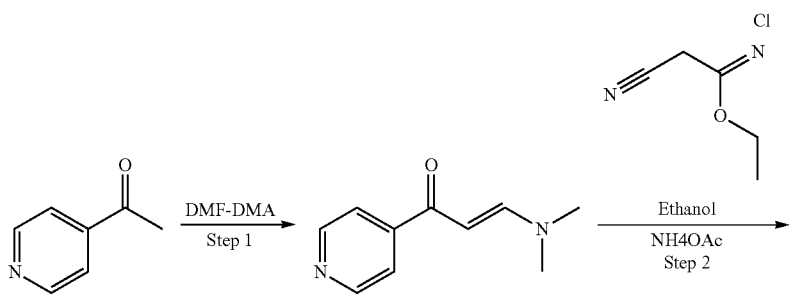

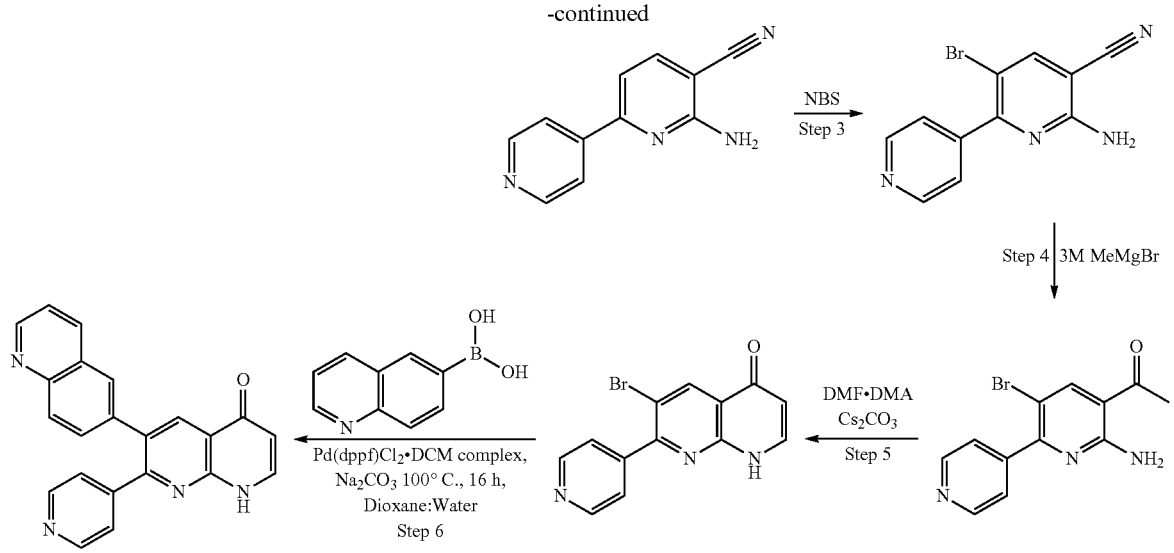

Step 1: Synthesis of (E)-3-(dimethylamino)-1-(pyridin-4-yl)prop-2-en-1-one

A mixture of DMF-DMA (21.9 g, 297.17 mmol, 3.6 eq) and 1-(pyridin-4-yl)ethan-1-one (10.0 g, 1.0 eq, 83 mmol) was heated at 100° C. for 16 h. The reaction mixture was then cooled to RT and diluted with cold water. The yellow precipitates were filtered under vacuum and washed with excess water followed by hexane. The yellow solid (14.8 g) was used as such for next step without further purification.
LCMS: 176 [M+1]+

Step 2: Synthesis of 6-amino-[2,4'-bipyridine]-5-carbonitrile

To a solution of (E)-3-(dimethylamino)-1-phenyl-prop-2-en-1-one (11.0 g, 62.5 mmol) in ethanol (200 mL) was added ethyl 2-cyanoethanimidate hydrochloride 11.1 g, 1.2 equiv, 75.0 mmol) and ammonium acetate (55.62 g, 625.0 mmol, 10 equiv) and the reaction mixture was allowed to stir at 85° C. for 16 h. Progress of the reaction was monitored by $^1$H NMR. Reaction mixture was cooled to RT, diluted with cold water (250 mL) and the solid was filtered. The solid was washed with hexane and dried under vacuum to afford the desired product (9.8 g, 80%)
LCMS: 196 [M+1]+

Step 3: Synthesis of 6-amino-3-bromo-[2,4'-bipyridine]-5-carbonitrile

To a stirred solution of 6-amino-[2,4'-bipyridine]-5-carbonitrile (11.0 g, 56.06 mmol, 1.0 equiv) in DMF (120 mL) was added NBS portion wise (9.97 g, 56.06 mmol, 1.0 equiv). The resulting solution was poured over ice to get the precipitates which were filtered under vacuum, washed with excess water and vacuum dried to get the desired product (9.8 g, 64%) which was used as such for next step without further purification.
LCMS: 275 [M+1]+

Step 4: Synthesis of 1-(6-amino-3-bromo-[2,4'-bipyridin]-5-yl)ethan-1-one

To a stirred solution of 6-amino-3-bromo-[2,4'-bipyridine]-5-carbonitrile (4.0 g, 14.59 mmol, 1.0 eq) in THF (60 mL) was added 3M MeMgBr in diethyl ether (35.0 ml, 291.8 mmol, 20.0 equiv) at 0° C. The resulting reaction mixture was stirred at 50° C. for 16 h. Reaction mixture was then cooled to 0° C. and quenched by adding dilute HCl. The acidic reaction mixture was neutralized by using aq. sodium bicarbonate solution and extracted by using ethyl acetate (2×75 mL). The combined organic layers were washed (brine), dried (anhydrous Na$_2$SO$_4$) and concentrated under vacuum to get the light green solid (2.27 g, 51%) which was used as such for next step without further purification.
LCMS: 292 [M+1]+

Step 5: Synthesis of 6-bromo-7-(pyridin-4-yl)-1,8-naphthyridin-4(1H)-one

To a solution of 1-(6-amino-3-bromo-[2,4'-bipyridin]-5-yl)ethan-1-one (1.3 g, 4.46 mmol, 1.0 eq) in DMF (10 mL) was added DMF.DMA (1.06 g, 8.92 mmol, 2.0 equiv). The reaction mixture was warmed to 100° C. After stirring for 3 h, Cs$_2$CO$_3$ (4.5 g, 13.78 mmol, 2.0 equiv) was added and the reaction was stirred for 16 h at 100° C. The reaction mixture was cooled to 0° C. and diluted with cold water. The resulting precipitates were filtered, washed with excess water and vacuum dried. The solid obtained was purified by normal phase silica gel flash chromatography to get the yellow solid (0.700 g, 54%).
LCMS: 302 [M+1]+

Step 6: Synthesis of 7-(pyridin-4-yl)-6-(quinolin-6-yl)-1,8-naphthyridin-4(1H)-one To a stirred solution of 6-bromo-7-(pyridin-4-yl)-1,8-naphthyridin-4(1H)-one (0.100 g, 0.33 mmol, 1.0 eq) and quinolin-6-ylboronic acid (0.068 g, 0.39 mmol, 1.2 eq) in dioxane (5 mL) was added 0.4 mL 2M aq. Na$_2$CO$_3$ (0.070 g, 0.66 mmol, 2.0 eq) under N$_2$. The reaction was purged with N$_2$ for 5 min. Following this Pd(dppf)Cl$_2$.DCM (0.014 g, 5 mol %) was added and N$_2$ was purged again for another 5 min. The reaction was then heated at 100° C. for 16 h. The reaction was allowed to cool to RT and extracted using ethyl acetate (2×30 mL). The combined organic layers were washed (brine), dried (anhydrous Na$_2$SO$_4$) and concentrated under vacuum to get the solid which was purified by supercritical fluid chromatography to get the desired product (0.063 g, 54%).

LCMS: 351 [M+1]$^+$ $^1$H NMR (400 MHz, DMSO-d$_6$) δ $^1$H NMR (400 MHz, DMSO-d$_6$ 7.3-7.4 (2H), 7.4-7.5 (1H), 7.5-7.6 (1H), 7.8-7.9 (1H) 8.0-8.1 (2H), 8.3-8.4 (1H) 8.5-8.6 (1H), 8.6-8.7 (1H), 8.9-9.0 (1H), 12.5-12.6 (1H).

Example S19. Synthesis of 6-(7-chloro-1H-benzo[d]imidazol-5-yl)-7-phenyl-1,8-naphthyridin-2(1H)-one (Compound No. 1.19)

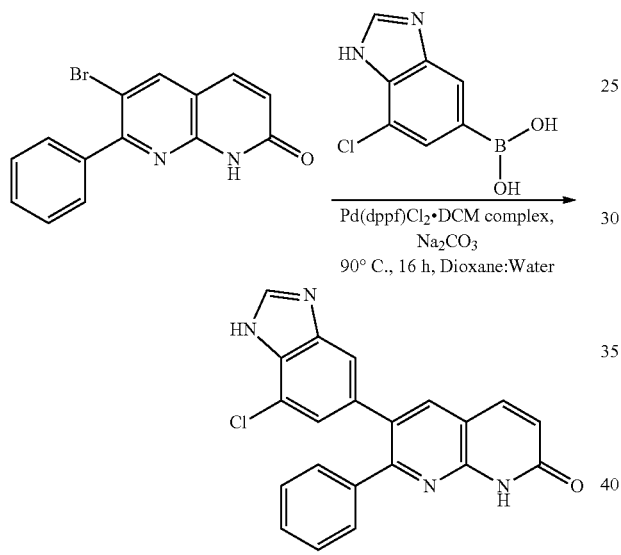

To a stirred solution of 6-bromo-7-phenyl-1,8-naphthyridin-2(1H)-one (0.100 g, 0.33 mmol, 1.0 equiv) and (7-chloro-1H-benzo[d]imidazol-5-yl)boronic acid (0.108 g, 0.39 mmol, 1.2 equiv) in dioxane (3 mL) was added Na$_2$CO$_3$ (0.069 g, 0.66 mmol, 2.0 equiv) and 1 mL water. The reaction was purged with N$_2$ for 5 min. To this reaction mixture was added Pd(dppf)Cl$_2$.DCM complex (0.014 g, 5 mol %) and N$_2$ was purged again for another 5 min. The reaction mixture was heated at 90° C. for 16 h. The reaction mixture was allowed to cool to RT and extracted using ethyl acetate (2×35 mL). The combined organic layers were washed (brine), dried (anhydrous Na$_2$SO$_4$) and concentrated under vacuum to get the solid residue which was purified by reversed phase column chromatography to get the desired product as off white solid (0.008 g, 7%).

LCMS: 373 [M+1]$^+$ $^1$H NMR (400 MHz, DMSO-d$_6$) δ 12.25 (br. s., 1H), 8.25 (s, 1H), 8.29 (s, 1H), 8.01 (d, J=9.65 Hz, 1H), 7.35 (d, J=7.45 Hz, 3H), 7.28 (d, J=7.02 Hz, 3H), 7.10 (s, 1H), 6.62 (d, J=9.21 Hz, 1H)

Example S20. Synthesis of 7-(pyridin-3-yl)-6-(quinolin-6-yl)-1,8-naphthyridin-4(1H)-one. (Compound No. 1.20)

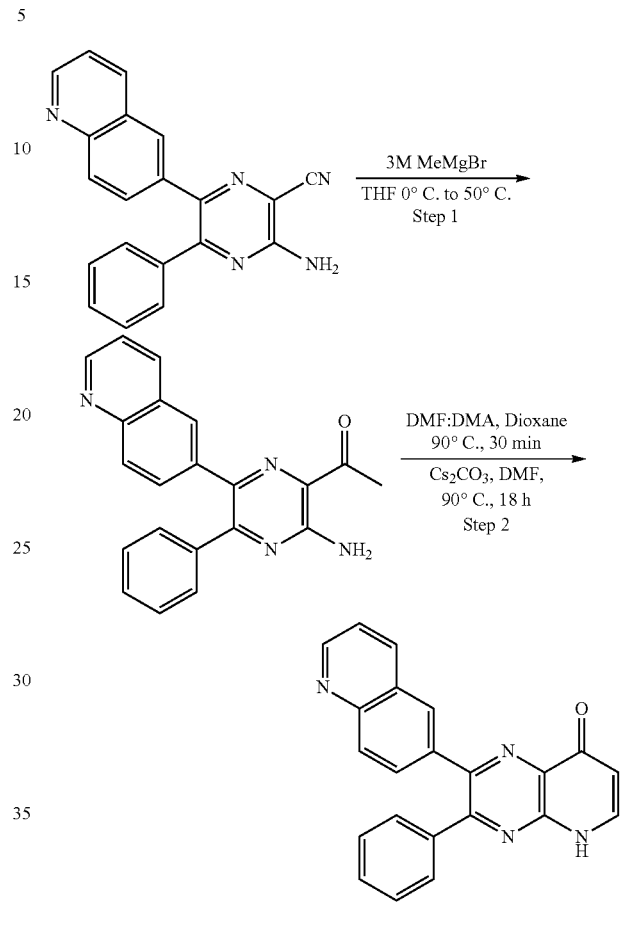

Step 1: 1-(3-amino-5-phenyl-6-(quinolin-6-yl)pyrazin-2-yl)ethan-1-one

To a stirred solution of 3-amino-5-phenyl-6-(quinolin-6-yl)pyrazine-2-carbonitrile (0.100 g, 0.32 mmol, 1.0 eq) in THF (5 mL) was added 3M MeMgBr in diethyl ether (1 mL, 0.360 g, 10.0 eq, 3.0 mmol) at 0° C. The resulting reaction mixture was stirred at 50° C. for 16 h. Reaction mixture was then cool to RT and acidified slowly with dilute HCl. The acidified reaction mixture was stirred for 1 h at 50° C. The reaction mixture was again allowed to cool to RT and extracted by using ethyl acetate (2×25 mL). The combined organic layers were washed (brine), dried (anhydrous Na$_2$SO$_4$) and concentrated under vacuum to get the desired product as light yellow solid (0.090 g, 97%)

LCMS: 291 [M+1]$^+$

Step 2: Synthesis of 7-(pyridin-3-yl)-6-(quinolin-6-yl)-1,8-naphthyridin-4(1H)-one To a solution of 1-(6-amino-3-(quinolin-6-yl)-2,3'-bipyridin-5-yl)ethanone (0.090 g, 0.31 mmol, 1.00 eq.), in 1,4 dioxane (5 mL), was added DMF:DMA (0.044 g, 0.37 mmol, 1.2 eq.). The reaction mixture was heated at 90° C. for 30 minute. The reaction was monitored by TLC and LCMS. The reaction solvent was evaporated under reduced pressure. The semisolid crude material obtained was redissolved in DMF (2 mL) and Cs$_2$CO$_3$ (0.150 g, 0.46 mmol, 1.5 eq.) was added. The reaction mixture was again heated at 90° C. for 18 h. The progress of the reaction was monitored by LCMS. The reaction mixture was diluted with ice cold water (25 mL) and extracted by using ethyl acetate (3×25 mL). The residue was purified by reverse phase column chromatography to afford the desired product (0.010 g, 10%).

LCMS: 351 [M+1]$^+$ $^1$H NMR (400 MHz, DMSO-d$_6$) δ 8.92 (d, J=3.07 Hz, 1H), 8.35 (d, J=7.45 Hz, 1H), 8.14 (br. s., 1H), 8.06 (d, J=5.26 Hz, 1H), 7.91 (d, J=8.77 Hz, 1H), 7.65 (d, J=7.02 Hz, 1H), 7.45-7.59 (m, 3H), 7.29-7.44 (m, 3H), 6.33 (d, J=7.02 Hz, 1H)

Example S21. Synthesis of 6-(benzo[d]oxazol-5-yl)-7-phenyl-1,8-naphthyridin-4(1H)-one (Compound No. 1.21)

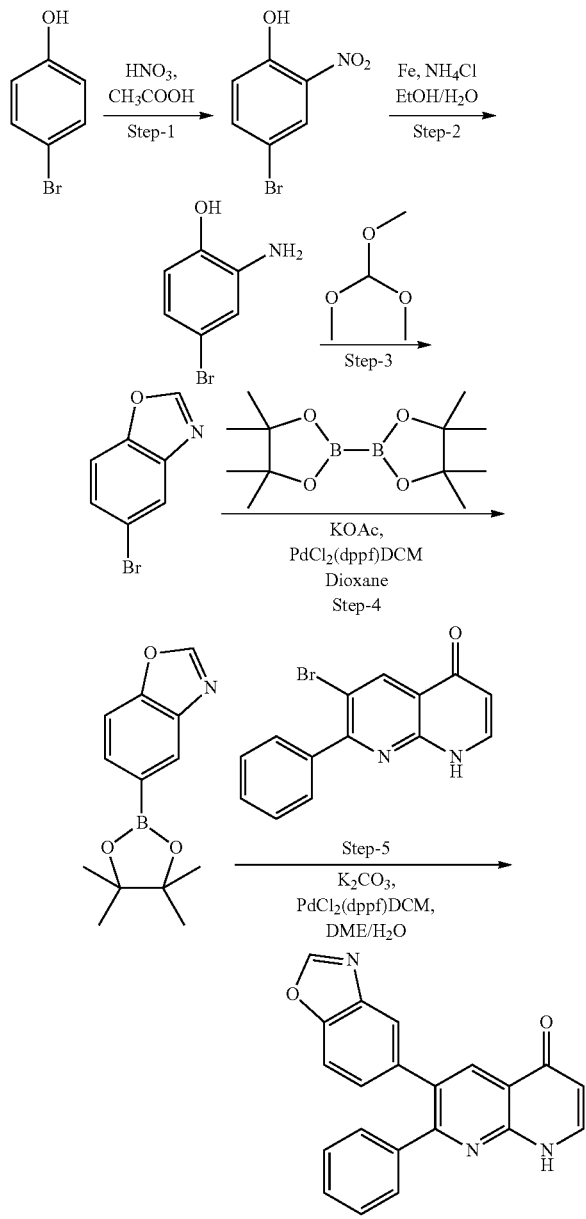

Step 1: Synthesis of 4-bromo-2-nitrophenol

To a solution of 6-bromophenol (5 g, 28.90 mmol, 1 eq.) in acetic acid (10 mL) was added nitric acid (1 mL) drop wise. Reaction mixture was stirred at RT for 5 min. The reaction was monitored by LCMS and found to be complete after 5 min. The reaction mixture was added with ice, the precipitated solid was filtered and dried to afford 4-bromo-2-nitrophenol (6 g, 95.23%) as yellow solid.

LCMS: 217 [M+1]$^+$

Step 2: Synthesis of 2-amino-4-bromophenol

To a solution of 4-bromo-2-nitrophenol (3 g, 13.76 mmol, 1 eq.) in ethanol-water (50 mL) was added ammonium chloride (2.1 g, 41.28 mmol, 3 eq.) and iron (2.3 g, 41.28 mmol. The reaction was stirred at 90° C. for 2 h. The reaction was monitored by LCMS and found to be complete after 2 h. The reaction mixture was cooled to RT, evaporated under reduced pressure to remove the solvent diluted with water (20 mL) and extracted with ethyl acetate (2×50 mL). Combined organic layer was washed with brine (20 mL) and dried over sodium sulfate. Removal of solvent under reduced pressure gave crude which was purified by Combi-Flash to obtain the 2-amino-4-bromophenol (2 g, 80%) as brown solid.

LCMS: 188 [M+1]$^+$

Step 3: Synthesis of 5-bromobenzo[d]oxazole

A solution of 2-amino-4-bromophenol (1.5, 7.90 mmol, 1 eq.) in methylorthoformate (10 mL) was stirred at 150° C. for 4-6 h. The reaction was monitored by LCMS and found to be complete after 6 h. The reaction mixture was cooled to RT, evaporated under reduced pressure to remove the solvent diluted with water (20 mL) and extracted with ethyl acetate (2×50 mL). Combined organic layer was washed with brine (20 mL) and dried over sodium sulfate. Removal of solvent under reduced pressure gave crude which was purified by Combi-Flash to obtain the 5-bromobenzo[d]oxazole (1.2 g, 80.0%) as yellow solid.

LCMS: 298 [M+1]$^+$

Step 4: Synthesis of 5-(4,4,5,5-tetramethyl-1,3,2-dioxaborolan-2-yl)benzo[d]oxazole To a solution of 5-bromobenzo[d]oxazole (1.2 g, 6.06 mmol, 1 eq.) in DMF (10 mL) was added 5-(4,4,5,5-bis(pinacolato)diboron (1.68 g, 1.66 mmol, 1.1 eq.), KOAc (1.7 g, 18.09 mmol, 3 eq.), PdCl$_2$(dppf).DCM (247 mg, 0.23 mmol, 0.05 eq.). The reaction mixture was deoxygenated with N$_2$ and the reaction mixture was stirred at 80° C. overnight. The reaction was monitored by LCMS and found to be complete after 18 h. The reaction mixture was cooled to RT, diluted with water (50 mL) and extracted with ethyl acetate (2×50 mL). Combined organic layer was washed with brine (20 mL) and dried over sodium sulfate. Removal of solvent under reduced pressure gave crude which was purified by Combi-Flash (0-100% EtOAC-Hexane) to afford the desired product (900 mg, 60%) as off white solid.

LCMS: 246 [M+1]

Step 5: Synthesis of 6-(benzo[d]oxazol-5-yl)-7-phenyl-1,8-naphthyridin-4(1H)-one To a solution of 6-bromo-7-phenylquinolin-4(1H)-one (100 mg, 0.40 mmol, 1 eq.) in DME-water (2 mL) was added 5-(4,4,5,5-tetramethyl-1,3,2-dioxaborolan-2-yl)benzo[d]oxazole (97 mg, 0.39 mmol, 1.2 eq.), Na$_2$CO$_3$ (70 mg, 0.66 mmol, 2.0 eq.), PdCl2(dppf).DCM (13.86 mg, 0.01 mmol, 0.05 eq.). The reaction mixture was deoxygenated with $N_2$ and the reaction mixture was stirred at 100° C. for 12 h. The reaction was monitored by LCMS and found to be complete after 12 h. The reaction mixture was cooled to RT, diluted with water (20 mL) and extracted with ethyl acetate (2×50 mL). Combined organic layer was washed with brine (20 mL) and dried over sodium sulfate. Removal of solvent under reduced pressure gave crude which was purified by reverse phase column chromatography to afford the desired product (10 mg, 9%) as off white solid.

LCMS: 340 [M+1]+

$^1$HNMR (400 MHz, DMSO-d$_6$) δ 12.40 (s, 1H), 8.72 (s, 1H), 8.40 (s, 1H), 8.20-8.00 (m, 2H), 7.70-7.62 (m, 2H), 7.40-7.20 (m, 5H), 6.18 (d, 1H).

Example S22. Synthesis of 6-(1-methyl-1H-benzo[d]imidazol-5-yl)-7-phenyl-1,8-naphthyridin-4(1H)-one (Compound No. 1.22)

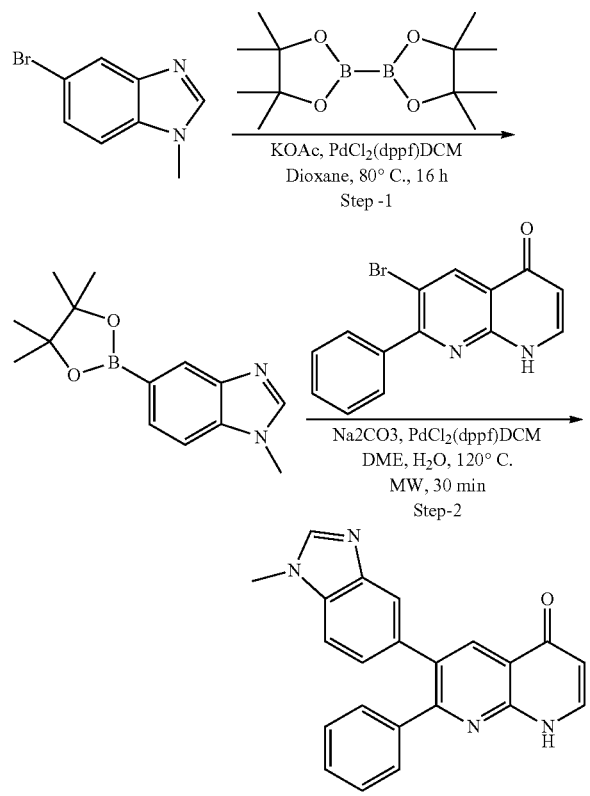

Step 1: Synthesis of 1-methyl-5-(4,4,5,5-tetramethyl-1,3,2-dioxaborolan-2-yl)-1H-benzo[d]imidazole To a solution of 5-bromo-1-methyl-1H-benzo[d]imidazole (200 mg, 0.33 mmol, 1 eq.) in 1,4-dioxane (10 mL) was added 5-(4,4,5,5-bis(pinacolato)diboron (287 mg, 1.13 mmol, 1.2 eq.), KOAc (276 mg, 2.82 mmol, 2 eq.), PdCl$_2$(dppf).DCM (76 mg, 0.09 mmol, 0.09 eq.). The reaction mixture was deoxygenated with $N_2$ and the reaction mixture was stirred at 80° C. for 16 h. The reaction was monitored by LCMS and found to be complete after 18 h. The reaction mixture was cooled to RT, diluted with water (50 mL) and extracted with ethyl acetate (2×50 mL). Combined organic layer was washed with brine (20 mL) and dried over sodium sulfate. Removal of solvent under reduced pressure gave crude which was purified by Combi-Flash (0-100% EtOAC-Hexane) to afford the desired product (120 mg, 49%) as brown oil.

LCMS: 259 [M+1]+

Step 2: Synthesis of 6-(1-methyl-1H-benzo[d]imidazol-5-yl)-7-phenyl-1,8-naphthyridin-4(1H)-one To a solution of 6-bromo-7-phenyl-1,8-naphthyridin-4 (1H)-one (100 mg, 0.40 mmol, 1 eq.) in DME-water (2 mL) was added 1-methyl-5-(4,4,5,5-tetramethyl-1,3,2-dioxaborolan-2-yl)-1H-benzo[d]imidazole (102 mg, 0.39 mmol, 1.2 eq.), K$_2$CO$_3$ (136 mg, 0.99 mmol, 3 eq.), PdCl$_2$(dppf).DCM (53 mg, 0.06 mmol, 0.2 eq.). The reaction mixture was deoxygenated with $N_2$ and the reaction mixture was stirred at 120° C. for 30 min microwave irradiation. The reaction was monitored by LCMS and found to be complete after 30 min. The reaction mixture was cooled to RT, diluted with water (20 mL) and extracted with ethyl acetate (2×50 mL). Combined organic layer was washed with brine (20 mL) and dried over sodium sulfate. Removal of solvent under reduced pressure gave crude which was purified by reverse phase column chromatography to afford the desired product (10 mg, 10%) as off white solid.

LCMS: 353 [M+1]+

$^1$HNMR (400 MHz, DMSO-d$_6$) δ 8.56 (s, 2H), 8.00 (s, 1H), 7.98-7.80 (m, 2H), 7.65 (m, 1H), 7.40-7.20 (m, 5H), 6.80 (s, 2H).

Example S23. Synthesis of 6-(8-methylquinolin-6-yl)-7-phenyl-1,8-naphthyridin-4(1H)-one (Compound No. 1.23)

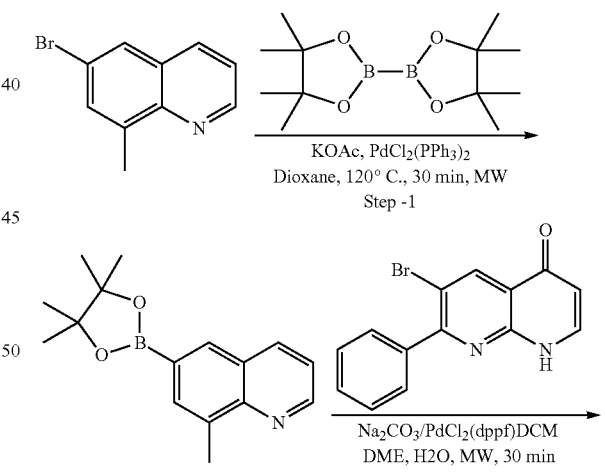

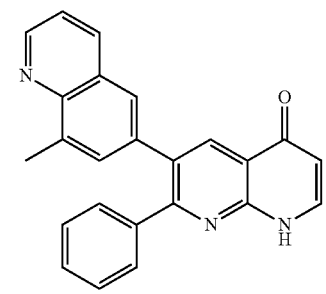

Step 1: Synthesis of 8-methyl-6-(4,4,5,5-tetramethyl-1,3,2-dioxaborolan-2-yl)quinoline To a solution of 6-bromo-8-methylquinoline (100 mg, 0.45 mmol, 1 eq.) in 1,4-dioxane (10 mL) was added 5-(4,4,5,5-bis(pinacolato)diboron (127 mg, 0.49 mmol, 1.1 eq.), KOAc (88 mg, 0.90 mmol, 2 eq.), PdCl$_2$(PPh$_3$)$_2$(15.7 mg, 0.02 mmol, 0.05 eq.). The reaction mixture was deoxygenated with N$_2$ and the reaction mixture was heated under microwave irradiation for 30 min at 120° C. The reaction was monitored by LCMS and found to be complete after 30 min. The reaction mixture was cooled to RT, diluted with water (10 mL) and extracted with ethyl acetate (2×20 mL). Combined organic layer was washed with brine (20 mL) and dried over sodium sulfate. Removal of solvent under reduced pressure gave crude (150 mg) which was carried to next step without any further purification.

LCMS: 269 [M+1]+

Step 2: Synthesis of 6-(8-methylquinolin-6-yl)-7-phenyl-1,8-naphthyridin-4(1H)-one To a solution of 6-bromo-7-phenyl-1,8-naphthyridin-4(1H)-one (100 mg, 0.33 mmol, 1 eq.) in DME-Water (2 mL) was added 8-methyl-6-(4,4,5,5-tetramethyl-1,3,2-dioxaborolan-2-yl)quinoline (107 mg, 0.39 mmol, 1.2 eq.), Na$_2$CO$_3$ (70 mg, 0.66 mmol, 2.0 eq.), PdCl$_2$(dppf).DCM (13. mg, 0.01 mmol, 0.05 eq.). The reaction mixture was deoxygenated with N$_2$ and the reaction mixture was stirred at 120° C. for 30 min under Microwave irradiation. The reaction was monitored by LCMS and found to be complete after 30 min. The reaction mixture was cooled to RT, diluted with water (20 mL) and extracted with ethyl acetate (2×50 mL). Combined organic layer was washed with brine (20 mL) and dried over sodium sulfate. Removal of solvent under reduced pressure gave crude which was purified by reverse phase column chromatography to afford the desired product (10 mg, 8%) as off white solid.

LCMS: 364 [M+1]+

$^1$HNMR (400 MHz, DMSO-d$_6$) δ 12.40 (s, 1H), 8.96 (d, 1H), 8.58 (d, 1H), 8.35 (d, 1H), 8.00 (d 1H), 7.80 (m, 1H), 7.50-7.20 (m, 7H), 6.20 (d, 1H), 2.60 (s, 3H).

Example S24. Synthesis of 6-(benzo[d]thiazol-6-yl)-7-phenyl-1,8-naphthyridin-4(1H)-one (Compound No. 1.24)

To a solution of 6-bromo-7-phenyl-1,8-naphthyridin-4(1H)-one (100 mg, 0.40 mmol, 1 eq.) in dioxane-water (10 mL) was added benzo[d]thiazol-6-ylboronic acid (86.0 mg, 0.48 mmol, 1.2 eq.), Na$_2$CO$_3$ (87 mg, 0.82 mmol, 2.5 eq.), and PdCl$_2$(dppf).DCM (13.4 mg, 0.01 mmol, 0.05 eq.). The reaction mixture was deoxygenated with N$_2$ and the reaction mixture was stirred at 120° C. for 30 min under microwave irradiation. The reaction mixture was cooled to RT, diluted with water (20 mL) and extracted with ethyl acetate (2×50 mL). Combined organic layer was washed with brine (20 mL) and dried over sodium sulfate. Removal of solvent under reduced pressure gave crude which was purified by reverse phase column chromatography to afford the desired product (3 mg 10%) as a light brown solid.

LCMS: 356 [M+1]+

$^1$HNMR (400 MHz, DMSO-d$_6$) δ 12.40 (s, 1H), 9.40 (s, 1H), 8.50 (s, 1H), 8.20 (s, 1H), 8.15-8.00 (m 2H), 7.43-7.18 (m, 6H), 6.20 (d, 1H).

Example S25. Synthesis of 7-(5-methylfuran-2-yl)-6-(quinolin-6-yl)-1,8-naphthyridin-4(1H)-one (Compound No. 1.25)

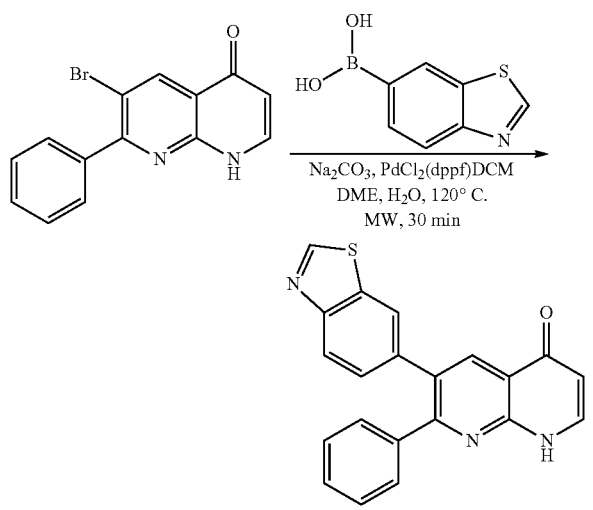

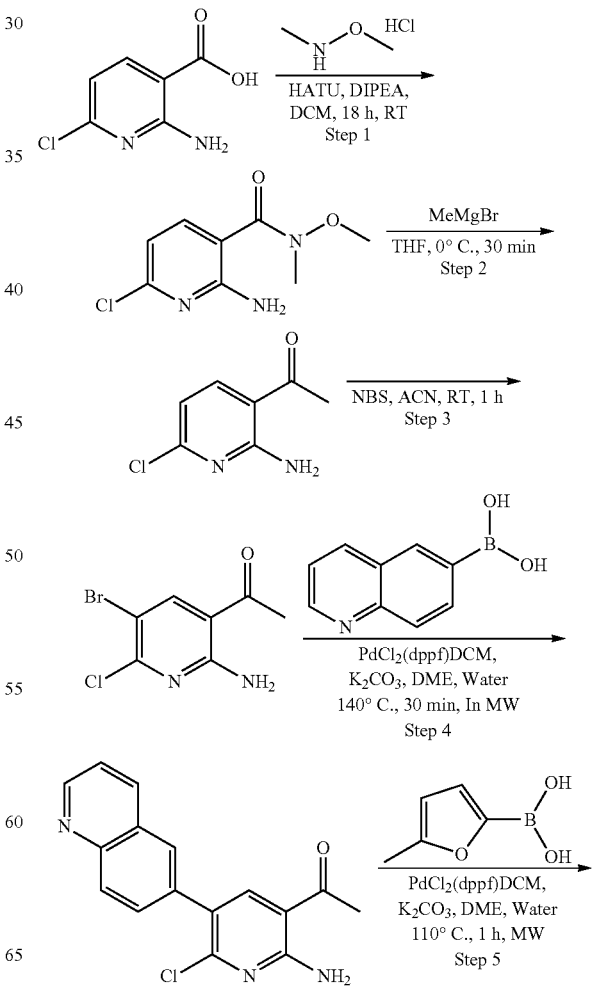

-continued

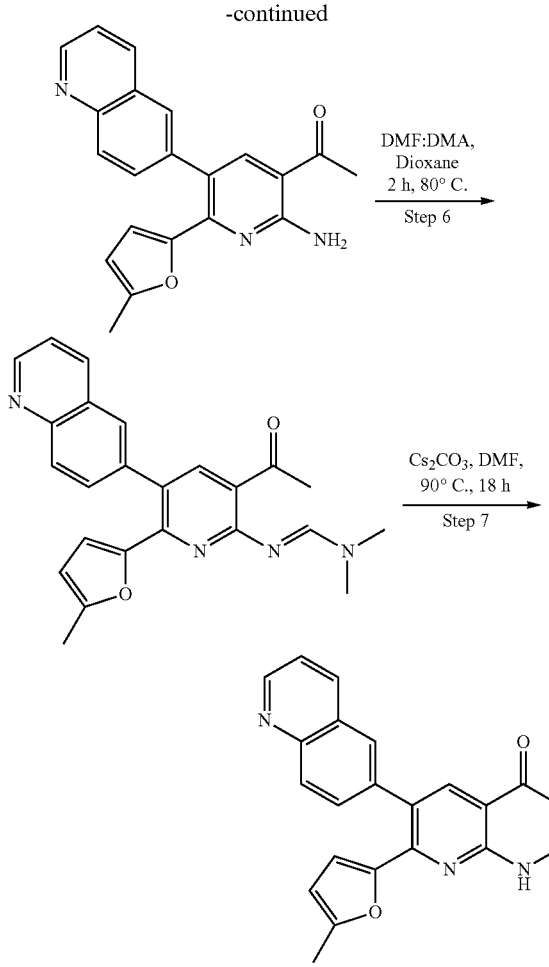

Step 1: Synthesis of 2-amino-6-chloro-N-methoxy-N-methylnicotinamide

To a stirred solution of 2-amino-6-chloronicotinic acid (1.136 g, 6.56 mmol, 1.0 eq) and N,O-dimethylhydroxylamine hydrochloride (0.965 g, 9.85 mmol, 1.5 eq) in DMF (20 mL) was added EDC (1.9 g, 9.85 mmol, 1.5 eq), HOBt (1.5 g, 9.85 mmol, 1.5 eq), and DIPEA (2.58 g, 20.0 mmol, 3.0 eq). The reaction was allowed to stir at RT for 16 h. The reaction mixture was then extracted using ethyl acetate (2×100 mL). the combined organic layer was washed (brine), dried (anhydrous sodium sulphate) and concentrated under vacuum to get the solid which was purified by normal phase flash column chromatography to get the desired product (1.0 g)
LCMS: 216 $[M+1]^+$

Step 2: Synthesis of 1-(2-amino-6-chloropyridin-3-yl)ethanone

To a solution of 2-amino-6-chloro-N-methoxy-N-methylnicotinamide (500 mg, 2.32 mmol, 1.00 eq) in THF (20 mL) was cooled to 0° C. and 3M MeMgBr in THF (2.713 mL, 3.5 mmol) was added at the same temperature. The reaction mixture was stirred at the same temperature for 30 min. Following this the reaction mixture was quenched using freshly prepared saturated solution of NH$_4$Cl (50 mL) and extracted using ethyl acetate (2×50 mL). The combined organic layer was dried over sodium sulfate and concentrated under reduced pressure to afford the desired product (300 mg, 47%).
LCMS: 171 $[M+1]^+$

Step 3: Synthesis of 1-(2-amino-5-bromo-6-chloropyridin-3-yl)ethanone

To a solution of 1-(2-amino-6-chloropyridin-3-yl)ethanone (1.5 g, 8.82 mmol, 1 eq.) in mixture of ACN (50 mL) was added N-bromosuccinimide (1.895 g, 10.58 mmol, 1.2 eq.). The reaction mixture was stirred at room temperature for 1 h. The reaction was monitored by TLC and NMR. The reaction solvent was evaporated under reduced pressure. The reaction mixture was diluted with water (100 mL) and extracted by ethyl acetate (2×50 mL). The organic layer was separated, washed water (5×20 mL) and brine and dried over anhydrous sodium sulfate. The solvent was evaporated under reduced pressure to afford (1.800 g, 85%) of 1-(2-amino-5-bromo-6-chloropyridin-3-yl)ethanone.
LCMS: 249 $[M+1]^+$

Step 4: Synthesis of 1-(2-amino-6-chloro-5-(quinolin-6-yl)pyridin-3-yl)ethanone To a solution of 1-(2-amino-5-bromo-6-chloropyridin-3-yl)ethanone (1.100 g, 4.40 mmol, 1 eq.) in DME (10 mL):water (1 mL) was added quinolin-6-ylboronic acid (0.756 g, 4.39 mmol, 1.0 eq.), K$_2$CO$_3$ (0.912 g, 6.6 mmol, 1.5 eq.), PdCl$_2$(dppf).DCM (0.179 g, 0.22 mmol, 0.05 eq.). The reaction mixture was deoxygenated using N$_2$ atmosphere and the reaction mixture was heated at 140° C. for 30 min. The reaction was monitored by TLC and LCMS. The reaction mixture was diluted with water (50 mL) and extracted using ethyl acetate (2×50 mL). The separated organic layer was dried over sodium sulfate and concentrated under reduced pressure. The crude product was purified by flash column chromatography to afford the desired product (350 mg, 26%).
LCMS: 298 $[M+1]^+$

Step 5: Synthesis of 1-(2-amino-6-(5-methylfuran-2-yl)-5-(quinolin-6-yl)pyridin-3-yl)ethanone To a solution of 1-(2-amino-6-chloro-5-(quinolin-6-yl)pyridin-3-yl)ethanone (200 mg, 0.67 mmol, 1 eq.) in DME (8 mL): water (2 mL) was added 5-methylfuran-2-ylboronic acid (109 mg, 0.87 mmol, 1.3 eq.), K$_2$CO$_3$ (139 mg, 1.006 mmol, 1.5 eq.), PdCl$_2$(dppf).DCM (27 mg, 0.03 mmol, 0.05 eq.). The reaction mixture was deoxygenated using N$_2$ atmosphere and the reaction mixture was heated at 110° C. for 1 h. The reaction was monitored by TLC and LCMS. The reaction mixture was diluted with water (50 mL) and extracted using ethyl acetate (2×50 mL). The separated organic layer was dried over sodium sulfate and concentrated under reduced pressure. The crude product was purified by flash column chromatography to afford the desired product (160 mg, 69%).
LCMS: 344 $[M+1]^+$

Step 6: Synthesis of (E)-N'-(3-acetyl-6-(5-methylfuran-2-yl)-5-(quinolin-6-yl)pyridin-2-yl)-N,N-dimethylformimidamide To a solution of 1-(2-amino-6-(5-methylfuran-2-yl)-5-(quinolin-6-yl)pyridin-3-yl)ethanone (100 mg, 0.29 mmol, 1 eq), in 1,4-dioxane (5 mL), was added DMF:DMA (346 mg, 2.91 mmol, 2.5 eq.). The reaction mixture was heated at 90° C. for 30 min. The reaction was monitored by TLC and LCMS. The reaction solvent was evaporated under reduced pressure to afford the desired product (100 mg, 86%).

LCMS: 399 [M+1]$^+$

Step 7: Synthesis of 7-(5-methylfuran-2-yl)-6-(quinolin-6-yl)-1,8-naphthyridin-4(1H)-one To a solution of N'-(3-acetyl-6-(5-methylfuran-2-yl)-5-(quinolin-6-yl)pyridin-2-yl)-N,N-dimethylformimidamide (100 mg, 0.25 mmol, 1 eq), in DMF (1 mL), was added Cs$_2$CO$_3$ (122 mg, 0.37 mmol, 1.5 eq). The reaction mixture was heated at 90° C. for 18 h. The reaction was monitored by LCMS. The reaction mixture was diluted with ice cold water (25 mL). The precipitation of product was observed and filtered as sold. The crude product was submitted to reverse phase column chromatography to afford the desired product (10 mg, 11%).

LCMS: 354 [M+1]$^+$ $^1$H NMR (400 MHz, DMSO-d$_6$) δ 3.20 (s, 3H), 5.98 (d, 1H), 6.10 (m, 2H), 7.60 (m, 1H), 7.70 (d, 1H), 7.98 (d, 1H), 8.05 (m, 2H), 8.30 (s, 1H), 8.42 (d, 1H), 8.98 (d, 1H), 12.40 (bs, 1H).

Example S26. Synthesis of 6-(8-methoxyquinolin-6-yl)-7-phenyl-1,8-naphthyridin-4(1H)-one (Compound No. 1.26)

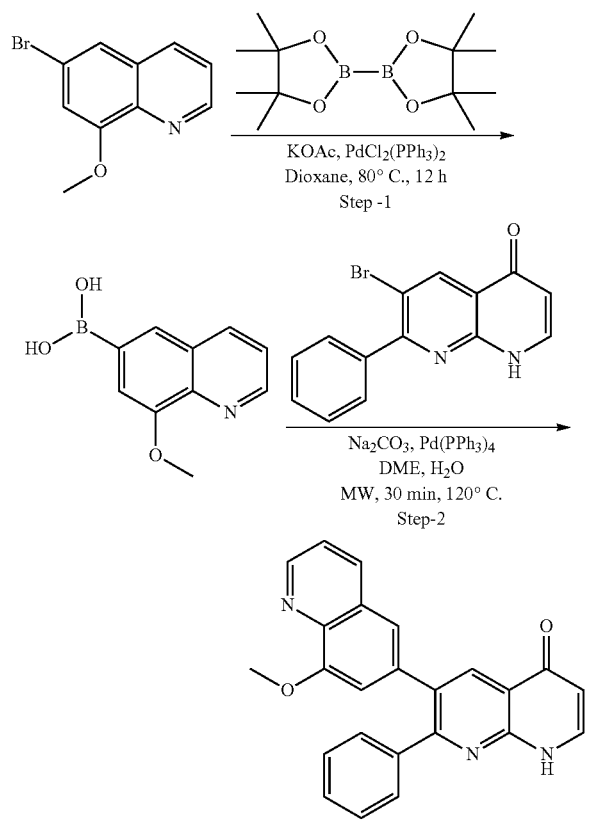

Step 1: Synthesis of 8-methoxyquinolin-6-ylboronic acid

To a solution of 6-6-bromo-8-methoxyquinoline (200 mg, 084 mmol, 1 eq.) in 1,4-dioxane (10 mL) was added 5-(4,4,5,5-bis(pinacolato)diboron (256 mg, 1.00 mmol, 1.2 eq.), KOAc (164 mg, 1.68 mmol, 2 eq), PdCl$_2$(PPh$_3$)$_2$ (68 mg, 0.168 mmol, 0.2 eq.). The reaction mixture was deoxygenated with N$_2$ and the reaction mixture was heated at 80° C. for 12 h. The reaction was monitored by LCMS and found to be complete after 12 h. The reaction mixture was cooled to RT, diluted with water (10 mL) and extracted with ethyl acetate (2×20 mL). Combined organic layer was washed with brine (20 mL) and dried over sodium sulfate. Removal of solvent under reduced pressure gave crude which was carried to next step without any purification to afford 8-methoxyquinolin-6-ylboronic acid. (120 mg) which was used directly to the next step.

LCMS: 204 [M+1]$^+$

Step 2: Synthesis of 6-(8-methoxyquinolin-6-yl)-7-phenyl-1,8-naphthyridin-4(1H)-one To a solution of 6-bromo-7-phenyl-1,8-naphthyridin-4(1H)-one (100 mg, 0.33 mmol, 1 eq.) in DME-water (2 mL) was added 8-methoxyquinolin-6-ylboronic acid (80.9 mg, 0.39 mmol, 1.2 eq.), K$_2$CO$_3$ (136.62 mg, 0.99 mmol, 3.0 eq.), PdCl$_2$(dppf).DCM (13.4 mg, 0.01 mmol, 0.05 eq.). The reaction mixture was deoxygenated with N$_2$ and the reaction mixture was stirred at 120° C. for 30 min in microwave. The reaction was monitored by LCMS and found to be complete after 30 min. The reaction mixture was cooled to RT, diluted with water (20 mL) and extracted with ethyl acetate (2×50 mL). Combined organic layer was washed with brine (20 mL) and dried over sodium sulfate. Removal of solvent under reduced pressure gave crude which was purified by reversed phase column chromatography to afford the desired product (10 mg, 8%) as off white solid.

LCMS: 380 [M+1]$^+$ $^1$HNMR (400 MHz, DMSO-d$_6$) δ 12.40 (s, 1H), 8.82 (d, 1H), 8.60 (s, 1H), 8.30 (d, 1H), 8.00 (d, 1H), 7.60-7.20 (m, 7H), 6.80 (s, 1H), 6.20 (d, 1H), 3.60 (s, 3H).

Example S27. Synthesis of 6-(1H-benzo[d]imidazol-5-yl)-7-(furan-2-yl)-1,8-naphthyridin-4(1H)-one (Compound No. 1.27)

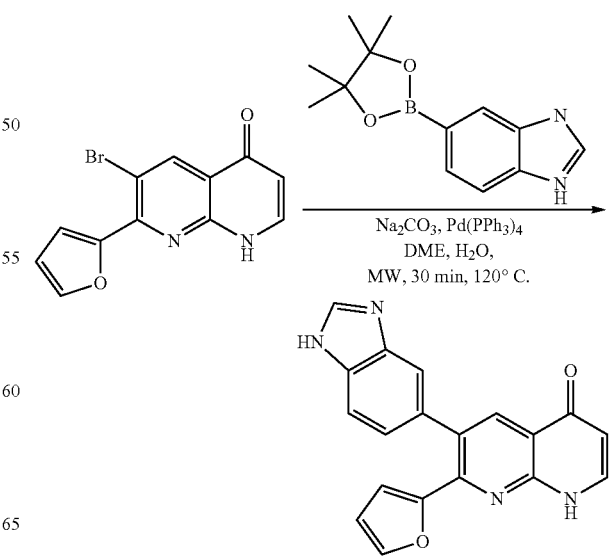

To a solution of 6-bromo-7-(furan-2-yl)-1,8-naphthyridin-4(1H)-one (100 mg, 0.33 mmol, 1 eq.) in DME-water (2 mL) was added 8-methoxyquinolin-6-ylboronic acid (80.9 mg, 0.39 mmol, 1.2 eq.), K$_2$CO$_3$ (136.62 mg, 0.99 mmol, 3.0 eq.), PdCl$_2$(dppf).DCM (13.4 mg, 0.01 mmol, 0.05 eq.). The reaction mixture was deoxygenated with N$_2$ and the reaction mixture was stirred at 120° C. for 30 min under microwave irradiation. The reaction was monitored by LCMS and found to be complete after 30 min. The reaction mixture was cooled to room temperature, diluted with water (20 mL) and extracted with ethyl acetate (2×50 mL). Combined organic layer was washed with brine (20 mL) and dried over sodium sulfate. Removal of solvent under reduced pressure gave crude which was purified by reverse phase column chromatography to afford the desired product (3 mg, 8%) as off-white solid.

LCMS: 329 [M+1]$^+$ $^1$HNMR (400 MHz, DMSO-d$_6$) δ 8.56 (s, 2H), 8.00 (s, 1H), 7.98-7.80 (m, 2H), 7.65 (m, 1H), 7.40-7.20 (m, 5H), 6.80 (s, 2H).

Example S28. Synthesis of 7-(pyridin-3-yl)-6-(quinolin-6-yl)-1,8-naphthyridin-4(1H)-one (Compound No. 1.28)

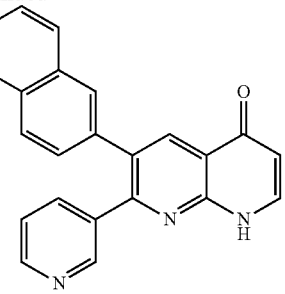

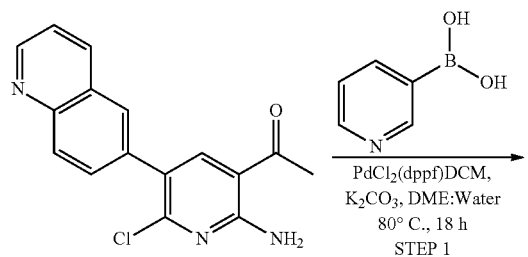

Step 1: Synthesis of 1-(6-amino-3-(quinolin-6-yl)-2,3'-bipyridin-5-yl)ethanone

To a solution of 1-(2-amino-6-chloro-5-(quinolin-6-yl)pyridin-3-yl)ethanone (100 mg, 0.33 mmol, 1 eq.) in DME (8 mL): water (2 mL) was added pyridin-3-ylboronic acid (49 mg, 0.40 mmol, 1.2 eq.), K$_2$CO$_3$ (69 mg, 0.50 mmol, 1.5 eq.), PdCl$_2$(dppf).DCM (13 mg, 0.015 mmol, 0.05 eq.). The reaction mixture was deoxygenated using N$_2$ atmosphere and the reaction mixture was heated at 80° C. for 18 h. The reaction was monitored by TLC and LCMS. The reaction mixture was diluted with water (50 mL) and extracted using ethyl acetate (2×50 mL). The separated organic layer was dried over sodium sulfate and concentrated under reduced pressure, to get the desired product (200 mg) which was used as such for next step without further purification.

LCMS: 341 [M+1]$^+$

Step 2: Synthesis of 7-(pyridin-3-yl)-6-(quinolin-6-yl)-1,8-naphthyridin-4(1H)-one To a solution of 1-(6-amino-3-(quinolin-6-yl)-2,3'-bipyridin-5-yl)ethanone (200 mg, 0.58 mmol, 1.00 eq.), in 1,4 dioxane (5 mL), was added DMF:DMA (346 mg, 2.91 mmol, 2.5 eq.). The reaction mixture was heated at 90° C. for 30 min. The reaction was monitored by TLC and LCMS. The reaction solvent was evaporated under reduced pressure. The semisolid crude material obtained was dissolved in DMF (2 mL) and Cs$_2$CO$_3$ (246 mg, 0.75 mmol, 1.5 eq.) was added. The reaction mixture was again heated at 90° C. for 18 h. The progress of the reaction was monitored by LCMS. The reaction mixture was diluted with ice cold water (25 mL) and the precipitates obtained were filtered under vacuum. The residue was purified by reversed phase column chromatography to afford the desired product (10 mg, 6%).

LCMS: 351 [M+1]$^+$ $^1$H NMR (400 MHz, DMSO-d$_6$) δ 6.20 (d, 1H), 7.38 (t, 1H), 7.50 (d, 1H), 7.58 (d, 1H), 7.78 (d, 1H), 7.90 (d, 1H), 8.02 (m, 2H), 8.38 (d, 1H), 8.50-8.60 (d, 1H), 8.58 (m, 2H), 8.98 (d, 1H), 12.42 (bs, 1H).

Example S29. Synthesis of 7-(5-methylfuran-2-yl)-6-(quinolin-6-yl)-1,8-naphthyridin-2(1H)-one (Compound No. 1.29)

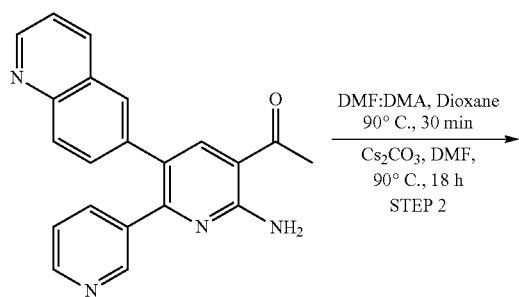

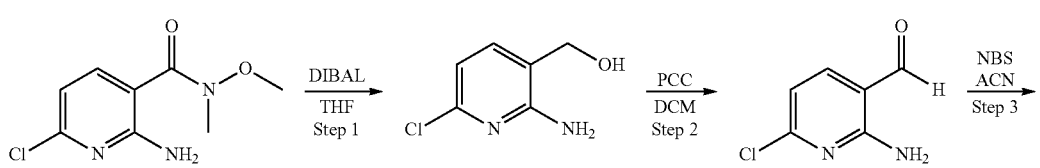

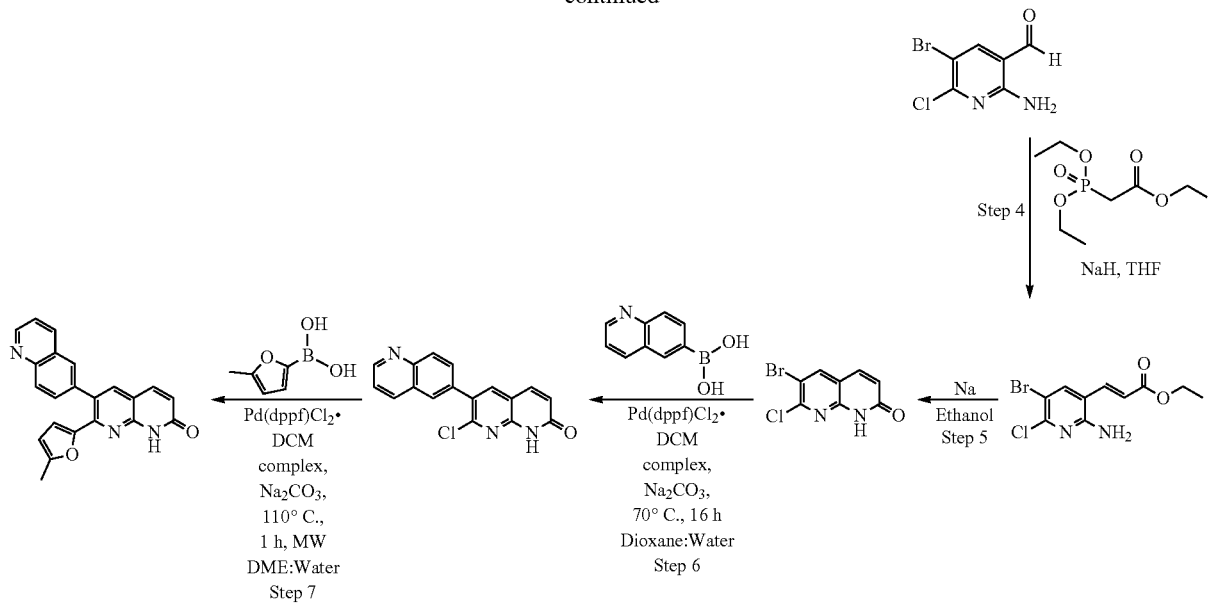

Step 1: Synthesis of (2-amino-6-chloropyridin-3-yl)methanol

To a stirred solution of 2-amino-6-chloro-N-methoxy-N-methylnicotinamide (1.0 g, 4.6 mmol, 1.0 eq) in THF (20 mL) was added 1M solution of DIBAL-H in toluene (23.14 mL, 5.0 eq) dropwise at 0° C. Progress of the reaction was monitored by TLC. To the reaction mixture was added aqueous NH$_4$Cl and extracted using ethyl acetate (3×75 mL). Combined organic layers were washed (brine), dried (anhydrous Na$_2$SO$_4$) and concentrated under vacuum to get the solid which was further triturated with pentane to give the desired product (0.330 g, 45%)

LCMS: 159 [M+1]$^+$

Step 2: Synthesis of 2-amino-6-chloronicotinaldehyde

To a solution of (2-amino-6-chloropyridin-3-yl)methanol (2.67 g, 16.83 mmol, 1.0 eq) in DCM (40 mL) was added PCC (7.26 g, 33.6 mmol, 2.0 eq) at 0° C., the reaction was allowed to stir at RT, progress of the reaction was monitored by TLC. After completion of the reaction the reaction was filtered through Celite. The filtrate were washed with brine and dried over sodium sulphate and concentrated under vacuum to get the desired product (1.92 g, 73%).

LCMS: 157 [M+1]$^+$

Step 3: Synthesis of 2-amino-5-bromo-6-chloronicotinaldehyde

To a stirred solution of 2-amino-6-chloronicotinaldehyde (1.8 g, 1.0 eq, 11.49 mmol) in ACN (20 mL) were added NBS (2.0 g, 1.0 eq, 11.49 mmol) at 0° C. The reaction mixture was allowed to stir at RT. The progress of the reaction was monitored by TLC. After complete conversion of the starting material the reaction mixture was concentrated under vacuum. Water was added and the reaction mixture was extracted using ethyl acetate (3×75 mL), the combined organics were washed with brine and dried over anhydrous sodium sulphate and concentrated under vacuum to get the desired product (1.8 g, 67%).

LCMS: 235 [M+1]$^+$

Step 4: Synthesis of ethyl (E)-3-(2-amino-5-bromo-6-chloropyridin-3-yl)acrylate In a 20 mL THF, NaH (1.8 g, 1.0 eq, 7.6 mmol) and TEPA (1.98 mL, 9.9 mmol, 1.3 eq) was added at 0° C. Followed by addition of 2-amino-5-bromo-6-chloronicotinaldehyde (1.8 g, 1.0 eq, 7.6 mmol) and the reaction mixture was allowed to stir at RT. The progress of the reaction was monitored by TLC. The reaction was quenched by adding water extracted by using ethyl acetate (3×100 mL). The combined organics were washed by brine and dried over sodium sulphate and concentrated under vacuum to give the desired product (1.035 g, 34%)

LCMS: 305 [M+1]$^+$

Step 5: Synthesis of 6-bromo-7-chloro-1,8-naphthyridin-2(1H)-one

To a freshly prepared sodium ethoxide (0.105 g Na metal in 10 mL ethanol) at 0° C. was added 20 mL solution of ethyl (E)-3-(2-amino-5-bromo-6-chloropyridin-3-yl)acrylate (1.035 g, 4.56 mmol, 1.0 eq) in ethanol and the reaction mixture was allowed to stir at RT for 16 h. The progress of the reaction was monitored by TLC. The reaction mixture was concentrated under vacuum and extracted with ethyl acetate (3×75 mL), the combined organic layers were washed with brine and dried over sodium sulphate and concentrated under vacuum to get the desired product (0.650 g, 55%)

LCMS: 259 [M+1]$^+$

Step 6: Synthesis of 7-chloro-6-(quinolin-6-yl)-1,8-naphthyridin-2(1H)-one

To a stirred solution of 6-bromo-7-chloro-1,8-naphthyridin-2(1H)-one (0.120 g, 0.46 mmol, 1.0 equiv) and quinolin-6-ylboronic acid (0.096 g, 0.56 mmol, 1.2 equiv) in dioxane (3 mL) was added Na₂CO₃ (0.097 g, 0.66 mmol, 2.0 equiv) and 1 mL water. The reaction was purged with N₂ for 5 min. To this reaction mixture was added Pd(dppf)Cl₂.DCM complex (0.019 g, 5 mol %) and N₂ was purged again for another 5 min. The reaction mixture was heated at 70° C. for 16 h. The reaction mixture was allowed to cool to RT and extracted using ethyl acetate (2×35 mL). The combined organic layers were washed (brine), dried (anhydrous Na₂SO₄) and concentrated under vacuum. The light brown solid obtained was triturated with pentane to give the desired product (0.100 g) which was used as such for next step without further purification.

LCMS: 308 [M+1]⁺

Step 7: Synthesis of 7-(5-methylfuran-2-yl)-6-(quinolin-6-yl)-1,8-naphthyridin-2(1H)-one To a stirred solution of 7-chloro-6-(quinolin-6-yl)-1,8-naphthyridin-2(1H)-one (0.100 g, 0.32 mmol, 1.0 equiv) and (5-methylfuran-2-yl)boronic acid (0.050 g, 0.38 mmol, 1.2 equiv) in dioxane (3 mL) was added Na₂CO₃ (0.062 g, 0.64 mmol, 2.0 equiv) and 1 mL water. The reaction was purged with N₂ for 5 min. To this reaction mixture was added Pd(dppf)Cl₂.DCM complex (0.015 g, 5 mol %) and N₂ was purged again for another 5 min. The reaction mixture was heated at 110° C. for 1 h under microwave irradiation. The reaction mixture was allowed to cool to RT and extracted using ethyl acetate (2×35 mL). The combined organic layers were washed (brine), dried (anhydrous Na₂SO₄) and concentrated under vacuum to get the solid residue which was purified by reversed phase column chromatography to get the desired product as off white solid (0.005 g, 5%).

LCMS: 354 [M+1]⁺

¹HNMR (400 MHz, METHANOL-d₄) δ 8.71 (d, J=2.63 Hz, 1H), 8.23 (d, J=7.45 Hz, 1H), 7.88 (t, J=4.17 Hz, 2H), 7.77 (s, 1H), 7.79 (s, 1H), 7.48-7.58 (m, 1H), 7.41 (dd, J=4.39, 8.33 Hz, 2H), 6.46 (d, J=9.65 Hz, 1H), 6.20 (d, J=3.07 Hz, 1H), 5.82 (d, J=3.07 Hz, 1H), 1.76-1.92 (m, 3H)

Example S30. Synthesis of 7-(3-methyl-1H-pyrazol-1-yl)-6-(quinolin-6-yl)-1,8-naphthyridin-4(1H)-one (Compound No. 1.92)

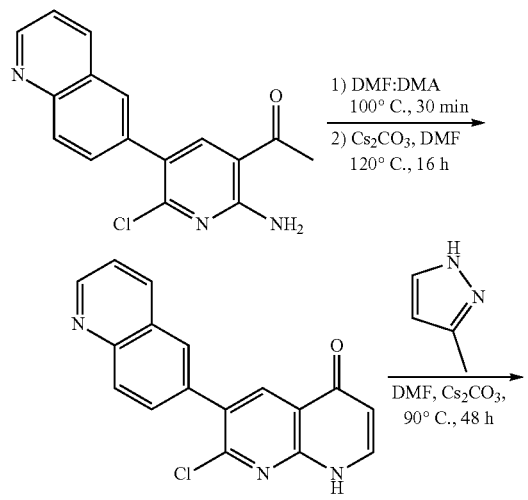

Step 1: Synthesis of 7-chloro-6-(quinolin-6-yl)-1,8-naphthyridin-4(1H)-one

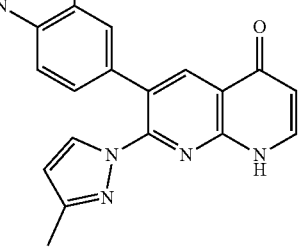

To a solution of 1-(2-amino-5-(quinolin-6-yl)pyridin-3-yl)ethanone (297 mg, 0.83 mmol, 1 eq), in 1,4 dioxane (10 mL), in DMF:DMA (150 mg, 1.25 mmol, 1.5 eq.). The reaction mixture was heated at 100° C. for 30 min. The reaction was monitored by TLC and LCMS. The reaction mixture was concentrated under reduced pressure. To this Cs₂CO₃ (820 mg, 2.5 mmol, 3.0 eq) and DMF (1 mL) was added. The reaction mixture was heated at 120° C. for 16 h. The reaction mixture was diluted with ice cold water (5 mL) and extracted with ethyl acetate (3×30 mL). The separated organic layer was washed with water (5×20 mL). The organic layer was dried over sodium sulfate and concentrated under reduced pressure. The crude product was purified by normal phase column chromatography to get the desired product (120 mg, 47%).

LCMS: 308 [M+1]⁺

Step-2: Synthesis of 7-(3-methyl-1H-pyrazol-1-yl)-6-(quinolin-6-yl)-1,8-naphthyridin-4(1H)-one To a stirred solution of 7-chloro-6-(quinolin-6-yl)-1,8-naphthyridin-4(1H)-one (120 mg, 0.39 mmol, 1 eq.) in DMF (2 mL) was added 3-methyl-1H-pyrazole (320 mg, 3.9 mmol, 10 eq.) and Cs₂CO₃ (380 mg, 1.16 mmol, 3 eq.). Resulting mixture was heated at 90° C. for 48 h, progress of the reaction was monitored by TLC and LCMS. On completion of the reaction, the reaction mixture was diluted with water (30 mL) and extracted with ethyl acetate (50 mL×2). Combined organic layers were washed with water (100 mL×2), dried with anhydrous Na₂SO₄ and concentrated under vacuum to get the solid residue which was purified by reversed phase column chromatography to get the desired product as off white solid (2 mg, 1%).

LCMS: 354 [M+1]⁺. ¹H NMR (400 MHz, DMSO-d₆) δ 12.47 (s, 1H), 9.05 (br. s., 1H), 8.65 (s, 1H), 8.60 (s, 1H), 8.19 (br. s., 1H), 8.11 (br. s., 1H), 7.93-8.04 (m, 2H), 7.76 (s, 1H), 7.47 (d, J=8.33 Hz, 1H), 6.31 (d, J=2.19 Hz, 1H), 6.19 (d, J=7.45 Hz, 1H), 1.96 (s, 3H).

Example S31. Synthesis of 6-(benzo[d]thiazol-6-yl)-7-(5-methylfuran-2-yl)-1,8-naphthyridin-4(1H)-one (Compound No. 1.98)

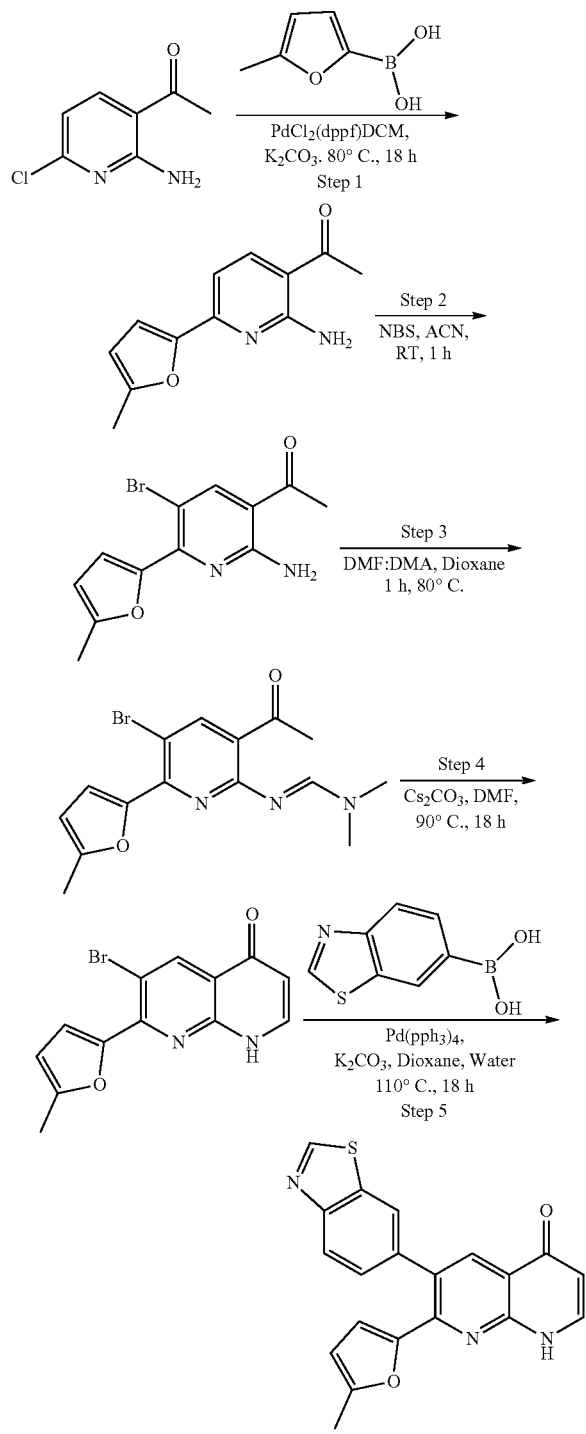

Step 1: Synthesis of 1-(2-amino-6-(5-methylfuran-2-yl)pyridin-3-yl)ethanone To a solution of 1-(2-amino-6-chloropyridin-3-yl)ethanone (600 mg, 3.52 mmol, 1 eq.) in DME (15 mL): water (3 mL) was added 5-methylfuran-2-ylboronic acid (485 mg, 3.88 mmol, 1.1 eq.), $K_2CO_3$ (731 mg, 5.29 mmol, 1.5 eq.), $PdCl_2(dppf)DCM$ (144 mg, 0.017 mmol, 0.05 eq.). The reaction mixture was deoxygenated using $N_2$ atmosphere and the reaction mixture was heated at 80° C. for 18 h. The reaction was monitored by TLC and LCMS. The reaction mixture was diluted with water (50 mL) and extracted using ethyl acetate (2×50 mL). The separated organic layer was dried over sodium sulfate and concentrated under reduced pressure. The crude product was purified using Combi-flash column chromatography to afford the desired product (150 mg, 20%).

LCMS: 217 $[M+1]^+$.

Step 2: Synthesis of 1-(2-amino-5-bromo-6-(5-methylfuran-2-yl)pyridin-3-yl)ethanone To a solution of 1-(2-amino-6-(5-methylfuran-2-yl)pyridin-3-yl)ethanone (150 mg, 0.69 mmol, 1 eq.) in mixture of ACN (10 mL) was added N-bromosuccinimide (160 mg, 0.89 mmol, 1.3 eq.). The reaction mixture was stirred at room temperature for 1 h. The reaction was monitored by TLC and NMR. The reaction solvent was evaporated under reduced pressure. The reaction mixture was diluted with water (100 mL) and extracted by ethyl acetate (2×50 mL). The organic layer was separated, washed water (5×20 mL) and brine and dried over anhydrous sodium sulfate. The solvent was evaporated under reduced pressure to afford the desired product (200 mg, 98%).

LCMS: 295 $[M+1]^+$.

Step 3: Synthesis of N'-(3-acetyl-5-bromo-6-(5-methylfuran-2-yl)pyridin-2-yl)-N,N-dimethylformimidamide To a solution of 1-(2-amino-5-bromo-6-(5-methylfuran-2-yl)pyridin-3-yl)ethanone (200 mg, 0.677 mmol, 1 eq), in 1,4 dioxane (10 mL), was added DMF:DMA (201 mg, 1.69 mmol, 2.5 eq.). The reaction mixture was heated at 80° C. for 60 min. The reaction was monitored by TLC and LCMS. The reaction solvent was evaporated under reduced pressure. The crude product was used in next step.

LCMS: 350 $[M+1]^+$.

Step 4: Synthesis of 6-bromo-7-(5-methylfuran-2-yl)-1,8-naphthyridin-4(1H)-one To a solution of N'-(3-acetyl-5-bromo-6-(5-methylfuran-2-yl)pyridin-2-yl)-N,N-dimethylformimidamide (200 mg, 0.57 mmol, 1 eq), in DMF (2 mL), was added $Cs_2CO_3$ (278 mg, 0.85 mmol, 1.5 eq). The reaction mixture was heated at 90° C. for 18 h. The reaction was monitored by LCMS. The reaction mixture was diluted with ice cold water (25 mL) and extracted with ethyl acetate (2×50 mL). The separated organic layer was washed with water (5×20 mL). The organic layer was dried over sodium sulfate and concentrated under reduced pressure to afford (150 mg, 86%) of 6-bromo-7-(5-methylfuran-2-yl)-1,8-naphthyridin-4(1H)-one.

LCMS: 305 $[M+1]^+$.

Step 5: Synthesis of 6-(benzo[d]thiazol-6-yl)-7-(5-methylfuran-2-yl)-1,8-naphthyridin-4(1H)-one To a solution of 6-bromo-7-(5-methylfuran-2-yl)-1,8-naphthyridin-4(1H)-one (100 mg, 0.33 mmol, 1 eq) in 1,4 dioxane (8 mL): water (2 mL) was added benzo[d]thiazol- 6-ylboronic acid (64 mg, 0.36 mmol, 1.1 eq.), K$_2$CO$_3$ (68 mg, 0.49 mmol, 1.5 eq.), Pd(PPh$_3$)$_4$(19 mg, 0.016 mmol, 0.05 eq.). The reaction mixture was deoxygenated using N$_2$ atmosphere and the reaction mixture was heated at 80° C. for 18 h. The reaction was monitored by TLC and LCMS. The reaction mixture was diluted with water (50 mL) and extracted using ethyl acetate (2×50 mL). The separated organic layer was dried over sodium sulfate and concentrated under reduced pressure. The crude product was purified using reverse phase column chromatography to afford the desired product as off-white solid (14 mg, 11%).

LCMS: 260 [M+1]$^+$. $^1$H NMR (400 MHz, DMSO-d$_6$) D 12.44 (d, J=4.82 Hz, 1H), 9.47 (s, 1H), 8.20-8.28 (m, 2H), 8.15 (d, J=8.33 Hz, 1H), 7.92-7.97 (m, 1H), 7.50 (dd, J=1.75, 8.33 Hz, 1H), 6.07-6.12 (m, 2H), 5.86 (d, J=3.51 Hz, 1H), 2.20 (s, 3H).

Example S32. Synthesis of 7-(1H-pyrazol-1-yl)-6-(quinolin-6-yl)-1,8-naphthyridin-2(1H)-one (Compound No. 1.99)

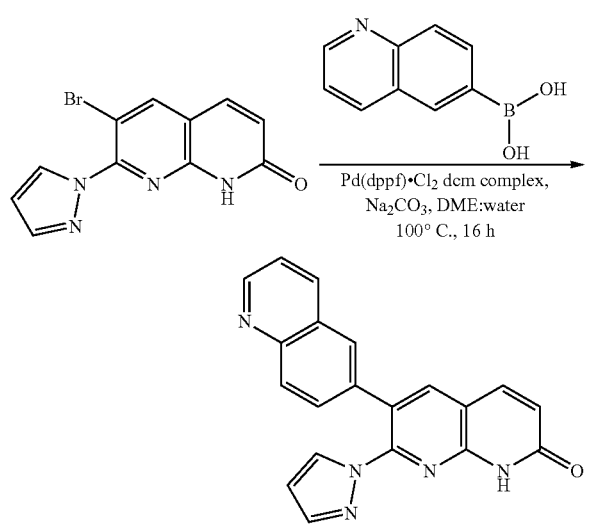

To a stirred solution of 6-bromo-7-(1H-pyrazol-1-yl)-1,8-naphthyridin-2(1H)-one (0.100 g, 0.34 mmol, 1.0 eq.) and quinolin-6-ylboronic acid (0.071 g, 0.41 mmol, 1.2 eq.) in DME (3 mL) was added Na$_2$CO$_3$ (0.072 g, 0.68 mmol, 2.0 eq.) and 1 mL water. The reaction was deoxygenated using N2 followed by addition of Pd(dppf)Cl$_2$.DCM complex (0.014 g, 5 mol %). The reaction mixture was deoxygenated again & heated at 100° C. for 16 h. The reaction mixture was allowed to cool to RT and extracted using ethyl acetate (3×25 mL). The combined organic layers were washed (brine), dried (anhydrous Na$_2$SO$_4$) and concentrated under vacuum to get the solid residue which was purified by reversed phase column chromatography to get the desired product as off white solid (0.015 g, 13%)

LCMS: 340 [M+1]$^+$. $^1$H NMR (400 MHz, DMSO-d$_6$) δ 8.85-8.95 (m, 1H), 8.48 (s, 1H), 8.32 (d, J=7.89 Hz, 1H), 8.19 (br. s., 1H), 8.05 (d, J=9.21 Hz, 1H), 7.81-7.93 (m, 2H), 7.46-7.59 (m, 2H), 7.31 (d, J=8.33 Hz, 1H), 6.67 (d, J=9.65 Hz, 1H), 6.46 (br. s., 1H).

Example S33. Synthesis of 7-(1H-pyrazol-1-yl)-6-(quinolin-6-yl)-1,8-naphthyridin-4(1H)-one (Compound No. 1.100)

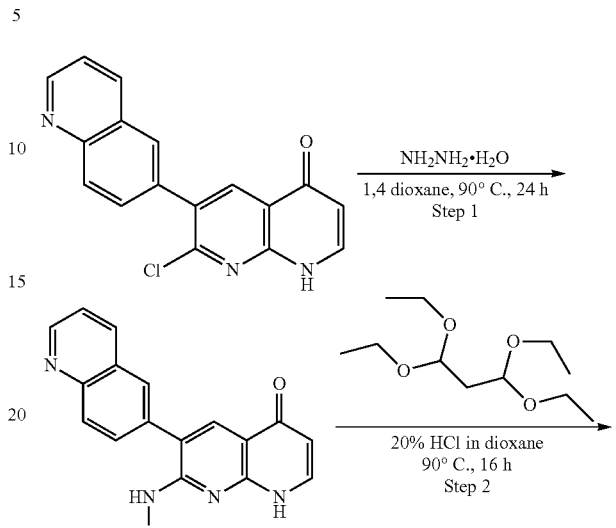

Step 1

To a stirred solution of 7-chloro-6-(quinolin-6-yl)-1,8-naphthyridin-4(1H)-one (90 mg, 0.29 mmol, 1.0 equiv) & hydrazine hydrate (22 mg, 0.43 mmol, 1.5 equiv) in dioxane (5 mL). The resulting mixture was heated at 90° C. for 16 h. The reaction mixture was allowed to cool to RT and concentrated under vacuum to get the solid residue (90 mg crude) which was used for next reaction without purification.

LCMS: 304 [M+1]$^+$.

Step 2

To a stirred solution of 7-hydrazinyl-6-(quinolin-6-yl)-1,8-naphthyridin-4(1H)-one (90 mg, 0.29 mmol, 1.0 equiv) & 1,1,3,3-tetraethoxypropane (97 mg, 0.44 mmol, 1.5 equiv) in dioxane (5 mL) was added 20% HCl in dioxane (0.3 ml). The reaction mixture was heated at 90° C. for 16 h. Progress of the reaction was monitored by LCMS. The reaction mixture was allowed to cool to RT & basified with solution of NaHCO$_3$ (10 mL) and extracted with ethyl acetate (20 mL×2). The combined organic layers were washed with water (50 mL) and brine solution (50 mL), dried (anhydrous Na$_2$SO$_4$) & concentrated under vacuum to get the solid residue which was purified by reversed phase column chromatography to get the desired product (13 mg, 13%).

LCMS: 340 [M+1]$^+$ $^1$H NMR (400 MHz, DMSO-d$_6$) δ 8.89 (d, J=3.95 Hz, 1H), 8.62 (s, 1H), 8.36 (d, J=8.33 Hz, 1H), 8.29 (d, J=2.19 Hz, 1H), 8.04 (d, J=7.45 Hz, 1H), 7.99

(br. s., 1H), 7.85 (d, J=8.33 Hz, 1H), 7.58-7.47 (m, 2H), 7.29 (d, J=8.77 Hz, 1H), 6.49 (br. s., 1H), 6.16 (d, J=7.45 Hz, 1H).

Example S34. Synthesis of 3-phenyl-2-(quinazolin-6-yl)pyrido[2,3-b]pyrazin-8(5H)-one (Compound No. 1.101)

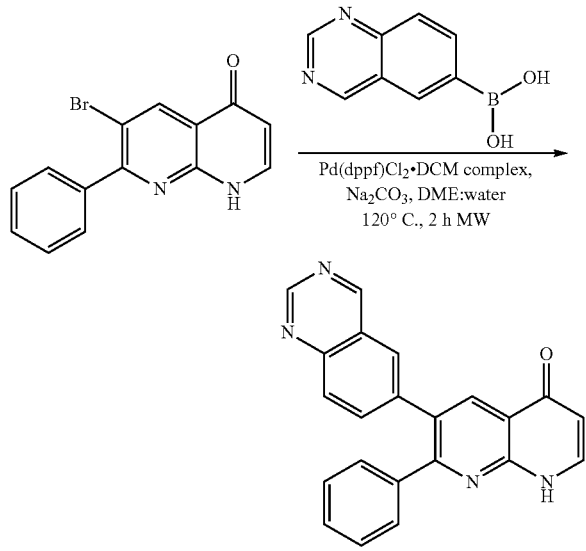

To a stirred solution of 2-bromo-3-phenylpyrido[2,3-b]pyrazin-8(5H)-one (0.100 g, 0.33 mmol, 1.0 eq.) in DME (20.0 mL) was added quinazolin-6-ylboronic acid (0.110 g, 0.43 mmol, 1.3 eq). The reaction mixture was deoxygenated using nitrogen gas. Pd(dppf)Cl$_2$ dcm complex (0.0.013 g, 0.05 eq 0.0.16 mmol) was then added. The reaction mixture was again purged with nitrogen & heated at 120° C. for 2 hours in microwave. Progress of the reaction was monitored by TLC and LCMS. Reaction mixture was allowed to cool to RT & quenched by adding aq. NaOH & extracted using ethyl acetate (3×100 mL) The combined organic layers were washed (brine), dried (anhydrous Na$_2$SO$_4$) & concentrated under vacuum to get the solid which was purified by normal phase column chromatography to get the desired product (0.0092 g, 8%).

LCMS: 351 [M+1]$^+$ $^1$H NMR (400 MHz, DMSO-d$_6$) δ 12.41 (d, J=5.70 Hz, 1H), 9.60 (s, 1H), 9.34-9.14 (m, 1H), 8.56 (s, 1H), 8.27 (d, J=1.75 Hz, 1H), 7.99-8.08 (m, 1H), 7.84 (d, J=8.77 Hz, 1H), 7.65 (dd, J=8.77, 1.75 Hz, 1H), 7.46-7.15 (m, 5H), 6.18 (d, J=7.45 Hz, 1H).

Example S35. Synthesis of 6-(3a,7a-dihydro-1H-indazol-5-yl)-7-phenyl-1,8-naphthyridin-4(1H)-one (Compound No. 1.102)

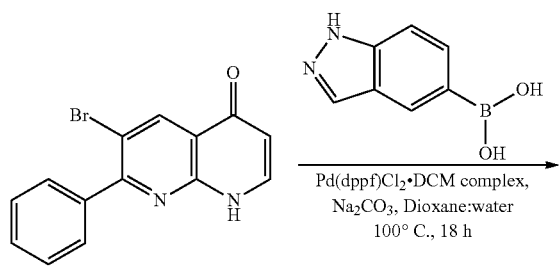

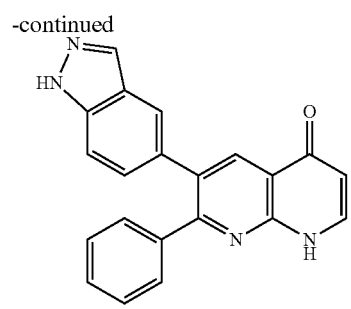

To a stirred solution of 6-bromo-7-phenyl-1,8-naphthyridin-4(1H)-one (0.150 g, 0.5 mmol, 1.0 eq.) and (1H-indazol-5-yl)boronic acid (0.146 g, 0.6 mmol, 1.2 eq.) in dioxane (4 mL) was added Na$_2$CO$_3$ (0.106 g, 1.0 mmol, 2.0 eq.) and 1 mL water. The reaction was purged with N$_2$ for 5 min. To this reaction mixture was added with Pd(dppf)Cl$_2$.DCM complex (0.021 g, 5 mol %) and N$_2$ was purged again for another 5 min. The reaction mixture was heated at 100° C. for 18 h. The reaction mixture was allowed to cool to RT and extracted using ethyl acetate (3×25 mL). The combined organic layers were washed (brine), dried (anhydrous Na$_2$SO$_4$) and concentrated under vacuum to get the solid residue which was purified by reversed phase column chromatography to get the desired product as off white solid (0.005 g, 3%)

LCMS: 339 [M+1]+$^1$H NMR (400 MHz, DMSO-d$_6$) δ 13.11 (br. s., 1H), 12.33 (br. s., 1H), 8.39 (s, 1H), 8.05 (br. s., 1H), 7.98 (br. s., 1H), 7.72 (s, 1H), 7.33-7.46 (m, 3H), 7.28 (d, J=7.02 Hz, 2H), 7.08 (d, J=8.33 Hz, 1H), 6.14 (d, J=7.45 Hz, 2H).

Example S36. Synthesis of 6-(3-chlorophenyl)-7-phenyl-1,8-naphthyridin-4(1H)-one (Compound No. 1.30)

To a solution of 6-bromo-7-phenyl-1,8-naphthyridin-4(1H)-one (100 mg, 0.33 mmol, 1 eq.) in 1,4-dioxane (8 mL): water (2 mL) was added 3-chlorophenylboronic acid (54 mg, 0.35 mmol, 1.05 eq.), Na$_2$CO$_3$ (70 mg, 0.66 mmol, 2 eq.), and Pd(PPh$_3$)$_4$ (9 mg, 0.008 mmol, 0.025 eq.). The reaction mixture was deoxygenated using N$_2$ and was allowed to heat at 80° C. for 18 h. The progress of the reaction was monitored by LCMS. The reaction mixture was diluted with water (50 mL) and extracted using ethyl acetate (2×50 mL). The separated organic layer was dried over sodium sulfate and concentrated under reduced pressure. The crude product was purified by reverse phase column chromatography to afford the desired product (25 mg, 23%)

LCMS: 333 [M+1]⁺. ¹H NMR (400 MHz, DMSO-d₆) δ 6.18 (d, 1H), 7.18 (d, 1H), 7.30-7.40 (m, 8H), 8.00 (d, 1H), 8.40 (s, 1H).

Example S37. Synthesis of 6-(3-chlorophenyl)-7-phenyl-1,8-naphthyridin-2(1H)-one (Compound No. 1.31)

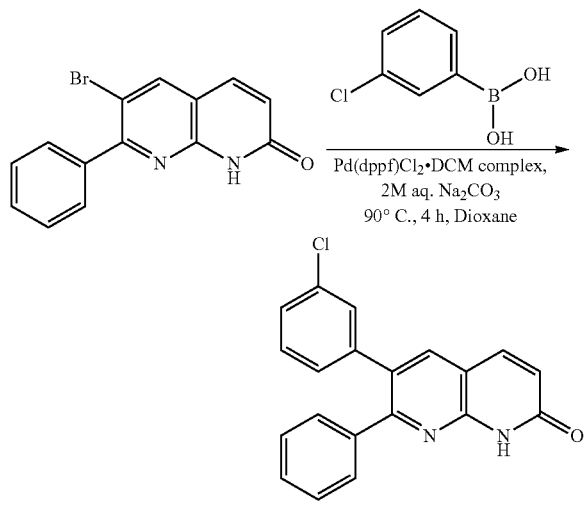

To a stirred solution of 6-bromo-7-phenyl-1,8-naphthyridin-2(1H)-one (0.120 g, 0.40 mmol, 1.0 equiv) and (3-chlorophenyl)boronic acid (0.075 g, 0.48 mmol, 1.2 equiv) in dioxane (4 mL) was added 2M aqueous Na₂CO₃ (0.085 g, 0.80 mmol, 2.0 equiv, 0.4 mL). The reaction was purged with N₂ for 5 min. To this reaction mixture was added Pd(dppf)Cl₂-DCM complex (0.016 g, 5 mol %) and N₂ was purged again for another 5 min. The reaction mixture was heated at 90° C. for 4 h. The reaction mixture was allowed to cool to RT and extracted using ethyl acetate (2×35 mL). The combined organic layers were washed (brine), dried (anhydrous Na₂SO₄) and concentrated under vacuum to get the solid residue which was purified by normal phase flash column chromatography (3% Methanol in DCM) to get the desired product as off white solid (0.020 g, 15%).

LCMS: 333 [M+1]⁺. ¹H NMR (400 MHz, DMSO-d₆) δ 8.23 (s, 1H), 8.00 (d, J=9.21 Hz, 1H), 7.22-7.42 (m, 8H), 7.06-7.17 (m, 1H), 6.63 (d, J=9.65 Hz, 1H).

Example S38. Synthesis of 6-(2-oxo-2,3-dihydro-1H-benzo[d]imidazol-5-yl)-7-phenyl-1,8-naphthyridin-2(1H)-one (Compound No. 1.32)

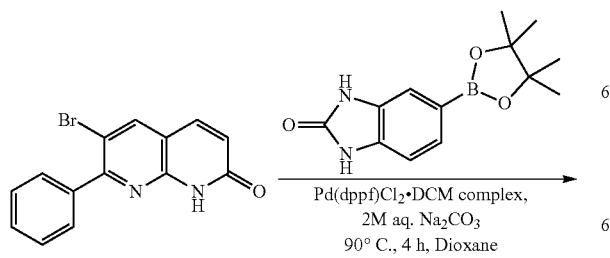

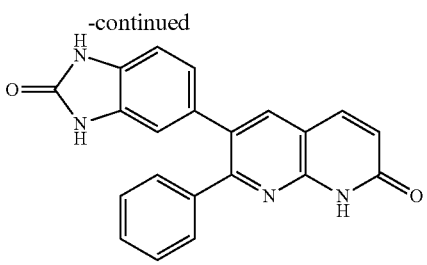

To a stirred solution of 6-bromo-7-phenyl-1,8-naphthyridin-2(1H)-one (0.120 g, 0.40 mmol, 1.0 equiv) and 5-(4,4,5,5-tetramethyl-1,3,2-dioxaborolan-2-yl)-1,3-dihydro-2H-benzo[d]imidazol-2-one (0.124 g, 0.48 mmol, 1.2 equiv) in dioxane (4 mL) was added 2M aqueous Na₂CO₃ (0.085 g, 0.80 mmol, 2.0 equiv, 0.4 mL). The reaction was purged with N₂ for 5 min. To this reaction mixture was added Pd(dppf)Cl₂-DCM complex (0.016 g, 5 mol %) and N₂ was purged again for another 5 min. The reaction mixture was heated at 90° C. for 4 h. The reaction mixture was allowed to cool to RT and extracted using ethyl acetate (2×35 mL). The combined organic layers were washed (brine), dried (anhydrous Na₂SO₄) and concentrated under vacuum to get the solid residue which was purified by reverse phase column chromatography to get the desired product (0.020 g, 14%).

LCMS: 355 [M+1]⁺. ¹H NMR (400 MHz, DMSO-d₆) δ 10.57 (br. s., 2H), 8.13 (s, 1H), 7.99 (d, J=9.65 Hz, 1H), 7.17-7.42 (m, 5H), 6.84 (d, J=7.89 Hz, 1H), 6.71-6.78 (m, 2H), 6.60 (d, J=9.21 Hz, 1H).

Example S39. Synthesis of 6-(2,6-dimethylpyridin-4-yl)-7-phenyl-1,8-naphthyridin-2(1H)-one (Compound No. 1.33)

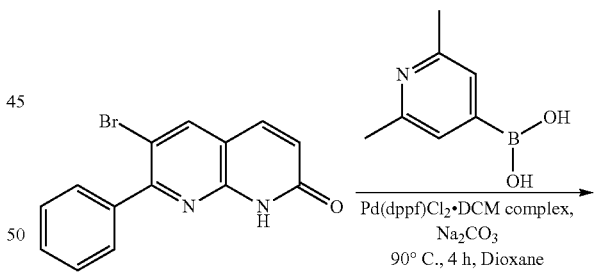

To a stirred solution of 6-bromo-7-phenyl-1,8-naphthyridin-2(1H)-one (0.120 g, 0.40 mmol, 1.0 equiv) and (2,6-dimethylpyridin-4-yl)boronic acid (0.073 g, 0.48 mmol, 1.2 equiv) in dioxane (2 mL) was added Na₂CO₃ (0.085 g, 0.80 mmol, 2.0 equiv) and 0.8 mL water. The reaction was purged with N₂ for 5 min. To this reaction mixture was added Pd(dppf)Cl₂-DCM complex (0.016 g, 5 mol %) and N₂ was purged again for another 5 min. The reaction mixture was heated at 90° C. for 4 h. The reaction mixture was allowed to cool to RT and extracted using ethyl acetate (2×35 mL). The combined organic layers were washed (brine), dried (anhydrous Na₂SO₄) and concentrated under vacuum to get the solid residue which was purified by reverse phase column chromatography to get the desired product as off white solid (0.020 g, 15%).

LCMS: 328 [M+1]⁺. ¹H NMR (400 MHz, DMSO-d₆) δ 12.28 (br. s., 1H), 8.22 (s, 1H), 8.00 (d, J=9.78 Hz, 1H), 7.26-7.44 (m, 5H), 6.86 (s, 2H), 6.63 (d, J=9.29 Hz, 1H), 2.32 (s, 6H)

Example S40. Synthesis of 7-phenyl-6-(pyridin-4-yl)-1,8-naphthyridin-2(1H)-one (Compound No. 1.34)

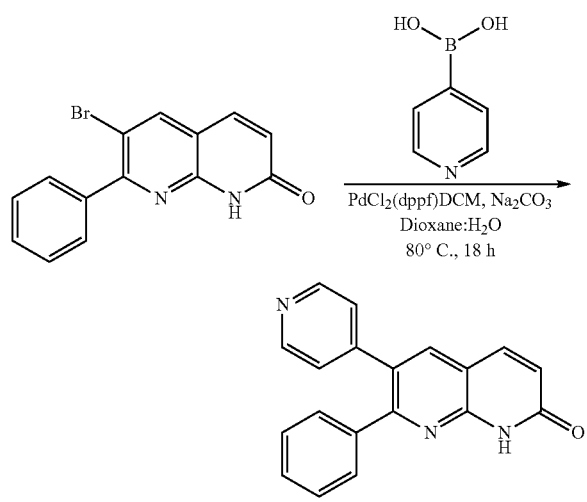

To a solution of 6-bromo-7-phenyl-1,8-naphthyridin-2 (1H)-one (100 mg, 0.33 mmol, 1 eq.) in 1,4-dioxane (8 mL): water (2 mL) was added pyridin-4-ylboronic acid (41 mg, 0.33 mmol, 1.00 eq.), Na₂CO₃ (70 mg, 0.66 mmol, 2 eq.), and PdCl₂(dppf)DCM complex (6 mg, 0.008 mmol, 0.025 eq.). The reaction mixture was deoxygenated using N₂ atmosphere and the reaction mixture was heated at 80° C. for 18 h. The reaction was monitored by NMR and LCMS. The reaction mixture was diluted with water (50 mL) and extracted using ethyl acetate (2×50 mL). The separated organic layer was dried over sodium sulfate and concentrated under reduced pressure. The crude product was purified by reverse phase column chromatography to afford (20 mg, 20%) as a desired product.

LCMS: 300 [M+1]⁺. ¹H NMR (400 MHz, DMSO-d₆) δ 6.62 (d, 1H), 7.20 (d, 2H), 7.30-7.40 (bs, 5H), 8.00 (d, 1H), 8.22 (s, 1H), 8.30 (d, 2H).

Example S41. Synthesis of 6-(3-chloro-5-methylphenyl)-7-phenyl-1,8-naphthyridin-2(1H)-one (Compound No. 1.35)

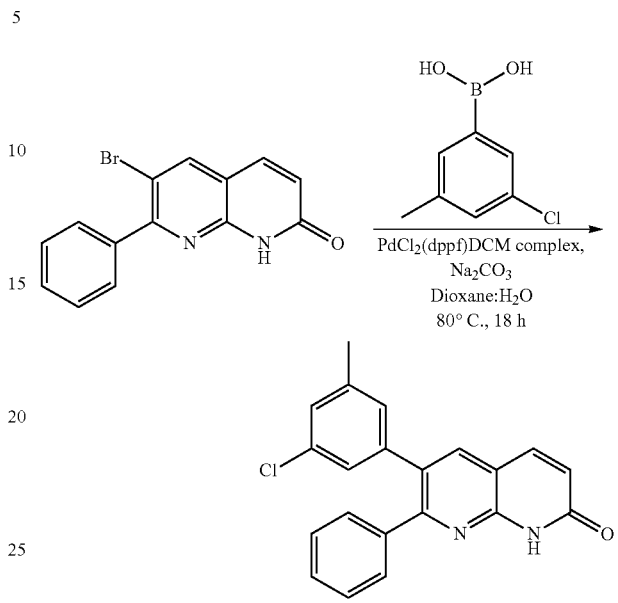

To a solution of 6-bromo-7-phenyl-1,8-naphthyridin-2 (1H)-one (100 mg, 0.33 mmol, 1 eq.) in 1,4-dioxane (8 mL): water (2 mL) was added 3-chloro-5-methylphenylboronic acid (41 mg, 0.33 mmol, 1.00 eq.), Na₂CO₃ (70 mg, 0.66 mmol, 2 eq.), PdCl₂(dppf)DCM complex (6 mg, 0.008 mmol, 0.025 eq.). The reaction mixture was deoxygenated using N₂ atmosphere and the reaction mixture was heated at 80° C. for 18 h. The reaction was monitored by NMR and LCMS. The reaction mixture was diluted with water (50 mL) and extracted using ethyl acetate (2×50 mL). The separated organic layer was dried over sodium sulfate and concentrated under reduced pressure. The crude product was purified by reverse phase column chromatography to afford (20 mg, 17%) as a desired product.

LCMS: ([M+1]+): 347. ¹H NMR (400 MHz, DMSO-d₆) δ 2.20 (s, 3H), 6.60 (d, 1H), 6.98-7.00 (d, 2H), 7.18 (s, 1H), 7.30-7.40 (s, 5H), 8.00 (s, 1H), 8.20 (s, 1H).

It is understood that compounds from the Table-1 (1.36-1.91, 1.93-1.97 and 1.103-2.023) may be synthesized by the General Synthetic Scheme 1, Scheme 2, Scheme 3, Scheme 4, Scheme 5 or present routes involving steps clearly familiar to those skilled in the art, wherein the substituents described in compounds of formula (I) herein can be varied with a choice of appropriate starting materials and reagents utilized in the steps presented.

Biological Examples

Example B1. Radioligand Binding Competition Assay

Binding of selected compounds to the adenosine $A_1$, $A_{2A}$, $A_{2B}$, and $A_3$ receptors was tested using a binding competition assay.

The general protocol for the radioligand binding competition assay was as follows. Competition binding was performed in duplicate in the wells of a 96 well plate (Master Block, Greiner, 786201) containing binding buffer (optimized for each receptor), membrane extracts (amount of protein/well optimized for each receptor), radiotracer (final concentration optimized for each receptor), and test compound. Nonspecific binding was determined by co-incubation with 200-fold excess of cold competitor. The samples were incubated in a final volume of 0.1 mL at 25° C. for 60 minutes and then filtered over filter plates. Filters were washed six times with 0.5 mL of ice-cold washing buffer (optimized for each receptor) and 50 µL of Microscint 20 (Packard) were added on each filter. The filter plates were sealed, incubated 15 min on an orbital shaker and scintillation counted with a TopCount for 30 sec/filter.

For the adenosine $A_{2A}$ receptor radioligand binding assay, the following modifications were made to the general protocol. GF/C filters (Perkin Elmer, 6005174), presoaked in 0.01% Brij for 2 h at room temperature were used. Filters were washed six times with 0.5 mL of ice-cold washing buffer (50 mM Tris pH 7.4) and 50 µL of Microscint 20 (Packard) was added in each well. The plates were then incubated for 15 min on an orbital shaker and then counted with a TopCount™ for 1 min/well.

Another radioligand binding assay was used to evaluate the binding affinity for the adenosine $A_{2A}$ receptor assay was performed in duplicate in the wells of a 384 plate. Assay buffer contained DPBS 500 mM, $MgCl_2$ 0.1 mM, and 1% DMSO. Membrane-bead suspension was prepared by mixing 25.98 µL of human adenosine $A_{2A}$ membrane preparation (Perkin Elmer, RBHA2AM400UA) at 33.4 pg/mL, 28 µL of ADA at 20 pg/mL, and 932 µL of SPA beads at 3.33 mg/mL) and incubated the mixture for 20 min at room temperature. Mixed 20 µL of radiotracer ($^3$H-SCH 58261) at 15 nM to each well containing test articles at various concentrations and centrifuge the plate at 1000 rpm for 1 minute. Added 30 µL of the membrane-bead suspension to each well. Sealed the plates and incubated for 1 hr at room temperature with vigorous mixing on a plate mixer. Plates were read on Microbeta$^2$ (Perkin Elmer, 2450-0010).

For the adenosine $A_1$ radioligand binding competition assay, a similar procedure was used except that the following reagents were used: CHO-K1-A1 cell membranes; binding buffer comprising HEPES 25 mM pH 7.4, $MgCl_2$ 5 mM, $CaCl_2$ 1 mM, NaCl 100 mM, saponin 10 g/mL; wash buffer comprising HEPES 25 mM pH 7.4, $MgCl_2$ 5 mM, $CaCl_2$ 1 mM, NaCl 100 mM; Unifilter GF/B—treated for 2 h with 0.5% PEI was the filter; and 1.6 nM of $^3$H-DPCPX was the tracer.

Similarly, the following reagents were used for the adenosine $A_{2B}$ radioligand binding competition assay: HEK-293-A2b cell membranes, 20 µg/well, preincubated 30 min at RT with g/mL Adenosine Deaminase; a binding buffer comprising HEPES 10 mM pH7.4, EDTA 1 mM, 0.5% BSA; a wash buffer comprising HEPES 10 mM pH7.4, EDTA 1 mM; a Unifilter GF/C—treated for 2 h with 0.5% PEI; and 10 nM $^3$H-DPCPX as the tracer.

For the adenosine $A_3$ radioligand binding competition assay, the following reagents were used: CHO-K1-A3 cell membranes, 1.5 µg/well; a binding buffer comprising HEPES 25 mM pH 7.4, $MgCl_2$ 5 mM, $CaCl_2$ 1 mM, 0.5% BSA; a wash buffer comprising HEPES 25 mM pH 7.4, $MgCl_2$ 5 mM, $CaCl_2$ 1 mM; a Unifilter GF/C—treated for 2 h with 0.5% BS; and 0.4 nM of $^{125}$I-AB-MECA as the tracer.

The results of the binding assay are shown in Table B1-1 and are shown as percent residual binding at a given concentration. Percent of residual binding means binding of a compound in the presence of competitor normalized to the amount of binding in the absence of competitor. The compounds tested showed a range of binding to the adenosine receptors tested. For example, compound 1 strongly bound to $A_{2A}$ (30% residual binding at a concentration of 100 nM), $A_1$ (−3% residual binding at 300 nM) and $A_{2B}$, (−9% residual binding at 300 nM) but weakly bound to $A_3$ (96% residual binding at 300 nM).

TABLE B1-1

| Compound No. | $A_{2A}$ radioligand binding competition assay % residual binding @ 3000/1000/300/100 nM | Radioligand binding competition assay % residual binding @ 300 nM ($A_1$/$A_{2b}$/$A_3$) | $A_{2A}$ binding IC$_{50}$ (nM) |
|---|---|---|---|
| 1.1 | ND/ND/54/83 | 1.6/17/95 | ND |
| 1.2 | ND/ND/60/77 | 0/0/83 | ND |
| 1.3 | 50/ND/ND/ND | ND | ND |
| 1.4 | 19/17/79/71 | ND | ND |
| 1.5 | 22/12/38/74 | 11/2/104 | 181 |
| 1.6 | 57/ND/ND/ND | ND | ND |
| 1.7 | 18/21/33/52 | 7/0/84 | ND |
| 1.8 | 106/ND/ND/ND | ND | ND |
| 1.9 | 70/ND/ND/ND | ND | ND |
| 1.10 | 60/ND/ND/ND | ND | ND |
| 1.11 | 51/ND/ND/ND | ND | ND |
| 1.12 | 14/ND/ND/ND | ND | ND |
| 1.13 | 29/ND/ND/ND | ND | ND |
| 1.14 | 5/ND/ND/ND | 13/0/87 | 33 |
| 1.15 | 45/ND/ND/ND | ND | ND |
| 1.16 | 76/ND/ND/ND | ND | ND |
| 1.17 | 14/ND/ND/ND | ND | ND |
| 1.18 | 38/ND/ND/ND | ND | ND |
| 1.19 | 25/ND/ND/ND | ND | ND |
| 1.20 | 36/ND/ND/ND | ND | ND |
| 1.21 | 54/ND/ND/ND | ND | ND |
| 1.22 | 69/ND/ND/ND | ND | ND |
| 1.23 | 22/ND/ND/ND | ND | ND |
| 1.24 | 16/ND/ND/ND | ND | ND |
| 1.25 | 0/ND/ND/ND | ND | ND |

ND = Not determined

TABLE B1-2

| Compound No. | A2a binding IC50 (nM) | A2a binding % inh @ 3000 nM | A2a binding % inh @ 1000/300/100/10/1 nM |
|---|---|---|---|
| 1.98 | ND | 85 | ND |
| 1.99 | ND | 57 | ND |
| 1.100 | ND | 78 | ND |
| 1.101 | ND | 72 | ND |
| 1.102 | ND | 77 | ND |
| 1.30 | ND | ND | ND/0/ND/ND/ND |
| 1.31 | ND | ND | ND/0/ND/ND/ND |
| 1.32 | ND | ND | ND/0/ND/ND/ND |
| 1.33 | ND | 30 | ND |
| 1.34 | ND | 30 | ND |
| 1.35 | ND | 0 | ND |

ND = Not determined

Example B2. cAMP Assay

The functional activity of compounds was tested using one of the two assays to detect the present of cAMP. Activation of G-protein coupled receptors (such as $A_{2A}$) results in activation of adenylcyclase which converts ATP into cAMP which is used as a downstream signaling molecule. Therefore, molecules which act as GPCR (or specifically $A_{2A}$ receptor) antagonists cause a decrease in intracellular cAMP concentration.

Both assays used HEK-293 cells expressing human recombinant adenosine $A_{2A}$ receptor were grown prior to the test in media without antibiotic. Assay 1: The cells were detached by gentle flushing with PBS-EDTA (5 mM EDTA), recovered by centrifugation and suspended in assay buffer (KRH: 5 mM KCl, 1.25 mM MgSO$_4$, 124 mM NaCl, 25 mM HEPES, 13.3 mM Glucose, 1.25 mM KH$_2$PO$_4$, 1.45 mM CaCl$_2$, 0.5 g/L BSA, supplemented with Rolipram).

12 μL of cells were mixed with 6 μL of the test compound at increasing concentrations and then incubated for 10 min. Thereafter 6 μL of the reference agonist was added at a final concentration corresponding to the historical EC$_{80}$. The plates were then incubated for 30 min at room temperature. After addition of the lysis buffer and 1 hour incubation, cAMP concentrations were estimated, according to the manufacturer specification, with the HTRF® kit.

Assay 2: 100 nL of test articles at 100× of final concentration were transferred to assay plate by Echo. Cells were washed twice with 5 mL of PBS 10 μL of cells were mixed with 5 mL PBS. After aspirating the PBS and adding 1.5 mL versine, cells were incubated at 37° C. for 2-5 min. After centrifugation, 4 mL of medium was added and adjusted cell density to 5,000 cells/well with stimulation buffer. 10 μL of cells were aliquoted to the assay plate, centrifuged at 1000 rpm for 1 minute, and incubated for 60 minutes at room temperature. 5 μL 4× Eu-cAMP tracer solution and 5 μL 4× Ulight™-anti-cAMP solution were added to assay plate, followed by centrifugation and 60-minute incubation at room temperature. Plates were read on EnVision.

| Compound No. | A2a cAMP IC$_{50}$ (nM) | A2a cAMP % inh @ 100 nM |
|---|---|---|
| 1.1 | 61 | ND |
| 1.2 | 22 | ND |
| 1.3 | ND | 50 |
| 1.4 | ND | 82 |
| 1.5 | 23 | ND |
| 1.6 | ND | 43 |
| 1.7 | ND | 81 |
| 1.8 | ND | 0 |
| 1.9 | ND | 30 |
| 1.10 | ND | 40 |
| 1.11 | ND | 49 |
| 1.12 | ND | 100 |
| 1.13 | 47.7 | ND |
| 1.14 | ND | 94 |
| 1.15 | ND | 54 |
| 1.16 | ND | 23 |
| 1.17 | ND | 85 |
| 1.18 | ND | 61 |
| 1.19 | ND | 74 |
| 1.20 | ND | 63 |
| 1.21 | ND | 45 |
| 1.22 | ND | 30 |
| 1.23 | ND | 77 |
| 1.24 | ND | 83 |
| 1.25 | 18.8 | ND |
| 1.26 | ND | 64 |
| 1.27 | ND | 88 |
| 1.28 | ND | 46 |
| 1.29 | ND | 77 |

ND = Not determined

| Compound No. | A2a cAMP IC$_{50}$ (nM) | A2a cAMP % inh @ 300/100 nM |
|---|---|---|
| 1.92 | 357 | ND |
| 1.98 | 17.2 | ND |
| 1.99 | 7307 | ND |
| 1.100 | 3223 | ND |
| 1.101 | 181.8 | ND |
| 1.102 | 292.4 | ND |
| 1.33 | ND | 60/ND |
| 1.34 | ND | 26/ND |
| 1.35 | ND | 12/ND |

ND = Not determined

Example B3: GTPγ$^{35}$S Scintillation Proximity Assay for A$_{2A}$ Receptor

A scintillation proximity assay (SPA) can be used to determine the kinetic profile of the binding of candidate molecules to the A$_{2A}$ receptor.

For antagonist testing, membranes extracts are prepared from HEK-293 cells expressing recombinant human A$_{2A}$ receptor are mixed with GDP (volume:volume) and are incubated in assay buffer comprising 20 mM HEPES pH 7.4; 100 mM NaCl, 10 μg/mL saponin, 5 mM MgCl$_2$ for at least 15 min on ice. In parallel, GTPγ[$^{35}$S] is mixed with the beads (volume:volume) just before starting the reaction. The following reagents are successively added in the wells of an Optiplate (Perkin Elmer): 25 μL of test compound or reference ligand, 25 μL of the membranes: GDP mix, 25 μL of reference agonist at historical EC$_{80}$ and 25 μL of GTPγ[$^{35}$S] (PerkinElmer NEG030X), diluted in assay buffer to give 0.1 nM. The plate is incubated at room temperature for 1 hour. Then, 20 μL of IGEPAL is added for 30 minutes at room temperature. Following this incubation, 20 μL of beads (PVT-anti rabbit (PerkinElmer, RPNQ0016)), diluted in assay buffer at 50 mg/mL (0.5 mg/10 μL) and 20 μL of an Anti-GαS/olf antibody are added for a final incubation of 3 hours at room temperature. Then the plates are centrifuged for 10 min at 2000 rpm, incubated at room temperature for 1 hour and counted for 1 min/well with a PerkinElmer TopCount reader.

Example B4: Human T Cell Activation Assay

Fresh human blood was diluted with the same volume of PBS and the buffy coat containing peripheral blood mononuclear cells (PBMCs) were prepared and resuspend in culture medium at a density of 2×10$^6$/mL. 2×10$^5$ PBMCs (in 100 μL) were plated to each well of 96-well flat bottom plate. 25 μL of 8× final concentration of 10-fold serial diluted compounds were added to indicated wells and incubate for 30 mins in 37° C./5% CO2. Beads included in T cell activation/expansion kit (Miltenyi biotec Cat#130-091-441) at a bead-to-cell ratio of 1:6 in 50 L were added to all well with the final concentration of DMSO at 0.1% and final volume at 200 μL. 60 μL of supernatant post 24 hr and 48 hr incubation was collected for TNF-α and IFN-γ concentration evaluation using TNF-α ELISA ready-set-go kit (eBioscience, Cat#88-7346-77) and IFN-γ ELISA ready-set-go kit (eBioscience, Cat#88-7316-77), respectively.

Example B5: cAMP Assay

CD8+ T-cells are isolated from peripheral blood mononuclear cells (PBMC) from normal donors using CD8+T lymphocyte enrichment kit.

In a 96-well plate coated with anti-CD3 antibody, CD8$^+$ T-cells (1×10$^5$) were cultured alone, with 3 μM of NECA, or in the presence of 1 μM of compound of the interest with or without 3 μM of NECA. The cells were incubated for 30 min at 37° C. and 5% CO$_2$, and the reaction was stopped by addition of 200 μL, 0.1 M hydrochloric acid. cAMP levels were determined by an ELISA kit.

Example B6: Anti-Tumor Activities in Immuno-Oncology Mouse Models

The anti-tumor activities of test articles will be evaluated in selective mouse models (e.g., syngeneic model, xenograft modle, or PDX) as a monotherapy or combination therapies.

Using MC-38 syngenic model as an example: female C57BL/6 mice are inoculated subcutaneously at right flank with MC-38 cells for tumor development. Five days after tumor inoculation, mice with tumor size ranging from 40-85 mm$^3$ are selected and assigned into sub-groups using stratified randomization with 10 mice per group based upon their tumor volumes. Mice receive pre-defined treatments include vehicle, test article at various doses alone, test article at various doses plus other anti-cancer therapy, and other anti-cancer therapy contro. Body weight and tumor sizes are measured three times per week during the treatment. Tumor volume will be expressed in mm$^3$ using the formula: V=0.5 a×b$^2$ where a and b are the long and short diameters of the tumor, respectively. The tumor sizes are used for the calculations of both tumor growth inhibition (TGI) and T/C values. When an individual animal reaches to the termination endpoint (e.g., with TV>1000 mm$^3$), the mouse are euthanized. The time from inoculation to the termination are deemed as its survival time. Survival curve are plotted by Kaplan-Meier method. At the end of study, plasma and tumor samples are collected to explore biomarkers.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed is:

1. A compound of Formula (I):

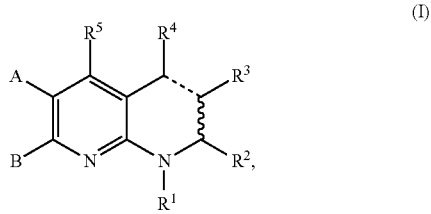

or a tautomer or isomer thereof, or a pharmaceutically acceptable salt of any of the foregoing, wherein:

$R^1$ is H or $C_1$-$C_6$ alkyl wherein the $C_1$-$C_6$ alkyl of $R^1$ is optionally substituted with oxo or $R^a$;

$R^2$ is H, $R^b$ or oxo;

$R^4$ is H, oxo, $C_1$-$C_6$ alkyl, $C_2$-$C_6$ alkenyl, $C_2$-$C_6$ alkynyl, halogen, —CN, —OR$^8$, —SR$^8$, —NO$_2$, —C=NH(OR$^8$), —C(O)R$^8$, —OC(O)R$^8$, —C(O)OR$^8$, —C(O)NR$^9$R$^{10}$, —OC(O)NR$^9$R$^{10}$, —NR$^8$C(O)OR$^9$, —NR$^8$C(O)NR$^9$R$^{10}$, —S(O)R$^8$, —S(O)$_2$R$^8$, —NR$^8$S(O)R$^9$, —C(O)NR$^8$S(O)R$^9$, —NR$^8$S(O)$_2$R$^9$, —C(O)NR$^8$S(O)$_2$R$^9$, —S(O)NR$^9$R$^{10}$, —S(O)$_2$NR$^9$R$^{10}$, —P(O)(OR$^9$)(OR$^{10}$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)OR$^8$, —($C_1$-$C_3$ alkylene)SR$^8$, —($C_1$-$C_3$ alkylene)NR$^9$R$^{10}$, —($C_1$-$C_3$ alkylene)CF$_3$, —($C_1$-$C_3$ alkylene)NO$_2$, —C=NH(OR$^8$), —($C_1$-$C_3$ alkylene)C(O)R$^8$, —($C_1$-$C_3$ alkylene)OC(O)R$^8$, —($C_1$-$C_3$ alkylene)C(O)OR$^8$, —($C_1$-$C_3$ alkylene)C(O)NR$^9$R$^{10}$, —($C_1$-$C_3$ alkylene)OC(O)NR$^9$R$^{10}$, —($C_1$-$C_3$ alkylene)NR$^8$C(O)R$^9$, —($C_1$-$C_3$ alkylene)NR$^8$C(O)OR$^9$, —($C_1$-$C_3$ alkylene)NR$^8$C(O)NR$^9$R$^{10}$, —($C_1$-$C_3$ alkylene)S(O)R$^8$, —($C_1$-$C_3$ alkylene)S(O)$_2$R$^8$, —($C_1$-$C_3$ alkylene)NR$^8$S(O)R$^9$, —C(O)($C_1$-$C_3$ alkylene)NR$^8$S(O)R$^9$, —($C_1$-$C_3$ alkylene)NR$^8$S(O)$_2$R$^9$, —($C_1$-$C_3$ alkylene)C(O)NR$^8$S(O)$_2$R$^9$, —($C_1$-$C_3$ alkylene)S(O)NR$^9$R$^{10}$, —($C_1$-$C_3$ alkylene)S(O)$_2$NR$^9$R$^{10}$, —($C_1$-$C_3$ alkylene)P(O)(OR$^9$)(OR$^{10}$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or -($C_1$-$C_3$ alkylene)($C_6$-$C_{14}$ aryl), each of which is independently optionally substituted by halogen, oxo, —OR$^{11}$, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —($C_1$-$C_3$ alkylene)OR$^{11}$, —($C_1$-$C_3$ alkylene)NR$^{11}$R$^{12}$, —($C_1$-$C_3$ alkylene)C(O)R$^{11}$, —($C_1$-$C_3$ alkylene)S(O)R$^{11}$, —($C_1$-$C_3$ alkylene)S(O)$_2$R$^{11}$, —($C_1$-$C_3$ alkylene)P(O)(OR$^{11}$)(OR$^{12}$), $C_3$-$C_8$ cycloalkyl, or $C_1$-$C_6$ alkyl optionally substituted by oxo, —OH or halogen;

$R^3$ and $R^5$ are each independently H or $R^c$;

each $R^a$, $R^b$, and $R^c$ is independently $C_1$-$C_6$ alkyl, $C_2$-$C_6$ alkenyl, $C_2$-$C_6$ alkynyl, halogen, —CN, —OR$^8$, —SR$^8$, —NR$^9$R$^{10}$, —NO$_2$, —C=NH(OR$^8$), —C(O)R$^8$, —OC(O)R$^8$, —C(O)OR$^8$, —C(O)NR$^9$R$^{10}$, —OC(O)NR$^9$R$^{10}$, —NR$^8$C(O)R$^9$, —NR$^8$C(O)OR$^9$, —NR$^8$C(O)NR$^9$R$^{10}$, —S(O)R$^8$, —S(O)$_2$R$^8$, —NR$^8$S(O)R$^9$, —C(O)NR$^8$S(O)R$^9$, —NR$^8$S(O)$_2$R$^9$, —C(O)NR$^8$S(O)$_2$R$^9$, —S(O)NR$^9$R$^{10}$, —S(O)$_2$NR$^9$R$^{10}$, —P(O)(OR$^9$)(OR$^{10}$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)OR$^8$, —($C_1$-$C_3$ alkylene)SR$^8$, —($C_1$-$C_3$ alkylene)NR$^9$R$^{10}$, —($C_1$-$C_3$ alkylene)CF$_3$, —($C_1$-$C_3$ alkylene)NO$_2$, —C=NH(OR$^8$), —($C_1$-$C_3$ alkylene)C(O)R$^8$, —($C_1$-$C_3$ alkylene)OC(O)R$^8$, —($C_1$-$C_3$ alkylene)C(O)OR$^8$, —($C_1$-$C_3$ alkylene)C(O)NR$^9$R$^{10}$, —($C_1$-$C_3$ alkylene)OC(O)NR$^9$R$^{10}$, —($C_1$-$C_3$ alkylene)NR$^8$C(O)R$^9$, —($C_1$-$C_3$ alkylene)NR$^8$C(O)OR$^9$, —($C_1$-$C_3$ alkylene)NR$^8$C(O)NR$^9$R$^{10}$, —($C_1$-$C_3$ alkylene)S(O)R$^8$, —($C_1$-$C_3$ alkylene)S(O)$_2$R$^8$, —($C_1$-$C_3$ alkylene)NR$^8$S(O)R$^9$, —C(O)($C_1$-$C_3$ alkylene)NR$^8$S(O)R$^9$, —($C_1$-$C_3$ alkylene)NR$^8$S(O)$_2$R$^9$, —($C_1$-$C_3$ alkylene)C(O)NR$^8$S(O)$_2$R$^9$, —($C_1$-$C_3$ alkylene)S(O)NR$^9$R$^{10}$, —($C_1$-$C_3$ alkylene)S(O)$_2$NR$^9$R$^{10}$, —($C_1$-$C_3$ alkylene)P(O)(OR$^9$)(OR$^{10}$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or -($C_1$-$C_3$ alkylene)($C_6$-$C_{14}$ aryl), wherein each $R^a$, $R^b$, and $R^c$ is independently optionally substituted by halogen, oxo, —OR$^{11}$, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —($C_1$-$C_3$ alkylene)OR$^{11}$, —($C_1$-$C_3$ alkylene)NR$^{11}$R$^{12}$, —($C_1$-$C_3$ alkylene)C(O)R$^{11}$, —($C_1$-$C_3$ alkylene)S(O)R$^{11}$, —($C_1$-$C_3$ alkylene)S(O)$_2$R$^{11}$, —($C_1$-$C_3$ alkylene)P(O)(OR$^{11}$)(OR$^{12}$), $C_3$-$C_8$ cycloalkyl, or $C_1$-$C_6$ alkyl optionally substituted by oxo, —OH or halogen;

wherein when $R^1$ is $C_1$-$C_6$ alkyl, $R^4$ is other than —NR$^9$R$^{10}$ and $R^3$ is other than —C(O)R$^8$;

------ is a single bond or a double bond, wherein when ------ is a double bond, $R^2$ is oxo;

⁓⁓⁓ is a single bond or a double bond, wherein when ⁓⁓⁓ is a double bond, $R^4$ is oxo;

one of ------ and ⁓⁓⁓ is a double bond and the other is a single bond;

A is $C_6$-$C_{12}$ aryl, 5- to 10-membered heteroaryl, 9- to 10-membered carbocycle, or 9- to 10-membered heterocycle, wherein the $C_6$-$C_{12}$ aryl, 5- to 10-membered heteroaryl or 9- to 10-membered carbocycle, or 9- to 10-membered heterocycle of A is optionally further substituted with $R^6$;

B is phenyl, 5- to 6-membered heteroaryl, 5- to 6-membered carbocycle, 5- to 6-membered heterocycle, or 9- to 10-membered heteroaryl, wherein the phenyl, 5- to 6-membered heteroaryl, 5- to 6-membered carbocycle, 5- to 6-membered heterocycle, or 9- to 10-membered heteroaryl of B is optionally further substituted with $R^7$;

wherein when B is 5- to 6-membered heterocycle, A is other than phenyl optionally further substituted with $R^6$ or pyridyl optionally further substituted with $R^6$;

each $R^6$ and $R^7$ is independently oxo, $C_1$-$C_6$ alkyl, $C_2$-$C_6$ alkenyl, $C_2$-$C_6$ alkynyl, halogen, —CN, —OR$^8$, —SR$^8$, —NR$^9$R$^{10}$, —NO$_2$, —C=NH(OR$^8$), —C(O)R$^8$, —OC(O)R$^8$, —C(O)OR$^8$, —C(O)NR$^9$R$^{10}$, —OC(O)NR$^9$R$^{10}$, —NR$^8$C(O)R$^9$, —NR$^8$C(O)OR$^9$, —NR$^8$C(O)NR$^9$R$^{10}$, —S(O)R$^8$, —S(O)$_2$R$^8$, —NR$^8$S(O)R$^9$, —C(O)NR$^8$S(O)R$^9$, —NR$^8$S(O)$_2$R$^9$, —C(O)NR$^8$S(O)$_2$R$^9$, —S(O)NR$^9$R$^{10}$, —S(O)$_2$NR$^9$R$^{10}$, —P(O)(OR$^9$)(OR$^{10}$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)OR$^8$, —($C_1$-$C_3$ alkylene)SR$^8$, —($C_1$-$C_3$ alkylene)NR$^9$R$^{10}$, —($C_1$-$C_3$ alkylene)CF$_3$, —($C_1$-$C_3$ alkylene)NO$_2$, —C=NH(OR$^8$), —($C_1$-$C_3$ alkylene)C(O)R$^8$, —($C_1$-$C_3$ alkylene)OC(O)R$^8$, —($C_1$-$C_3$ alkylene)C(O)OR$^8$, —($C_1$-$C_3$ alkylene)C(O)NR$^9$R$^{10}$, —($C_1$-$C_3$ alkylene)OC(O)NR$^9$R$^{10}$, —($C_1$-$C_3$ alkylene)NR$^8$C(O)R$^9$, —($C_1$-$C_3$ alkylene)NR$^8$C(O)OR$^9$, —($C_1$-$C_3$ alkylene)NR$^8$C(O)NR$^9$R$^{10}$, —($C_1$-$C_3$ alkylene)S(O)R$^8$, —($C_1$-$C_3$ alkylene)S(O)$_2$R$^8$, —($C_1$-$C_3$ alkylene)NR$^8$S(O)R$^9$, —C(O)($C_1$-$C_3$ alkylene)NR$^8$S(O)R$^9$, —($C_1$-$C_3$ alkylene)NR$^8$S(O)$_2$R$^9$, —($C_1$-$C_3$ alkylene)C(O)NR$^8$S(O)$_2$R$^9$, —($C_1$-$C_3$ alkylene)S(O)NR$^9$R$^{10}$, —($C_1$-$C_3$ alkylene)S(O)$_2$NR$^9$R$^{10}$, —($C_1$-$C_3$ alkylene)P(O)(OR$^9$)(OR$^{10}$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or -($C_1$-$C_3$ alkylene)($C_6$-$C_{14}$ aryl), wherein each $R^6$ and $R^7$ is independently optionally substituted by halogen, oxo, —OR$^{11}$, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —($C_1$-$C_3$ alkylene)OR$^{11}$, —($C_1$-$C_3$ alkylene)NR$^{11}$R$^{12}$, —($C_1$-$C_3$ alkylene)C(O)R$^{11}$, —($C_1$-$C_3$ alkylene)S(O)R$^{11}$, —($C_1$-$C_3$ alkylene)S(O)$_2$R$^{11}$, —($C_1$-$C_3$ alkylene)P(O)(OR$^{11}$)(OR$^{12}$), $C_3$-$C_8$ cycloalkyl, or $C_1$-$C_6$ alkyl optionally substituted by oxo, —OH or halogen;

$R^8$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl, 3-6-membered heterocyclyl, —($C_1$-$C_3$ alkylene)($C_3$-$C_6$ cycloalkyl), —($C_1$-$C_3$ alkylene)($C_6$-$C_{14}$ aryl), —($C_1$-$C_3$ alkylene)(5-6-membered heteroaryl), or -($C_1$-$C_3$ alkylene)(3-6-membered heterocyclyl), wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl, 3-6-membered heterocyclyl, —($C_1$-$C_3$ alkylene)($C_3$-$C_6$ cycloalkyl), —($C_1$-$C_3$ alkylene)($C_6$-$C_{14}$ aryl), —($C_1$-$C_3$ alkylene)(5-6-membered heteroaryl), and -($C_1$-$C_3$ alkylene)(3-6-membered heterocyclyl) are independently optionally substituted by halogen, oxo, —CN, —OR$^{13}$, —NR$^{13}$R$^{14}$, —P(O)(OR$^{13}$)(OR$^{14}$), phenyl optionally substituted by halogen, or $C_1$-$C_6$ alkyl optionally substituted by halogen, —OH or oxo;

$R^9$ and $R^{10}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heterocyclyl, 3-6 membered heterocyclyl, —($C_1$-$C_3$ alkylene)NR$^{11}$R$^{12}$, $C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl) or -($C_1$-$C_3$ alkylene)($C_6$ aryl), wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5-6-membered heteroaryl, 3-6 membered heterocyclyl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl) and —($C_1$-$C_3$ alkylene)($C_6$ aryl) are independently optionally substituted by halogen, oxo, —CN, —OR$^{13}$, —NR$^{13}$R$^{14}$ or $C_1$-$C_6$ alkyl optionally substituted by halogen, —OH or oxo;

or $R^9$ and $R^{10}$ are taken together with the atom to which they attached to form a 3-6 membered heterocyclyl optionally substituted by halogen, oxo, —OR$^{13}$, —NR$^3$R$^{14}$ or $C_1$-$C_6$ alkyl optionally substituted by halogen, oxo or —OH;

$R^{11}$ and $R^{12}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^{11}$ and $R^{12}$ are taken together with the atom to which they attached to form a 3-6 membered heterocyclyl optionally substituted by halogen, oxo or $C_1$-$C_6$ alkyl optionally substituted by halogen or oxo; and $R^{13}$ and $R^{14}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^{13}$ and $R^{14}$ are taken together with the atom to which they attached to form a 3-6 membered heterocyclyl optionally substituted by halogen, oxo or $C_1$-$C_6$ alkyl optionally substituted by oxo or halogen.

2. The compound of claim 1, or a tautomer or isomer thereof, or a pharmaceutically acceptable salt of any of the foregoing, wherein:

$R^1$ is H or $C_1$-$C_6$ alkyl wherein the $C_1$-$C_6$ alkyl of $R^1$ is optionally substituted with oxo or $R^a$;

$R^2$ is H, $R^b$ or oxo;

$R^4$ is H, oxo, $C_1$-$C_6$ alkyl, $C_2$-$C_6$ alkenyl, $C_2$-$C_6$ alkynyl, halogen, —CN, —OR$^8$, —SR$^8$, —NO$_2$, —C=NH(OR$^8$), —C(O)R$^8$, —OC(O)R$^8$, —C(O)OR$^8$, —C(O)NR$^9$R$^{10}$, —OC(O)NR$^9$R$^{10}$, —NR$^8$C(O)R$^9$, —NR$^8$C(O)OR$^9$, —NR$^8$C(O)NR$^9$R$^{10}$, —S(O)R$^8$, —S(O)$_2$R$^8$, —NR$^8$S(O)R$^9$, —C(O)NR$^8$S(O)R$^9$, —NR$^8$S(O)$_2$R$^9$, —C(O)NR$^8$S(O)$_2$R$^9$, —S(O)NR$^9$R$^{10}$, —S(O)$_2$NR$^9$R$^{10}$, —P(O)(OR$^9$)(OR$^{10}$), $C_3$-$C_6$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)OR$^8$, —($C_1$-$C_3$ alkylene)SR$^8$, —($C_1$-$C_3$ alkylene)NR$^9$R$^{10}$, —($C_1$-$C_3$ alkylene)CF$_3$, —($C_1$-$C_3$ alkylene)NO$_2$, —C=NH(OR$^8$), —($C_1$-$C_3$ alkylene)C(O)R$^8$, —($C_1$-$C_3$ alkylene)OC(O)R$^8$, —($C_1$-$C_3$ alkylene)C(O)OR$^8$, —($C_1$-$C_3$ alkylene)C(O)NR$^9$R$^{10}$, —($C_1$-$C_3$ alkylene)OC(O)NR$^9$R$^{10}$, —($C_1$-$C_3$ alkylene)NR$^8$C(O)R$^9$, —($C_1$-$C_3$ alkylene)NR$^8$C(O)OR$^9$, —($C_1$-$C_3$ alkylene)NR$^8$C(O)NR$^9$R$^{10}$, —($C_1$-$C_3$ alkylene)S(O)R$^8$, —($C_1$-$C_3$ alkylene)S(O)$_2$R$^8$, —($C_1$-$C_3$ alkylene)NR$^8$S(O)R$^9$, —C(O)($C_1$-$C_3$ alkylene)NR$^8$S(O)R$^9$, —($C_1$-$C_3$ alkylene)NR$^8$S(O)$_2$R$^9$, —($C_1$-$C_3$ alkylene)C(O)NR$^8$S(O)$_2$R$^9$, —($C_1$-$C_3$ alkylene)S(O)NR$^9$R$^{10}$, —($C_1$-$C_3$ alkylene)S(O)$_2$NR$^9$R$^{10}$, —($C_1$-$C_3$ alkylene)P(O)(OR$^9$)(OR$^{10}$), —($C_1$-$C_3$ alkylene)($C_3$-$C_6$ cycloalkyl), —($C_1$-$C_3$ alkylene)(3-12-membered heterocyclyl), —($C_1$-$C_3$ alkylene)(5-10-membered heteroaryl) or -($C_1$-$C_3$ alkylene)($C_6$-$C_{14}$ aryl), each of which is independently optionally substituted by halogen, oxo, —OR$^{11}$, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —(C$_1$-C$_3$ alkylene)OR$^{11}$, —(C$_1$-C$_3$ alkylene)NR$^{11}$R$^{12}$, —(C$_1$-C$_3$ alkylene)C(O)R$^{11}$, —(C$_1$-C$_3$ alkylene)S(O)R$^{11}$, —(C$_1$-C$_3$ alkylene)S(O)$_2$R$^{11}$, —(C$_1$-C$_3$ alkylene)P(O)(OR$^{11}$)(OR$^{12}$), C$_3$-C$_8$ cycloalkyl, or C$_1$-C$_6$ alkyl optionally substituted by oxo, —OH or halogen;

R$^3$ and R$^5$ are each independently H or R$^c$;

each R$^a$, R$^b$, and R$^c$ is independently C$_1$-C$_6$ alkyl, C$_2$-C$_6$ alkenyl, C$_2$-C$_6$ alkynyl, halogen, —CN, —OR$^8$, —SR$^8$, —NR$^9$R$^{10}$, —NO$_2$, —C=NH(OR$^8$), —C(O)R$^8$, —OC(O)R$^8$, —C(O)OR$^8$, —C(O)NR$^9$R$^{10}$, —OC(O)NR$^9$R$^{10}$, —NR$^8$C(O)R$^9$, —NR$^8$C(O)OR$^9$, —NR$^8$C(O)NR$^9$R$^{10}$, —S(O)R$^8$, —S(O)$_2$R$^8$, —NR$^8$S(O)R$^9$, —C(O)NR$^8$S(O)R$^9$, —NR$^8$S(O)$_2$R$^9$, —C(O)NR$^8$S(O)$_2$R$^9$, —S(O)NR$^9$R$^{10}$, —S(O)$_2$NR$^9$R$^{10}$, —P(O)(OR$^9$)(OR$^{10}$), C$_3$-C$_6$ cycloalkyl, 3-12-membered heterocyclyl, 5- to 10-membered heteroaryl, C$_6$-C$_{14}$ aryl, —(C$_1$-C$_3$ alkylene)CN, —(C$_1$-C$_3$ alkylene)OR$^8$, —(C$_1$-C$_3$ alkylene)SR$^8$, —(C$_1$-C$_3$ alkylene)NR$^9$R$^{10}$, —(C$_1$-C$_3$ alkylene)CF$_3$, —(C$_1$-C$_3$ alkylene)NO$_2$, —C=NH(OR$^8$), —(C$_1$-C$_3$ alkylene)C(O)R$^8$, —(C$_1$-C$_3$ alkylene)OC(O)R$^8$, —(C$_1$-C$_3$ alkylene)C(O)OR$^8$, —(C$_1$-C$_3$ alkylene)C(O)NR$^9$R$^{10}$, —(C$_1$-C$_3$ alkylene)OC(O)NR$^9$R$^{10}$, —(C$_1$-C$_3$ alkylene)NR$^8$C(O)R$^9$, —(C$_1$-C$_3$ alkylene)NR$^8$C(O)OR$^9$, —(C$_1$-C$_3$ alkylene)NR$^8$C(O)NR$^9$R$^{10}$, —(C$_1$-C$_3$ alkylene)S(O)R$^8$, —(C$_1$-C$_3$ alkylene)S(O)$_2$R$^8$, —(C$_1$-C$_3$ alkylene)NR$^8$S(O)R$^9$, —C(O)(C$_1$-C$_3$ alkylene)NR$^8$S(O)R$^9$, —(C$_1$-C$_3$ alkylene)NR$^8$S(O)$_2$R$^9$, —(C$_1$-C$_3$ alkylene)C(O)NR$^8$S(O)$_2$R$^9$, —(C$_1$-C$_3$ alkylene)S(O)NR$^9$R$^{10}$, —(C$_1$-C$_3$ alkylene)S(O)$_2$NR$^9$R$^{10}$, —(C$_1$-C$_3$ alkylene)P(O)(OR$^9$)(OR$^{10}$), —(C$_1$-C$_3$ alkylene)(C$_3$-C$_6$ cycloalkyl), —(C$_1$-C$_3$ alkylene)(3-12-membered heterocyclyl), —(C$_1$-C$_3$ alkylene)(5-10-membered heteroaryl) or -(C$_1$-C$_3$ alkylene)(C$_6$-C$_{14}$ aryl), wherein each R$^a$, R$^b$, and R$^c$ is independently optionally substituted by halogen, oxo, —OR$^{11}$, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —(C$_1$-C$_3$ alkylene)OR$^{11}$, —(C$_1$-C$_3$ alkylene)NR$^{11}$R$^{12}$, —(C$_1$-C$_3$ alkylene)C(O)R$^{11}$, —(C$_1$-C$_3$ alkylene)S(O)R$^{11}$, —(C$_1$-C$_3$ alkylene)S(O)$_2$R$^{11}$, —(C$_1$-C$_3$ alkylene)P(O)(OR$^{11}$)(OR$^{12}$), C$_3$-C$_8$ cycloalkyl, or C$_1$-C$_6$ alkyl optionally substituted by oxo, —OH or halogen;

wherein when R$^1$ is C$_1$-C$_6$ alkyl, R$^4$ is other than —NR$^9$R$^{10}$ and R$^3$ is other than —OC(O)R$^8$;

------ is a single bond or a double bond, wherein when ------- is a double bond, R$^2$ is oxo;

⁓⁓⁓ is a single bond or a double bond, wherein when ⁓⁓⁓ is a double bond, R$^4$ is oxo;

one of ------ and ⁓⁓⁓ is a double bond and the other is a single bond;

A is C$_6$-C$_{12}$ aryl, 5- to 10-membered heteroaryl, 9- to 10-membered carbocycle, or 9- to 10-membered heterocycle, wherein the C$_6$-C$_{12}$ aryl, 5- to 10-membered heteroaryl or 9- to 10-membered carbocycle, or 9- to 10-membered heterocycle of A is optionally further substituted with R$^6$;

B is phenyl, 5- to 6-membered heteroaryl, 5- to 6-membered carbocycle, 5- to 6-membered heterocycle, or 9- to 10-membered heteroaryl, wherein the phenyl, 5- to 6-membered heteroaryl, 5- to 6-membered carbocycle, 5- to 6-membered heterocycle, or 9- to 10-membered heteroaryl of B is optionally further substituted with R$^7$;

wherein when B is 5- to 6-membered heterocycle, A is other than phenyl optionally further substituted with R$^6$ or pyridyl optionally further substituted with R$^6$;

each R$^6$ and R$^7$ is independently oxo, C$_1$-C$_6$ alkyl, C$_2$-C$_6$ alkenyl, C$_2$-C$_6$ alkynyl, halogen, —CN, —OR$^8$, —SR$^8$, —NR$^9$R$^{10}$, —NO$_2$, —C=NH(OR$^8$), —C(O)R$^8$, —OC(O)R$^8$, —C(O)OR$^8$, —C(O)NR$^9$R$^{10}$, —OC(O)NR$^9$R$^{10}$, —NR$^8$C(O)R$^9$, —NR$^8$C(O)OR$^9$, —NR$^8$C(O)NR$^9$R$^{10}$, —S(O)R$^8$, —S(O)$_2$R$^8$, —NR$^8$S(O)R$^9$, —C(O)NR$^8$S(O)R$^9$, —NR$^8$S(O)$_2$R$^9$, —C(O)NR$^8$S(O)$_2$R$^9$, —S(O)NR$^9$R$^{10}$, —S(O)$_2$NR$^9$R$^{10}$, —P(O)(OR$^9$)(OR$^{10}$), C$_3$-C$_6$ cycloalkyl, 3-12-membered heterocyclyl, 5- to 10-membered heteroaryl, C$_6$-C$_{14}$ aryl, —(C$_1$-C$_3$ alkylene)CN, —(C$_1$-C$_3$ alkylene)OR$^8$, —(C$_1$-C$_3$ alkylene)SR$^8$, —(C$_1$-C$_3$ alkylene)NR$^9$R$^{10}$, —(C$_1$-C$_3$ alkylene)CF$_3$, —(C$_1$-C$_3$ alkylene)NO$_2$, —C=NH(OR$^8$), —(C$_1$-C$_3$ alkylene)C(O)R$^8$, —(C$_1$-C$_3$ alkylene)OC(O)R$^8$, —(C$_1$-C$_3$ alkylene)C(O)OR$^8$, —(C$_1$-C$_3$ alkylene)C(O)NR$^9$R$^{10}$, —(C$_1$-C$_3$ alkylene)OC(O)NR$^9$R$^{10}$, —(C$_1$-C$_3$ alkylene)NR$^8$C(O)R$^9$, —(C$_1$-C$_3$ alkylene)NR$^8$C(O)OR$^9$, —(C$_1$-C$_3$ alkylene)NR$^8$C(O)NR$^9$R$^{10}$, —(C$_1$-C$_3$ alkylene)S(O)R$^8$, —(C$_1$-C$_3$ alkylene)S(O)$_2$R$^8$, —(C$_1$-C$_3$ alkylene)NR$^8$S(O)R$^9$, —C(O)(C$_1$-C$_3$ alkylene)NR$^8$S(O)R$^9$, —(C$_1$-C$_3$ alkylene)NR$^8$S(O)$_2$R$^9$, —(C$_1$-C$_3$ alkylene)C(O)NR$^8$S(O)$_2$R$^9$, —(C$_1$-C$_3$ alkylene)S(O)NR$^9$R$^{10}$, —(C$_1$-C$_3$ alkylene)S(O)$_2$NR$^9$R$^{10}$, —(C$_1$-C$_3$ alkylene)P(O)(OR$^9$)(OR$^{10}$), —(C$_1$-C$_3$ alkylene)(C$_3$-C$_6$ cycloalkyl), —(C$_1$-C$_3$ alkylene)(3-12-membered heterocyclyl), —(C$_1$-C$_3$ alkylene)(5-10-membered heteroaryl) or -(C$_1$-C$_3$ alkylene)(C$_6$-C$_{14}$ aryl), wherein each R$^6$ and R$^7$ is independently optionally substituted by halogen, oxo, —OR$^{11}$, —NR$^{11}$R$^{12}$, —C(O)R$^{11}$, —CN, —S(O)R$^{11}$, —S(O)$_2$R$^{11}$, —P(O)(OR$^{11}$)(OR$^{12}$), —(C$_1$-C$_3$ alkylene)OR$^{11}$, —(C$_1$-C$_3$ alkylene)NR$^{11}$R$^{12}$, —(C$_1$-C$_3$ alkylene)C(O)R$^{11}$, —(C$_1$-C$_3$ alkylene)S(O)R$^{11}$, —(C$_1$-C$_3$ alkylene)S(O)$_2$R$^{11}$, —(C$_1$-C$_3$ alkylene)P(O)(OR$^{11}$)(OR$^{12}$), C$_3$-C$_8$ cycloalkyl, or C$_1$-C$_6$ alkyl optionally substituted by oxo, —OH or halogen;

R$^8$ is independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl or 3-6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl and 3-6-membered heterocyclyl are independently optionally substituted by halogen, oxo, —CN, —OR$^{13}$, —NR$^{13}$R$^{14}$, —P(O)(OR$^{13}$)(OR$^{14}$), phenyl optionally substituted by halogen, or C$_1$-C$_6$ alkyl optionally substituted by halogen, —OH or oxo;

R$^9$ and R$^{10}$ are each independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl or 3-6 membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5-6-membered heteroaryl and 3-6 membered heterocyclyl are independently optionally substituted by halogen, oxo, —CN, —OR$^{13}$, —NR$^{13}$R$^{14}$ or C$_1$-C$_6$ alkyl optionally substituted by halogen, —OH or oxo;

or R$^9$ and R$^{10}$ are taken together with the atom to which they attached to form a 3-6 membered heterocyclyl optionally substituted by halogen, oxo, —OR$^{13}$, —NR$^3$R$^{14}$ or C$_1$-C$_6$ alkyl optionally substituted by halogen, oxo or —OH;

R$^{11}$ and R$^{12}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{11}$ and R$^{12}$ are taken together with the atom to which they attached to form a 3-6 membered heterocyclyl optionally substituted by halogen, oxo or C$_1$-C$_6$ alkyl optionally substituted by halogen or oxo; and R$^{13}$ and R$^{14}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{13}$ and R$^{14}$ are taken together with the atom to which they attached to form a 3-6 membered heterocyclyl optionally substituted by halogen, oxo or C$_1$-C$_6$ alkyl optionally substituted by oxo or halogen.

3. The compound of claim 1, or a tautomer or isomer thereof, or a pharmaceutically acceptable salt of any of the foregoing, wherein R$^1$ is H or methyl.

4. The compound of claim 1, or a tautomer or isomer thereof, or a pharmaceutically acceptable salt of any of the foregoing, wherein R$^5$ is H, C$_1$-C$_6$ alkyl, halogen, —CN, or —OR$^8$.

5. The compound of claim 1, wherein the compound is of the Formula (II):

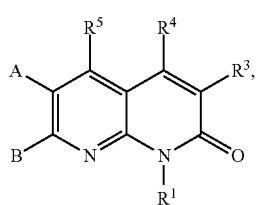

(II)

or a tautomer or isomer thereof, or a pharmaceutically acceptable salt of any of the foregoing, wherein A, B, R$^1$, R$^3$, R$^4$, and R$^5$ are as defined for Formula (I).

6. The compound of claim 5, or a tautomer or isomer thereof, or a pharmaceutically acceptable salt of any of the foregoing, wherein at least one of R$^3$, R$^4$, and R$^5$ is not H.

7. The compound of claim 5, or a tautomer or isomer thereof, or a pharmaceutically acceptable salt of any of the foregoing, wherein at least one of R$^3$, R$^4$, and R$^5$ is C$_1$-C$_6$ alkyl, halogen, C$_6$-C$_{14}$ aryl, —CN, or —OR$^8$.

8. The compound of claim 5, or a tautomer or isomer thereof, or a pharmaceutically acceptable salt of any of the foregoing, wherein R$^1$, R$^3$, R$^4$, and R$^5$ are each H.

9. The compound of claim 1, wherein the compound is of the Formula (III):

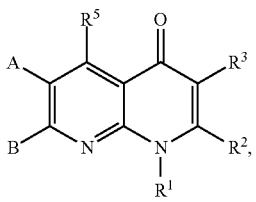

(III)

or a tautomer or isomer thereof, or a pharmaceutically acceptable salt of any of the foregoing, wherein A, B, R$^1$, R$^2$, R$^3$, and R$^5$ are as defined for Formula (I).

10. The compound of claim 1, or a tautomer or isomer thereof, or a pharmaceutically acceptable salt of any of the foregoing, wherein at least one of R$^2$, R$^3$, and R$^5$ is not H.

11. The compound of claim 9, or a tautomer or isomer thereof, or a pharmaceutically acceptable salt of any of the foregoing, wherein at least one of R$^2$, R$^3$, and R$^5$ is C$_1$-C$_6$ alkyl, halogen, C$_6$-C$_{14}$ aryl, —CN, or —OR$^8$.

12. The compound of claim 9, or a tautomer or isomer thereof, or a pharmaceutically acceptable salt of any of the foregoing, wherein R$^1$, R$^2$, R$^3$, and R$^5$ are each H.

13. The compound of claim 1, or a tautomer or isomer thereof, or a pharmaceutically acceptable salt of any of the foregoing, wherein R$^1$ is H.

14. The compound of claim 1, or a tautomer or isomer thereof, or a pharmaceutically acceptable salt of any of the foregoing, wherein A is C$_6$-C$_{12}$ aryl optionally further substituted with R$^6$.

15. The compound of claim 14, or a tautomer or isomer thereof, or a pharmaceutically acceptable salt of any of the foregoing, wherein A is phenyl or naphthyl, optionally substituted with R$^6$.

16. The compound of claim 1, or a tautomer or isomer thereof, or a pharmaceutically acceptable salt of any of the foregoing, wherein A is 5- to 10-membered heteroaryl optionally further substituted with R$^6$.

17. The compound of claim 1, or a tautomer or isomer thereof, or a pharmaceutically acceptable salt of any of the foregoing, wherein A is

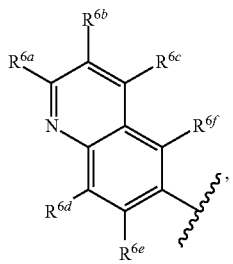

wherein R$^{6a}$, R$^{6b}$, R$^{6c}$, R$^{6d}$, R$^{6e}$, and R$^{6f}$ are each independently H, C$_1$-C$_6$ alkyl, halogen, —CN, or —OC$_1$-C$_6$ alkyl.

18. The compound of claim 1, or a tautomer or isomer thereof, or a pharmaceutically acceptable salt of any of the foregoing, wherein A is

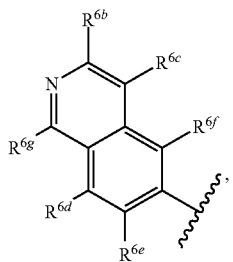

wherein R$^{6b}$, R$^{6c}$, R$^{6d}$, R$^{6e}$, R$^{6f}$, and R$^{6g}$ are each independently H, C$_1$-C$_6$ alkyl, halogen, —CN, or —OC$_1$-C$_6$ alkyl.

19. The compound of claim 1, or a tautomer or isomer thereof, or a pharmaceutically acceptable salt of any of the foregoing, wherein A is

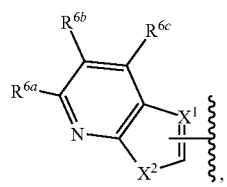

wherein $X^1$ is selected from the group consisting of N, C, and CH; $X^2$ is selected from the group consisting of NH, O, and S; and $R^{6a}$, $R^{6b}$, and $R^{6c}$ are each independently H, $C_1$-$C_6$ alkyl, halogen, —CN, or —$OC_1$-$C_6$ alkyl.

20. The compound of claim 1, or a tautomer or isomer thereof, or a pharmaceutically acceptable salt of any of the foregoing, wherein A is

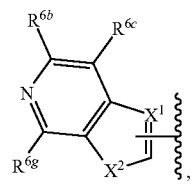

wherein $X^1$ is selected from the group consisting of N, C, and CH; $X^2$ is selected from the group consisting of NH, O, and S; and $R^{6g}$, $R^{6b}$, and $R^{6c}$ are each independently H, $C_1$-$C_6$ alkyl, halogen, —CN, or —$OC_1$-$C_6$ alkyl.

21. The compound of claim 16, or a tautomer or isomer thereof, or a pharmaceutically acceptable salt of any of the foregoing, wherein A is selected from the group consisting of pyridyl, quinolinyl, isoquinolinyl, quinoxalinyl, cinnolinyl, quinazolinyl, naphthyridinyl, benzoxazolyl, benzothiazolyl, benzoimidazoyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridazinyl, pyrimidinyl, pyrazinyl, triazinyl, tetrazinyl, indolyl, isoindolyl, indazolyl, benzotriazolyl, benzofuranyl, benzoisoxazolyl, benzoxadiazolyl, benzothiophenyl, benzoisothiazolyl, benzothiadiazolyl, pyrrolopyridinyl, pyrazolopyridinyl, imidazopyridinyl, triazolopyridinyl, furopyridinyl, oxazolopyridinyl, isoxazolopyridinyl, oxadiazolopyridinyl, thienopyridinyl, thiazolopyridinyl, isothiazolopyridinyl, thiadiazolopyridinyl, thienopyridinyl, phthalazinyl, pyrazolothiazolyl, pyrazolothiazolyl and imidazothiazolyl, each optionally substituted with $R^6$.

22. The compound of claim 16, or a tautomer or isomer thereof, or a pharmaceutically acceptable salt of any of the foregoing, wherein A is selected from the group consisting of:

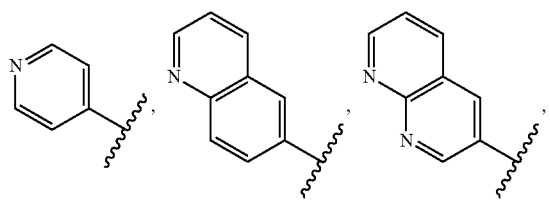

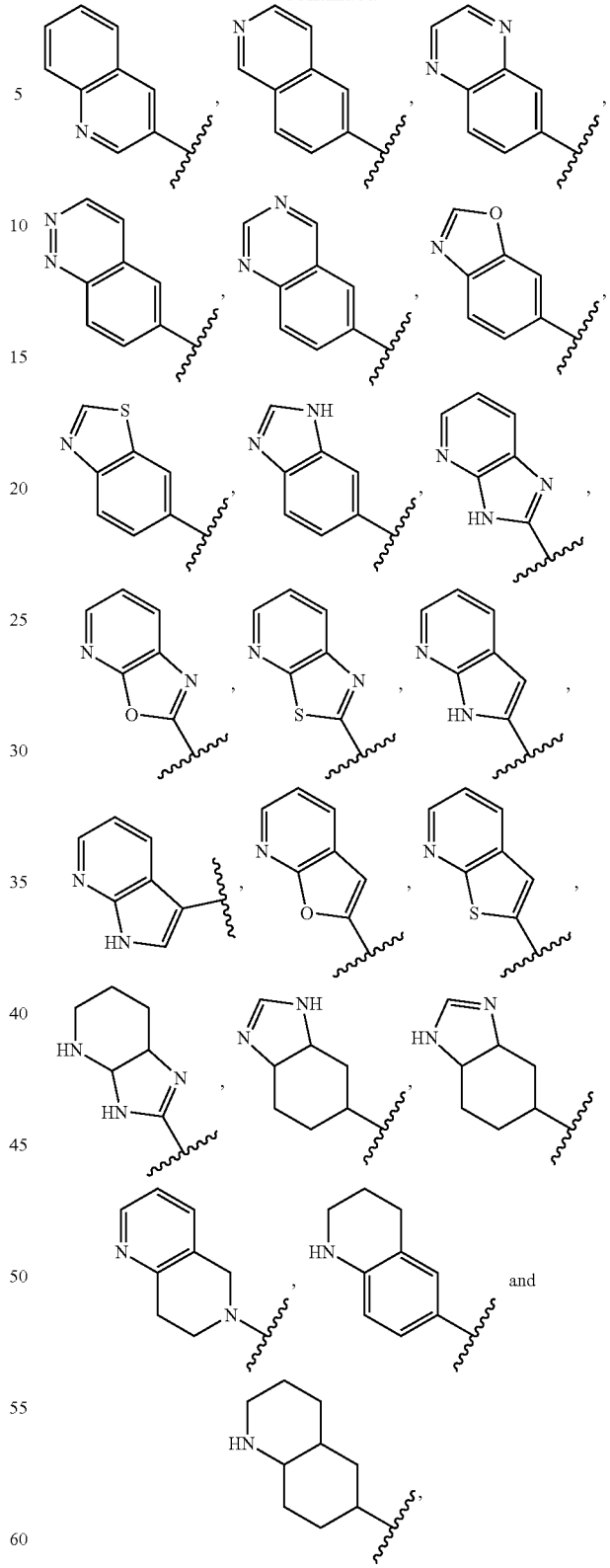

each optionally substituted with $R^6$.

23. The compound of claim 1, or a tautomer or isomer thereof, or a pharmaceutically acceptable salt of any of the foregoing, wherein A is a 9- to 10-membered carbocycle optionally further substituted with $R^6$.

24. The compound of claim 23, or a tautomer or isomer thereof, or a pharmaceutically acceptable salt of any of the foregoing, wherein A is selected from the group consisting of decahydronaphthalenyl, octahydroindenyl, 1,2,3,4-tetrahydronaphthalenyl, and 2,3-dihydroindenyl, each optionally substituted with $R^6$.

25. The compound of claim 1, or a tautomer or isomer thereof, or a pharmaceutically acceptable salt of any of the foregoing, wherein A is a 9- to 10-membered heterocycle optionally further substituted with $R^6$.

26. The compound of claim 24, or a tautomer or isomer thereof, or a pharmaceutically acceptable salt of any of the foregoing, wherein A is selected from the group consisting of tetrahydroquinolinyl, tetrahydroisoquinolinyl, decahydroquinolinyl, decahydroisoquinolinyl, indolinyl, isoindolinyl, tetrahydronaphthyridinyl and hexahydrobenzoimidazolyl, each optionally further substituted with $R^6$.

27. The compound of claim 1, or a tautomer or isomer thereof, or a pharmaceutically acceptable salt of any of the foregoing, wherein A is selected from the group consisting of

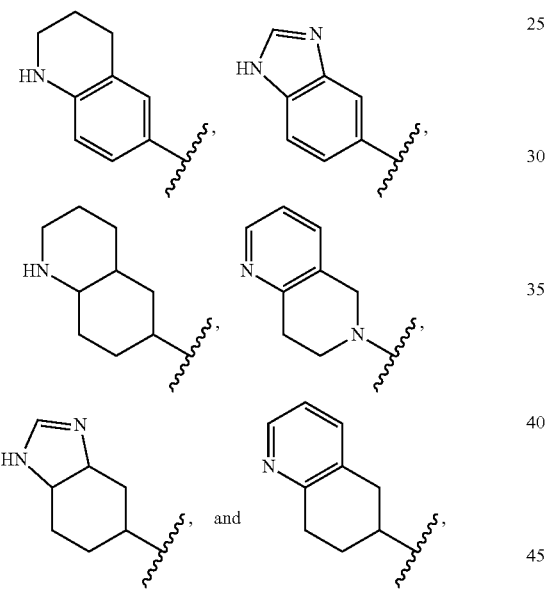

each optionally substituted with $R^6$.

28. The compound of claim 14, or a tautomer or isomer thereof, or a pharmaceutically acceptable salt of any of the foregoing, wherein each $R^6$ is independently selected from the group consisting of halogen, —CN, —$OR^8$, —$SR^8$, —$NR^9R^{10}$, —$NO_2$, —$C(O)R^8$, —$C(O)OR^8$, —$C(O)NR^9R^{10}$, —$C(O)NR^8S(O)_2R^9$, —$OC(O)R^8$, —$OC(O)NR^9R^{10}$, —$NR^8C(O)R^9$, —$NR^8C(O)NR^9R^{10}$, —$S(O)R^8$, —$S(O)_2R^8$, $C_3$-$C_6$ cycloalkyl and $C_1$-$C_6$ alkyl optionally substituted by halogen.

29. The compound of claim 28, or a tautomer or isomer thereof, or a pharmaceutically acceptable salt of any of the foregoing, wherein each $R^6$ is independently selected from the group consisting of $C_1$-$C_6$ alkyl, halogen, —CN, and —$OR^8$.

30. The compound of claim 1, or a tautomer or isomer thereof, or a pharmaceutically acceptable salt of any of the foregoing, wherein A is selected from the group consisting of:

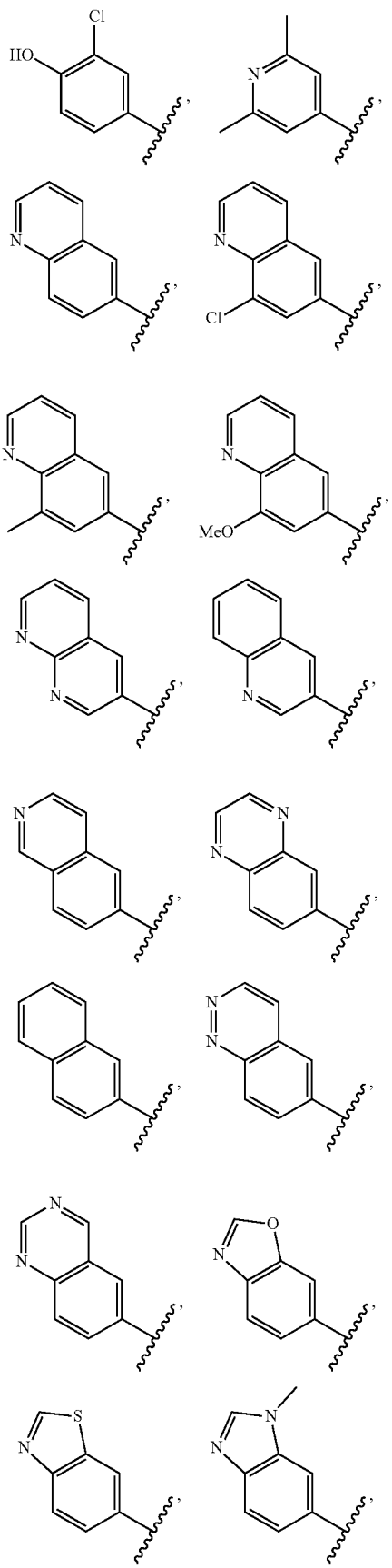

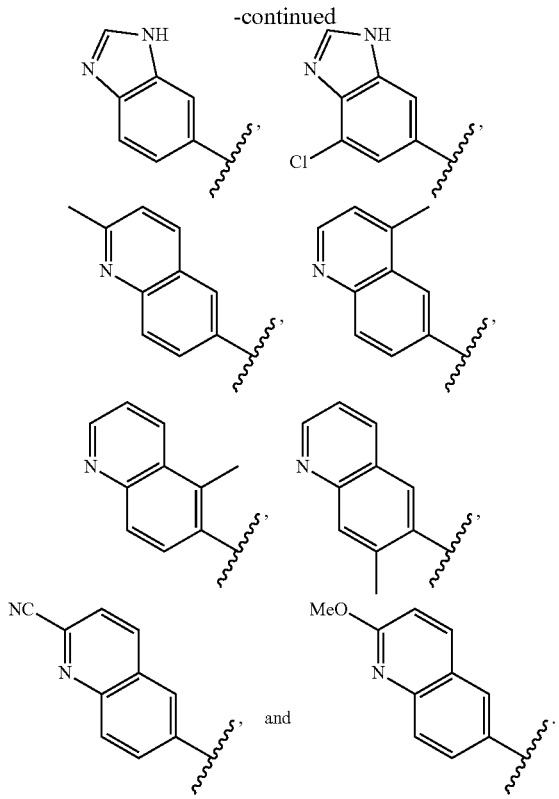

31. The compound of claim 1, or a tautomer or isomer thereof, or a pharmaceutically acceptable salt of any of the foregoing, wherein B is phenyl, optionally further substituted with $R^7$.

32. The compound of claim 1, or a tautomer or isomer thereof, or a pharmaceutically acceptable salt of any of the foregoing, wherein B is 5- to 6-membered heteroaryl optionally further substituted with $R^7$.

33. The compound of claim 32, or a tautomer or isomer thereof, or a pharmaceutically acceptable salt of any of the foregoing, wherein B is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each optionally substituted with $R^7$.

34. The compound of claim 32, or a tautomer or isomer thereof, or a pharmaceutically acceptable salt of any of the foregoing, wherein B is furanyl, pyridinyl, oxazoyl, or oxadiazoyl, each optionally substituted with $R^7$.

35. The compound of claim 1, or a tautomer or isomer thereof, or a pharmaceutically acceptable salt of any of the foregoing, wherein B is a 5- to 6-membered fully saturated carbocycle optionally further substituted with $R^7$.

36. The compound of claim 35, or a tautomer or isomer thereof, or a pharmaceutically acceptable salt of any of the foregoing, wherein B is cyclopentyl or cyclohexyl, optionally further substituted with $R^7$.

37. The compound of claim 1, or a tautomer or isomer thereof, or a pharmaceutically acceptable salt of any of the foregoing, wherein B is a 5- to 6-membered fully saturated heterocycle optionally further substituted with $R^7$.

38. The compound of claim 37, or a tautomer thereof or isomer thereof, or a pharmaceutically acceptable salt of any of the foregoing, wherein B is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, thiomorpholinyl optionally further substituted with $R^7$.

39. The compound of claim 1, or a tautomer or isomer thereof, or a pharmaceutically acceptable salt of any of the foregoing, wherein B is a 9- to 10-membered heteroaryl optionally further substituted with $R^7$.

40. The compound of claim 39, or a tautomer or isomer thereof, or a pharmaceutically acceptable salt of any of the foregoing, wherein B is selected from the group consisting of pyridyl, quinolinyl, isoquinolinyl, quinoxalinyl, cinnolinyl, quinazolinyl, naphthyridinyl, benzoxazolyl, benzothiazolyl, benzoimidazoyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridazinyl, pyrimidinyl, pyrazinyl, triazinyl, tetrazinyl, indolyl, isoindolyl, indazolyl, benzotriazolyl, benzofuranyl, benzoisoxazolyl, benzoxadiazolyl, benzothiophenyl, benzoisothiazolyl, benzothiadiazolyl, pyrrolopyridinyl, pyrazolopyridinyl, imidazopyridinyl, triazolopyridinyl, furopyridinyl, oxazolopyridinyl, isoxazolopyridinyl, oxadiazolopyridinyl, thienopyridinyl, thiazolopyridinyl, isothiazolopyridinyl, thiadiazolopyridinyl, thienopyridinyl, phthalazinyl, pyrazolothiazolyl, pyrazolothiazolyl and imidazothiazolyl, each optionally substituted with $R^7$.

41. The compound of claim 1, or a tautomer or isomer thereof, or a pharmaceutically acceptable salt of any of the foregoing, wherein each $R^7$ is independently selected from the group consisting of halogen, —CN, —$OR^8$, —$SR^8$, —$NR^9R^{10}$, —$NO_2$, —$C(O)R^8$, —$C(O)OR^8$, —$C(O)NR^9R^{10}$, —$C(O)NR^8S(O)_2R^9$, —$OC(O)R^8$, —$OC(O)NR^9R^{10}$, —$NR^8C(O)R^9$, —$NR^8C(O)NR^9R^{10}$, —$S(O)R^8$, —$S(O)_2R^8$, $C_3$-$C_6$ cycloalkyl and $C_1$-$C_6$ alkyl optionally substituted by halogen.

42. The compound of claim 41, or a tautomer or isomer thereof, or a pharmaceutically acceptable salt of any of the foregoing, wherein $R^7$ is halogen.

43. The compound of claim 1, or a tautomer or isomer thereof, or a pharmaceutically acceptable salt of any of the foregoing, wherein B is selected from the group consisting of:

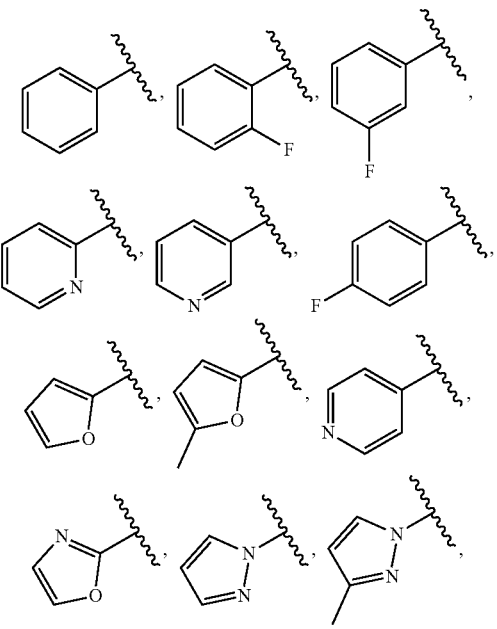

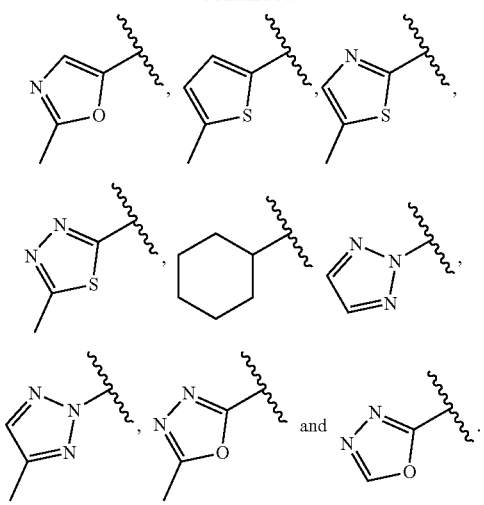
44. A compound selected from the group consisting of
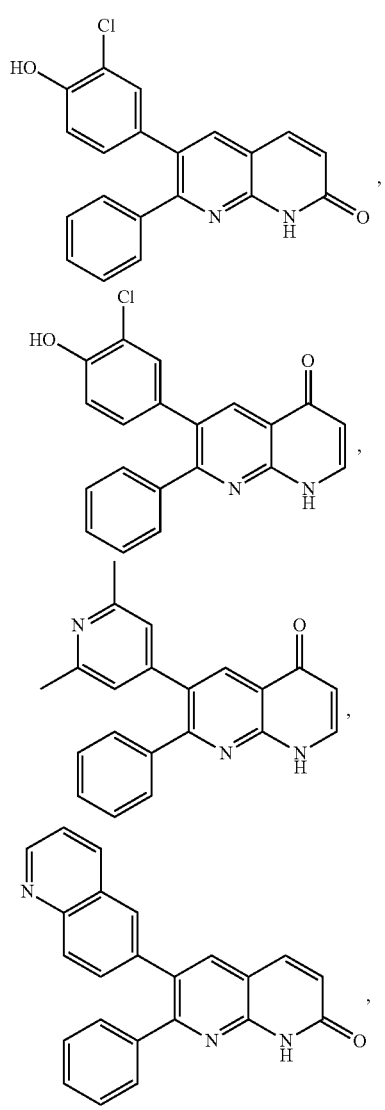
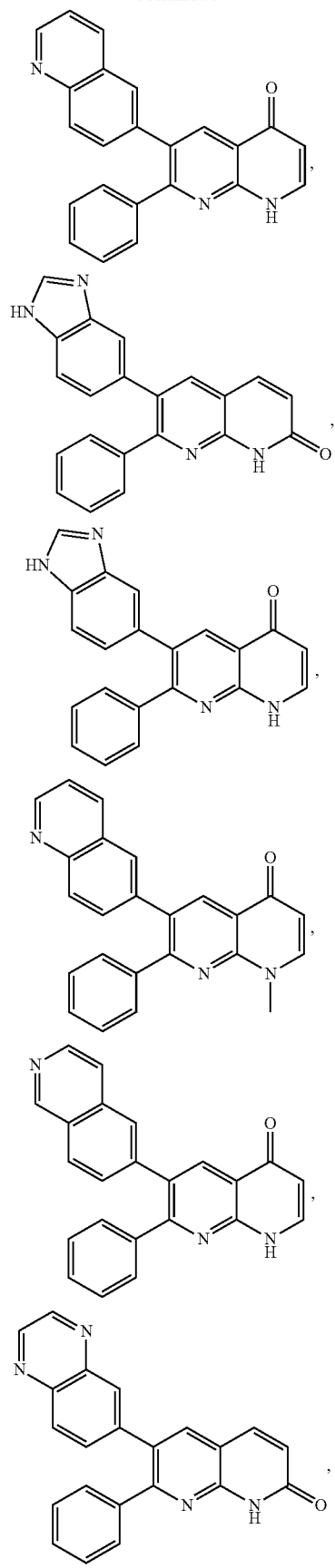

595
-continued
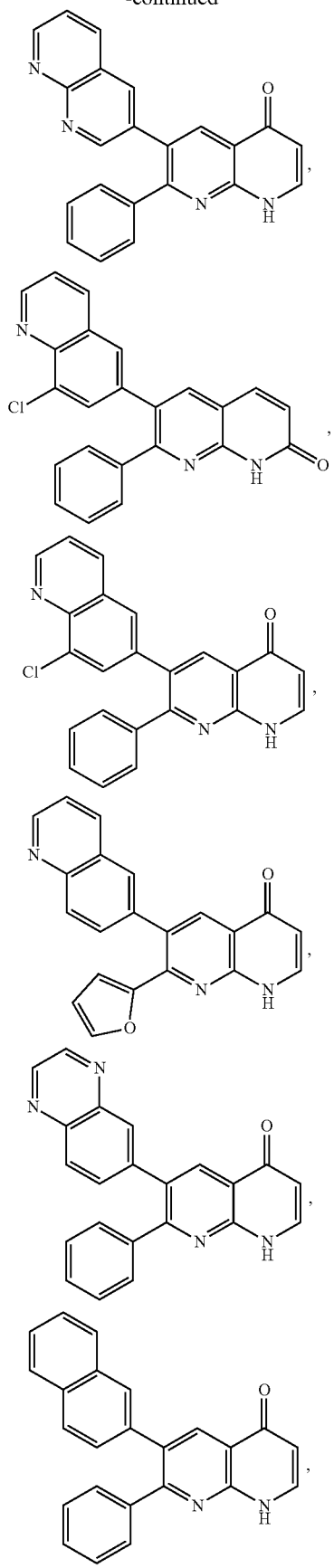
596
-continued
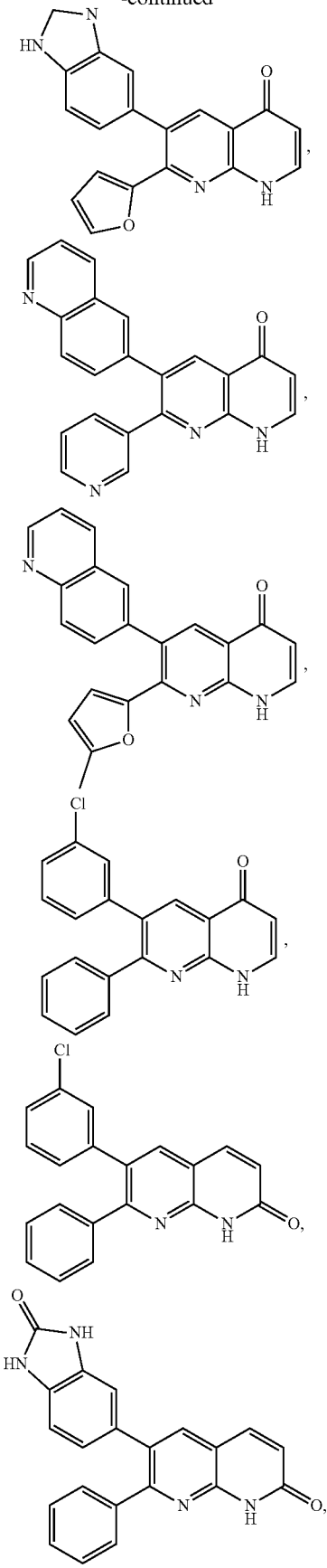

-continued
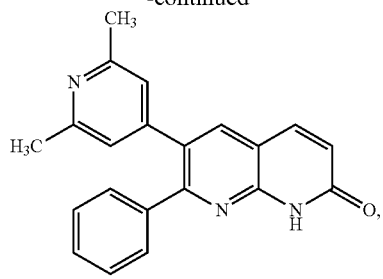
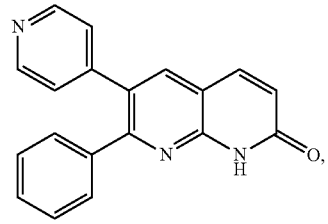
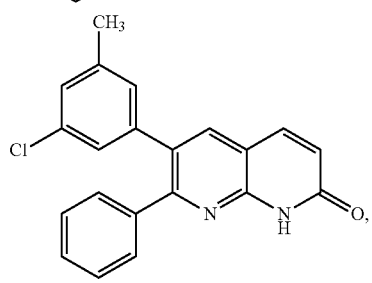
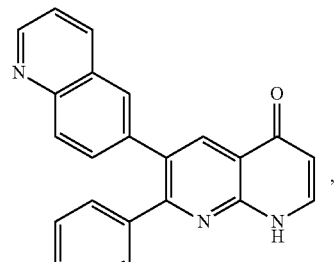
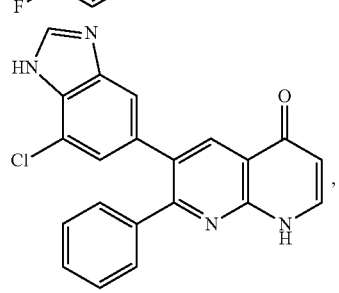
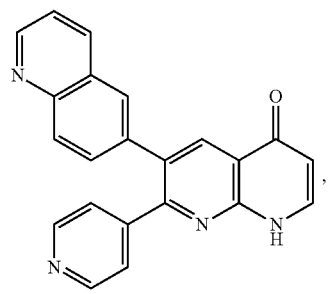
-continued
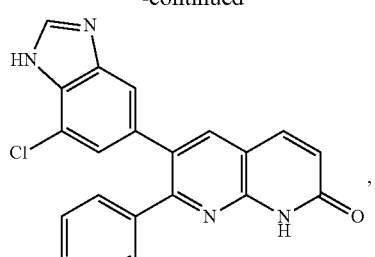
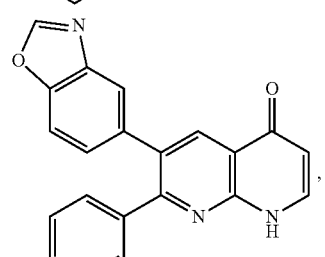
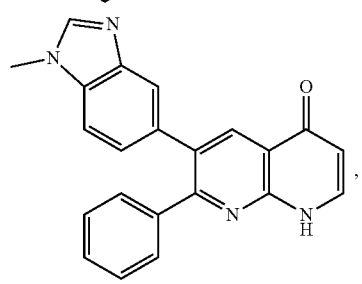
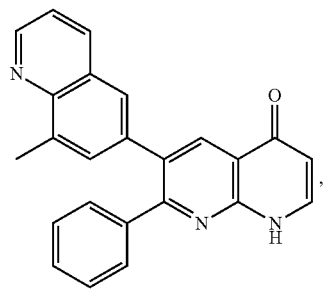
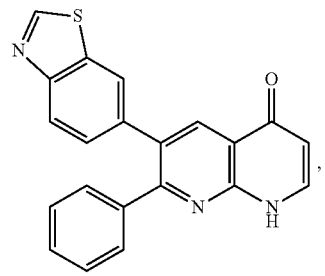
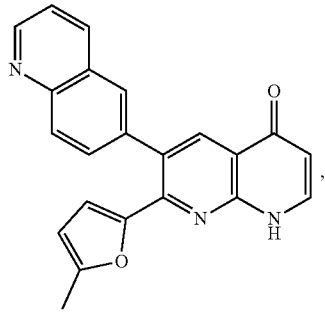

599
-continued
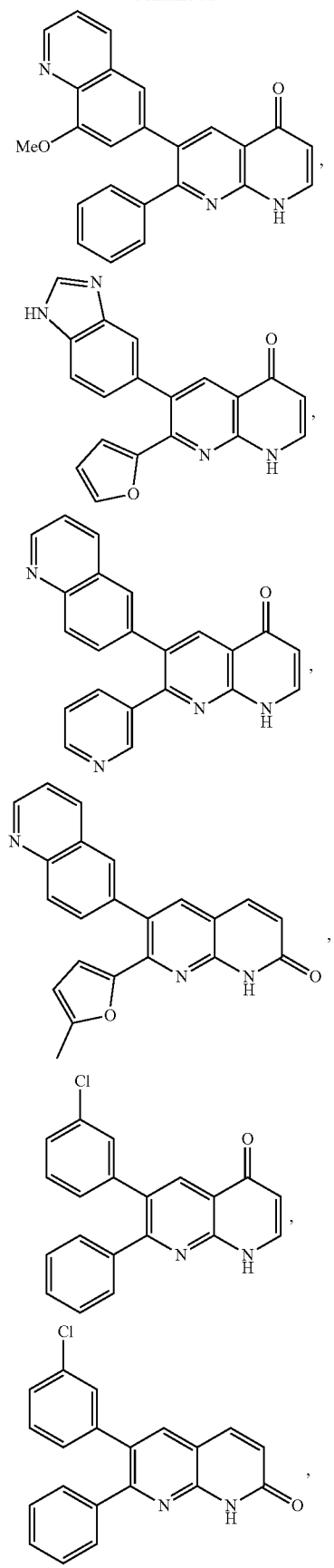
600
-continued
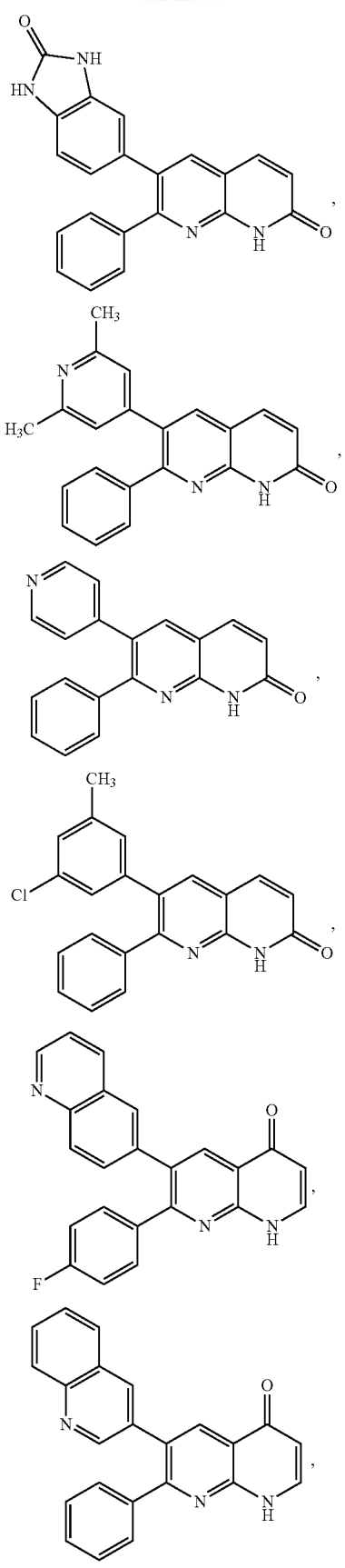

601
-continued
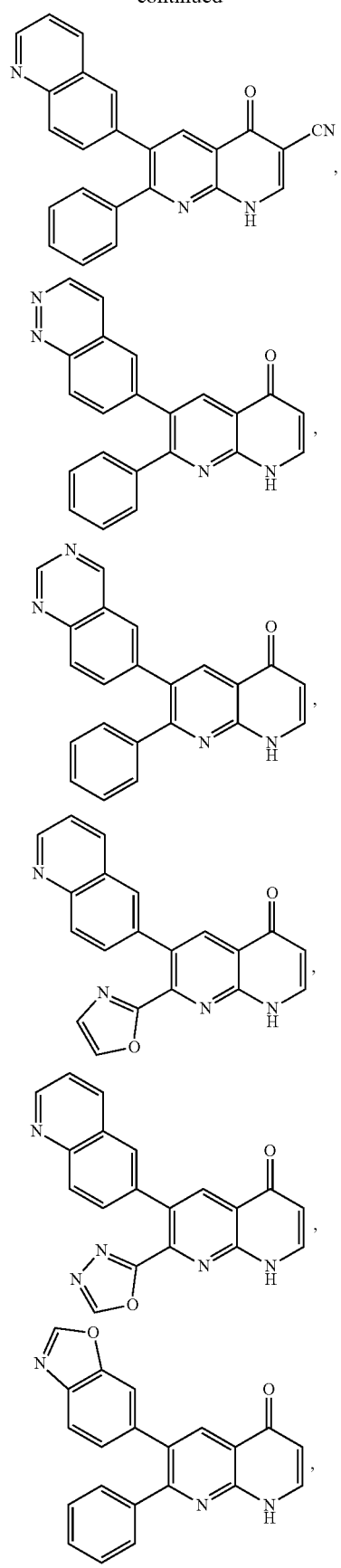
602
-continued
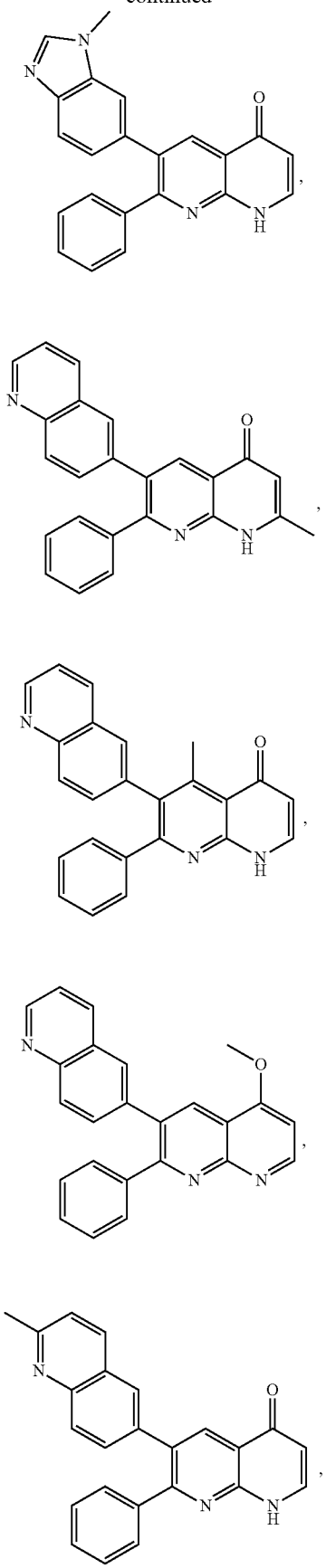

603
-continued
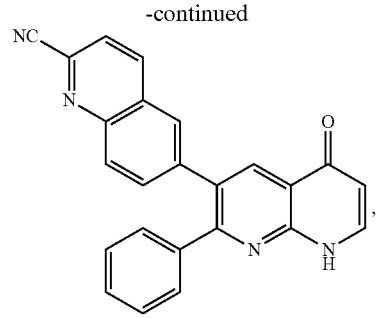
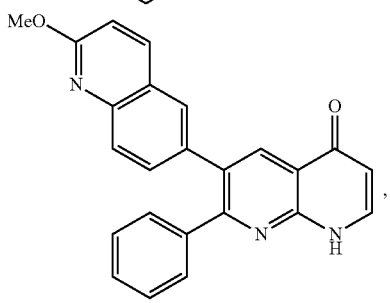
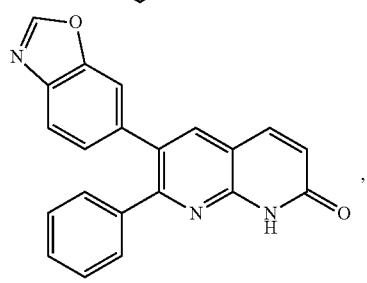
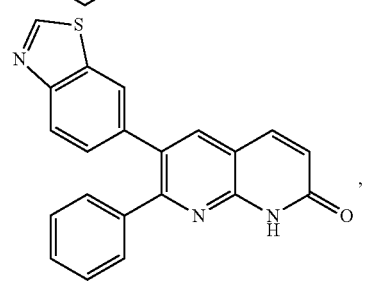
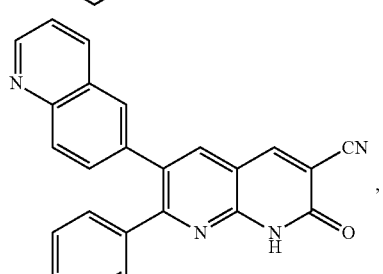
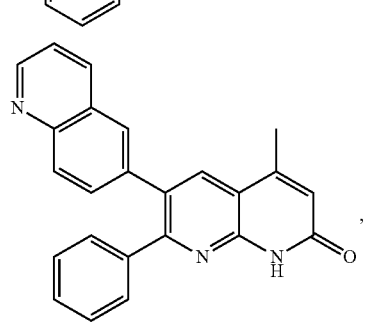
604
-continued
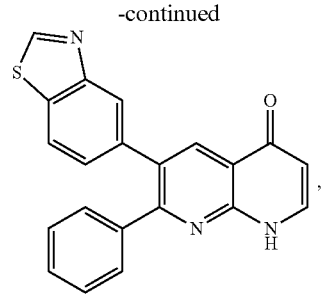
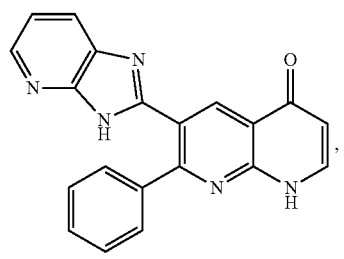
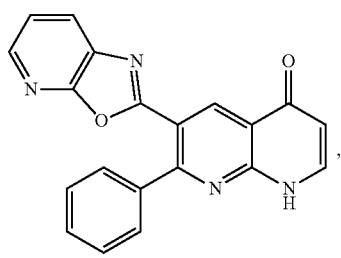
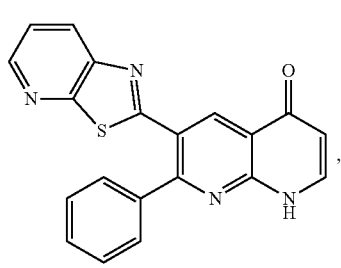
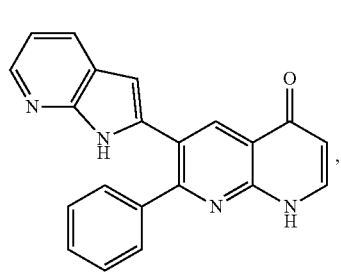
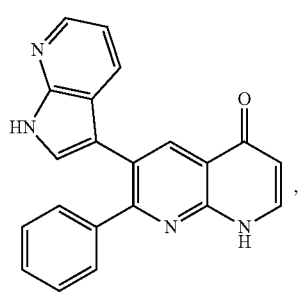

605
-continued
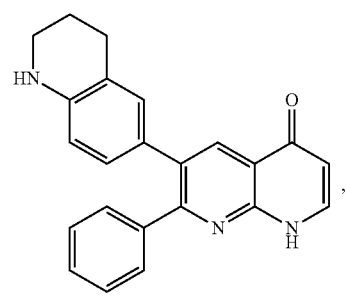,
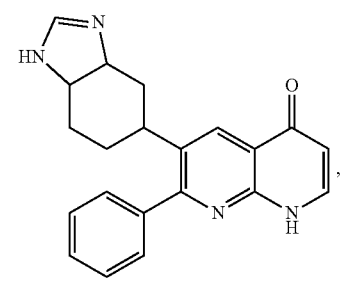,
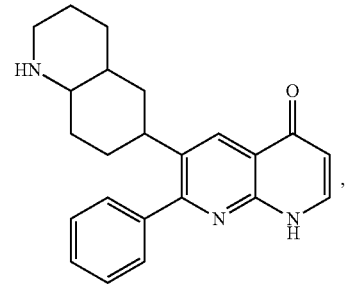,
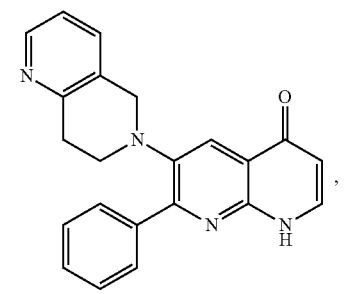,
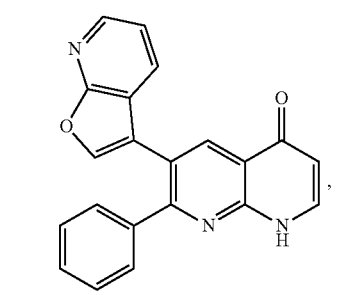,
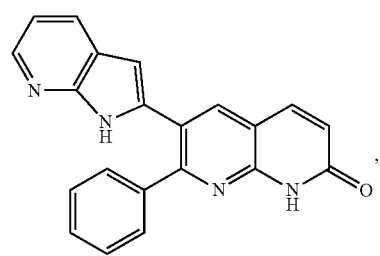,
606
-continued
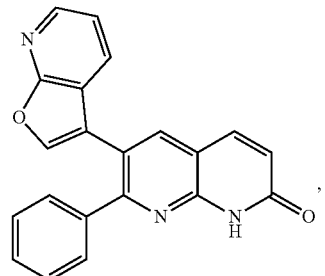,
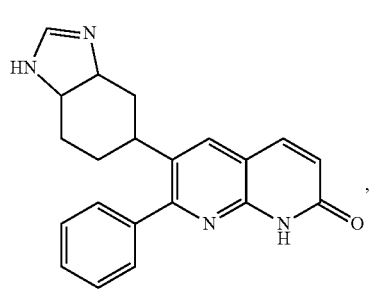,
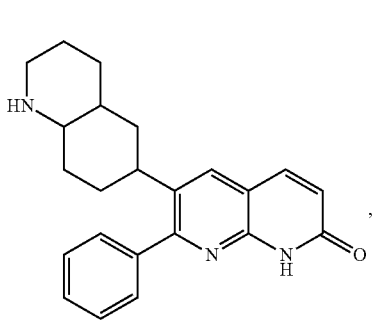,
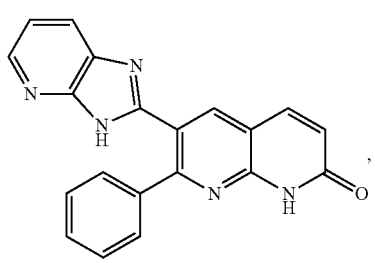,
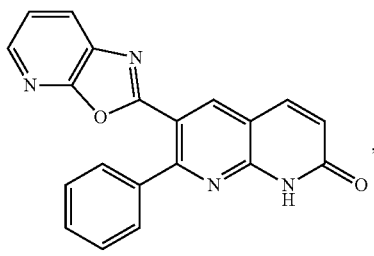,
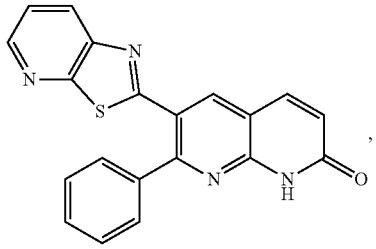,

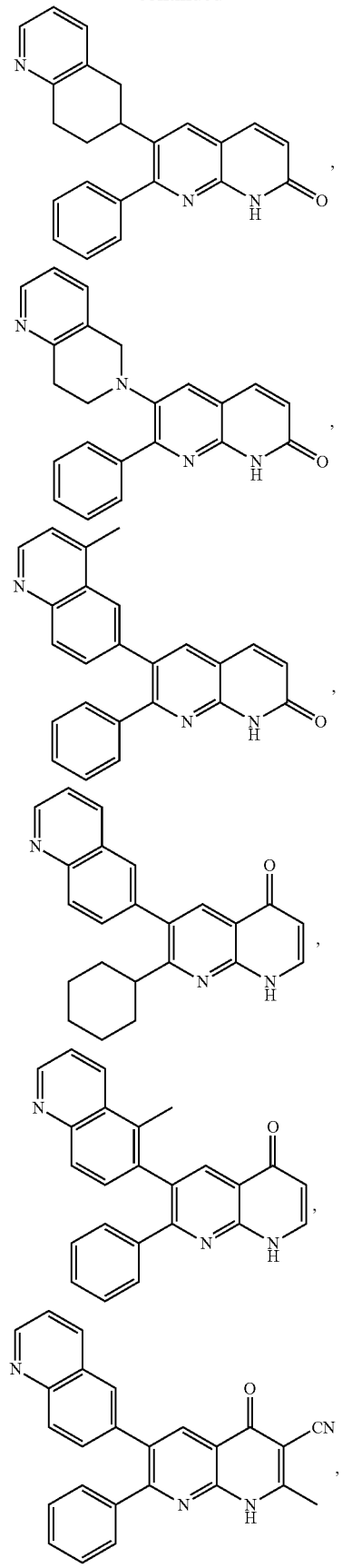
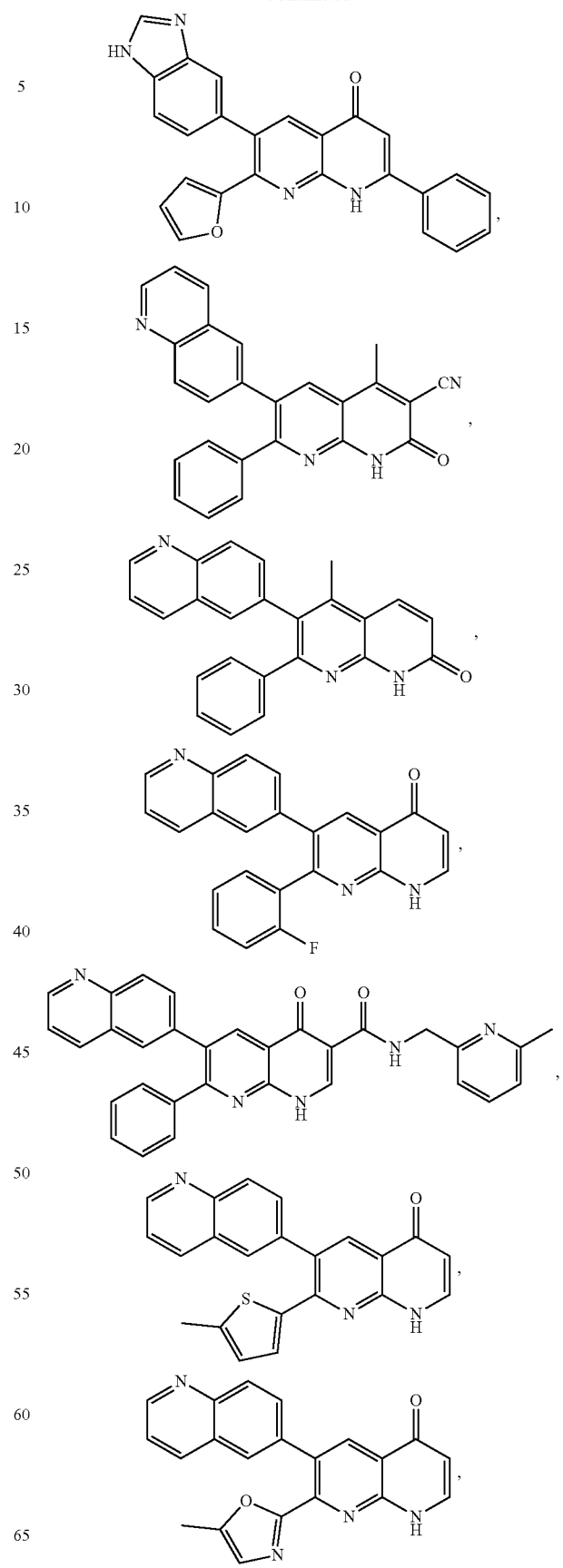

609
-continued
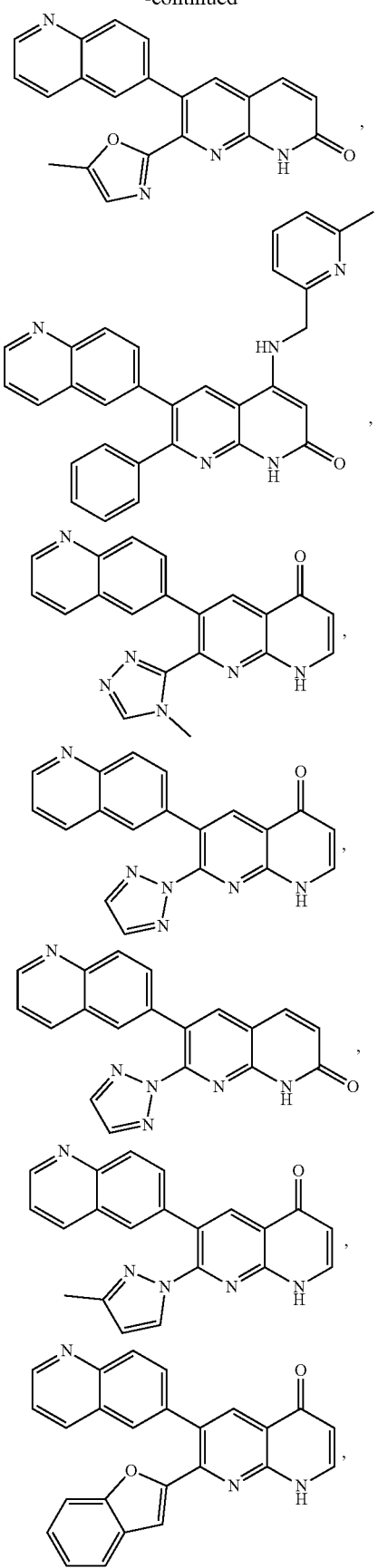
610
-continued
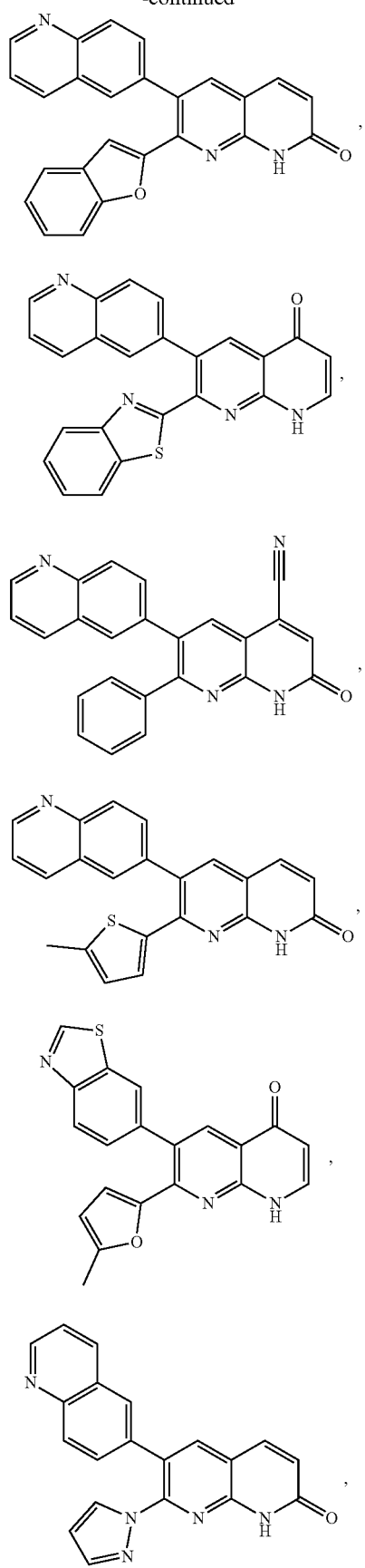

611
-continued
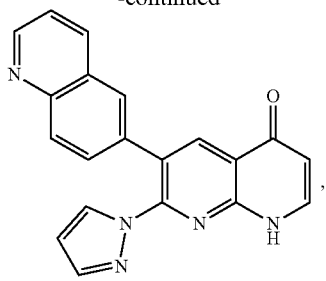
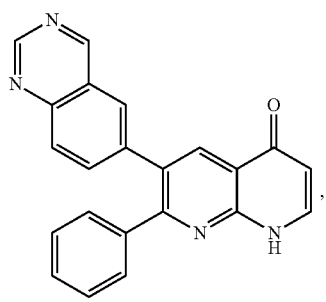
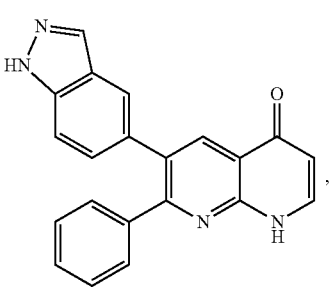
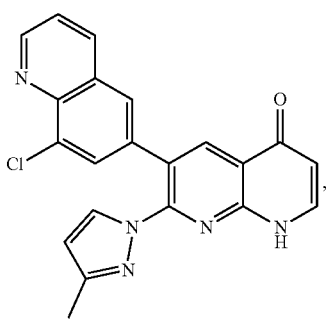
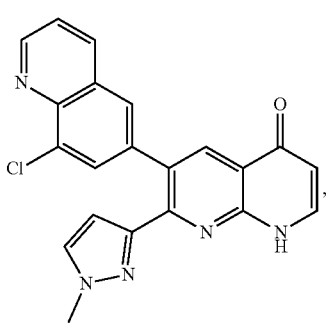
612
-continued
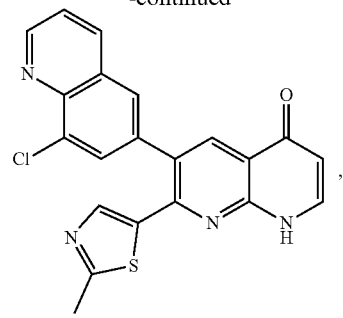
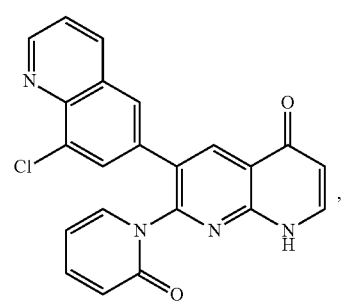
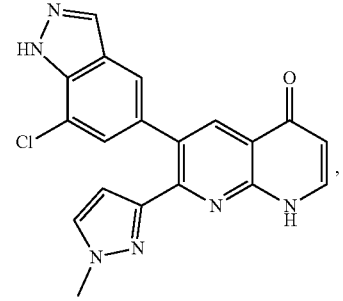
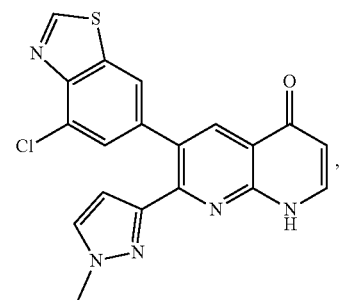
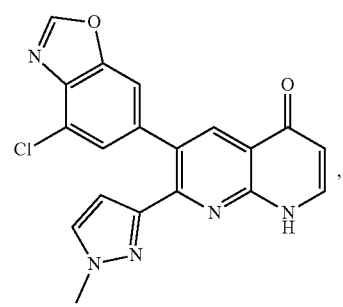

613
-continued
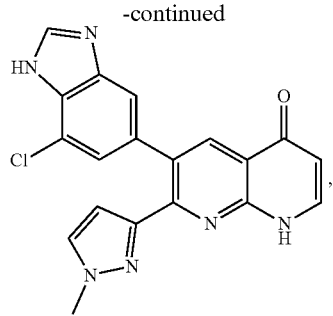
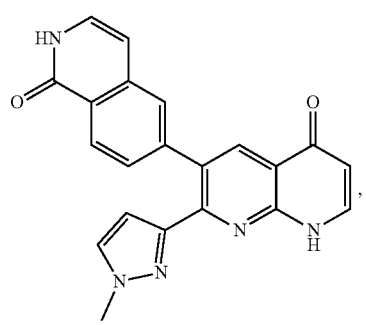
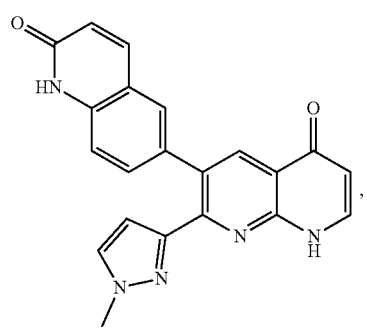
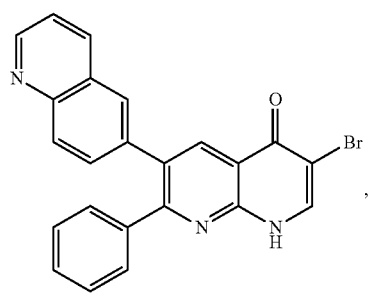
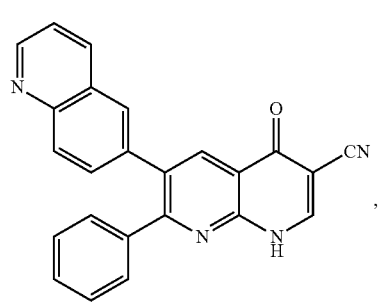
614
-continued
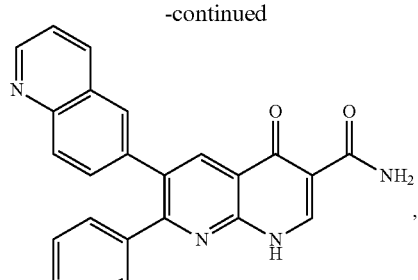
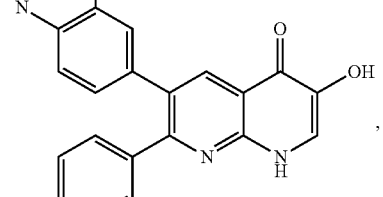
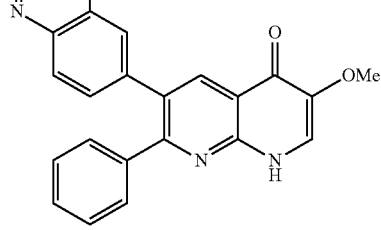
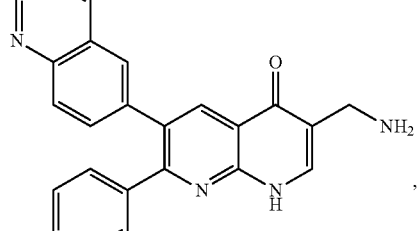
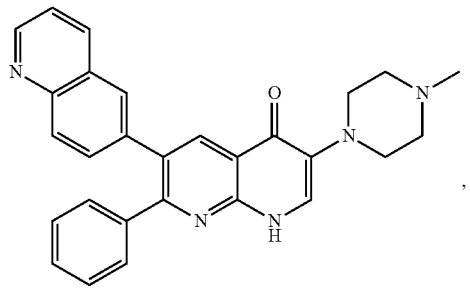
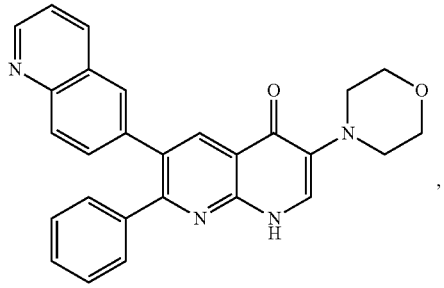

615
-continued
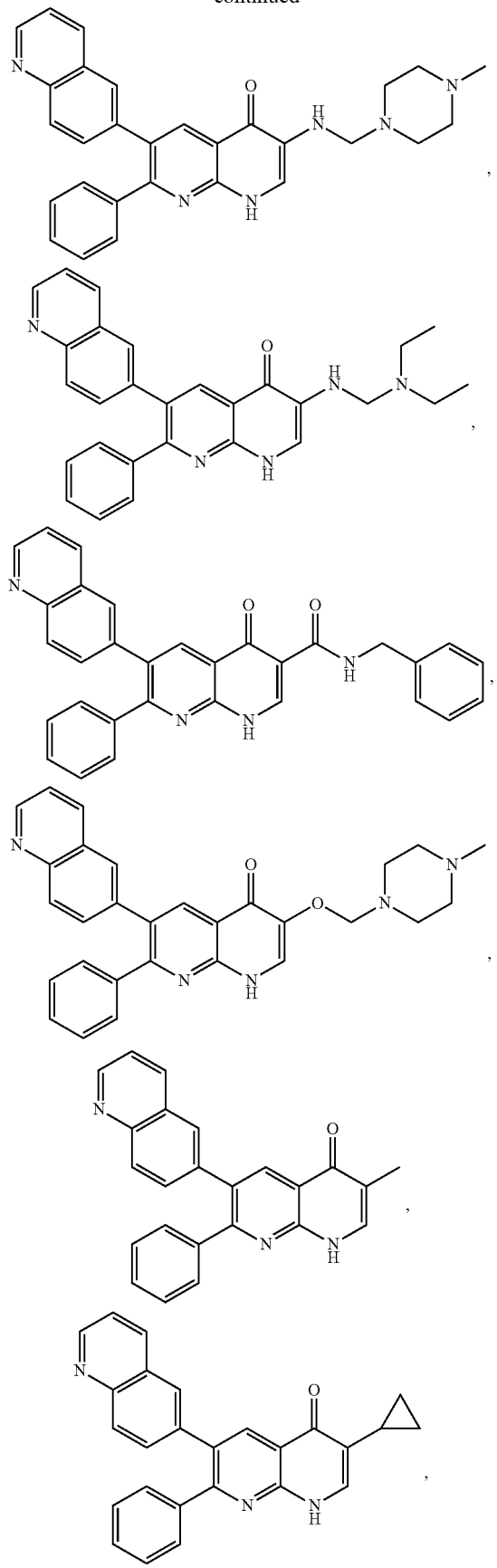
616
-continued
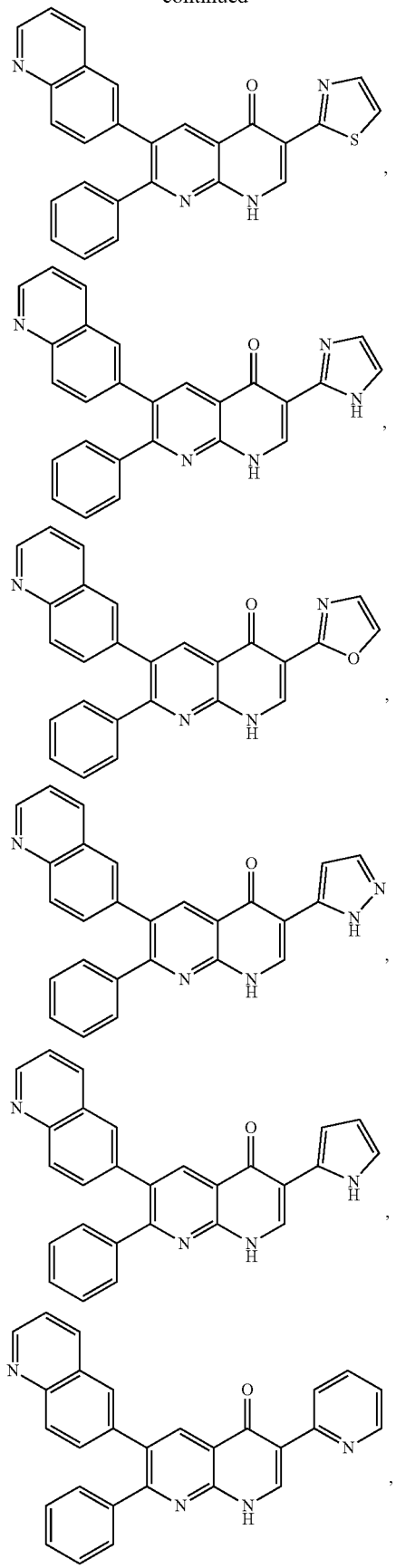

617
-continued
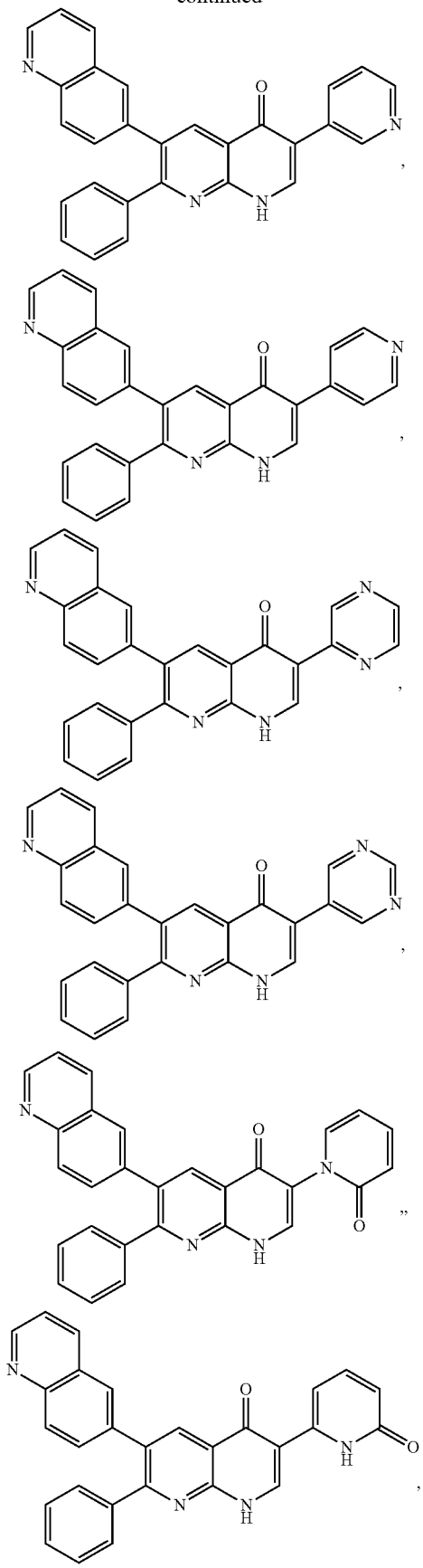
618
-continued
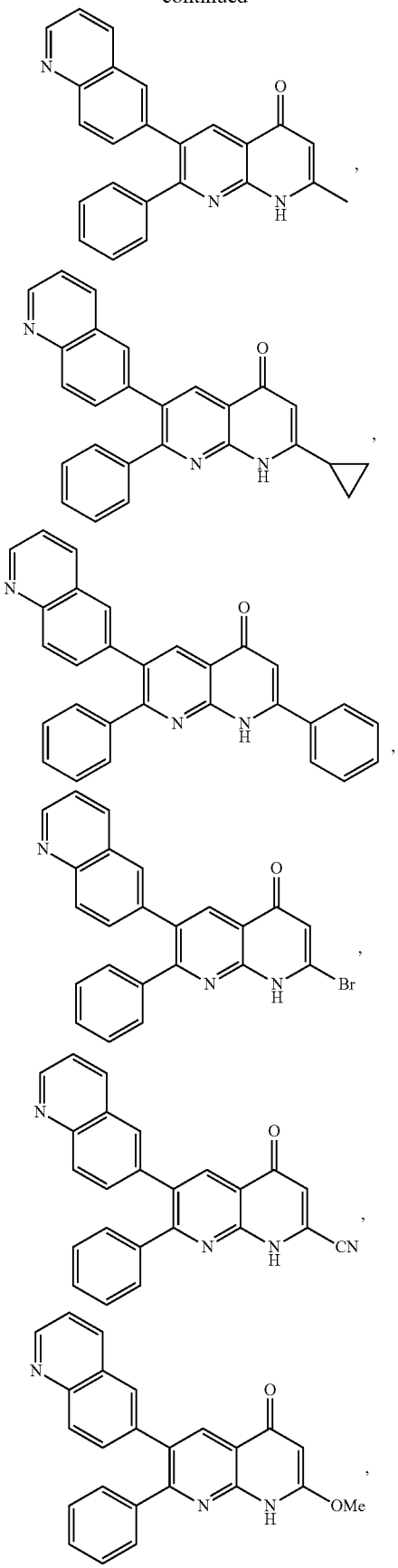

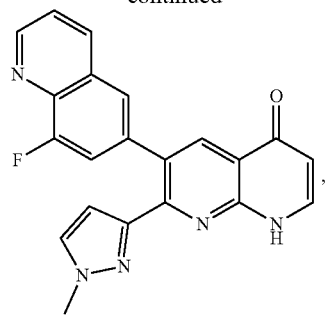,
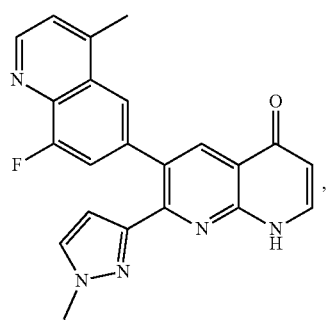,
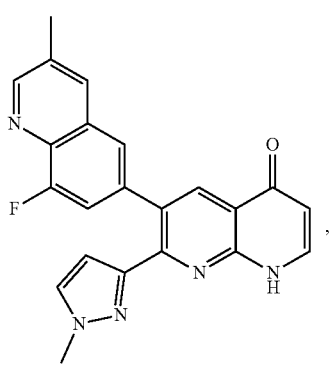,
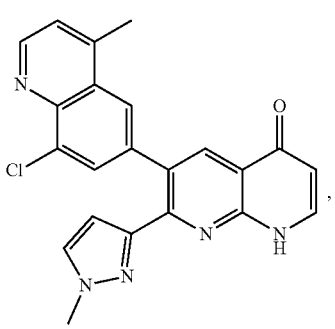,
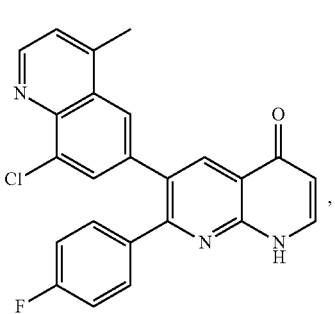,
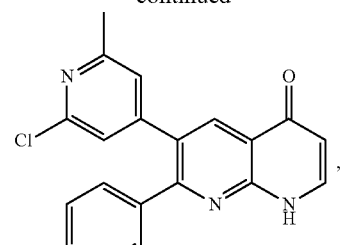,
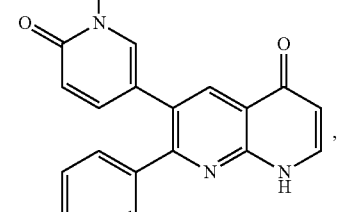,
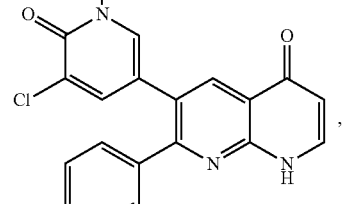,
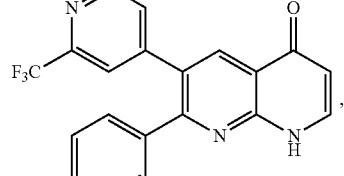,
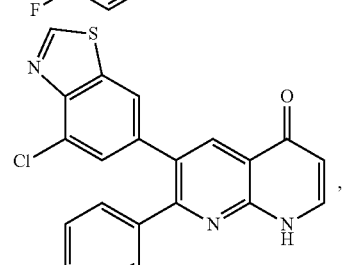,
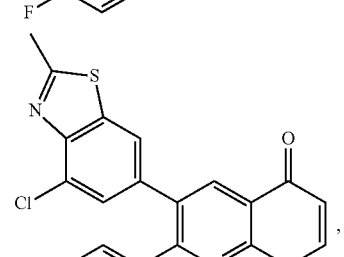, 621
-continued 622
-continued

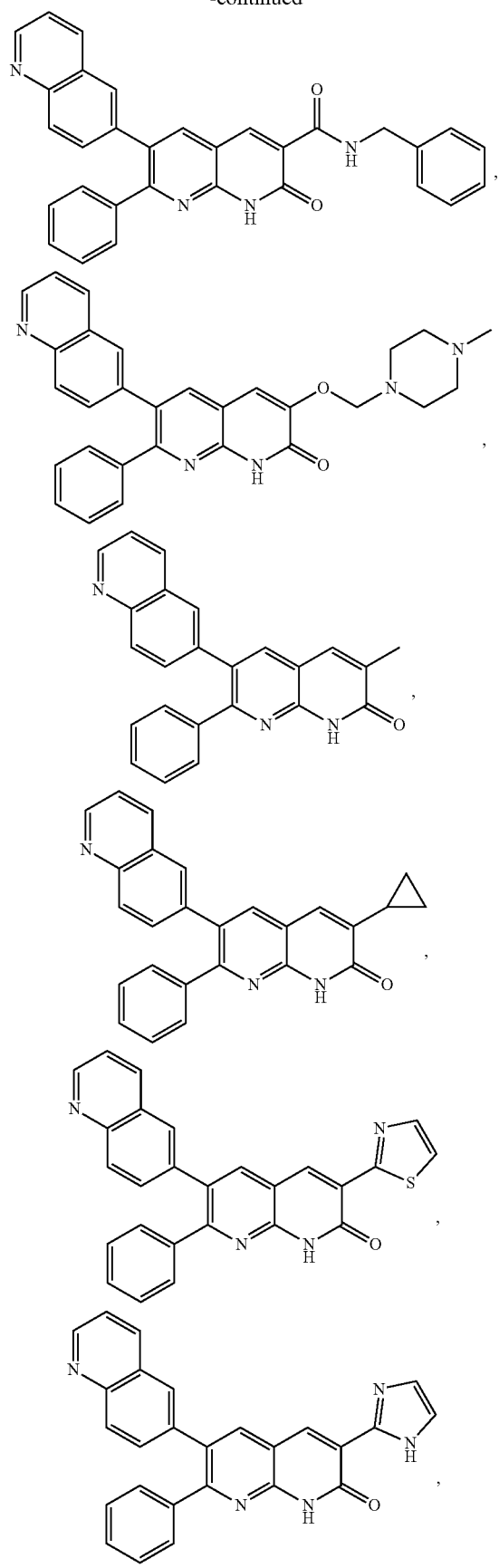
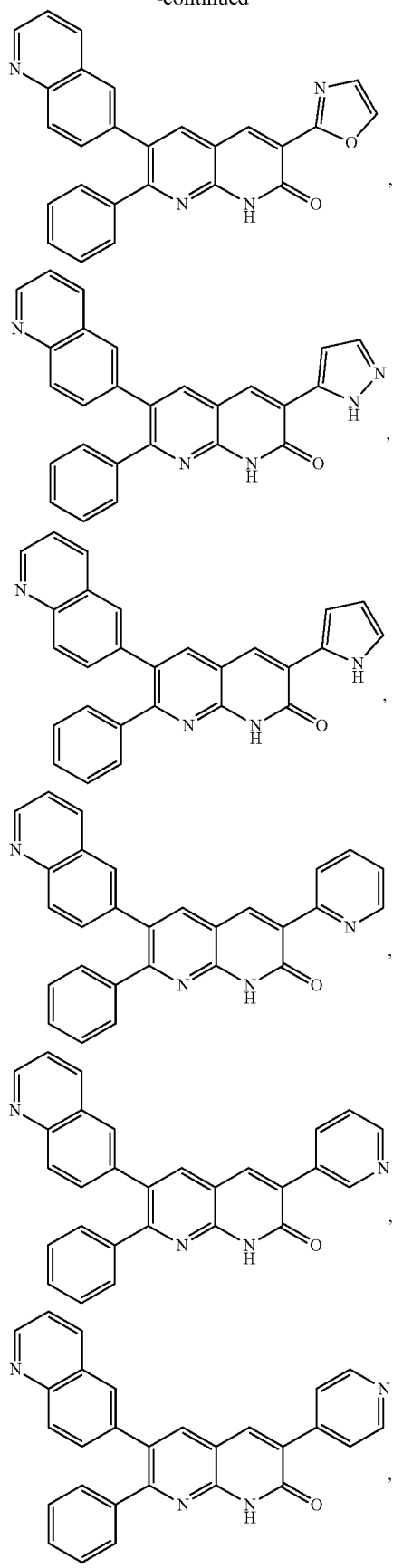

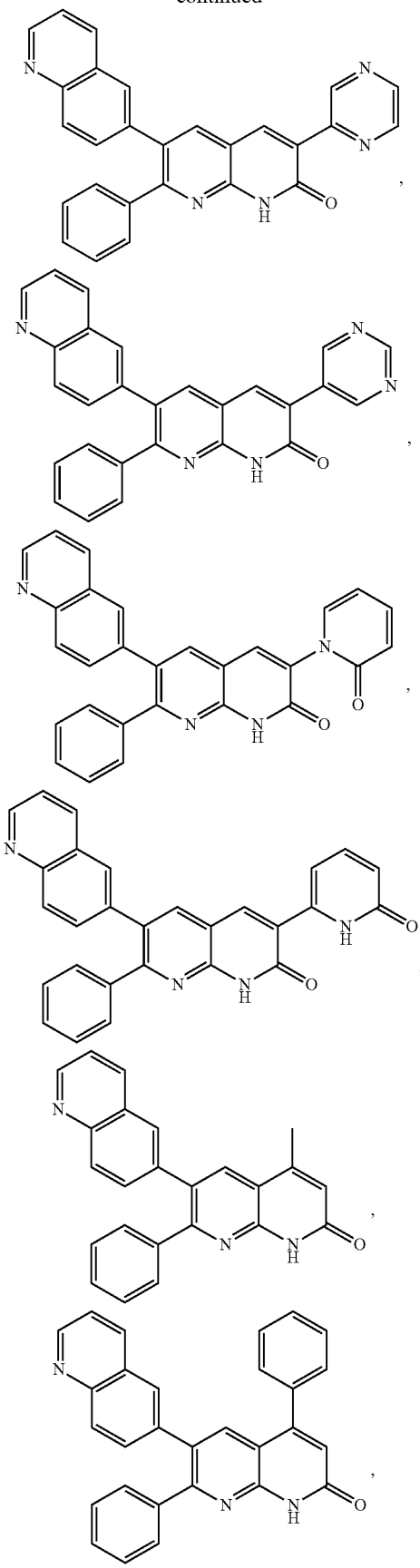
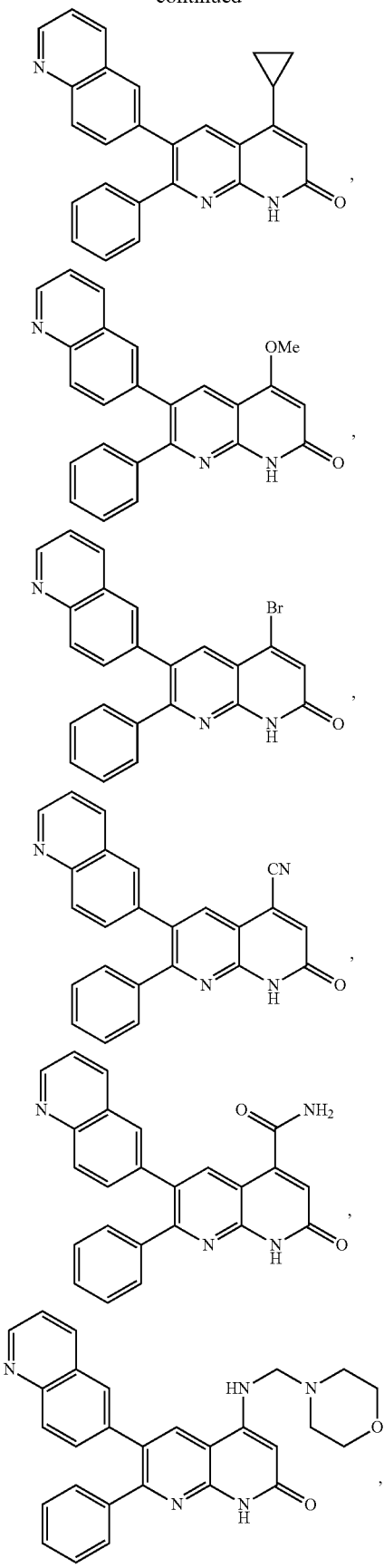

627
-continued
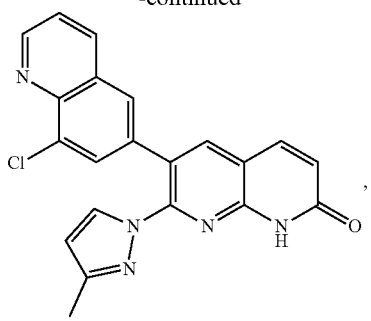
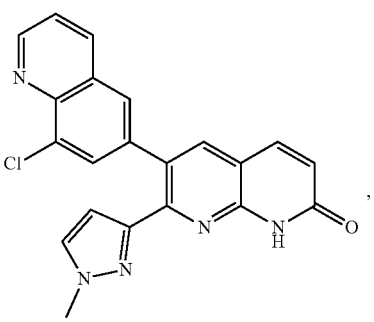
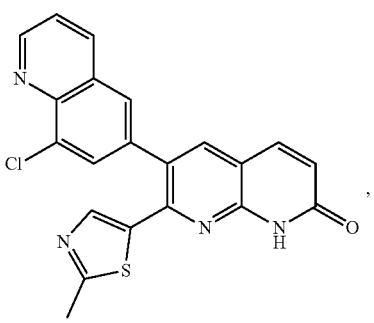
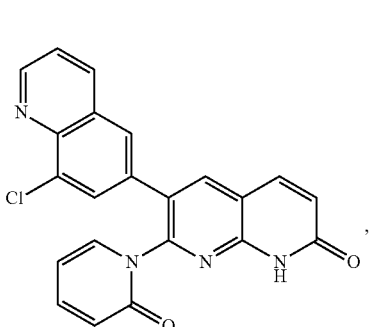
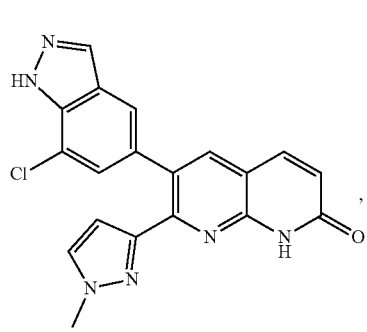
628
-continued
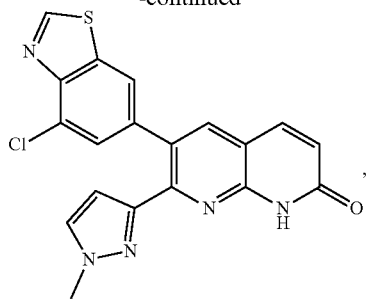
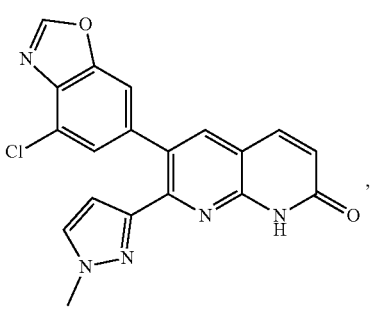
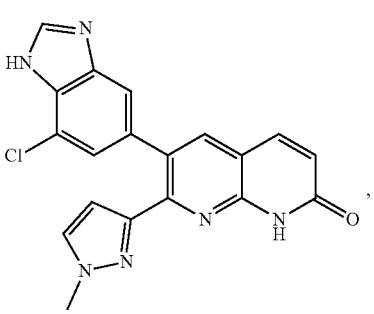
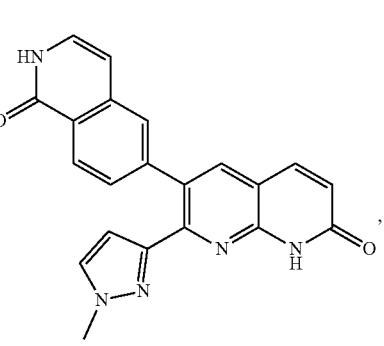
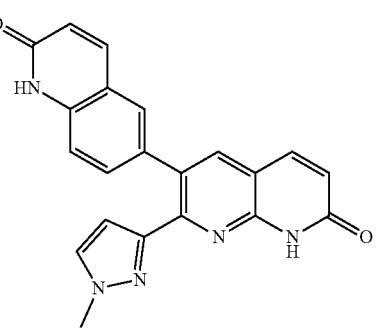

-continued
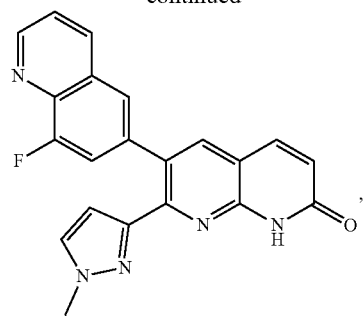,
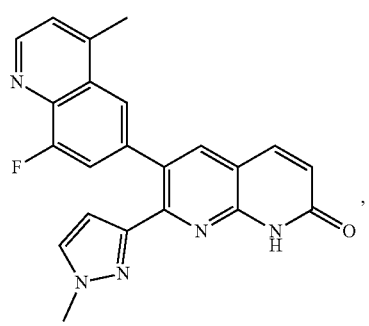,
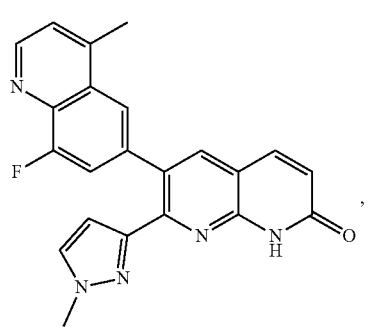,
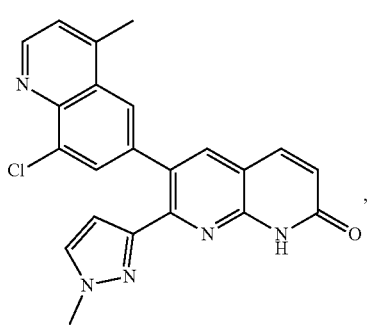,
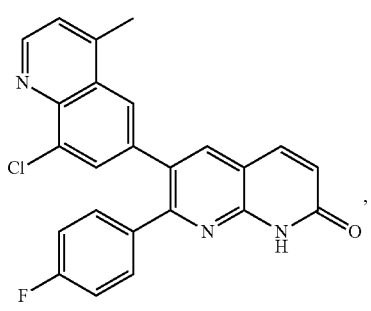,
-continued
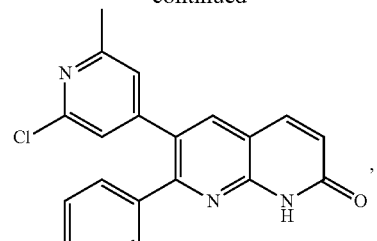,
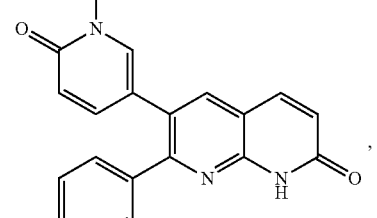,
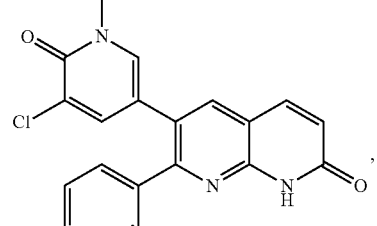,
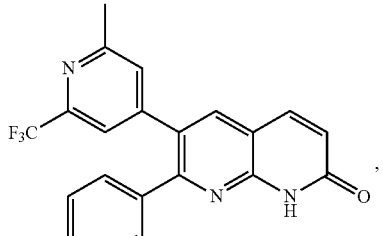,
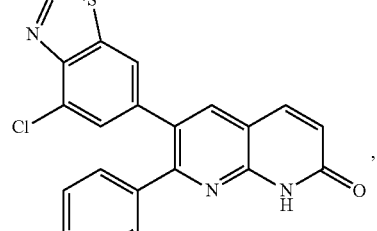,
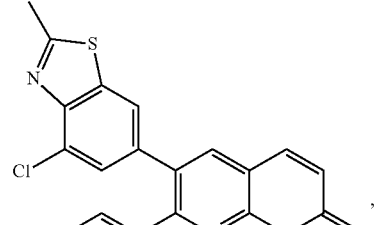,

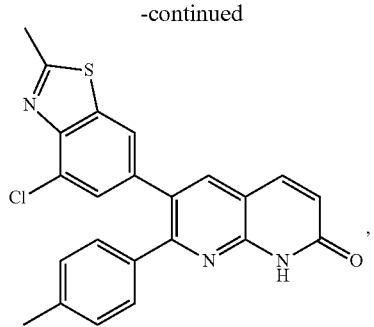
,
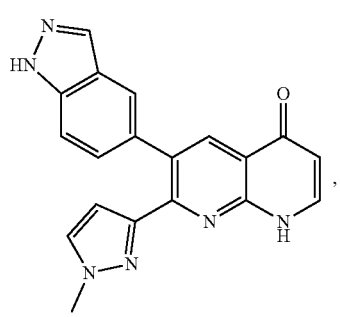
,
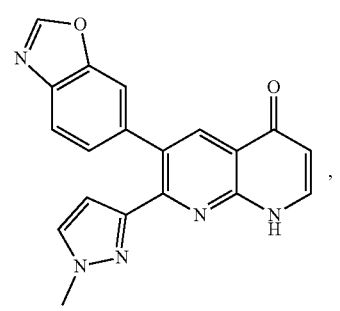
,
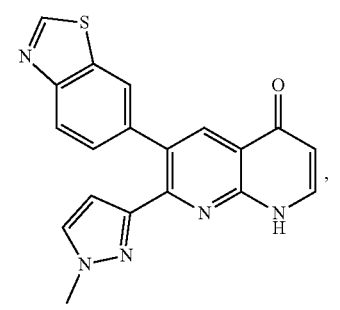
,
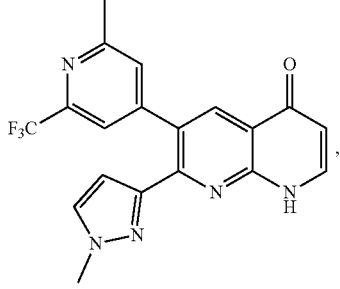
,
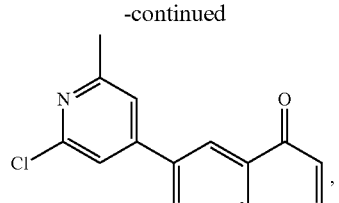
,
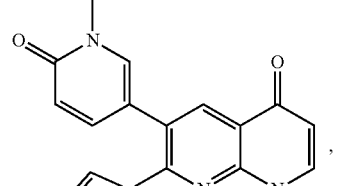
,
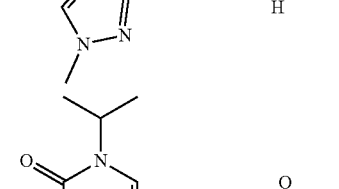
,
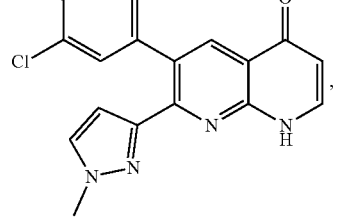
,
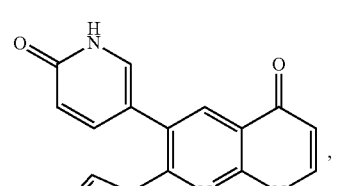
,
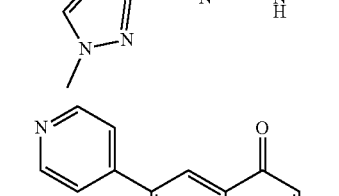
,
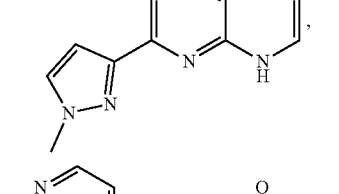
,
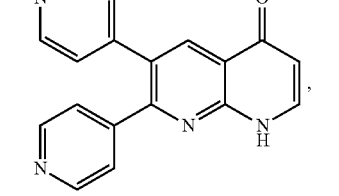
, 633
-continued
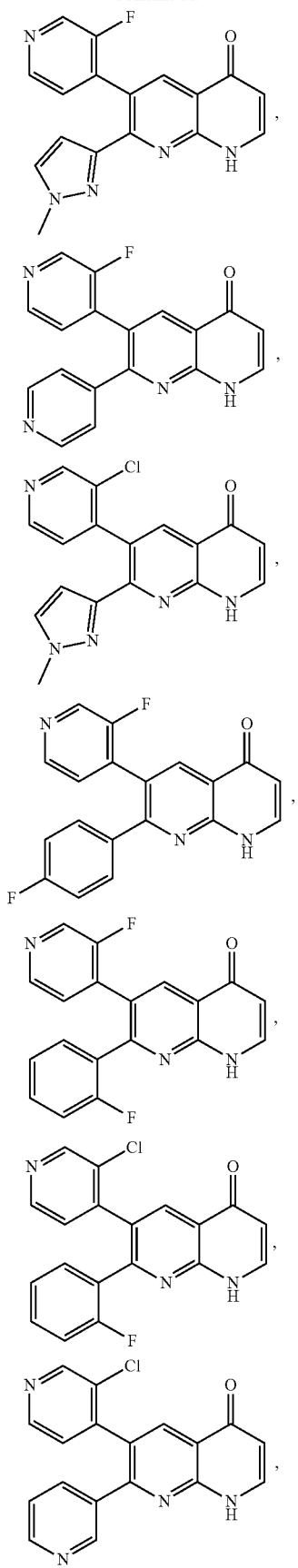
634
-continued
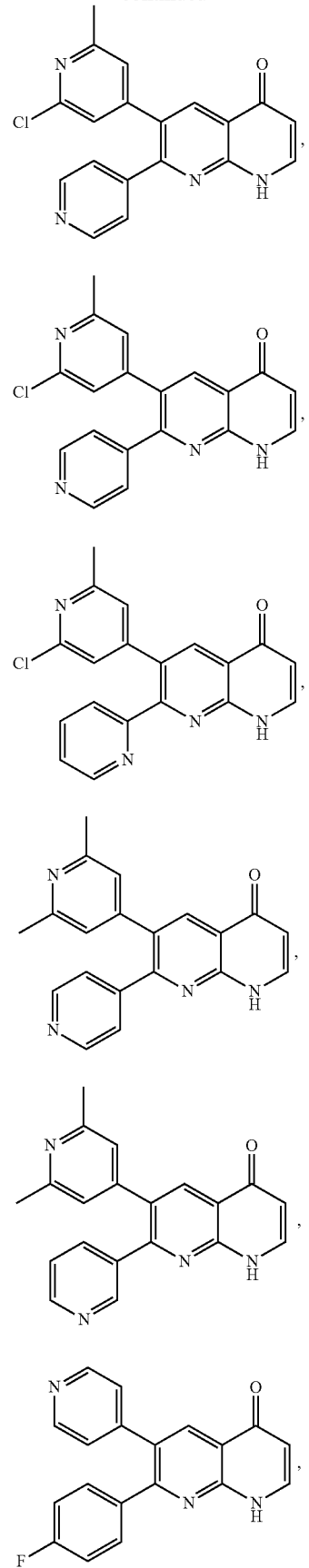

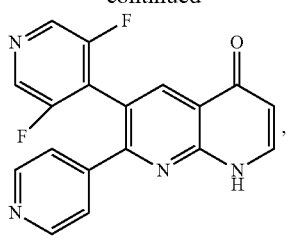,
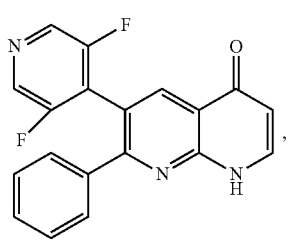,
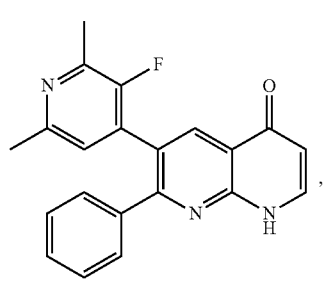,
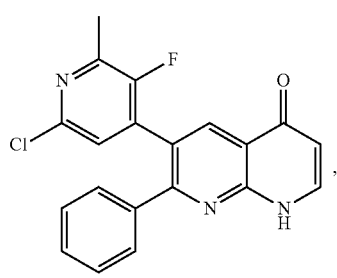,
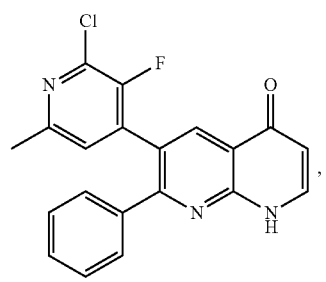,
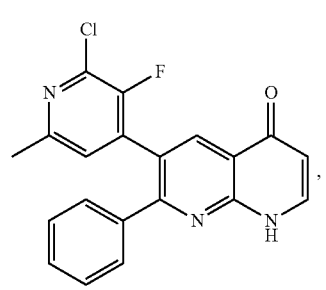,
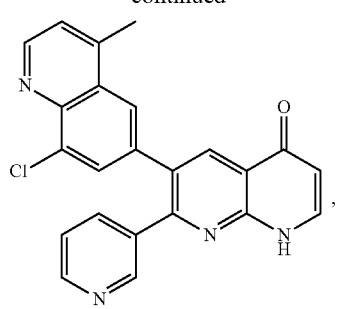,
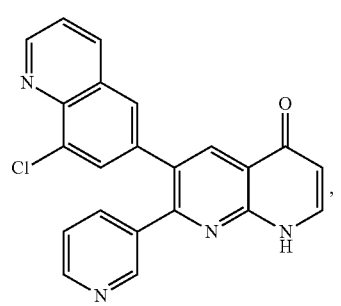,
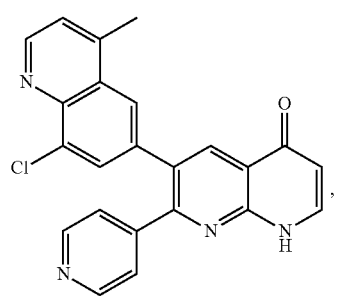,
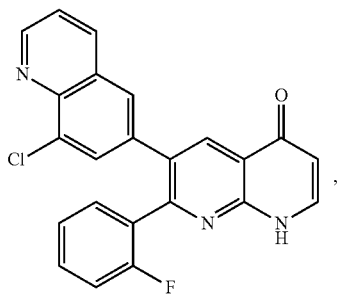,
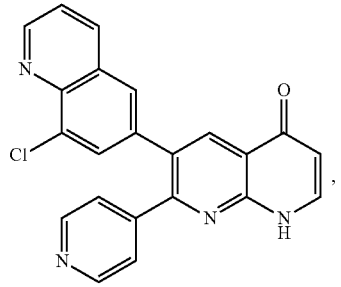, -continued
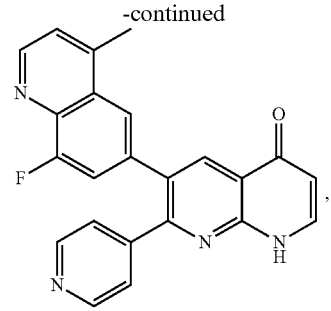
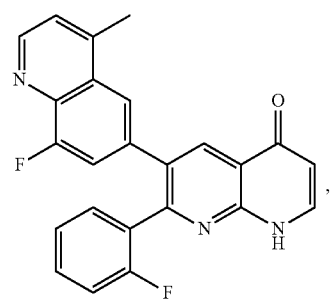
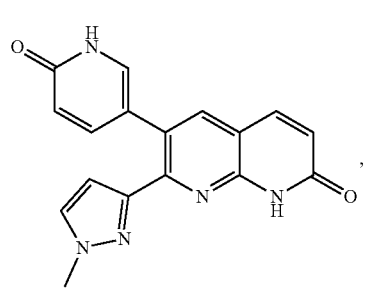
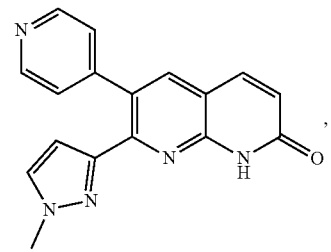
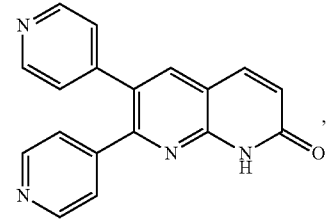
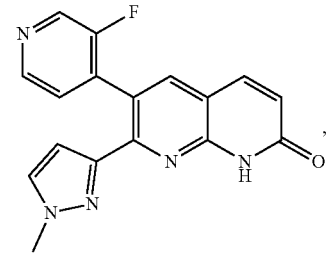
-continued
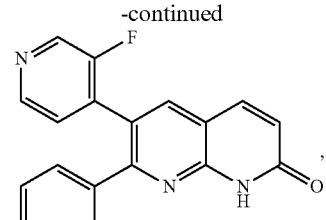
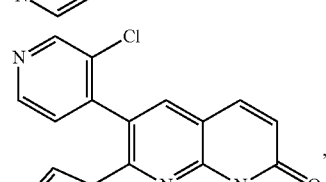
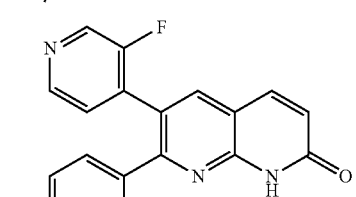
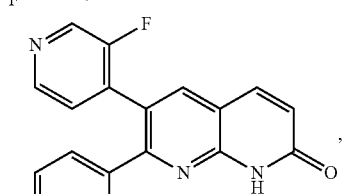
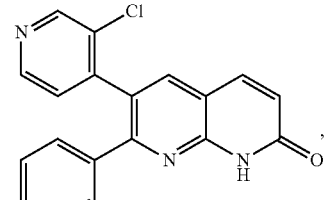
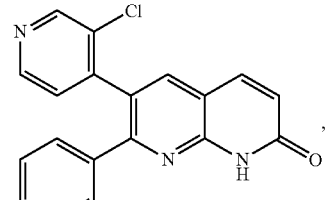
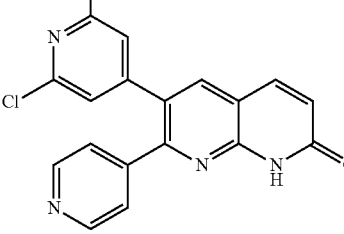

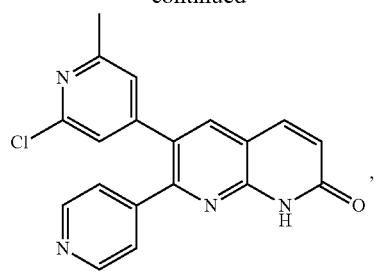
,
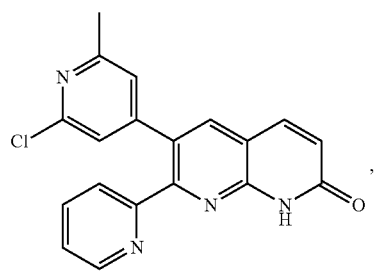
,
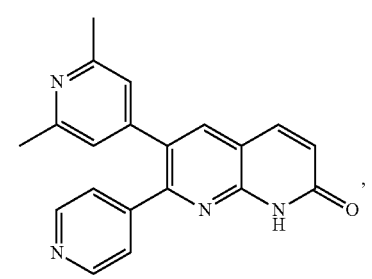
,
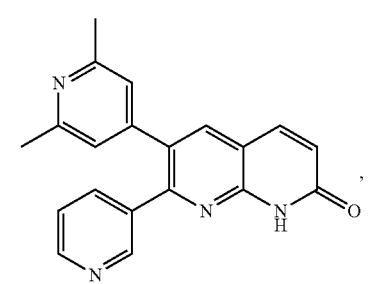
,
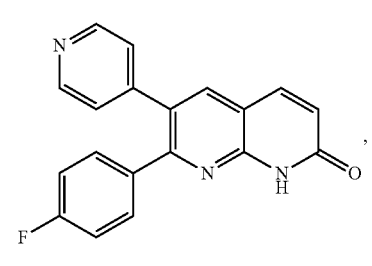
,
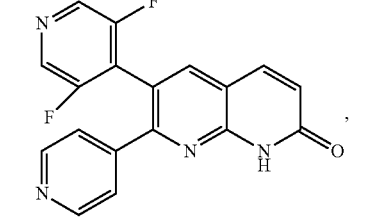
,
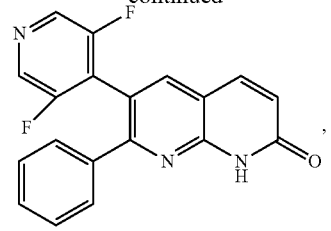
,
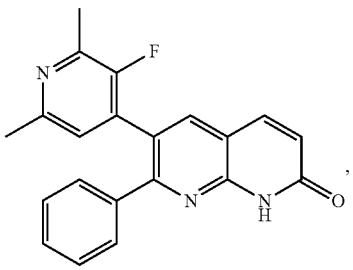
,
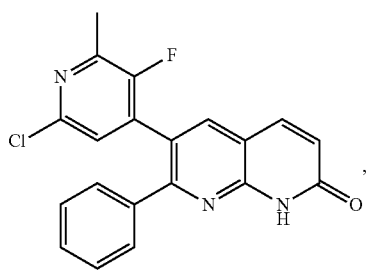
,
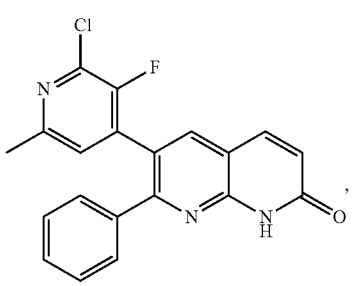
,
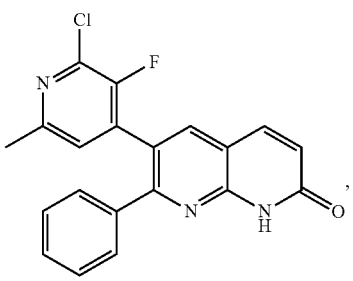
,
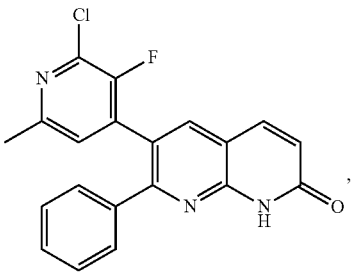
,

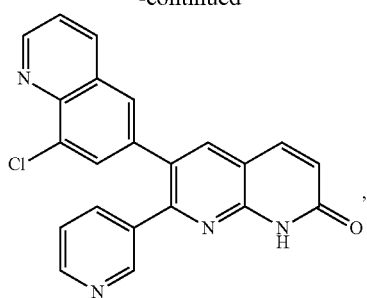
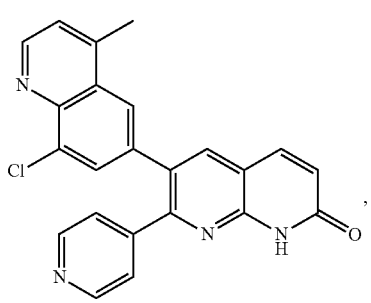
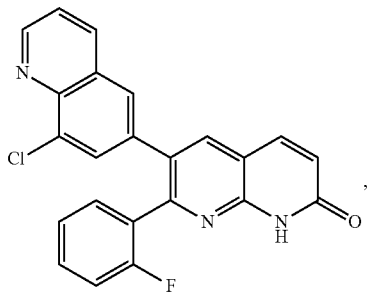
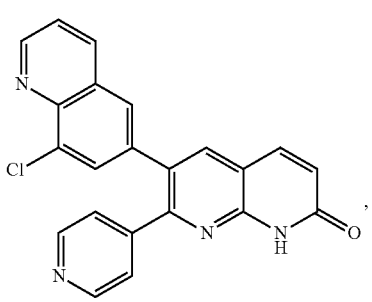
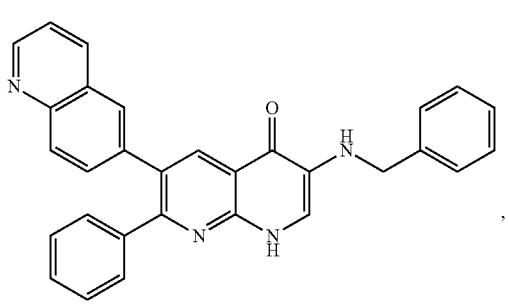
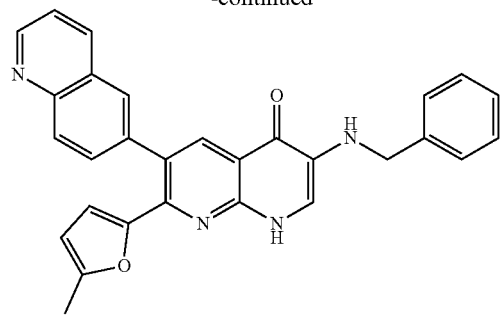
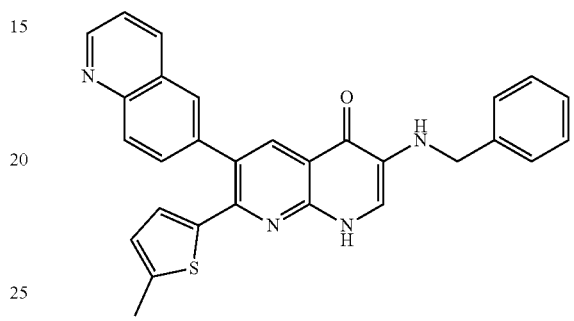
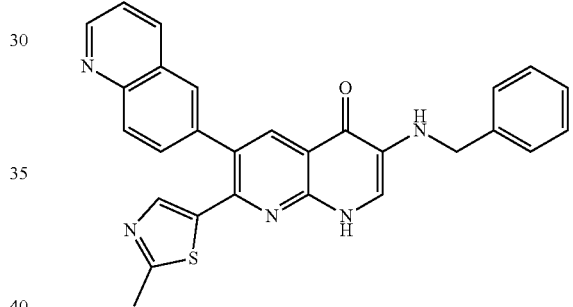
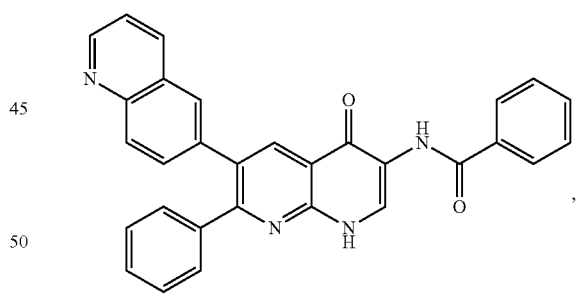
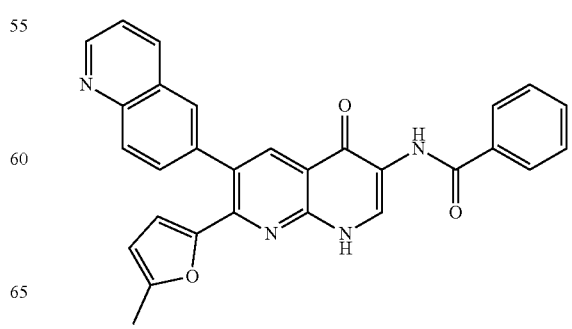

643
-continued
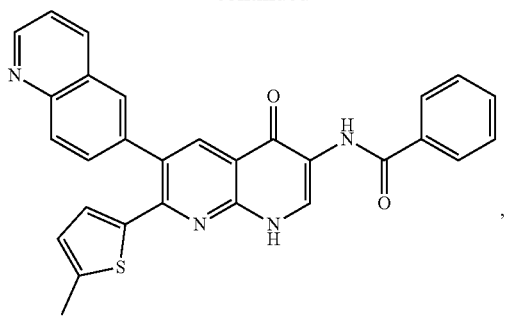,
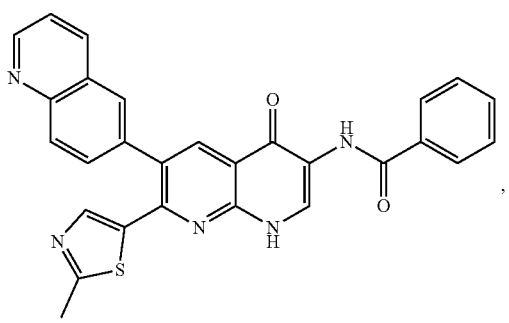,
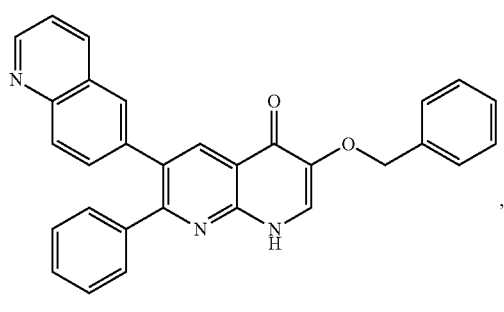,
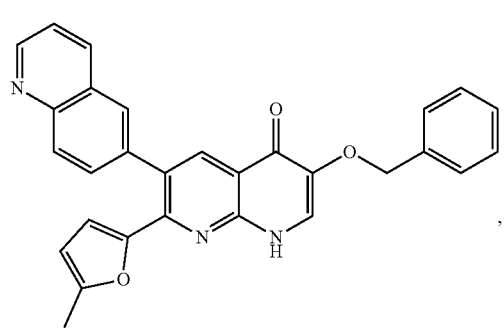,
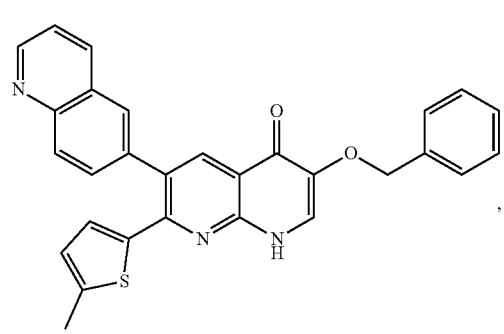,
644
-continued
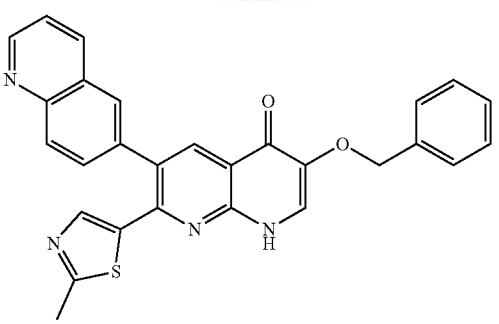,
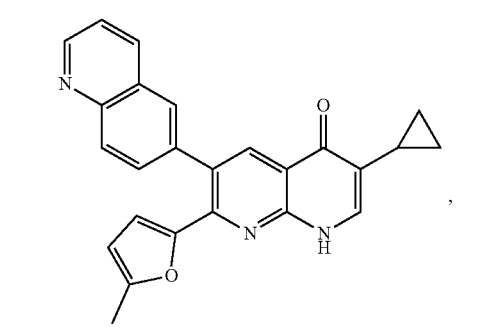,
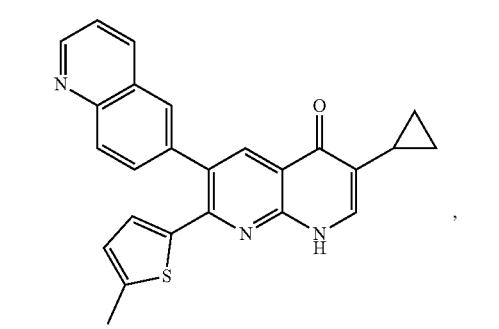,
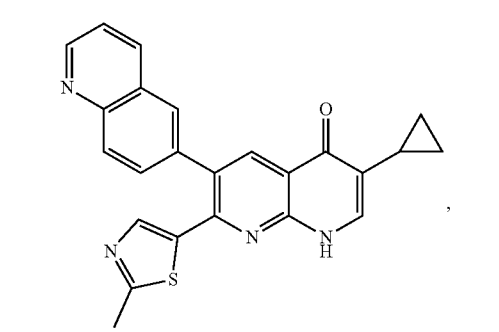,
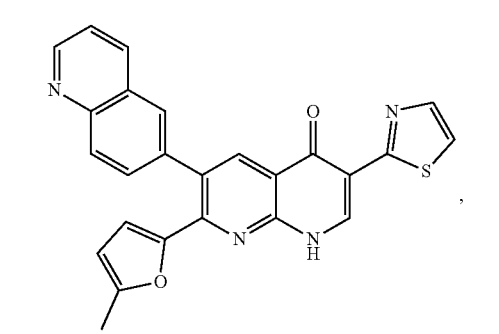, 645
-continued
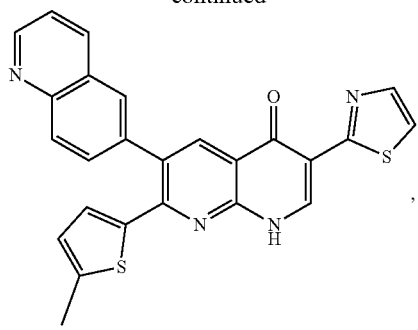,
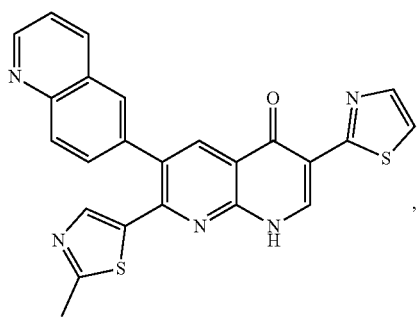,
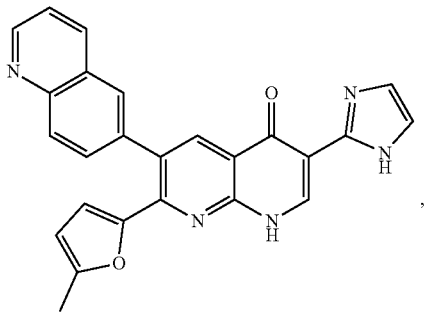,
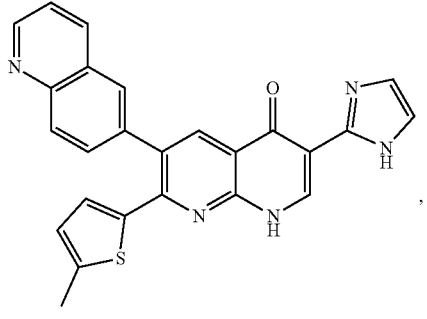,
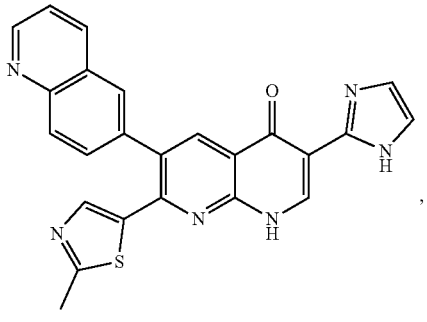,
646
-continued
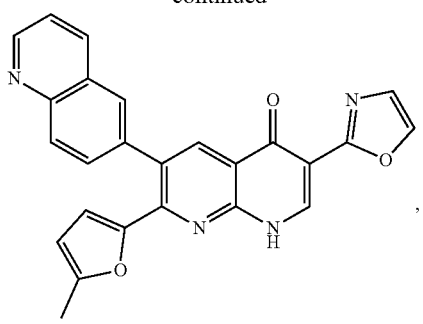,
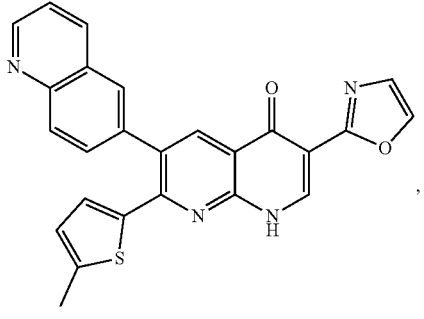,
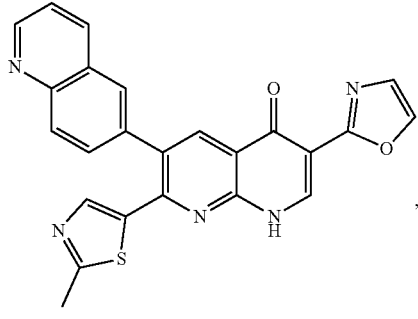,
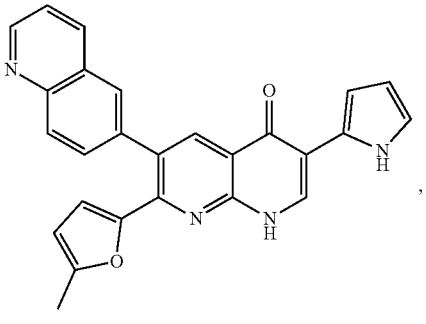,
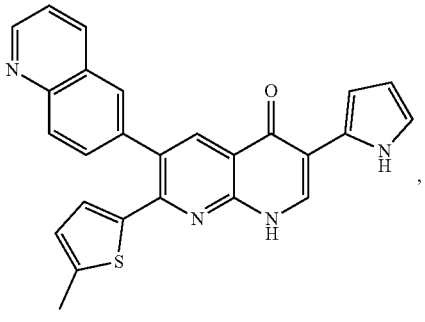, 647
-continued
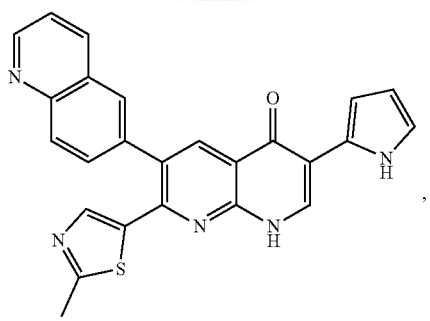
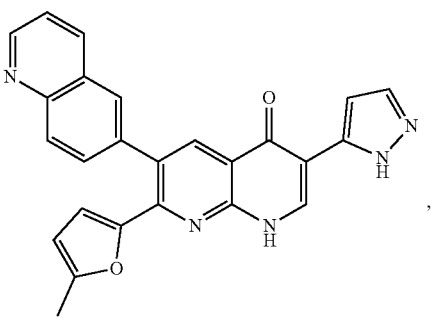
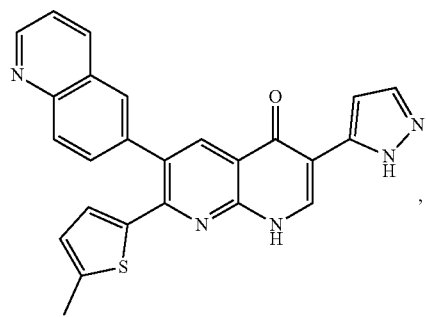
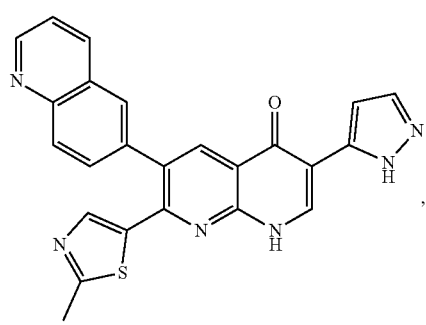
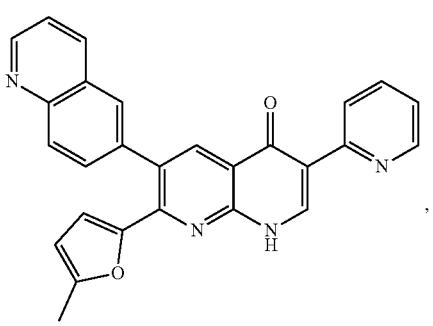
648
-continued
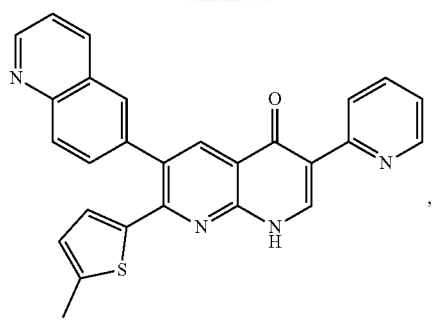
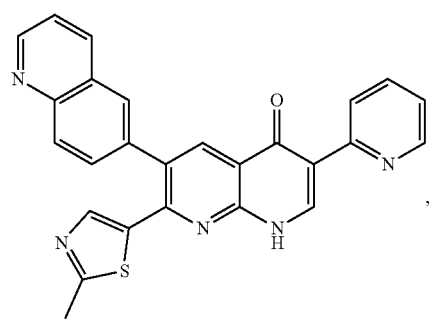
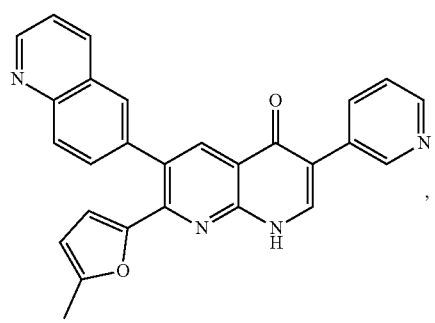
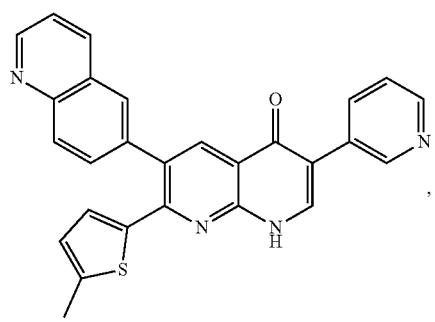
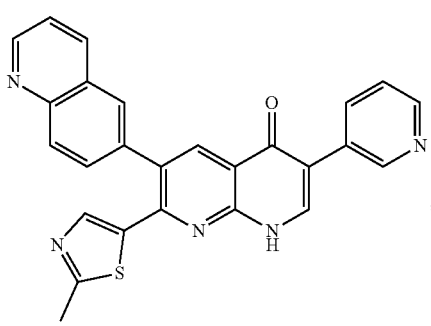

649
-continued
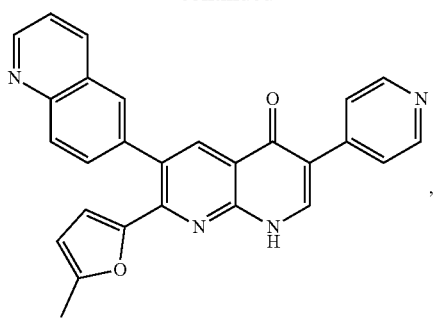
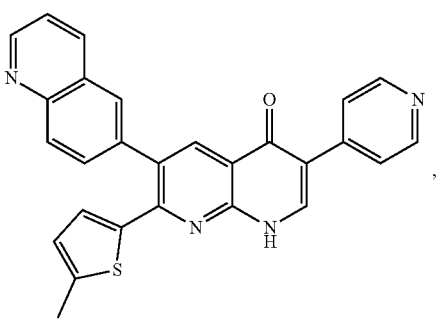
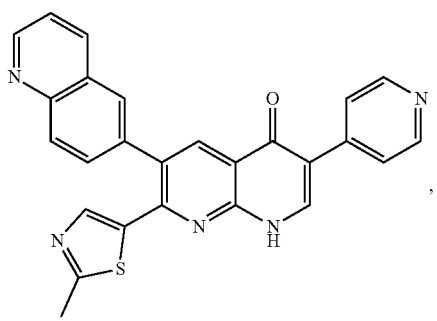
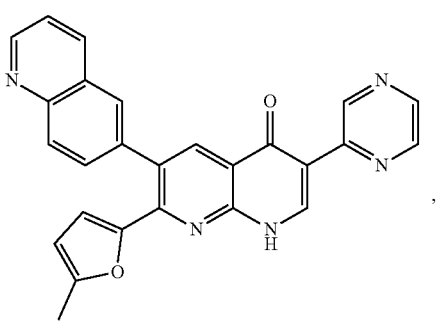
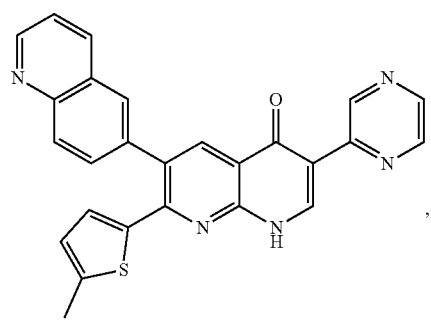
650
-continued
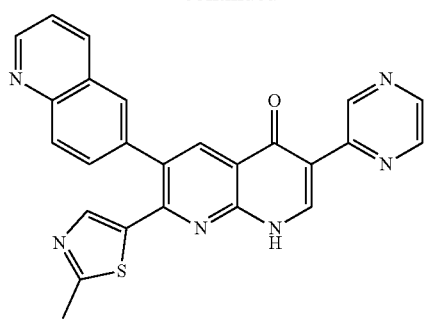
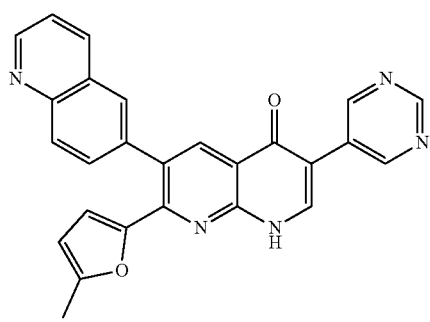
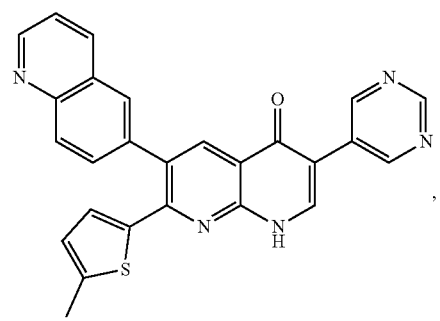
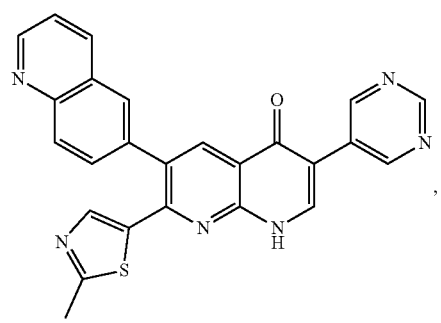
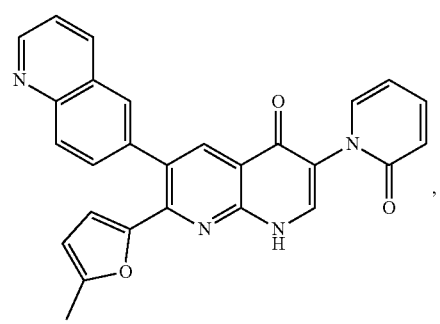

-continued
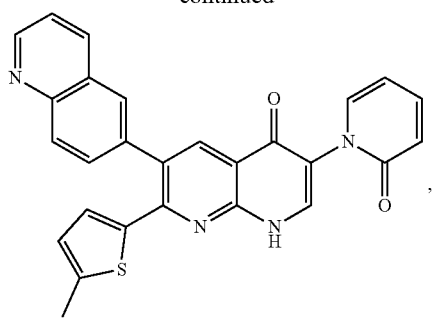,
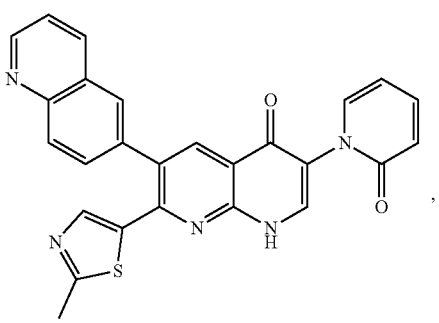,
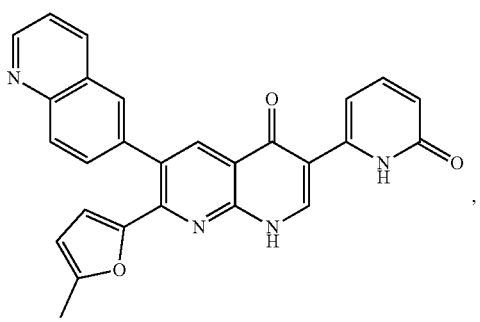,
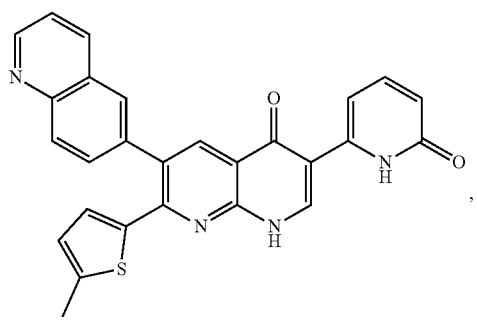,
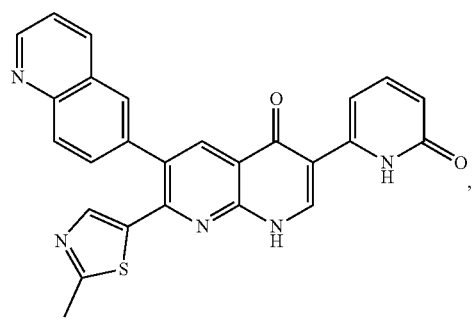,
-continued
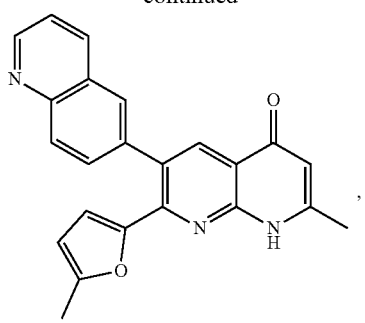,
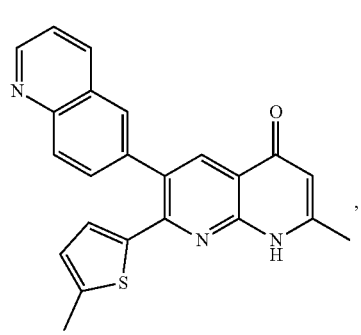,
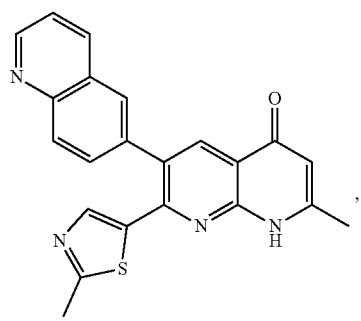,
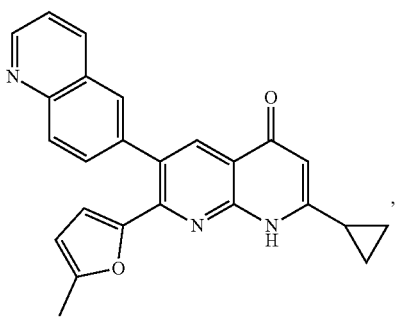,
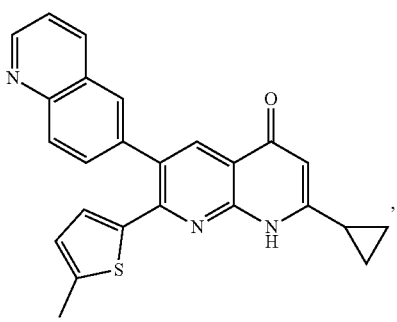, 653
-continued
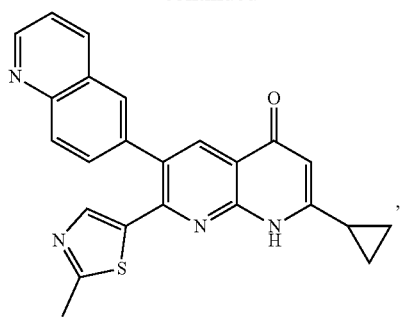,
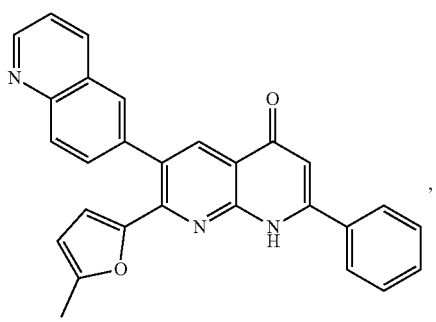,
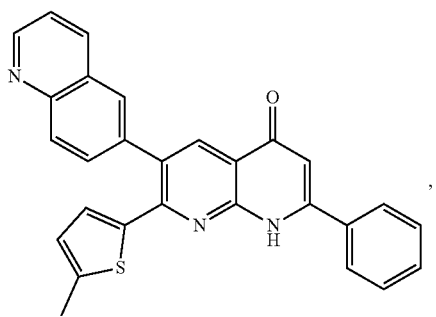,
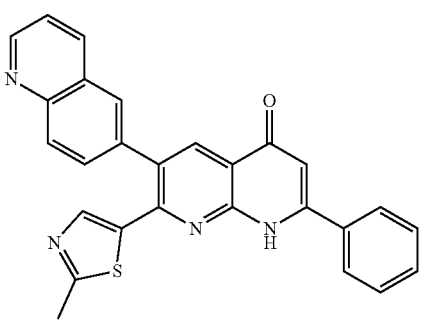,
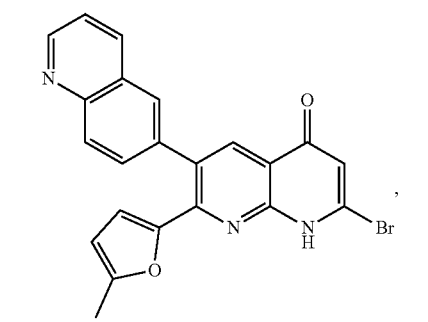,
654
-continued
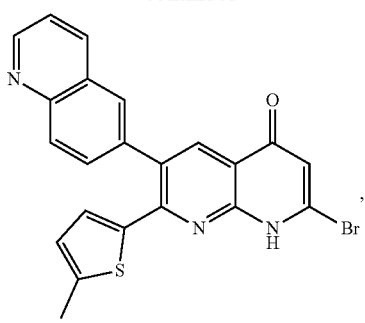,
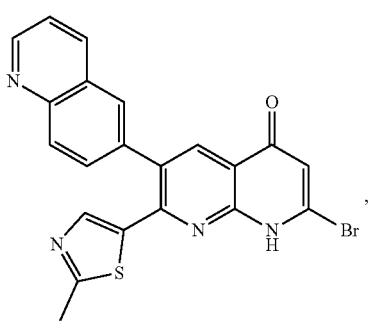,
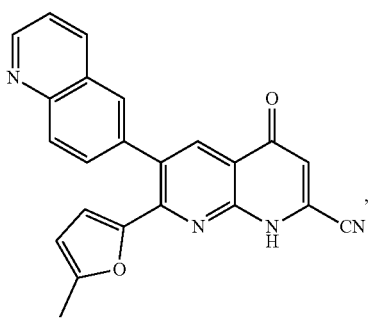,
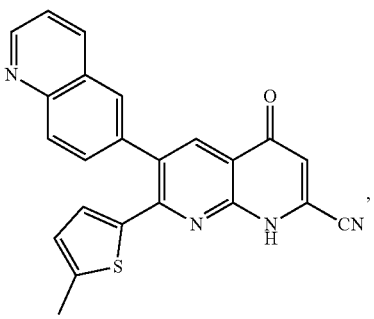,
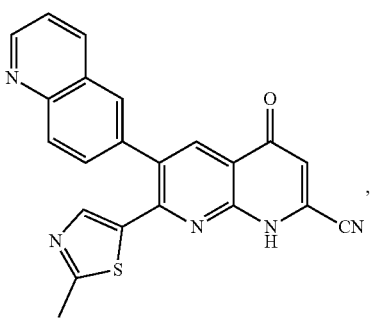, 655
-continued
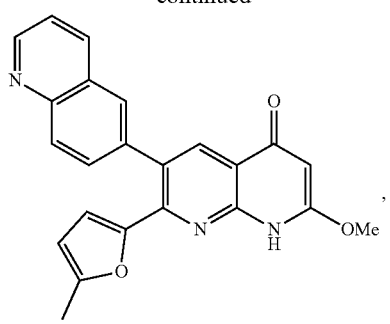,
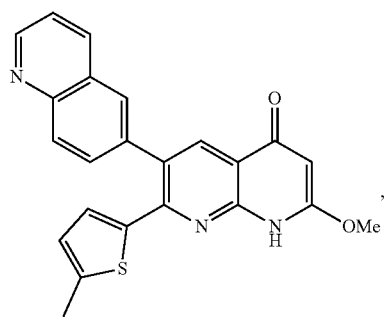,
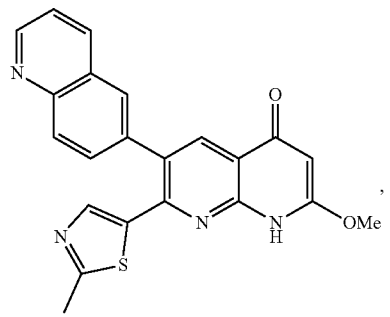,
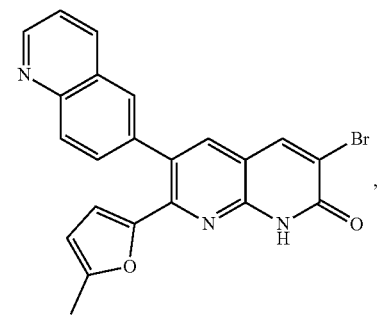,
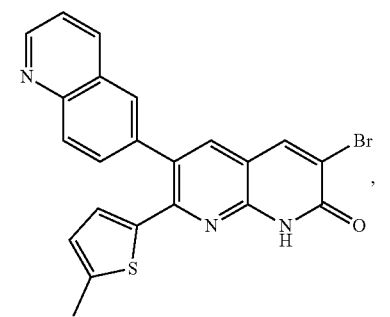,
656
-continued
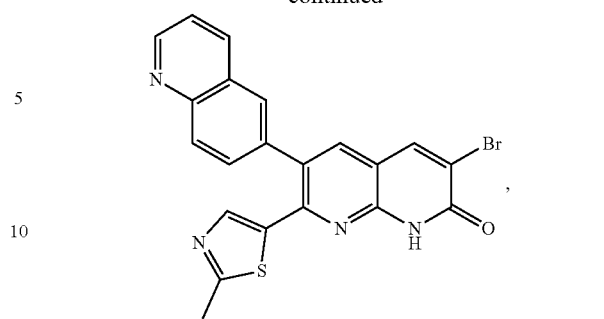,
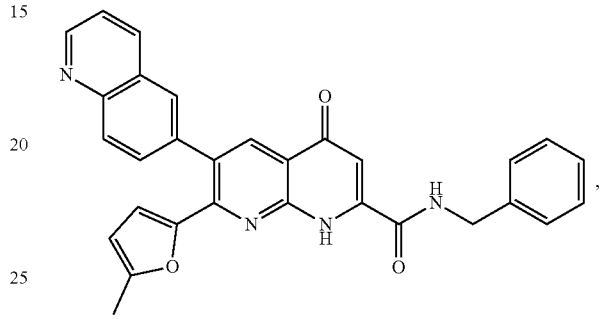,
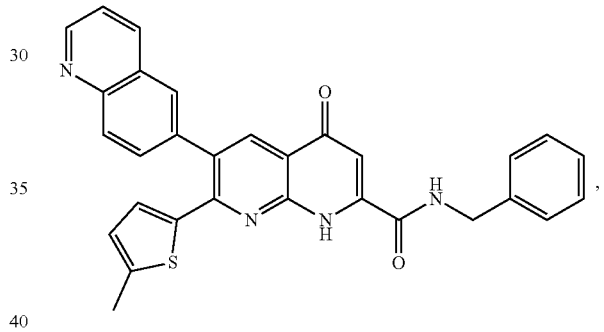,
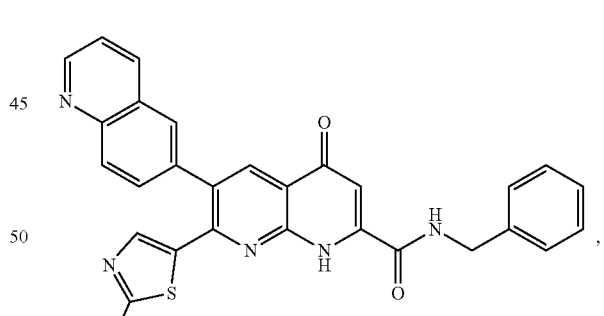,
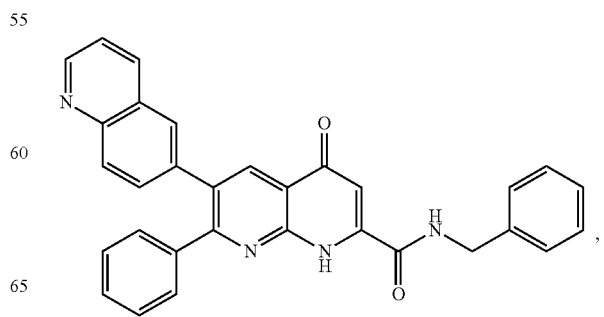, 657
-continued 658
-continued 659
-continued
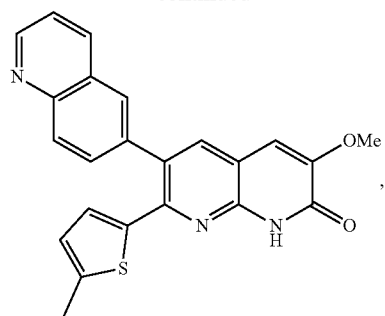
,
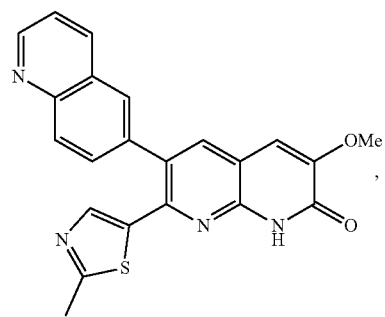
,
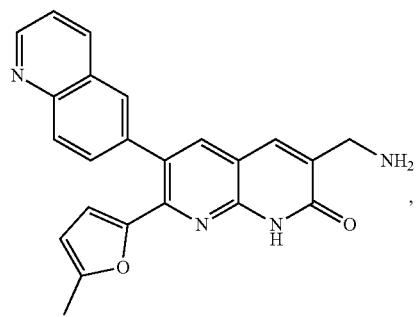
,
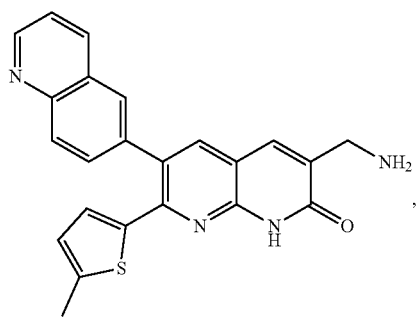
,
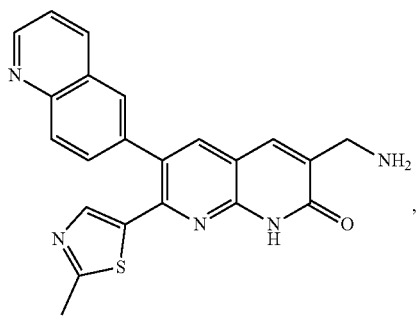
,
660
-continued
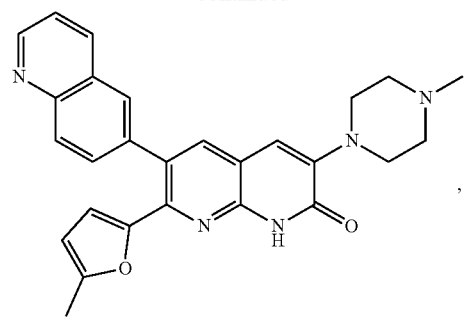
,
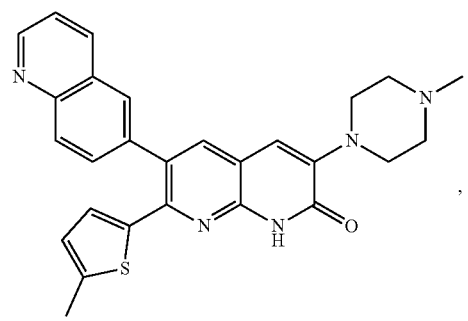
,
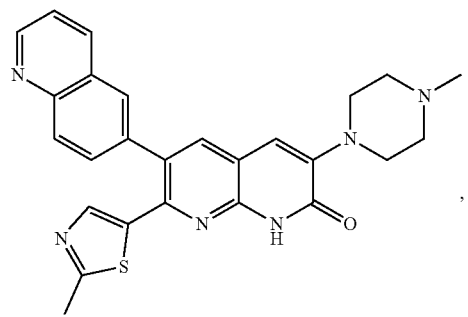
,
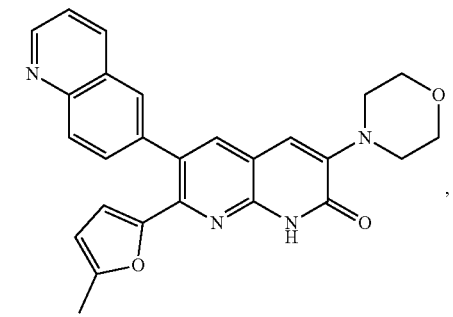
,
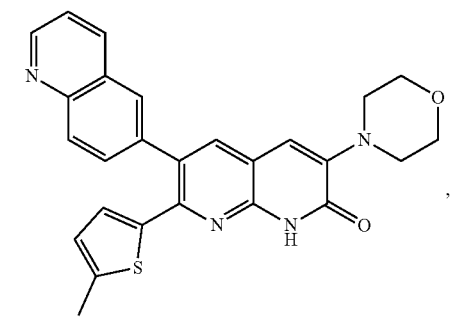
, 661
-continued
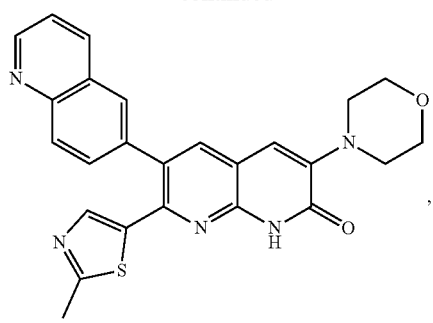
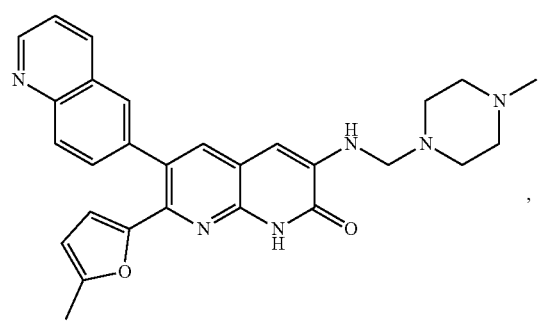
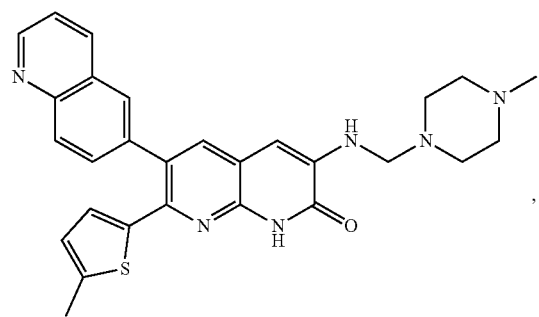
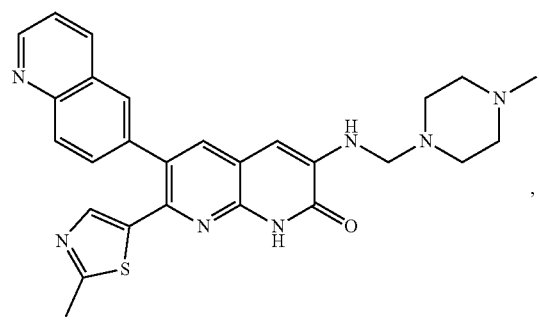
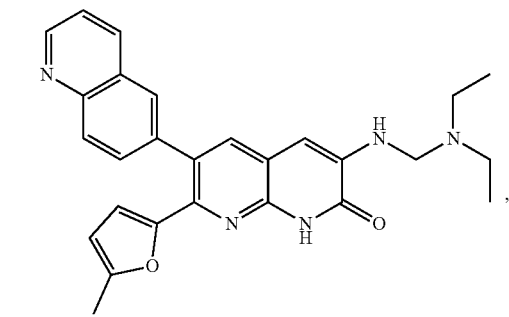
662
-continued
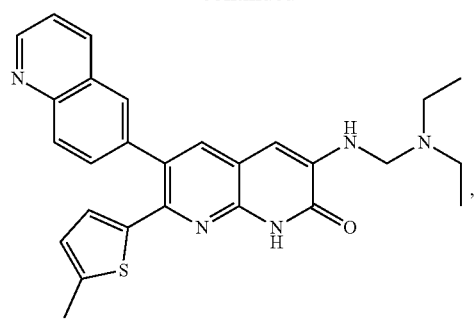
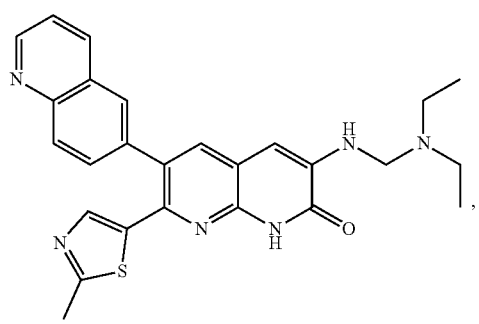
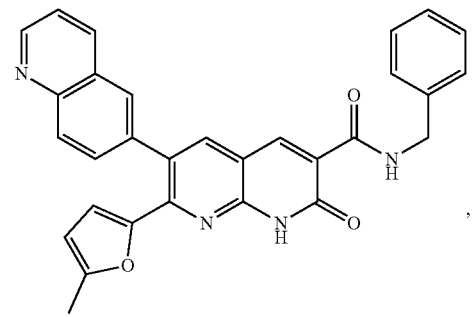
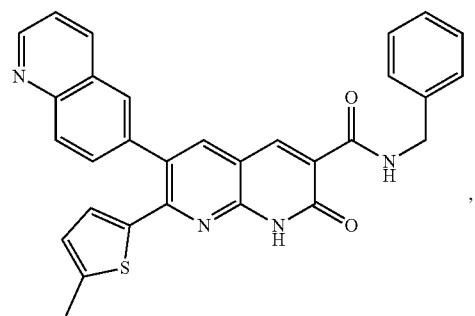
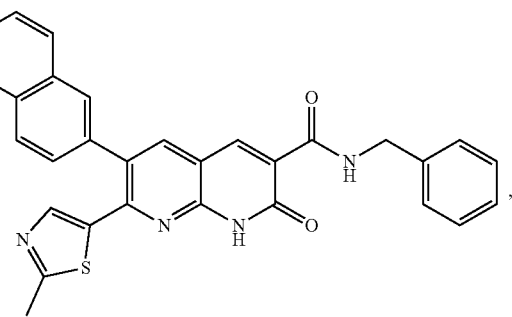

663
-continued
664
-continued
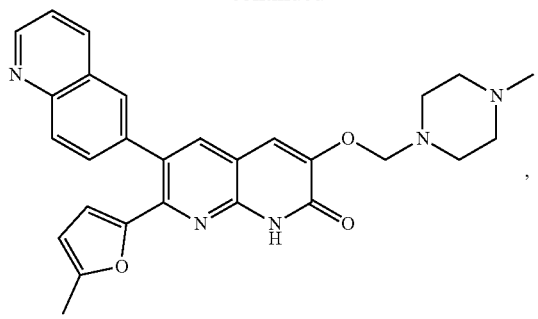
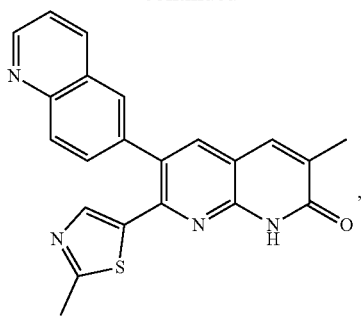

665
-continued
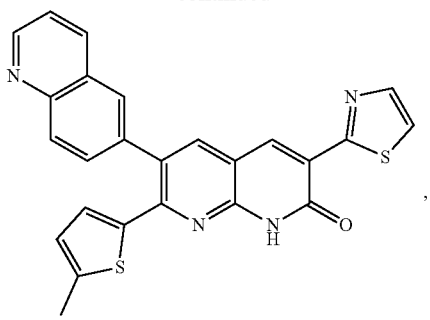
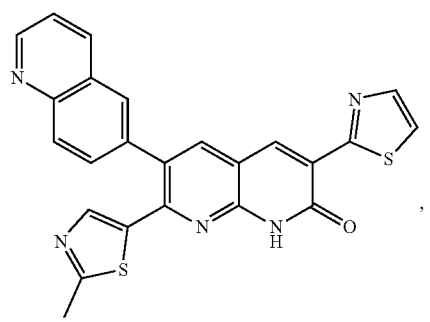
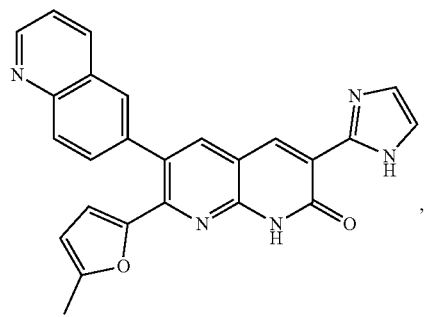
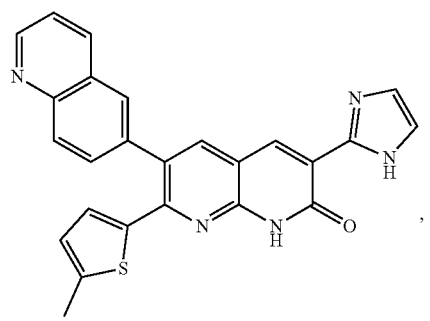
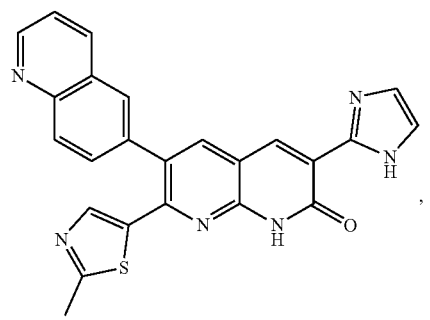
666
-continued
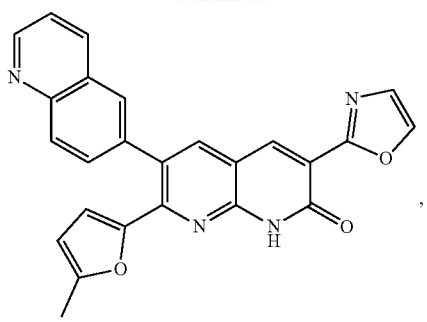
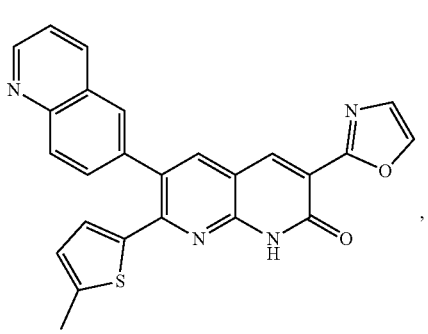
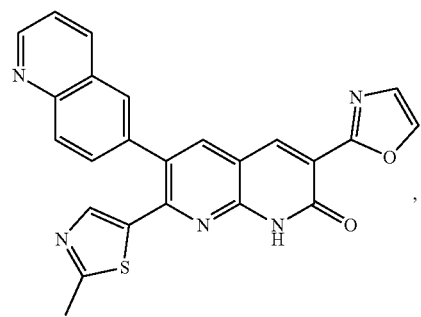
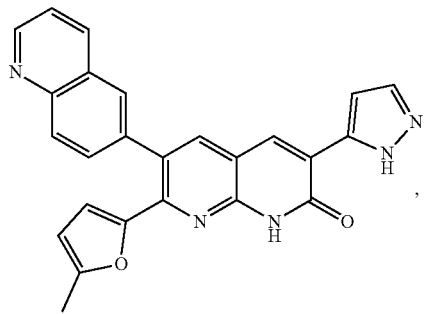
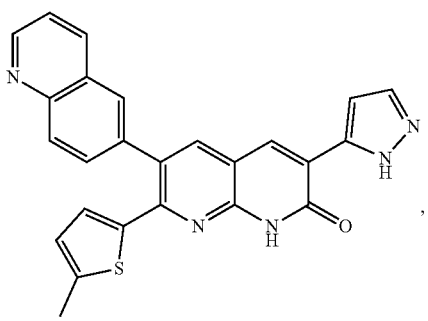

667
-continued
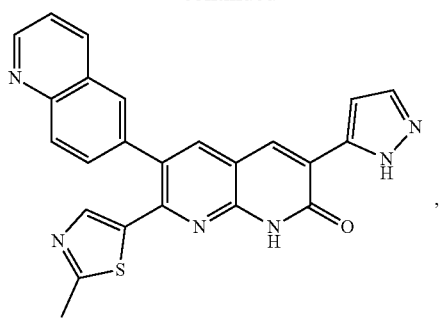
,
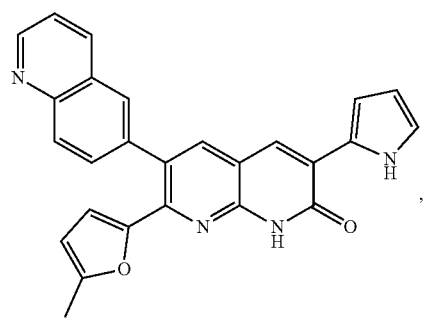
,
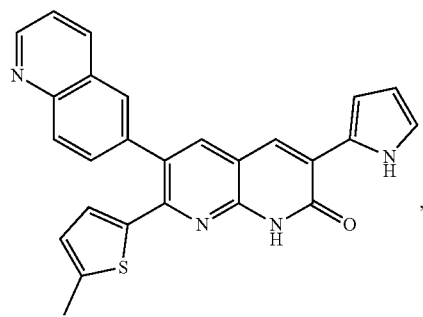
,
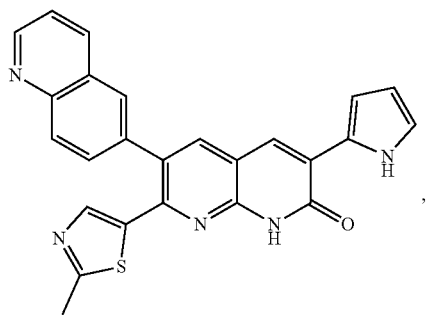
,
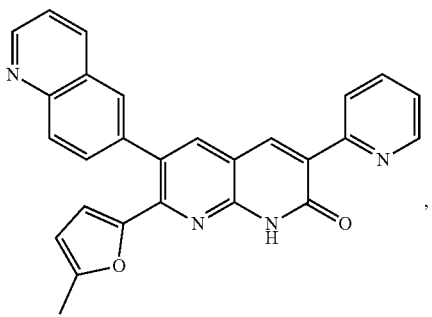
,
668
-continued
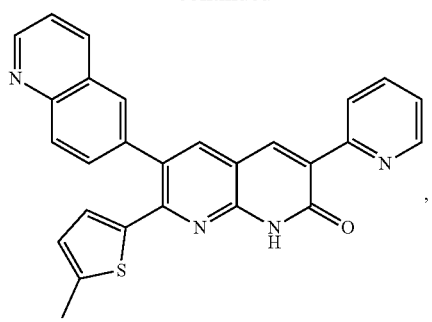
,
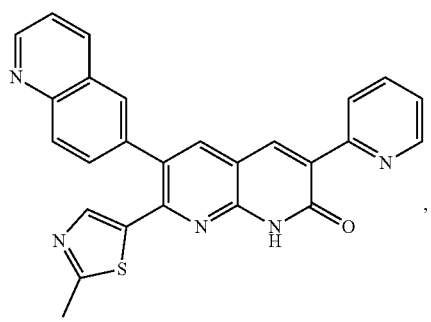
,
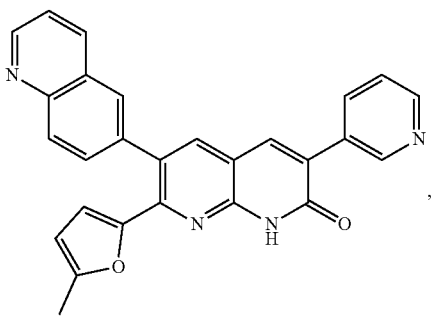
,
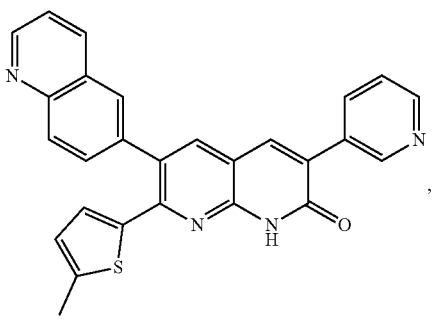
,
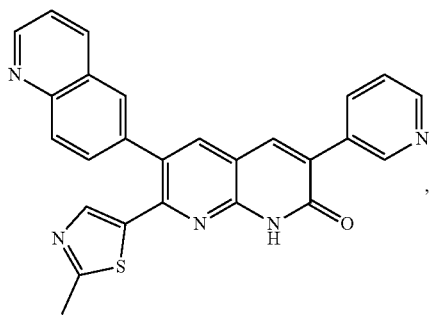
, 669
-continued
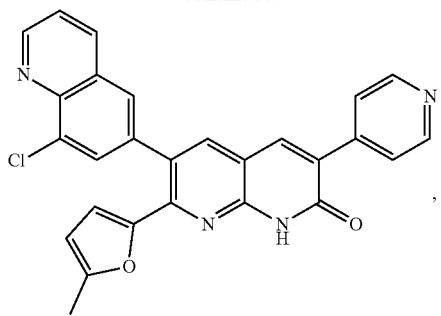
,
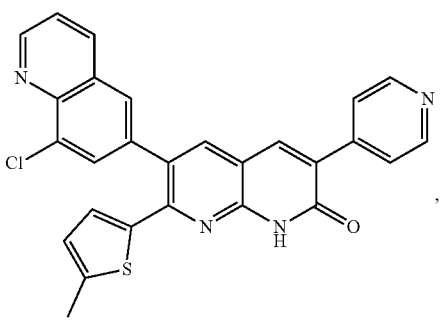
,
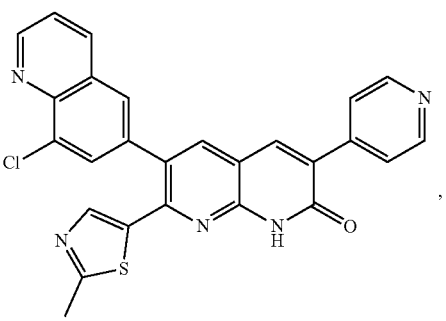
,
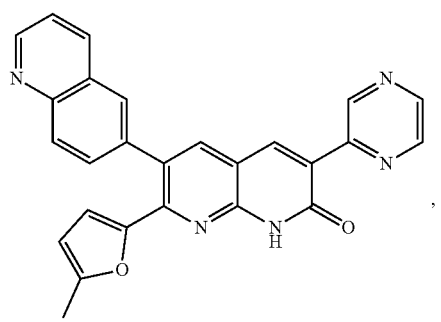
,
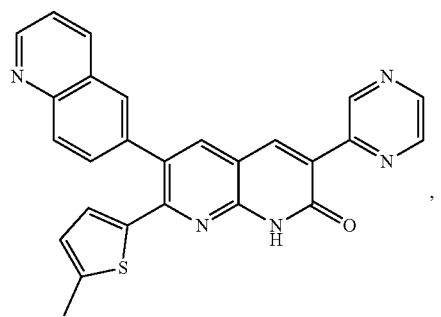
,
670
-continued
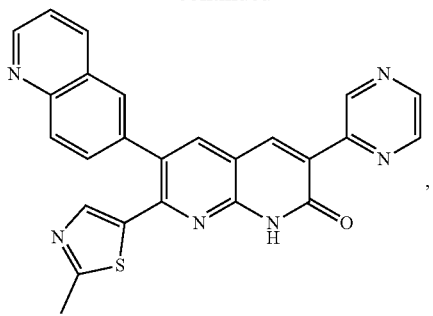
,
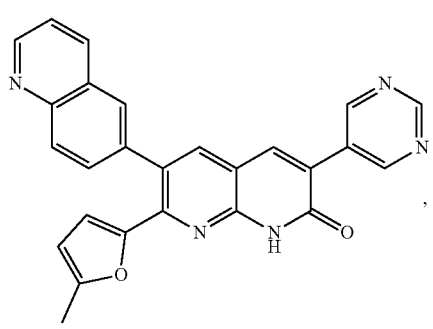
,
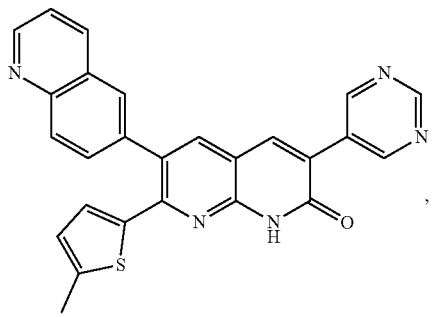
,
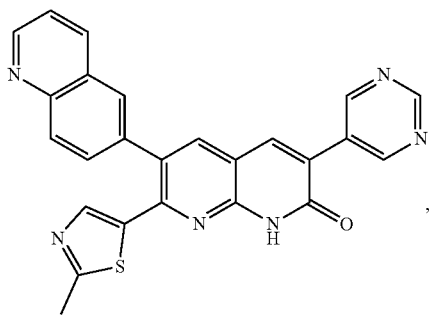
,
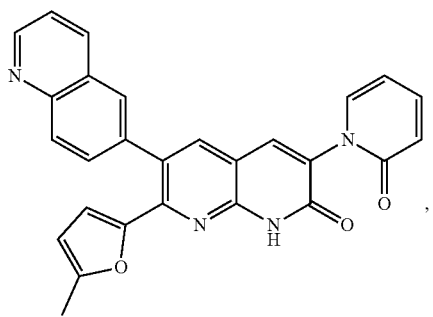
,

671
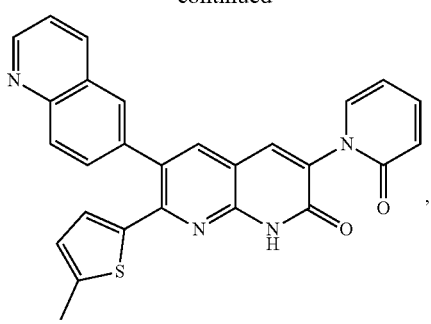,
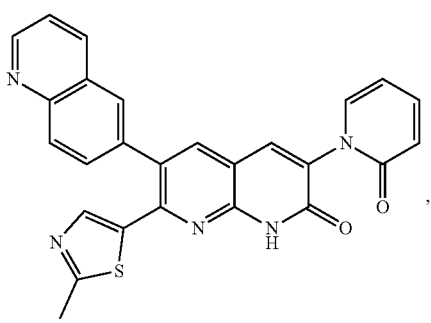,
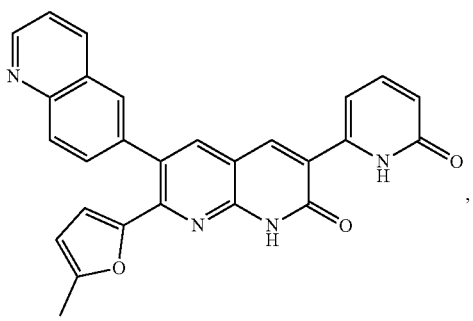,
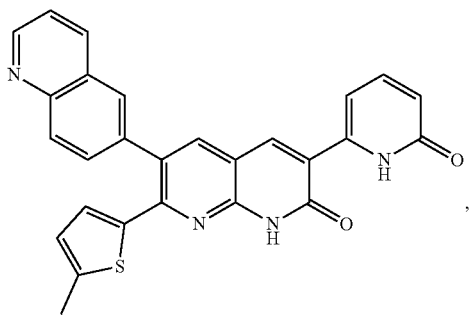,
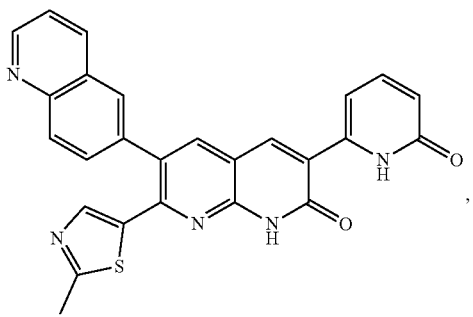,
672
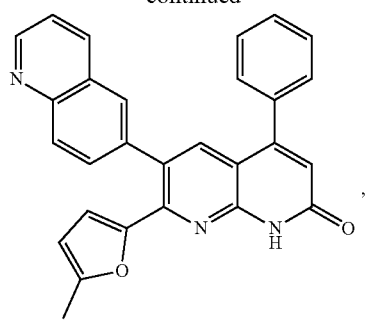,
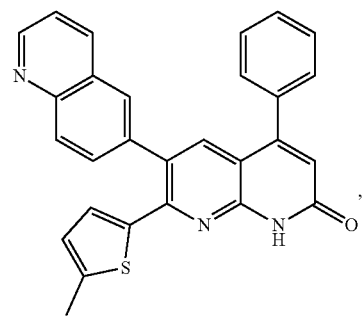,
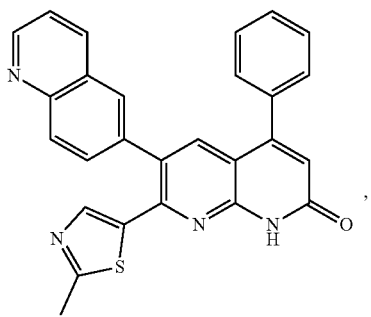,
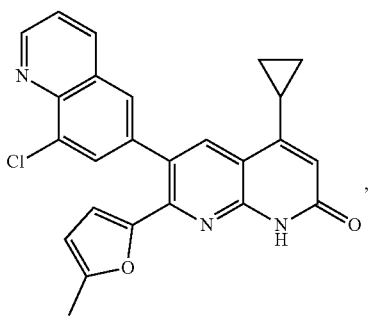,
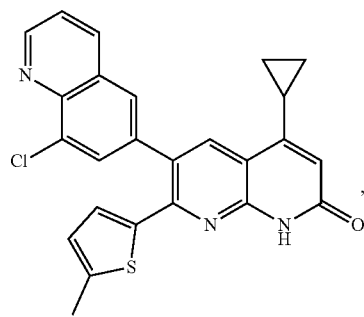,

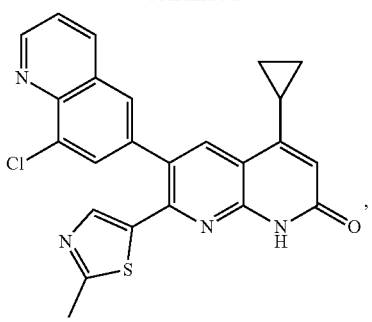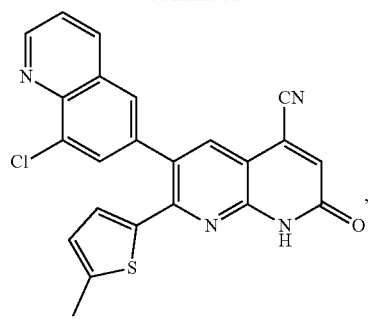

675 676
-continued -continued
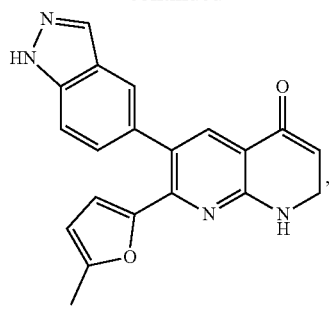
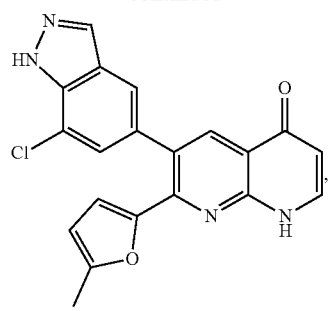

677
-continued
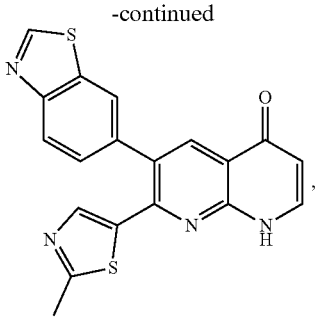
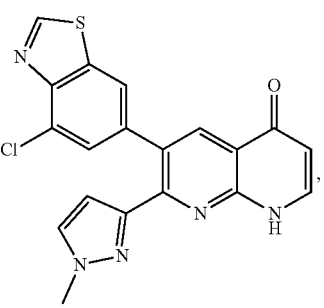
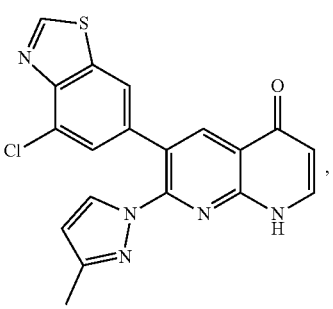
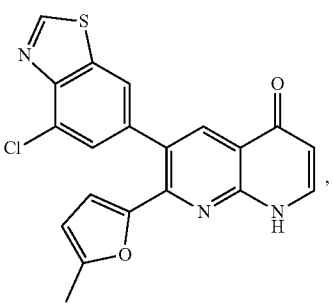
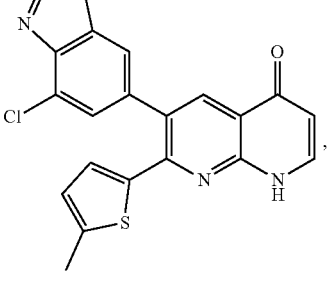
678
-continued
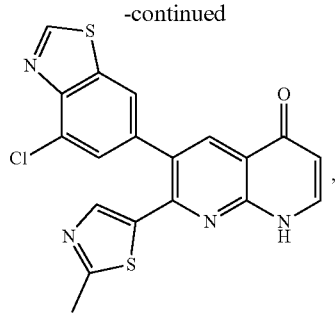
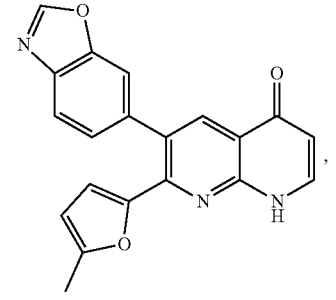
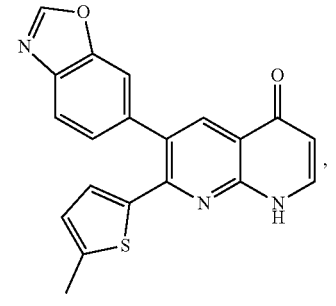
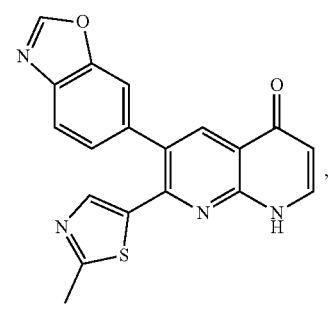
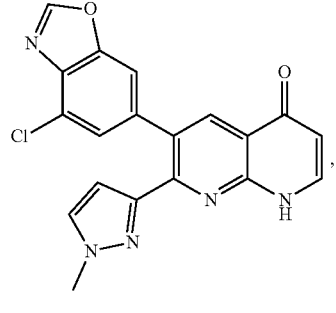

679
-continued
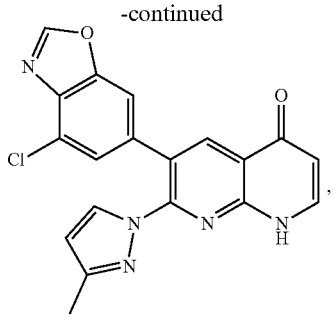
,
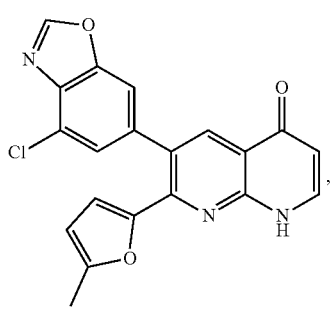
,
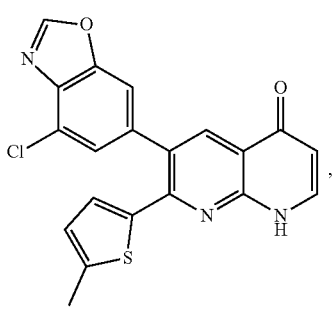
,
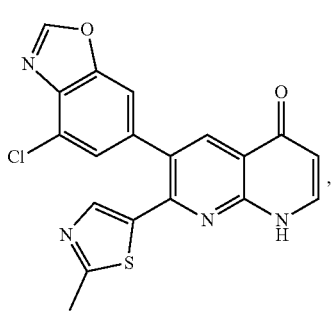
,
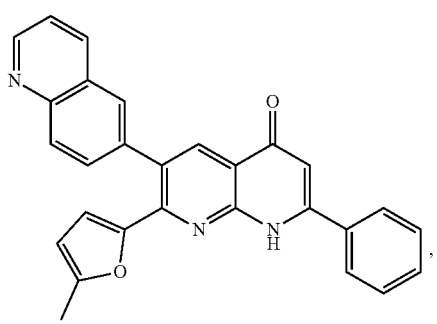
,
680
-continued
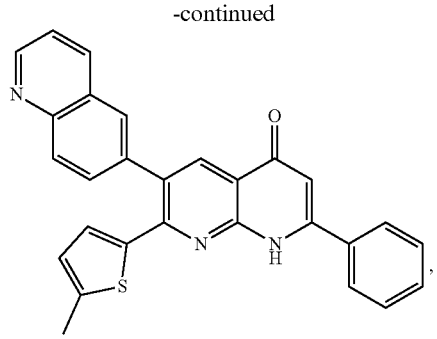
,
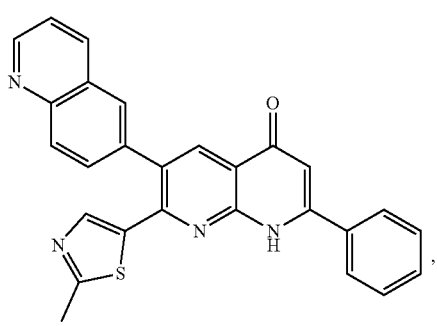
,
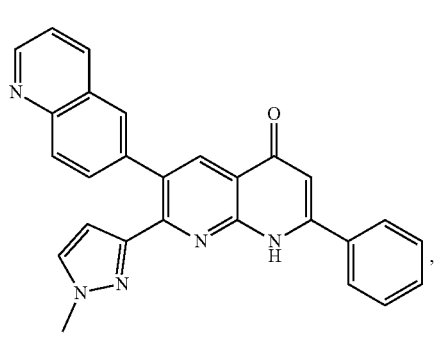
,
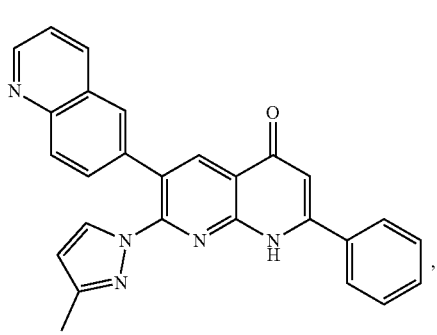
,
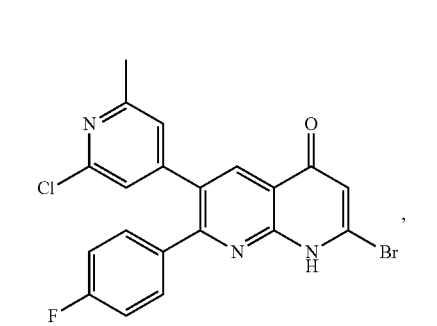
,

681
-continued
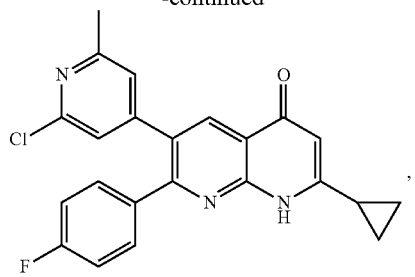
,
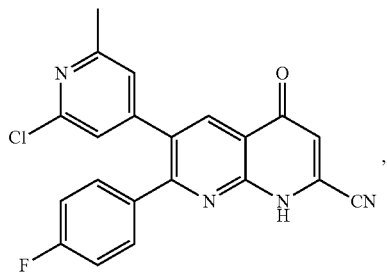
,
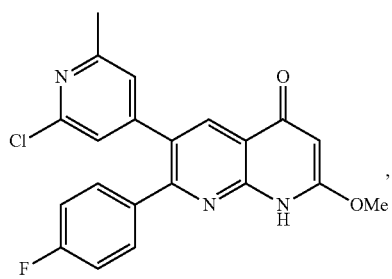
,
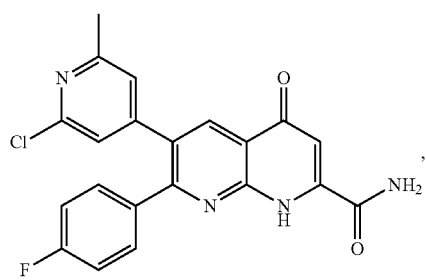
,
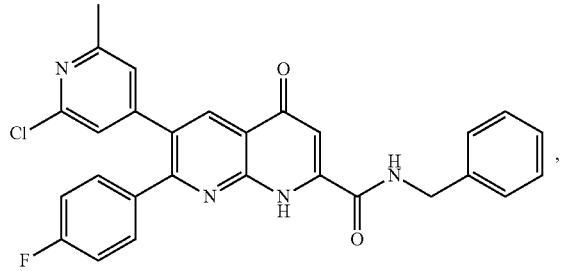
,
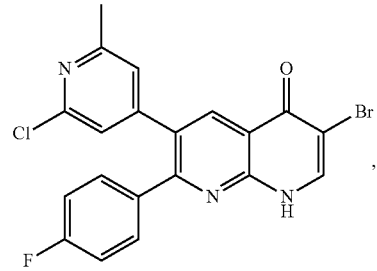
,
682
-continued
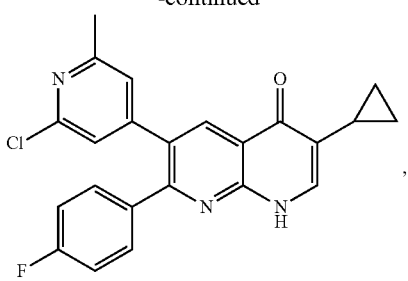
,
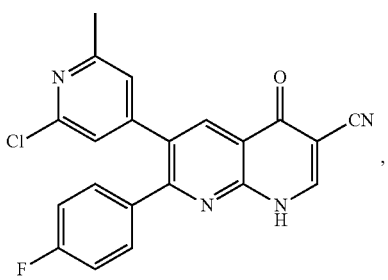
,
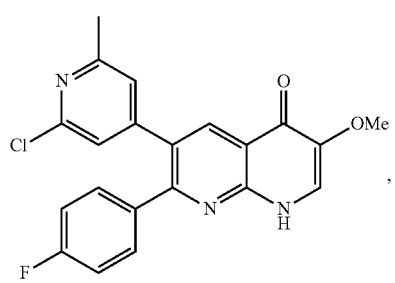
,
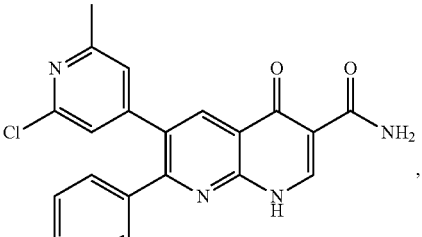
,
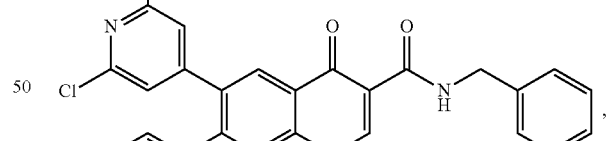
,
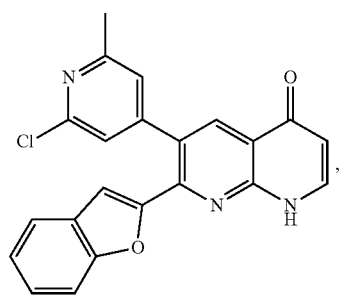
, 683
-continued
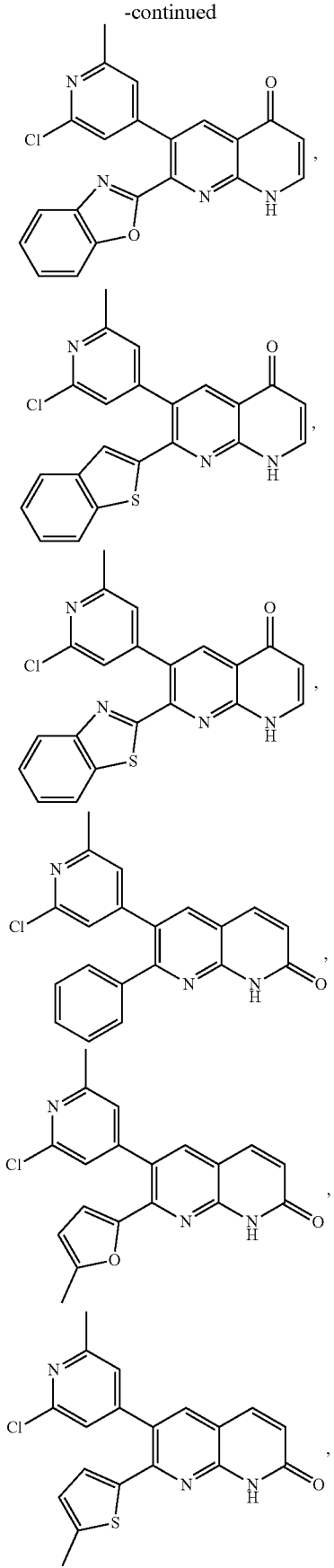
684
-continued
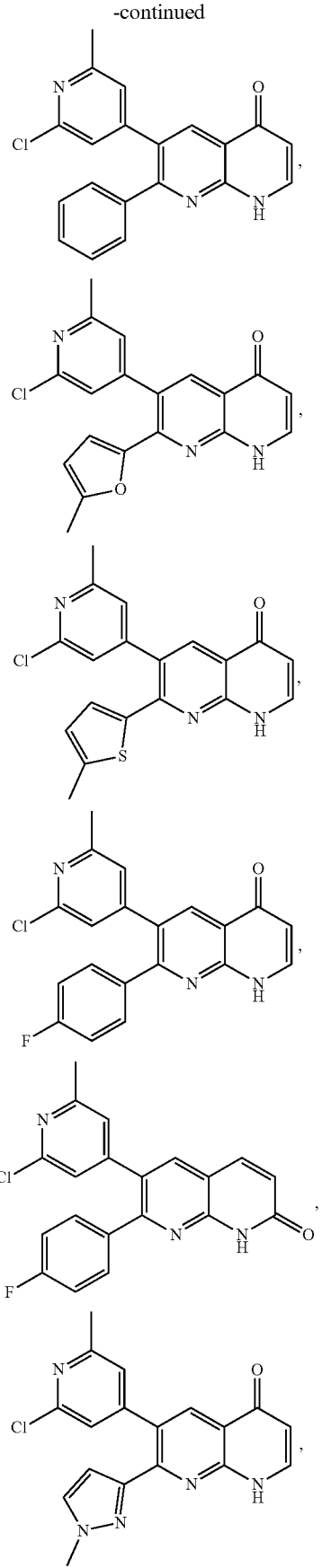

-continued
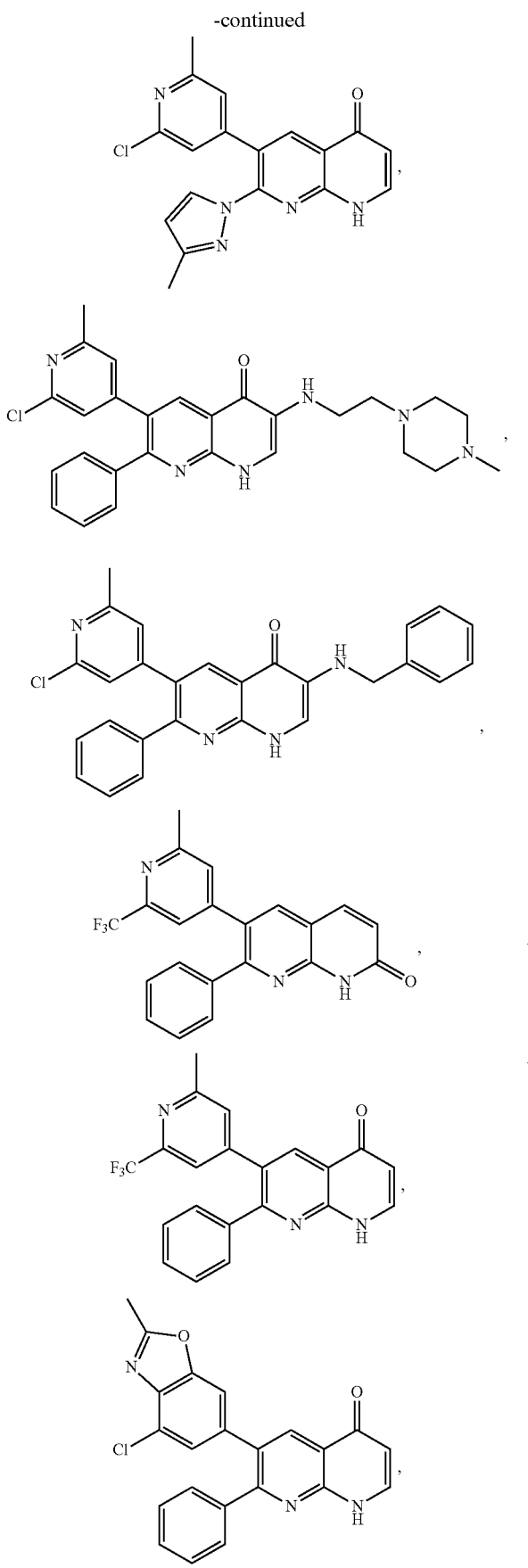
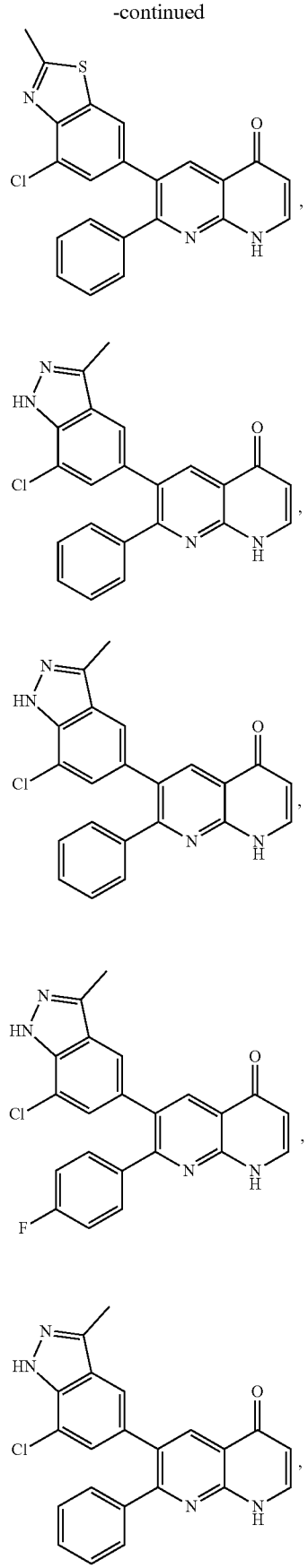

687
-continued
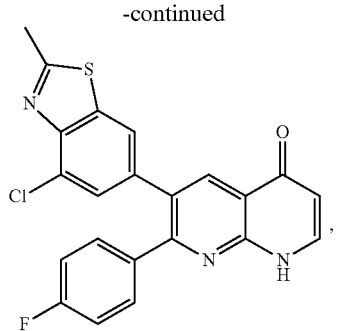
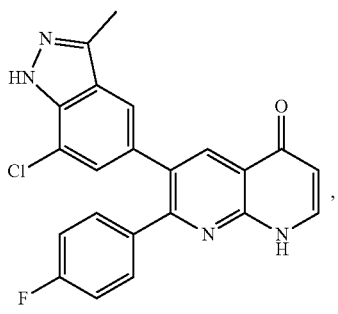
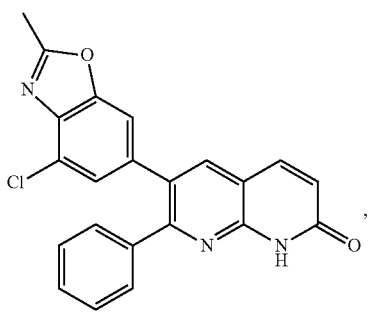
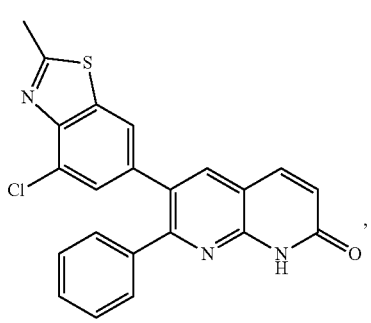
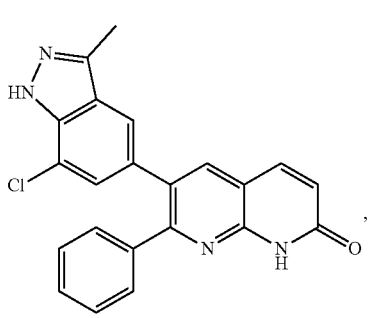
688
-continued
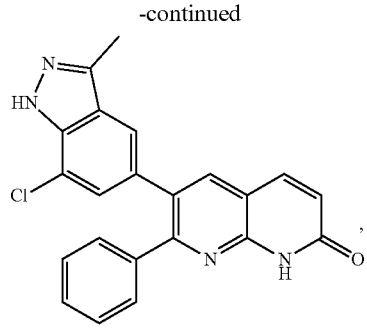
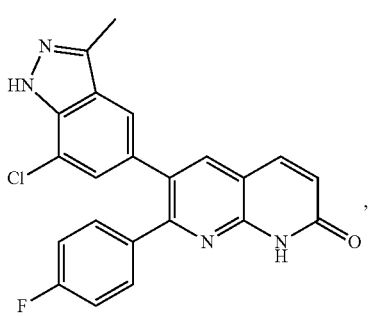
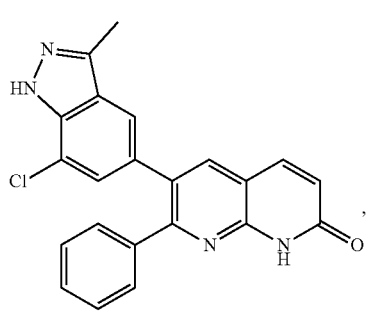
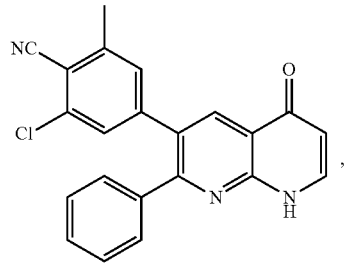
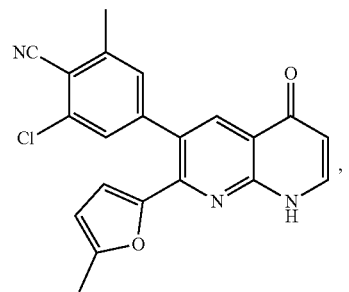

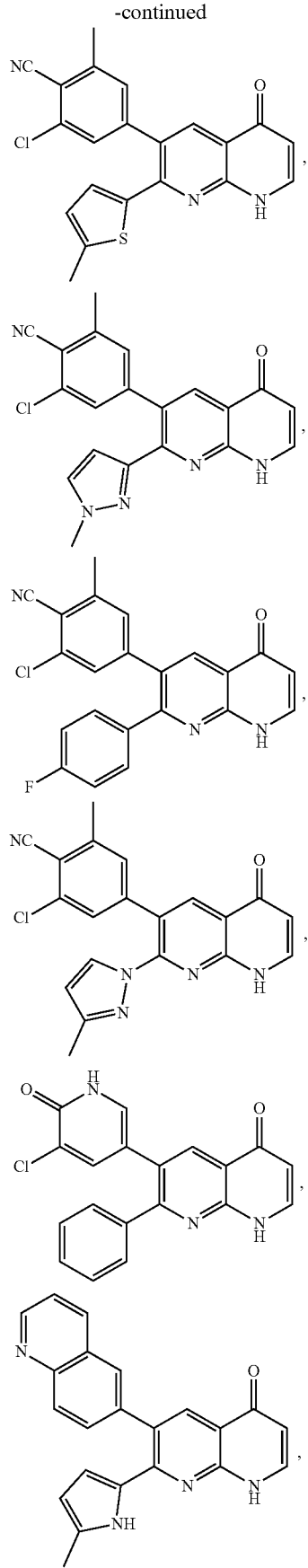
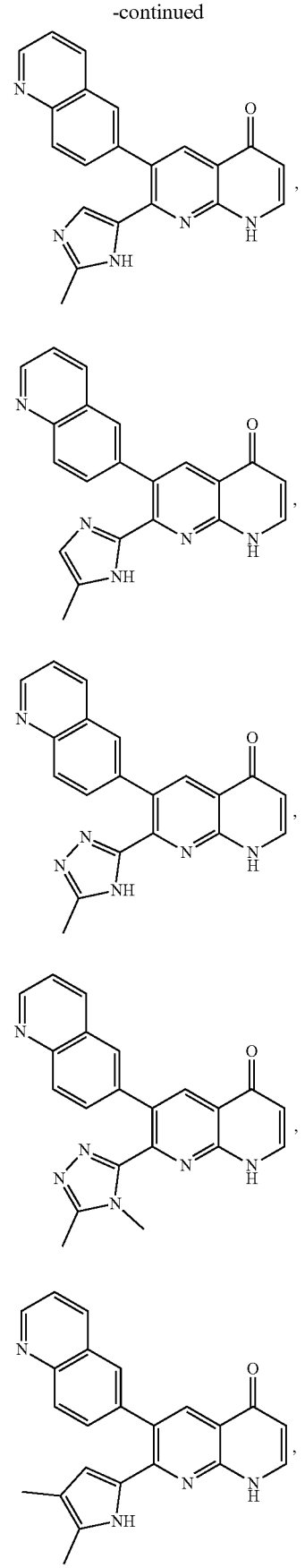

691
-continued
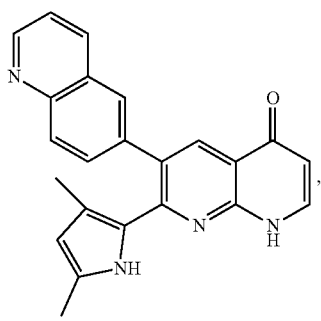,
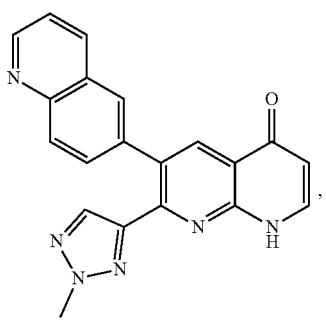,
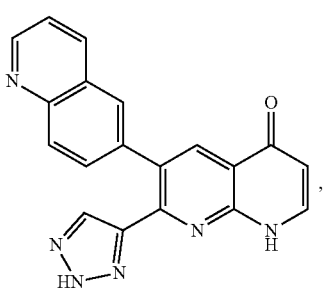,
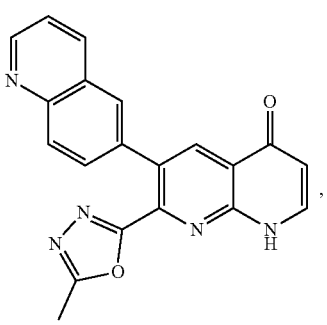,
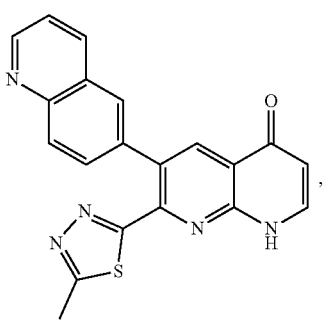,
692
-continued
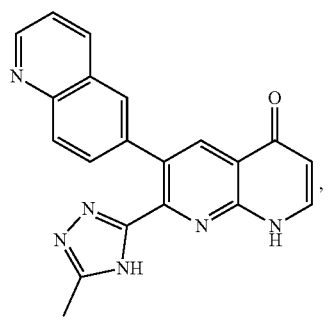,
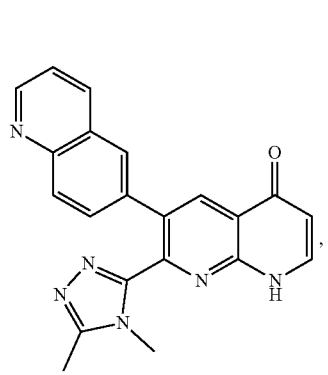,
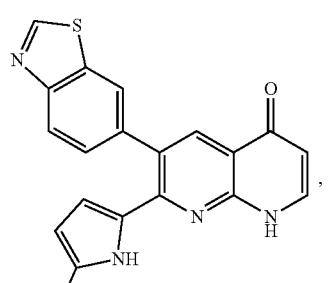,
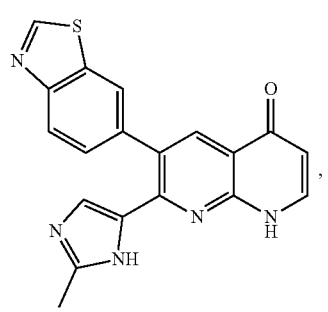,
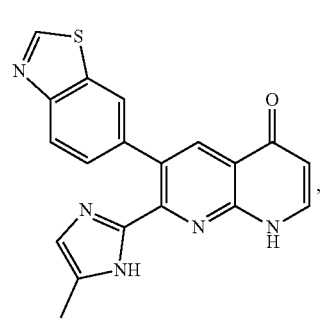, -continued
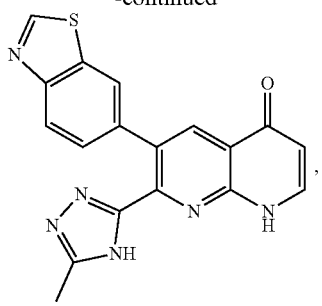
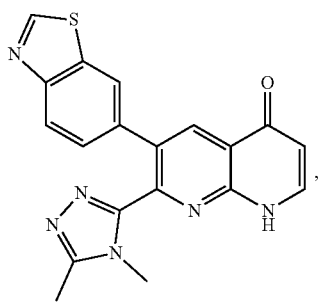
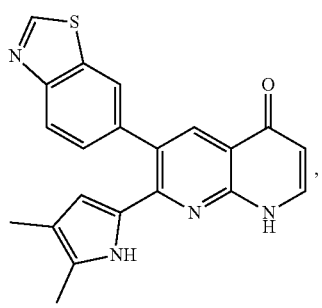
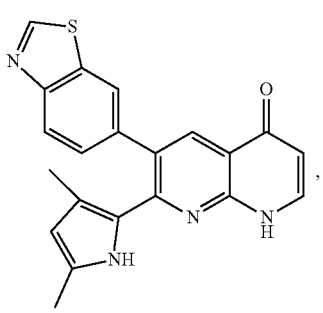
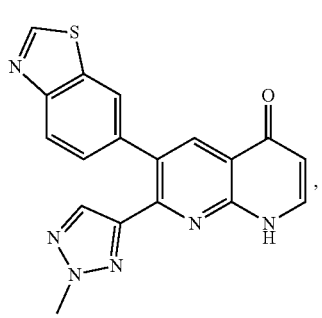
-continued
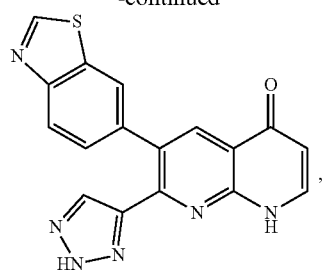
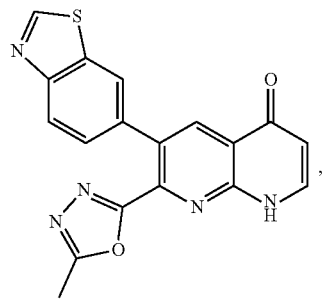
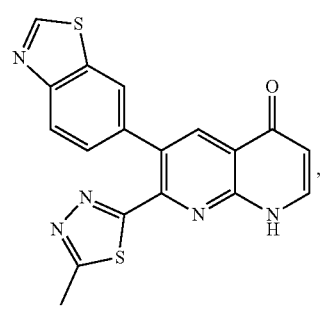
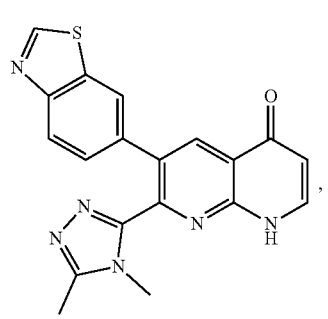

695
-continued
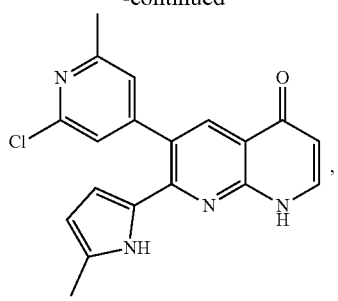
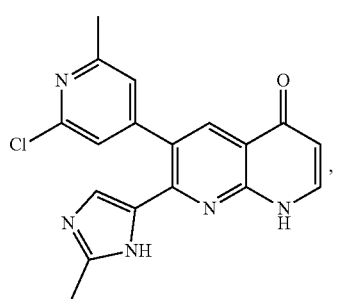
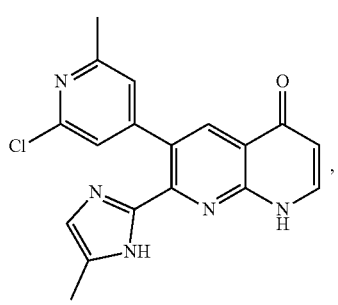
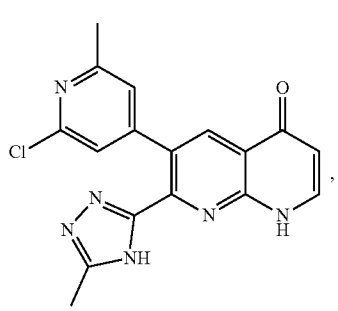
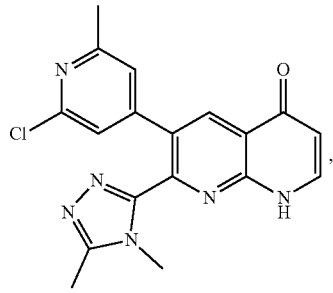
696
-continued
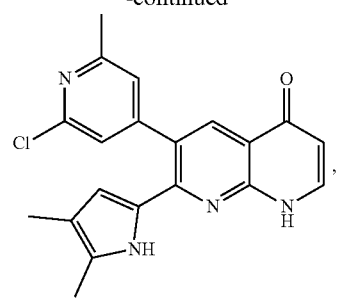
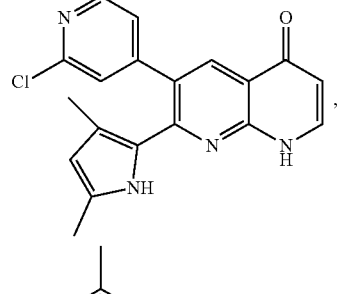
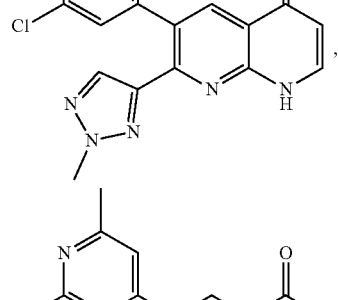
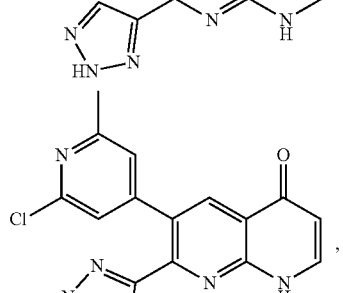
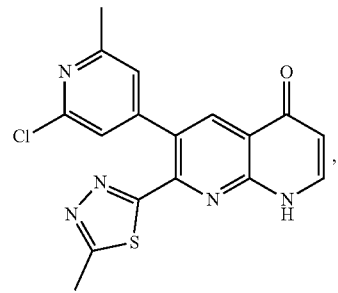

697
-continued
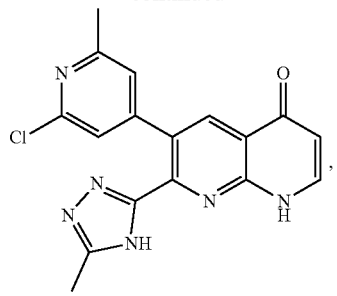
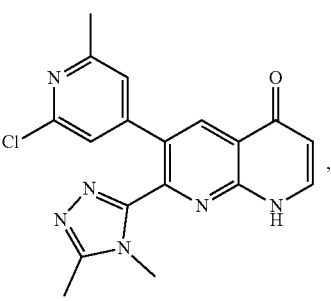
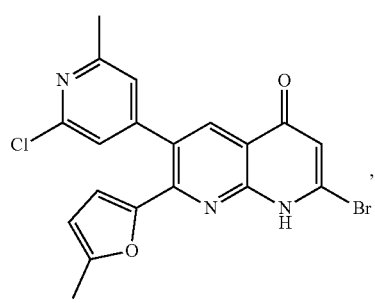
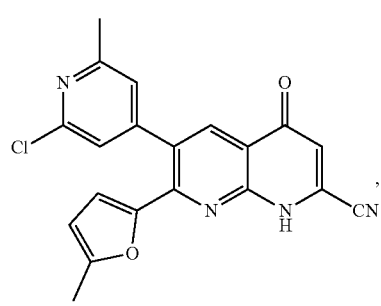
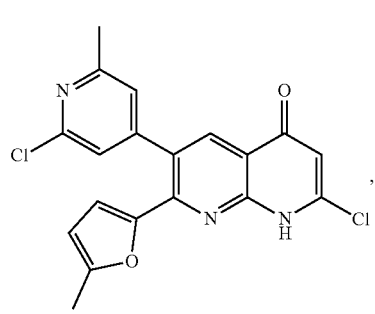
698
-continued
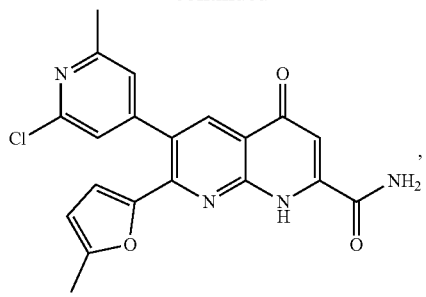
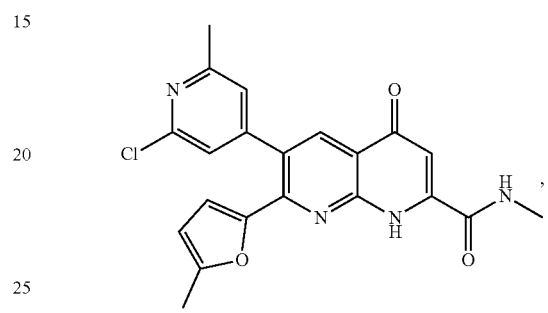
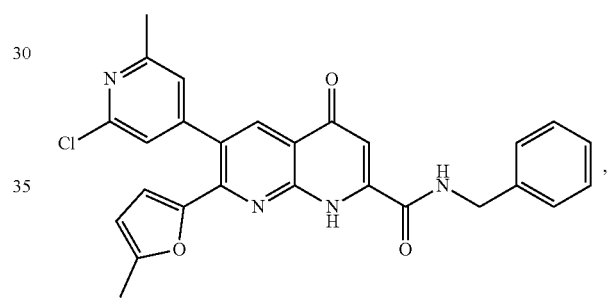
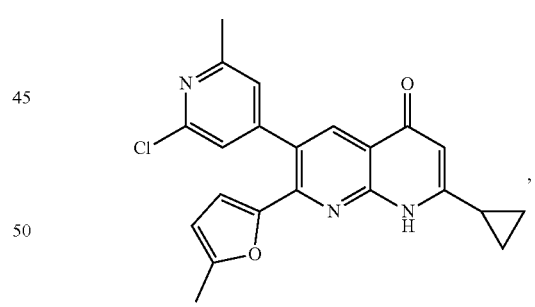
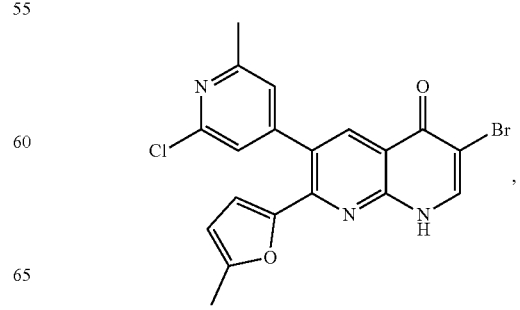

699
-continued
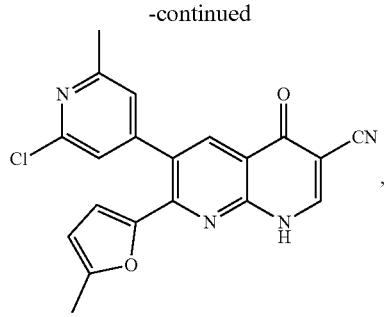
,
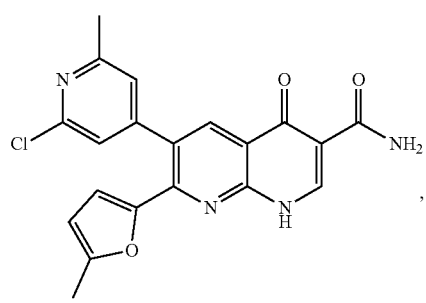
,
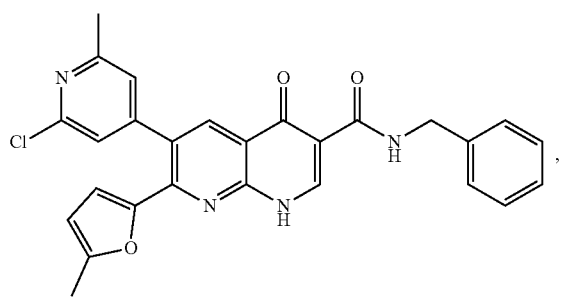
,
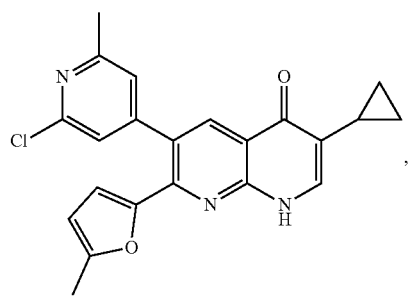
,
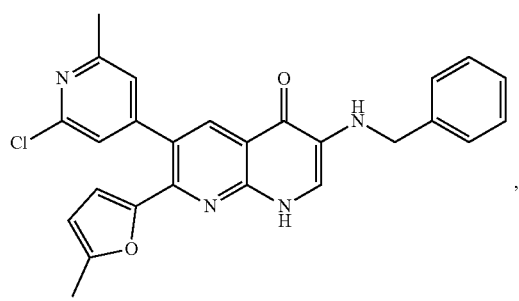
,
700
-continued
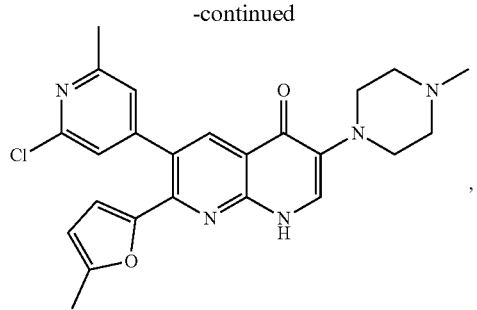
,
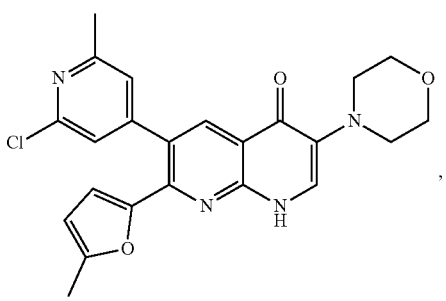
,
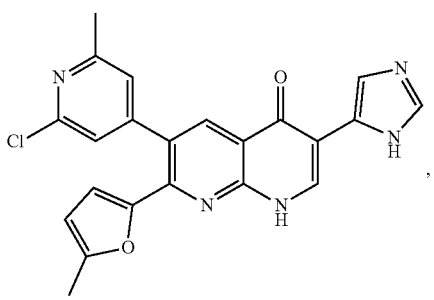
,
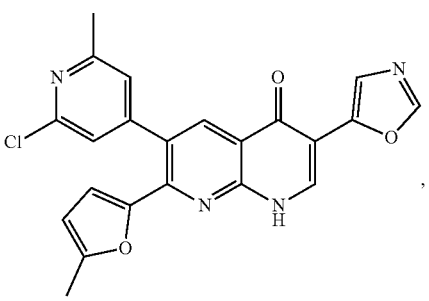
,
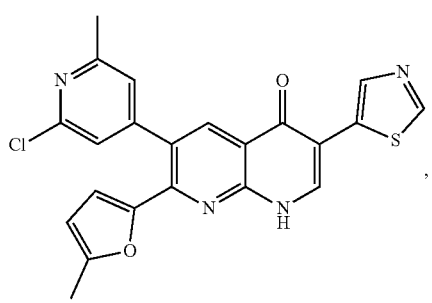
, 701
-continued
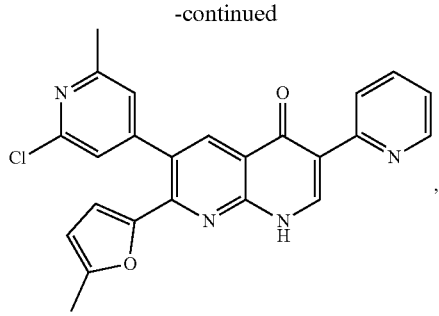,
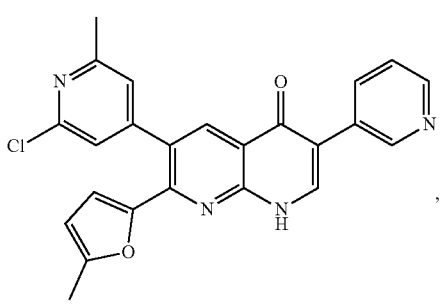,
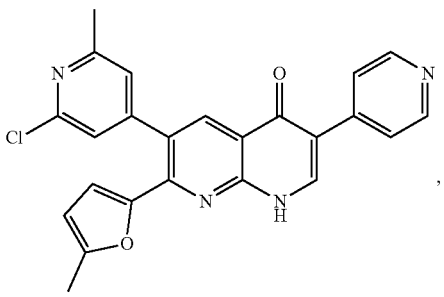,
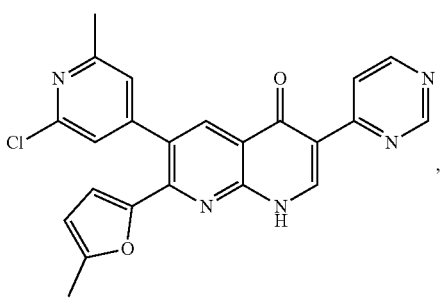,
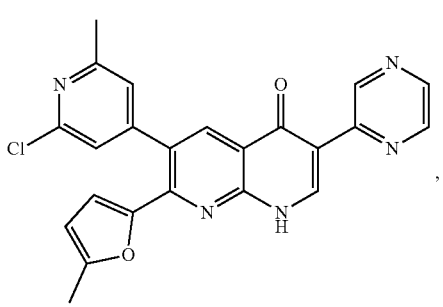,
702
-continued
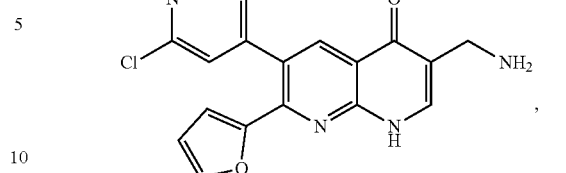,
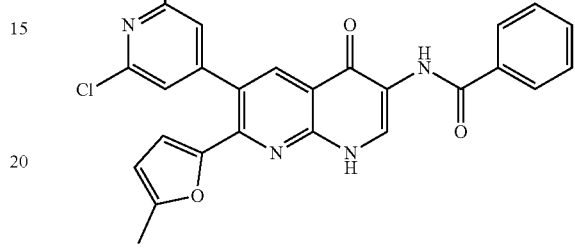,
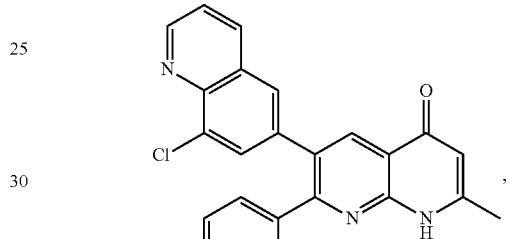,
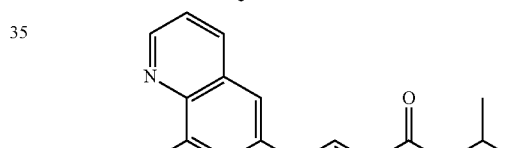,
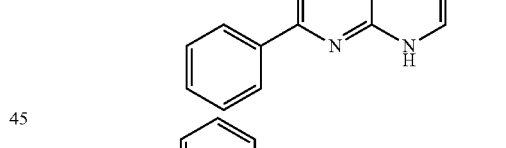,
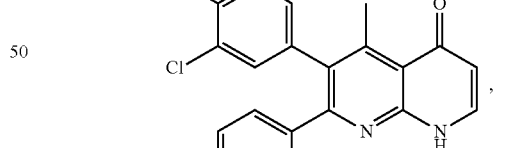, 703
-continued
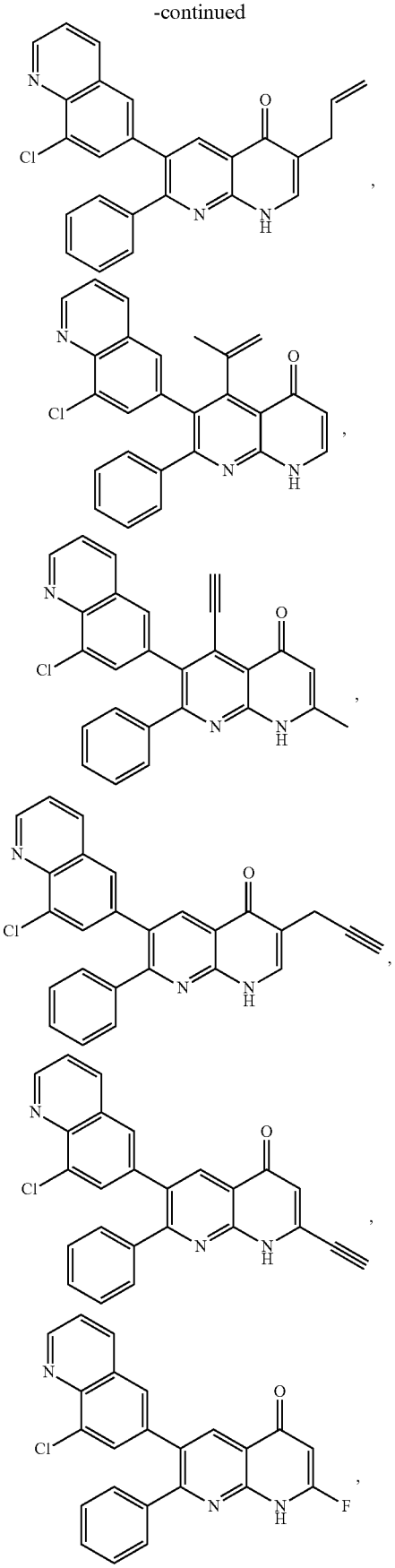
704
-continued
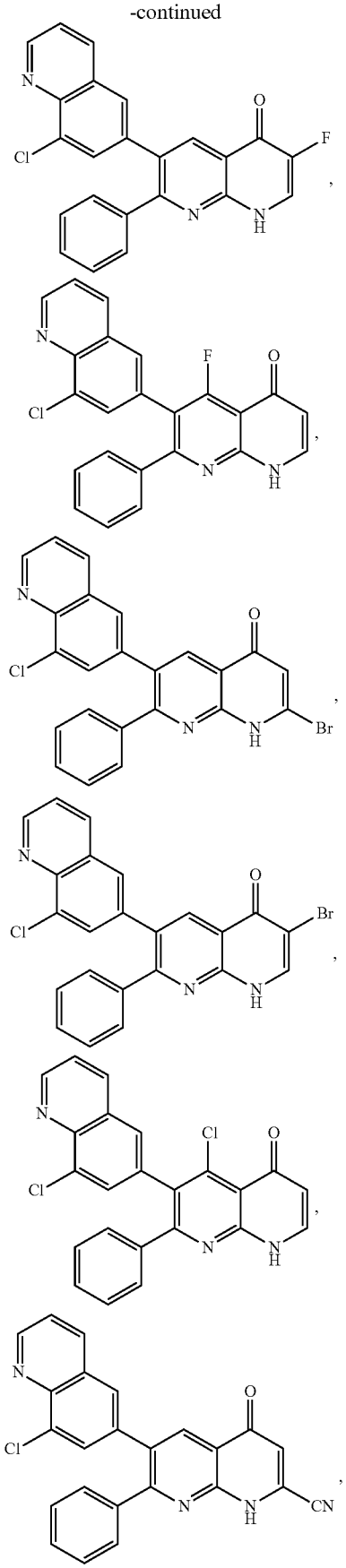

705
-continued
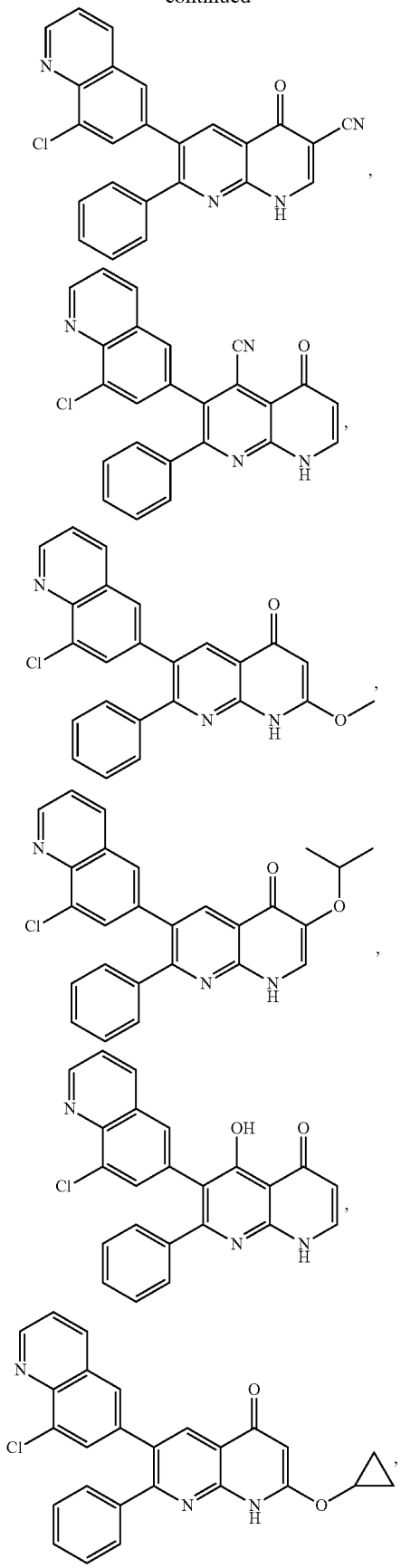
706
-continued
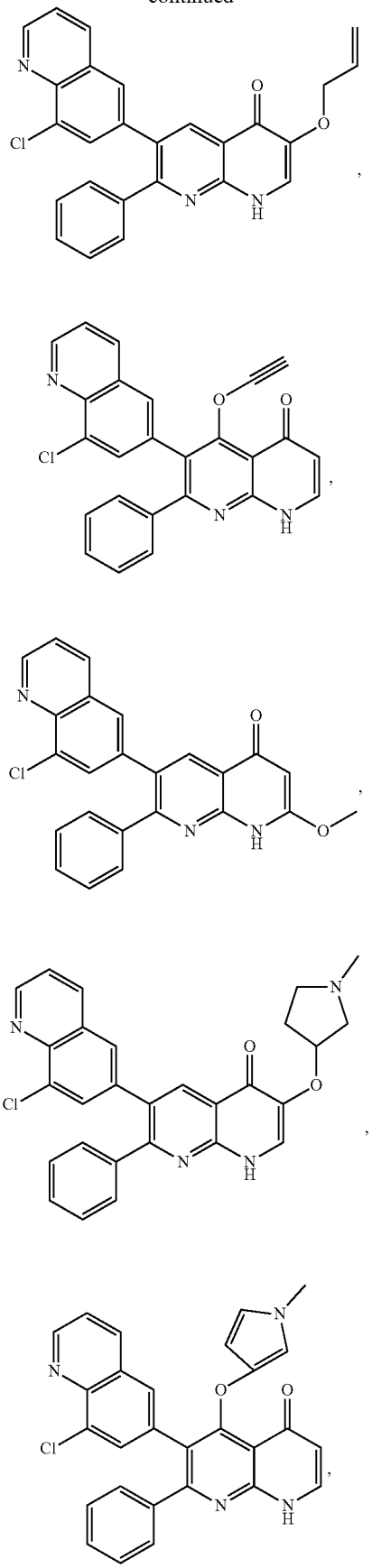

707
-continued
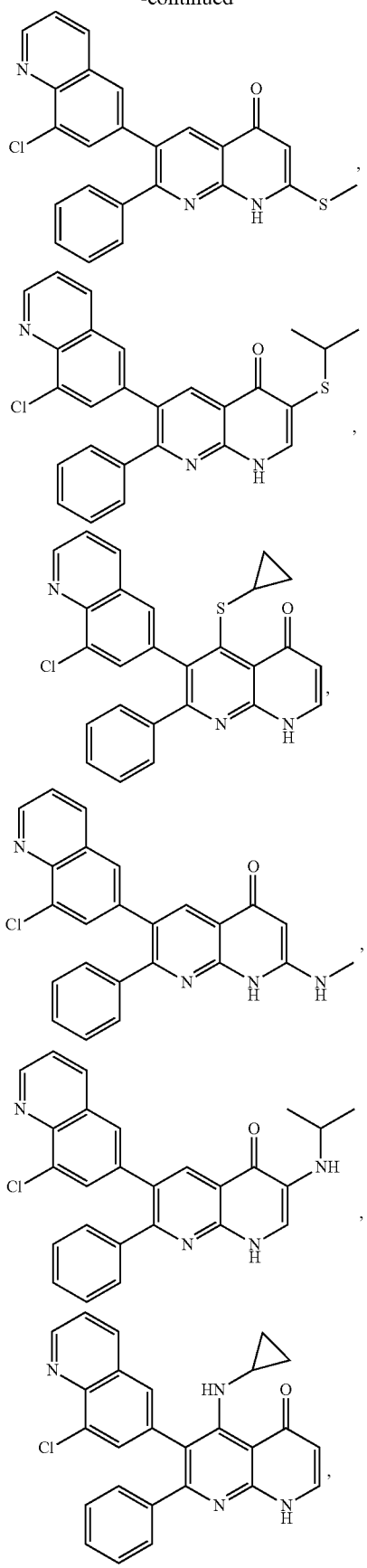
708
-continued
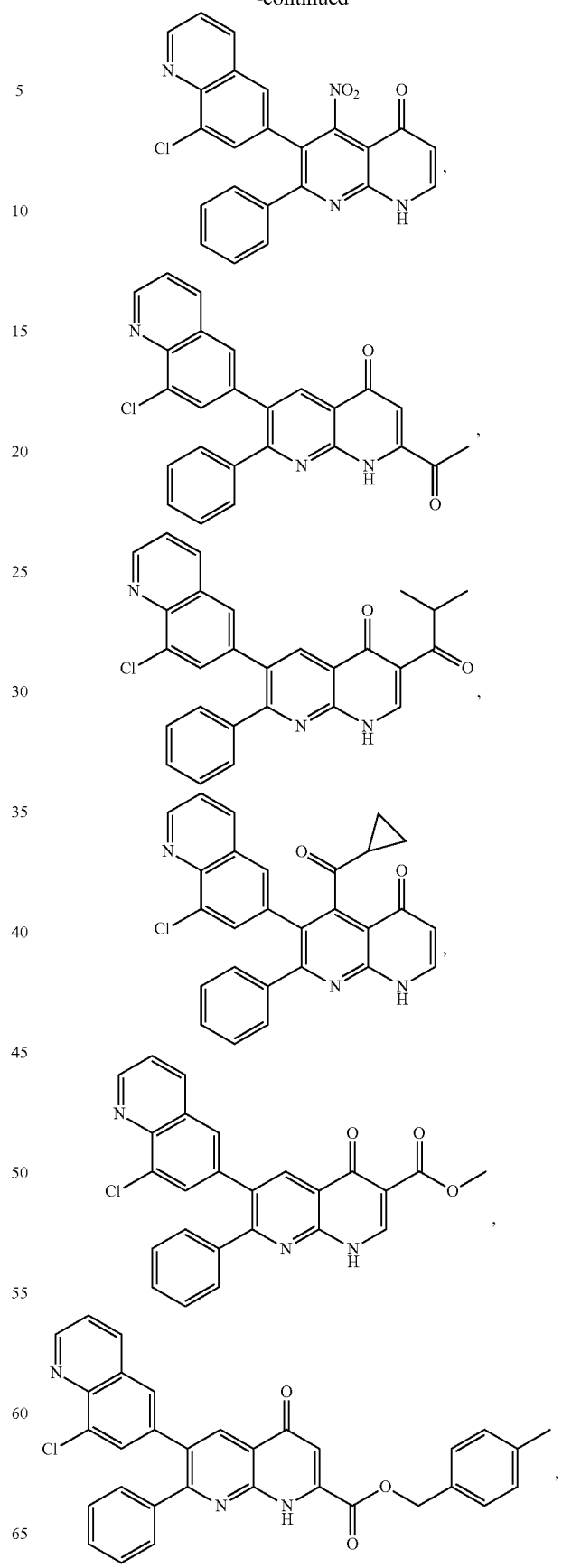

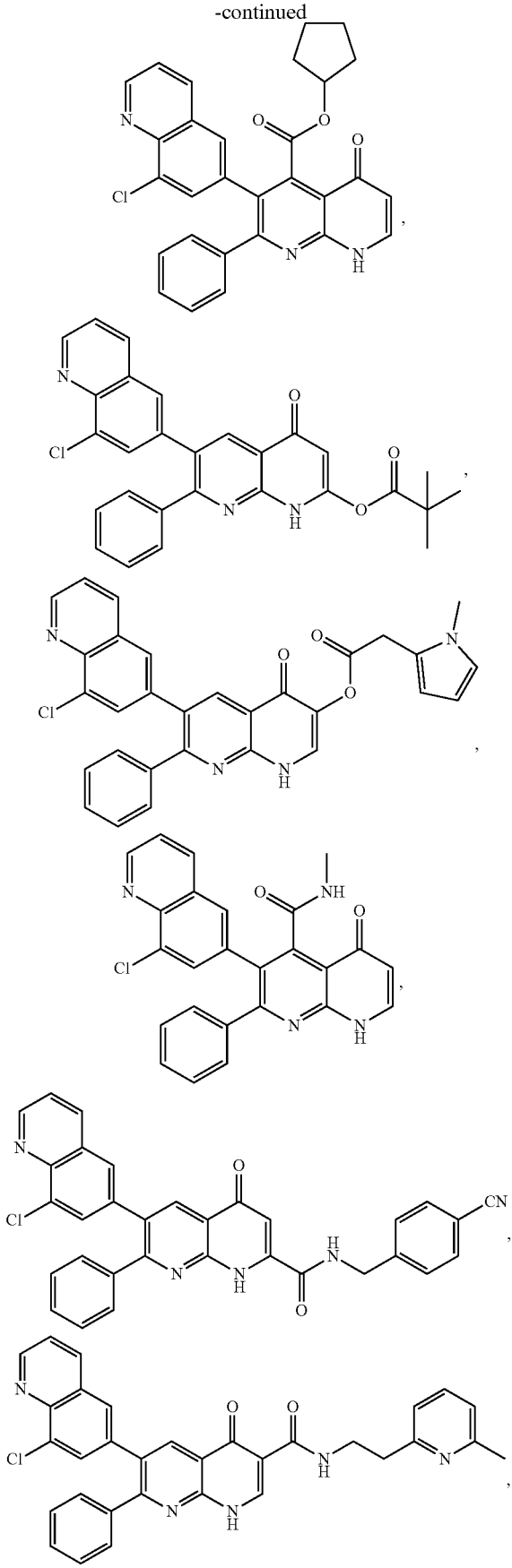
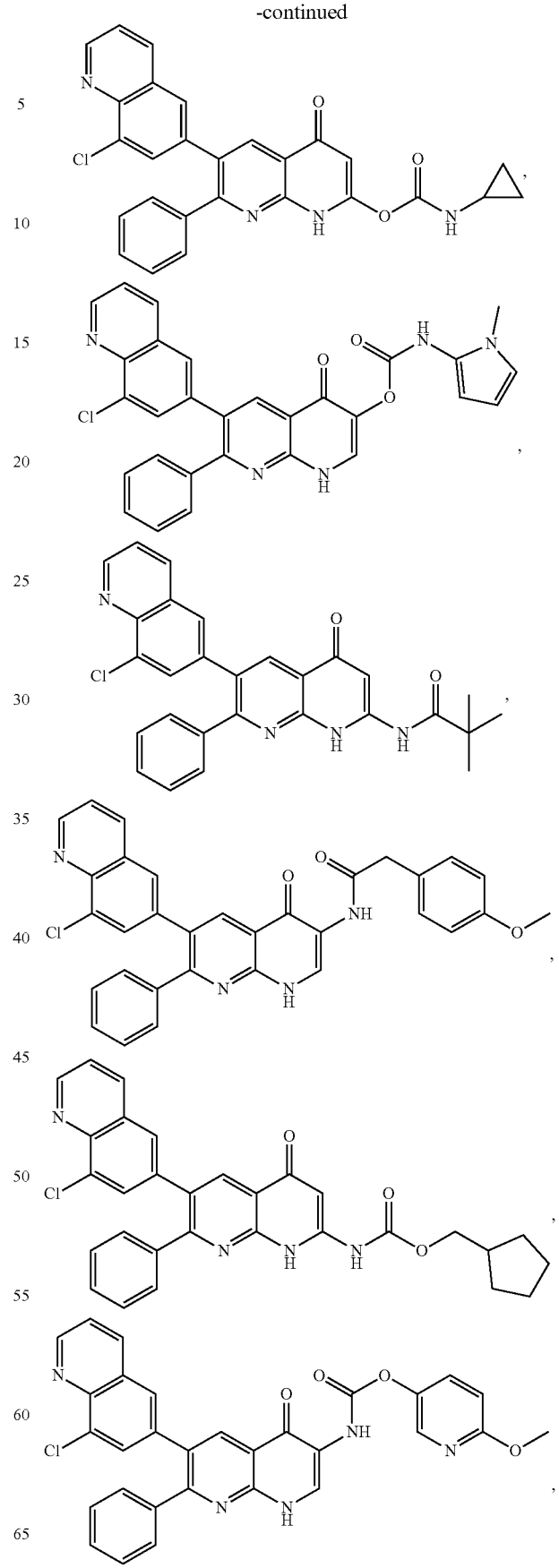

711
-continued
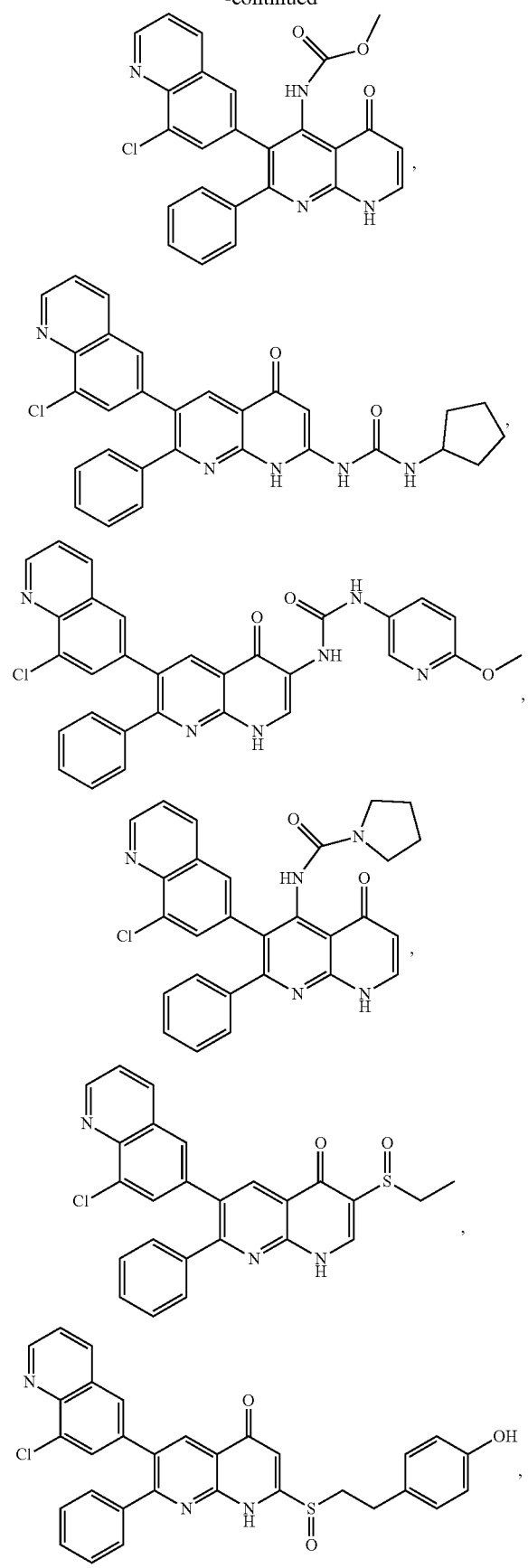
712
-continued
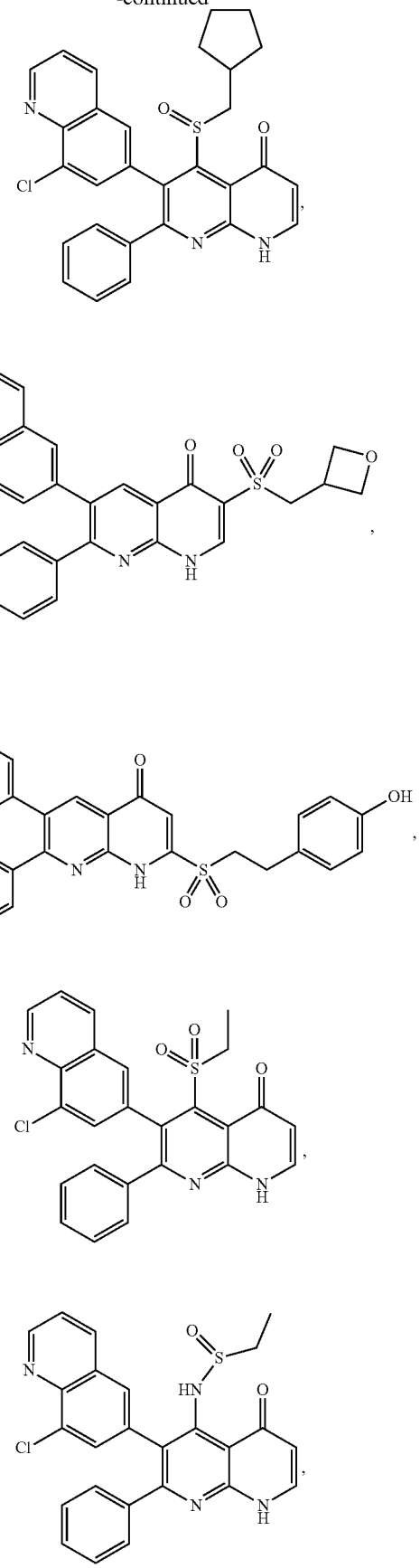

713
-continued
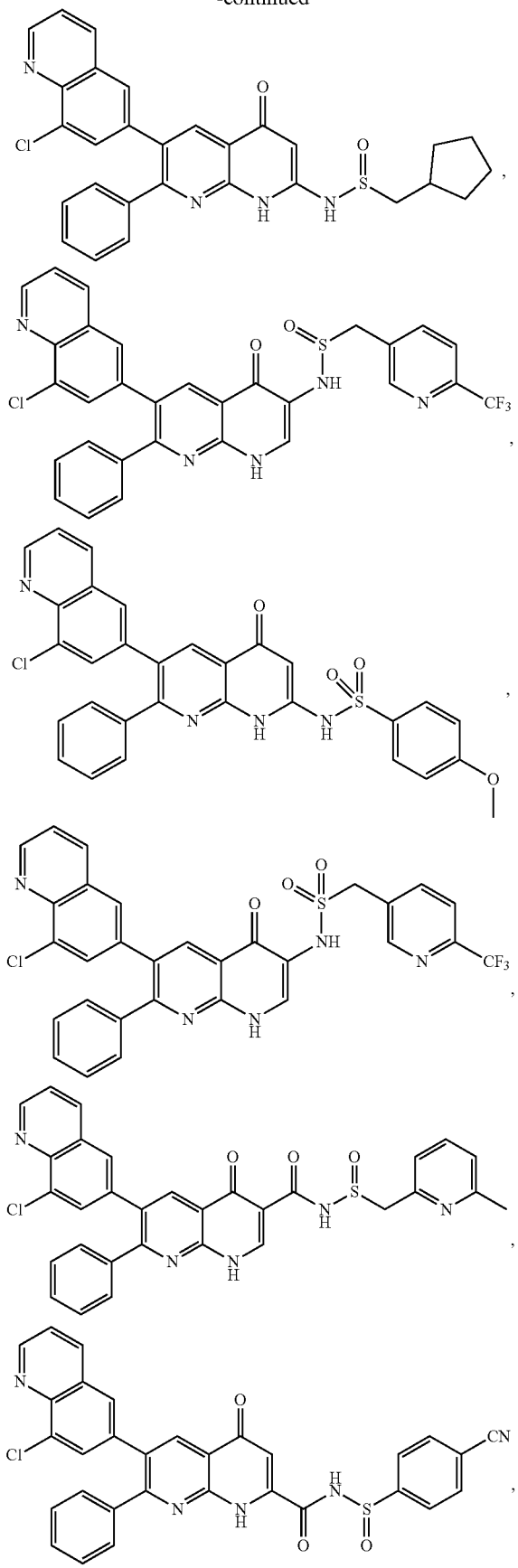
714
-continued
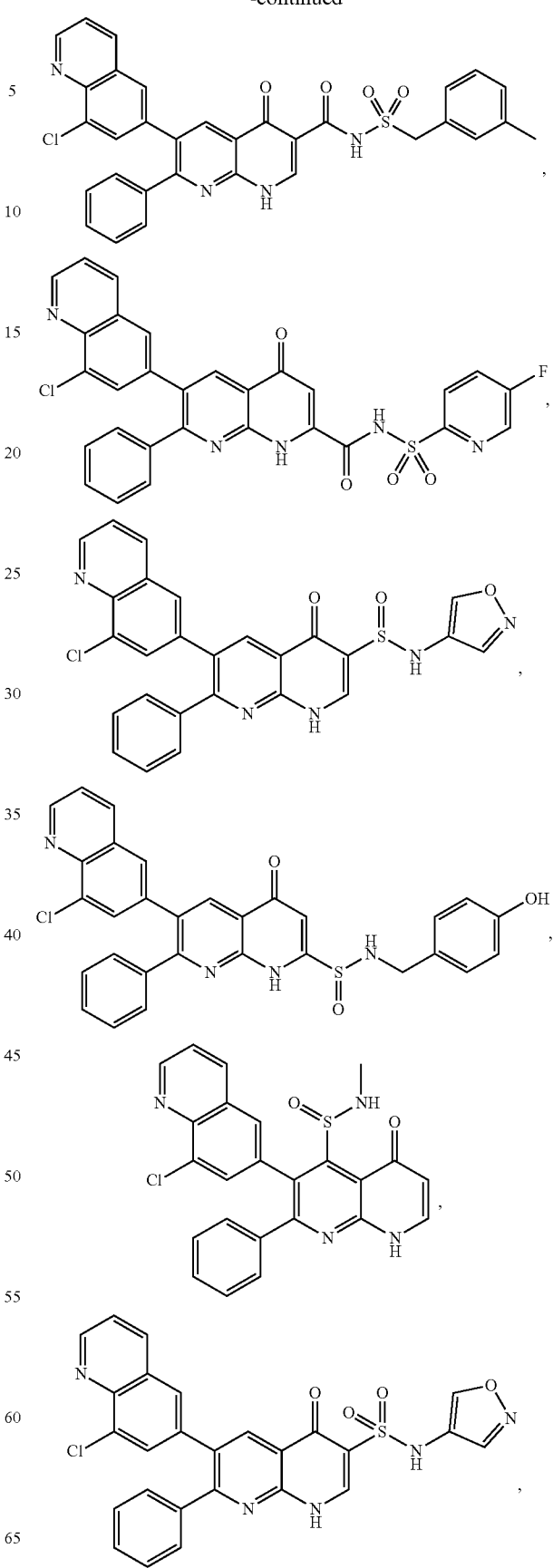

715
-continued
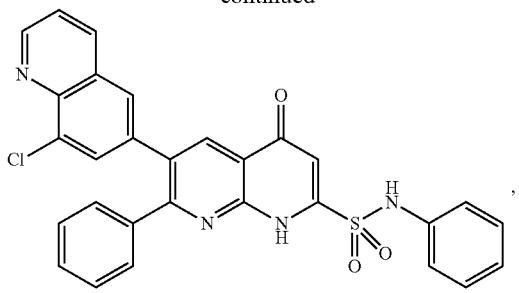
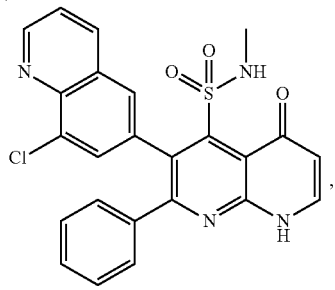
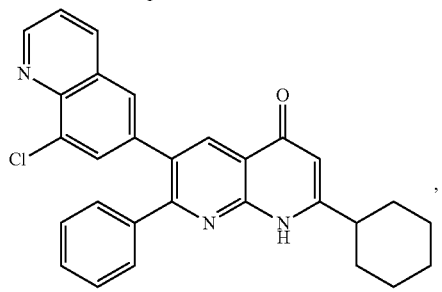
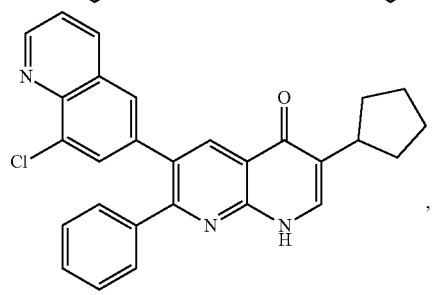
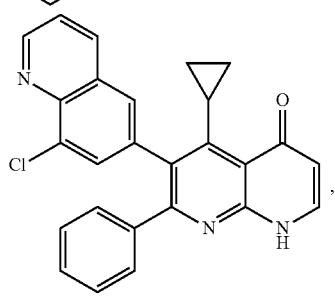
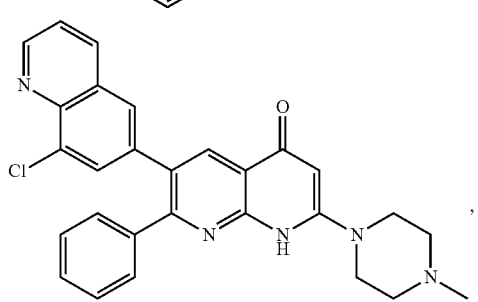
716
-continued
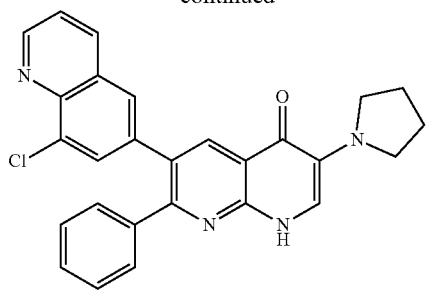
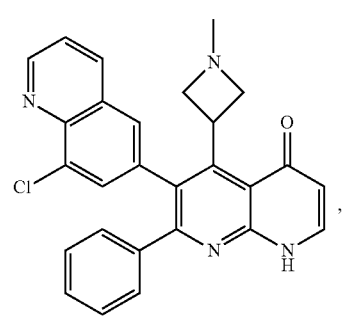
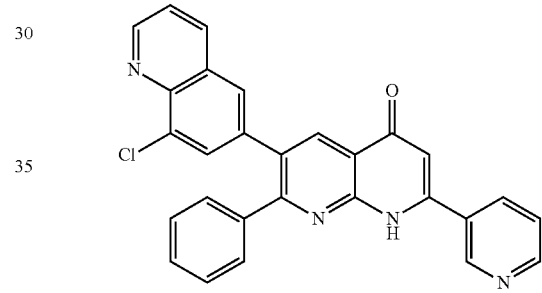
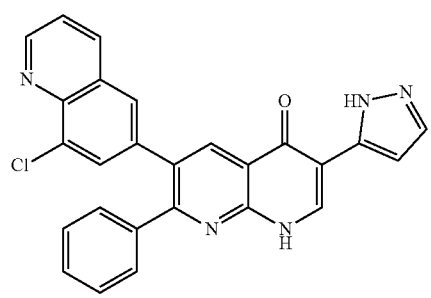
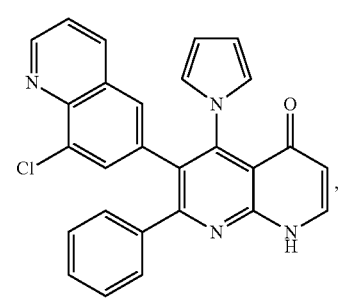

717
-continued
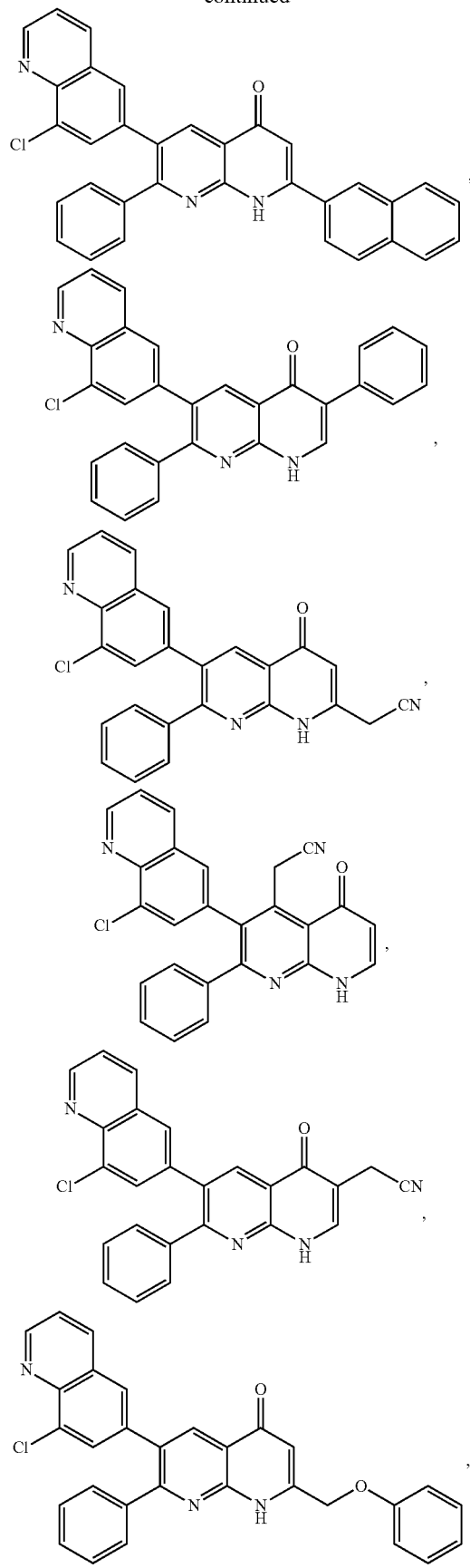
718
-continued
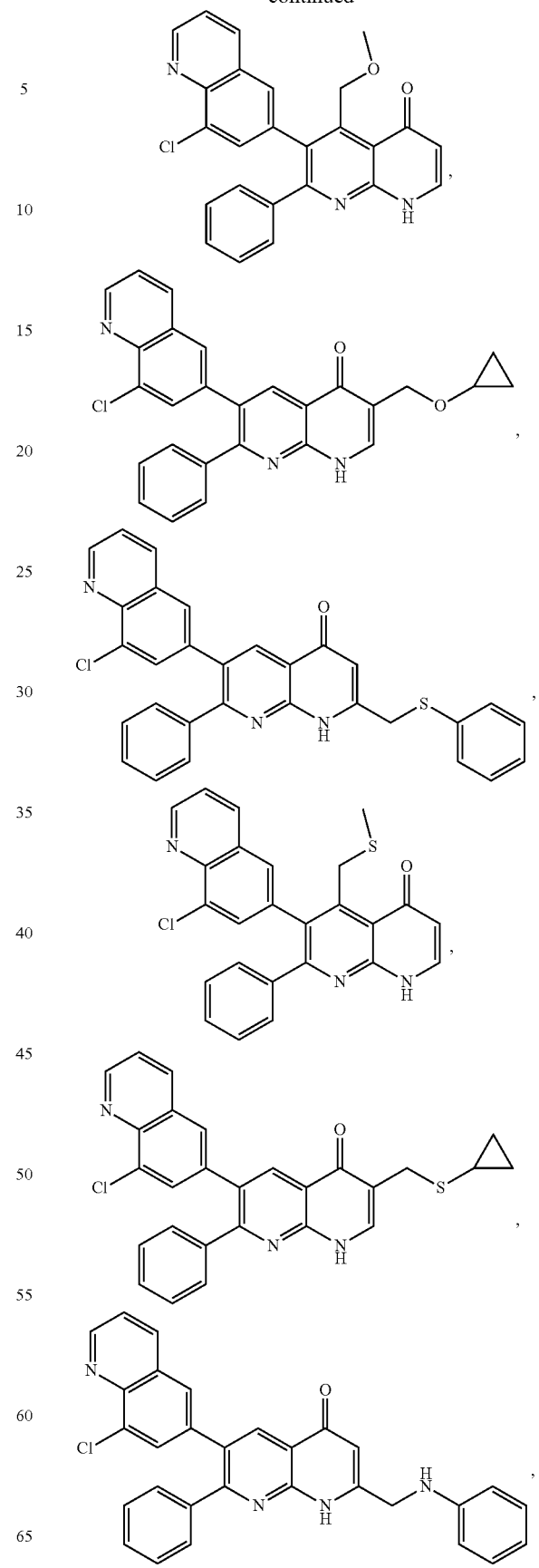

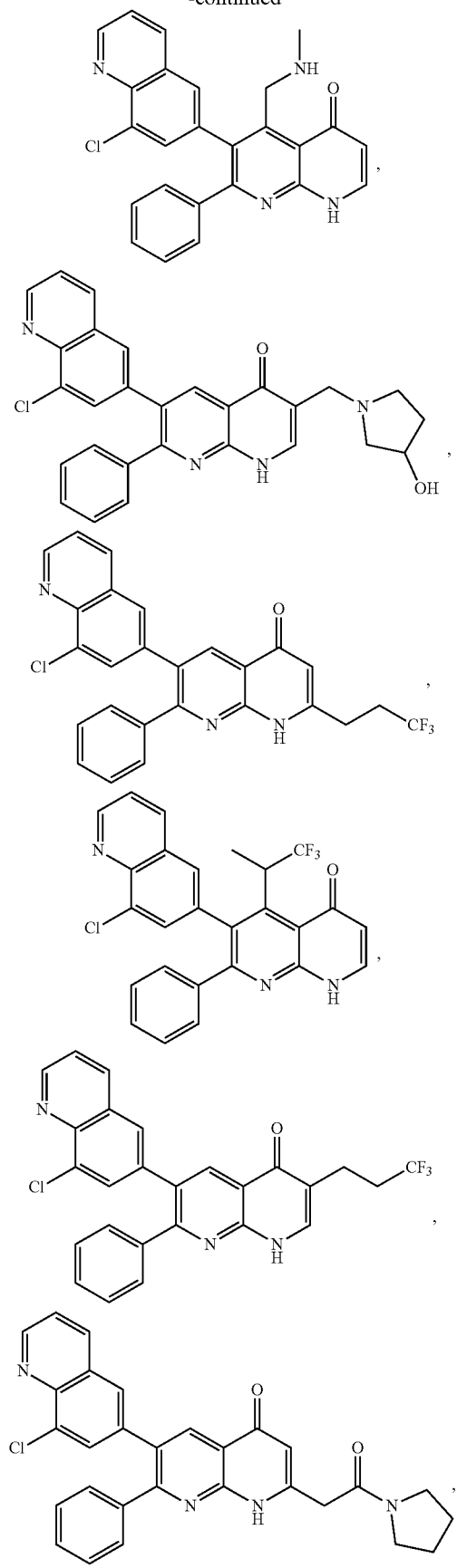
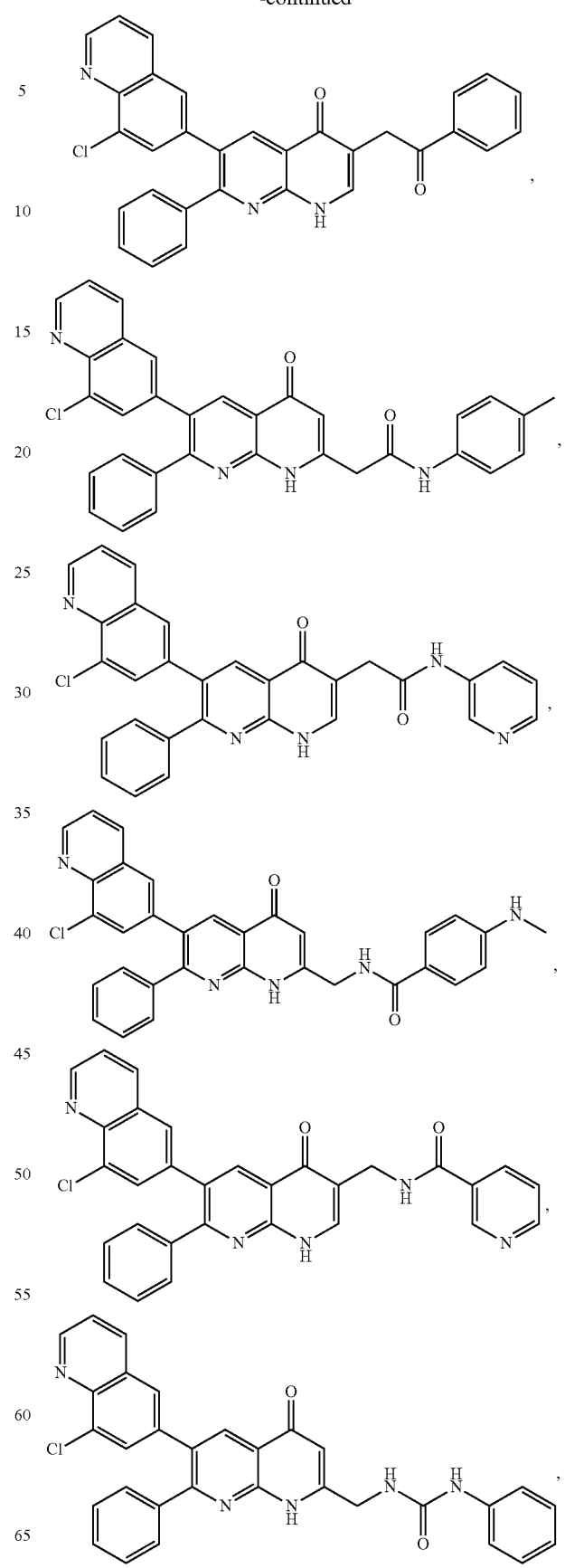

721
-continued
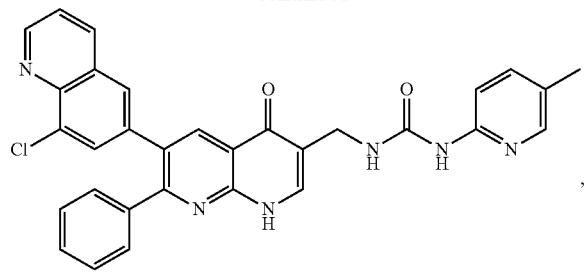
,
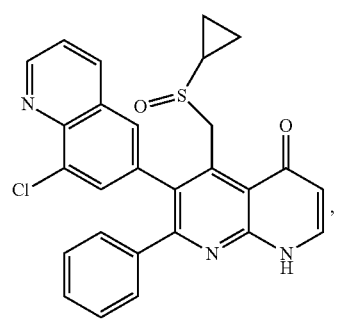
,
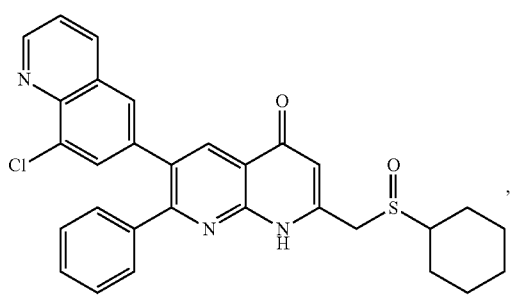
,
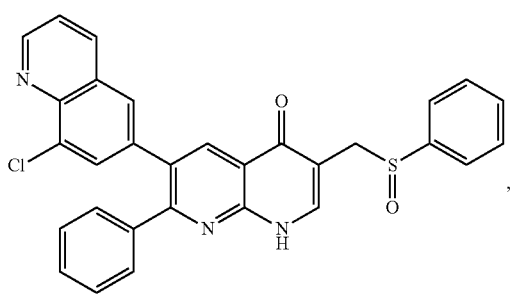
,
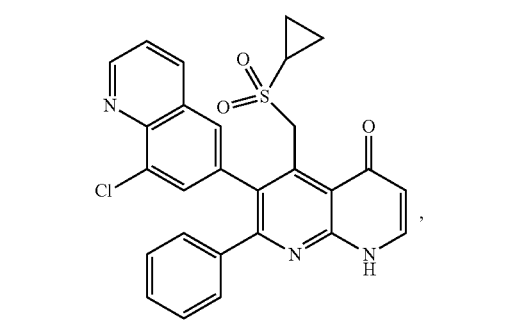
,
722
-continued
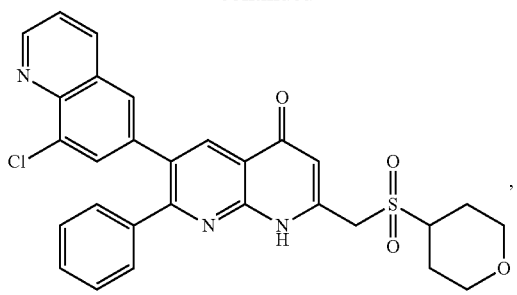
,
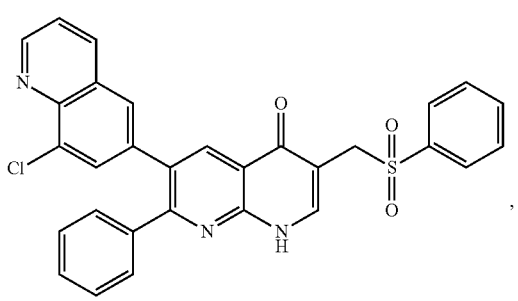
,
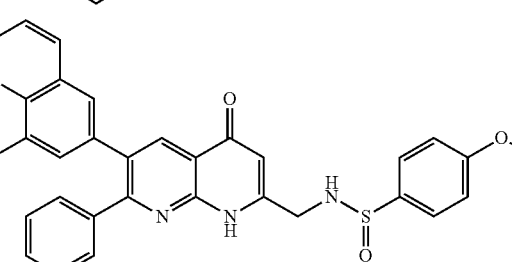
,
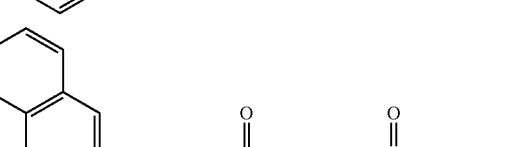
,
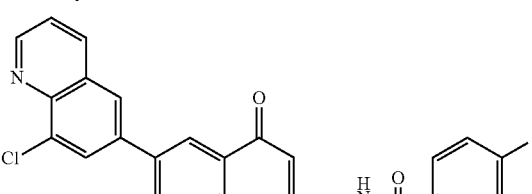
,
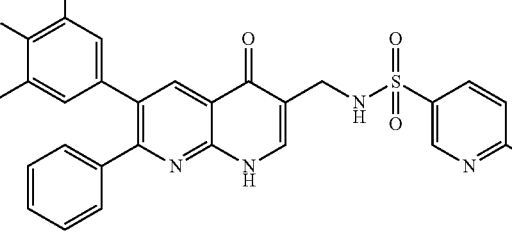
,

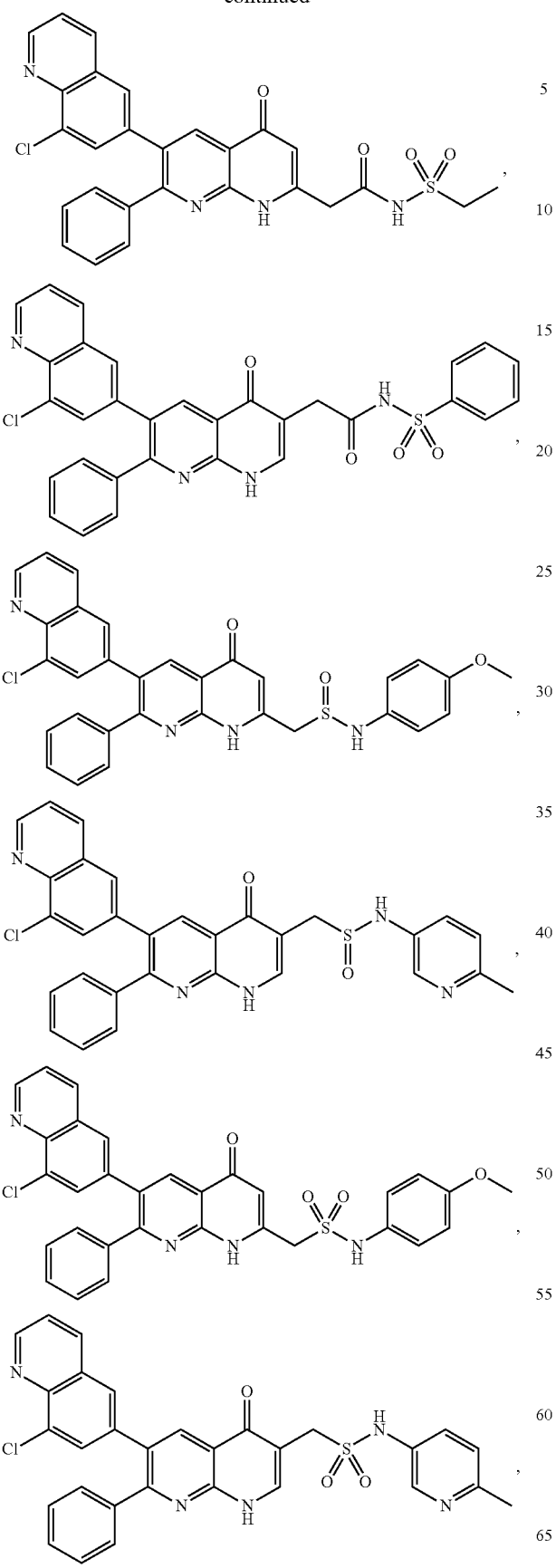
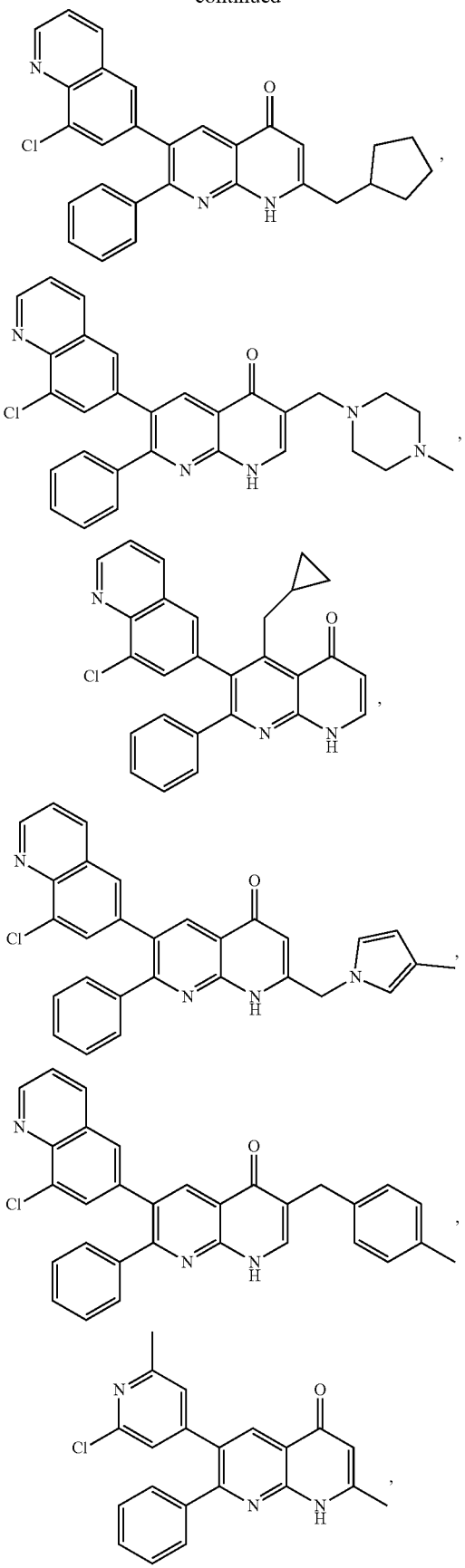

725
-continued
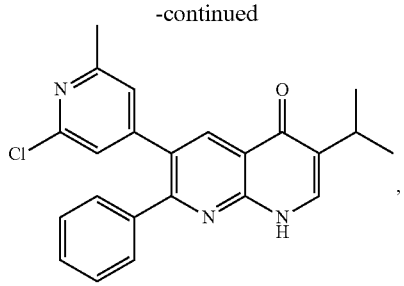,
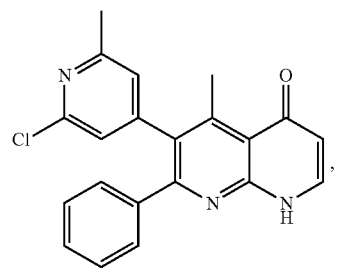,
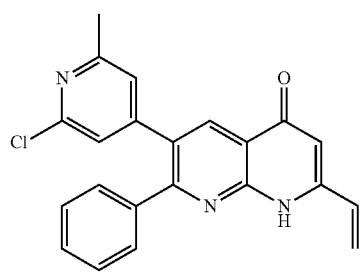,
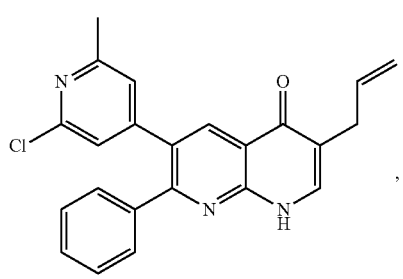,
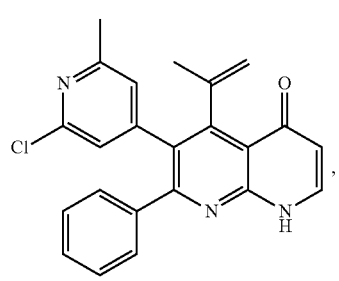,
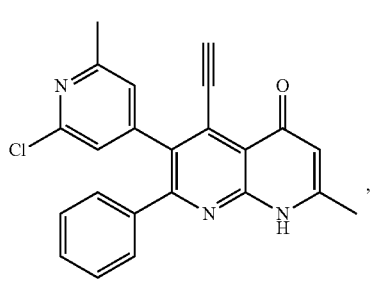,
726
-continued
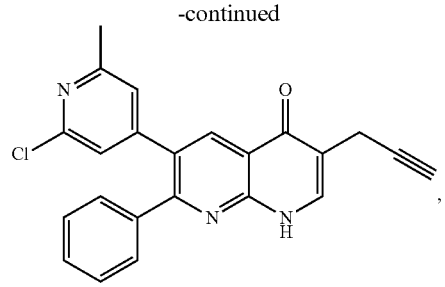,
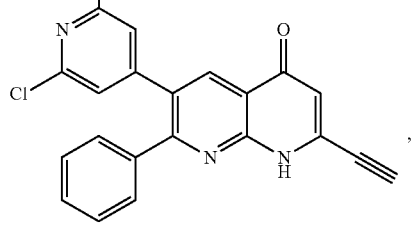,
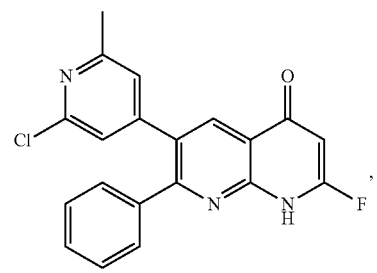,
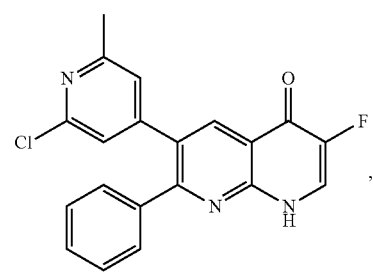,
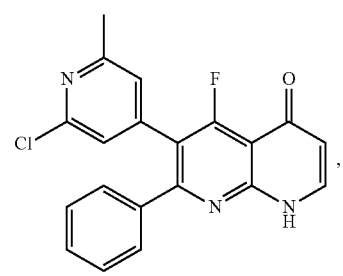,
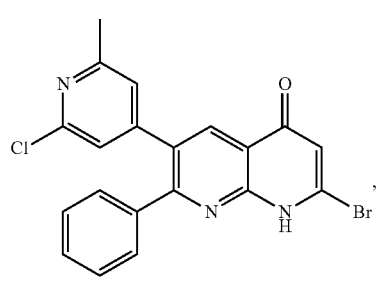, 727
-continued
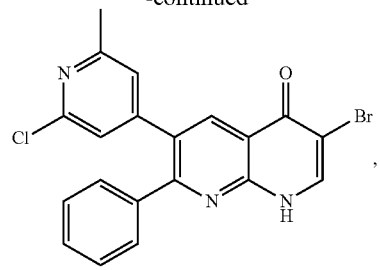,
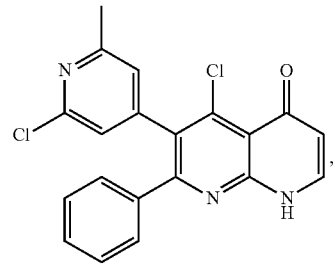,
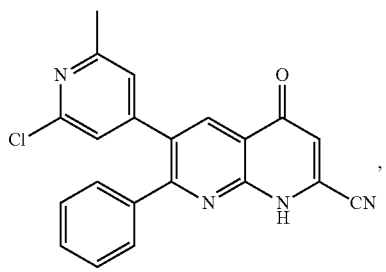,
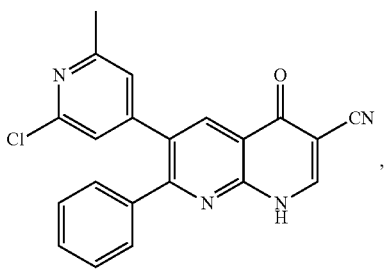,
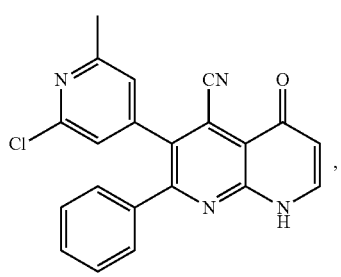,
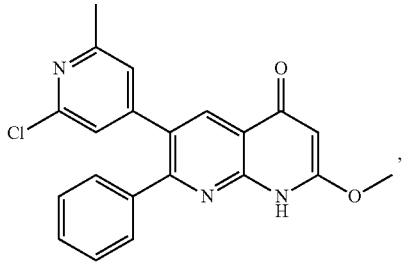,
728
-continued
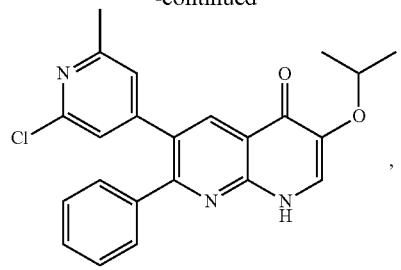,
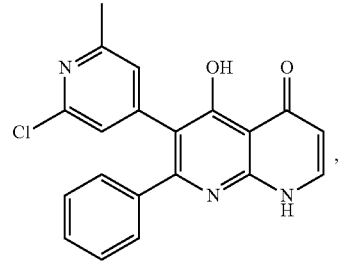,
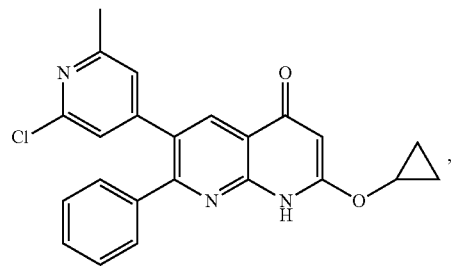,
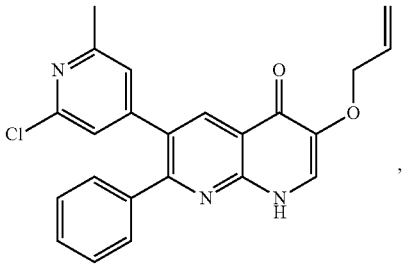,
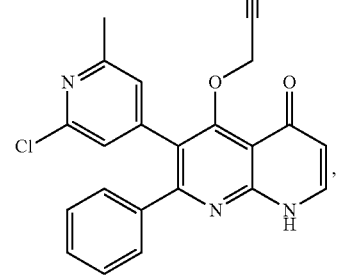,
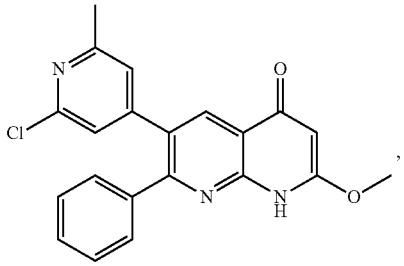,

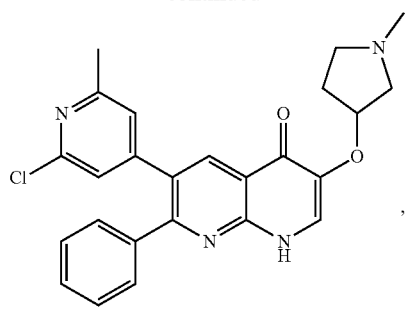,
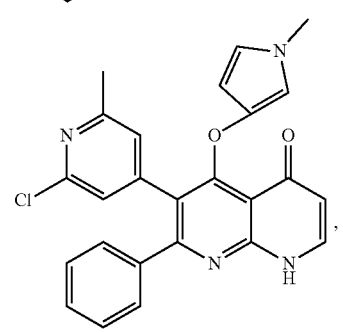,
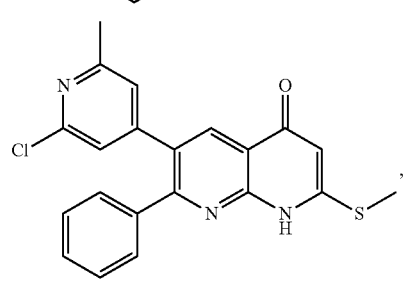,
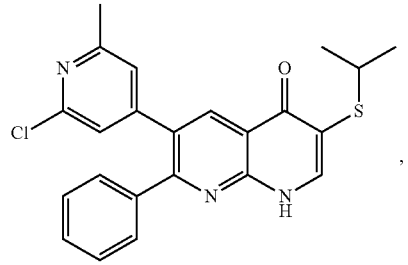,
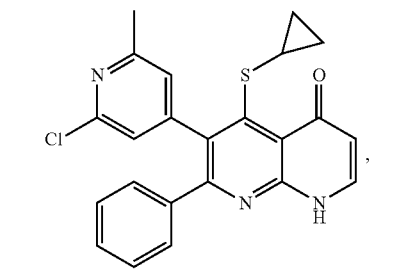,
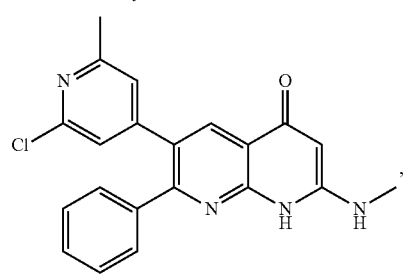,
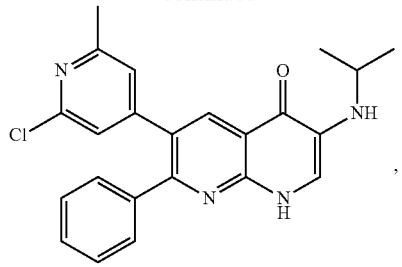,
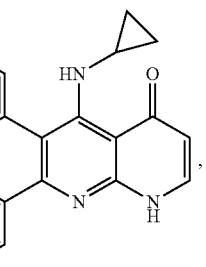,
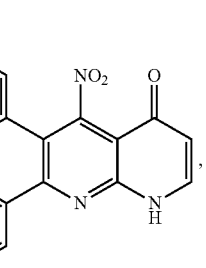,
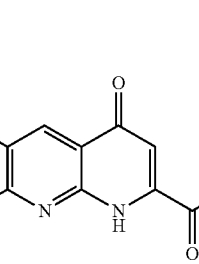,
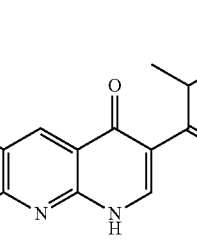,
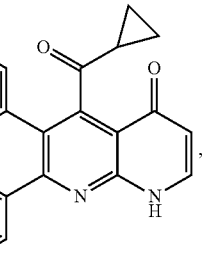, 731
-continued
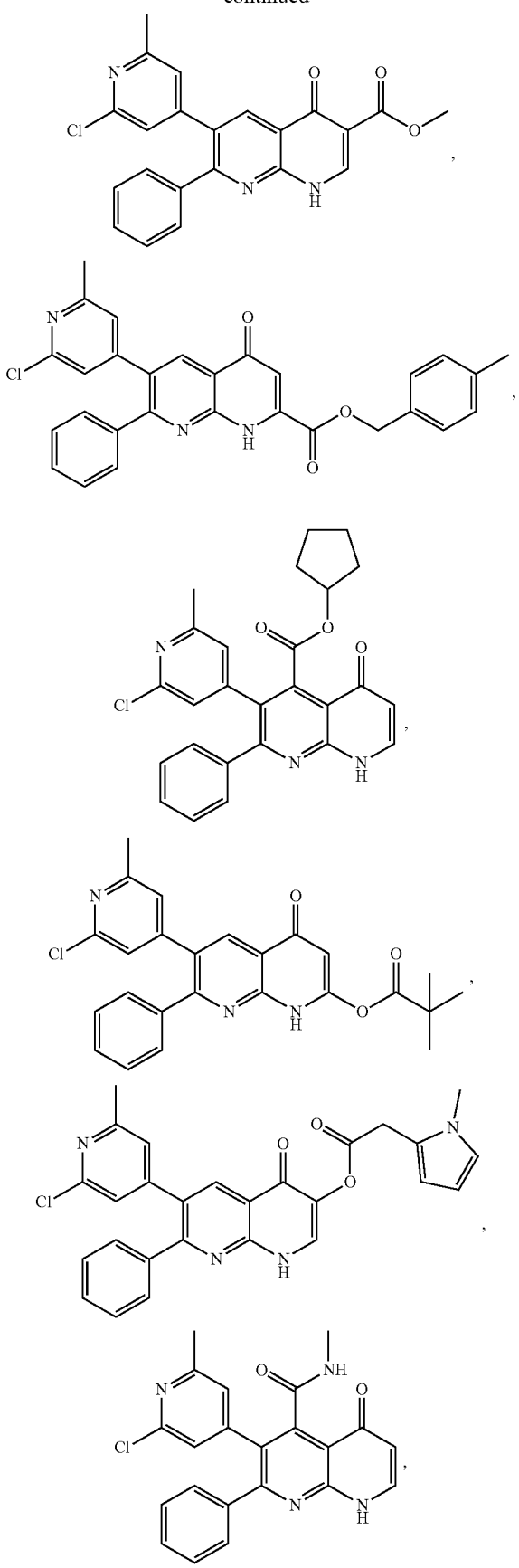
732
-continued
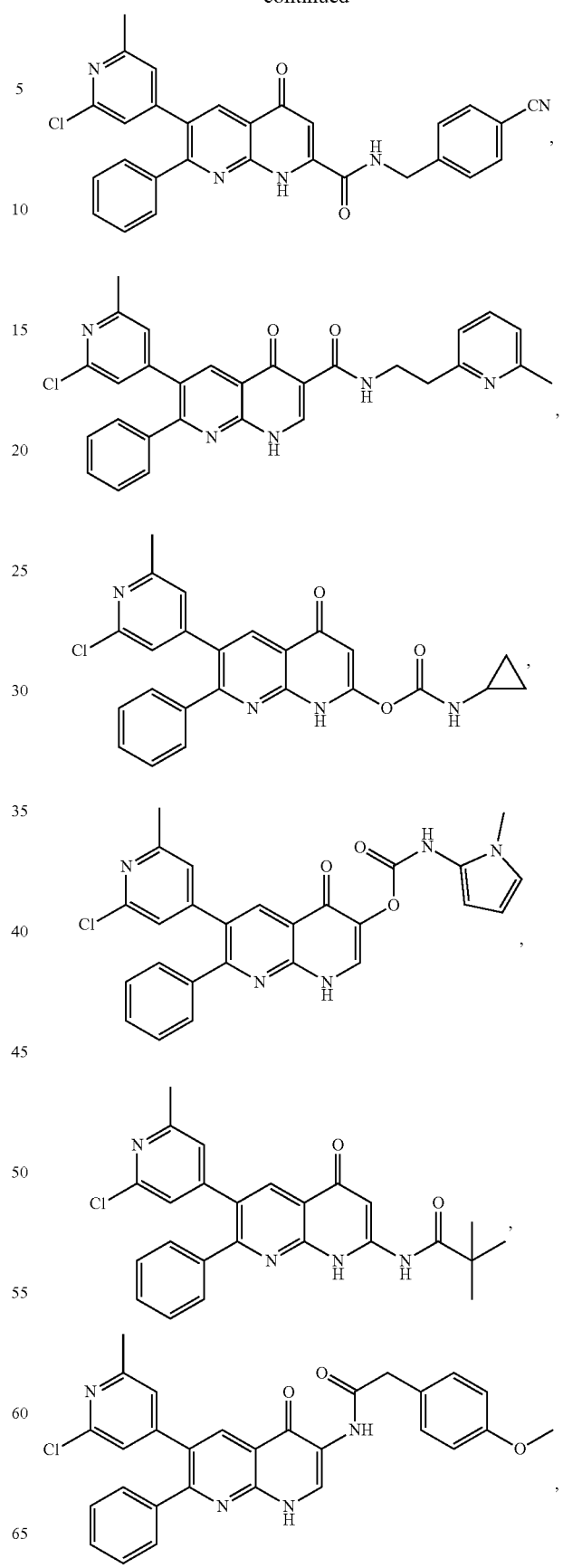

733
-continued
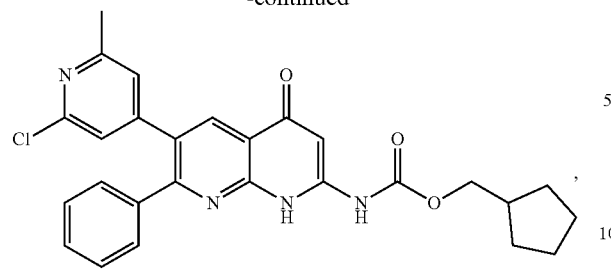,
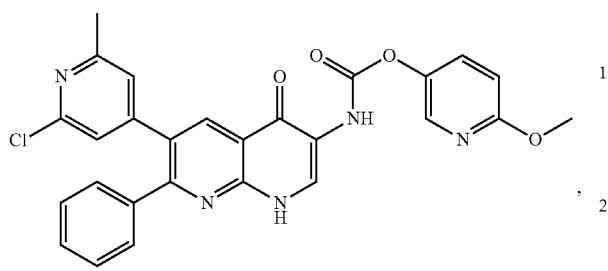,
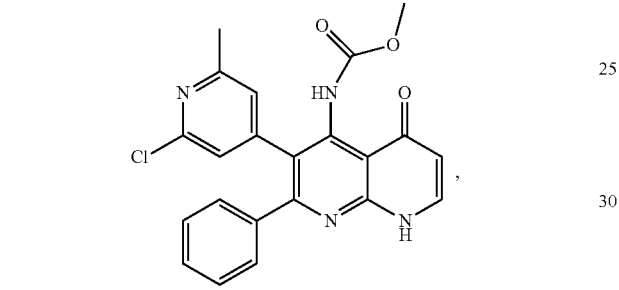,
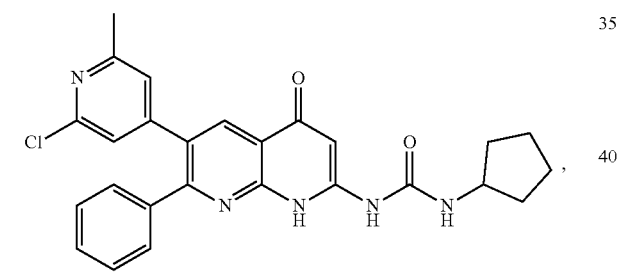,
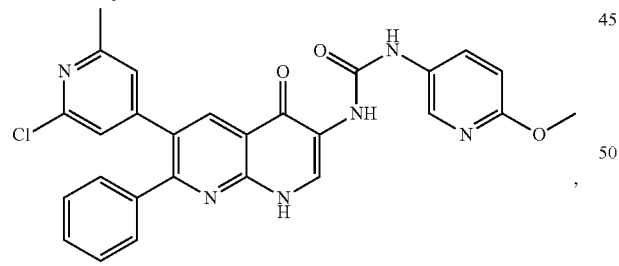,
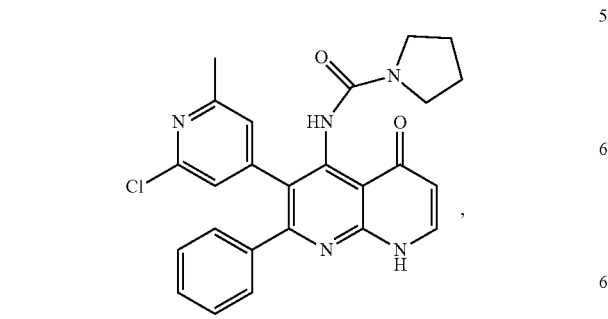,
734
-continued
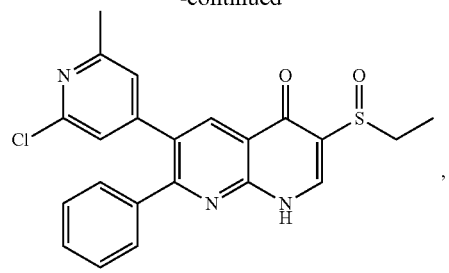,
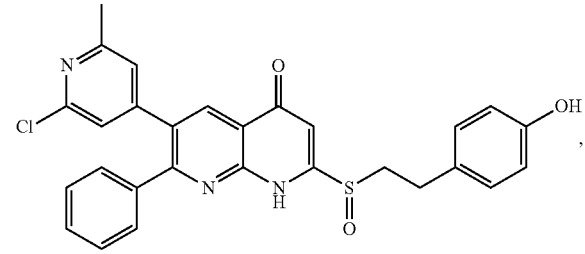,
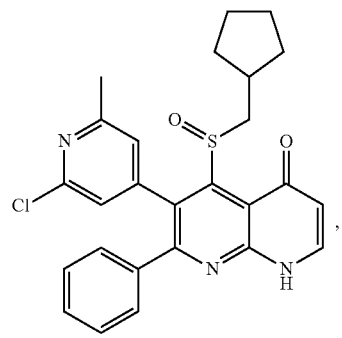,
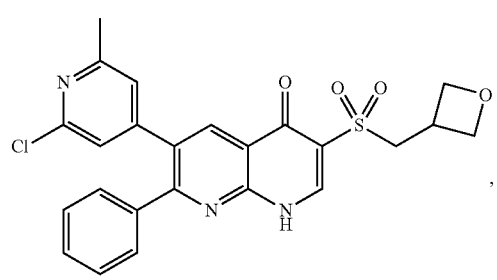,
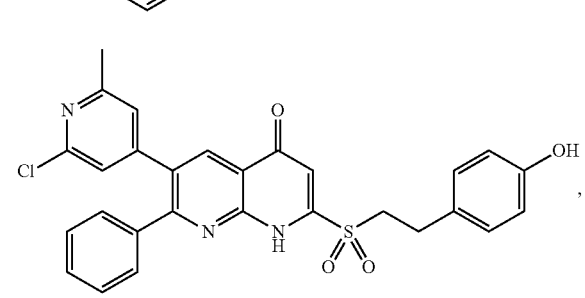,
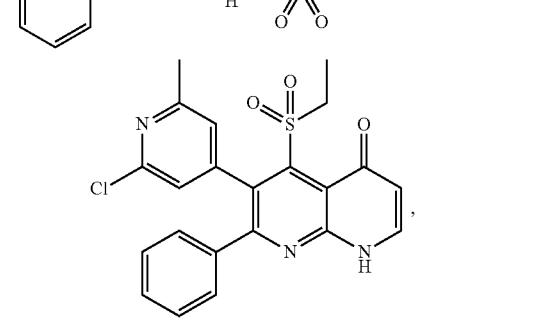, 735
-continued
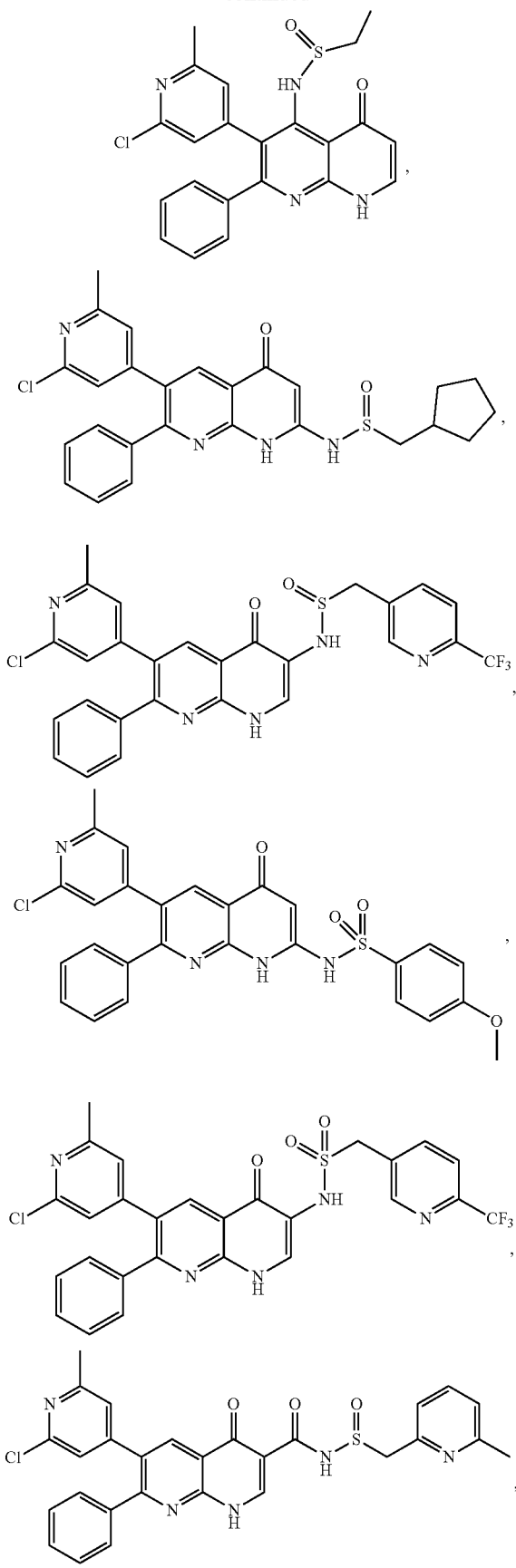
736
-continued
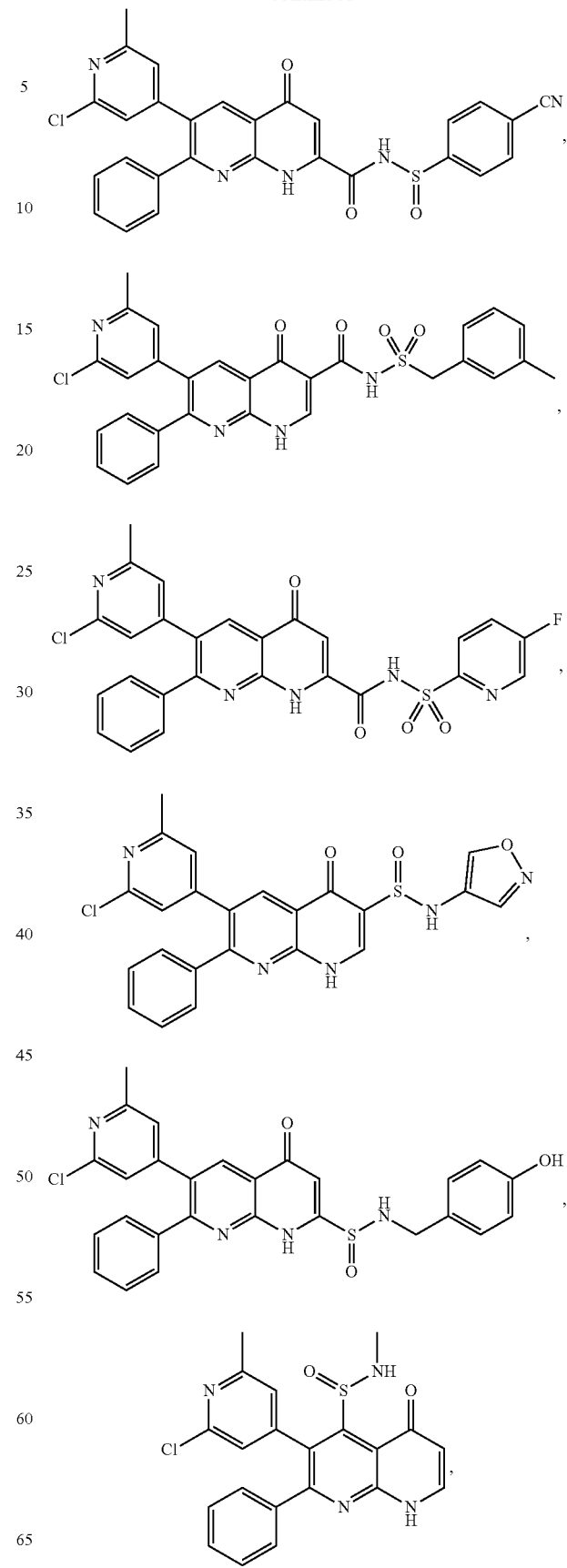

737
-continued
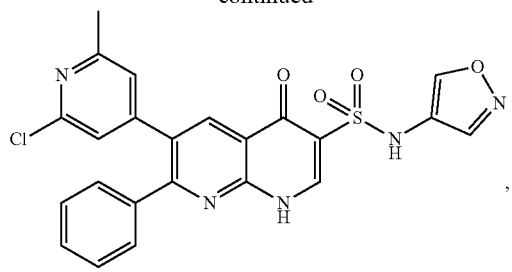,
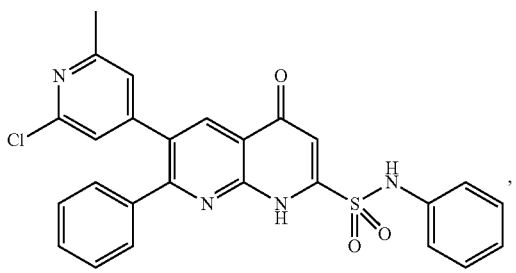,
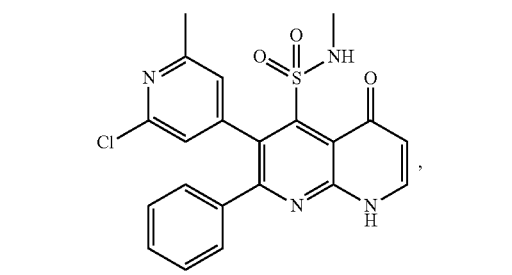,
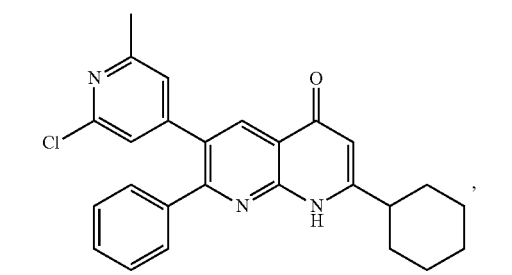,
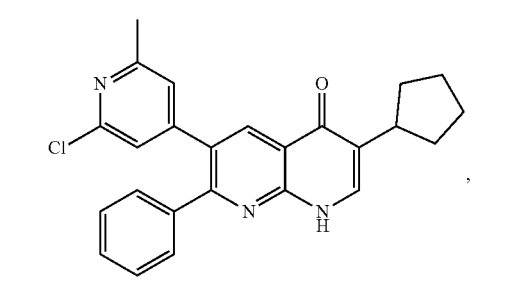,
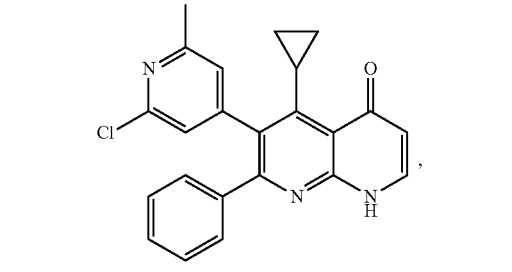,
738
-continued
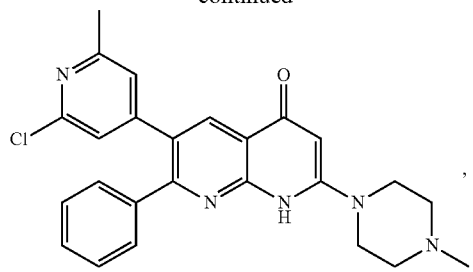,
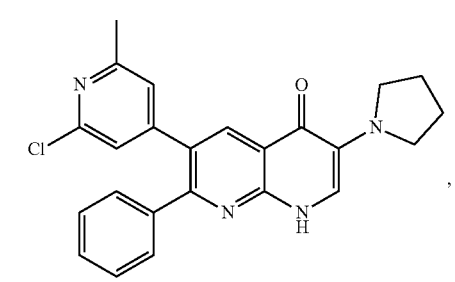,
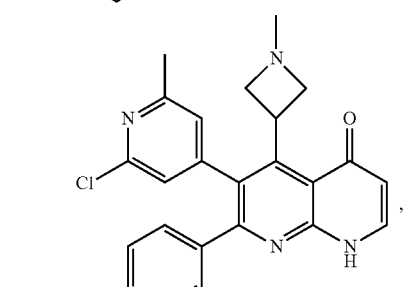,
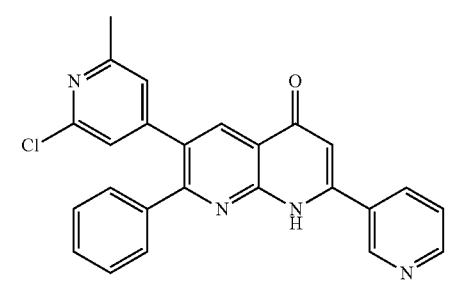,
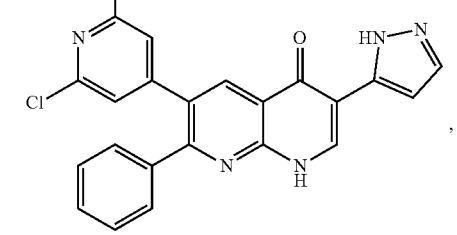,
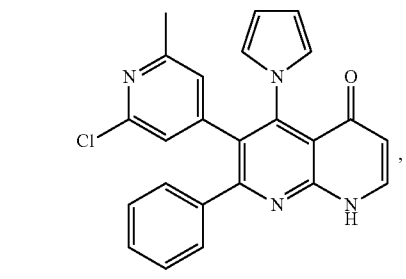, 739
-continued
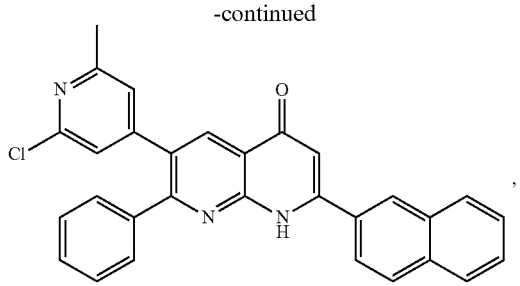
,
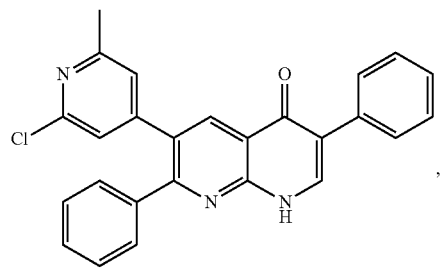
,
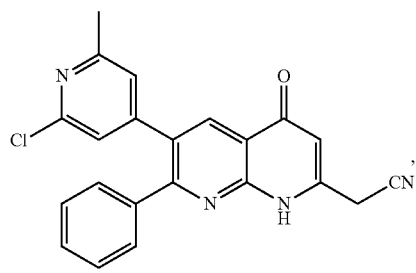
,
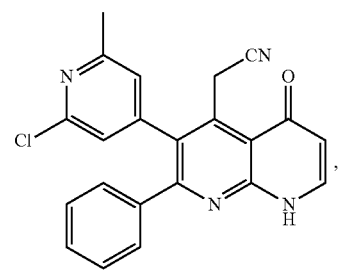
,
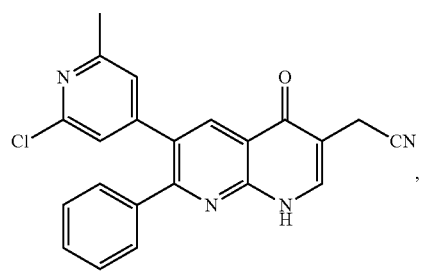
,
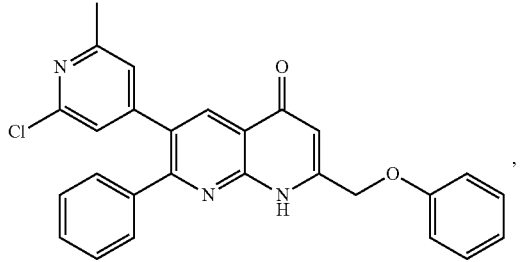
,
740
-continued
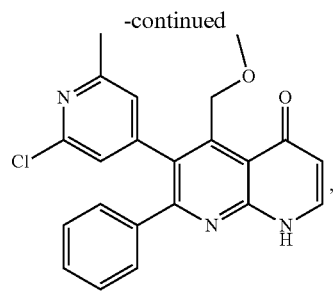
,
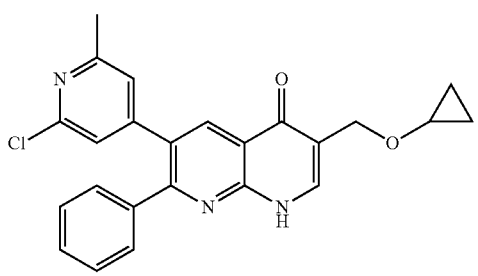
,
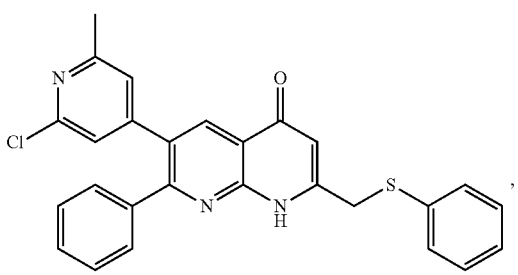
,
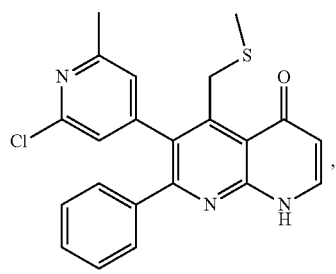
,
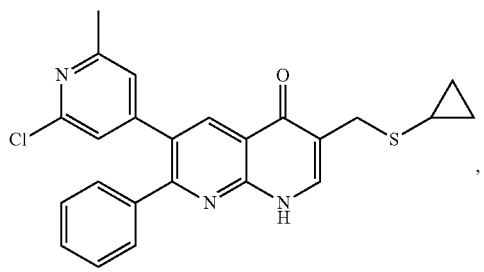
,
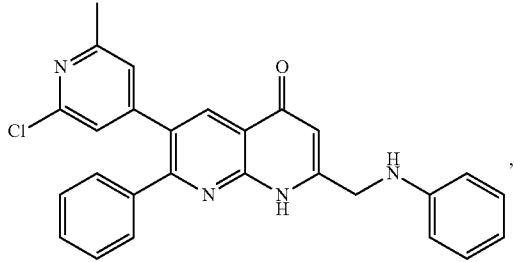
, 741
-continued
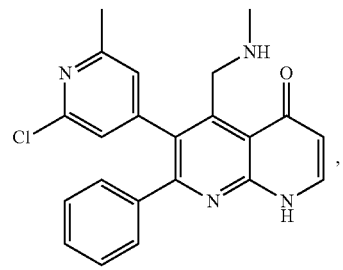,
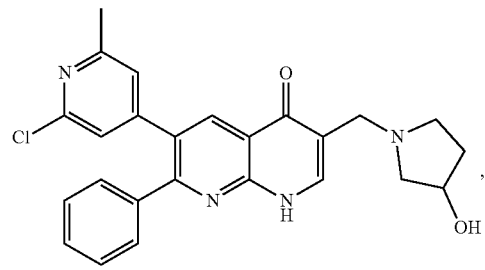,
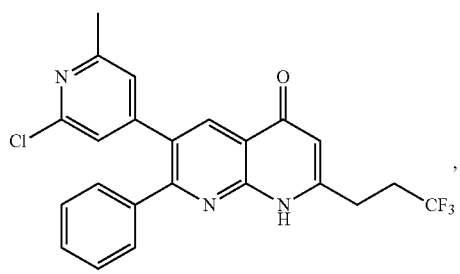,
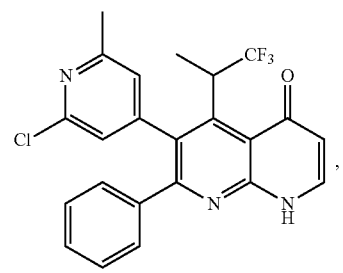,
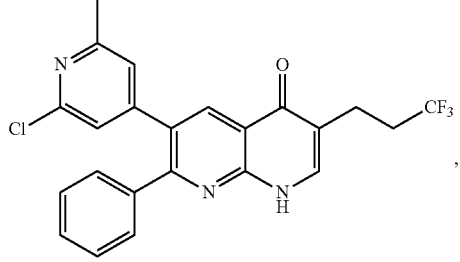,
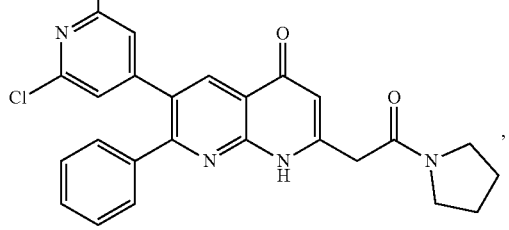,
742
-continued
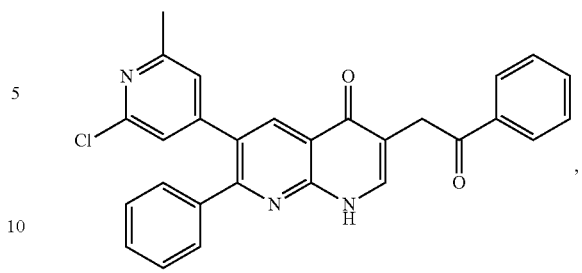,
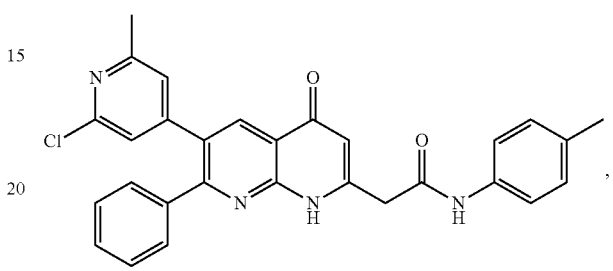,
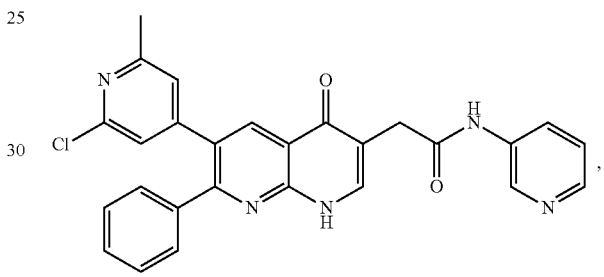,
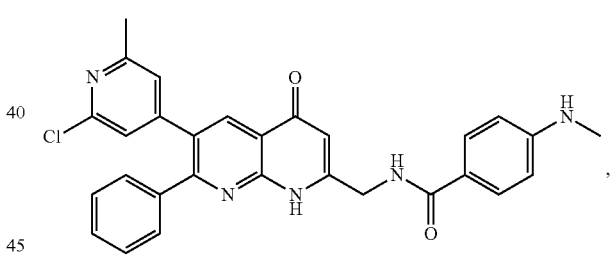,
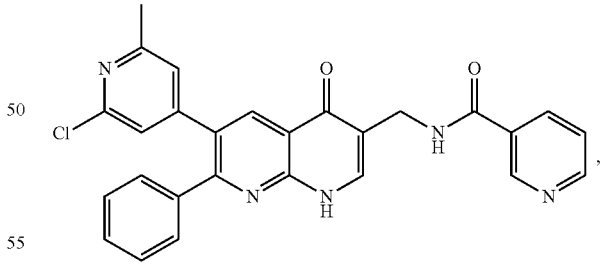,
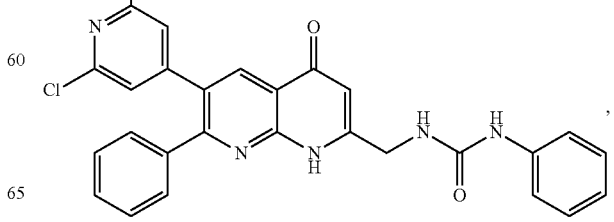, 743
-continued
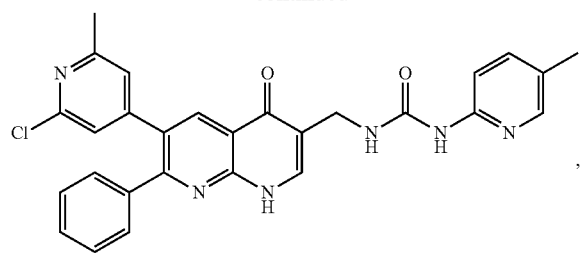
,
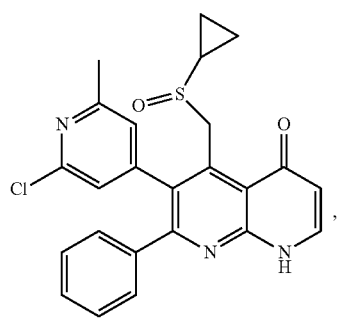
,
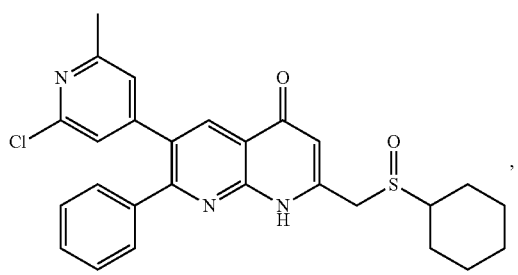
,
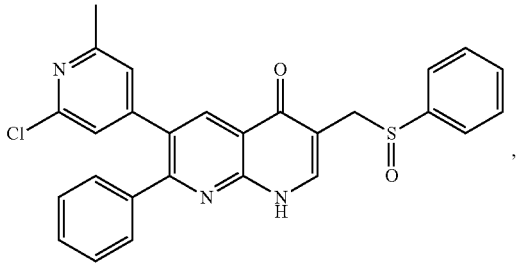
,
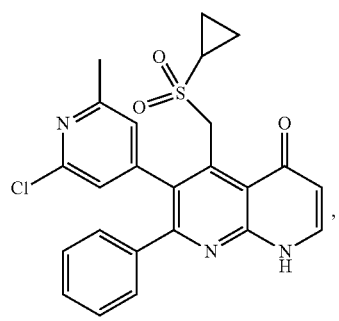
,
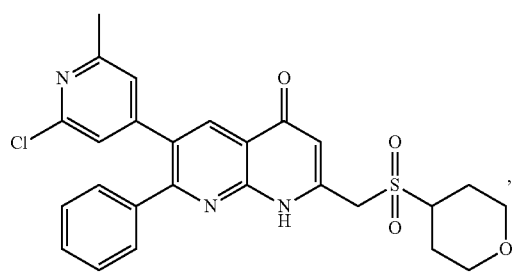
,
744
-continued
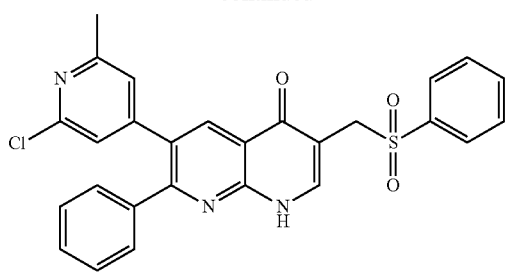
,
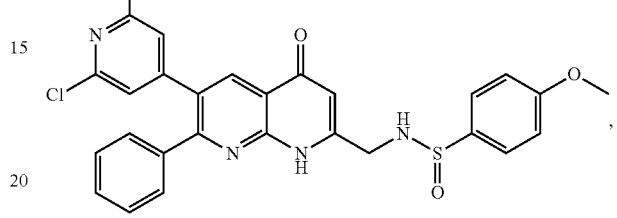
,
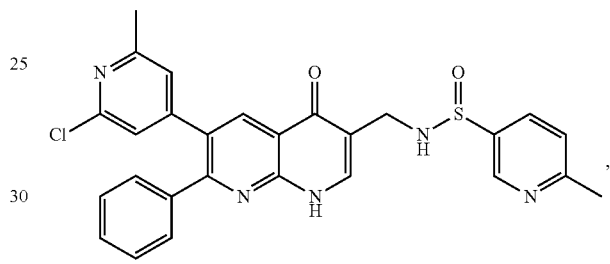
,
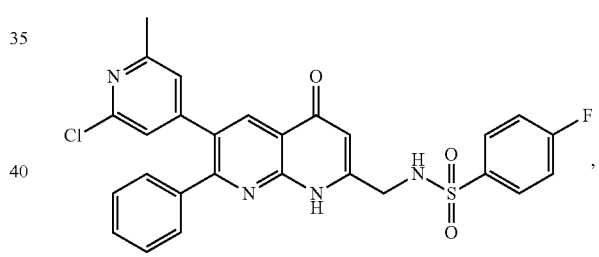
,
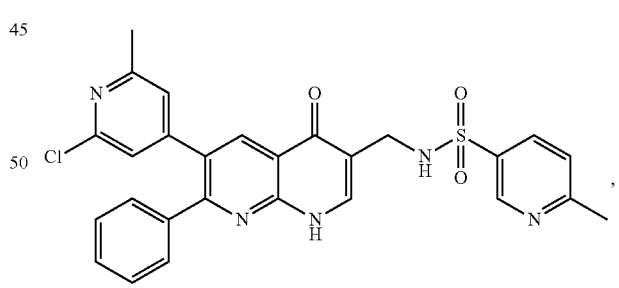
,
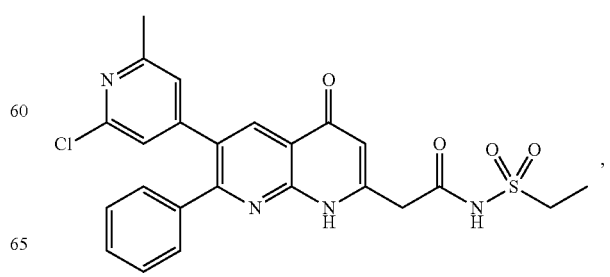
, 745
-continued
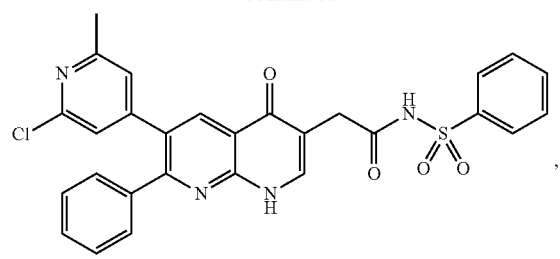,
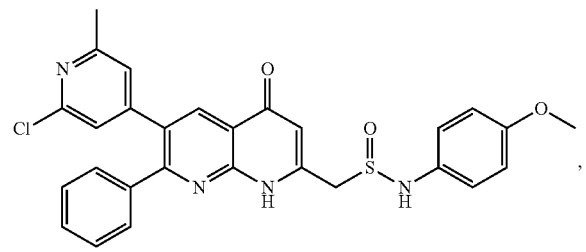,
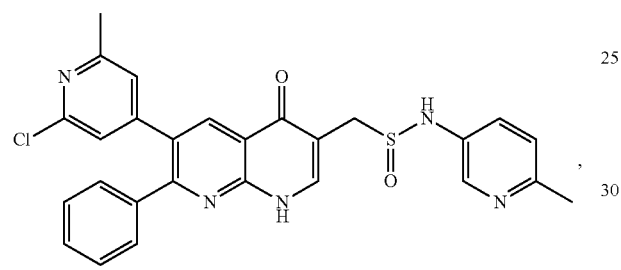,
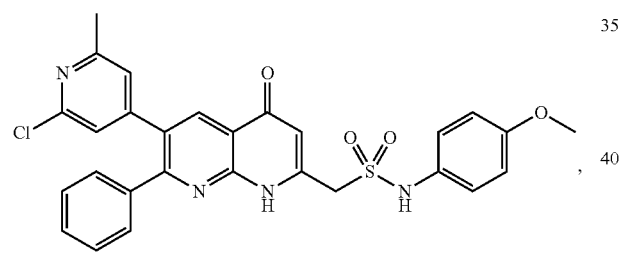,
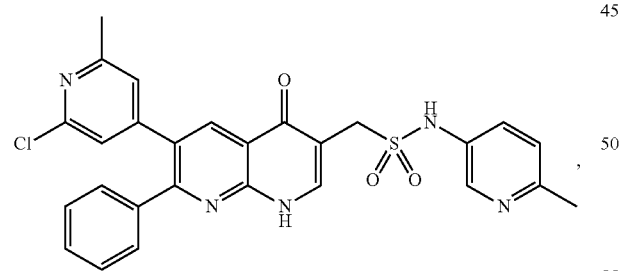,
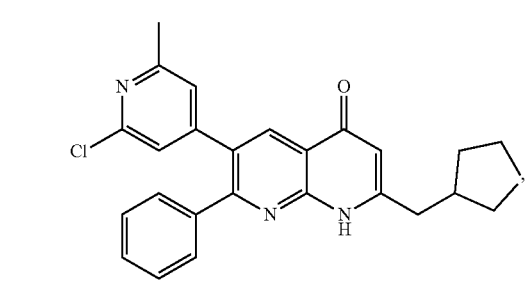,
746
-continued
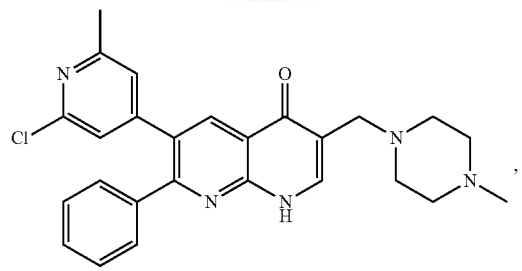,
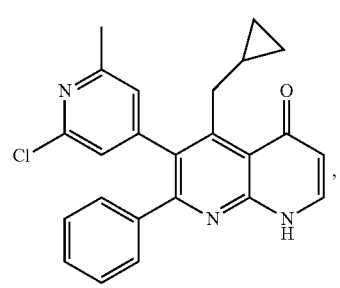,
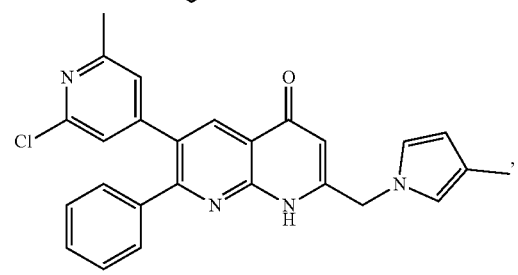,
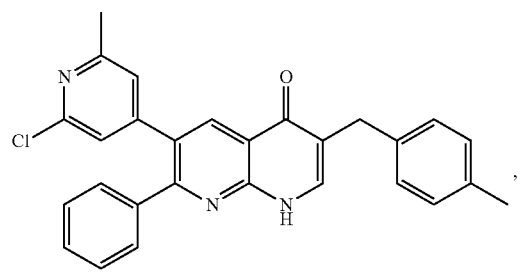,
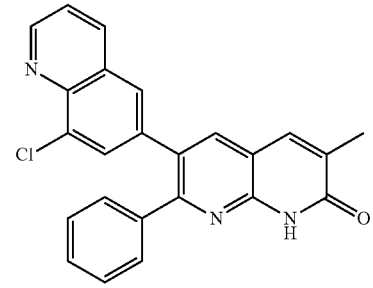,
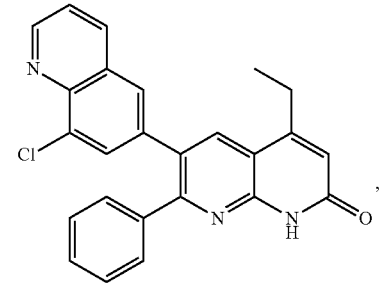, 747
-continued
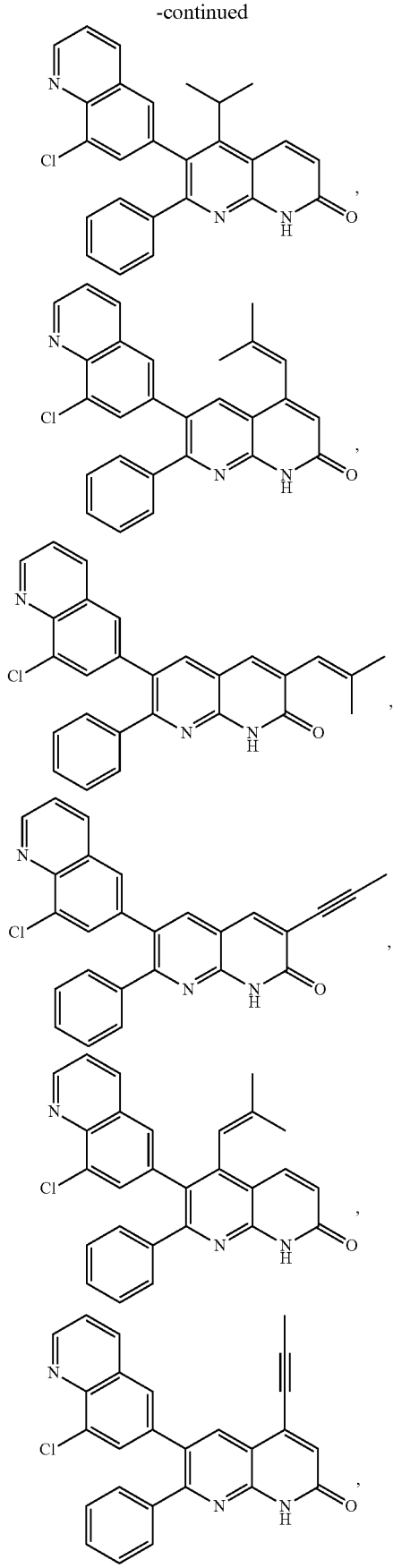
748
-continued
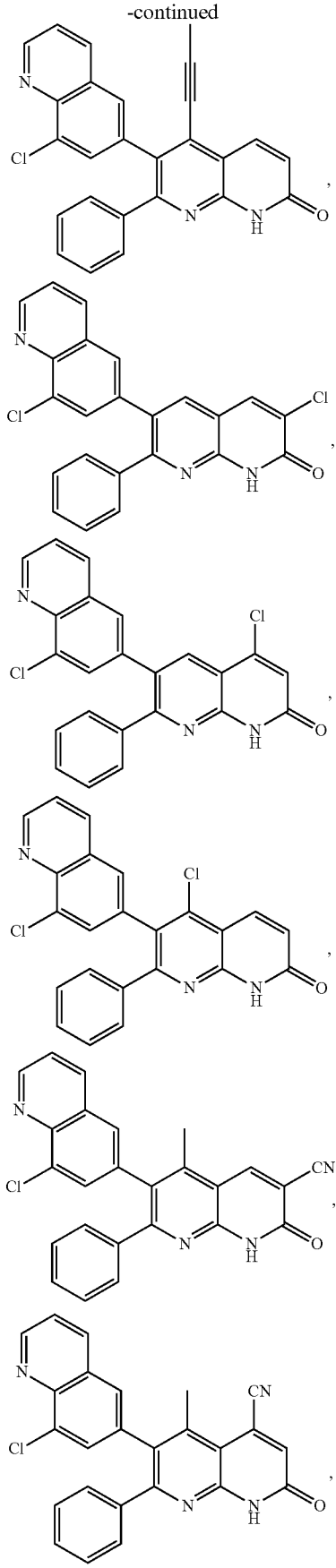

749
-continued
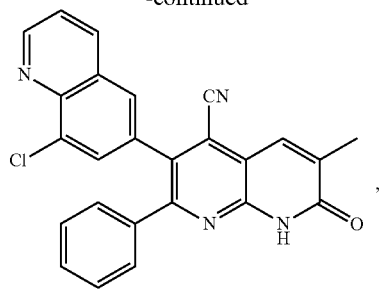
,
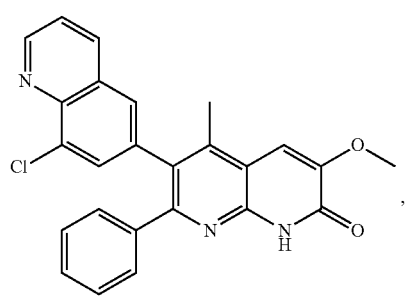
,
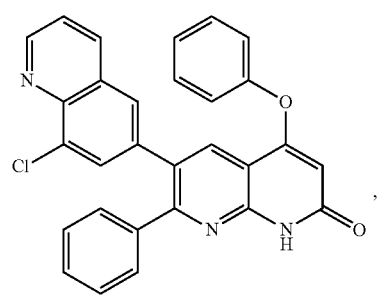
,
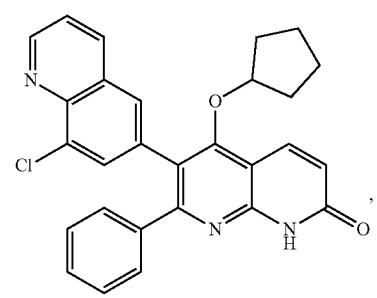
,
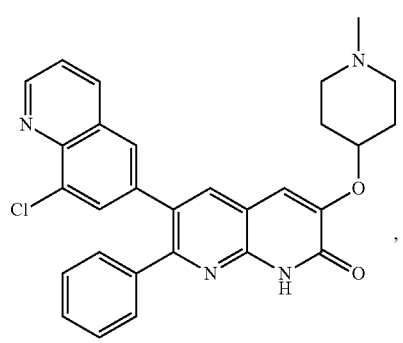
,
750
-continued
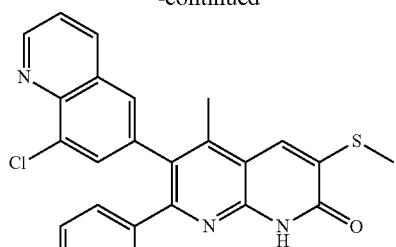
,
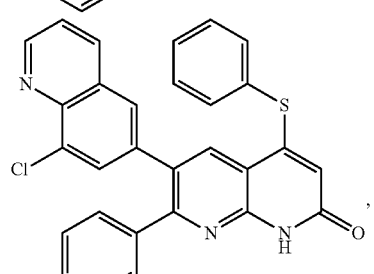
,
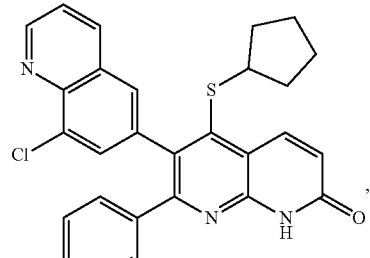
,
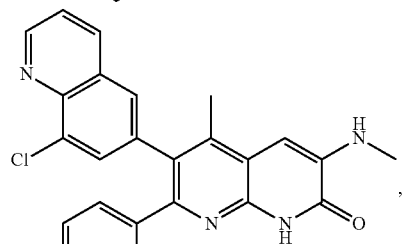
,
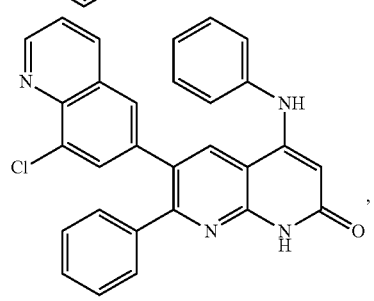
,
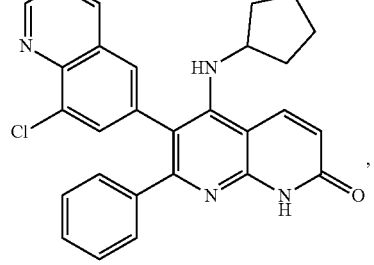
, 751
-continued
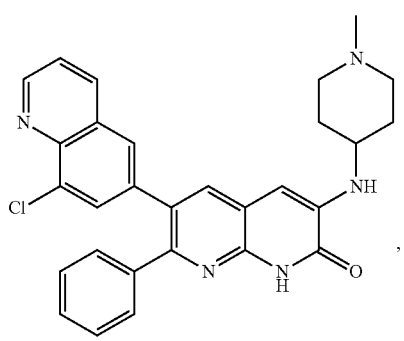
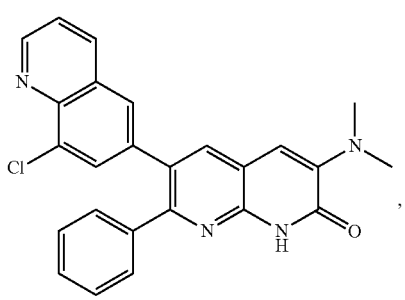
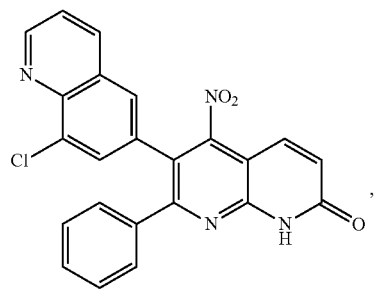
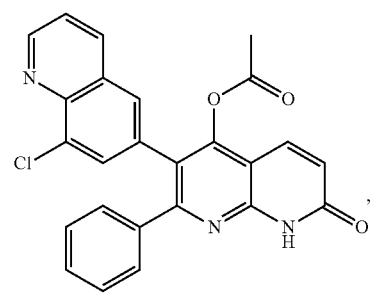
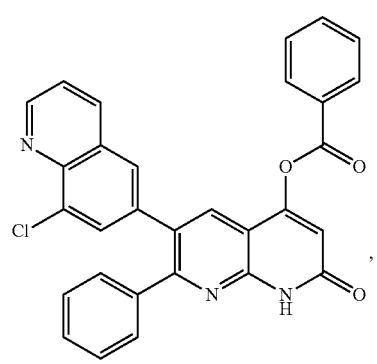
752
-continued
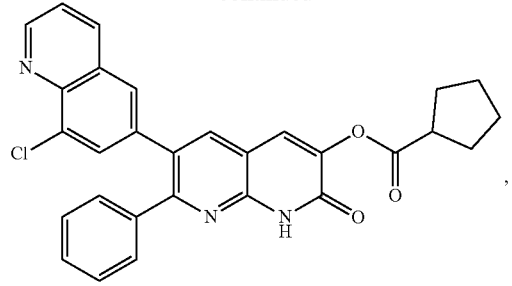
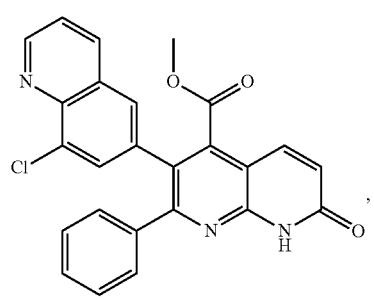
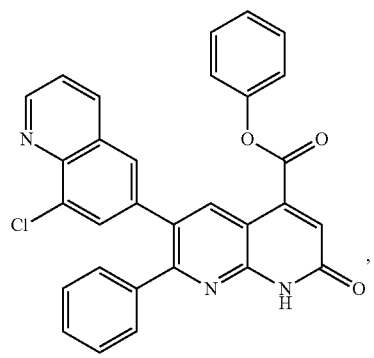
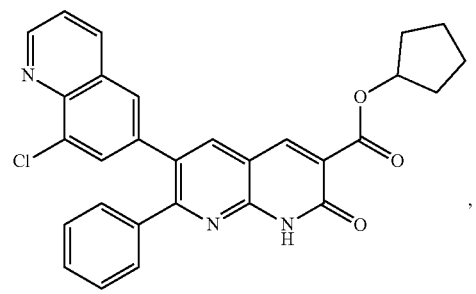
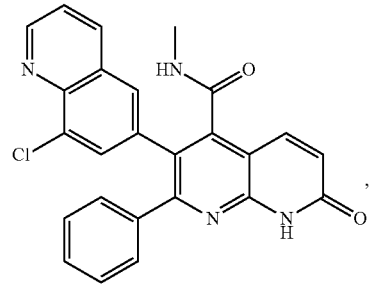

753
-continued
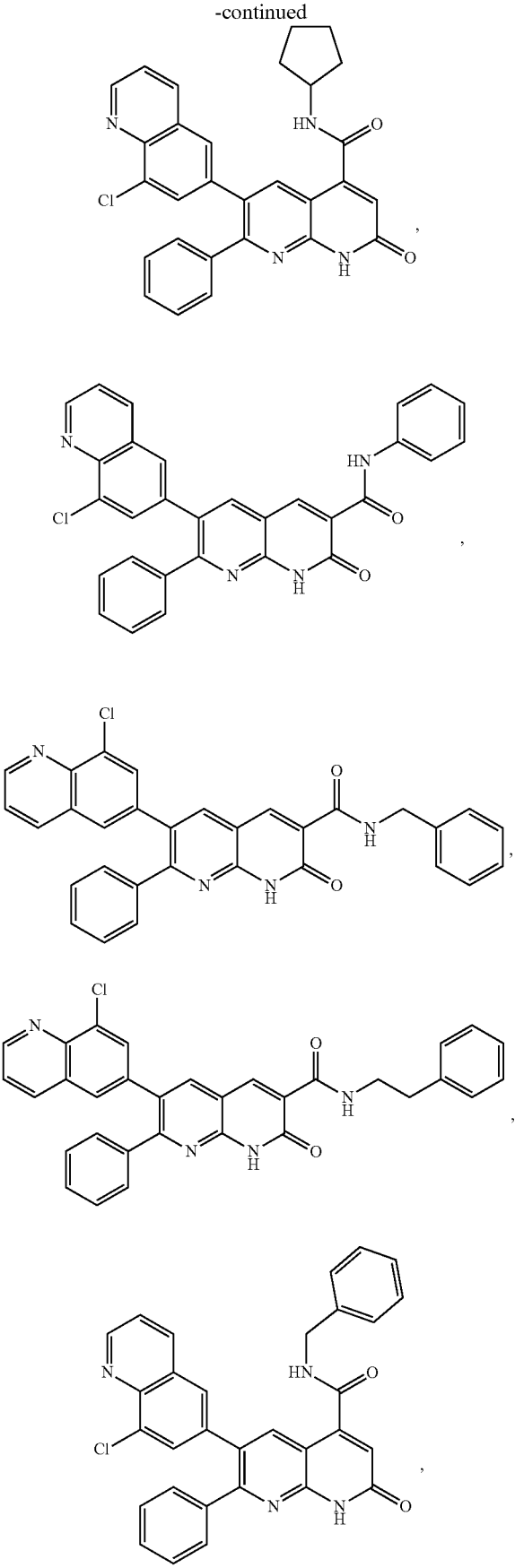
754
-continued
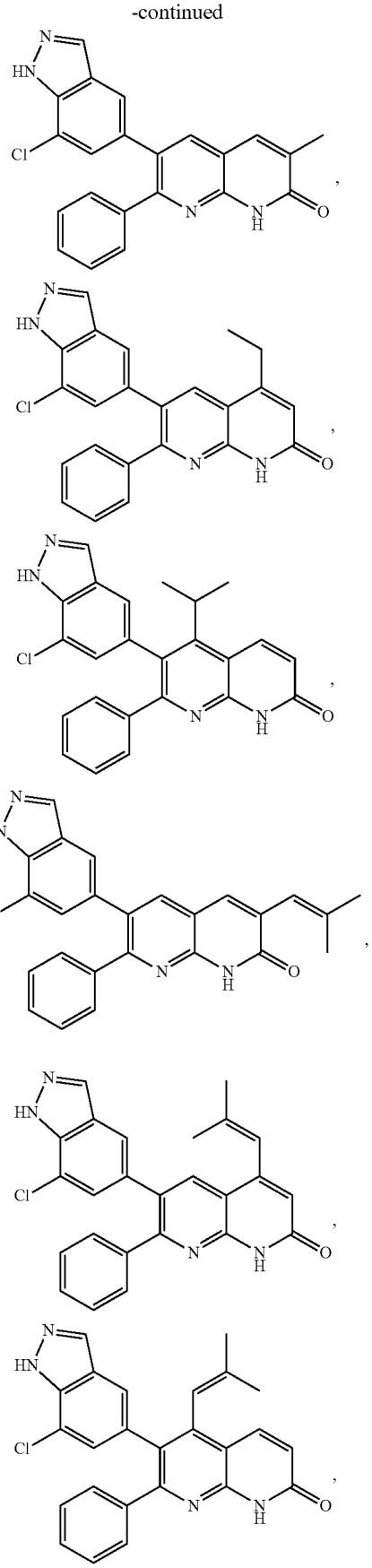

755
-continued
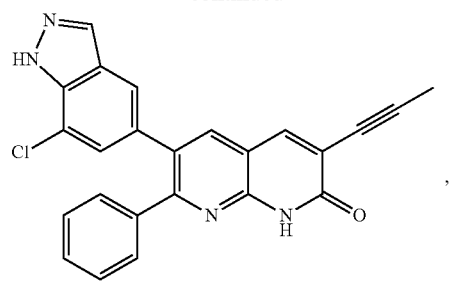
,
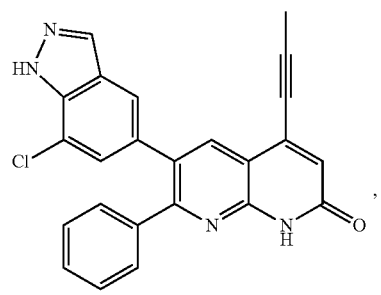
,
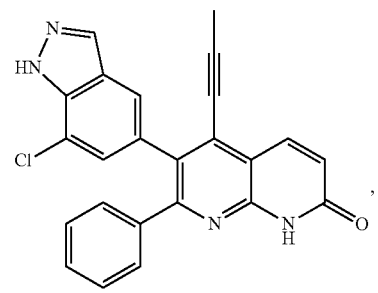
,
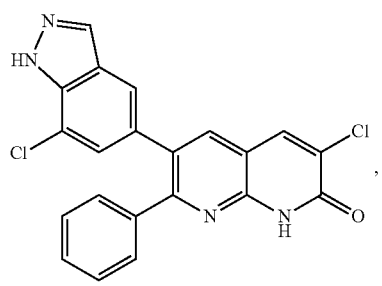
,
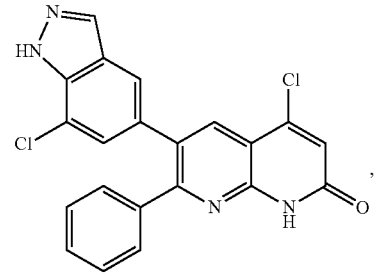
,
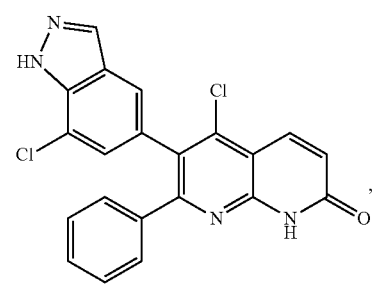
,
756
-continued
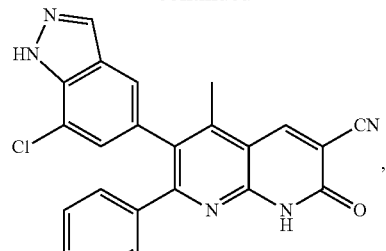
,
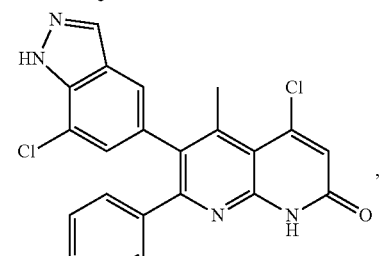
,
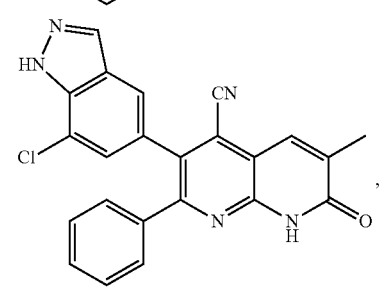
,
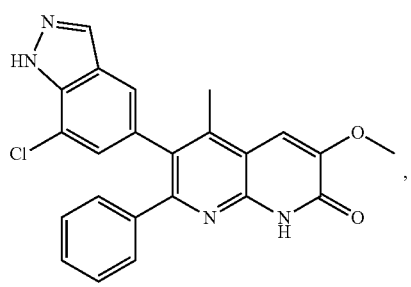
,
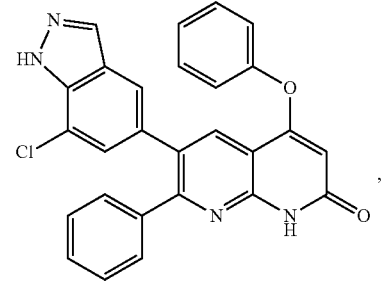
,
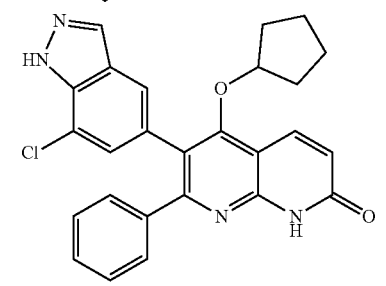
, 757
-continued
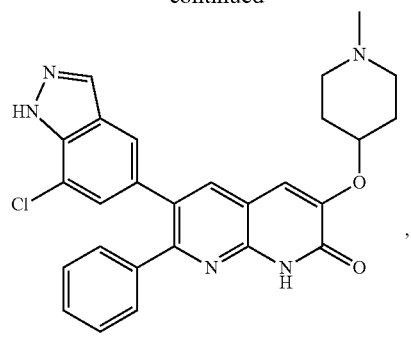,
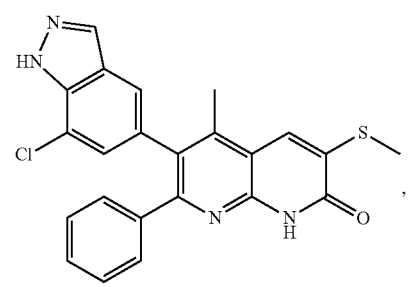,
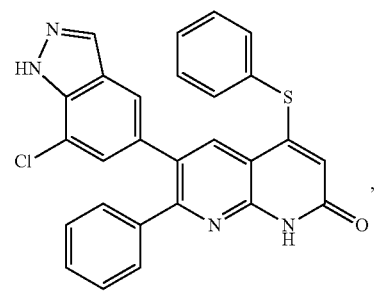,
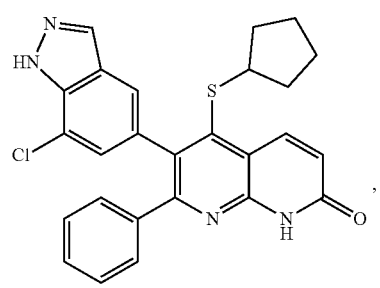,
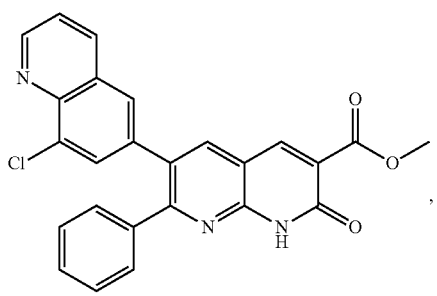,
758
-continued
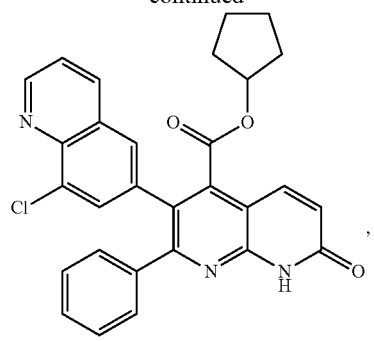,
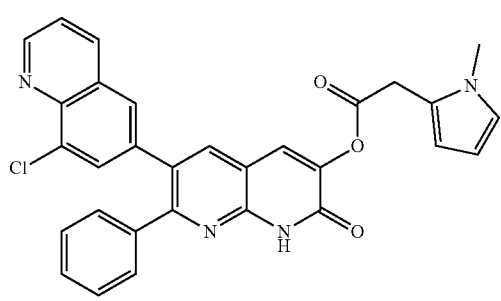,
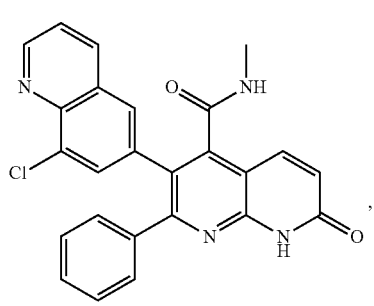,
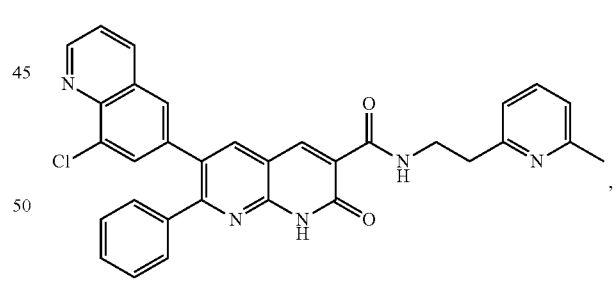,
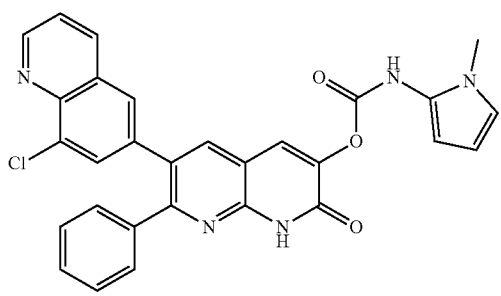,

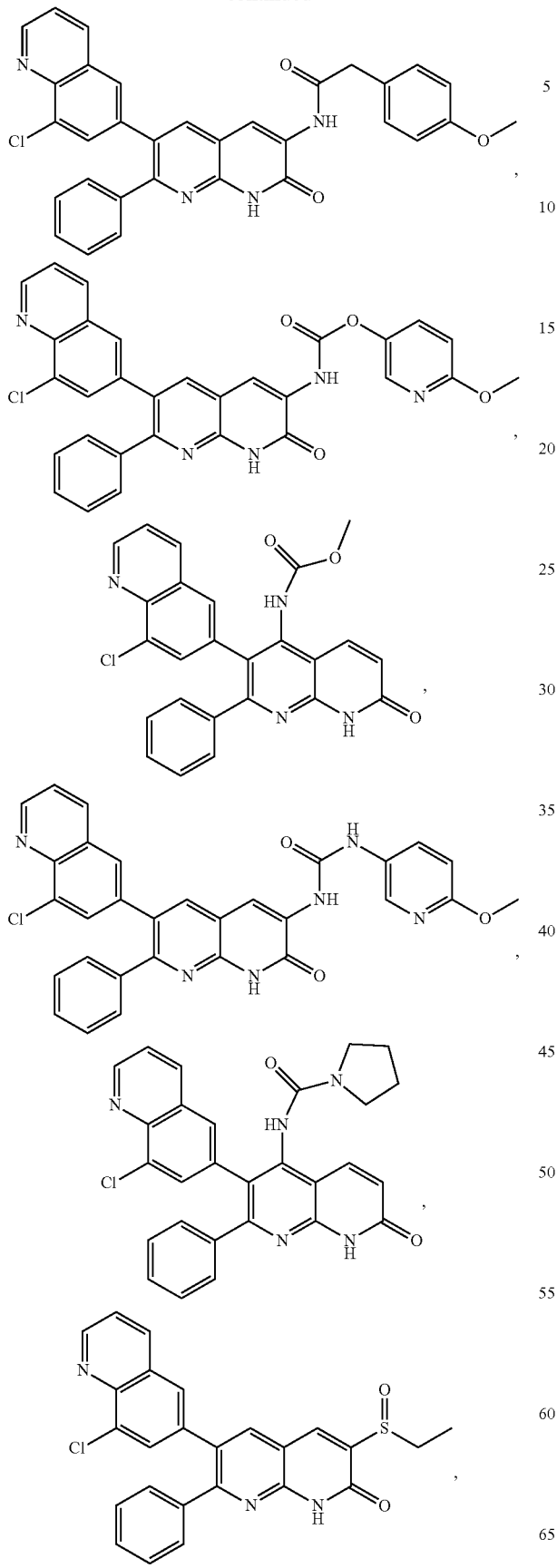
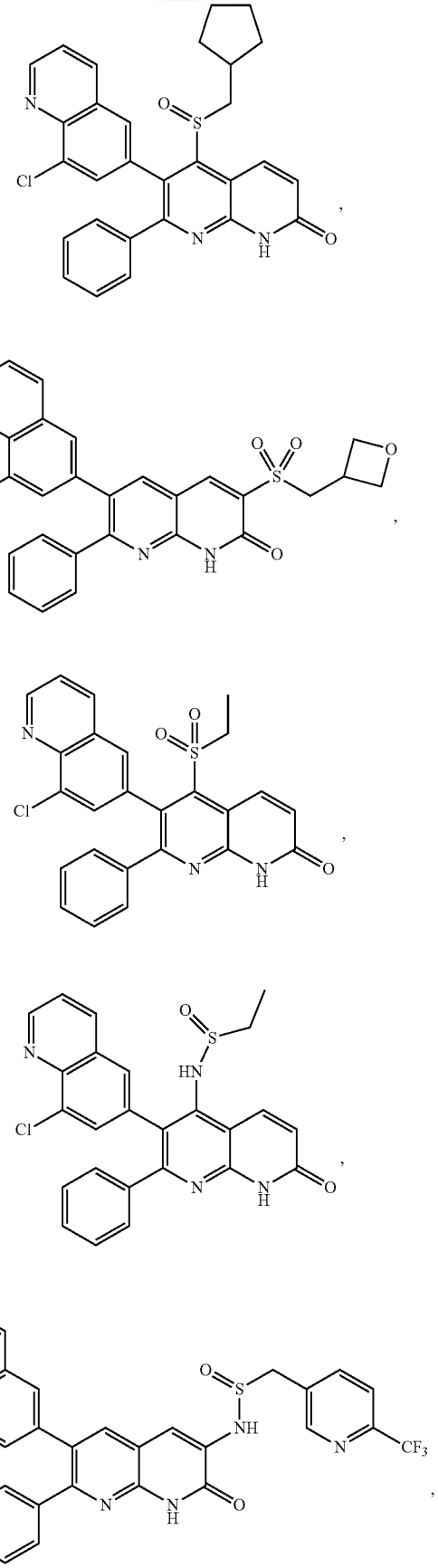

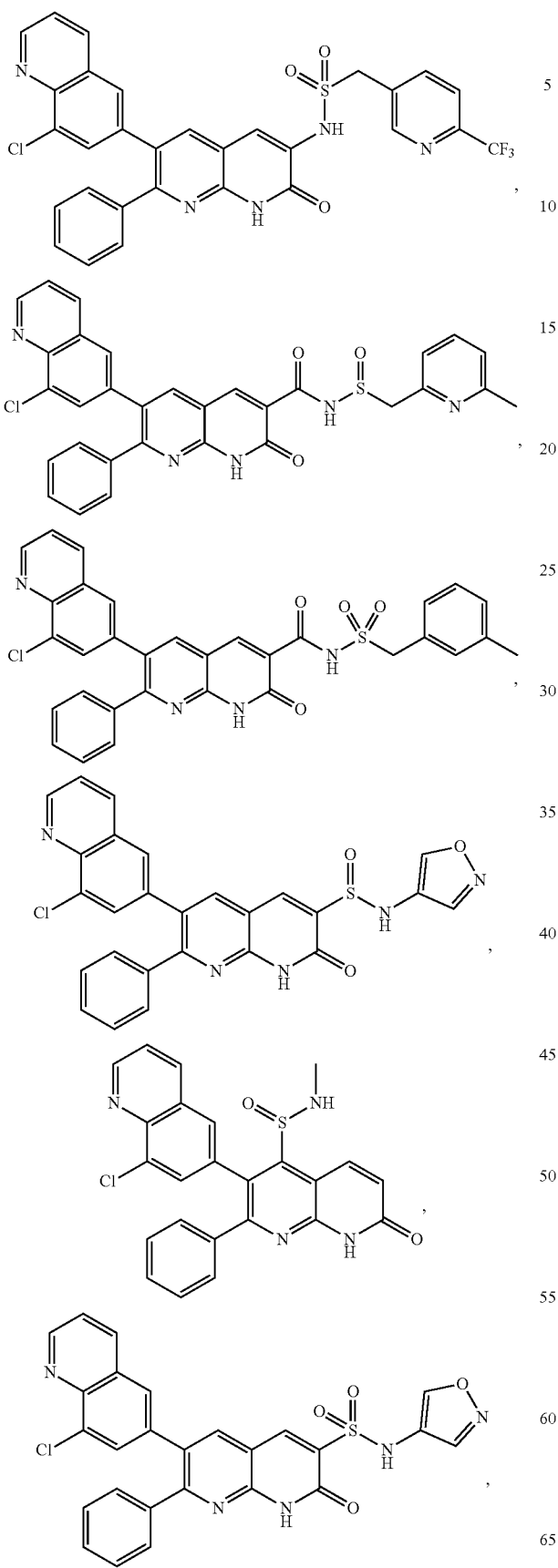
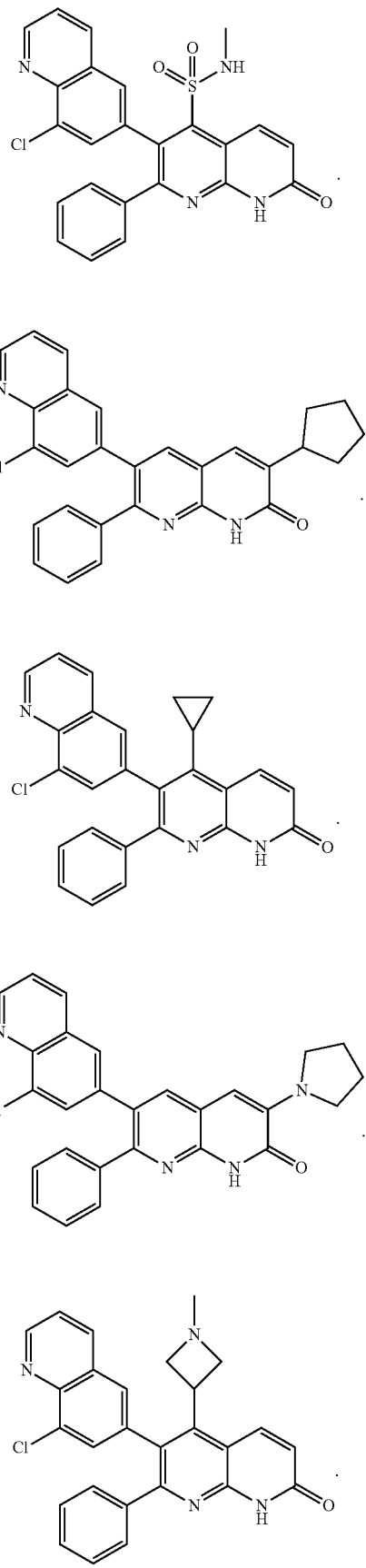

763
-continued
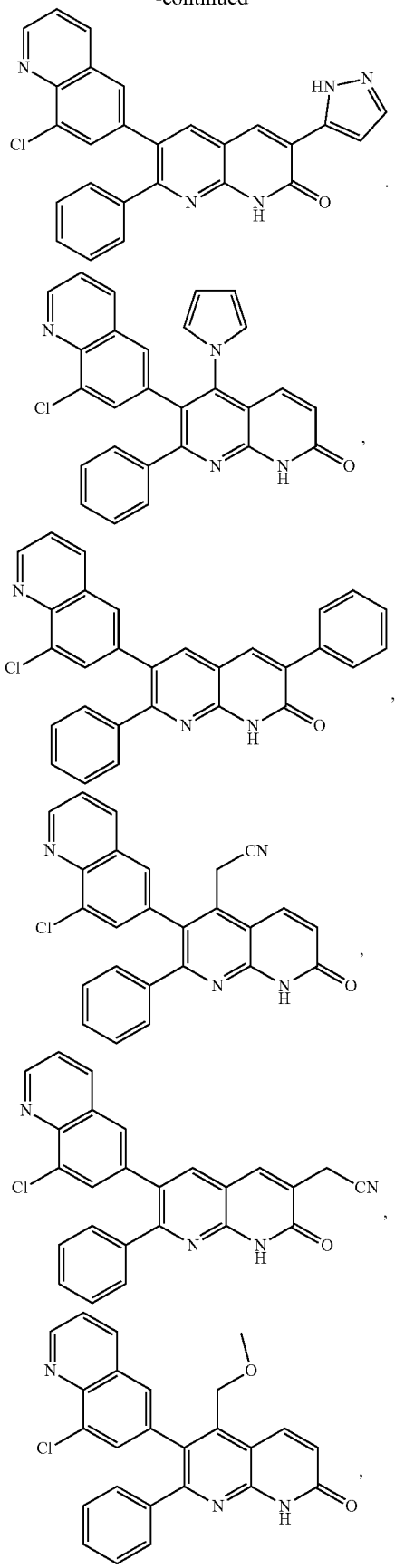
764
-continued
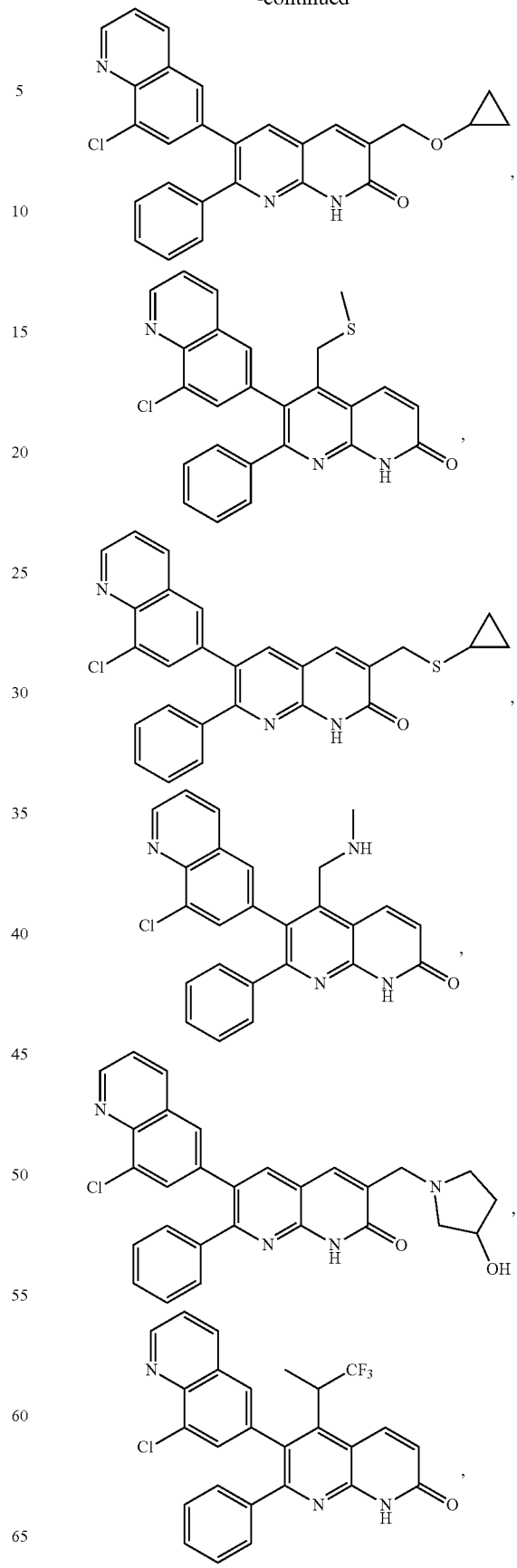

765
-continued
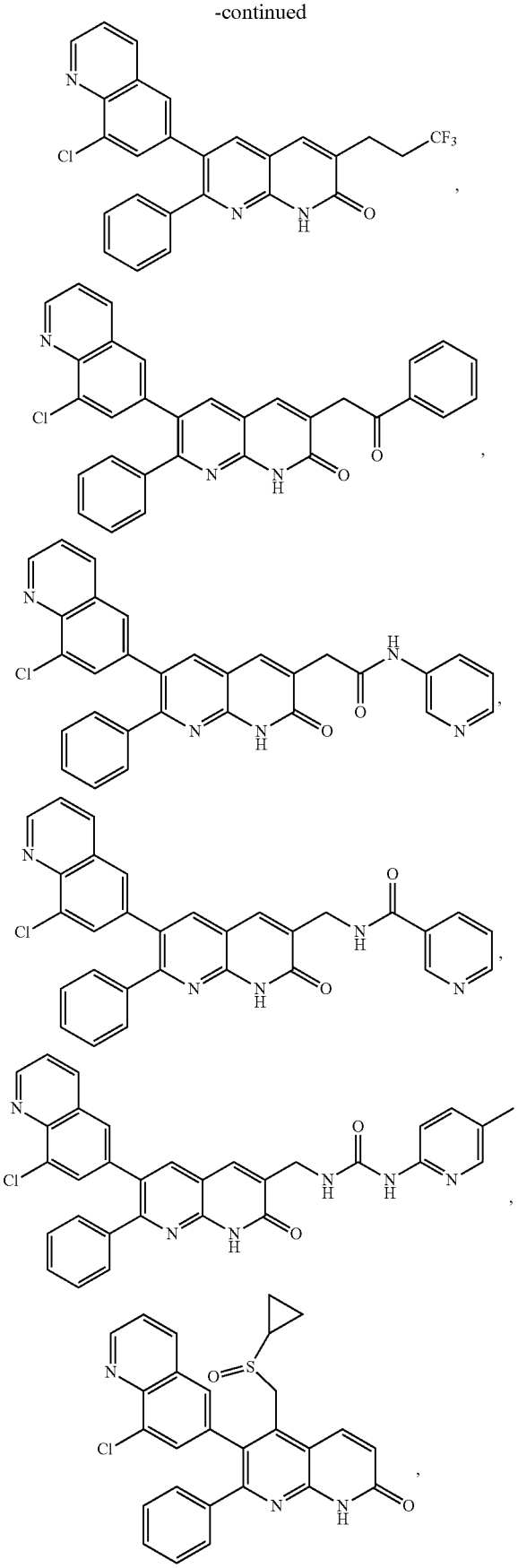
766
-continued
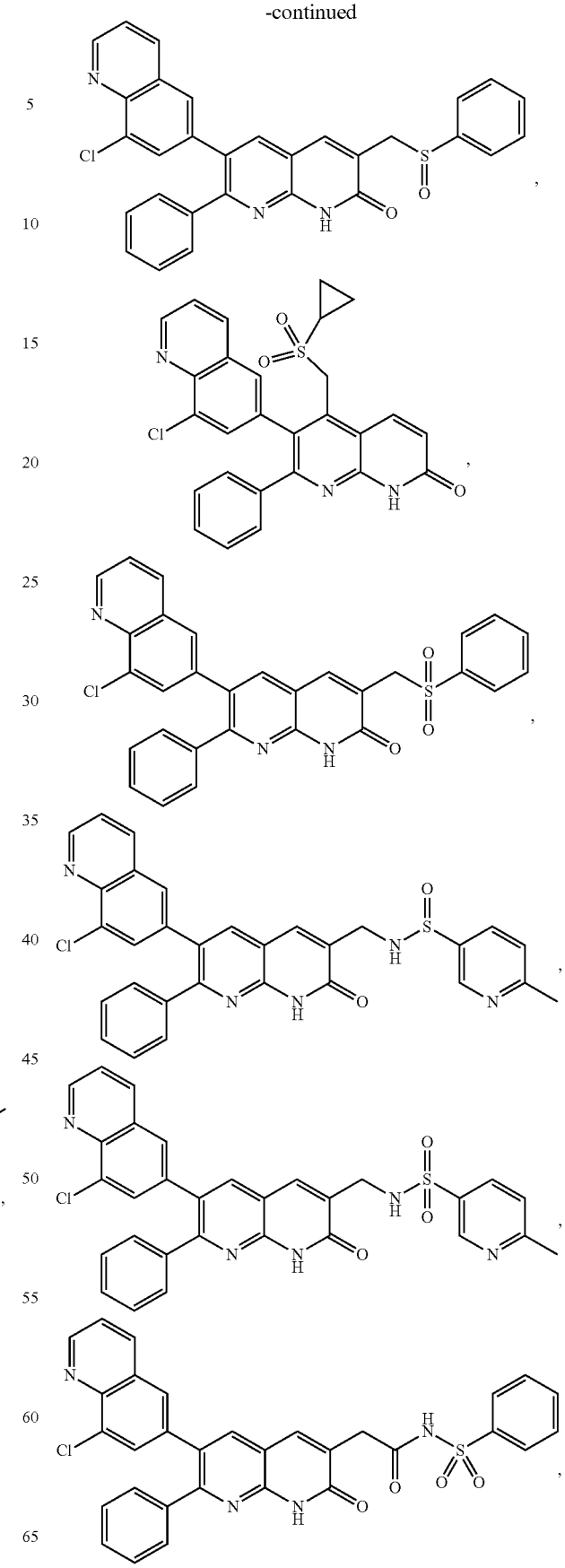

767
-continued
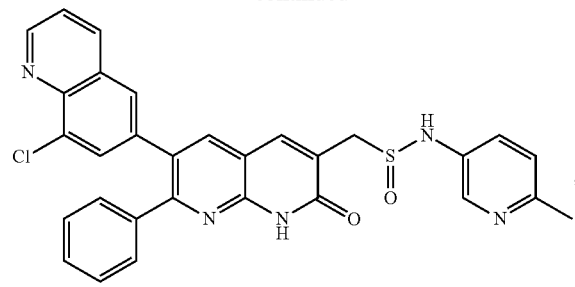
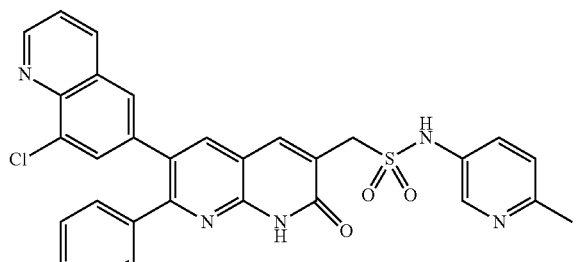
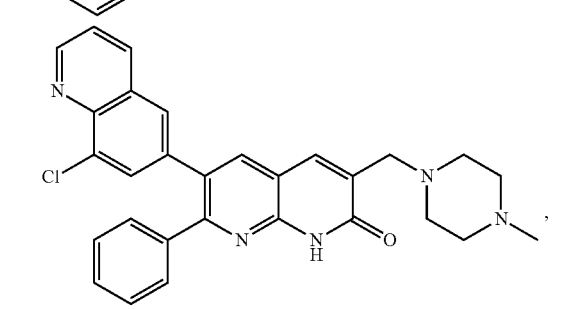
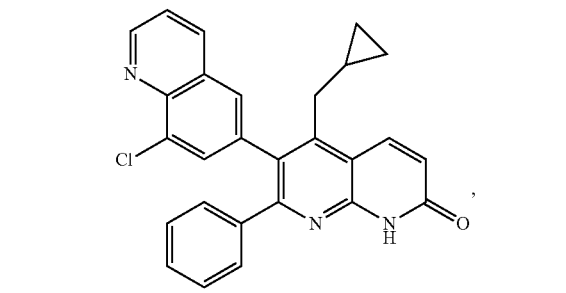
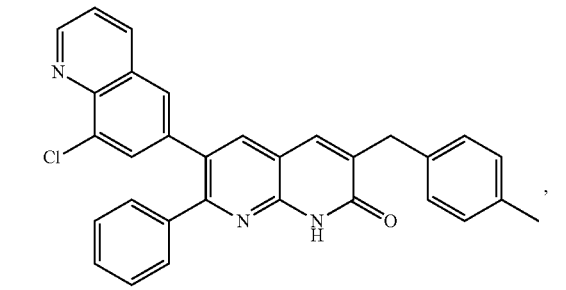
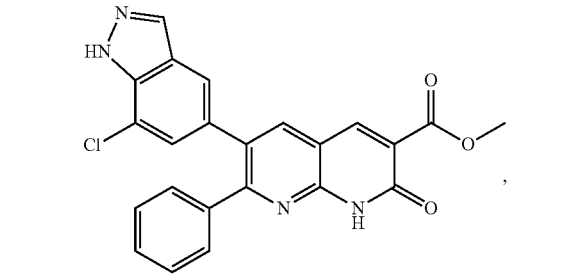
768
-continued
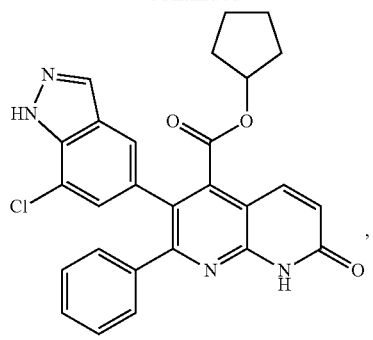
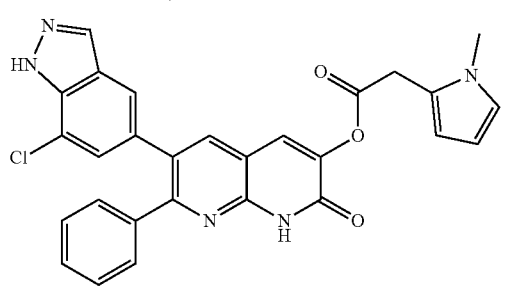
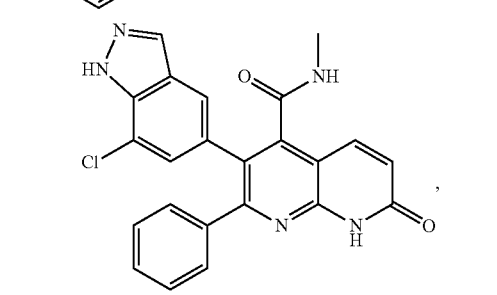
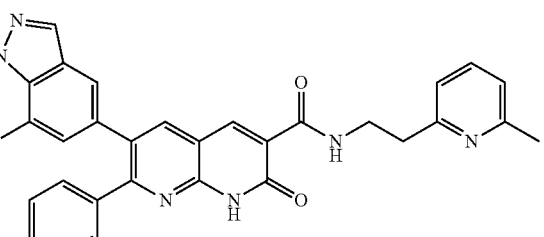
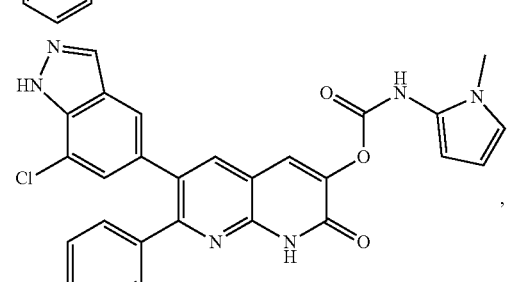
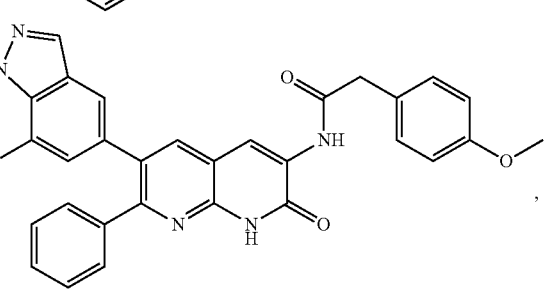

769
-continued
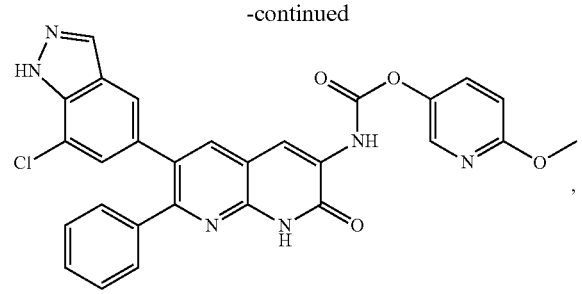,
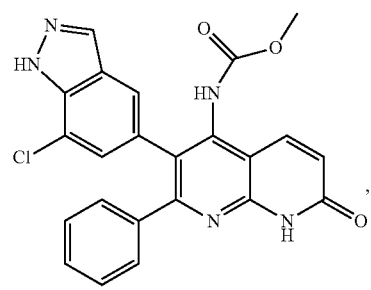,
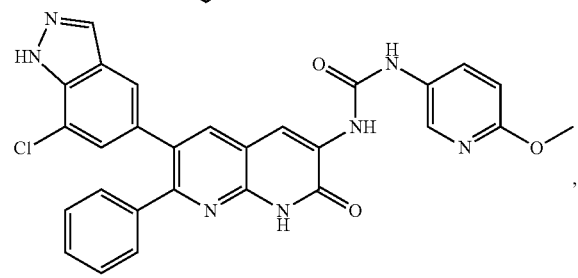,
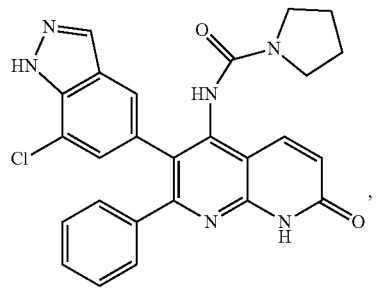,
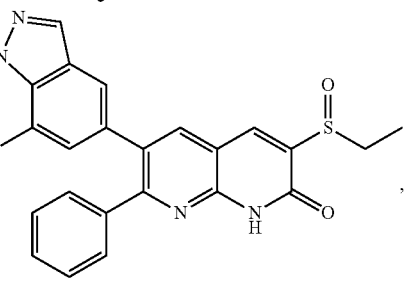,
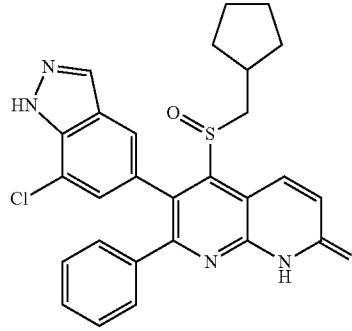,
770
-continued
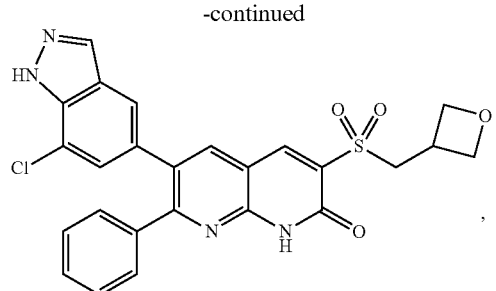,
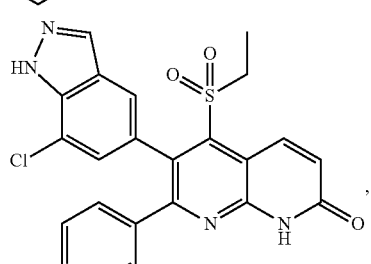,
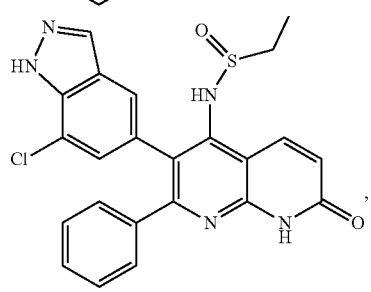
,
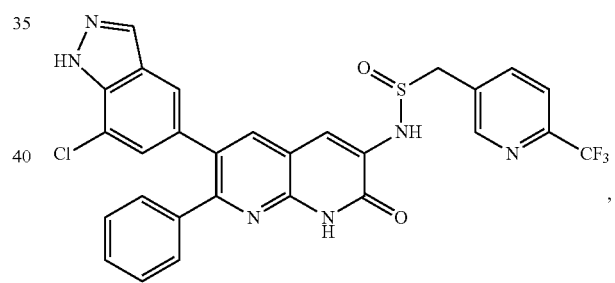,
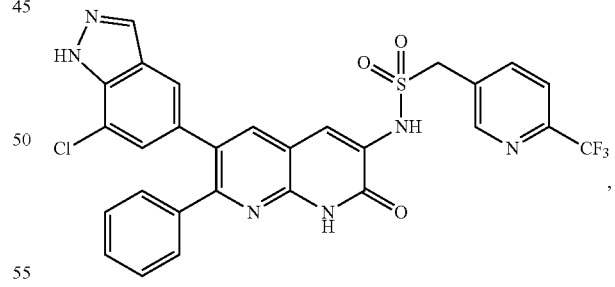,
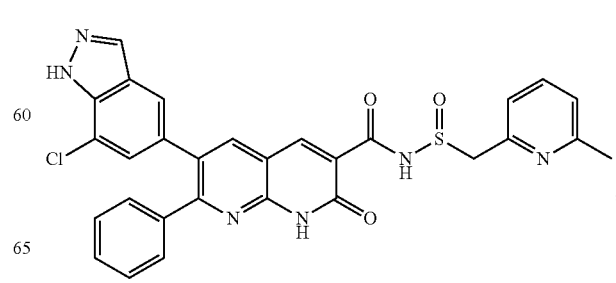, 771
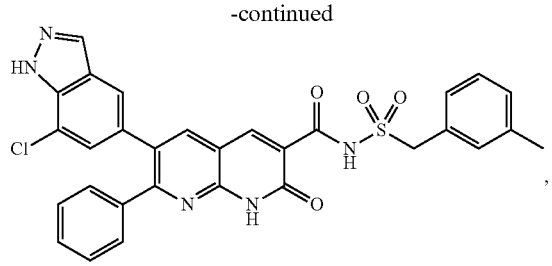
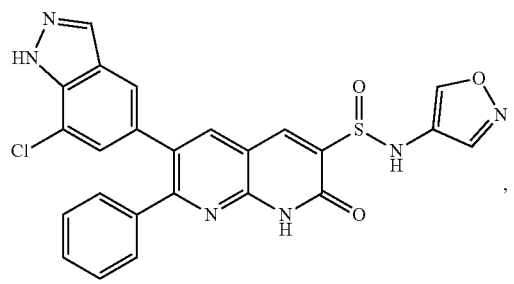
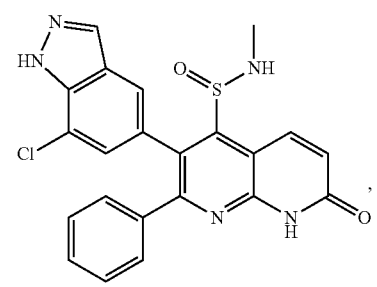
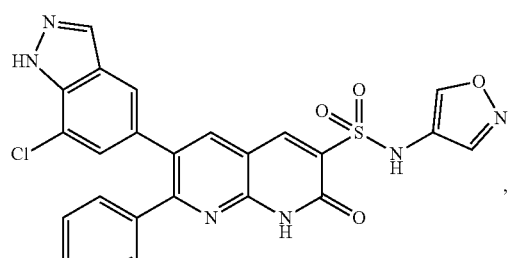
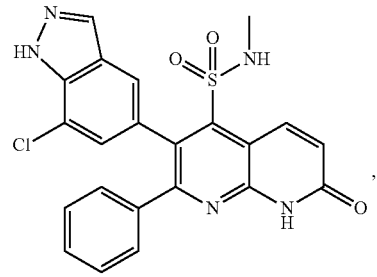
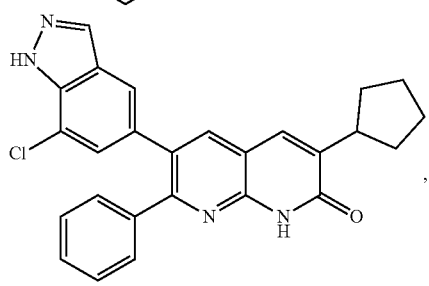
772
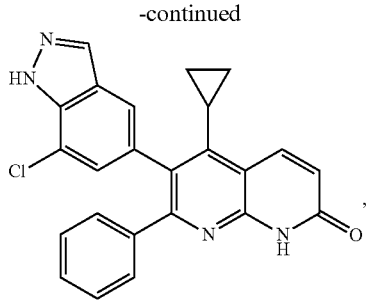
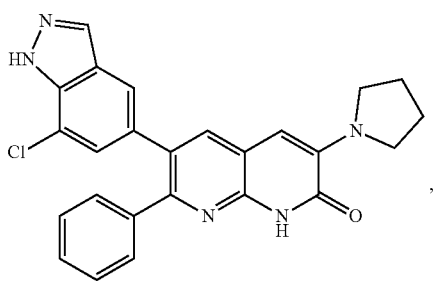
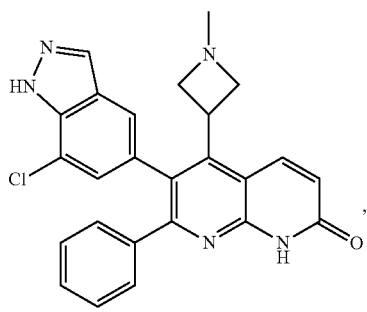
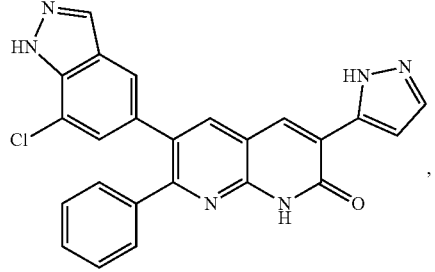
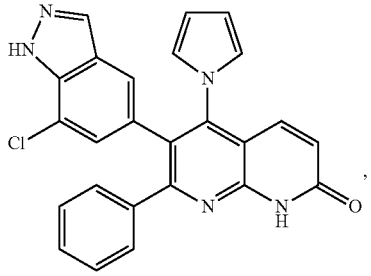
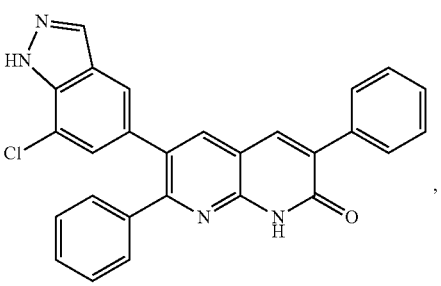

773
-continued
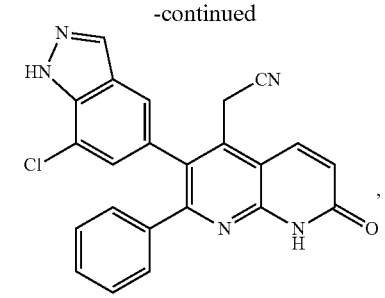
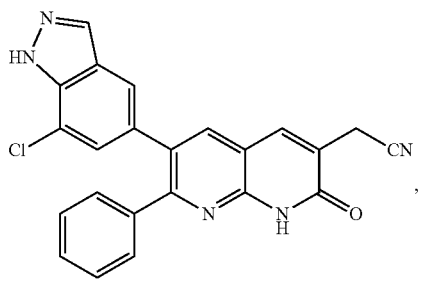
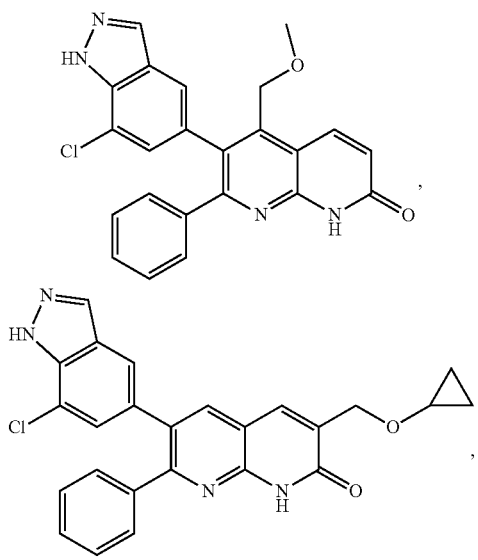
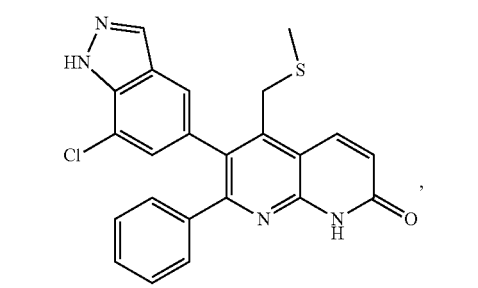
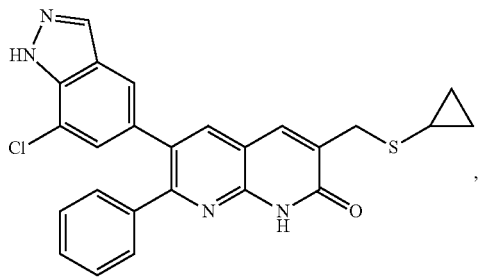
774
-continued
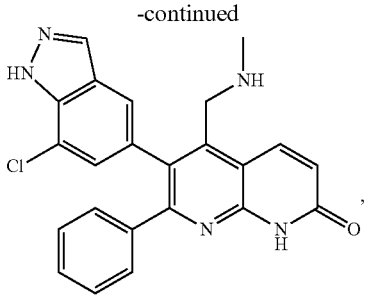
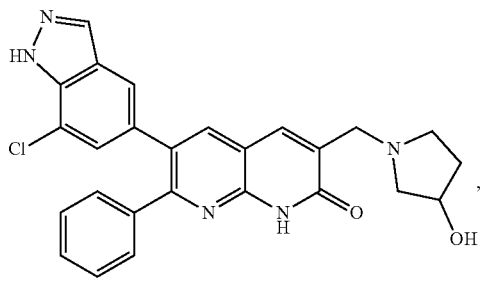
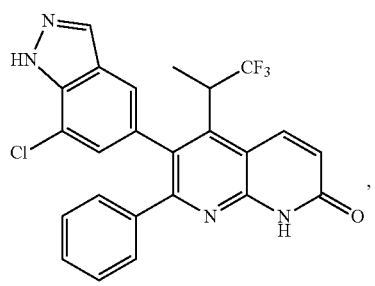
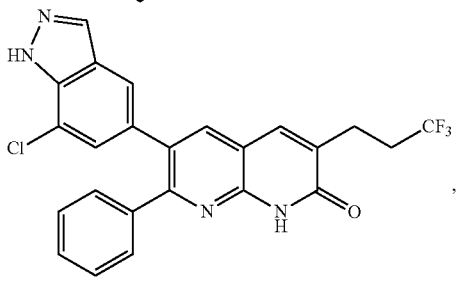
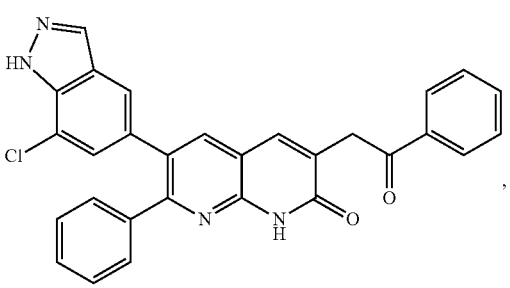
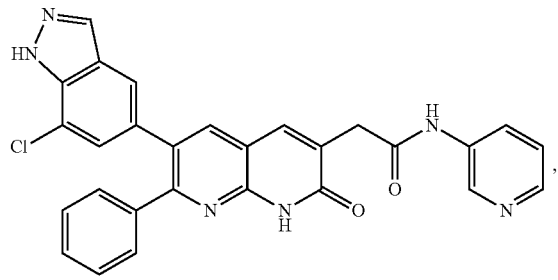

775
-continued
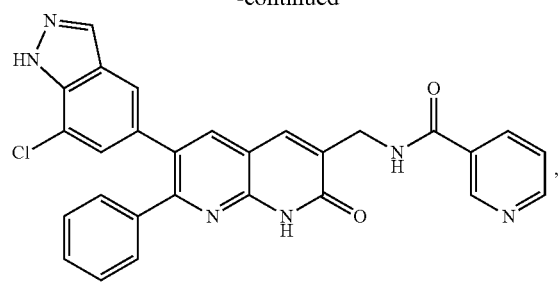
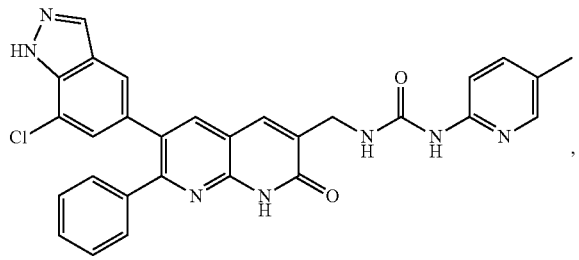
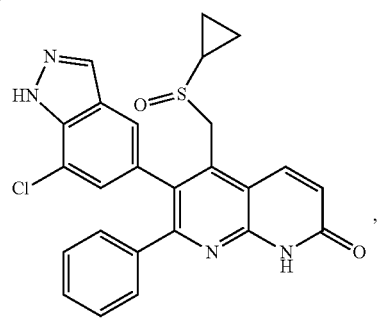
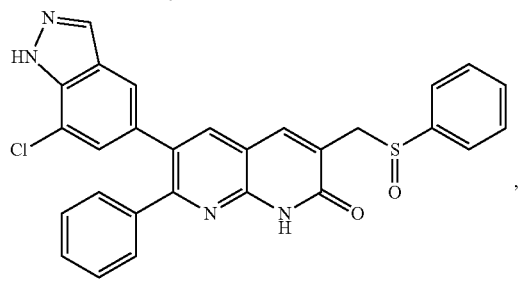
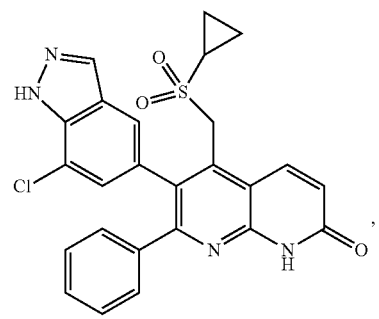
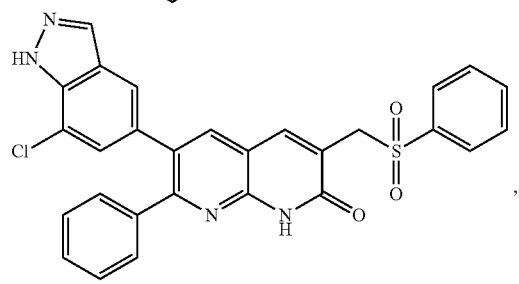
776
-continued
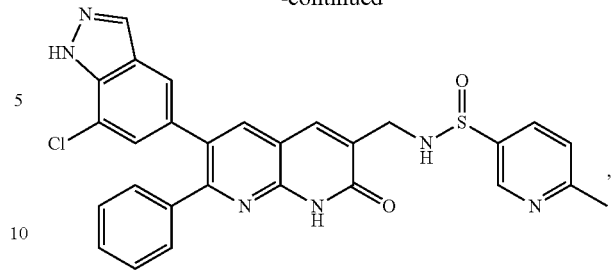
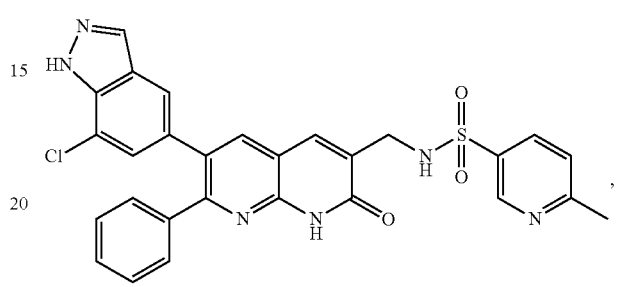
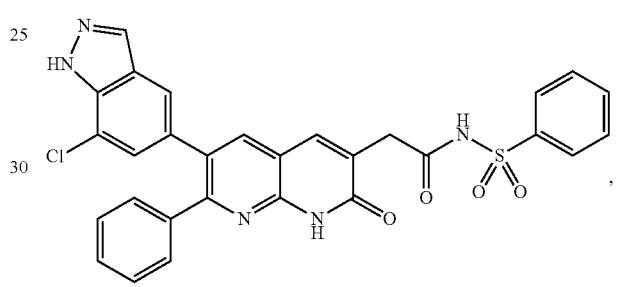
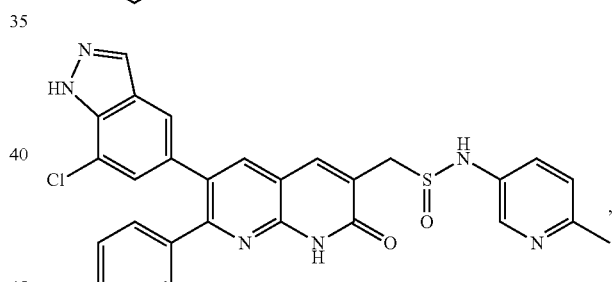
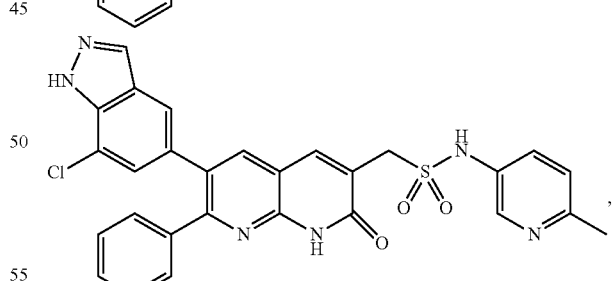
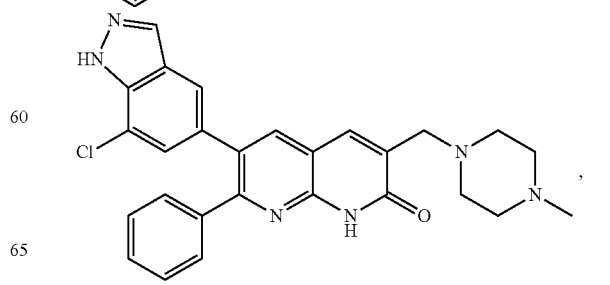

777
-continued
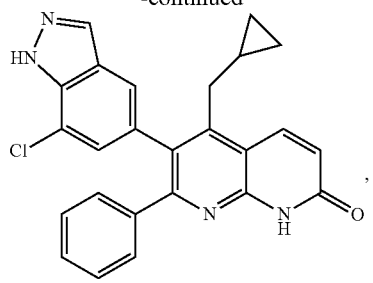,
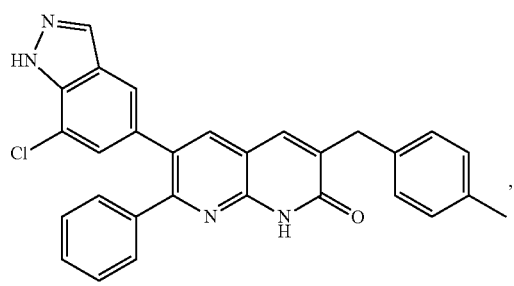,
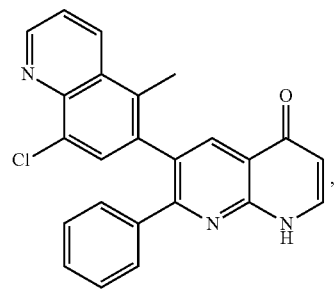,
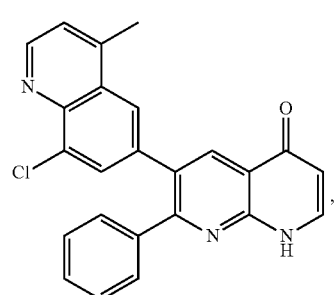,
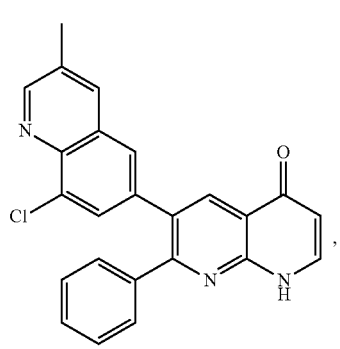,
778
-continued
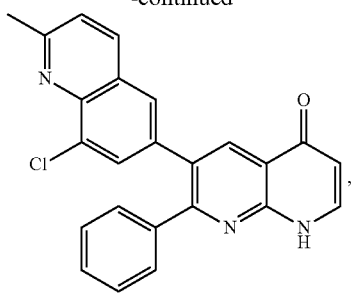,
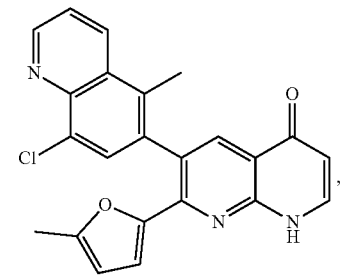,
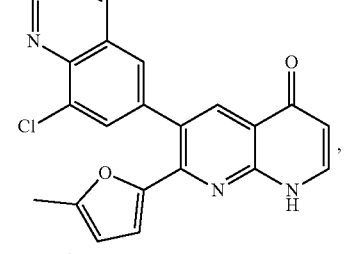,
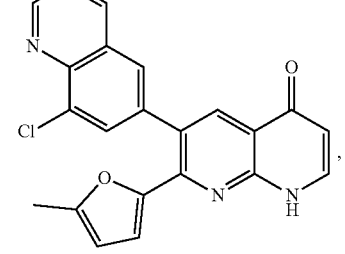,
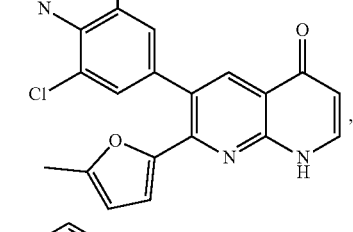,
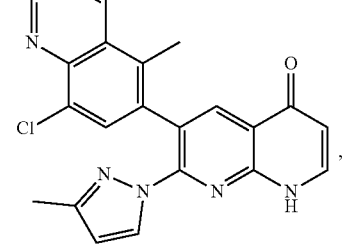, -continued
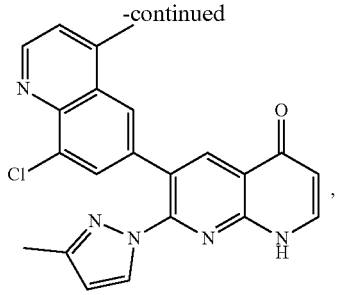
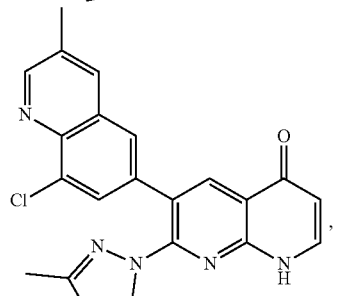
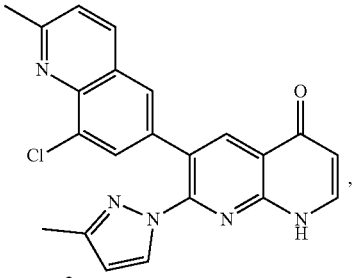
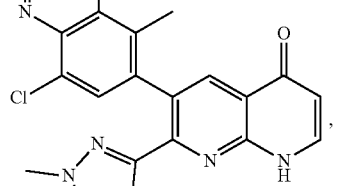
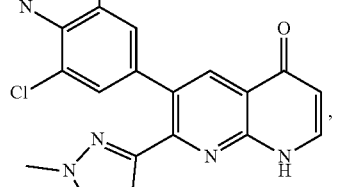
-continued
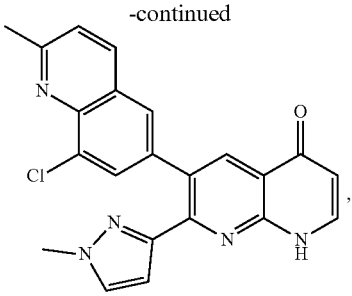
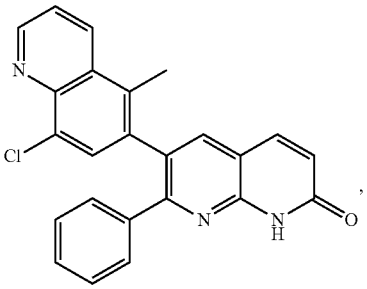
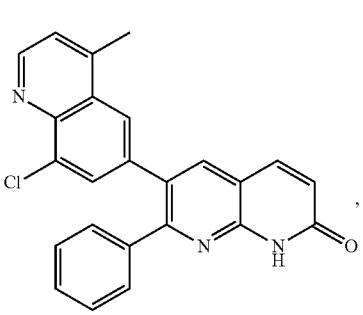
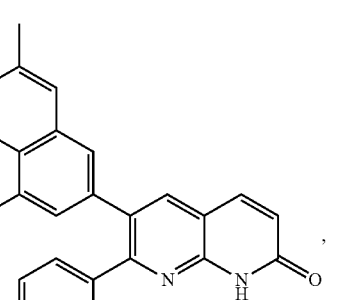, and
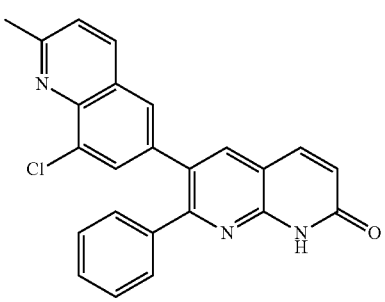
or a tautomer or isomer thereof, or a pharmaceutically acceptable salt of any of the foregoing.
45. The compound of claim 44, wherein the compound is selected from in the group consisting of

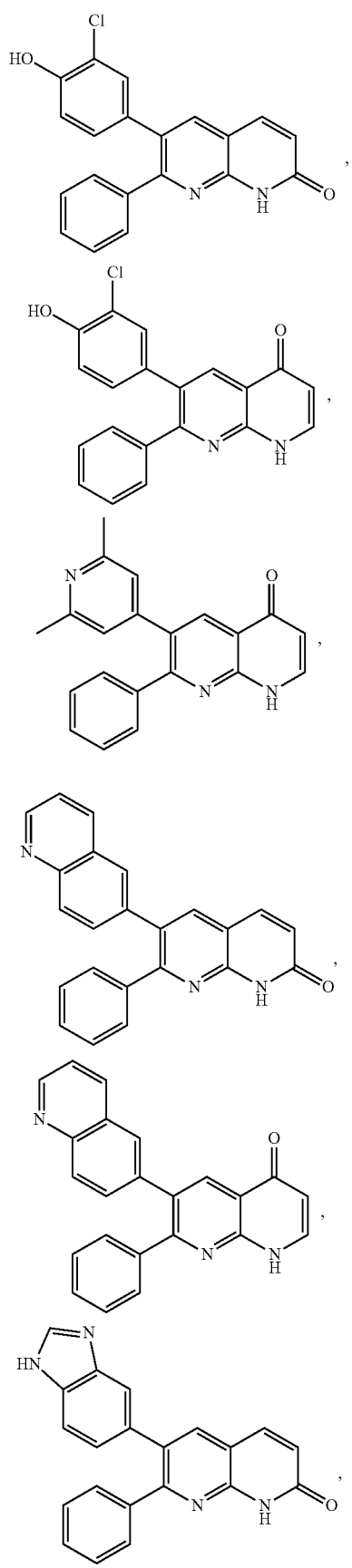
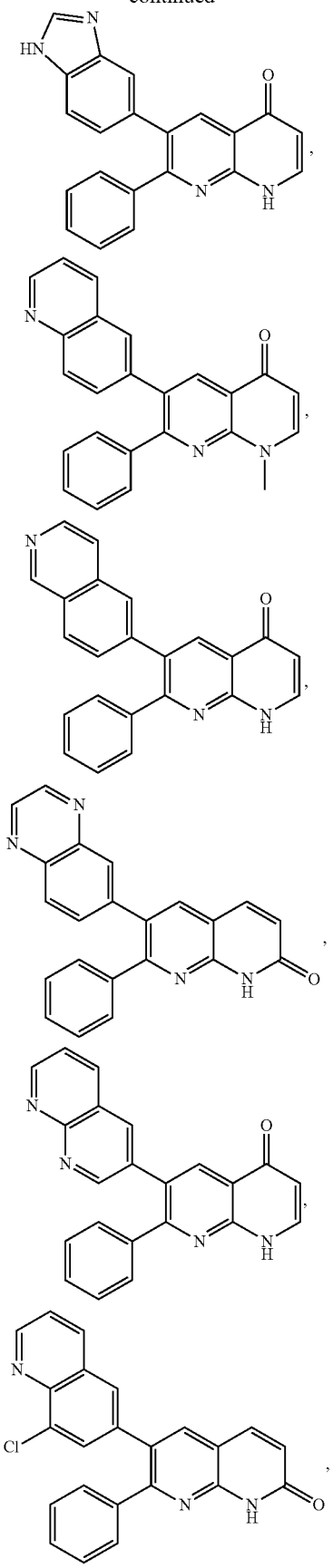

783
-continued
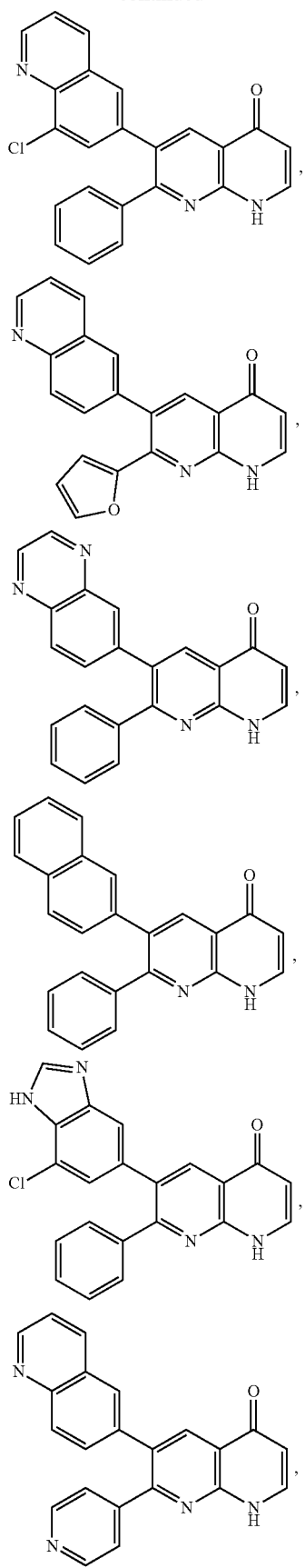
784
-continued
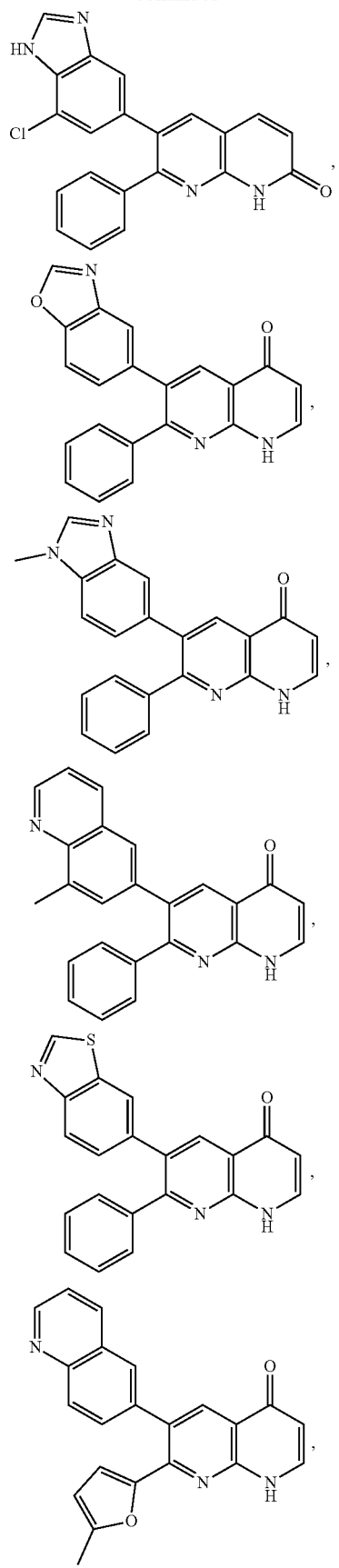

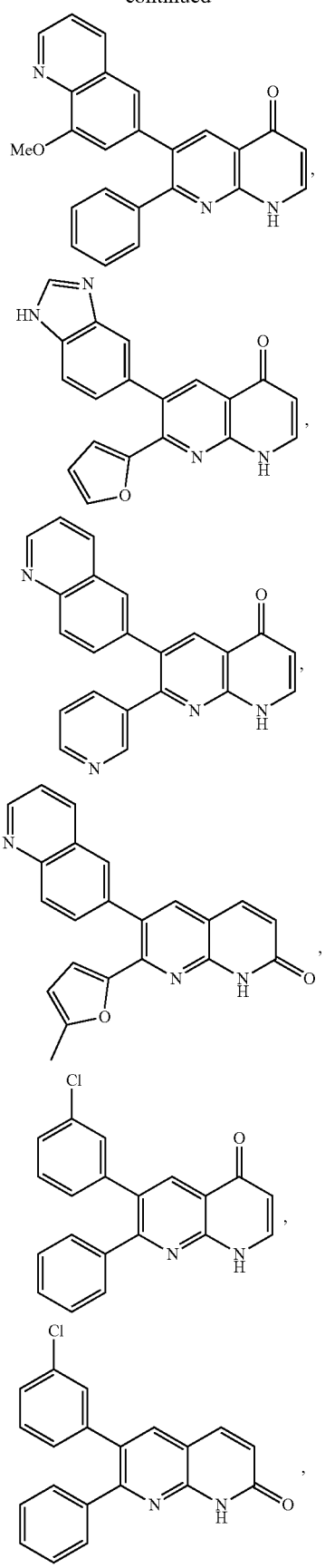
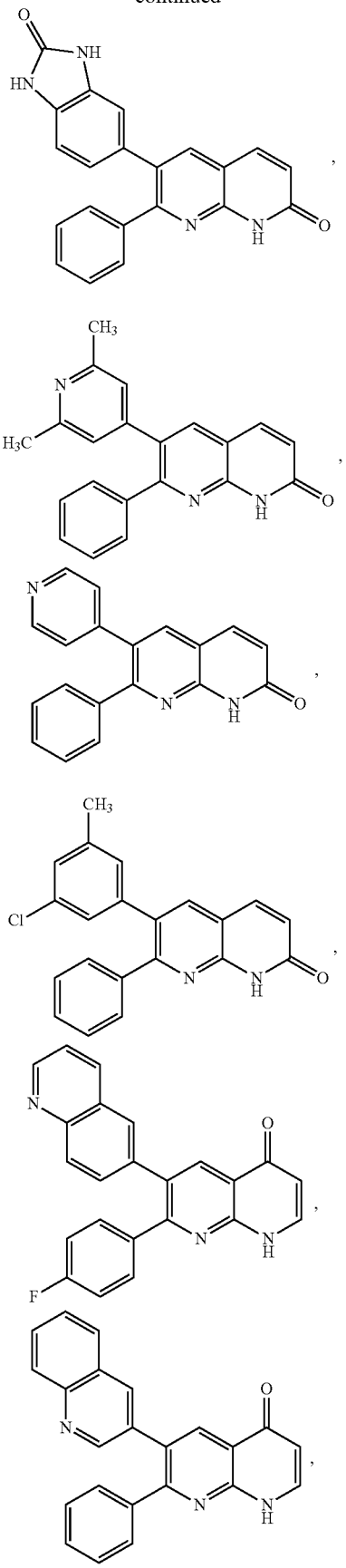

787
-continued
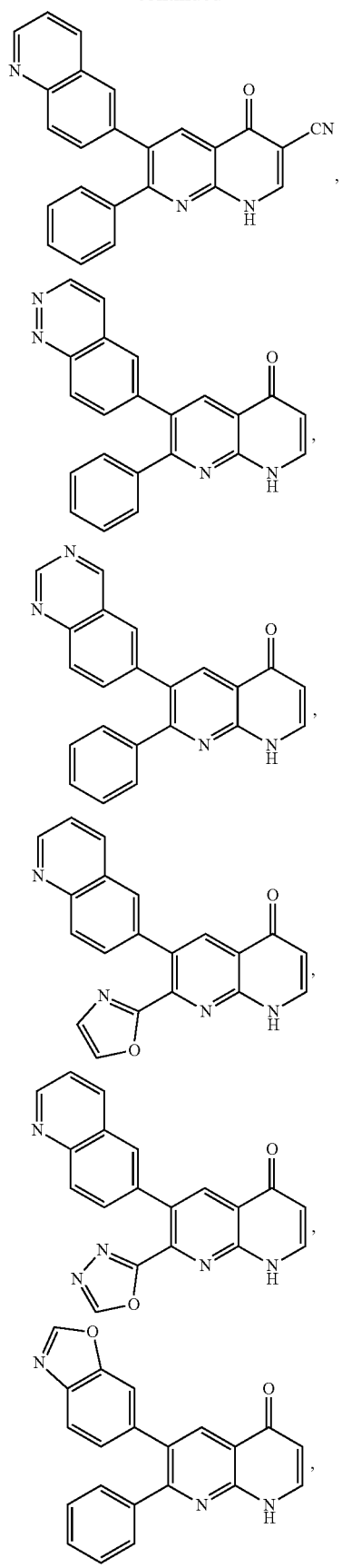
788
-continued
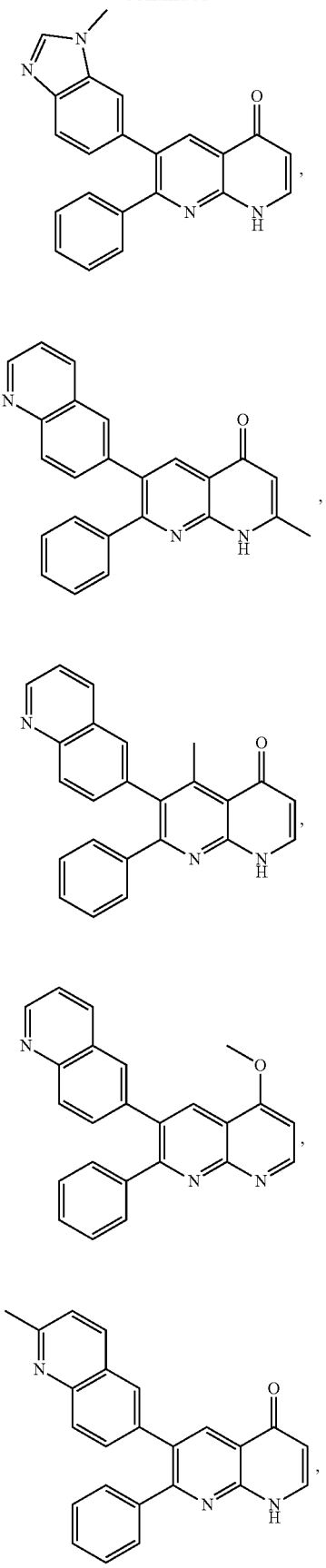

789
-continued
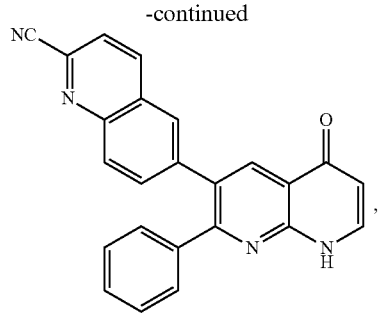
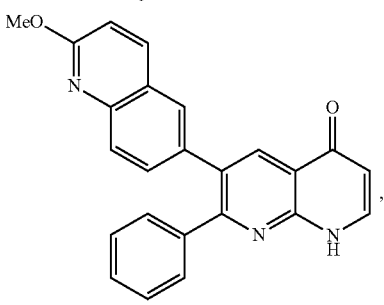
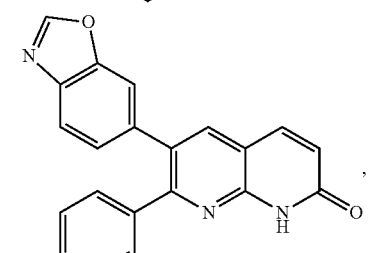
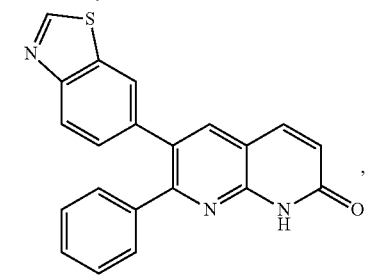
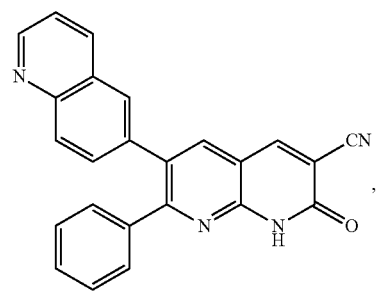
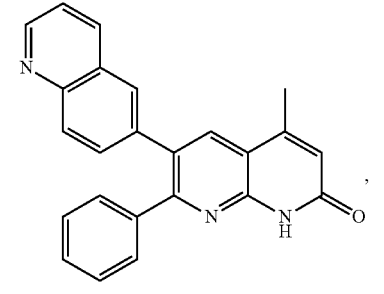
790
-continued
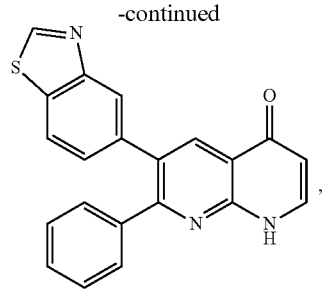
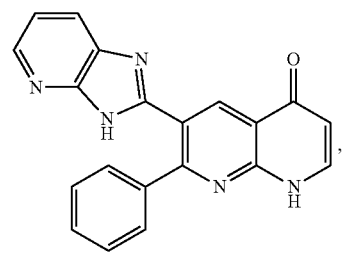
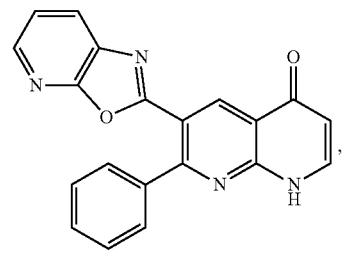
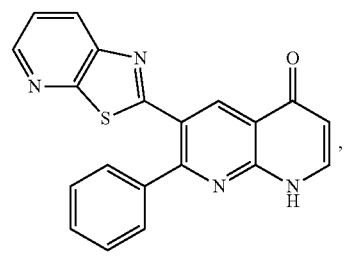
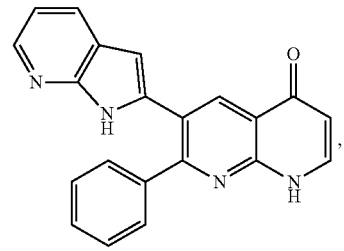
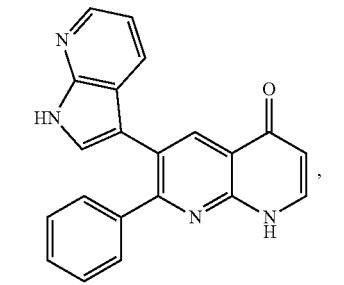

791
-continued
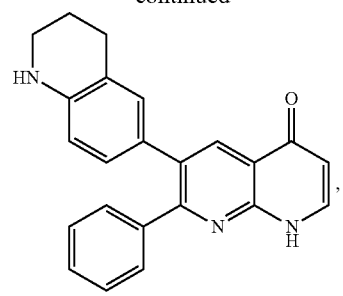,
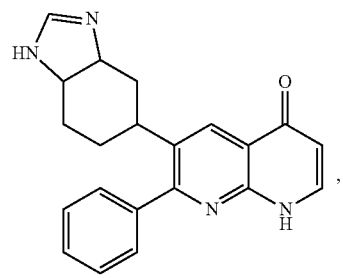,
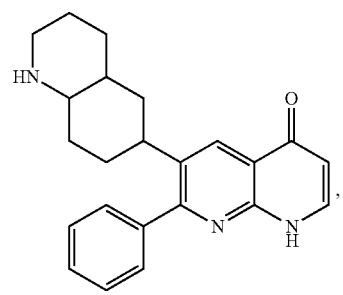,
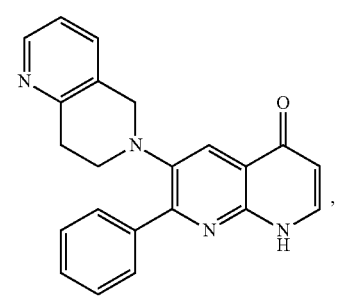,
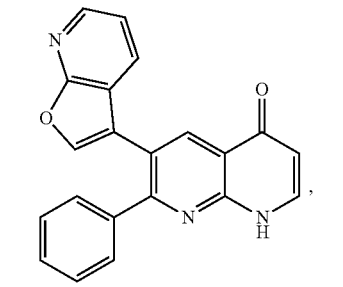,
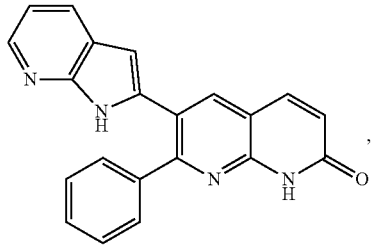,
792
-continued
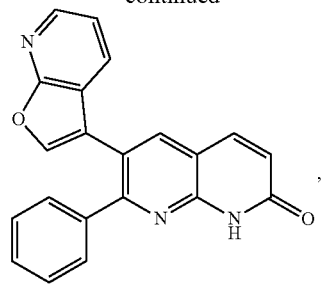,
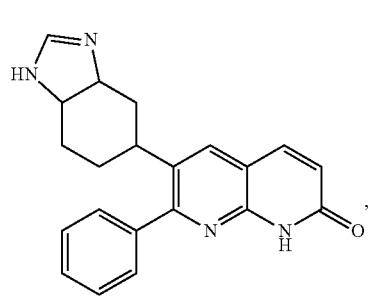,
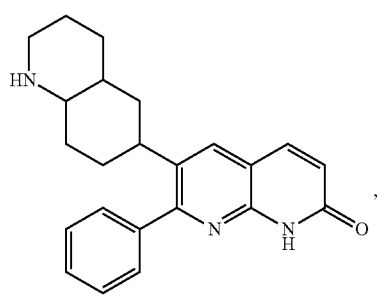,
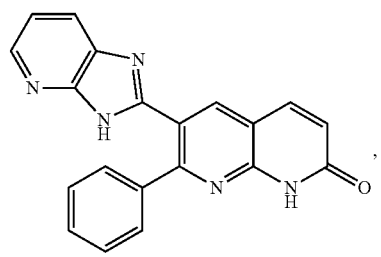,
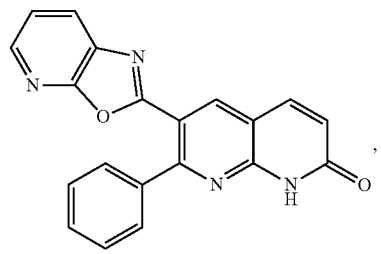,
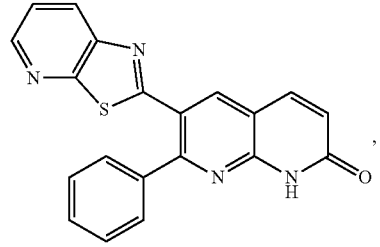,

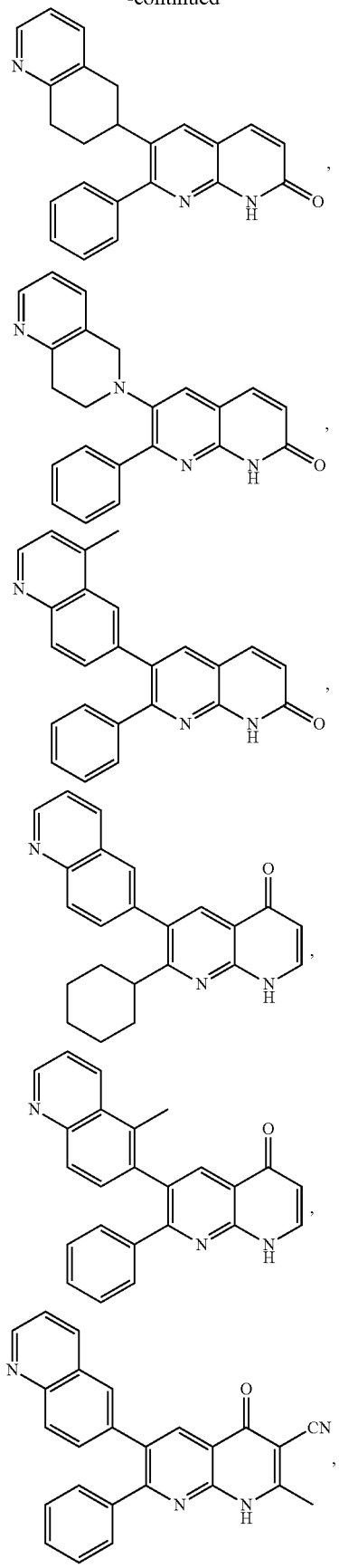
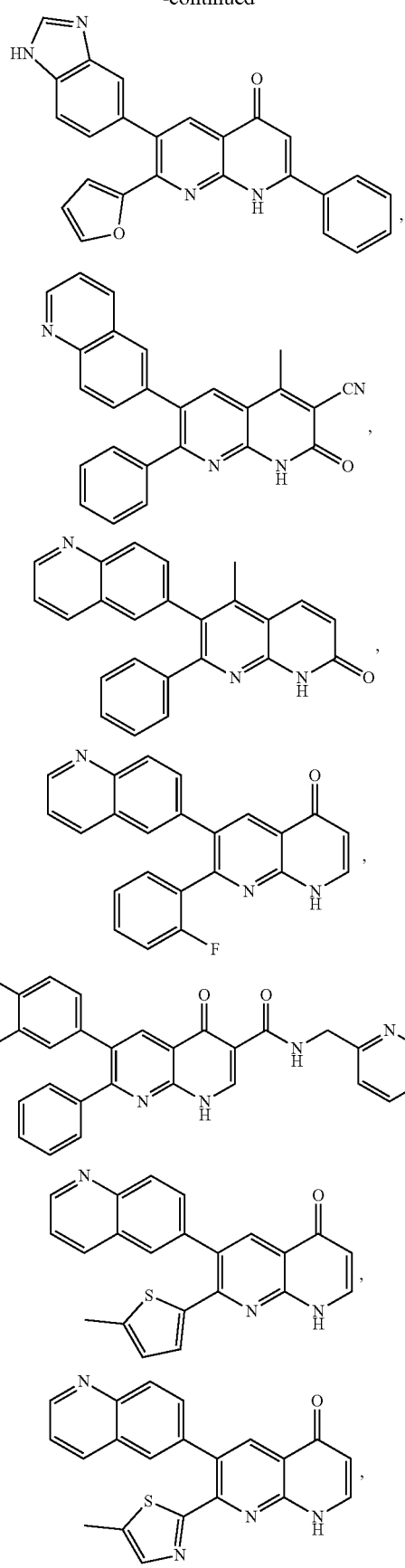

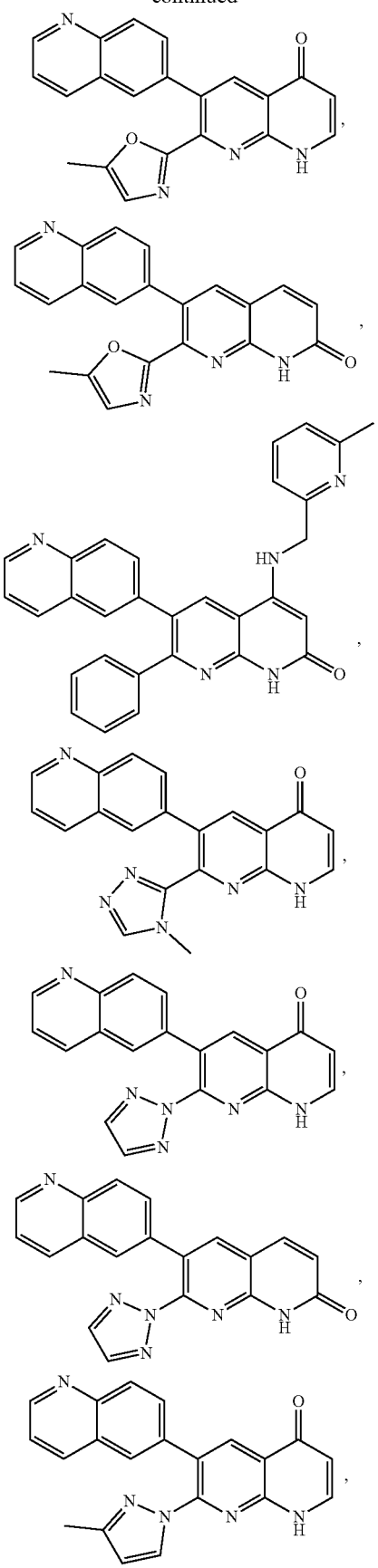
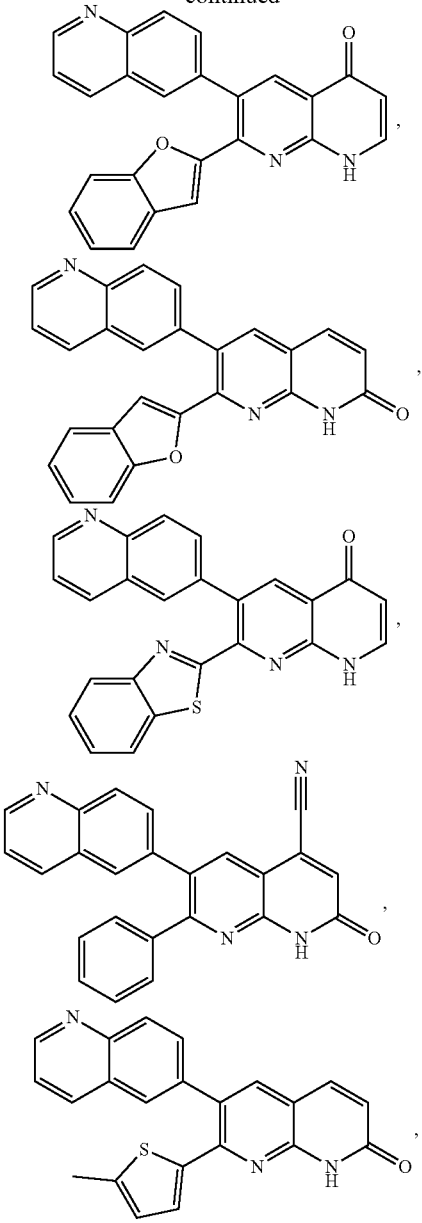

or a tautomer or isomer thereof, or a pharmaceutically acceptable salt of any of the foregoing.

46. The compound of claim 44, or a pharmaceutically acceptable salt thereof.

47. A pharmaceutical composition comprising a compound of claim 1, or a tautomer or isomer thereof, or a pharmaceutically acceptable salt of any of the foregoing, and a pharmaceutically acceptable carrier.

48. A method of treating cancer in an individual in need thereof comprising administering to the individual a therapeutically effective amount of a compound of claim 1, or a tautomer or isomer thereof, or a pharmaceutically acceptable salt of any of the foregoing.

49. A method of inhibiting adenosine receptors of subtypes $A_{2a}$, $A_{2b}$ or $A_3$ in a cell, comprising administering a compound of claim 1, or a tautomer or isomer thereof, or a pharmaceutically acceptable salt of any of the foregoing, to the cells.

50. The method of claim 49, wherein the adenosine receptors are of subtype $A_{2a}$.

51. A kit comprising a compound of claim 1, or a tautomer or isomer thereof, or a pharmaceutically acceptable salt of any of the foregoing.

52. The compound of claim 44, wherein the compound is selected from the group consisting of:

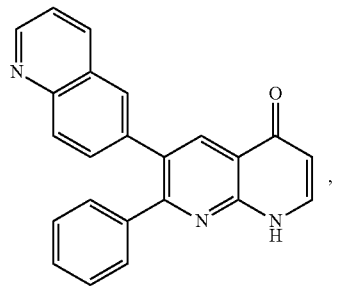 [SMILES: O=c1cc[nH]c2nc(-c3ccccc3)c(-c3ccc4cnccc4c3)cc12]

,

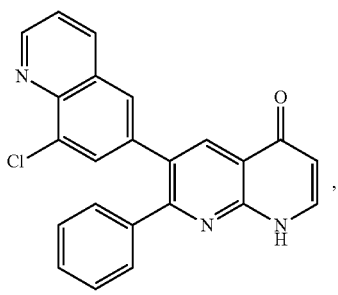 [SMILES: O=c1cc[nH]c2nc(-c3ccccc3)c(-c3cc(Cl)c4ncccc4c3)cc12]

,

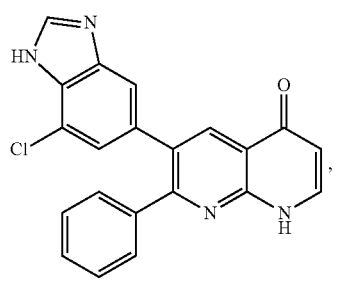

,

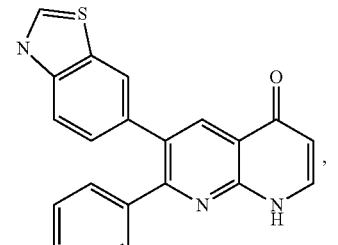

,

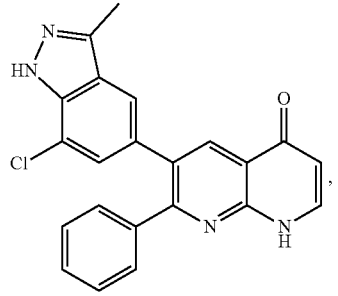

,

-continued

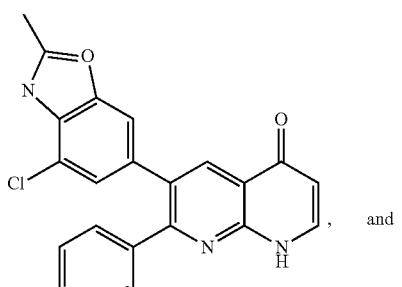

, and

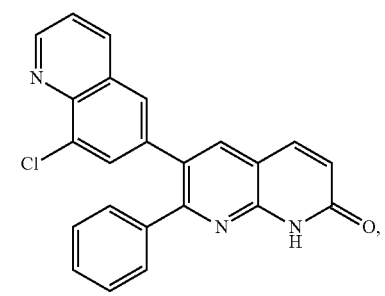

, or a pharmaceutically acceptable salt thereof.

53. The compound of claim 44, wherein the compound is selected from the group consisting of:

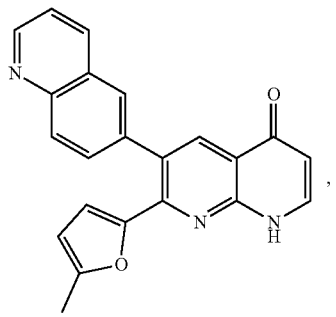

,

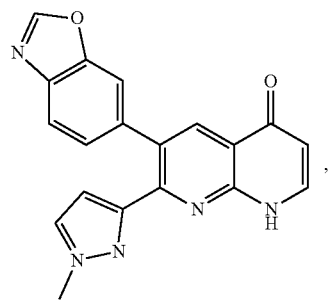

,

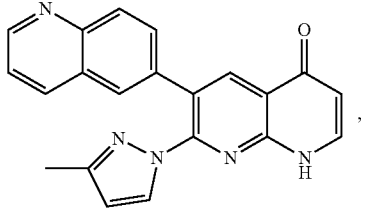

,

-continued
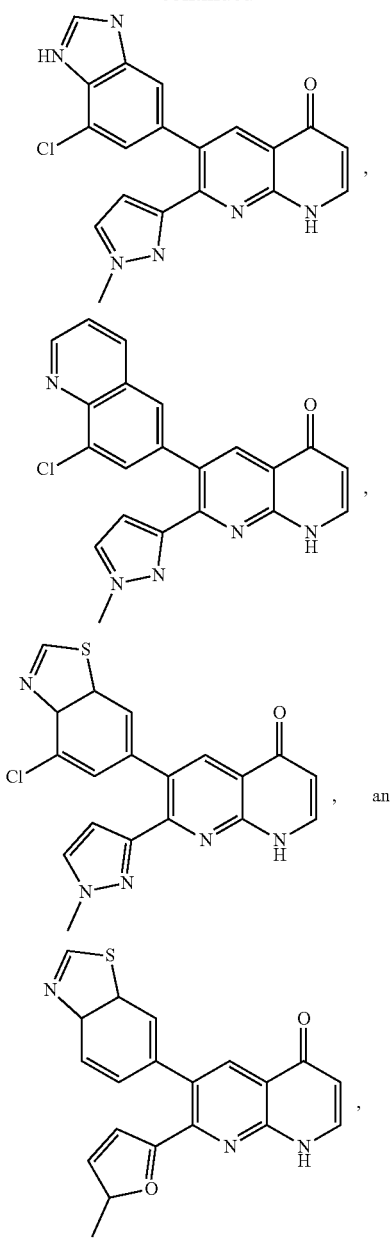
or a pharmaceutically acceptable salt thereof.
54. The compound of claim 44, wherein the compound is selected from the group consisting of:
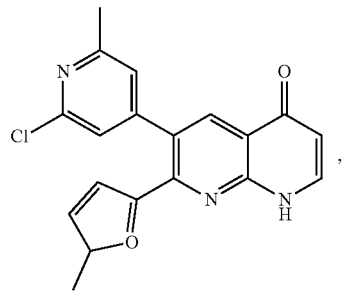
-continued
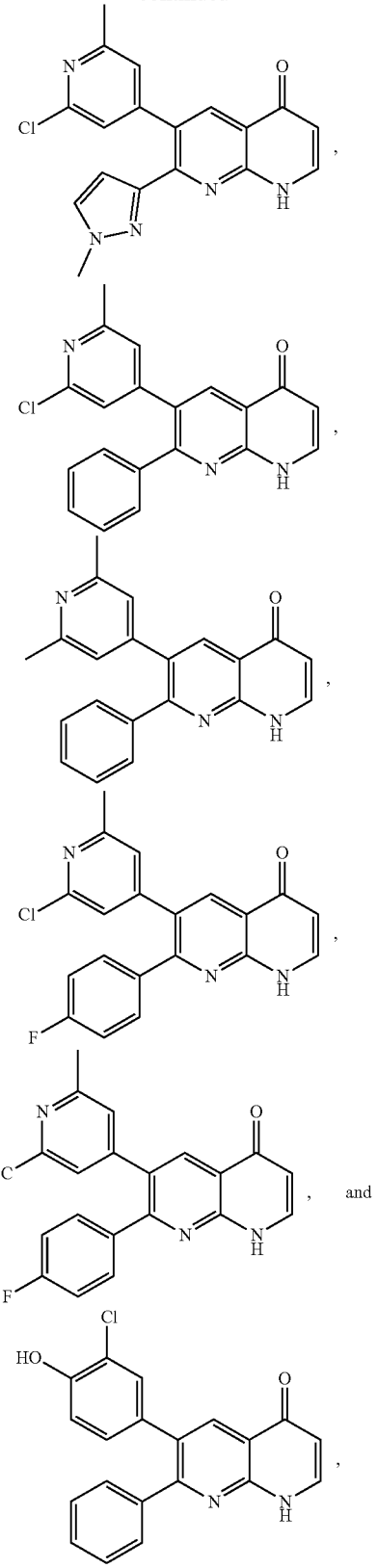
or a pharmaceutically acceptable salt thereof.
55. The compound of claim 44, wherein the compound is selected from the group consisting of:

801
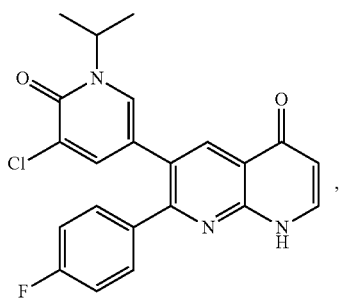
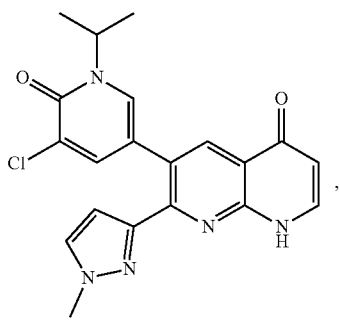
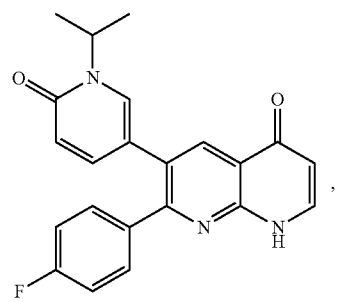
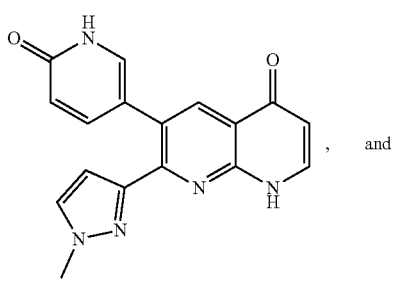 and
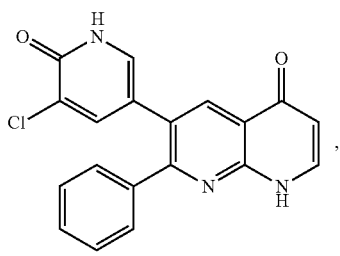
or a pharmaceutically acceptable salt thereof.
56. The compound of claim 44, wherein the compound is selected from the group consisting of:
802
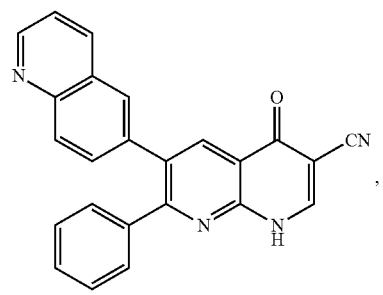
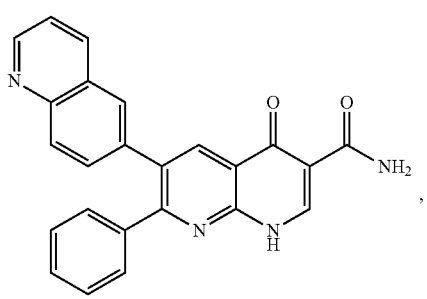
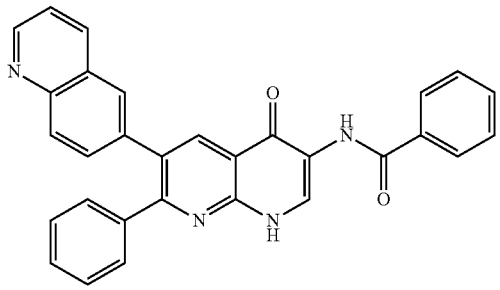
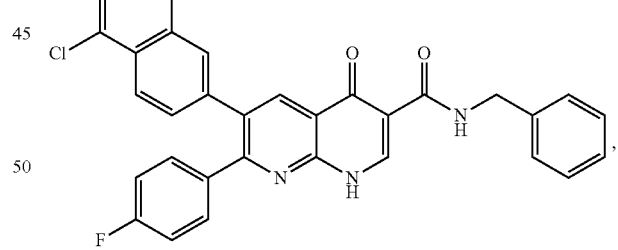
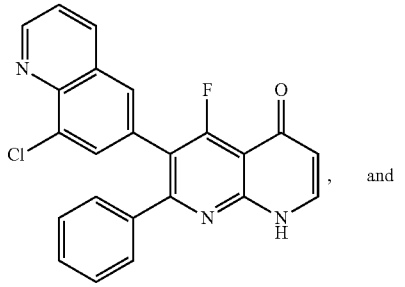 and -continued

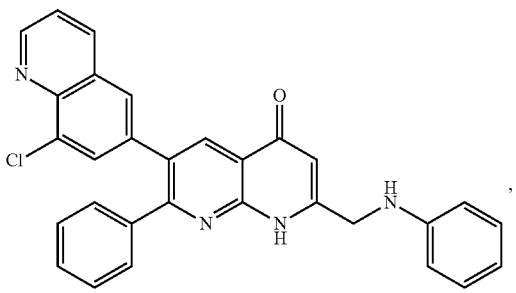

or a pharmaceutically acceptable salt thereof.

57. The compound of claim 44, wherein the compound is

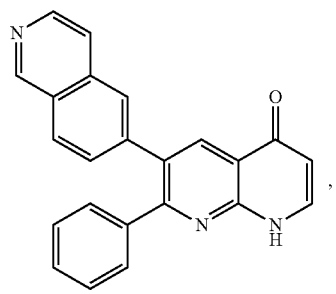

or a pharmaceutically acceptable salt thereof.

58. The compound of claim 44, wherein the compound is

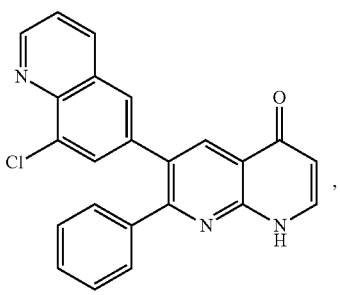

or a pharmaceutically acceptable salt thereof.

59. The compound of claim 44, wherein the compound is

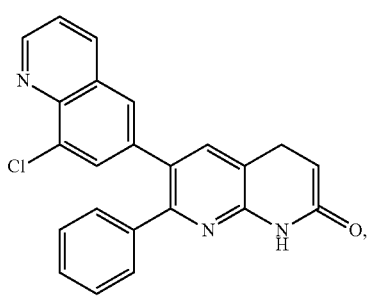

or a pharmaceutically acceptable salt thereof.

60. The compound of claim 44, wherein the compound is

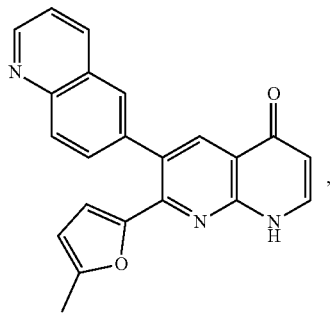 [SMILES: Cc1ccc(-c2nc3[nH]ccc(=O)c3cc2-c2ccc3ncccc3c2)o1]

or a pharmaceutically acceptable salt thereof.

61. The compound of claim 44, wherein the compound is

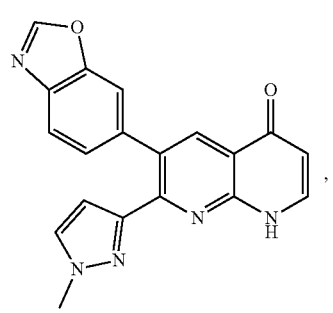 [SMILES: Cn1ccc(-c2nc3[nH]ccc(=O)c3cc2-c2ccc3ncoc3c2)n1]

or a pharmaceutically acceptable salt thereof.

62. The compound of claim 44, wherein the compound is

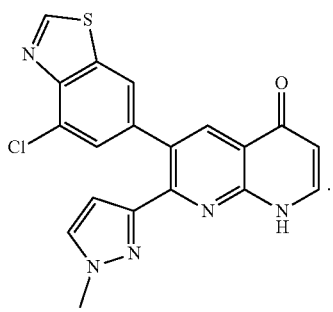 [SMILES: Cn1ccc(-c2nc3[nH]ccc(=O)c3cc2-c2cc(Cl)c3ncsc3c2)n1 ; "."]

or a pharmaceutically acceptable salt thereof.

63. The compound of claim 44, wherein the compound is

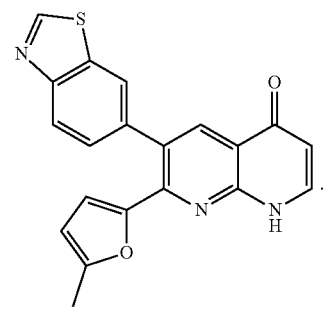 [SMILES: Cc1ccc(-c2nc3[nH]ccc(=O)c3cc2-c2ccc3ncsc3c2)o1 ; "."]

or a pharmaceutically acceptable salt thereof.

64. The compound of claim 44, wherein the compound is

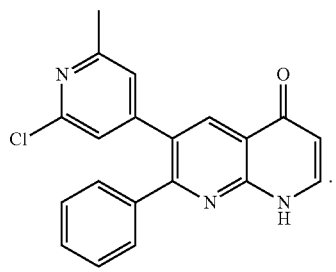 [SMILES: Cc1cc(-c2cc3c(=O)cc[nH]c3nc2-c2ccccc2)cc(Cl)n1 ; "."]

or a pharmaceutically acceptable salt thereof.

65. The compound of claim 44, or a pharmaceutically acceptable salt thereof, wherein the compound is

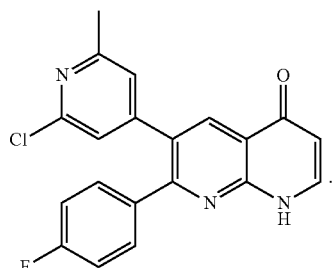

or a pharmaceutically acceptable salt thereof.

66. The compound of claim 44, wherein the compound is

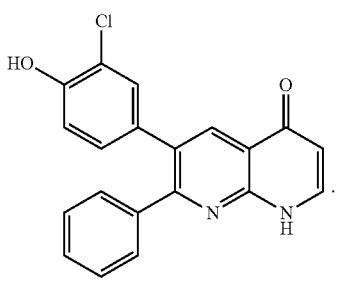 [SMILES: O=c1cc[nH]c2nc(-c3ccccc3)c(-c3ccc(O)c(Cl)c3)cc12 ; "."]

or a pharmaceutically acceptable salt thereof.

67. The compound of claim 44, wherein the compound is

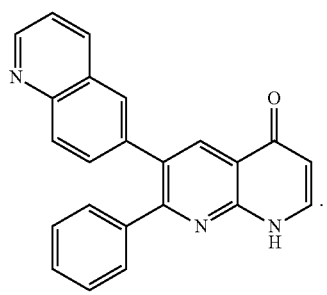 [SMILES: O=c1cc[nH]c2nc(-c3ccccc3)c(-c3ccc4ncccc4c3)cc12 ; "."]

68. The compound of claim 44, wherein the compound is

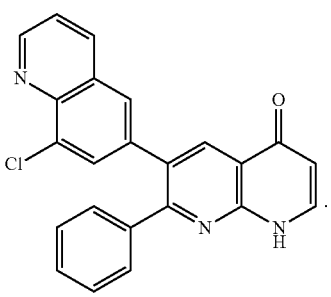 [SMILES: O=c1cc[nH]c2nc(-c3ccccc3)c(-c3cc(Cl)c4ncccc4c3)cc12 ; "."]

69. The compound of claim 44, wherein the compound is

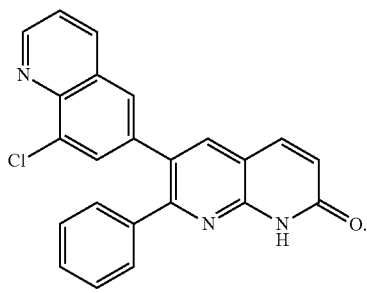 [SMILES: O=c1ccc2cc(-c3cc(Cl)c4ncccc4c3)c(-c3ccccc3)nc2[nH]1]

70. The compound of claim 44, wherein the compound is

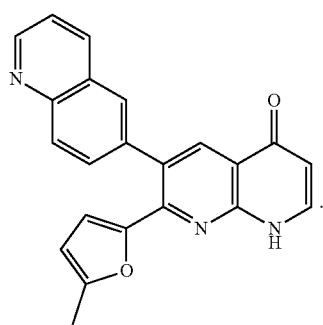 [SMILES: Cc1ccc(-c2nc3[nH]ccc(=O)c3cc2-c2ccc3ncccc3c2)o1 ; "."]

71. The compound of claim 44, wherein the compound is
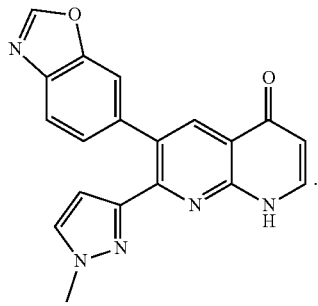 [SMILES: Cn1ccc(-c2nc3[nH]ccc(=O)c3cc2-c2ccc3ncoc3c2)n1 ; "."]
72. The compound of claim 44, wherein the compound is
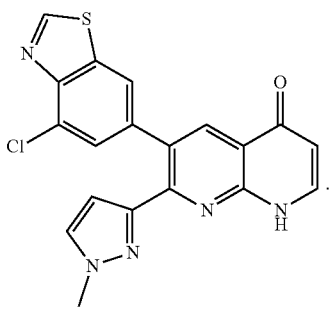 [SMILES: Cn1ccc(-c2nc3[nH]ccc(=O)c3cc2-c2cc(Cl)c3ncsc3c2)n1 ; "."]
73. The compound of claim 44, wherein the compound is
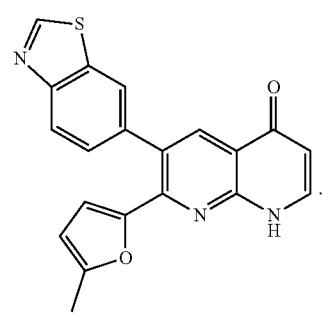 [SMILES: Cc1ccc(-c2nc3[nH]ccc(=O)c3cc2-c2ccc3ncsc3c2)o1 ; "."]
74. The compound of claim 44, wherein the compound is
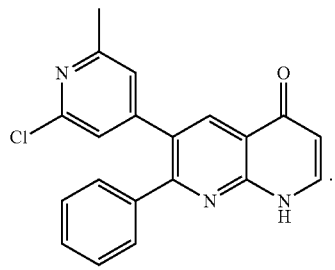 [SMILES: Cc1cc(-c2cc3c(=O)cc[nH]c3nc2-c2ccccc2)cc(Cl)n1 ; "."]
75. The compound of claim 44, or a pharmaceutically acceptable salt thereof, wherein the compound is
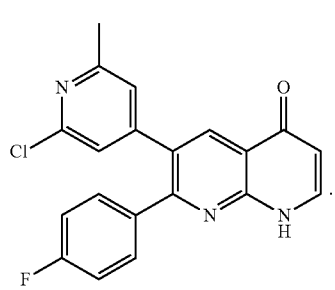 [SMILES: Cc1cc(-c2cc3c(=O)cc[nH]c3nc2-c2ccc(F)cc2)cc(Cl)n1 ; "."]
76. The compound of claim 44, wherein the compound is
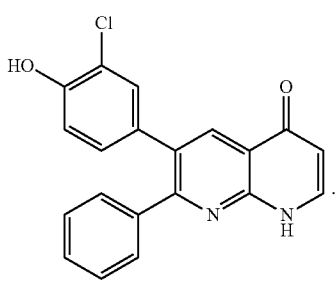
* * * * *